US012435266B2

(12) United States Patent
Watabe et al.

(10) Patent No.: US 12,435,266 B2
(45) Date of Patent: Oct. 7, 2025

(54) MATERIAL FOR HOLE-TRANSPORT LAYER, MATERIAL FOR HOLE-INJECTION LAYER, ORGANIC COMPOUND, LIGHT-EMITTING DEVICE, LIGHT-EMITTING APPARATUS, ELECTRONIC DEVICE, AND LIGHTING DEVICE

(71) Applicant: SEMICONDUCTOR ENERGY LABORATORY CO., LTD., Atsugi (JP)

(72) Inventors: Takeyoshi Watabe, Kanagawa (JP); Tomohiro Kubota, Kanagawa (JP); Airi Ueda, Kanagawa (JP); Satoshi Seo, Kanagawa (JP); Nobuharu Ohsawa, Kanagawa (JP); Yuko Kubota, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 0 days.

(21) Appl. No.: 16/919,291

(22) Filed: Jul. 2, 2020

(65) Prior Publication Data

US 2021/0005814 A1 Jan. 7, 2021

(30) Foreign Application Priority Data

| | | |
|---|---|---|
| Jul. 5, 2019 | (JP) | 2019-126017 |
| Jan. 31, 2020 | (JP) | 2020-015450 |
| Apr. 3, 2020 | (JP) | 2020-067192 |
| Apr. 28, 2020 | (JP) | 2020-078898 |

(51) Int. Cl.

| | |
|---|---|
| ***H01L 51/00*** | (2006.01) |
| ***C07C 211/61*** | (2006.01) |
| ***C09K 11/06*** | (2006.01) |
| ***H10K 85/60*** | (2023.01) |
| *H10K 50/15* | (2023.01) |
| *H10K 50/17* | (2023.01) |
| *H10K 101/20* | (2023.01) |
| *H10K 101/25* | (2023.01) |

(52) U.S. Cl.

CPC ............ *C09K 11/06* (2013.01); *C07C 211/61* (2013.01); *H10K 85/633* (2023.02); *C07C 2601/14* (2017.05); *C07C 2601/20* (2017.05); *C07C 2603/18* (2017.05); *C07C 2603/97* (2017.05); *C09K 2211/1007* (2013.01); *C09K 2211/1011* (2013.01); *C09K 2211/1014* (2013.01); *H10K 50/15* (2023.02); *H10K 50/17* (2023.02); *H10K 85/615* (2023.02); *H10K 85/626* (2023.02); *H10K 2101/20* (2023.02); *H10K 2101/25* (2023.02)

(58) Field of Classification Search

None

See application file for complete search history.

(56) References Cited

U.S. PATENT DOCUMENTS

| | | | | |
|---|---|---|---|---|
| 8,642,190 B2 | 2/2014 | Ogita et al. | | |
| 8,691,398 B2 | 4/2014 | Yamada et al. | | |
| 9,051,239 B2 | 6/2015 | Osaka et al. | | |
| 9,115,055 B2 | 8/2015 | Horikiri et al. | | |
| 9,496,503 B2 | 11/2016 | Takeda et al. | | |
| 9,634,263 B2 | 4/2017 | Ogita et al. | | |
| 9,818,984 B2 | 11/2017 | Mizuno | | |
| 10,556,864 B2 | 2/2020 | Nomura et al. | | |
| 10,941,108 B2 | 3/2021 | Jeong et al. | | |
| 12,139,446 B2 * | 11/2024 | Seo | H10K 85/633 | |
| 2007/0207346 A1 * | 9/2007 | Saitoh | C09K 11/06 | 257/E51.032 |
| 2008/0166591 A1 | 7/2008 | Yamada et al. | | |
| 2009/0066227 A1 * | 3/2009 | Okinaka | H10K 85/633 | 313/504 |
| 2009/0160323 A1 | 6/2009 | Nomura et al. | | |
| 2009/0302758 A1 * | 12/2009 | Saitoh | C09K 11/06 | 313/506 |

(Continued)

FOREIGN PATENT DOCUMENTS

| | | | |
|---|---|---|---|
| CN | 105111143 A * | 12/2015 | C07D 219/02 |
| CN | 107148408 A | 9/2017 | |

(Continued)

OTHER PUBLICATIONS

KR20190035567 machine translation, downloaded Dec. 27, 2021 from Google patents.*

JPH11162649 machine translation downloaded Feb. 11, 2023.*

S. Kim et al., International Nanoelectronics Conference, 3rd, Hong Kong, China, 678-678 (2010) (Year: 2010).*

CAS Abstract and Indexed Compounds, Jeong et al., US 2019/0016666 (Jan. 17, 2019) (Year: 2019).*

International Union of Pure and Applied Chemistry, Compendium of Chemical Terminology (IUPAC), Gold Book (2012) (Year: 2012).*

(Continued)

*Primary Examiner* — Alexander R Pagano

(74) *Attorney, Agent, or Firm* — Fish & Richardson P.C.

(57) ABSTRACT

A material for a hole-transport layer includes a monoamine compound. The first aromatic group, the second aromatic group, and the third aromatic group are bonded to the nitrogen atom of the monoamine compound. The first and second aromatic groups each independently include 1 to 3 benzene rings. One or both of the first and second aromatic groups have one or more hydrocarbon groups each having 1 to 12 carbon atoms each forming a bond only by the $sp^3$ hybrid orbitals. The total number of the carbon atoms in the hydrocarbon group in the first or second aromatic group is 6 or more. The total number of the carbon atoms in all of the hydrocarbon groups in the first and second aromatic groups is 8 or more. The third aromatic group is a substituted or unsubstituted monocyclic condensed ring or a substituted or unsubstituted bicyclic or tricyclic condensed ring.

6 Claims, 114 Drawing Sheets

(56) References Cited

U.S. PATENT DOCUMENTS

| | | | | |
|---|---|---|---|---|
| 2010/0104969 | A1 | 4/2010 | Mochizuki et al. | |
| 2013/0207046 | A1* | 8/2013 | Pflumm | C07D 219/02 252/500 |
| 2015/0329772 | A1 | 11/2015 | Heil et al. | |
| 2018/0009751 | A1 | 1/2018 | Nomura et al. | |
| 2019/0016666 | A1* | 1/2019 | Jeong | H10K 85/6572 |
| 2021/0317069 | A1* | 10/2021 | Seo | C07C 211/61 |
| 2022/0077391 | A1* | 3/2022 | Ohsawa | C07C 211/61 |
| 2022/0216445 | A1* | 7/2022 | Seo | H10K 30/451 |
| 2023/0037397 | A1* | 2/2023 | Watabe | A47L 9/2857 |
| 2023/0180501 | A1* | 6/2023 | Kawano | H10K 50/16 257/40 |
| 2023/0225149 | A1* | 7/2023 | Watabe | H10K 85/631 257/40 |
| 2023/0276647 | A1* | 8/2023 | Kawano | H10K 85/636 257/40 |
| 2023/0320130 | A1* | 10/2023 | Watabe | H10K 59/879 257/40 |
| 2023/0337462 | A1* | 10/2023 | Ueda | H10K 50/11 |
| 2024/0023431 | A1* | 1/2024 | Watabe | C09K 11/06 |
| 2024/0049578 | A1* | 2/2024 | Watabe | H05B 33/10 |

FOREIGN PATENT DOCUMENTS

| | | | | | |
|---|---|---|---|---|---|
| CN | 108623479 | A | * | 10/2018 | C07C 209/10 |
| CN | 108623481 | A | | 10/2018 | |
| CN | 111196822 | B | * | 2/2024 | C07F 7/0816 |
| JP | 11-162649 | A | | 6/1999 | |
| JP | 11-282181 | A | | 10/1999 | |
| JP | 2005-120030 | A | | 5/2005 | |
| JP | 2007-318063 | A | | 12/2007 | |
| JP | 2008-019238 | A | | 1/2008 | |
| JP | 2008-162910 | A | | 7/2008 | |
| JP | 2009-091304 | A | | 4/2009 | |
| JP | 2011-098903 | A | | 5/2011 | |
| JP | 2014-207356 | A | | 10/2014 | |
| JP | 2016-509592 | | | 3/2016 | |
| JP | 2018-181916 | A | | 11/2018 | |
| JP | 2019-505566 | | | 2/2019 | |
| KR | 2013-0060953 | A | | 6/2013 | |
| KR | 2016032521 | A | * | 3/2016 | C07C 15/20 |
| KR | 2017-0080432 | A | | 7/2017 | |
| KR | 20190035567 | | * | 9/2018 | C07C 211/61 |
| KR | 2018-0137315 | A | | 12/2018 | |
| KR | 2019-0007789 | A | | 1/2019 | |
| WO | WO-2007/072741 | | | 6/2007 | |
| WO | WO-2007/072952 | | | 6/2007 | |
| WO | WO-2011/055493 | | | 5/2011 | |
| WO | WO-2013/081410 | | | 6/2013 | |
| WO | WO-2017/116167 | | | 7/2017 | |
| WO | WO-2017/116168 | | | 7/2017 | |

OTHER PUBLICATIONS

R. Silverstein et al., Spectrometric Identification of Organic Compounds, 175-176 (5th ed., Wiley, 1991) (Year: 1991).*

International Union of Pure and Applied Chemistry, Compendium of Chemical Terminology (IUPAC), Gold Book, p. 115 of 1622 (2012) (Year: 2012).*

Lee.J et al., "Synergetic electrode architecture for efficient graphene-based flexible organic light-emitting diodes", Nature Communications, Jun. 2, 2016, vol. 7, pp. 11791-1-11791-9.

Taiwanese Office Action (Application No. 109122382) Dated Feb. 23, 2024.

* cited by examiner

MATERIAL FOR HOLE-TRANSPORT LAYER, MATERIAL FOR HOLE-INJECTION LAYER, ORGANIC COMPOUND, LIGHT-EMITTING DEVICE, LIGHT-EMITTING APPARATUS, ELECTRONIC DEVICE, AND LIGHTING DEVICE

BACKGROUND OF THE INVENTION

1. Field of the Invention

Embodiments of the present invention relate to an organic compound, a light-emitting element, a light-emitting device, a display module, a lighting module, a display device, a light-emitting apparatus, an electronic device, and a lighting device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

2. Description of the Related Art

Light-emitting devices (organic EL devices) including organic compounds and utilizing electroluminescence (EL) have been put to more practical use. In the basic structure of such light-emitting devices, an organic compound layer containing a light-emitting material (an EL layer) is interposed between a pair of electrodes. Carriers are injected by application of voltage to the element, and recombination energy of the carriers is used, whereby light emission can be obtained from the light-emitting material.

Such light-emitting devices are of self-light-emitting type and thus have advantages over liquid crystal displays, such as high visibility and no need for backlight when used as pixels of a display, and are suitable as flat panel display devices. Displays including such light-emitting devices are also highly advantageous in that they can be thin and lightweight. Moreover, such light-emitting devices also have a feature that response speed is extremely fast.

Since light-emitting layers of such light-emitting devices can be successively formed two-dimensionally, planar light emission can be achieved. This feature is difficult to realize with point light sources typified by incandescent lamps and LEDs or linear light sources typified by fluorescent lamps; thus, the light-emitting devices also have great potential as planar light sources, which can be applied to lighting devices and the like.

Displays or lighting devices including light-emitting devices are suitable for a variety of electronic devices as described above, and research and development of light-emitting devices have progressed for more favorable characteristics.

Low outcoupling efficiency is often a problem in an organic EL device. In particular, the attenuation due to reflection which is caused by a difference in refractive index between adjacent layers is a main cause of a reduction in device efficiency. In order to reduce this effect, a structure including a layer formed using a low refractive index material in an EL layer (see Non-Patent Document 1, for example) has been proposed.

A light-emitting device having this structure can have higher outcoupling efficiency and higher external quantum efficiency than a light-emitting device having a conventional structure; however, it is not easy to form such a layer with a low refractive index in an EL layer without adversely affecting other critical characteristics of the light-emitting device. This is because a low refractive index is in a trade-off relationship with a high carrier-transport property or high reliability of a light-emitting device including a layer with a low refractive index. This problem is caused because the carrier-transport property and reliability of an organic compound largely depend on an unsaturated bond, and an organic compound having many unsaturated bonds tends to have a high refractive index.

REFERENCE

Patent Document 1

Japanese Published Patent Application No. H11-282181

Patent Document 2

Japanese Published Patent Application No. 2009-91304

Patent Document 3

United States Patent Application Publication No. 2010/104969

Non-Patent Document 1

Jaeho Lee et al., "Synergetic electrode architecture for efficient graphene-based flexible organic light-emitting diodes", nature COMMUNICATIONS, Jun. 2, 2016, DOI: 10.1038/ncomms 11791.

SUMMARY OF THE INVENTION

An object of one embodiment of the present invention is to provide a novel material for a hole-transport layer. Another object of one embodiment of the present invention is to provide a material for a hole-transport layer with a low refractive index. Another object of one embodiment of the present invention is to provide a material for a hole-transport layer with a low refractive index and a carrier-transport property. Another object of one embodiment of the present invention is to provide a material for a hole-transport layer with a low refractive index and a hole-transport property.

An object of one embodiment of the present invention is to provide a novel material for a hole-injection layer. Another object of one embodiment of the present invention is to provide a material for a hole-injection layer with a low refractive index. Another object of one embodiment of the present invention is to provide a material for a hole-injection layer with a low refractive index and a carrier-transport property. Another object of one embodiment of the present invention is to provide a material for a hole-injection layer with a low refractive index and a hole-transport property.

An object of one embodiment of the present invention is to provide a novel organic compound. Another object of one embodiment of the present invention is to provide a novel organic compound having a carrier-transport property. Another object of one embodiment of the present invention is to provide a novel organic compound having a hole-transport property. An object of one embodiment of the present invention is to provide a novel organic compound with a low refractive index. Another object of one embodiment of the present invention is to provide a novel organic compound with a low refractive index and a carrier-transport property. Another object of one embodiment of the present invention is to provide a novel organic compound with a low refractive index and a hole-transport property.

Another object of one embodiment of the present invention is to provide a light-emitting device having high emission efficiency. Another object of one embodiment of the present invention is to provide a light-emitting device, a light-emitting apparatus, an electronic device, and a display device each having low power consumption.

Note that the descriptions of these objects do not preclude the existence of other objects. One embodiment of the present invention does not necessarily achieve all the objects listed above. Other objects will be apparent from and can be derived from the descriptions of the specification, the drawings, the claims, and the like.

It is only necessary that at least one of the above-described objects be achieved in the present invention.

One embodiment of the present invention is a material for a hole-transport layer including an aromatic amine compound. The glass transition temperature of the aromatic amine compound is higher than or equal to 90° C. A layer including the aromatic amine compound has a refractive index of higher than or equal to 1.5 and lower than or equal to 1.75. Another embodiment of the present invention is a material for a hole-transport layer including an aromatic amine compound. The glass transition temperature of the aromatic amine compound is higher than or equal to 90° C. The proportion of carbon atoms each forming a bond only by the $sp^3$ hybrid orbitals to the total number of carbon atoms in the molecule of the aromatic amine compound is higher than or equal to 23% and lower than or equal to 55%. Another embodiment of the present invention is a material for a hole-transport layer including an aromatic amine compound. The glass transition temperature of the aromatic amine compound is higher than or equal to 90° C. An integral value of signals at lower than 4 ppm exceeds an integral value of signals at 4 ppm or higher in results of H-NMR measurement conducted on the aromatic amine compound.

Note that the aromatic amine compound is preferably a triarylamine compound. The glass transition temperature is preferably higher than or equal to 100° C., further preferably higher than or equal to 110° C., still further preferably higher than or equal to 120° C.

Another embodiment of the present invention is a material for a hole-transport layer including a monoamine compound, the monoamine compound including a first aromatic group, a second aromatic group, and a third aromatic group. The first aromatic group, the second aromatic group, and the third aromatic group are bonded to a nitrogen atom of the monoamine compound. A layer including the monoamine compound has a refractive index of higher than or equal to 1.5 and lower than or equal to 1.75.

Another embodiment of the present invention is a material for a hole-transport layer including a monoamine compound, the monoamine compound including a first aromatic group, a second aromatic group, and a third aromatic group. The first aromatic group, the second aromatic group, and the third aromatic group are bonded to a nitrogen atom of the monoamine compound. The proportion of carbon atoms each forming a bond only by the $sp^3$ hybrid orbitals to the total number of carbon atoms in the molecule is higher than or equal to 23% and lower than or equal to 55%.

Another embodiment of the present invention is a material for a hole-transport layer including a monoamine compound, the monoamine compound including a first aromatic group, a second aromatic group, and a third aromatic group. The first aromatic group, the second aromatic group, and the third aromatic group are bonded to a nitrogen atom of the monoamine compound. An integral value of signals at lower than 4 ppm exceeds an integral value of signals at 4 ppm or higher in results of $^1$H-NMR measurement conducted on the monoamine compound.

Another embodiment of the present invention is any of the above materials for a hole-transport layer in which a layer including the monoamine compound has a refractive index of higher than or equal to 1.5 and lower than or equal to 1.75.

Another embodiment of the present invention is any of the above materials for a hole-transport layer, in which the monoamine compound has at least one fluorene skeleton.

Another embodiment of the present invention is any of the above materials for a hole-transport layer, in which one or more of the first aromatic group, the second aromatic group, and the third aromatic group are a fluorene skeleton.

Another embodiment of the present invention is any of the materials for a hole-transport layer, in which the molecular weight of the monoamine compound is greater than or equal to 400 and less than or equal to 1000.

Another embodiment of the present invention is a material for a hole-transport layer including a monoamine compound. A first aromatic group, a second aromatic group, and a third aromatic group are bonded to a nitrogen atom of the monoamine compound. The first aromatic group and the second aromatic group each independently include 1 to 3 benzene rings. One or both of the first aromatic group and the second aromatic group include one or more hydrocarbon groups each having 1 to 12 carbon atoms each forming a bond only by the $sp^3$ hybrid orbitals. The total number of the carbon atoms contained in the hydrocarbon group in the first aromatic group or the second aromatic group is 6 or more. The total number of the carbon atoms contained in all of the hydrocarbon groups in the first aromatic group and the second aromatic group is 8 or more. The third aromatic group is a substituted or unsubstituted monocyclic condensed ring or a substituted or unsubstituted bicyclic or tricyclic condensed ring.

Another embodiment of the present invention is any of the above materials for a hole-transport layer, in which the third aromatic group has 6 to 13 carbon atoms in a ring.

Another embodiment of the present invention is any of the above materials for a hole-transport layer, in which a layer including the monoamine compound has a refractive index of higher than or equal to 1.5 and lower than or equal to 1.75.

Another embodiment of the present invention is any of the above materials for a hole-transport layer, in which the third aromatic group includes a fluorene skeleton.

Another embodiment of the present invention is any of the above materials for a hole-transport layer, in which the third aromatic group is a fluorene skeleton.

Another embodiment of the present invention is any of the above materials for a hole-transport layer, in which the total number of the carbon atoms each forming a bond only by the $sp^3$ hybrid orbitals contained in all of the hydrocarbon groups in the first aromatic group and the second aromatic group is 36 or less.

Another embodiment of the present invention is any of the above materials for a hole-transport layer, in which the total number of the carbon atoms each forming a bond only by the $sp^3$ hybrid orbitals contained in all of the hydrocarbon groups in the first aromatic group and the second aromatic group is 12 or more.

Another embodiment of the present invention is any of the above materials for a hole-transport layer, in which the total number of the carbon atoms each forming a bond only by the $sp^3$ hybrid orbitals contained in all of the hydrocarbon groups in the first aromatic group and the second aromatic group is 30 or less.

Another embodiment of the present invention is any of the above materials for a hole-transport layer, in which the hydrocarbon group having 1 to 12 carbon atoms each forming a bond only by the $sp^3$ hybrid orbitals is an alkyl group having 3 to 8 carbon atoms or a cycloalkyl group having 6 to 12 carbon atoms.

Another embodiment of the present invention is any of the above materials for a hole-transport layer, in which the first aromatic group, the second aromatic group, and the third aromatic group are each a hydrocarbon ring.

Another embodiment of the present invention is a material for a hole-injection layer including a monoamine compound, the monoamine compound including a first aromatic group, a second aromatic group, and a third aromatic group. The first aromatic group, the second aromatic group, and the third aromatic group are bonded to a nitrogen atom of the monoamine compound. A layer including the monoamine compound has a refractive index of higher than or equal to 1.5 and lower than or equal to 1.75.

Another embodiment of the present invention is a material for a hole-injection layer including a monoamine compound, the monoamine compound including a first aromatic group, a second aromatic group, and a third aromatic group. The first aromatic group, the second aromatic group, and the third aromatic group are bonded to a nitrogen atom of the monoamine compound. The proportion of carbon atoms each forming a bond only by the $sp^3$ hybrid orbitals to the total number of carbon atoms in the molecule is higher than or equal to 23% and lower than or equal to 55%.

Another embodiment of the present invention is a material for a hole-injection layer including a monoamine compound, the monoamine compound including a first aromatic group, a second aromatic group, and a third aromatic group. The first aromatic group, the second aromatic group, and the third aromatic group are bonded to a nitrogen atom of the monoamine compound. An integral value of signals at lower than 4 ppm exceeds an integral value of signals at 4 ppm or higher in results of $^1$H-NMR measurement conducted on the monoamine compound.

Another embodiment of the present invention is any of the above materials for a hole-injection layer, in which a layer including the monoamine compound has a refractive index of higher than or equal to 1.5 and lower than or equal to 1.75.

Another embodiment of the present invention is any of the above materials for a hole-injection layer, in which the monoamine compound has at least one fluorene skeleton.

Another embodiment of the present invention is any of the above materials for a hole-injection layer, in which one or more of the first aromatic group, the second aromatic group, and the third aromatic group are a fluorene skeleton.

Another embodiment of the present invention is any of the above materials for a hole-injection layer, in which the molecular weight of the monoamine compound is greater than or equal to 400 and less than or equal to 1000.

Another embodiment of the present invention is a material for a hole-injection layer including a monoamine compound. A first aromatic group, a second aromatic group, and a third aromatic group are bonded to a nitrogen atom of the monoamine compound. The first aromatic group and the second aromatic group each independently include 1 to 3 benzene rings. One or both of the first aromatic group and the second aromatic group include one or more hydrocarbon groups each having 1 to 12 carbon atoms each forming a bond only by the $sp^3$ hybrid orbitals. The total number of the carbon atoms contained in the hydrocarbon group in the first aromatic group or the second aromatic group is 6 or more. The total number of the carbon atoms contained in all of the hydrocarbon groups in the first aromatic group and the second aromatic group is 8 or more. The third aromatic group is a substituted or unsubstituted monocyclic condensed ring or a substituted or unsubstituted bicyclic or tricyclic condensed ring.

Another embodiment of the present invention is any of the above materials for a hole-injection layer, in which the third aromatic group has 6 to 13 carbon atoms in a ring.

Another embodiment of the present invention is any of the above materials for a hole-injection layer, in which a layer including the monoamine compound has a refractive index of higher than or equal to 1.5 and lower than or equal to 1.75.

Another embodiment of the present invention is any of the above materials for a hole-injection layer, in which the third aromatic group includes a fluorene skeleton.

Another embodiment of the present invention is any of the above materials for a hole-injection layer, in which the third aromatic group is a fluorene skeleton.

Another embodiment of the present invention is any of the above materials for a hole-injection layer, in which the total number of the carbon atoms each forming a bond only by the $sp^3$ hybrid orbitals contained in all of the hydrocarbon groups in the first aromatic group and the second aromatic group is 36 or less.

Another embodiment of the present invention is any of the above materials for a hole-injection layer, in which the total number of the carbon atoms each forming a bond only by the $sp^3$ hybrid orbitals contained in all of the hydrocarbon groups in the first aromatic group and the second aromatic group is 12 or more.

Another embodiment of the present invention is any of the above materials for a hole-injection layer, in which the total number of the carbon atoms each forming a bond only by the $sp^3$ hybrid orbitals contained in all of the hydrocarbon groups in the first aromatic group and the second aromatic group is 30 or less.

Another embodiment of the present invention is any of the above materials for a hole-injection layer, in which the hydrocarbon group having 1 to 12 carbon atoms each forming a bond only by the $sp^3$ hybrid orbitals is an alkyl group having 3 to 8 carbon atoms or a cycloalkyl group having 6 to 12 carbon atoms.

Another embodiment of the present invention is any of the above materials for a hole-injection layer, in which the first aromatic group, the second aromatic group, and the third aromatic group are each a hydrocarbon ring.

Note that the glass transition temperature of the monoamine compound included in any of the above materials for a hole-transport layer or a hole-injection layer is preferably higher than or equal to 90° C. The glass transition temperature is further preferably higher than or equal to 100° C., still further preferably higher than or equal to 110° C., still further preferably higher than or equal to 120° C.

Another embodiment of the present invention is an organic compound represented by a general formula (G1) shown below.

[Chemical Formula 1]

(G1)

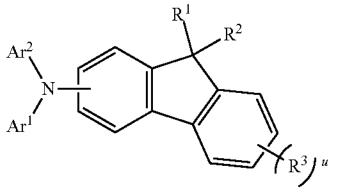

Note that in the general formula (G1), $Ar^1$ and $Ar^2$ each independently represent a substituent with a benzene ring or a substituent in which 2 or 3 benzene rings are bonded to each other. One or both of $Ar^1$ and $Ar^2$ have one or more hydrocarbon groups each having 1 to 12 carbon atoms each forming a bond only by the $sp^3$ hybrid orbitals. The total number of the carbon atoms contained in all of the hydrocarbon groups in $Ar^1$ and $Ar^2$ is 8 or more and the total number of the carbon atoms contained in the hydrocarbon group in $Ar^1$ or $Ar^2$ is 6 or more. In the case where a plurality of straight-chain alkyl groups each having 1 or 2 carbon atoms are included as the hydrocarbon groups in $Ar^1$ or $Ar^2$, the alkyl groups may be bonded to each other to form a ring. In the general formula (G1), $R^1$ and $R^2$ each independently represent an alkyl group having 1 to 4 carbon atoms. $R^1$ and $R^2$ may be bonded to each other to form a ring. $R^3$ represents an alkyl group having 1 to 4 carbon atoms, and u is an integer of 0 to 4.

Another embodiment of the present invention is an organic compound represented by a general formula (G2) shown below.

Note that in the general formula (G2), n, m, p, and r each independently represent 1 or 2, and s, t, and u each independently represent an integer of 0 to 4. Note that n+p and m+r are each independently 2 or 3. $R^4$ and $R^5$ each independently represent hydrogen or a hydrocarbon group having 1 to 3 carbon atoms. $R^{10}$ to $R^{14}$ and $R^{20}$ to $R^{24}$ each independently represent hydrogen or a hydrocarbon group having 1 to 12 carbon atoms each forming a bond only by the $sp^3$ hybrid orbitals. The total number of the carbon atoms contained in $R^{10}$ to $R^{14}$ and $R^{20}$ to $R^{24}$ is 8 or more and the total number of the carbon atoms contained in either $R^{10}$ to $R^{14}$ or $R^{20}$ to $R^{24}$ is 6 or more. $R^1$, $R^2$, and $R^3$ each independently represent an alkyl group having 1 to 4 carbon atoms. In the case where n is 2, the kind and number of substituents and the position of bonds in one phenylene group may be the same as or different from those of the other phenylene group. In the case where m is 2, the kind and number of substituents and the position of bonds in one phenylene group may be the same as or different from those of the other phenylene group. In the case where p is 2, the kind and number of substituents and the position of bonds in one phenyl group may be the same as or different from those of the other phenyl group. In the case where r is 2, the kind and number of substituents and the position of bonds in one phenylene group may be the same as or different from those of the other phenylene group. In the case where s is an integer of 2 to 4, $R^4$s are the same or different. In the case where t is an integer of 2 to 4, $R^{5s}$ are the same or different. In the case where u is an integer of 2 to 4, $R^3$s are the same or different. $R^1$ and $R^2$ may be bonded to each other to form a ring. Adjacent groups among $R^4$, $R^5$, $R^{10}$ to $R^{14}$, and $R^{20}$ to $R^{24}$ may be bonded to each other to form a ring.

[Chemical Formula 2]

(G2)

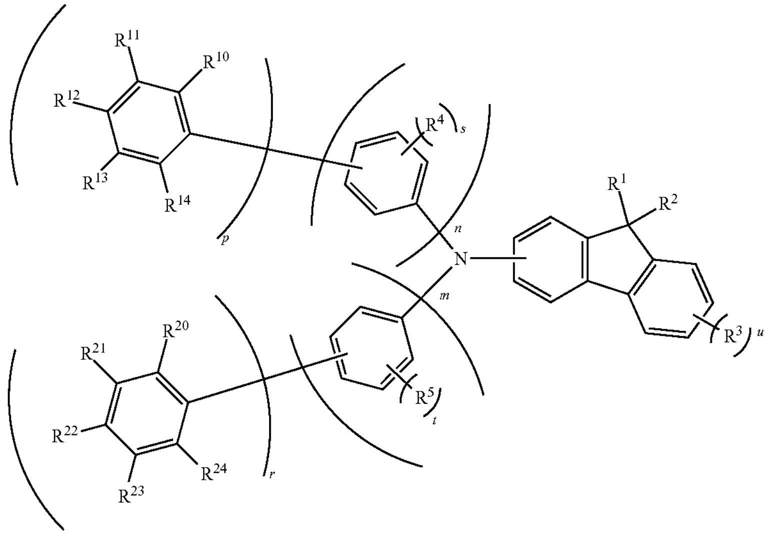

Another embodiment of the present invention is any of the above organic compounds in which t is 0.

Another embodiment of the present invention is an organic compound represented by a general formula (G3) shown below.

[Chemical Formula 3]

(G3)

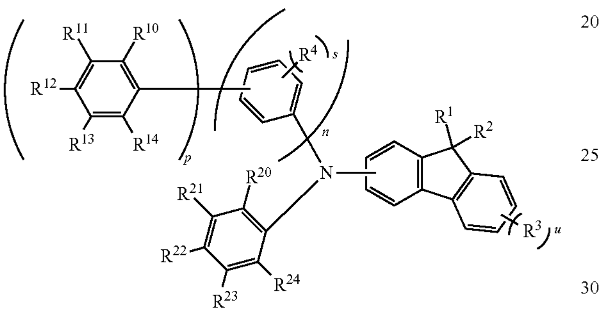

Note that in the general formula (G3), n and p each independently represent 1 or 2, and s and u each independently represent an integer of 0 to 4. Note that n+p is 2 or 3. $R^{10}$ to $R^{14}$ and $R^{20}$ to $R^{24}$ each independently represent hydrogen or a hydrocarbon group having 1 to 12 carbon atoms each forming a bond only by the $sp^3$ hybrid orbitals. The total number of the carbon atoms contained in $R^{10}$ to $R^{14}$ and $R^{20}$ to $R^{24}$ is 8 or more and the total number of the carbon atoms contained in either $R^{10}$ to $R^{14}$ or $R^{20}$ to $R^{24}$ is 6 or more. $R^1$, $R^2$, and $R^3$ each independently represent an alkyl group having 1 to 4 carbon atoms. $R^4$ represents hydrogen or an alkyl group having 1 to 3 carbon atoms. In the case where n is 2, the kind and number of substituents and the position of bonds in one phenylene group may be the same as or different from those of the other phenylene group. In the case where p is 2, the kind and number of substituents and the position of bonds in one phenyl group may be the same as or different from those of the other phenyl group. In the case where s is an integer of 2 to 4, $R^{4}$s are the same or different. In the case where u is an integer of 2 to 4, $R^{3}$s are the same or different. $R^1$ and $R^2$ may be bonded to each other to form a ring. Adjacent groups among $R^4$, $R^{10}$ to $R^{14}$, and $R^{20}$ to $R^{24}$ may be bonded to each other to form a ring.

Another embodiment of the present invention is any of the above organic compounds in which s is 0.

Another embodiment of the present invention is an organic compound represented by a general formula (G4) shown below.

[Chemical Formula 4]

(G4)

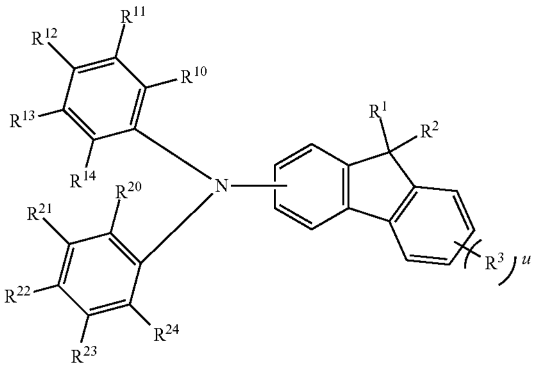

Note that in the general formula (G4), u represents an integer of 0 to 4. $R^{10}$ to $R^{14}$ and $R^{20}$ to $R^{24}$ each independently represent hydrogen or a hydrocarbon group having 1 to 12 carbon atoms each forming a bond only by the $sp^3$ hybrid orbitals. The total number of the carbon atoms contained in $R^{10}$ to $R^{14}$ and $R^{20}$ to $R^{24}$ is 8 or more and the total number of the carbon atoms contained in either $R^{10}$ to $R^{14}$ or $R^{20}$ to $R^{24}$ is 6 or more. $R^1$, $R^2$, and $R^3$ each independently represent an alkyl group having 1 to 4 carbon atoms. In the case where u is an integer of 2 to 4, $R^{3}$s are the same or different. $R^1$ and $R^2$ may be bonded to each other to form a ring. Adjacent groups among $R^{10}$ to $R^{14}$ and $R^{20}$ to $R^{24}$ may be bonded to each other to form a ring.

Another embodiment of the present invention is any of the above organic compounds in which u is 0.

Another embodiment of the present invention is any of the above organic compounds in which $R^{10}$ to $R^{14}$ and $R^{20}$ to $R^{24}$ are each independently any of hydrogen, a tert-butyl group, and a cyclohexyl group.

Another embodiment of the present invention is any of the above organic compounds in which at least three of $R^{10}$ to $R^{14}$ and at least three of $R^{20}$ to $R^{24}$ are each hydrogen.

Another embodiment of the present invention is any of the above organic compounds in which $R^{10}$, R, $R^{13}$, $R^{14}$, $R^{20}$, $R^{21}$, $R^{23}$, and $R^{24}$ are each hydrogen and $R^{12}$ and $R^{22}$ are each a cyclohexyl group.

Another embodiment of the present invention is any of the above organic compounds in which $R^{10}$, $R^{12}$, $R^{14}$, $R^{20}$, $R^{21}$, $R^{23}$, and $R^{24}$ are each hydrogen, $R^{11}$ and $R^{13}$ are each a tert-butyl group, and $R^{22}$ is a cyclohexyl group.

Another embodiment of the present invention is any of the above organic compounds in which $R^{10}$, R, $R^{14}$, $R^{20}$, $R^{22}$, and $R^{24}$ are each hydrogen and $R^{11}$, $R^{13}$, $R^{21}$ and $R^{23}$ are each a tert-butyl group.

Another embodiment of the present invention is a light-emitting device using any of the above materials for a hole-transport layer in a hole-transport layer.

Another embodiment of the present invention is a light-emitting device using any of the above materials for a hole-injection layer in a hole-injection layer.

Another embodiment of the present invention is a light-emitting device using any of the above organic compounds.

Another embodiment of the present invention is a light-emitting device using one or more of the above material for a hole-transport layer, the above material for a hole-injection layer, and the above organic compound, and containing an organic compound having a naphthobisbenzofuran skeleton or a naphthobisbenzothiophene skeleton in a light-emitting layer.

Another embodiment of the present invention is an electronic device including any of the above light-emitting devices, and at least one of a sensor, an operation button, a speaker, and a microphone.

Another embodiment of the present invention is a light-emitting apparatus including any of the above light-emitting devices, and at least one of a transistor and a substrate.

Another embodiment of the present invention is a lighting device including any of the above light-emitting devices and a housing.

Note that the light-emitting apparatus in this specification includes, in its category, an image display device that uses a light-emitting device. The light-emitting apparatus may include a module in which a light-emitting device is provided with a connector such as an anisotropic conductive film or a tape carrier package (TCP), a module in which a printed wiring board is provided at the end of a TCP, and a module in which an integrated circuit (IC) is directly mounted on a light-emitting device by a chip on glass (COG) method. Furthermore, a lighting device or the like may include the light-emitting apparatus.

According to one embodiment of the present invention, a novel material for a hole-transport layer can be provided. According to one embodiment of the present invention, a material for a hole-transport layer with a low refractive index can be provided. According to another embodiment of the present invention, a material for a hole-transport layer with a low refractive index and a carrier-transport property can be provided. According to another embodiment of the present invention, a material for a hole-transport layer with a low refractive index and a hole-transport property can be provided.

According to one embodiment of the present invention, a novel material for a hole-injection layer can be provided. According to one embodiment of the present invention, a material for a hole-injection layer with a low refractive index can be provided. According to another embodiment of the present invention, a material for a hole-injection layer with a low refractive index and a carrier-transport property can be provided. According to another embodiment of the present invention, a material for a hole-injection layer with a low refractive index and a hole-transport property can be provided.

According to one embodiment of the present invention, a novel organic compound can be provided. According to another embodiment of the present invention, a novel organic compound having a carrier-transport property can be provided. According to another embodiment of the present invention, a novel organic compound having a hole-transport property can be provided. According to one embodiment of the present invention, an organic compound with a low refractive index can be provided. According to another embodiment of the present invention, an organic compound with a low refractive index and a carrier-transport property can be provided. According to another embodiment of the present invention, an organic compound with a low refractive index and a hole-transport property can be provided.

According to another embodiment of the present invention, a light-emitting device having high emission efficiency can be provided. According to another embodiment of the present invention, a light-emitting device, a light-emitting apparatus, an electronic device, and a display device each having low power consumption can be provided.

Note that the descriptions of these effects do not preclude the existence of other effects. One embodiment of the present invention does not necessarily achieve all the effects listed above. Other effects will be apparent from and can be derived from the descriptions of the specification, the drawings, the claims, and the like.

BRIEF DESCRIPTION OF THE DRAWINGS

In the accompanying drawings:

FIGS. 7A, 7B1, 7B2, and 7C illustrate electronic devices;

FIGS. 119A and 119B are $^1$H-NMR charts of mmtBumTPtBuPAF;

FIG. 120 shows an absorption spectrum and an emission spectrum of mmtBumTPtBuPAF in a toluene solution;

Figure 121:
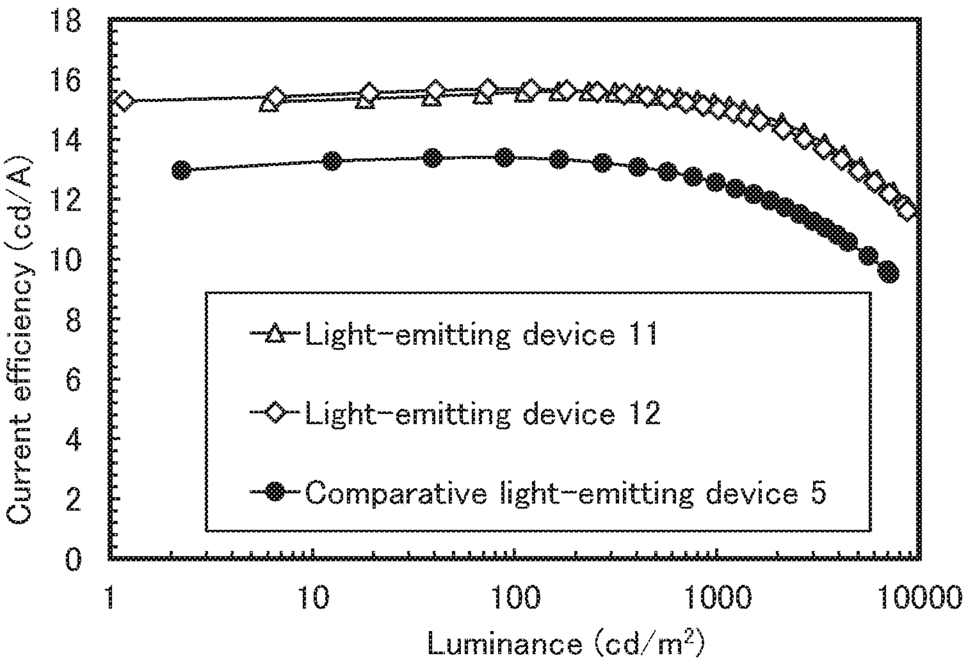
Figure 122:
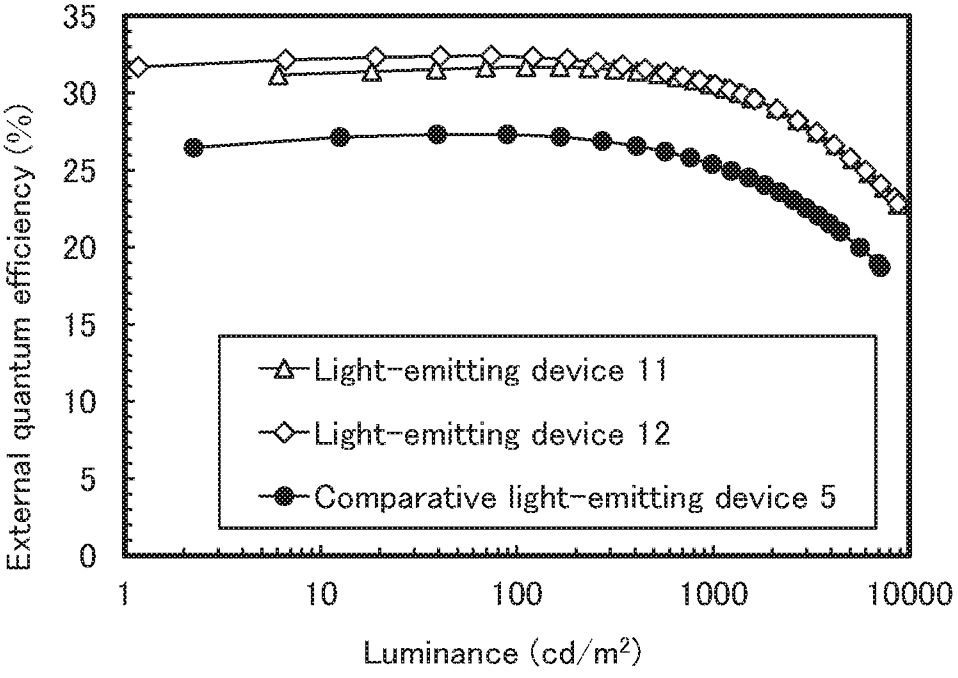
Figure 123:
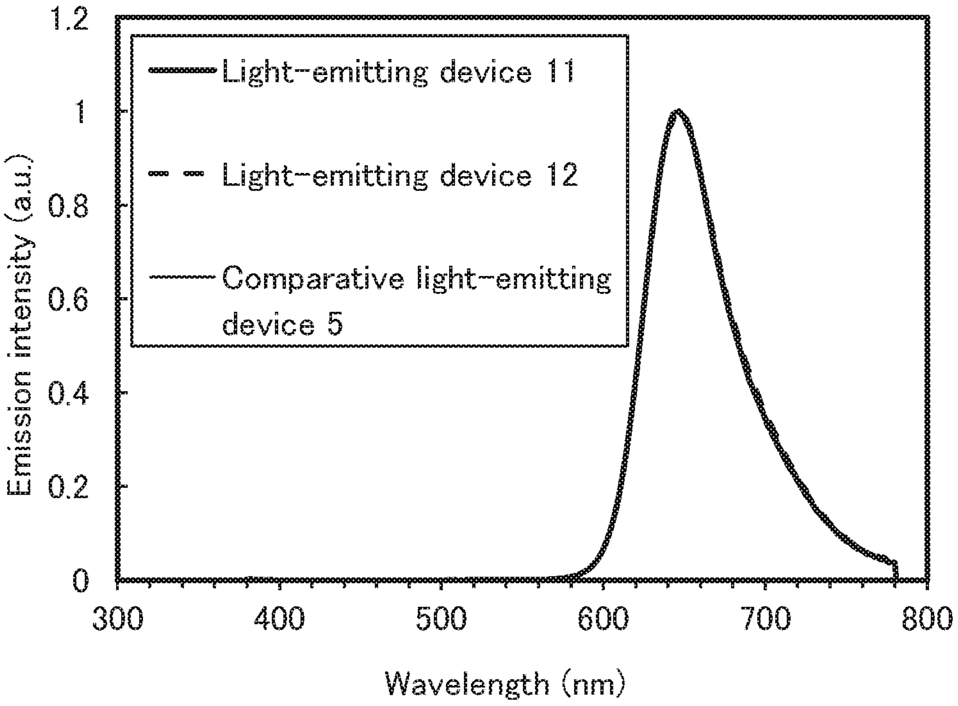
Figure 124:
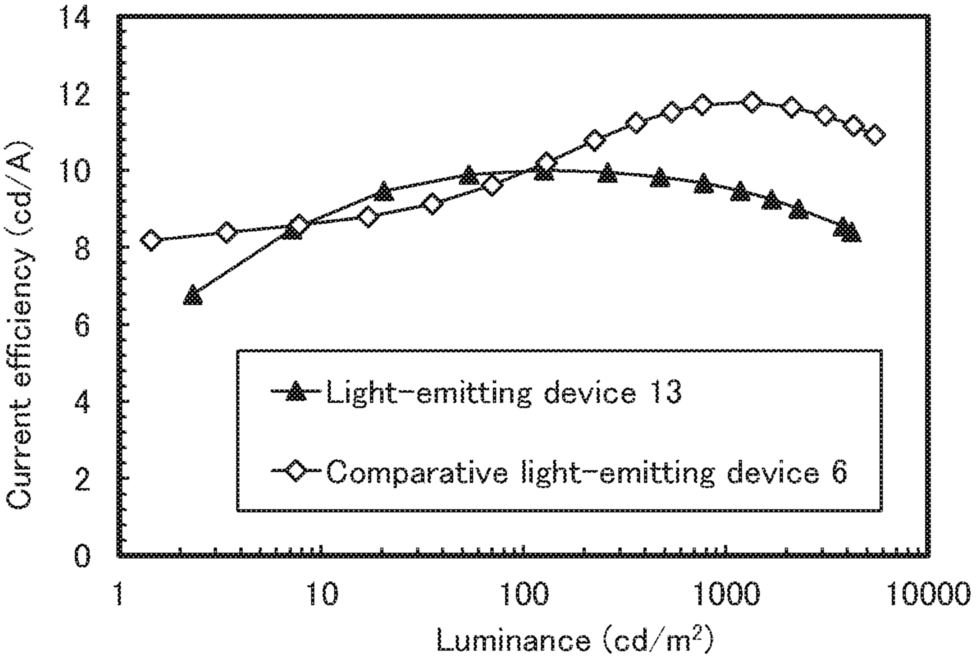
Figure 125:
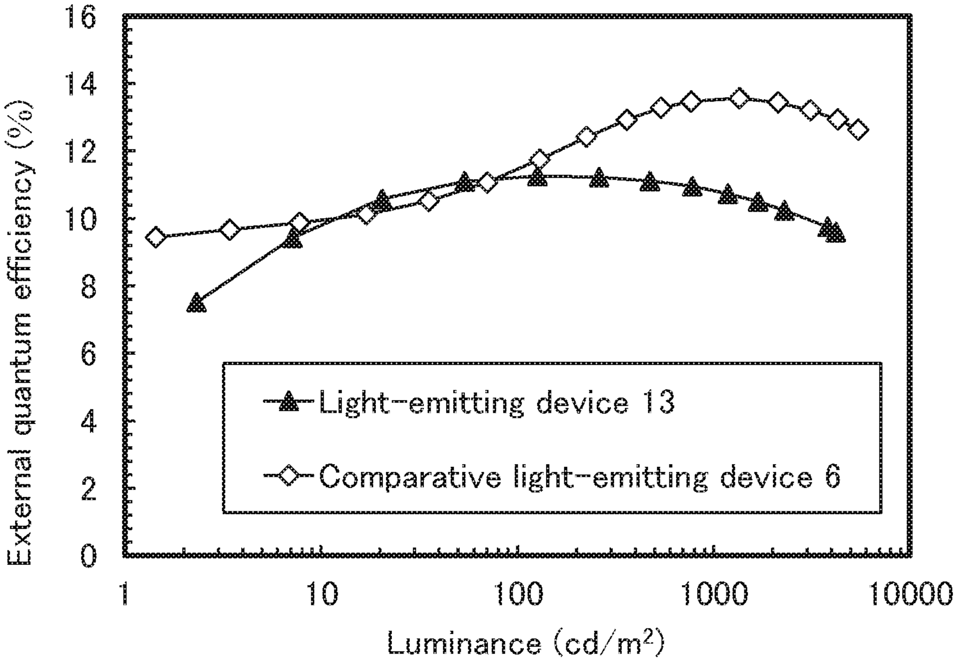
Figure 126:
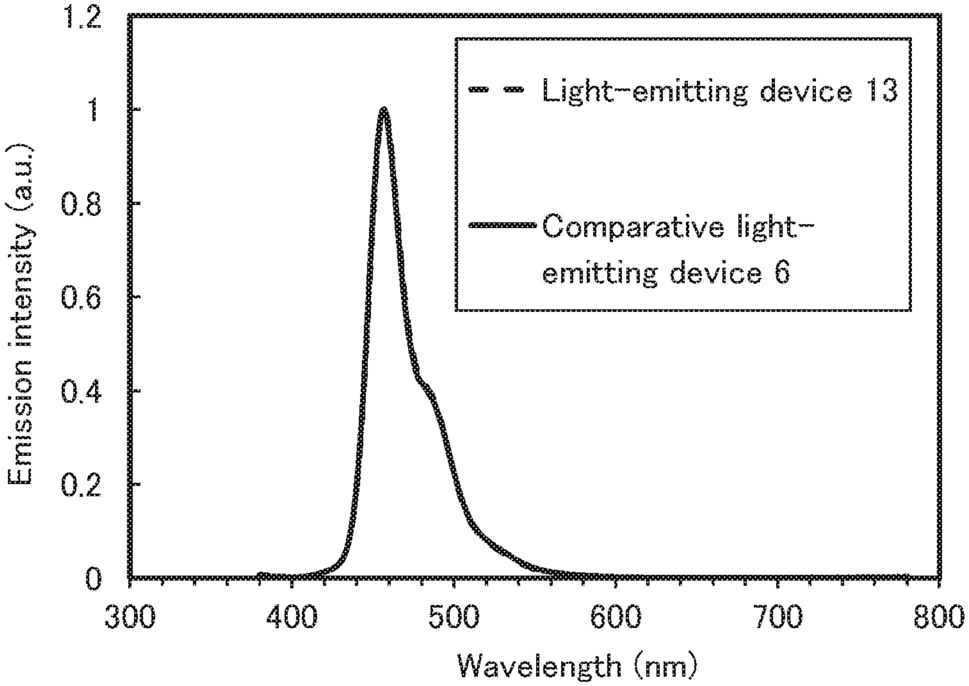
Figure 127:
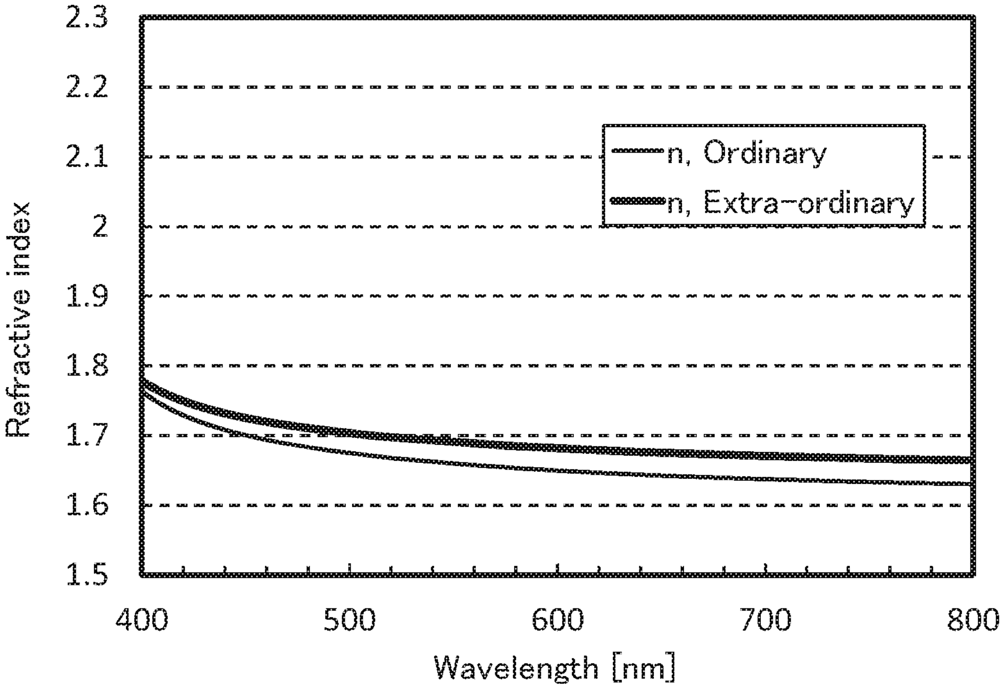
Figure 128:
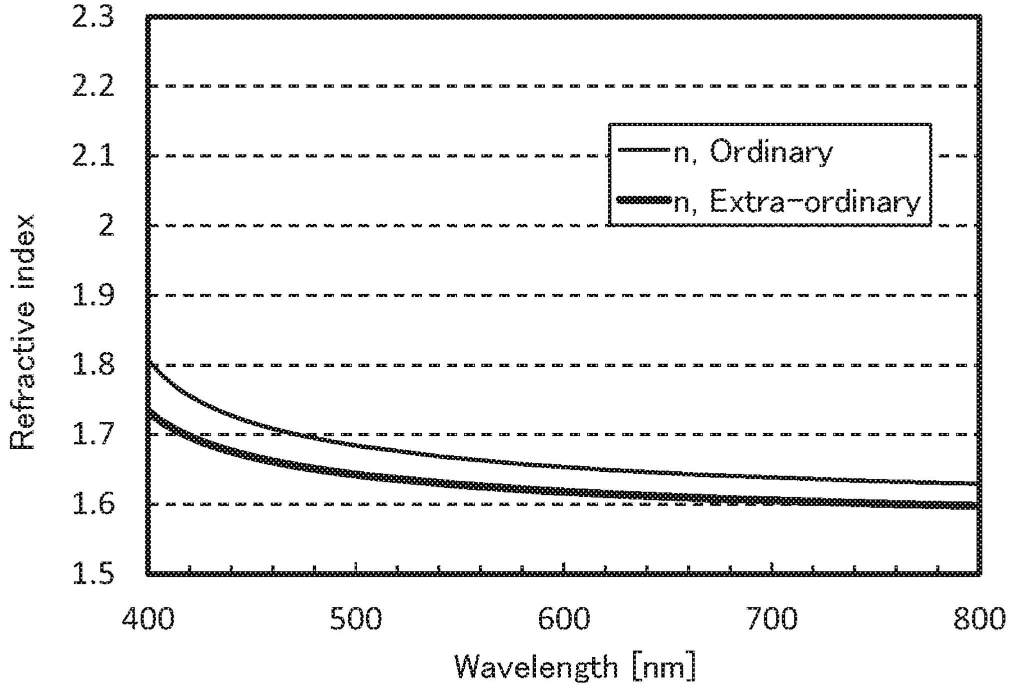
Figure 129:
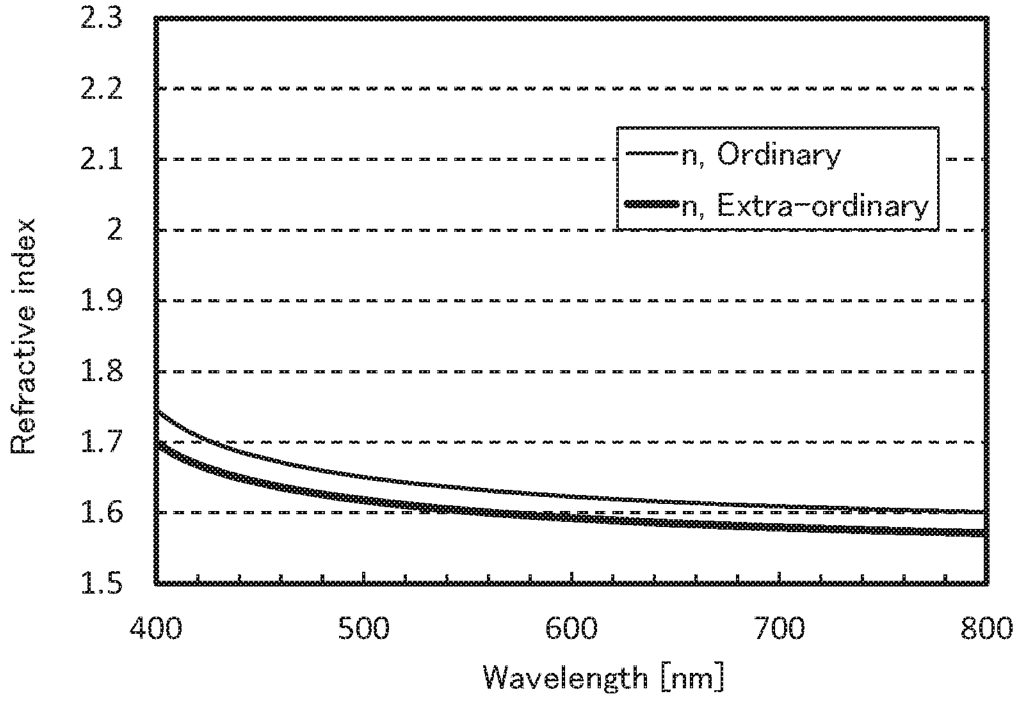
Figure 130:
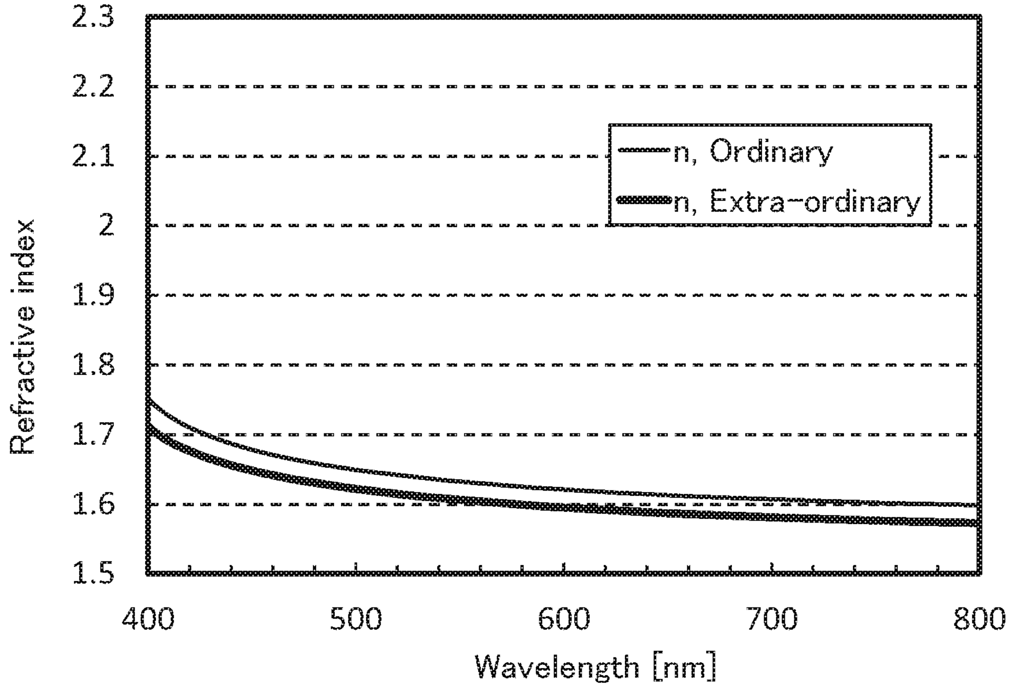
Figure 131:
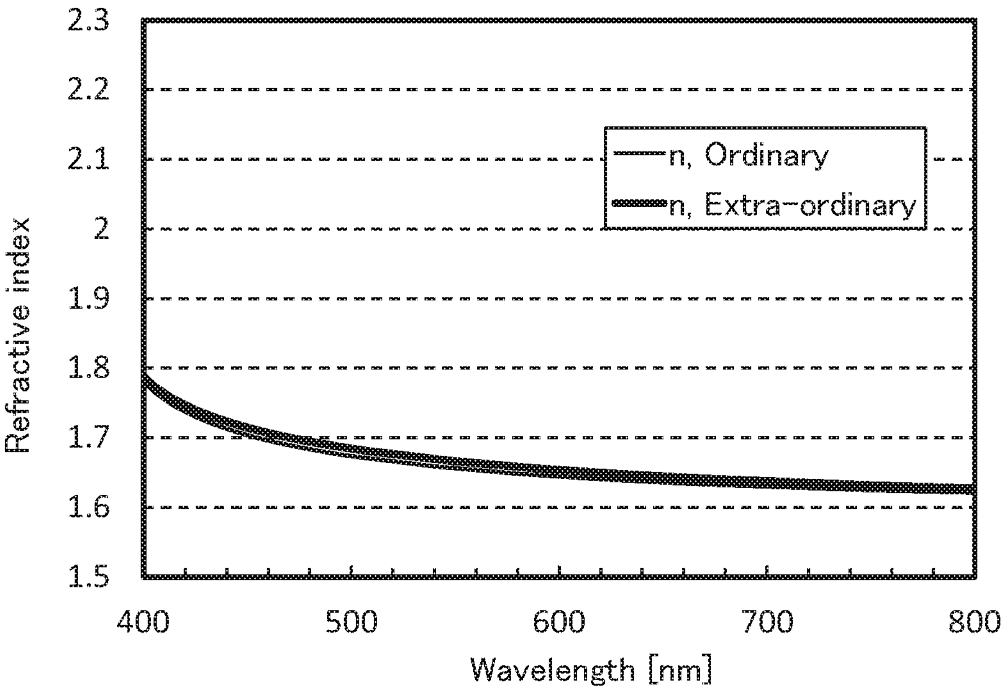

FIG. 121 shows the current efficiency-luminance characteristics of a light-emitting device 11, a light-emitting device 12, and a comparative light-emitting device 5;

FIG. 122 shows the external quantum efficiency-luminance characteristics of the light-emitting device 11, the light-emitting device 12, and the comparative light-emitting device 5;

FIG. 123 shows the emission spectra of the light-emitting device 11, the light-emitting device 12, and the comparative light-emitting device 5;

FIG. 124 shows the current efficiency-luminance characteristics of a light-emitting device 13 and a comparative light-emitting device 6;

FIG. 125 shows the external quantum efficiency-luminance characteristics of the light-emitting device 13 and the comparative light-emitting device 6;

FIG. 126 shows the emission spectra of the light-emitting device 13 and the comparative light-emitting device 6;

FIG. 127 shows measurement data of refractive indices of mmtBumTPFA;

FIG. 128 shows measurement data of refractive indices of mmtBumTPFBi;

FIG. 129 shows measurement data of refractive indices of mmtBumTPoFBi;

FIG. 130 shows measurement data of refractive indices of mmtBumBichPAF;

FIG. 131 shows measurement data of refractive indices of mmtBumBioFBi; and

Figure 132:
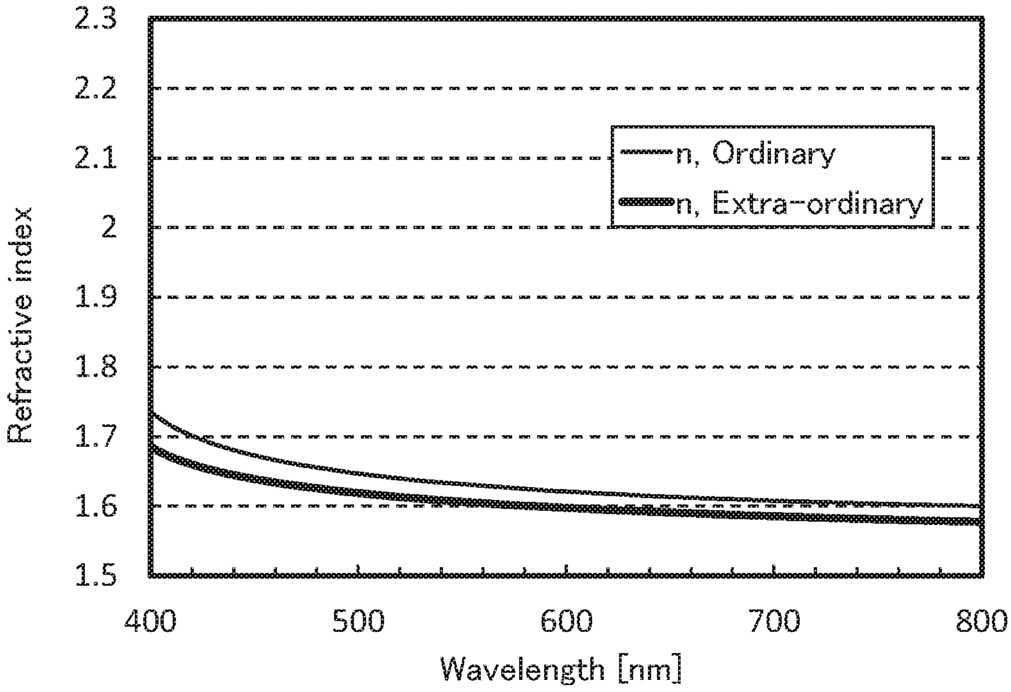

FIG. 132 shows measurement data of refractive indices of mmtBumTPtBuPAF.

DETAILED DESCRIPTION OF THE INVENTION

Embodiments of the present invention will be described in detail below with reference to the drawings. Note that the present invention is not limited to the following description, and it will be readily appreciated by those skilled in the art that modes and details of the present invention can be modified in various ways without departing from the spirit and scope of the present invention. Therefore, the present invention should not be construed as being limited to the description in the following embodiments.

Embodiment 1

Among organic compounds that have a carrier-transport property and can be used for an organic EL device, 1,1-bis-(4-bis(4-methyl-phenyl)-amino-phenyl)-cyclohexane (abbreviation: TAPC), which is a material with a low refractive index, is known. The use of such a material with a low refractive index for the EL layer enables a light-emitting device to have high external quantum efficiency; therefore, with TAPC, high external quantum efficiency of a light-emitting device can be expected.

In general, a high carrier-transport property and a low refractive index have a trade-off relationship. This is because the carrier-transport property of an organic compound largely depend on an unsaturated bond, and an organic compound having many unsaturated bonds tends to have a high refractive index. TAPC has both a carrier-transport property and a low refractive index in an exquisite balance; however, in a compound including 1,1-disubstituted cyclohexane such as TAPC, two bulky substituents are bonded to a carbon atom of cyclohexane, which causes larger steric repulsion and unstability of the molecule itself, leading to disadvantage in reliability. In addition, TAPC has a skeleton structure including cyclohexane and simple benzene rings, and thus has a low glass transition temperature (Tg) and a heat resistance problem.

One of the possible methods for obtaining a hole-transport material with high heat resistance and high reliability is introducing an unsaturated hydrocarbon group, particularly a cyclic unsaturated hydrocarbon group, into a molecule. Meanwhile, in order to obtain a material with a low refractive index, a substituent with low molecular refraction is preferably introduced into the molecule. Examples of the substituent include a saturated hydrocarbon group and a cyclic saturated hydrocarbon group.

However, a saturated hydrocarbon group and a cyclic saturated hydrocarbon group usually lower a carrier-transport property, and thus a carrier-transport property and a low refractive index have a trade-off relation in general. In addition, it is not easy to increase the glass transition temperature for higher heat resistance and to improve the reliability at the time of driving while both the carrier-transport property and the low-refractive index are achieved. In order to overcome such a trade-off, the present inventors have found an aromatic amine compound having a high glass transition temperature, in which the proportion of carbon atoms each forming a bond only by the $sp^3$ hybrid orbitals is within a certain range. The present inventors also have found that such an aromatic amine compound is useful as a material for a hole-transport layer or a hole-injection layer, especially that of a light-emitting device or a photoelectric conversion device.

That is, one embodiment of the present invention is a material for a hole-transport layer or a hole-injection layer including an aromatic amine compound with a glass transition temperature of higher than or equal to 90° C. A layer including the aromatic amine compound has a refractive index of higher than or equal to 1.5 and lower than or equal to 1.75. In the aromatic amine compound, the proportion of carbon atoms each forming a bond only by the $sp^3$ hybrid orbitals to the total number of carbon atoms in the molecule is preferably higher than or equal to 23% and lower than or equal to 55%.

A substituent including the carbon atoms each forming a bond only by the $sp^3$ hybrid orbitals is what is called a saturated hydrocarbon group or a cyclic saturated hydrocarbon group, and thus has a low molecular refraction. Thus, the aromatic amine compound, in which the proportion of the carbon atoms each forming a bond only by the $sp^3$ hybrid orbitals to the total number of the carbon atoms in the molecule is higher than or equal to 23% and lower than or equal to 55%, can be used as a material for a hole-transport layer or a hole-injection layer with a low refractive index.

Note that the aromatic amine compound is preferably a triarylamine compound. The glass transition temperature is preferably higher than or equal to 100° C., further preferably higher than or equal to 110° C., and still further preferably higher than or equal to 120° C.

A material used as a carrier-transport material for an organic EL device preferably has a skeleton with a high carrier-transport property, and an aromatic amine skeleton is particularly preferable because of its high hole-transport property. For a higher carrier-transport property, two amine skeletons can be introduced as another method. However, as in the above-described TAPC, the diamine structure sometimes adversely affects the reliability depending on the substituents arranged around the amine skeletons.

As a compound that overcomes the trade-off and has a carrier-transport property, a low refractive index, and a high reliability, the present inventors have found a monoamine compound in which the proportion of carbon atoms each forming a bond only by the $sp^3$ hybrid orbitals is within a certain range. In particular, the monoamine compound has high reliability equivalent to those of conventional materials for a hole-transport layer or a hole-injection layer with a normal refractive index. Furthermore, the monoamine compound can have more favorable characteristics when the number or position of the substituents containing the carbon atoms each forming a bond only by the $sp^3$ hybrid orbitals is adjusted.

That is, one embodiment of the present invention is a material for a hole-transport layer and a hole-injection layer including a monoamine compound, in which a first aromatic group, a second aromatic group, and a third aromatic group are directly bonded to the nitrogen atom of the amine. A layer including the monoamine compound has a refractive index of higher than or equal to 1.5 and lower than or equal to 1.75. In the monoamine compound, the proportion of carbon atoms each forming a bond only by the $sp^3$ hybrid orbitals to the total number of carbon atoms in the molecule is preferably higher than or equal to 23% and lower than or equal to 55%.

A substituent including carbon atoms each forming a bond only by the $sp^3$ hybrid orbitals is what is called a saturated hydrocarbon group or a cyclic saturated hydrocarbon group, and thus has low molecular refraction. Thus, the monoamine compound, in which the proportion of the carbon atoms each forming a bond only by the $sp^3$ hybrid orbitals to the total number of the carbon atoms in the molecule is higher than or equal to 23% and lower than or equal to 55%, can be used as a material for a hole-transport layer and a hole-injection layer with a low refractive index.

Note that the refractive index of the layer including the aromatic amine compound or the monoamine compound is a refractive index at a peak wavelength of the light emitted from a light-emitting device including the amine compound, or at an emission peak wavelength of a light-emitting substance contained in the light-emitting device. In the case where the light-emitting device is provided with a light-adjusting structure such as a color filter, the emission peak wavelength of the light emitted from the light-emitting device is a peak wavelength of the light not passing through the structure. The emission peak wavelength of the light-emitting substance is calculated from a PL spectrum in a solution state. Since the dielectric constant of the organic compound included in the EL layer of the light-emitting device is approximately 3, in order to prevent inconsistency with the emission spectrum of the light-emitting device, the dielectric constant of the solvent for the light-emitting substance is preferably greater than or equal to 1 and less than or equal to 10, more preferably greater than or equal to 2 and less than or equal to 5 at room temperature. Specific examples include hexane, benzene, toluene, diethyl ether, ethyl acetate, chloroform, chlorobenzene, and dichloromethane. It is more preferable that the solvent have high solubility, versatility, and a dielectric constant greater than or equal to 2 and less than or equal to 5 at room temperature. For example, the solvent is preferably toluene or chloroform. In the case where a specific light-emitting device is not used, the refractive index of the layer including the aromatic amine compound or the monoamine compound may be a refractive index measured using light with a wavelength of a blue light-emitting region (from 455 nm to 465 nm). In addition, the ordinary refractive index of the layer including the aromatic amine compound or the monoamine compound of one embodiment of the present invention measured using light with a wavelength of 633 nm, which is usually used for the measurement of a refractive index, is higher than or equal to 1.45 and lower than or equal to 1.70. In the case where the material has an anisotropy, the ordinary refractive index and the extraordinary refractive index are different from each other in some cases. When a thin film to be measured is in such a state, anisotropy analysis can be performed to separately calculate the ordinary refractive index and the extraordinary refractive index. In this specification, when the measured material has both the ordinary refractive index and the extraordinary refractive index, the ordinary refractive index is used as an indicator.

Furthermore, it is preferable that the integral value of signals at lower than 4 ppm exceed the integral value of signals at 4 ppm or higher in the results of $^1$H-NMR measurement conducted on the aromatic amine compound or the monoamine compound. The signals at lower than 4 ppm represent hydrogen in chain or cyclic saturated hydrocarbon groups, and the integral value of the signals exceeding the integral value of the signals at 4 ppm or higher indicates that there are more hydrogen atoms constituting saturated hydrocarbon groups than those constituting unsaturated groups. Thus, the proportion of the carbon atoms each forming a bond only by the $sp^3$ hybrid orbitals in the molecule can be estimated. Here, carbon in the unsaturated hydrocarbon group has a smaller number of bonds for hydrogen; for example, the number of bonds for hydrogen is greatly different between benzene ($C_6H_6$) and cyclohexane ($C_6H_{12}$). Considering the difference, the integral value of the signals at lower than 4 ppm exceeding the integral value of the signals at 4 ppm or higher obtained in the $^1$H-NMR measurement indicates that approximately one-third of carbon atoms in the molecule exist in the saturated hydrocarbon group. As a result, the aromatic amine compound or the monoamine compound is an organic compound with a low refractive index and thus can be suitably used as a material for a hole-transport layer and a hole-injection layer.

In addition, the monoamine compound preferably has at least one fluorene skeleton. The monoamine compound having a fluorene skeleton can have a high hole-transport property, and thus enables a light-emitting device including the monoamine compound as a material for a hole-transport layer and/or a hole-injection layer to have low driving voltage. The fluorene skeleton corresponds to any of the first to third aromatic groups. Furthermore, it is preferable that the fluorene skeleton be directly bonded to the nitrogen atom of the amine, because this contributes to a shallower HOMO level of the molecule and easier hole transfer.

In the case where the monoamine compound is deposited by evaporation, the molecular weight is preferably greater than or equal to 400 and less than or equal to 1000.

Note that the above-described monoamine compound enables high Tg when including a cyclic saturated hydrocarbon group or a rigid tertiary hydrocarbon group, and thus can be a material having high heat resistance. In general, a compound to which a saturated hydrocarbon group, especially a chain saturated hydrocarbon group is introduced tends to have lower Tg and melting point than a compound to which an aromatic group or a heteroaromatic group (with substantially the same number of carbon atoms as the saturated hydrocarbon group, for example) is introduced. The lower Tg sometimes leads to lower heat resistance of an organic EL material. An EL device including the organic EL material is desired to show stable properties under various circumstances in our life; thus, a material with high Tg is preferably selected from materials having substantially the same properties.

The above-described monoamine compound will be described in more detail.

The monoamine compound is a triarylamine derivative in which the first aromatic group, the second aromatic group, and the third aromatic group are bonded to the nitrogen atom of the amine.

The first aromatic group and the second aromatic group each include one to three benzene rings. In addition, it is preferable that the first aromatic group and the second aromatic group be each a hydrocarbon group. In other words, the first aromatic group and the second aromatic group are preferably a phenyl group, a biphenyl group, a terphenyl group, or a naphthylphenyl group. The first aromatic group or the second aromatic group is preferably a terphenyl group, in which case Tg and heat resistance are increased.

In the case where the first aromatic group or the second aromatic group includes two or three benzene rings, the two or three benzene rings are preferably bonded to each other to form a substituent. It is preferable that one or both of the first and second aromatic groups be a substituent in which two or three benzene rings are bonded to each other, that is, a biphenyl group or a terphenyl group, in which case Tg and heat resistance are increased. It is further preferable that both of the first and second aromatic groups be each a biphenyl group or a terphenyl group.

One or both of the first and second aromatic groups include one or more hydrocarbon groups having 1 to 12 carbon atoms each forming a bond only by the $sp^3$ hybrid orbitals.

Note that in the monoamine compound, the hydrocarbon group(s) having 1 to 12 carbon atoms each forming a bond only by the $sp^3$ hybrid orbitals is/are included in one or both of the first and second aromatic groups; however, the total number of the carbon atoms in the hydrocarbon group(s) in one of the aromatic groups is 6 or more. Furthermore, the total number of the carbon atoms in all of the hydrocarbon groups in the first and second aromatic groups is 8 or more, preferably 12 or more. When the hydrocarbon group with low molecular refraction is bonded in the above manner, the monoamine compound can be an organic compound with a low refractive index.

Furthermore, the total number of the carbon atoms each forming a bond only by the $sp^3$ hybrid orbitals in all of the hydrocarbon groups in the first and second aromatic groups is preferably 36 or less, further preferably 30 or less so that the carrier-transport property is maintained high. As described above, a larger number of 7 electrons due to unsaturated bonds of carbon atoms are advantageous in carrier transportation.

As the hydrocarbon group having 1 to 12 carbon atoms each forming a bond only by the $sp^3$ hybrid orbitals, an alkyl group having 3 to 8 carbon atoms or a cycloalkyl group having 6 to 12 carbon atoms is preferable. Specifically, it is possible to use a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a heptyl group, an octyl group, a cyclohexyl group, a 4-methylcyclohexyl group, a cycloheptyl group, a cyclooctyl group, a cyclononyl group, a cyclodecyl group, a decahydronaphthyl group, a cycloundecyl group, a cyclododecyl group, and the like. It is particularly preferable to use a tert-butyl group, a cyclohexyl group, or a cyclododecyl group.

The third aromatic group is a substituted or unsubstituted monocyclic condensed ring or a substituted or unsubstituted bicyclic or tricyclic condensed ring. Since the refractive index tends to increase with an increase in the number of the condensed rings, using an aromatic group with a small number of condensed rings enables the refractive index to be maintained low. Similarly, an increase in the number of the condensed rings leads to absorption and emission of light in the visible region that are to be observed, and thus using an aromatic group with a small number of condensed rings can reduce the influence of the absorption and emission of light. Note that the third aromatic group preferably has 6 to 13 carbon atoms in a ring to maintain the low refractive index. Specific examples of the aromatic group that can be used as the third aromatic group include a benzene ring, a naphthalene ring, a fluorene ring, and an acenaphthylene ring. In particular, the third aromatic group preferably includes a fluorene ring and further preferably is a fluorene ring, in which case the hole-transport property can be favorable.

The monoamine compound having the above-described structure is an organic compound with a hole-transport property and a low refractive index, and thus can be suitably used as a material for a hole-transport layer or a hole-injection layer of an organic EL device. Furthermore, an organic EL device using the material for a hole-transport layer or a hole-injection layer has a hole-transport layer or a hole-injection layer with a low refractive index, and thus can be a light-emitting device having high emission efficiency, i.e., high external quantum efficiency, high current efficiency, and a high blue index. Furthermore, since the organic EL device uses the monoamine compound as the material for a hole-transport layer or a hole-injection layer and the number of aromatic groups bonded to the saturated hydrocarbon group is limited, the steric repulsion can be reduced to improve the stability of the molecule, so that the organic EL device can be a light-emitting device having a long lifetime.

It is preferable that the glass transition temperature of the monoamine compound included in a hole-transport layer or a hole-injection layer be higher than or equal to 90° C. The glass transition temperature is further preferably higher than or equal to 100° C., still further preferably higher than or equal to 110° C., yet further preferably higher than or equal to 120° C.

It is particularly preferable that the monoamine compound be an organic compound represented by the following general formula (G1).

[Chemical Formula 5]

(G1)

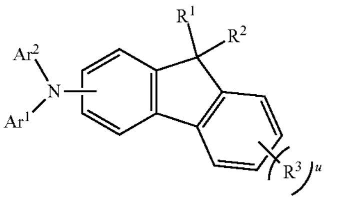

Note that in the general formula (G1), $Ar^1$ and $Ar^2$ each independently represent a substituent with a benzene ring or a substituent in which two or three benzene rings are bonded to each other. Specific examples of $Ar^1$ and $Ar^2$ include a phenyl group, a biphenyl group, a terphenyl group, and a naphthylphenyl group. A phenyl group is particularly preferable to lower the refractive index and maintain the carrier-transport property of the nitrogen atom.

Note that one or both of $Ar^1$ and $Ar^2$ have one or more hydrocarbon groups each having 1 to 12 carbon atoms each forming a bond only by the $sp^3$ hybrid orbitals. The total number of the carbon atoms in all of the hydrocarbon groups is 8 or more, and the total number of the carbon atoms in the hydrocarbon group(s) in $A^1$ or $Ar^2$ is 6 or more. As the hydrocarbon group having 1 to 12 carbon atoms each forming a bond only by the $sp^3$ hybrid orbitals, an alkyl group having 3 to 8 carbon atoms or a cycloalkyl group having 6 to 12 carbon atoms is preferable. Specifically, it is possible to use a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a heptyl group, an octyl group, a cyclohexyl group, a 4-methylcyclohexyl group, a cycloheptyl group, a cyclooctyl group, a cyclononyl group, a cyclodecyl group, a decahydronaphthyl group, a cycloundecyl group, a cyclododecyl group, and the like. It is particularly preferable to use a t-butyl group, a cyclohexyl group, or a cyclododecyl group.

Note that in the case where a plurality of straight-chain alkyl groups each having 1 or 2 carbon atoms are included as the hydrocarbon groups in $Ar^1$ or $Ar^2$, the straight-chain alkyl groups may be bonded to each other to form a ring.

In the above general formula (G1), $R^1$ and $R^2$ each independently represent an alkyl group having 1 to 4 carbon atoms. Note that $R^1$ and $R^2$ may be bonded to each other to form a ring. $R^3$ represents an alkyl group having 1 to 4 carbon atoms, and u is an integer of 0 to 4.

The organic compound of one embodiment of the present invention can also be represented by the following general formulae (G2) to (G4).

[Chemical Formula 6]

(G2)

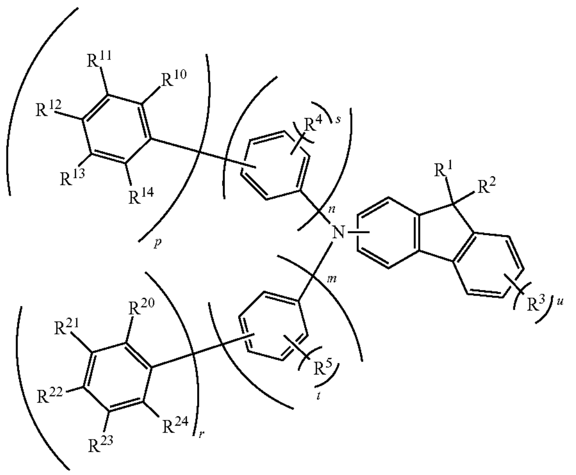

Note that in the general formula (G2), n, m, p, and r each independently represent 1 or 2 and s, t, and u each independently represent an integer of 0 to 4. In addition, n+p and m+r are each independently 2 or 3. It is preferable that s, t, and u be each 0.

In the general formula (G2), $R^1$, $R^2$, and $R^3$ each independently represent an alkyl group having 1 to 4 carbon atoms, and $R^4$ and $R^5$ each independently represent hydrogen or a hydrocarbon group having 1 to 3 carbon atoms. Examples of the hydrocarbon group having 1 to 3 carbon atoms include a methyl group, an ethyl group, and a propyl group. Examples of the hydrocarbon group having 1 to 4 carbon atoms include a butyl group in addition to the above groups.

$R^{10}$ to $R^{14}$ and $R^{20}$ to $R^{24}$ each independently represent hydrogen or a hydrocarbon group having 1 to 12 carbon atoms each forming a bond only by the $sp^3$ hybrid orbitals. As the hydrocarbon group having 1 to 12 carbon atoms each forming a bond only by the $sp^3$ hybrid orbitals, an alkyl group having 3 to 8 carbon atoms or a cycloalkyl group having 6 to 12 carbon atoms is preferable. Specifically, it is possible to use a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a heptyl group, an octyl group, a cyclohexyl group, a 4-methylcyclohexyl group, a cycloheptyl group, a cyclooctyl group, a cyclononyl group, a cyclodecyl group, a decahydronaphthyl group, a cycloundecyl group, a cyclododecyl group, and the like. It is particularly preferable to use a t-butyl group, a cyclohexyl group, or a cyclododecyl group.

Note that the total number of the carbon atoms in $R^{10}$ to $R^{14}$ and $R^{20}$ to $R^{24}$ is 8 or more, and the total number of the carbon atoms in either $R^{10}$ to $R^{14}$ or $R^{20}$ to $R^{24}$ is 6 or more.

In the general formula (G2), in the case where n is 2, the kind and number of substituents and the position of bonds in one phenylene group may be the same as or different from those of the other phenylene group. In the case where m is 2, the kind and number of substituents and the position of bonds in one phenylene group may be the same as or different from those of the other phenylene group. In the case where p is 2, the kind and number of substituents and the position of bonds in one phenyl group may be the same as or different from those of the other phenyl group. In the case where r is 2, the kind and number of substituents and the position of bonds in one phenylene group may be the same as or different from those of the other phenylene group.

Furthermore, in the case where s is an integer of 2 to 4, $R^4$s may be the same or different. In the case where t is an integer of 2 to 4, $R^5$s may be the same or different. In the case where u is an integer of 2 to 4, R's may be the same or different. Note that $R^1$ and $R^2$ may be bonded to each other to form a ring, and adjacent groups among $R^4$, $R^5$, $R^{10}$ to $R^{14}$, and $R^{20}$ to $R^{24}$ may be bonded to each other to form a ring.

[Chemical Formula 7]

(G3)

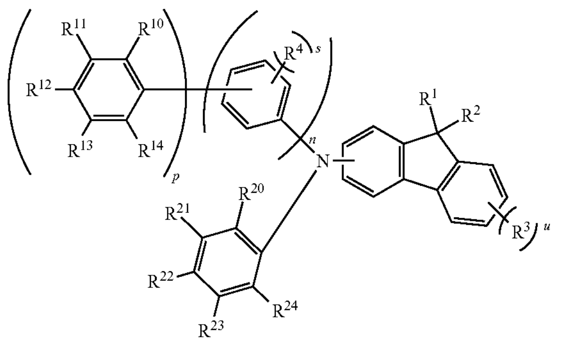

In the general formula (G3), $R^1$, $R^2$, and $R^3$ each independently represent an alkyl group having 1 to 4 carbon atoms, and $R^4$ represents hydrogen or a hydrocarbon group having 1 to 3 carbon atoms. Examples of the hydrocarbon group having 1 to 3 carbon atoms include a methyl group, an ethyl group, and a propyl group. Examples of the hydrocarbon group having 1 to 4 carbon atoms include a butyl group in addition to the above groups.

Note that n and p each independently represent 1 or 2, and s and u each independently represent an integer of 0 to 4. Note that n+p is 2 or 3. Note that s and u are each 0.

$R^{10}$ to $R^{14}$ and $R^{20}$ to $R^{24}$ each independently represent hydrogen or a hydrocarbon group having 1 to 12 carbon atoms each forming a bond only by the $sp^3$ hybrid orbitals. As the hydrocarbon group having 1 to 12 carbon atoms each forming a bond only by the $sp^3$ hybrid orbitals, an alkyl group having 3 to 8 carbon atoms or a cycloalkyl group having 6 to 12 carbon atoms is preferable. Specifically, it is possible to use a propyl group, a butyl group, a pentyl group, a hexyl group, an octyl group, a cyclohexyl group, a cycloheptyl group, a cyclooctyl group, a cyclononyl group, a cyclodecyl group, a cycloundecyl group, a cyclododecyl group, and the like. It is particularly preferable to use a t-butyl group, a cyclohexyl group, or a cyclododecyl group.

Note that the total number of the carbon atoms in $R^{10}$ to $R^{14}$ and $R^{20}$ to $R^{24}$ is 8 or more, and the total number of the carbon atoms in either $R^{10}$ to $R^{14}$ or $R^{20}$ to $R^{24}$ is 6 or more.

Note that in the case where n is 2, the kind and number of substituents and the position of bonds in one phenylene group may be the same as or different from those of the other phenylene group. In the case where p is 2, the kind and number of substituents and the position of bonds in one phenyl group may be the same as or different from those of the other phenyl group. Furthermore, in the case where s is an integer of 2 to 4, $R^4$s may be the same or different. In the case where u is an integer of 2 to 4, $R^3$s may be the same or different. Note that $R^1$ and $R^2$ may be bonded to each other to form a ring, and adjacent groups among $R^4$, $R^{10}$ to $R^{14}$, and $R^{20}$ to $R^{24}$ may be bonded to each other to form a ring.

[Chemical Formula 8]

(G4)

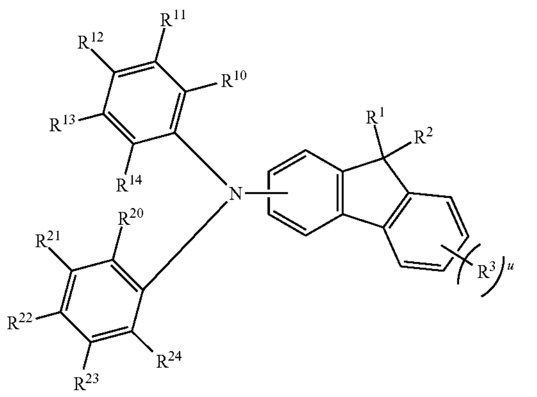

In the general formula (G4), u is an integer of 0 to 4. Note that u is preferably 0.

Furthermore, $R^{10}$ to $R^{14}$ and $R^{20}$ to $R^{24}$ each independently represent hydrogen or a hydrocarbon group having 1 to 12 carbon atoms each forming a bond only by the $sp^3$ hybrid orbitals. As the hydrocarbon group having 1 to 12 carbon atoms each forming a bond only by the $sp^3$ hybrid orbitals, an alkyl group having 3 to 8 carbon atoms or a cycloalkyl group having 6 to 12 carbon atoms is preferable. Specifically, it is possible to use a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a heptyl group, an octyl group, a cyclohexyl group, a 4-methylcyclohexyl group, a cycloheptyl group, a cyclooctyl group, a cyclononyl group, a cyclodecyl group, a decahydronaphthyl group, a cycloundecyl group, a cyclododecyl group, and the like. It is particularly preferable to use a t-butyl group, a cyclohexyl group, or a cyclododecyl group.

Note that the total number of the carbon atoms in $R^{10}$ to $R^{14}$ and $R^{20}$ to $R^{24}$ is 8 or more, and the total number of the carbon atoms in either $R^{10}$ to $R^{14}$ or $R^{20}$ to $R^{24}$ is 6 or more.

In addition, $R^1$, $R^2$, and $R^3$ each independently represent an alkyl group having 1 to 4 carbon atoms. Note that in the case where u is an integer of 2 to 4, $R^3$s may be the same or different. Note that $R^1$ and $R^2$ may be bonded to each other to forma ring, and adjacent groups among $R^{10}$ to $R^{14}$ and $R^{20}$ to $R^{24}$ may be bonded to each other to form a ring.

In the general formulae (G2) to (G4), it is preferable that $R^{10}$ to $R^{14}$ and $R^{20}$ to $R^{24}$ be each any of hydrogen, a tert-butyl group, and a cyclohexyl group to lower the refractive index. In addition, in the general formulae (G2) to (G4), at least three of $R^{10}$ to $R^{14}$ and at least three of $R^{20}$ to $R^{24}$ are preferably hydrogen not to lower the carrier-transport property.

Furthermore, it is preferable that $R^{10}$, R, $R^{13}$, $R^{14}$, $R^{20}$, $R^{21}$, $R^{23}$, and $R^{24}$ be each hydrogen and $R^{12}$ and $R^{22}$ be each a cyclohexyl group.

It is also preferable that $R^{10}$, $R^{12}$, $R^{14}$, $R^{20}$, $R^{21}$, $R^{23}$, and $R^{24}$ be each hydrogen, $R^{11}$ and $R^{13}$ be each a tert-butyl group, and $R^{22}$ be a cyclohexyl group.

It is also preferable that $R^{10}$, $R^{12}$, $R^{14}$, $R^{20}$, $R^{22}$, and $R^{24}$ be each hydrogen, and R, $R^{13}$, $R^{21}$, and $R^{23}$ be each a tert-butyl group.

The organic compound of one embodiment of the present invention with the above-described structure has a hole-transport property and a low refractive index, and thus can be suitably used as a material for a hole-transport layer or a hole-injection layer of an organic EL device. Furthermore, an organic EL device using the material for a hole-transport layer or a hole-injection layer has a hole-transport layer or a hole-injection layer with a low refractive index, and thus can be a light-emitting device having high emission efficiency, i.e., high external quantum efficiency, high current efficiency, and a high blue index. Furthermore, the organic EL device uses the monoamine compound as the material for a hole-transport layer or a hole-injection layer, so that the organic EL device can be a light-emitting device having a long lifetime.

Specific examples of the organic compound having the above structure are shown below.

[Chemical Formula 9]

(100)

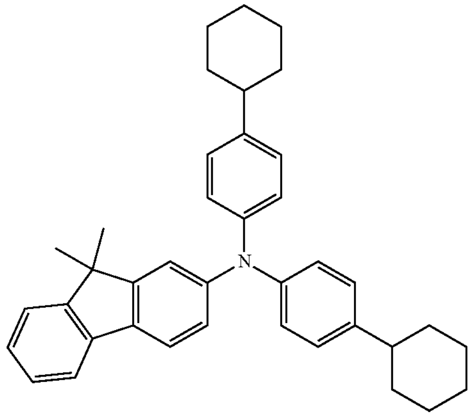

(101)

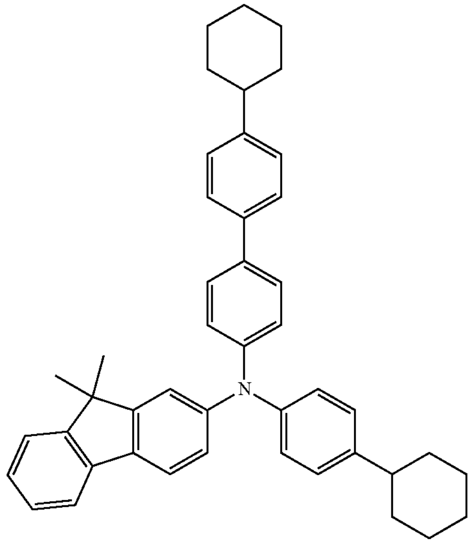

(102)

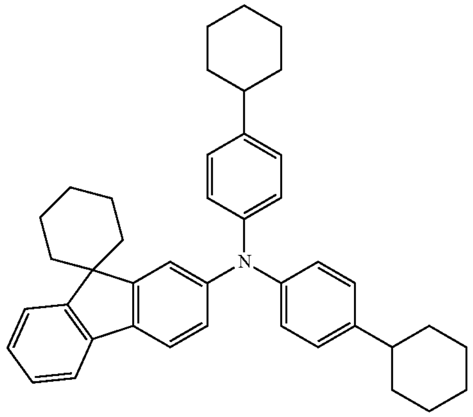

-continued
(103)
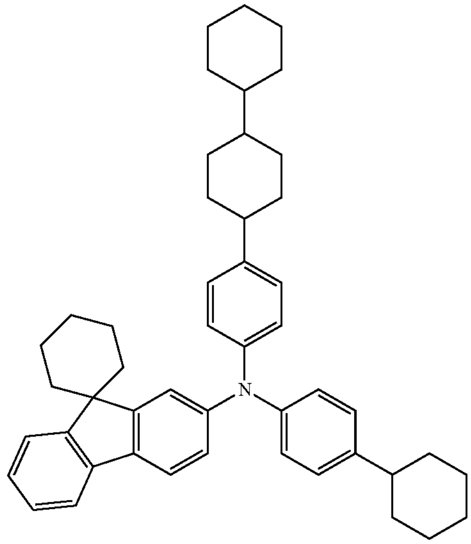
(104)
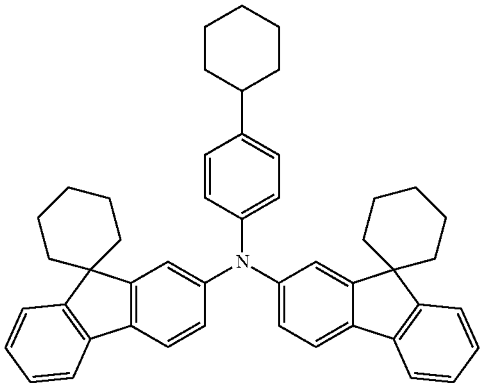
(105)
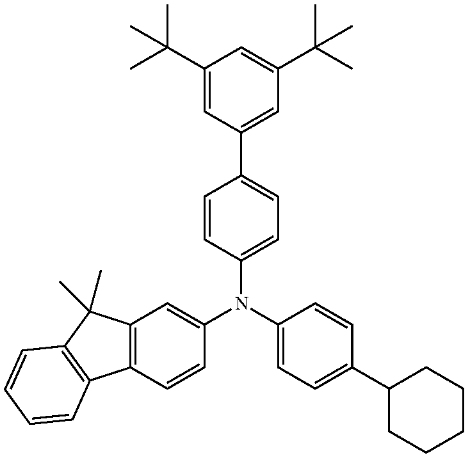
-continued
(106)
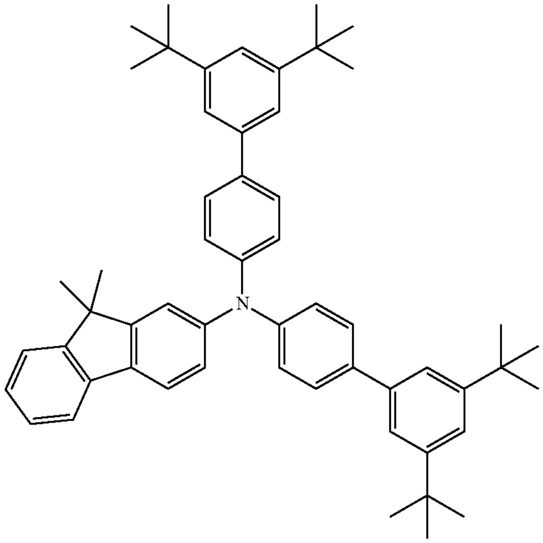
(107)
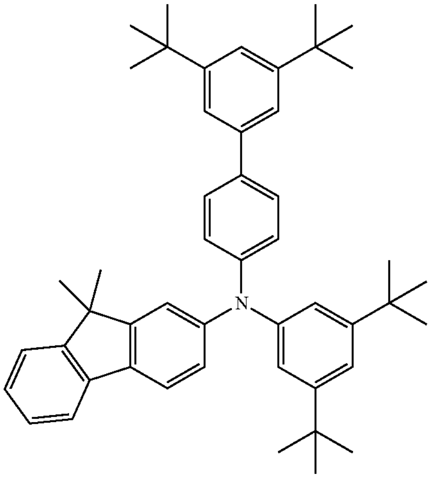
(108)
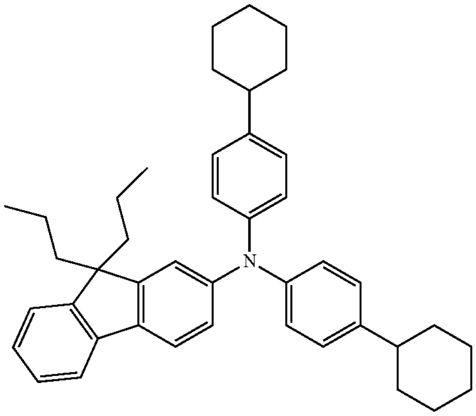

-continued
(109)
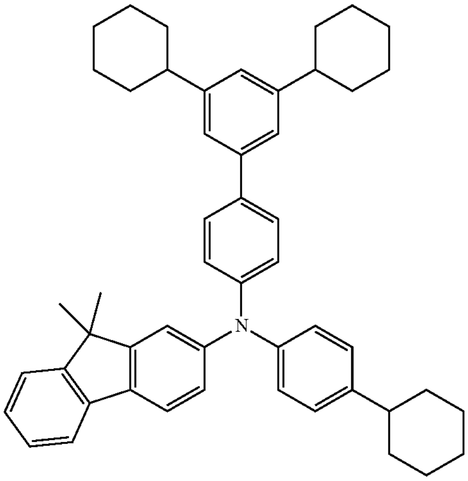
(110)
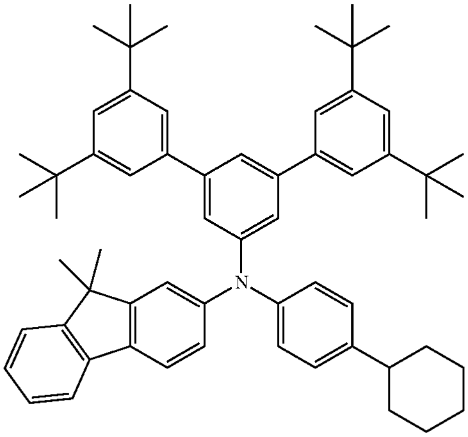
(111)
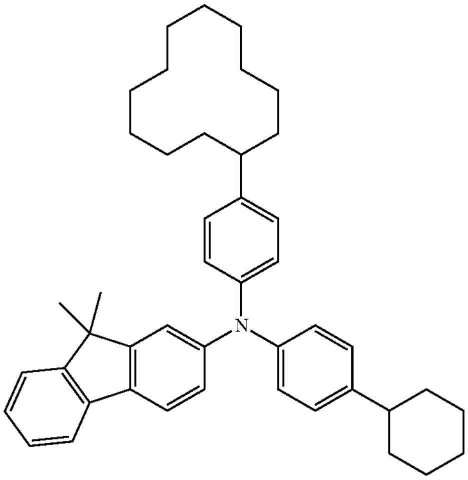
-continued
[Chemical Formula 10]
(112)
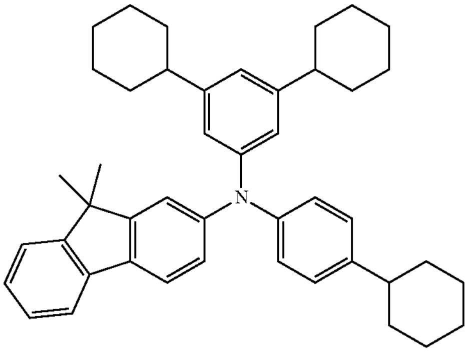
(113)
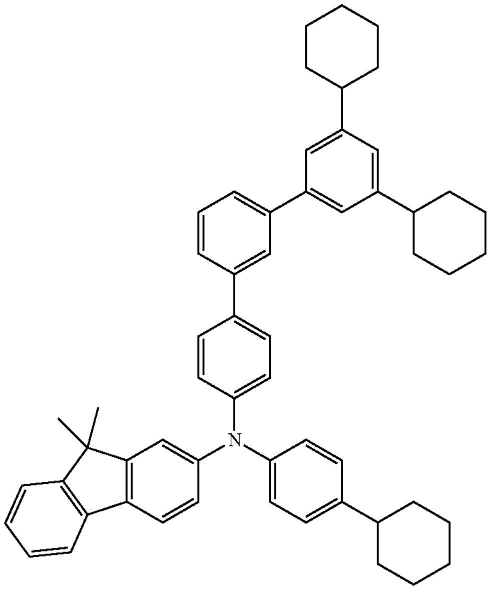
(114)
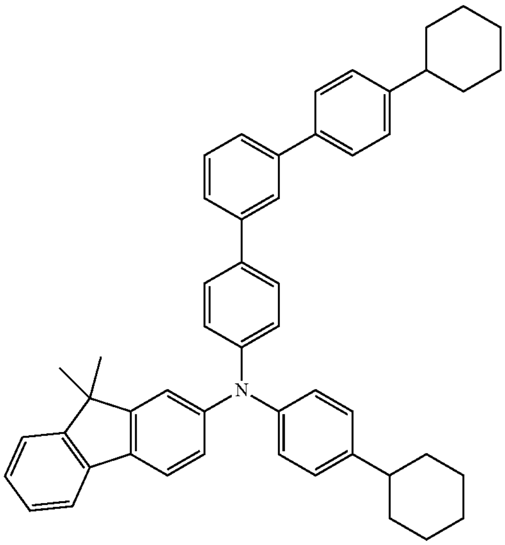

-continued
(115)
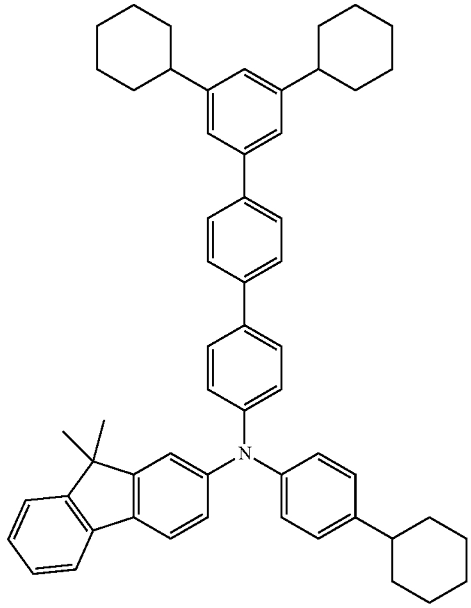
(116)
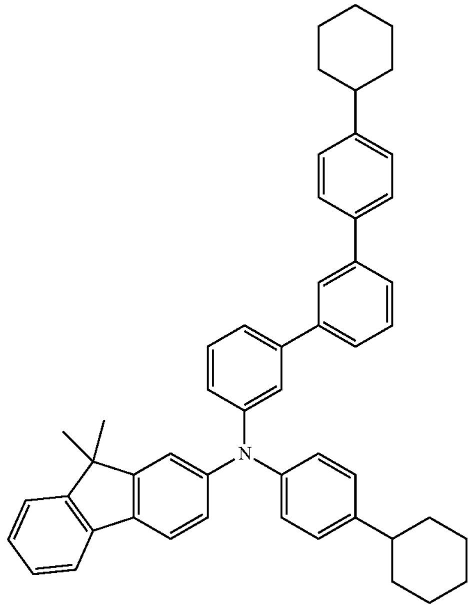
-continued
(117)
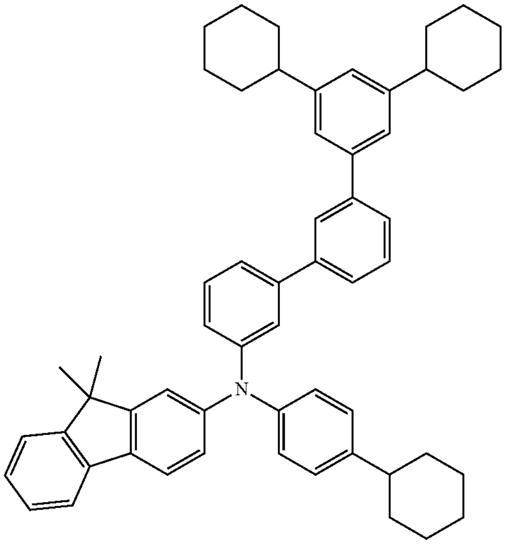
(118)
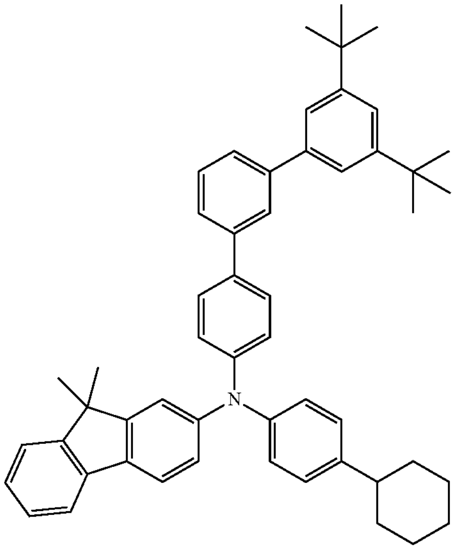

-continued
(119)
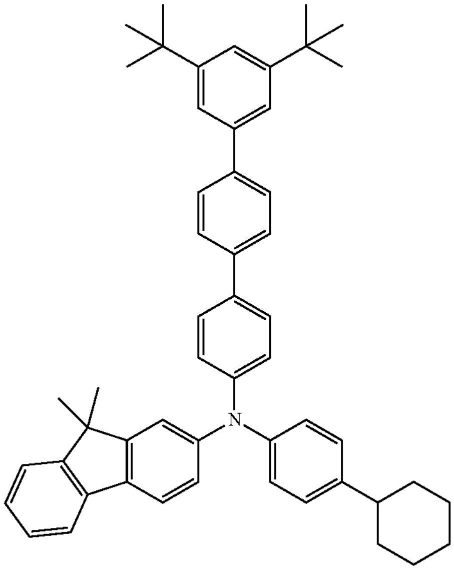
(120)
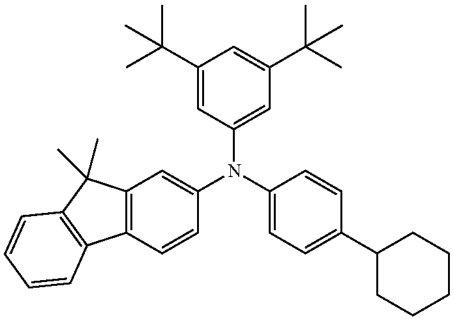
(121)
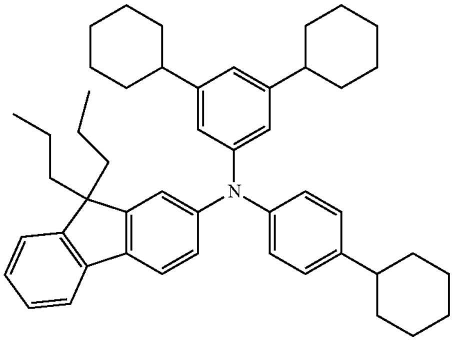
-continued
(122)
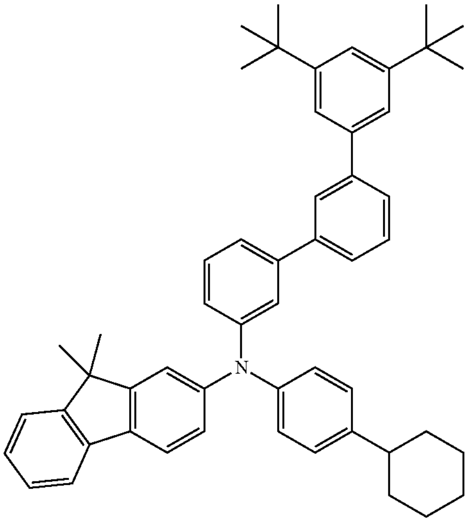
[Chemical Formula 11]
(123)
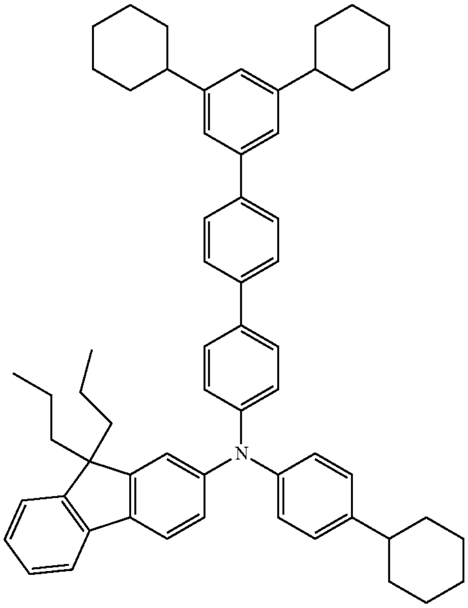

-continued
(124)
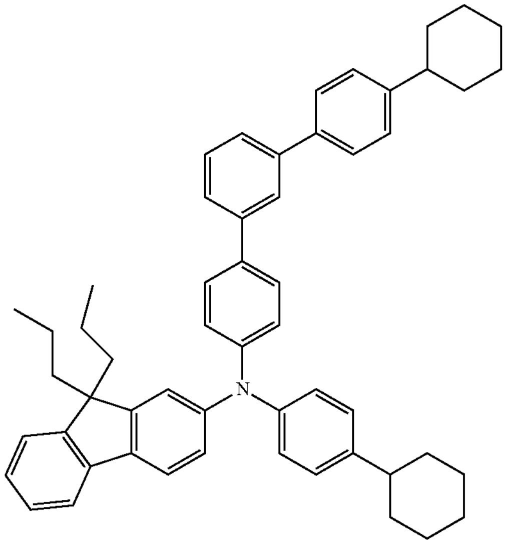
(125)
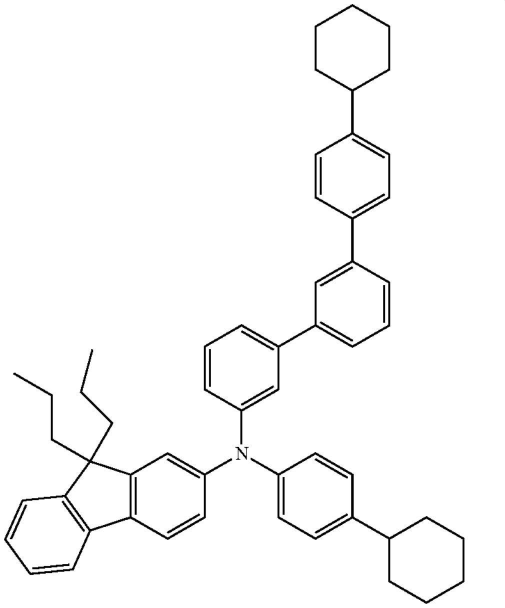
-continued
(126)
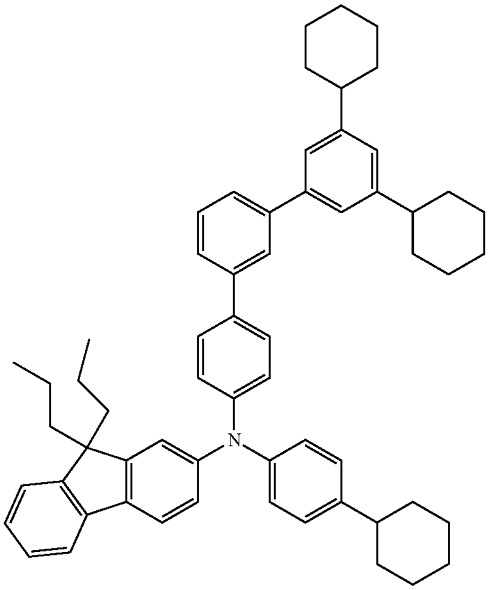
(127)
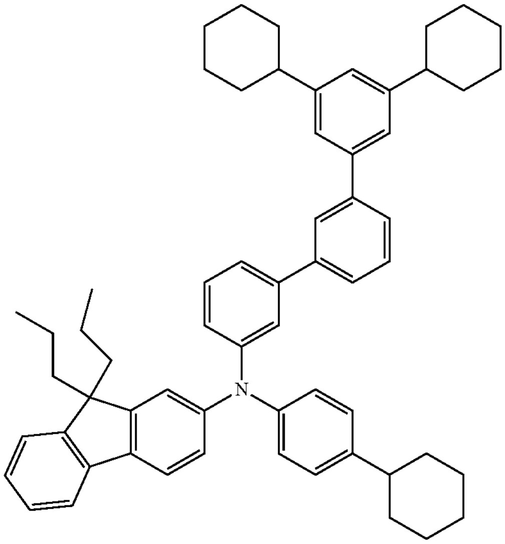
(128)
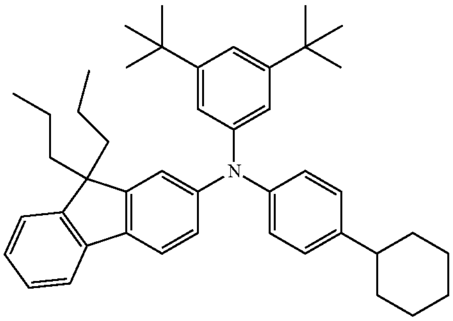

-continued
(129)
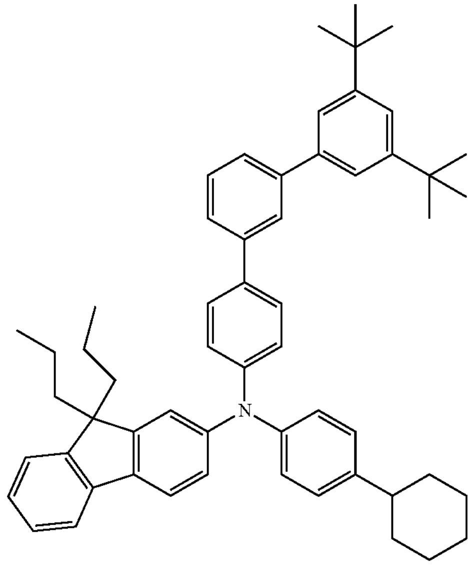
(130)
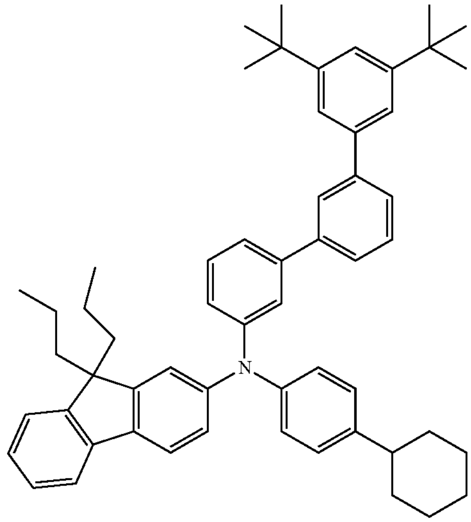
(131)
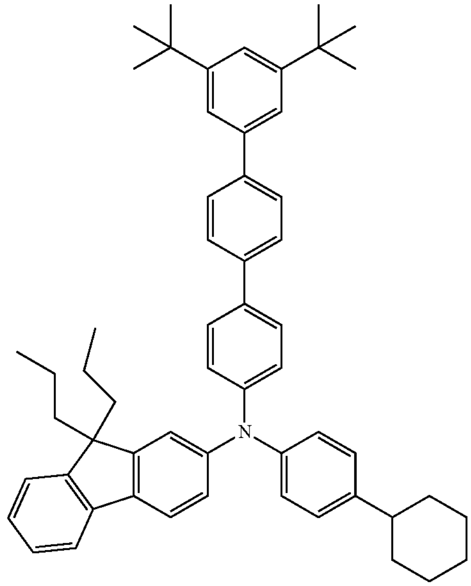
-continued
[Chemical Formula 12]
(132)
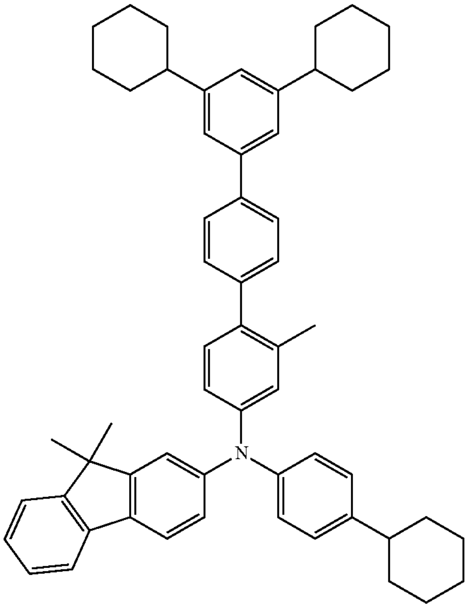
(133)
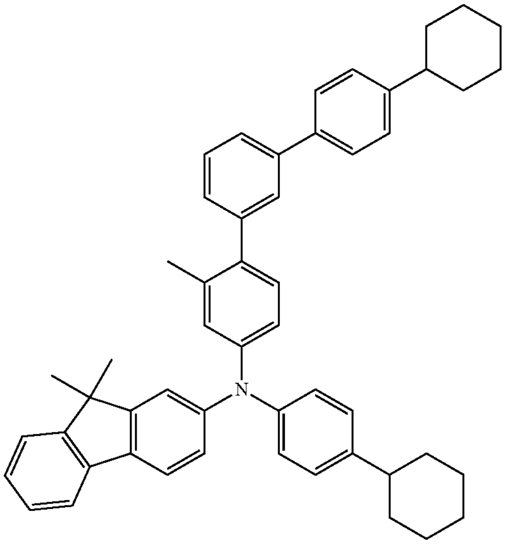

-continued
(134)
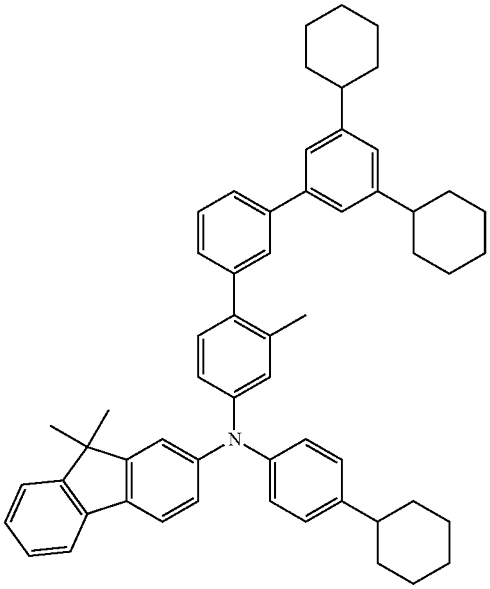
(135)
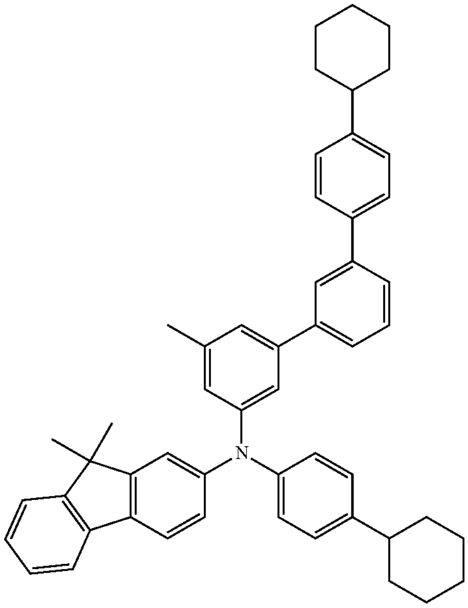
-continued
(136)
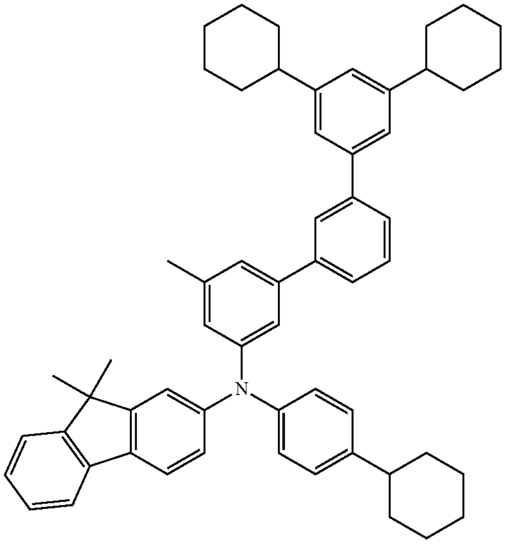
(137)
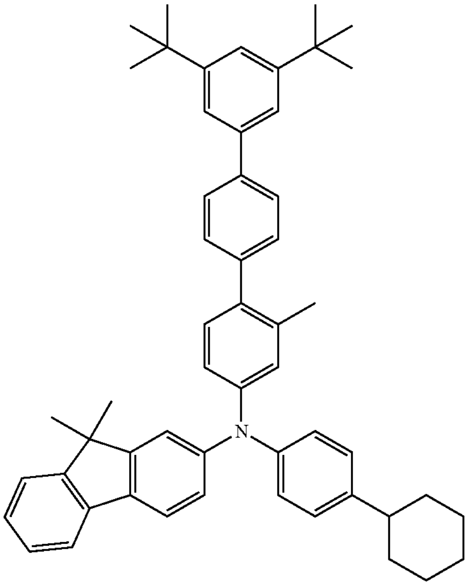
(138)
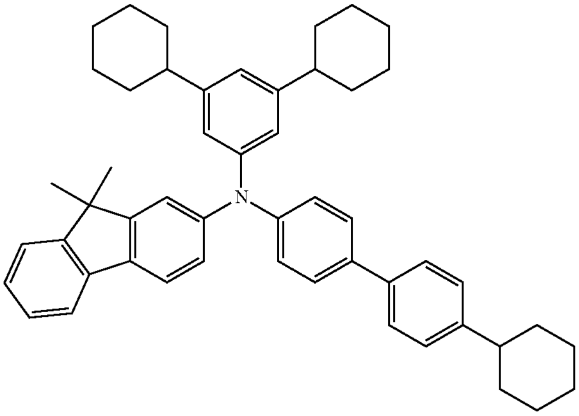

-continued
(139)
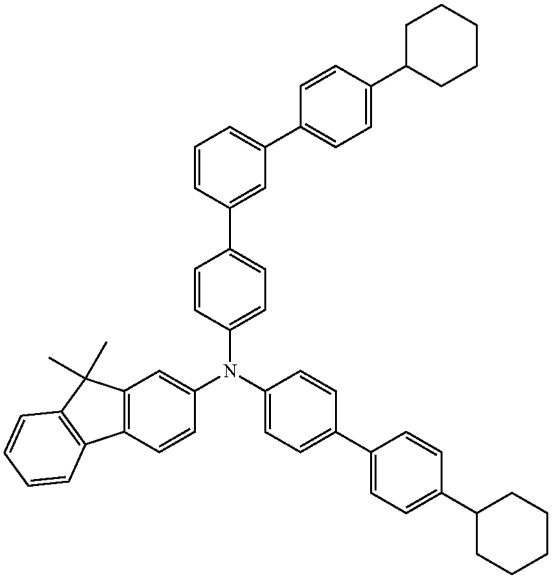
(140)
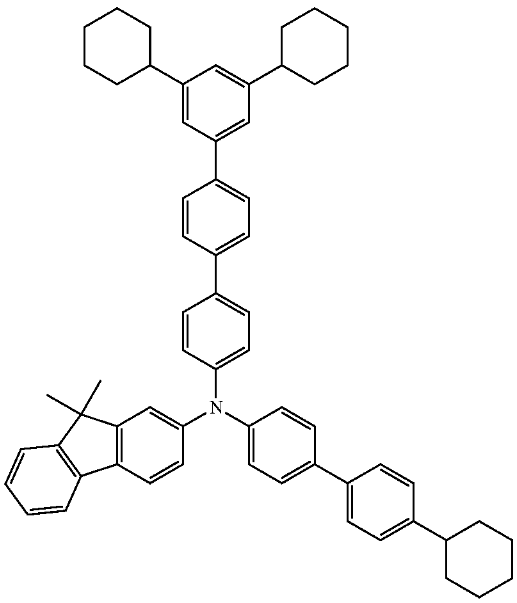
-continued
[Chemical Formula 13]
(141)
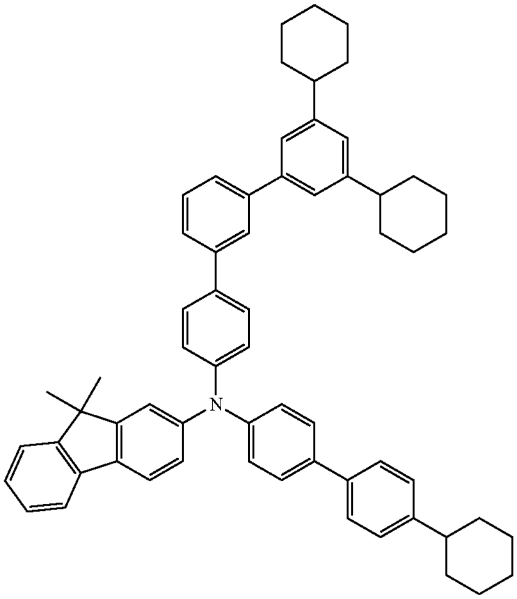
(142)
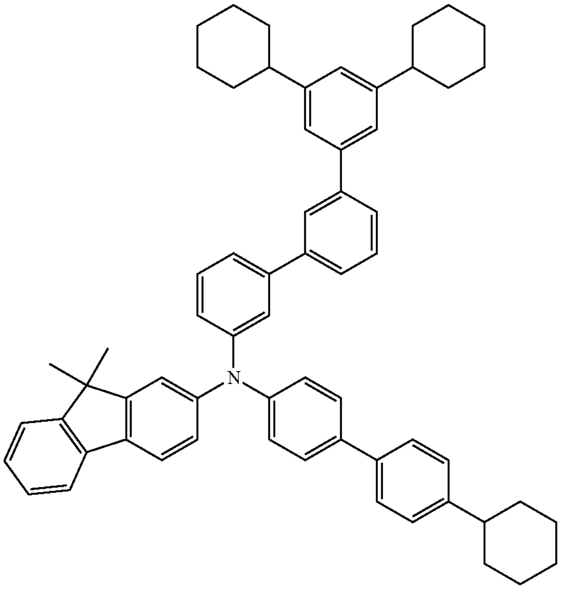

-continued
(143)
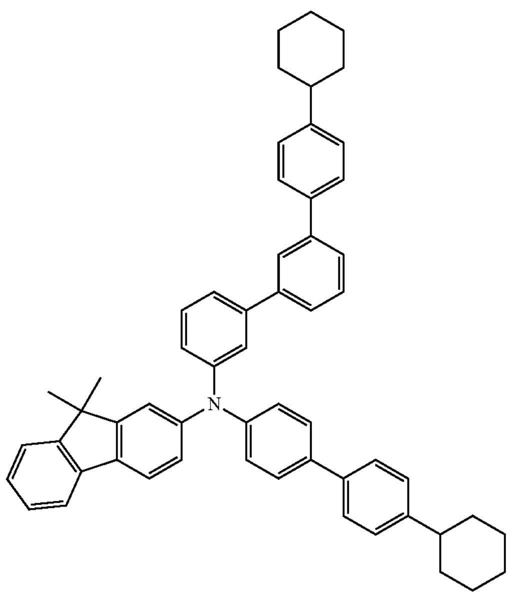
(144)
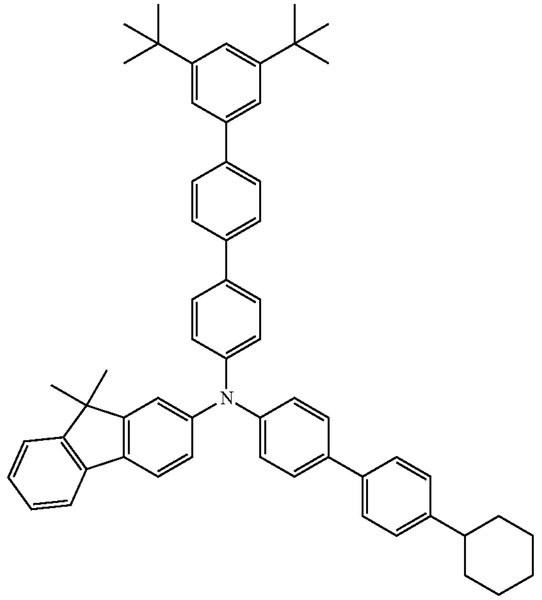
(145)
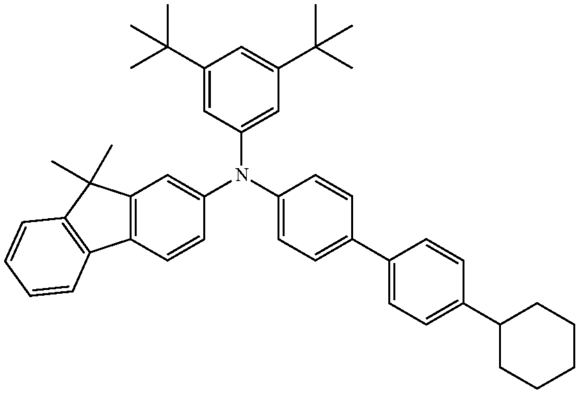
-continued
(146)
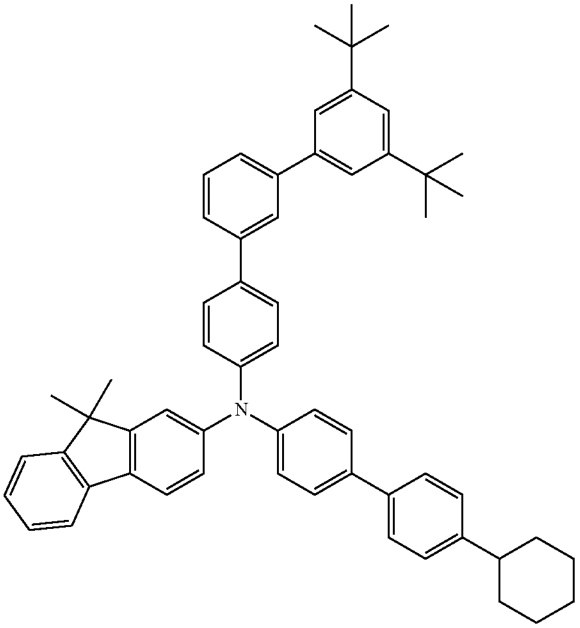
(147)
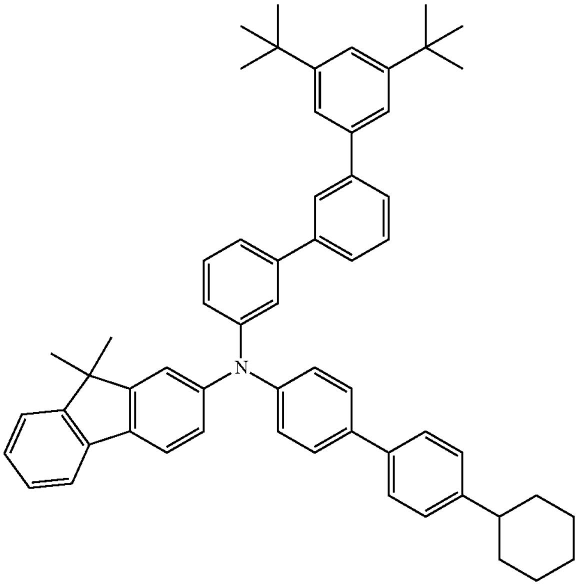

-continued
(148)
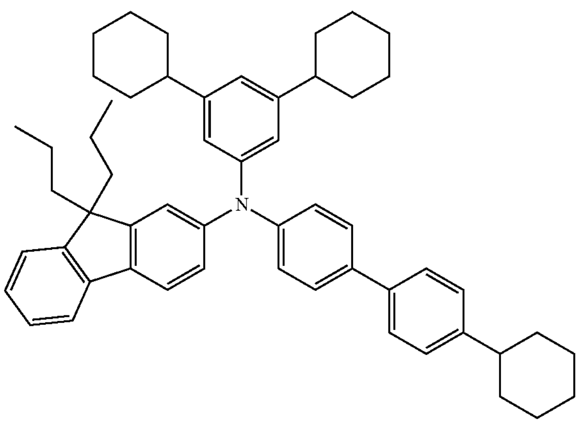
(149)
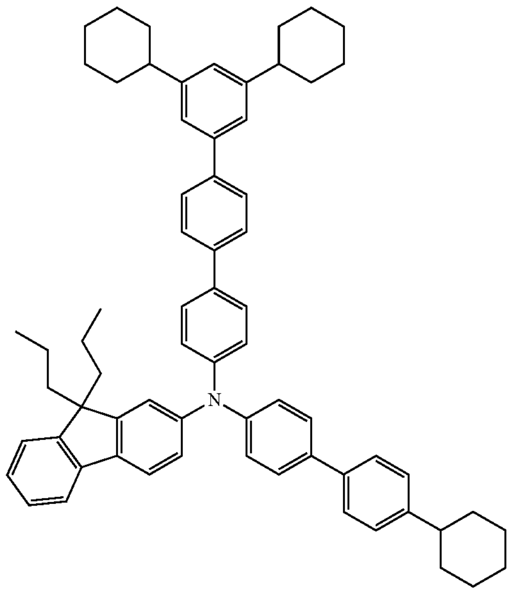
-continued
[Chemical Formula 14]
(150)
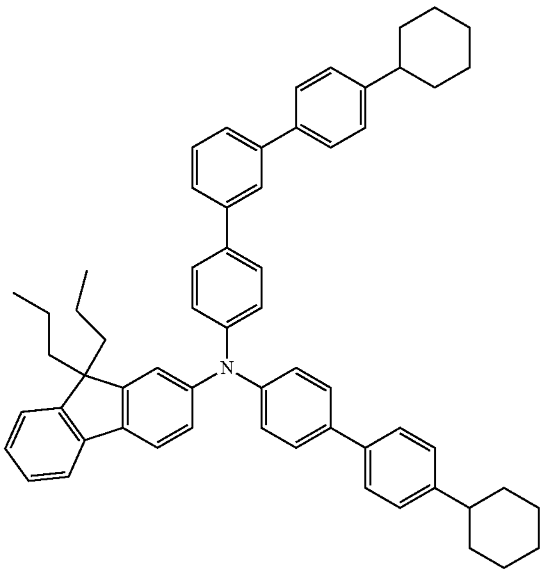
(151)
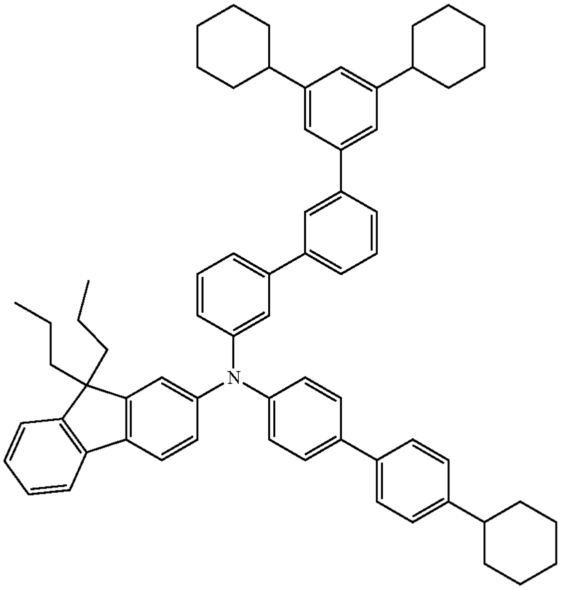
(152)
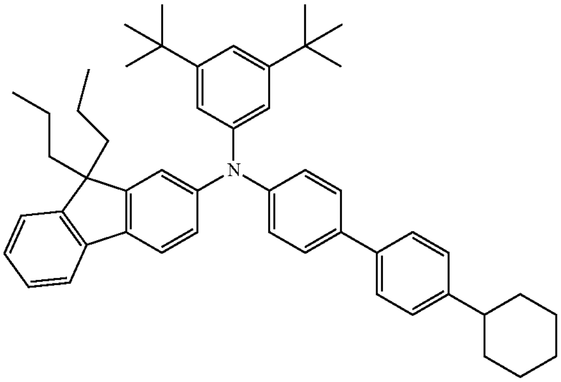

-continued
(153)
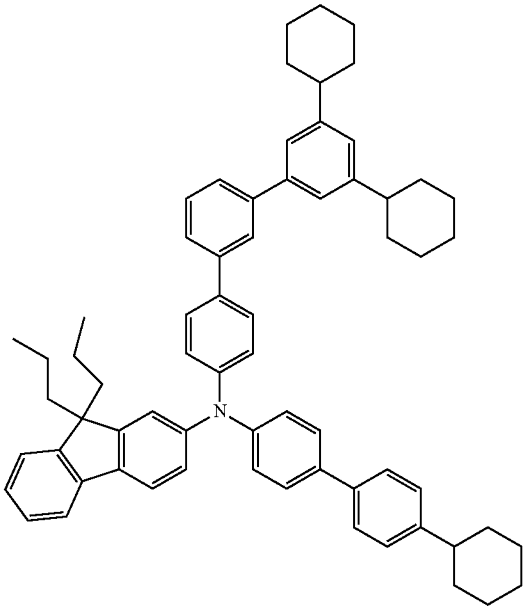
(154)
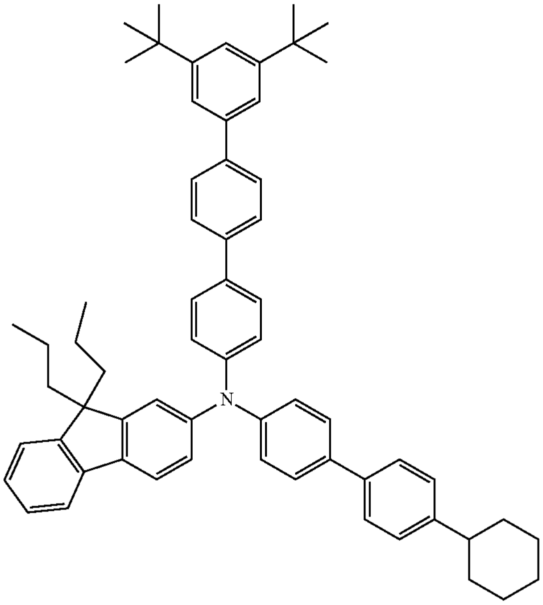
-continued
(155)
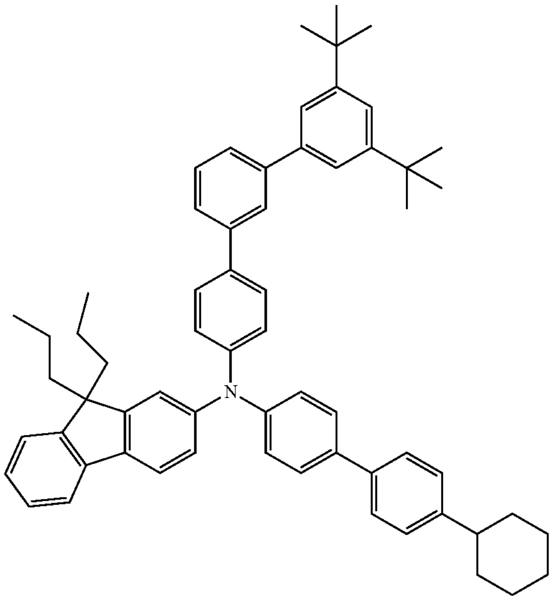
(156)
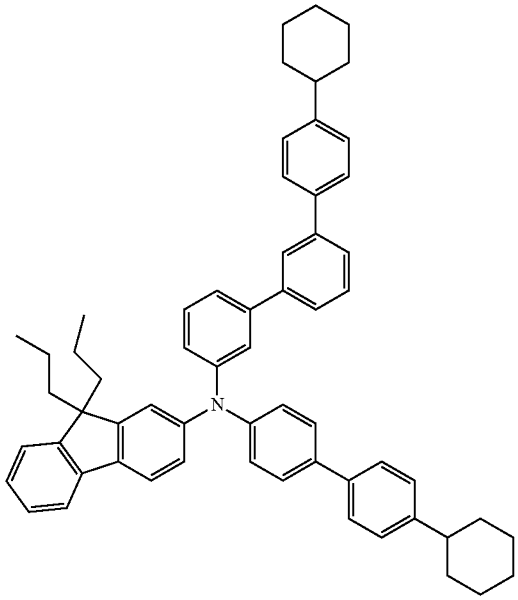

-continued
(157)
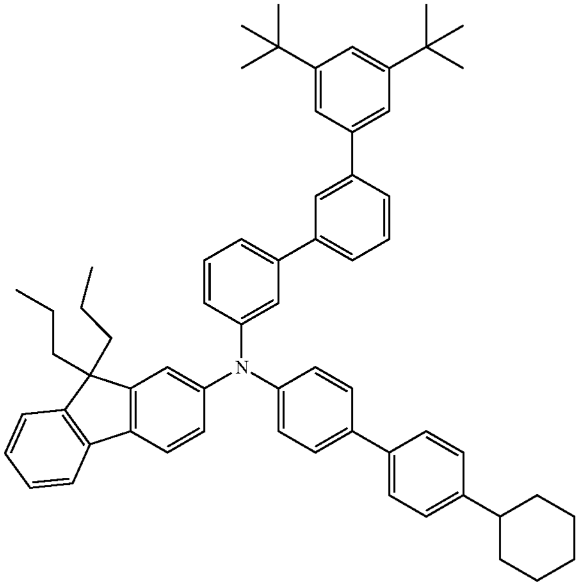
(158)
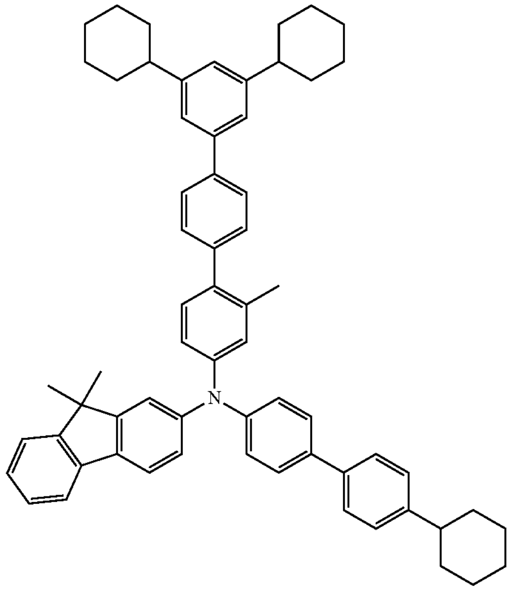
-continued
[Chemical Formula 15]
(159)
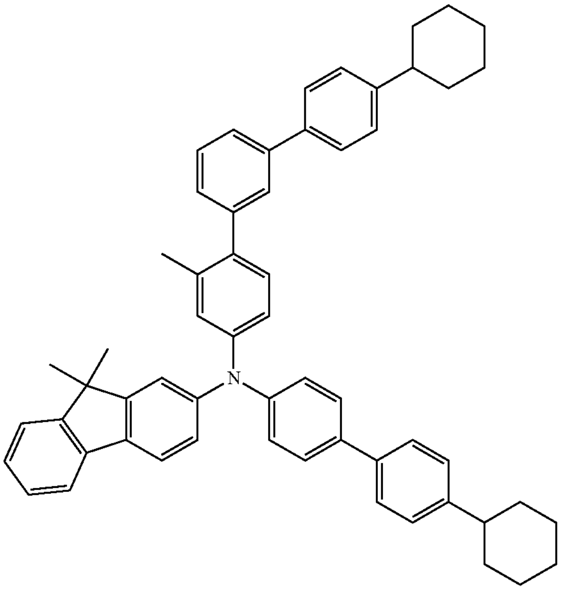
(160)
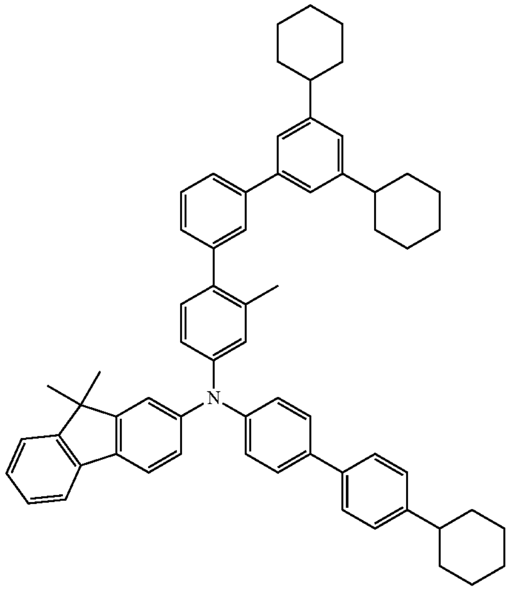

-continued
(161)
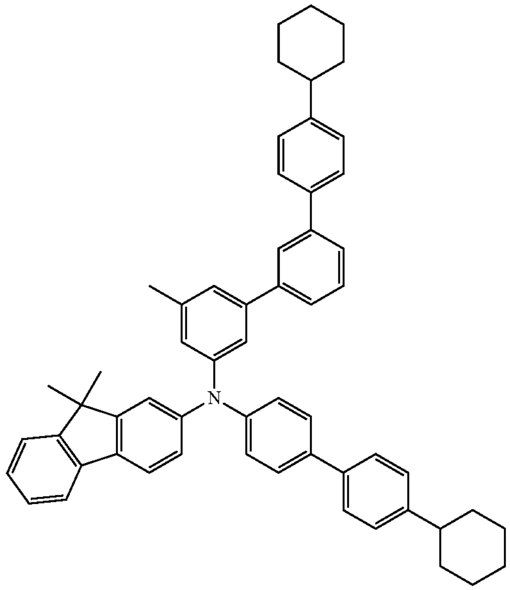
(162)
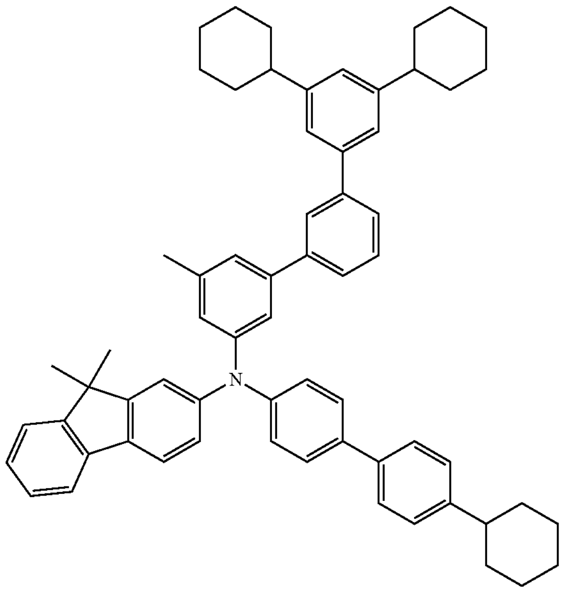
-continued
(163)
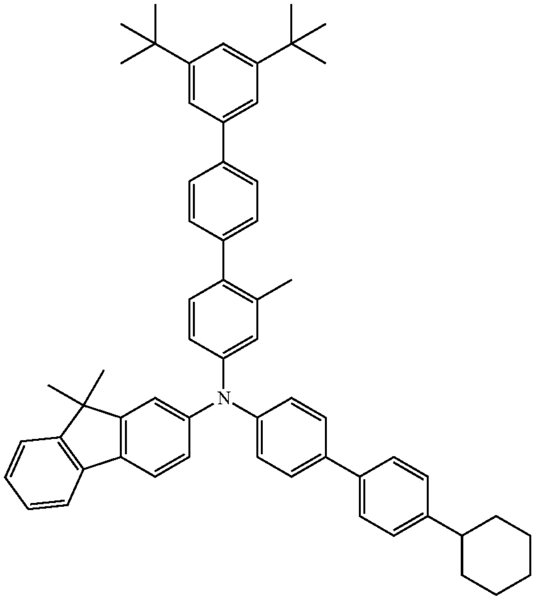
(164)
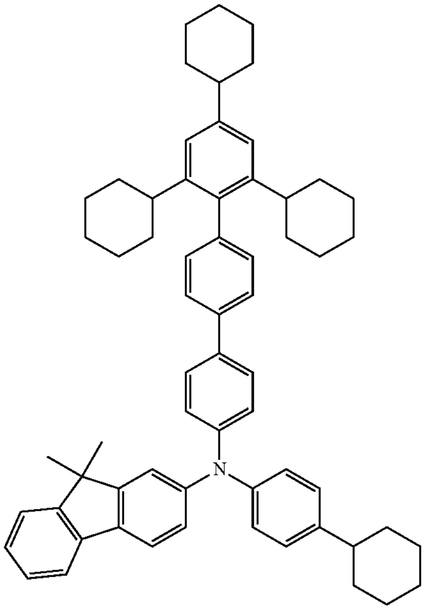

-continued
(165)
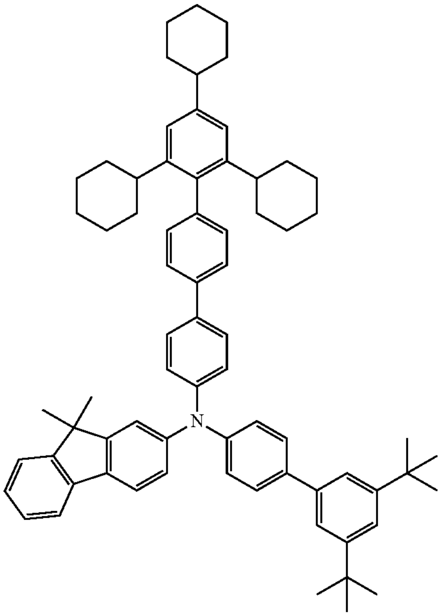
[Chemical Formula 16]
(166)
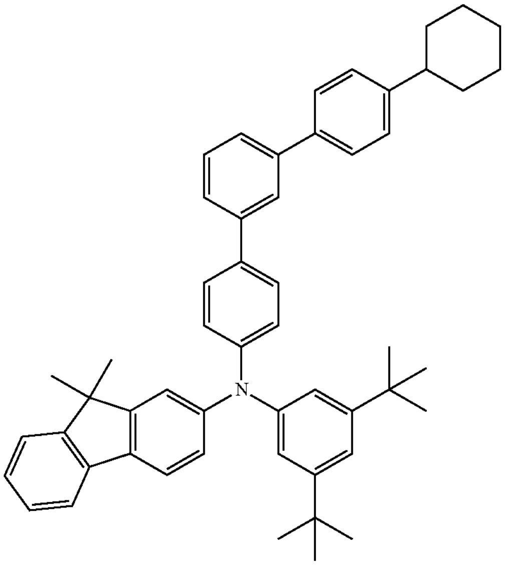
-continued
(167)
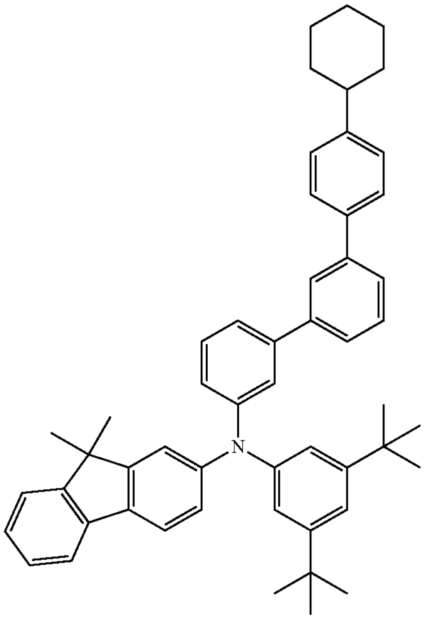
(168)
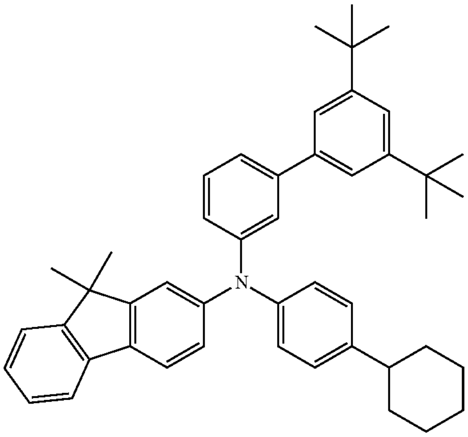
(169)
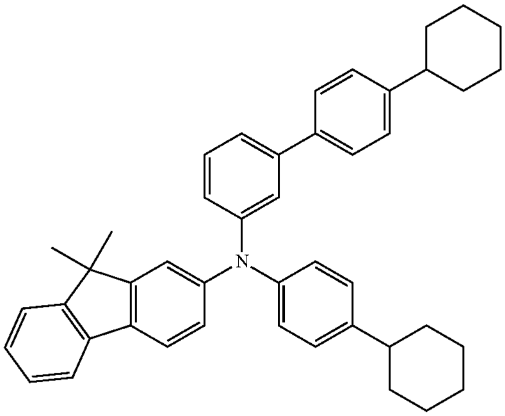

-continued
(170)
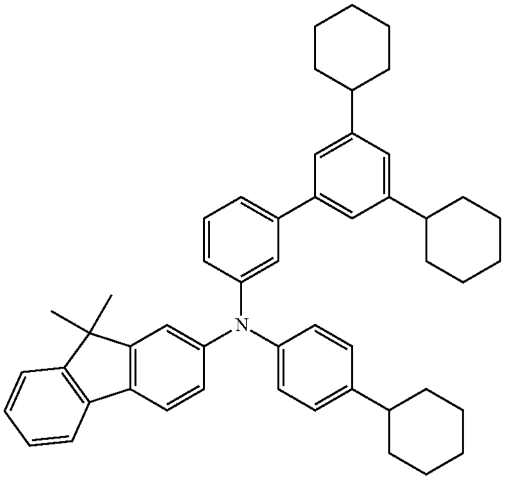
(171)
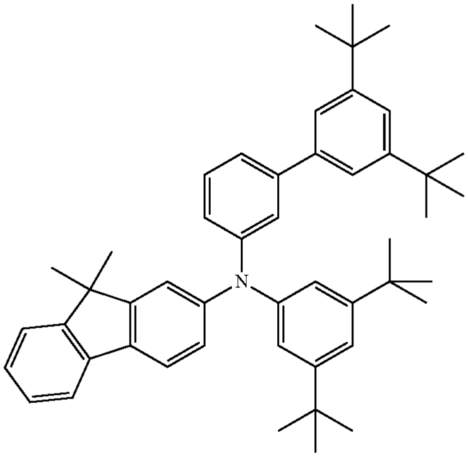
(172)
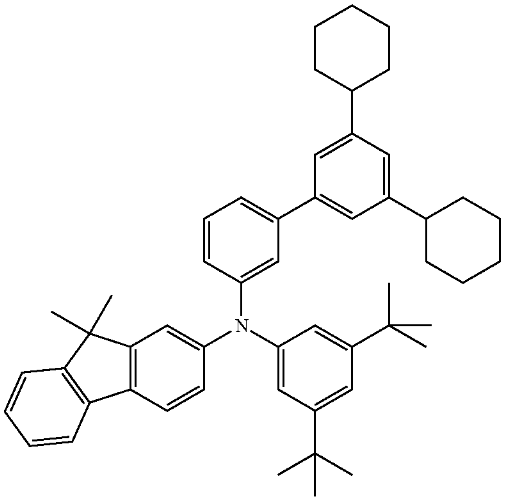
-continued
(173)
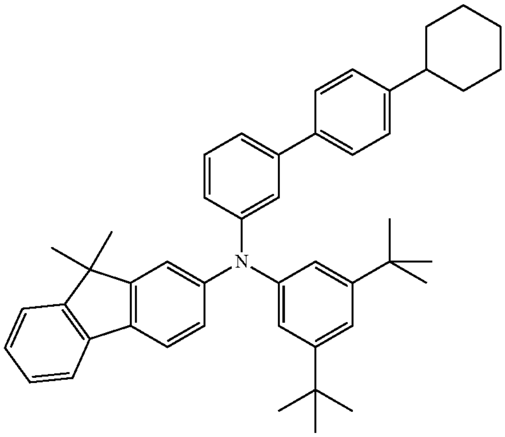
(174)
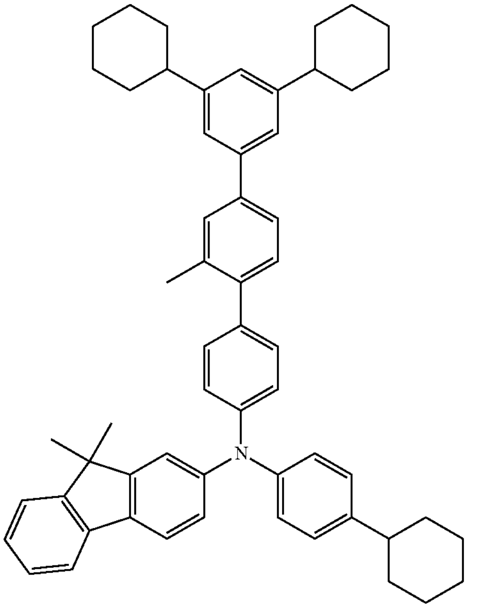
(175)
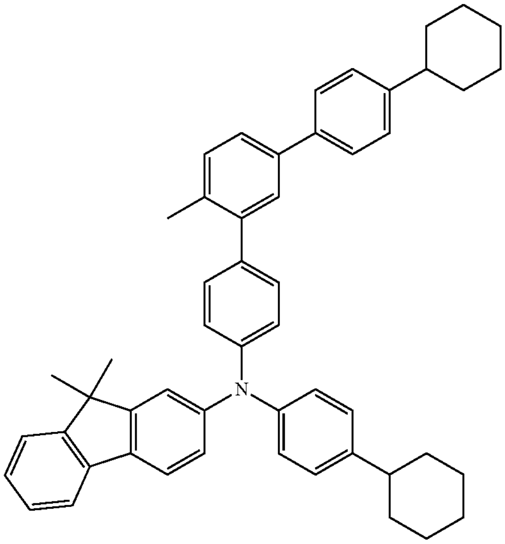

-continued
[Chemical Formula 17]
(176)
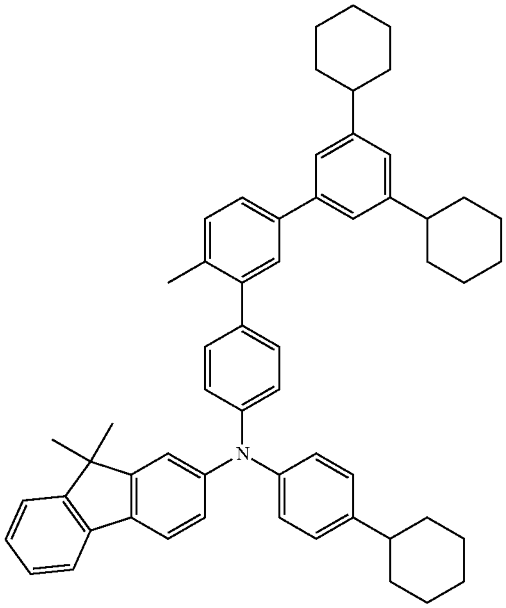
(177)
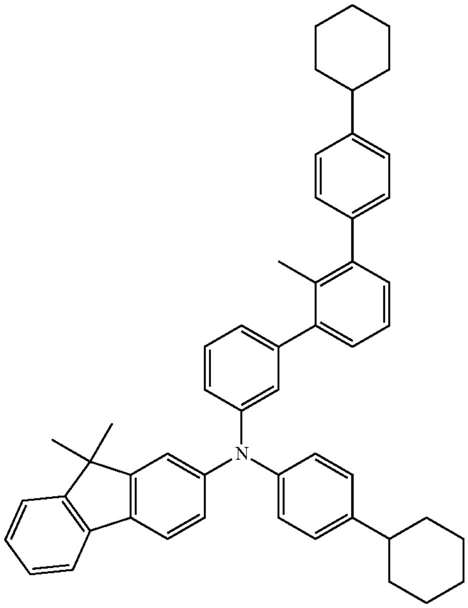
-continued
(178)
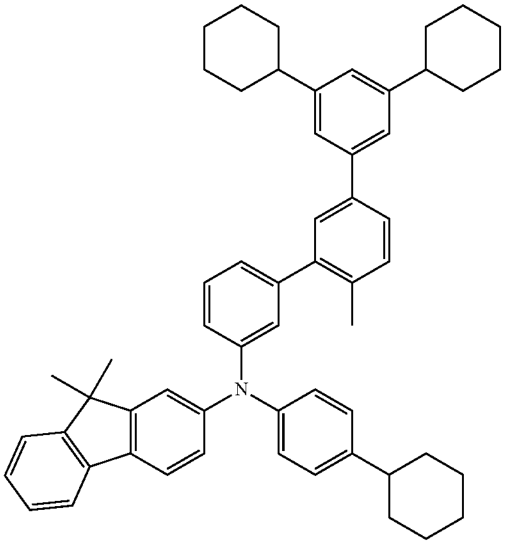
(179)
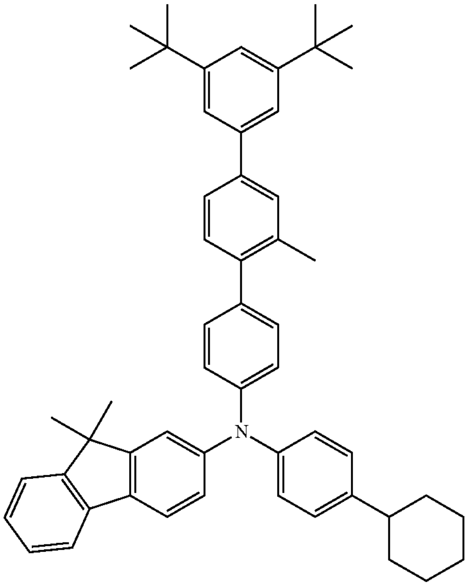

-continued
(180)
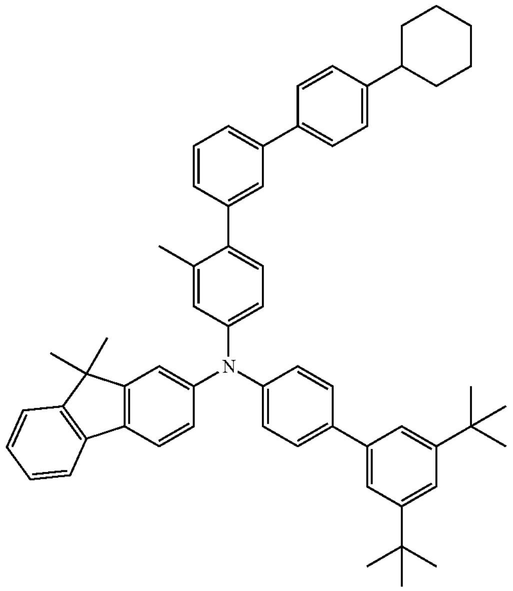
(181)
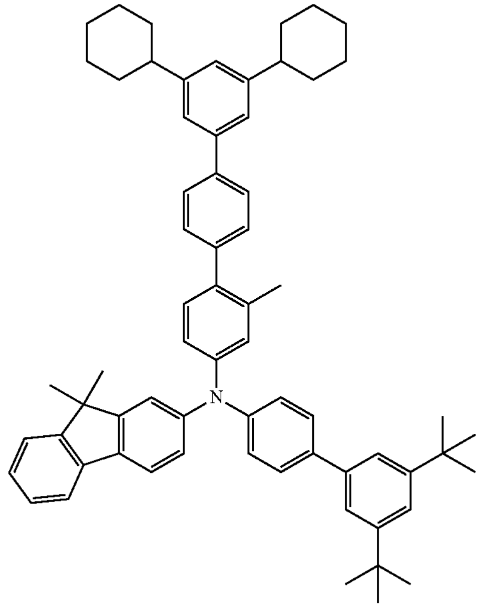
-continued
(182)
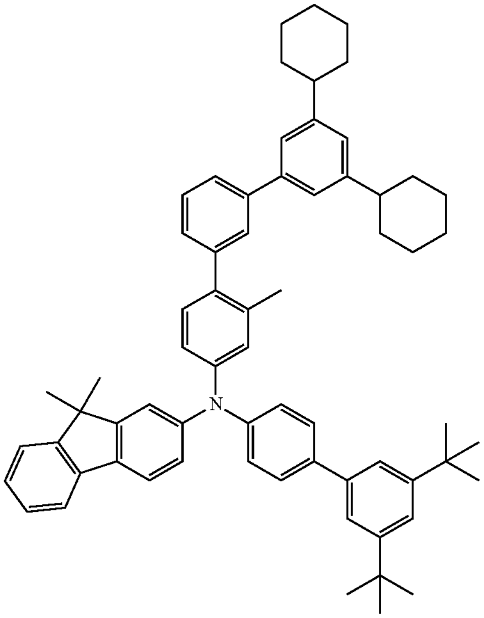
[Chemical Formula 18]
(183)
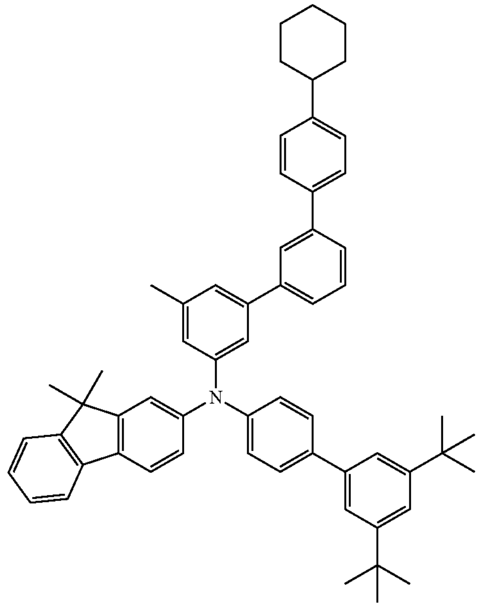

-continued
(184)
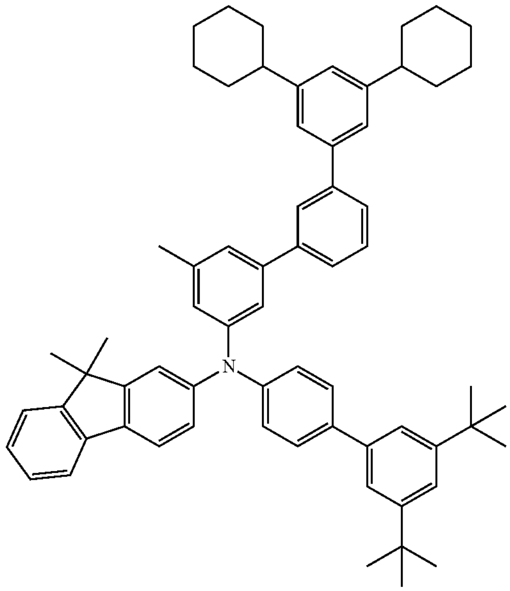
(185)
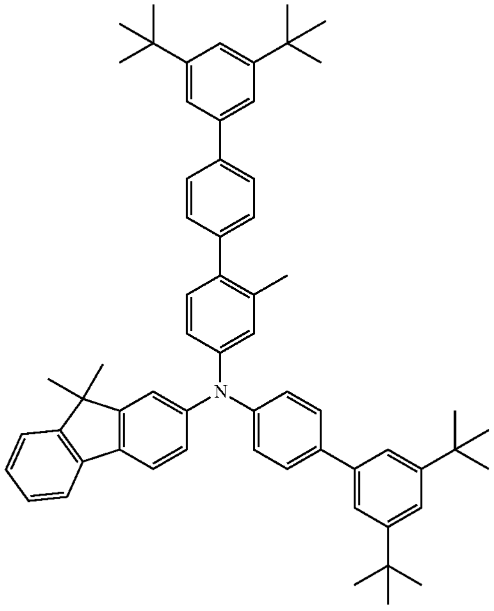
-continued
(186)
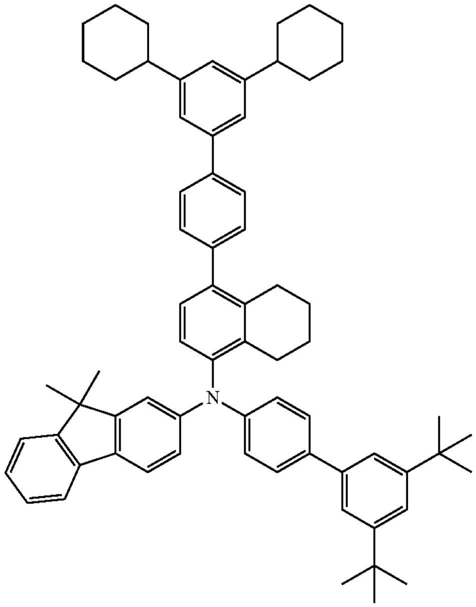
(187)
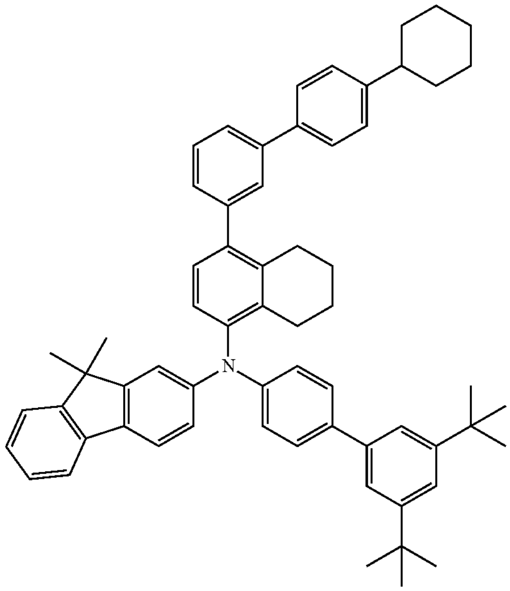

-continued
(188)
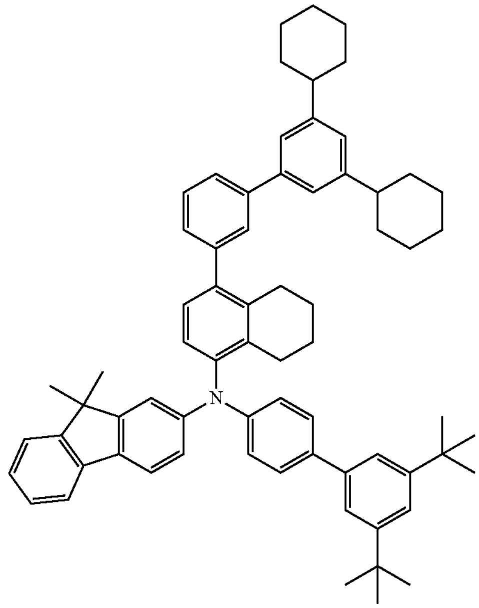
[Chemical Formula 19]
(189)
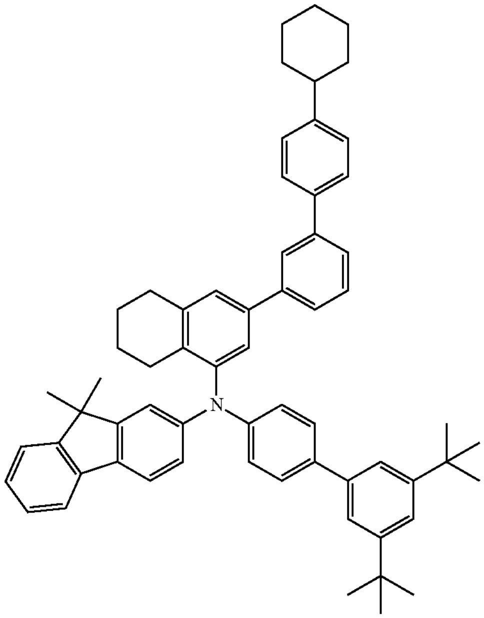
-continued
(190)
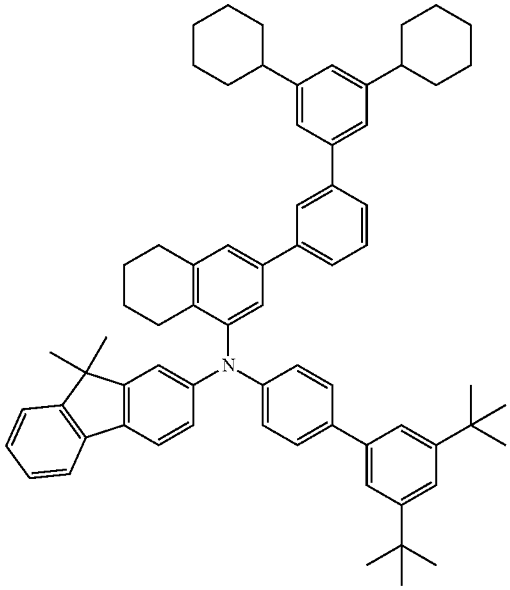
(191)
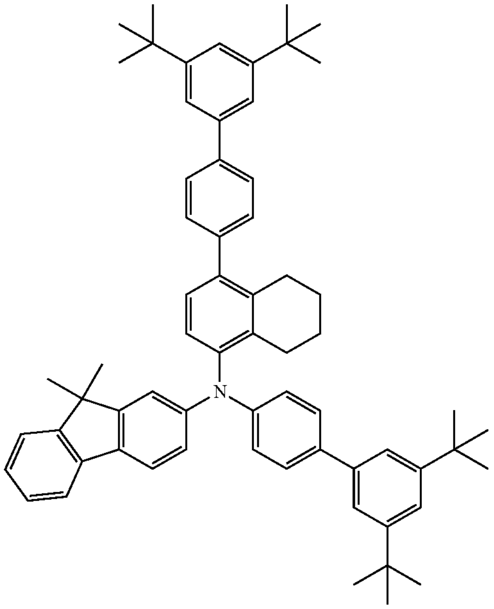

-continued
(192)
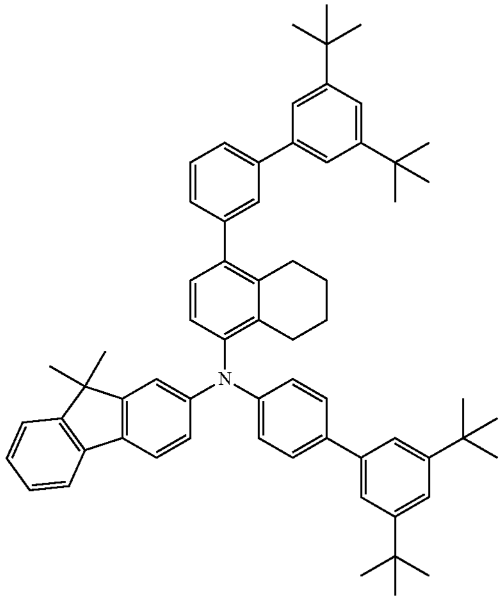
(193)
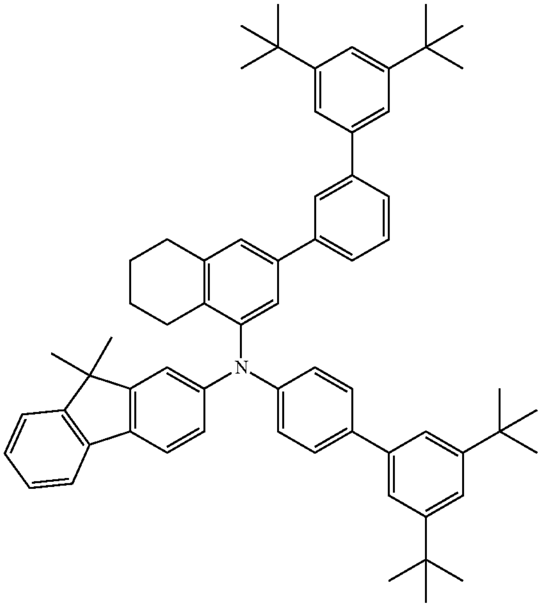
-continued
(194)
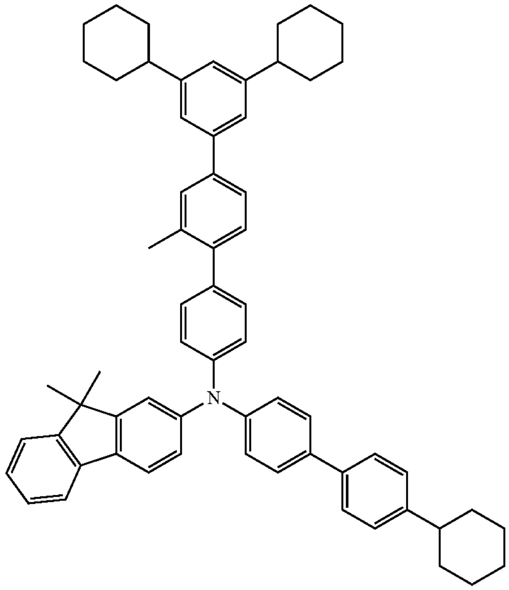
(195)
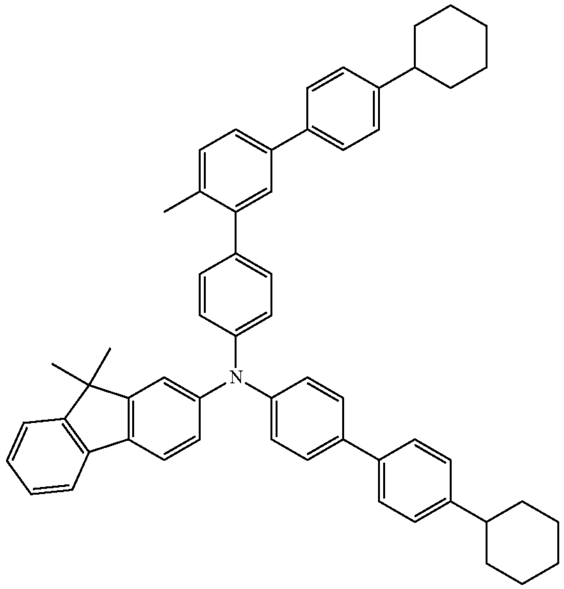

-continued
(196)
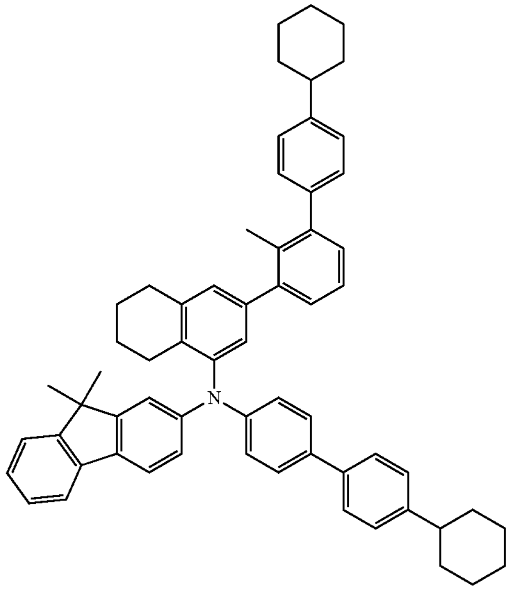
(197)
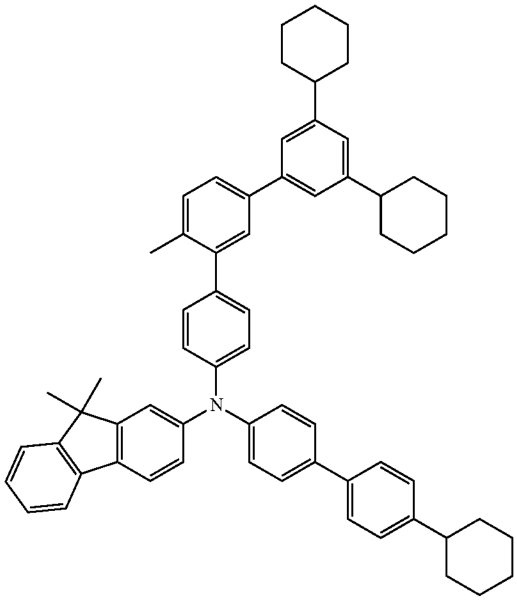
-continued
[Chemical Formula 20]
(198)
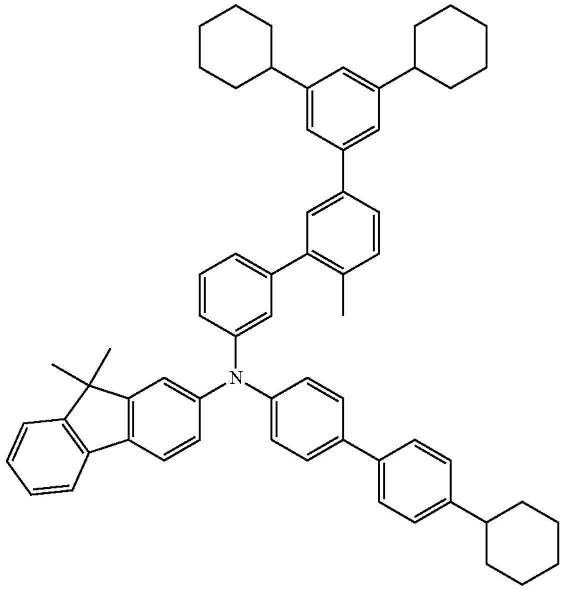
(199)
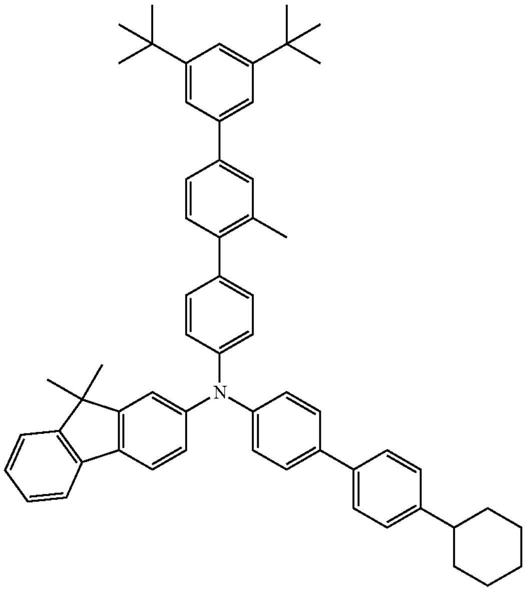

-continued
(200)
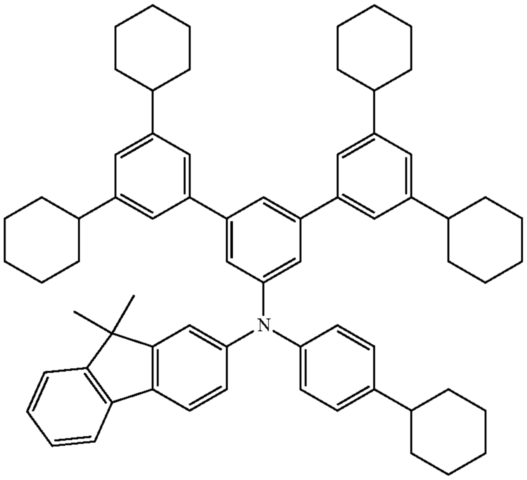
(201)
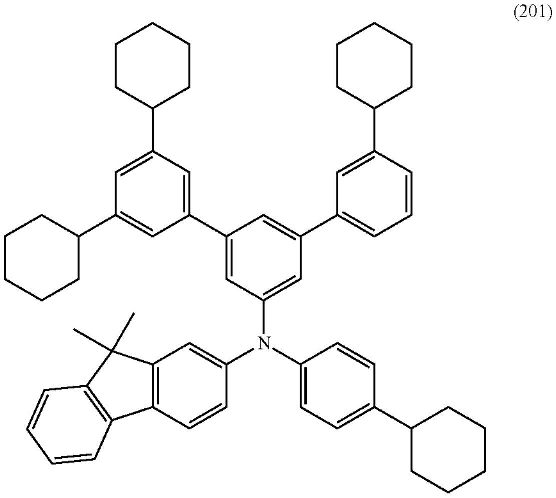
(202)
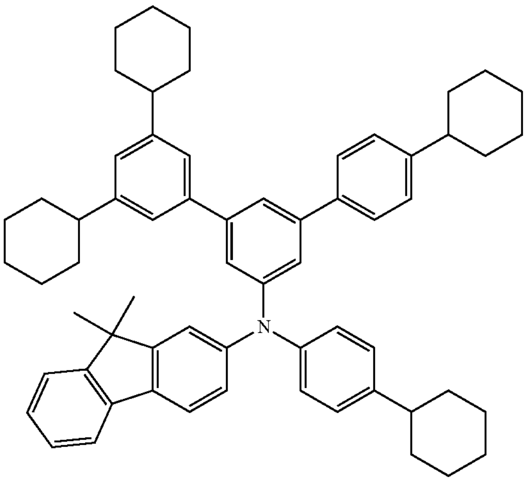
-continued
(203)
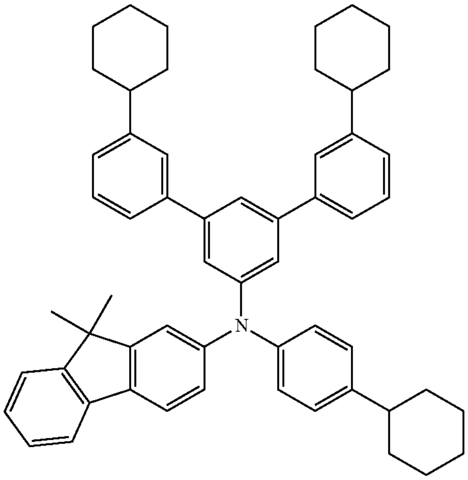
(204)
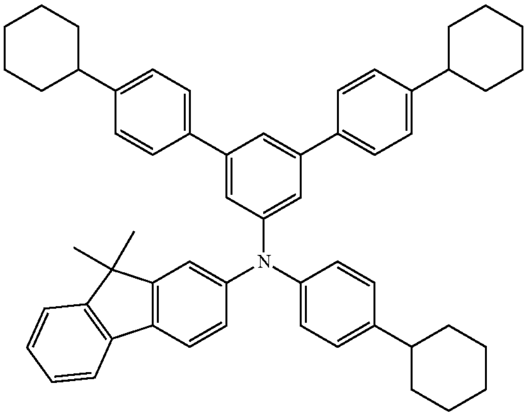
[Chemical Formula 21]
(205)
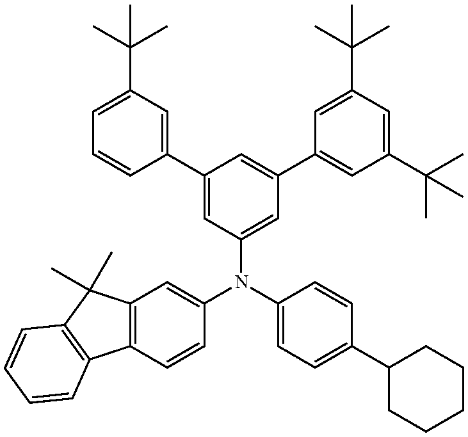

-continued
(206)
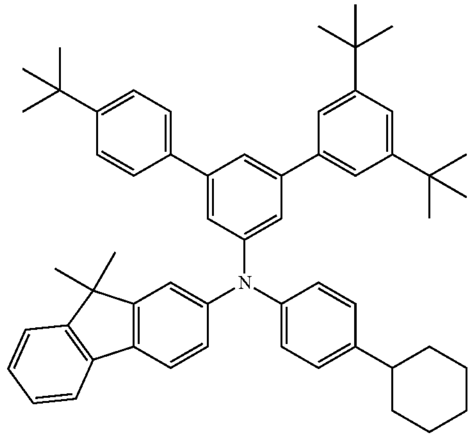
(207)
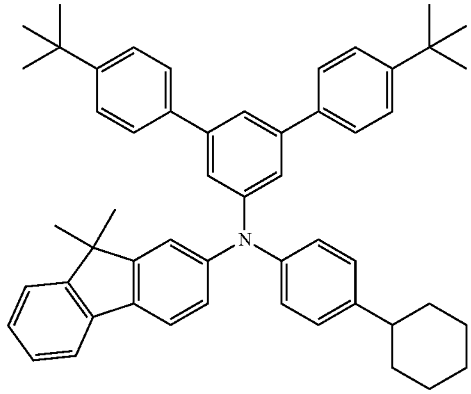
(208)
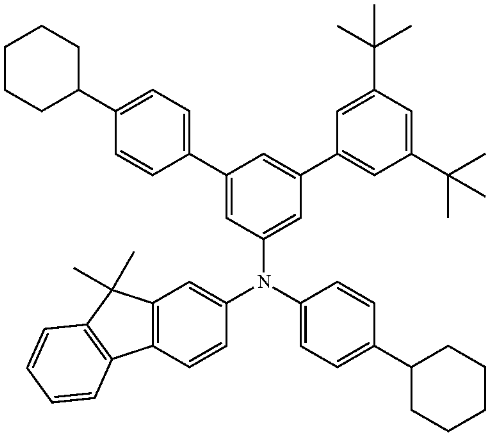
-continued
(209)
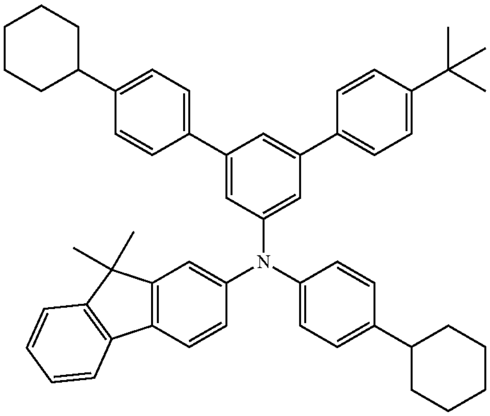
(210)
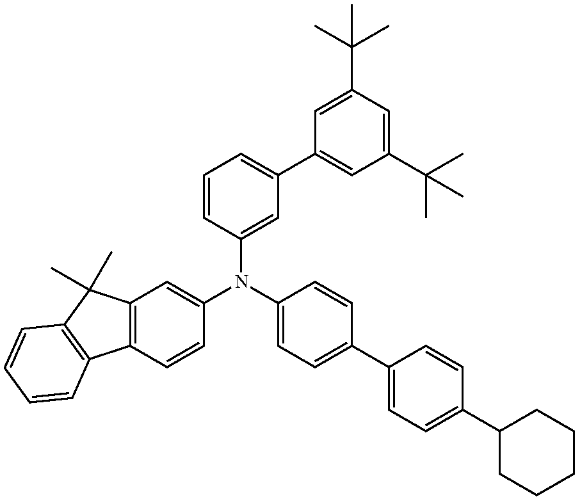
(211)
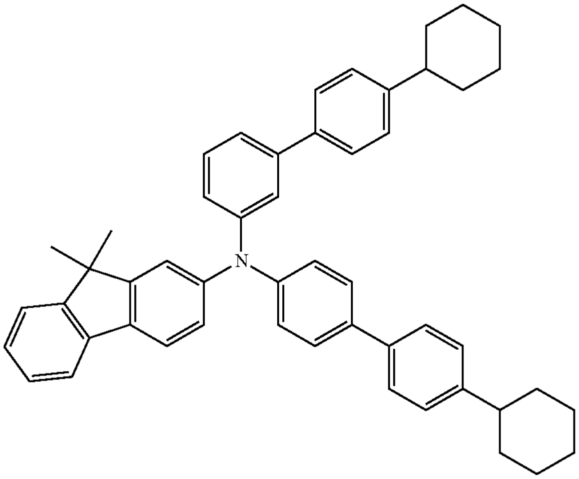

-continued
(212)
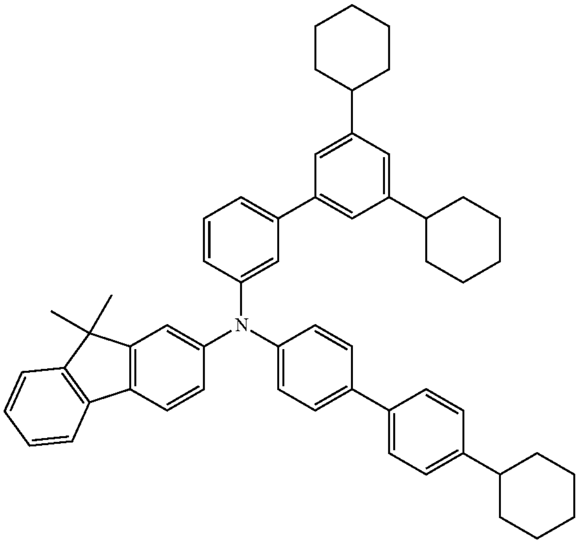
(213)
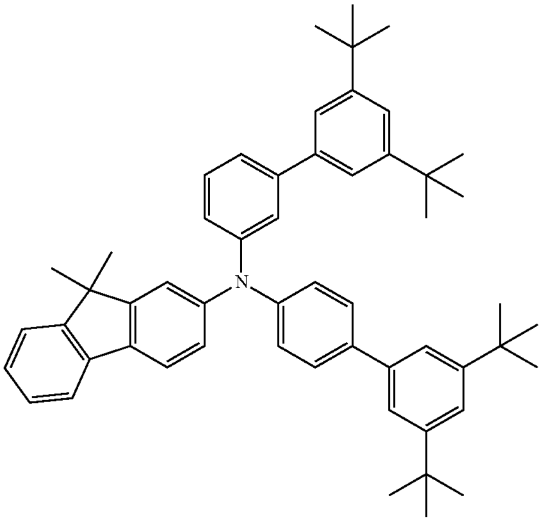
(214)
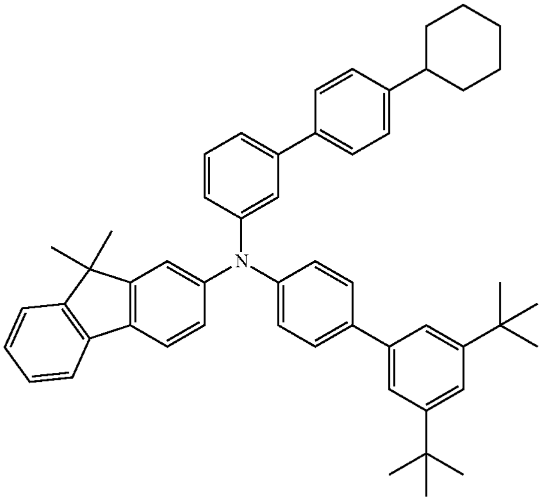
-continued
(215)
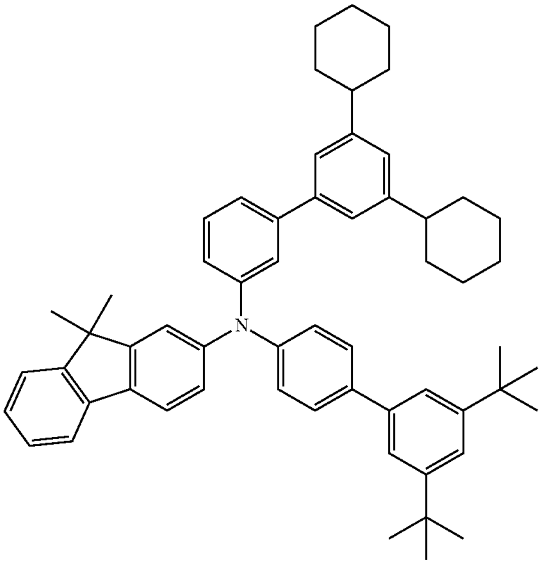
(216)
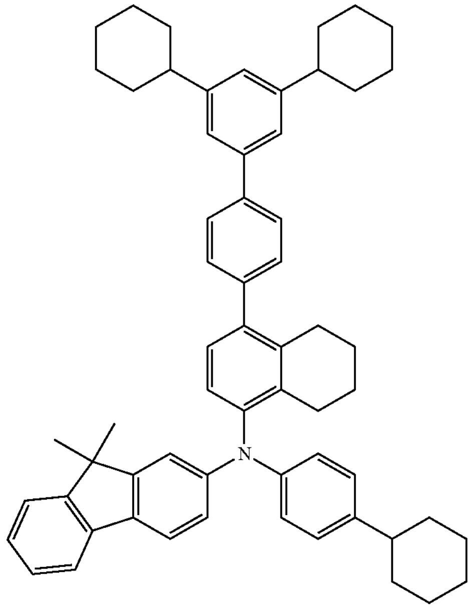

-continued
[Chemical Formula 22]
(217)
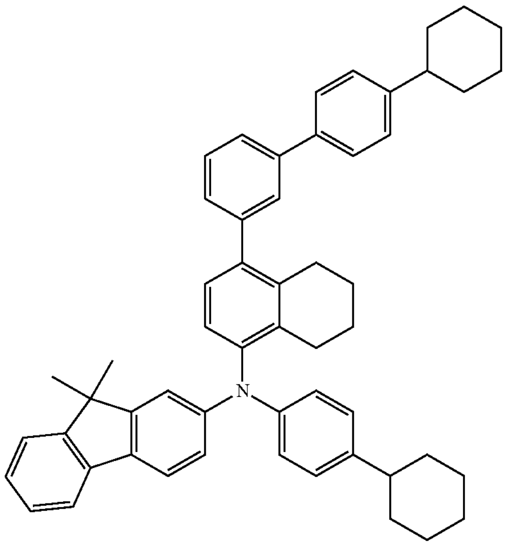
(218)
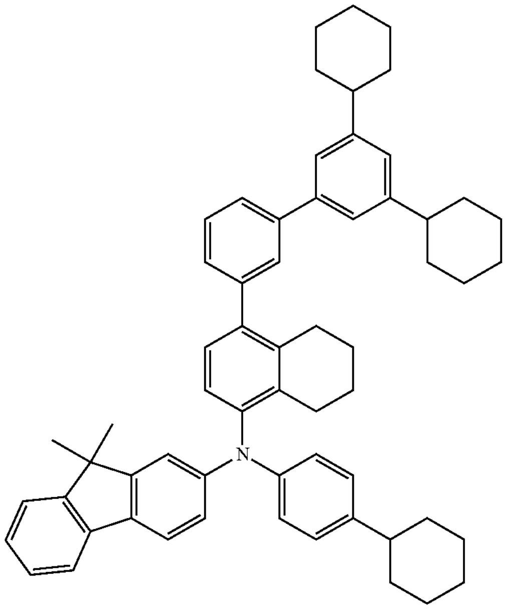
-continued
(219)
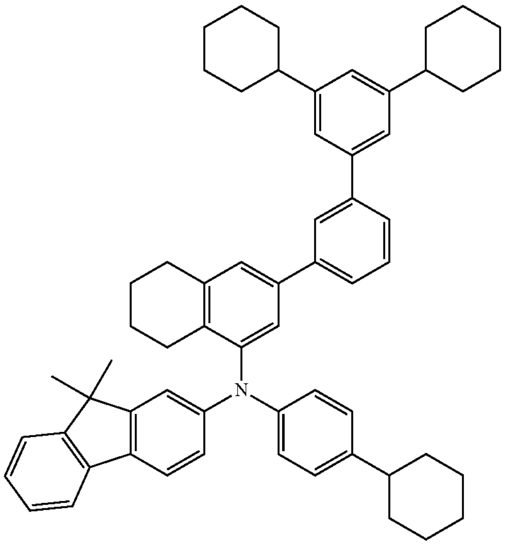
(220)
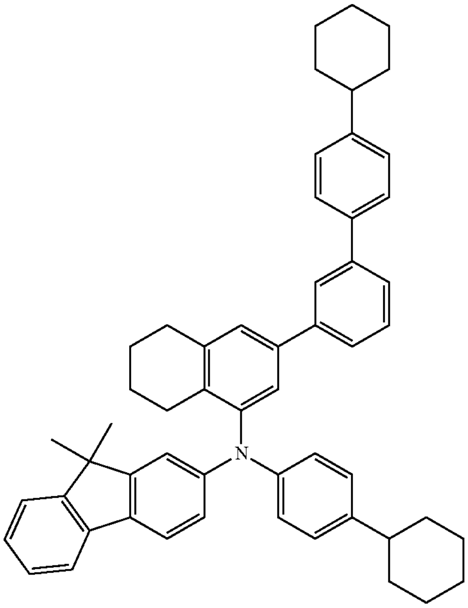

-continued
(221)
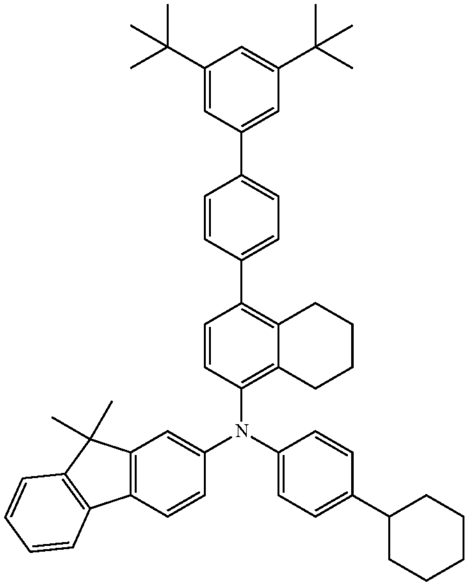
(222)
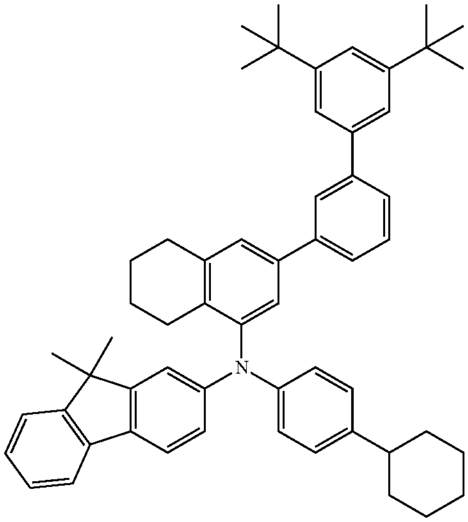
-continued
(223)
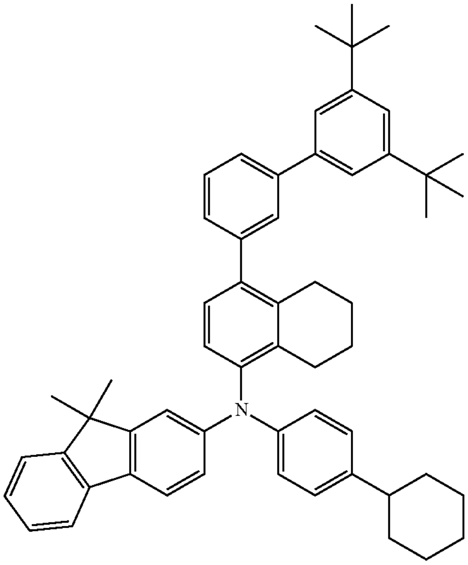
(224)
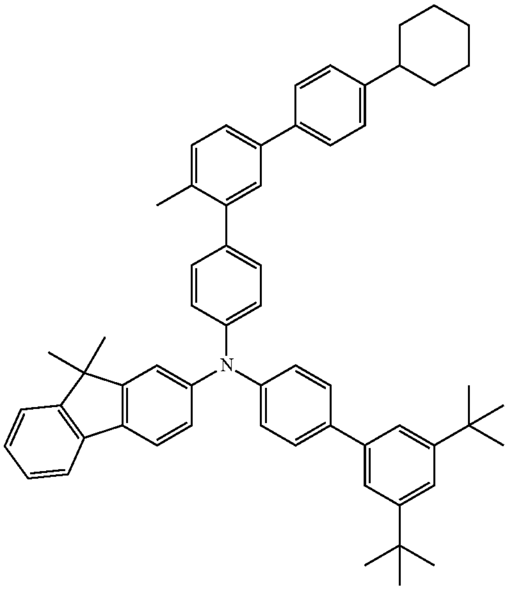

-continued
(225)
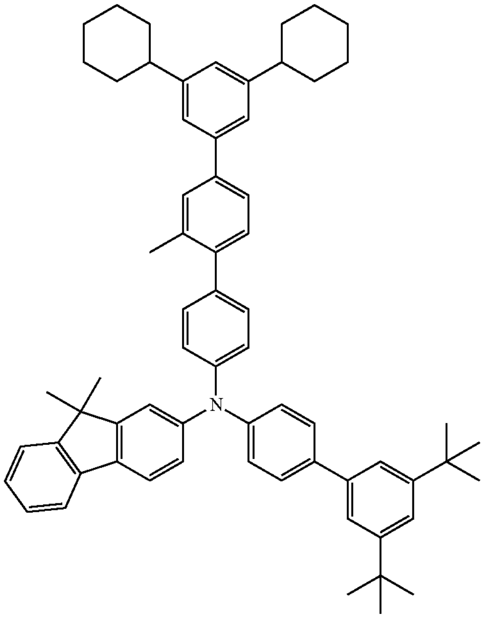
-continued
[Chemical Formula 23]
(227)
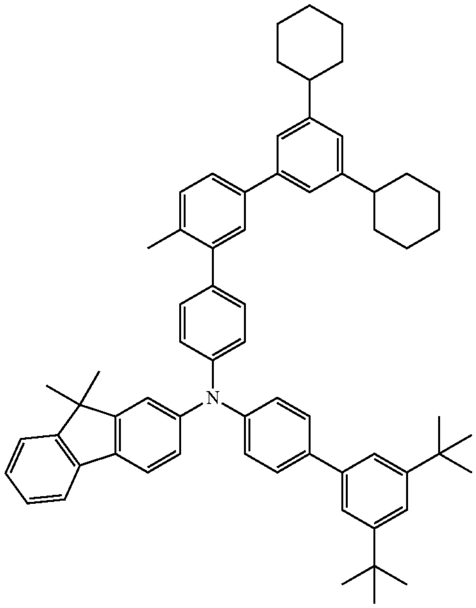
(226)
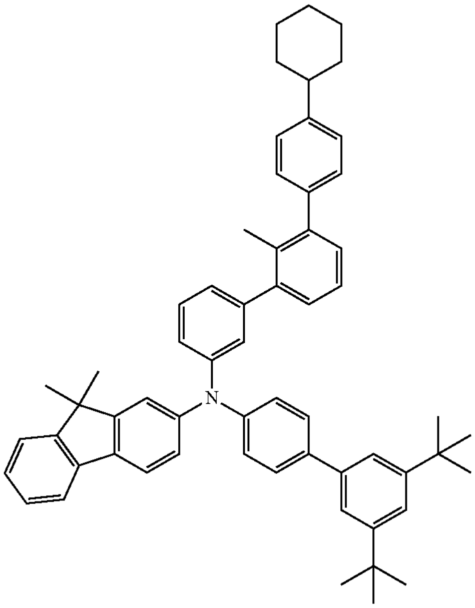
(228)
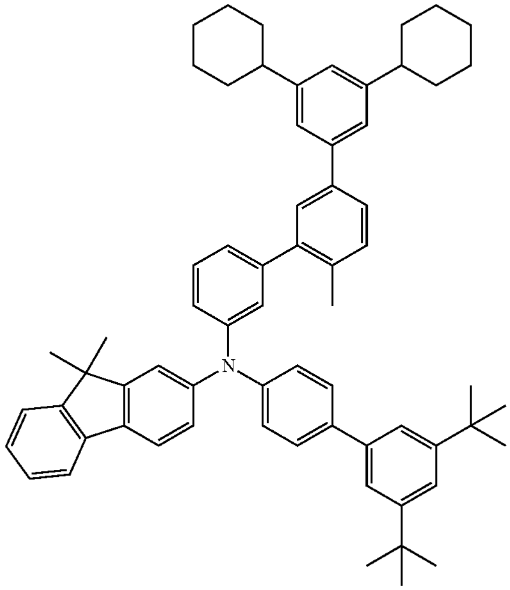

-continued
(229)
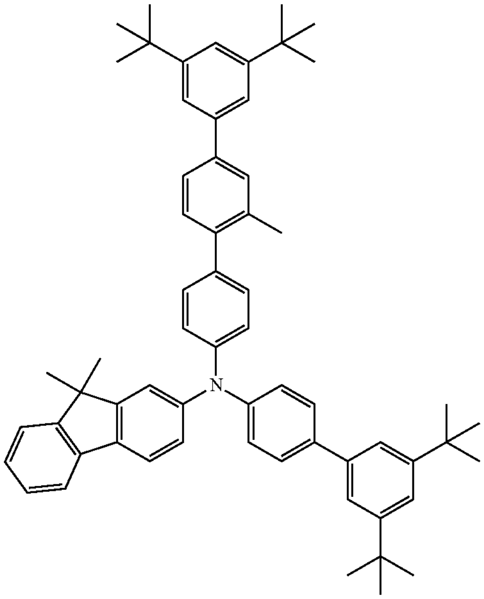
(230)
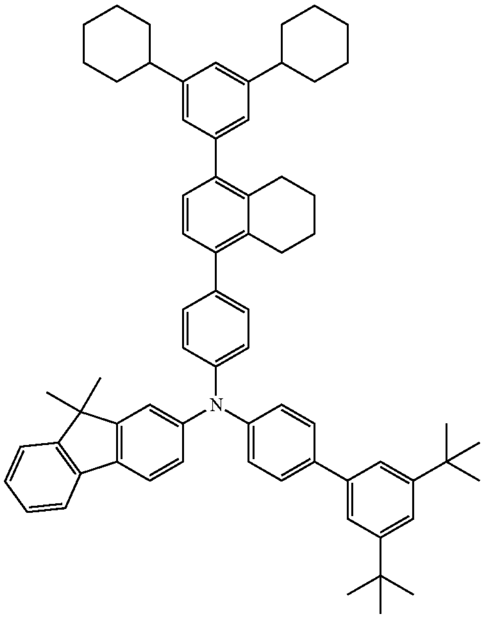
-continued
(231)
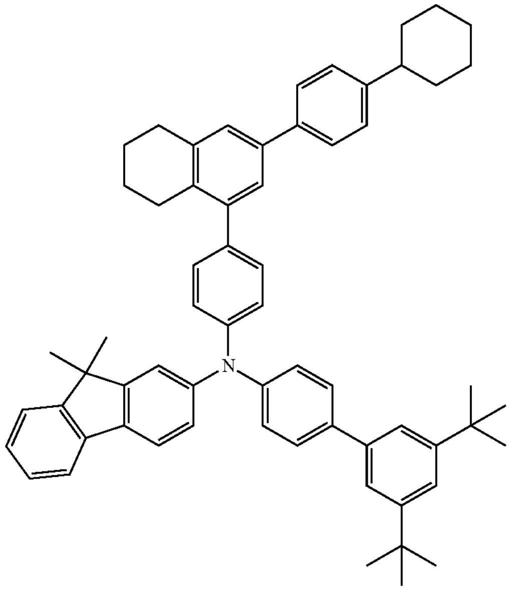
(232)
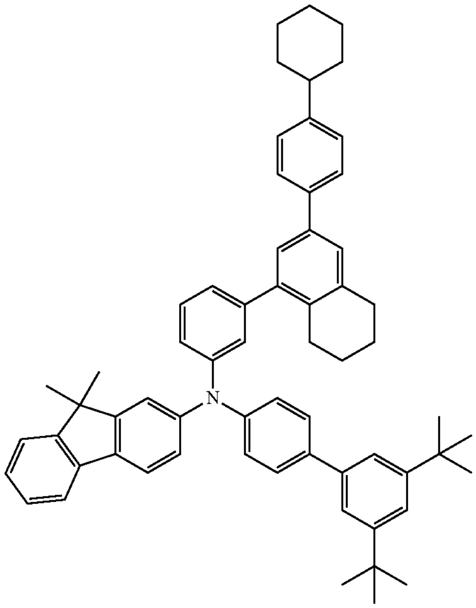

-continued
(233)
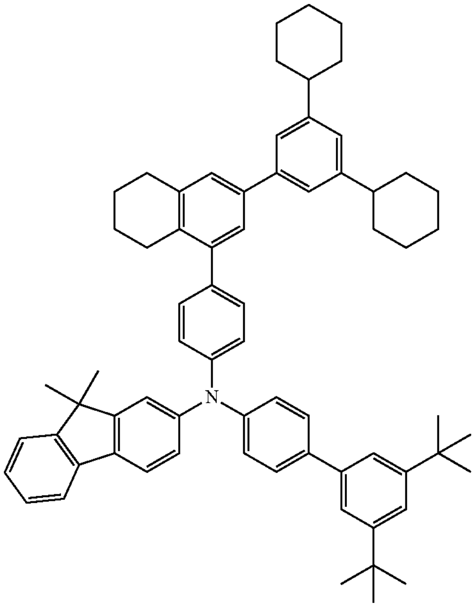
-continued
(235)
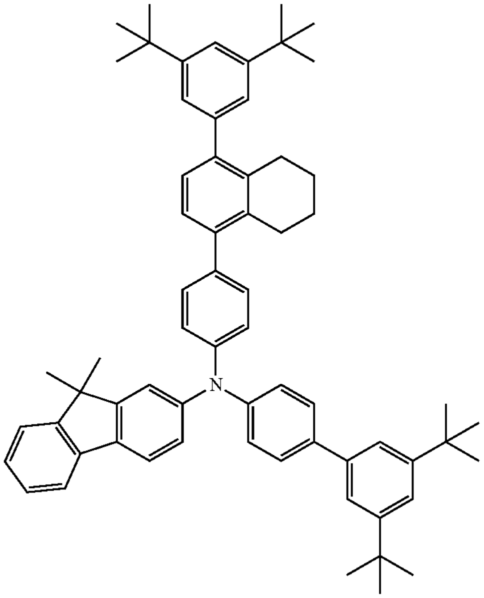
[Chemical Formula 24]
(234)
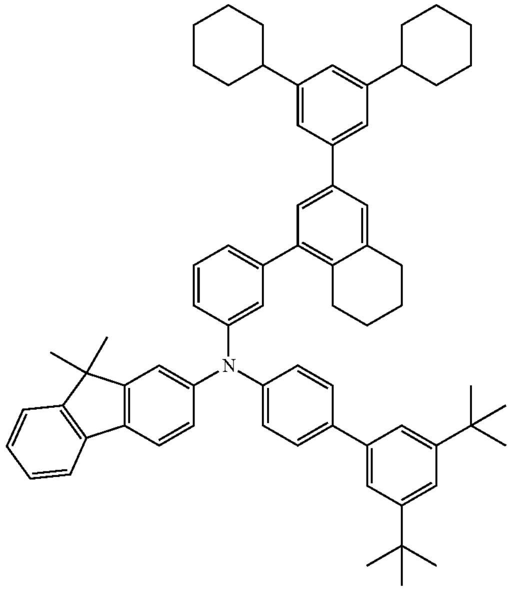
(236)
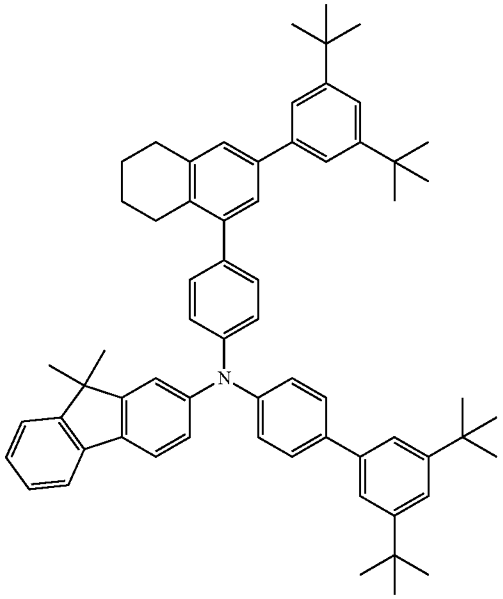

-continued
(237)
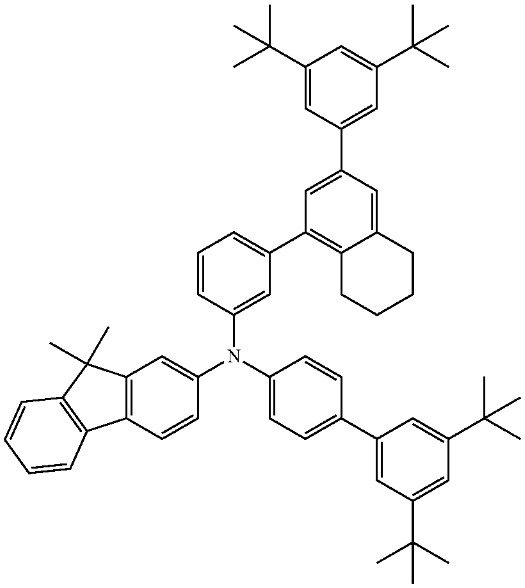
(238)
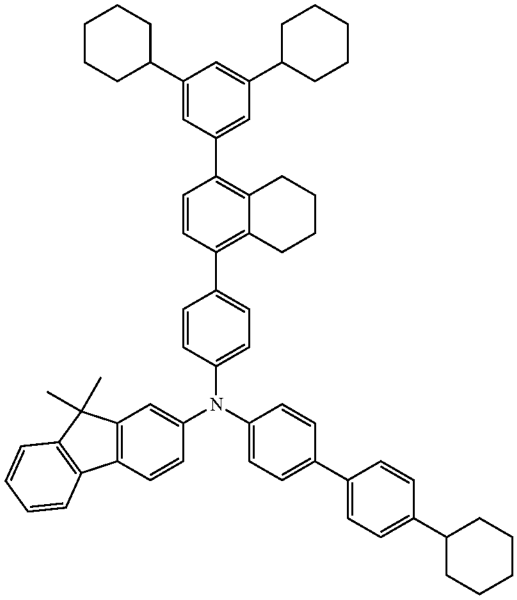
-continued
(239)
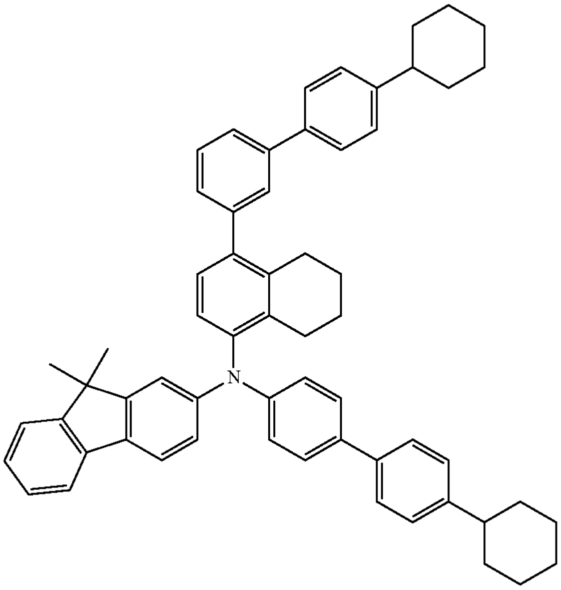
(240)
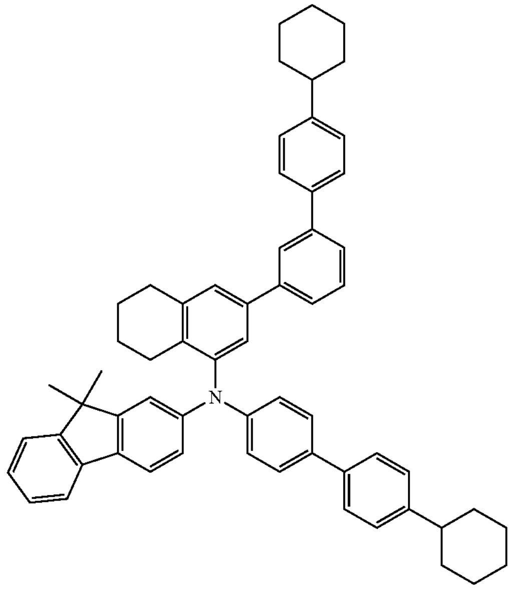

-continued
(241)
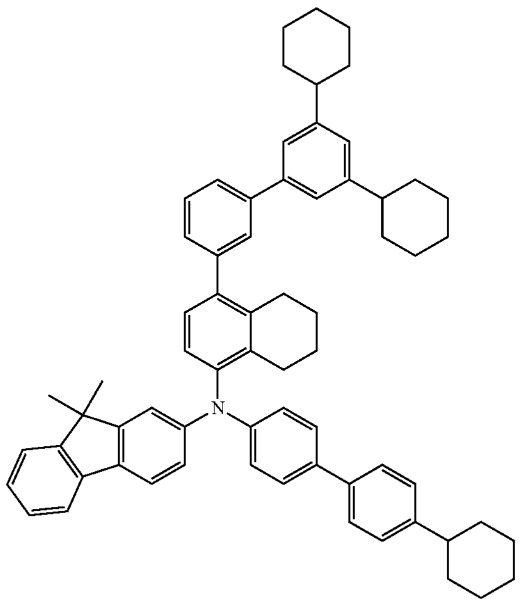
(242)
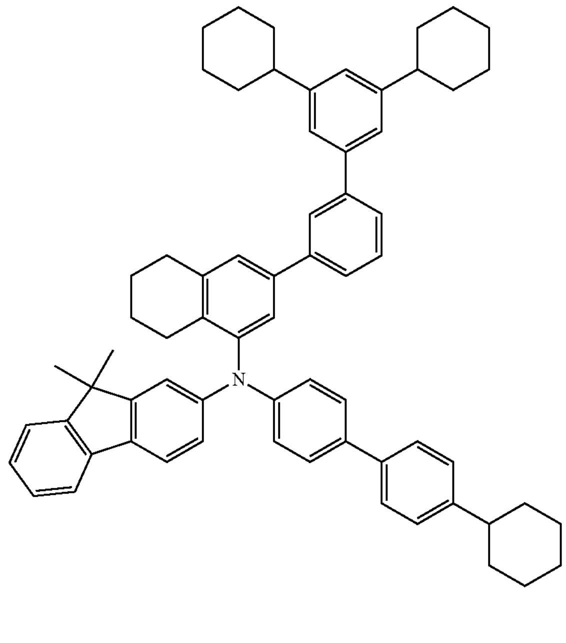
-continued
[Chemical Formula 25]
(243)
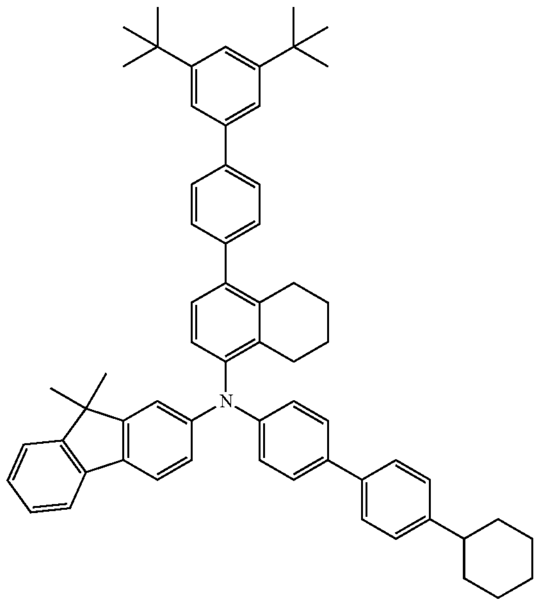
(244)
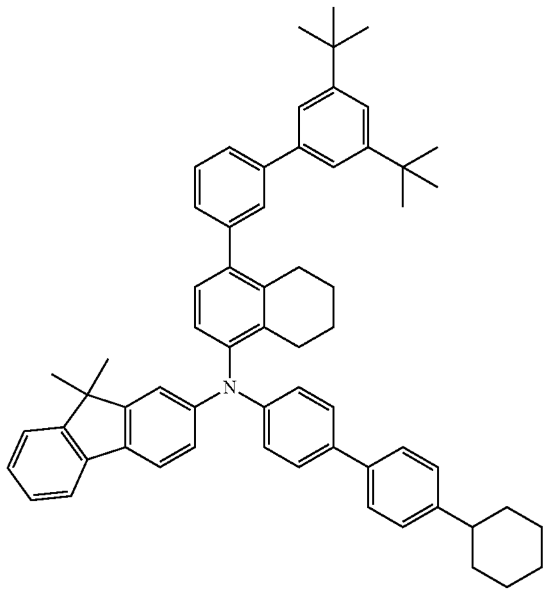

-continued
(245)
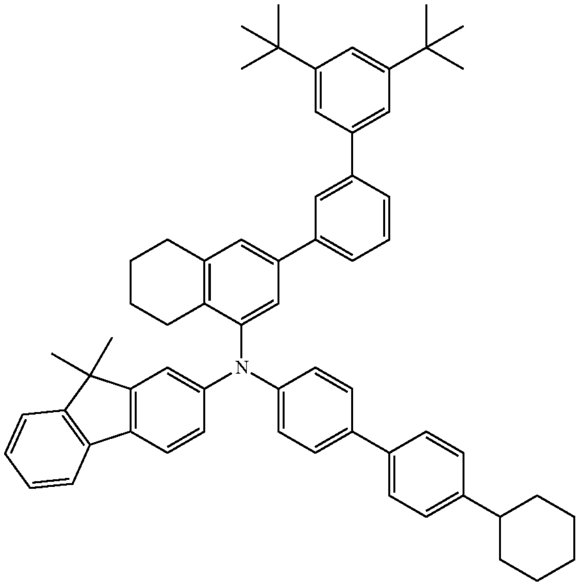
(246)
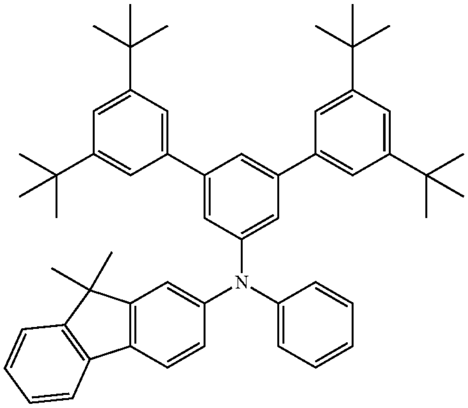
(247)
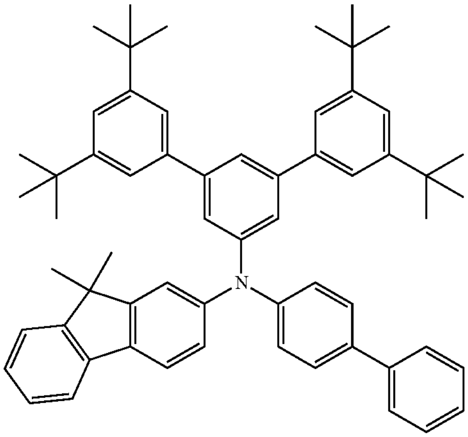
-continued
(248)
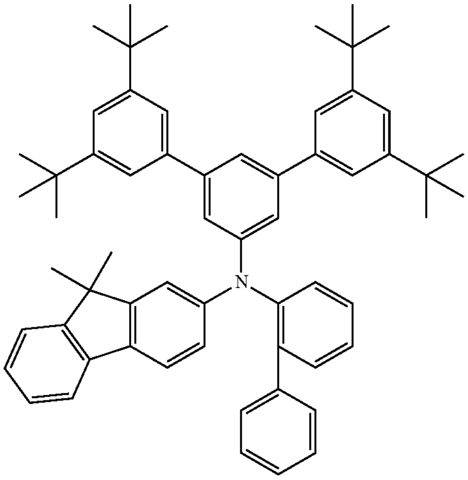
(249)
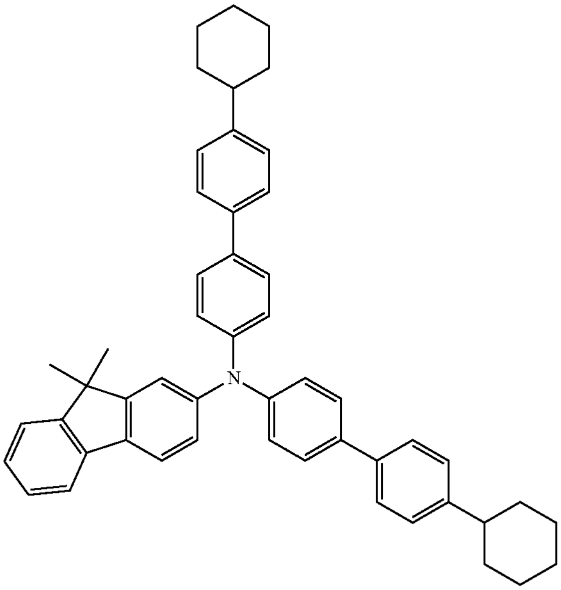

-continued
(250)
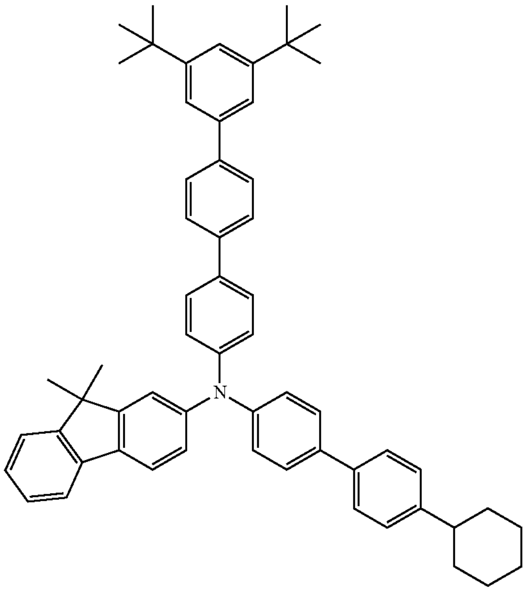
(251)
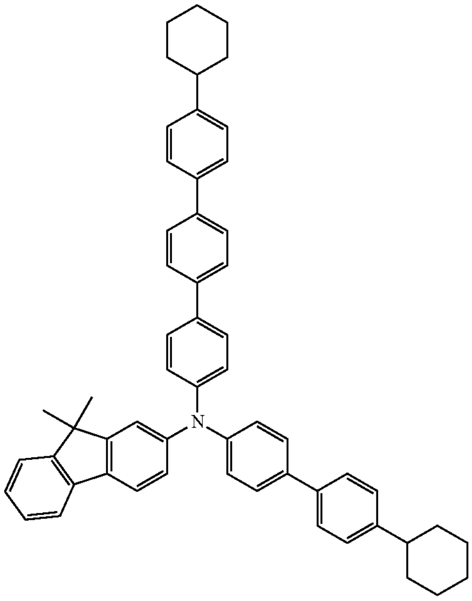
-continued
(252)
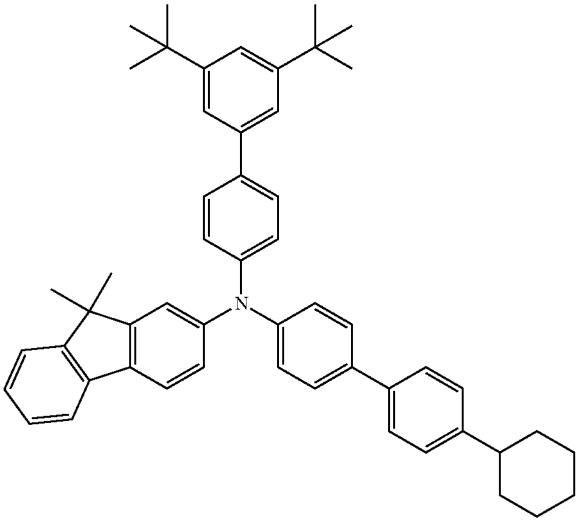
(252)
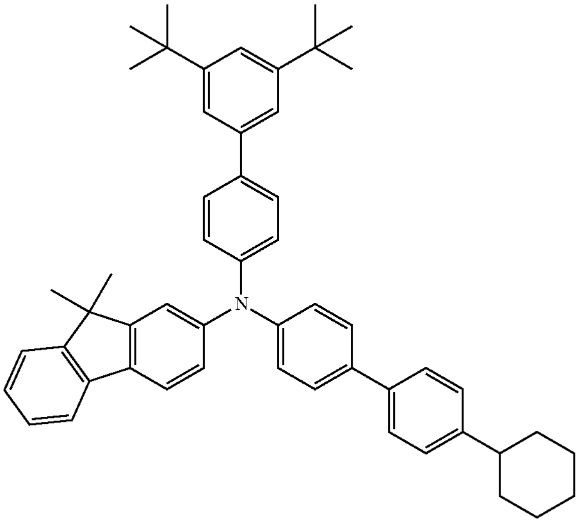

-continued
[Chemical Formula 26]
(253)
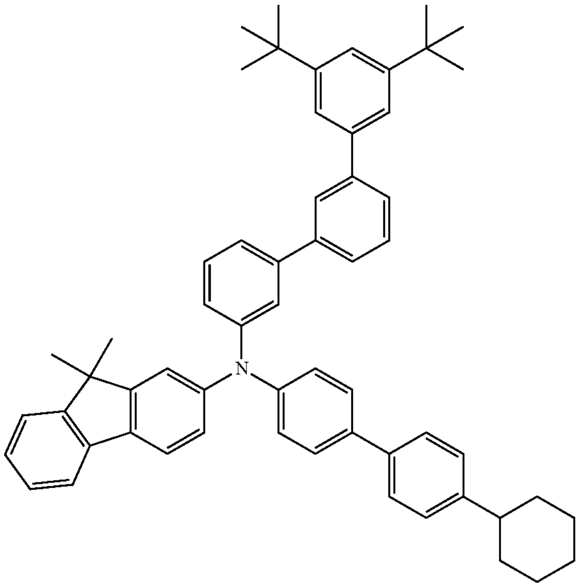
(254)
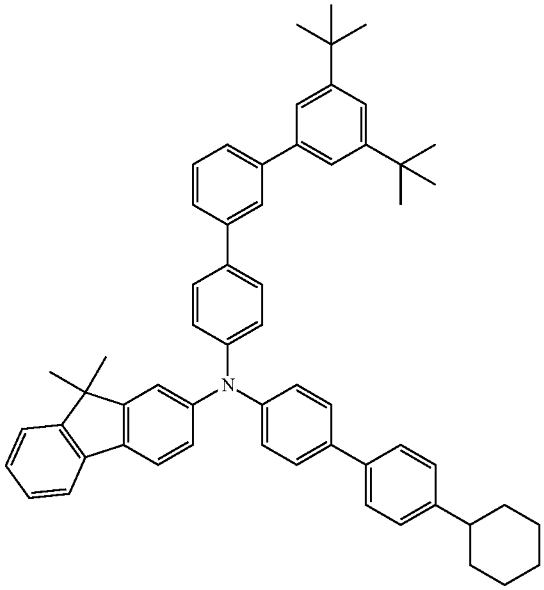
-continued
(255)
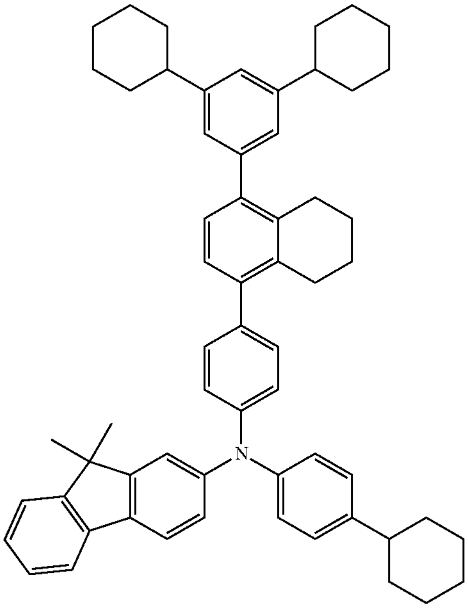
(256)
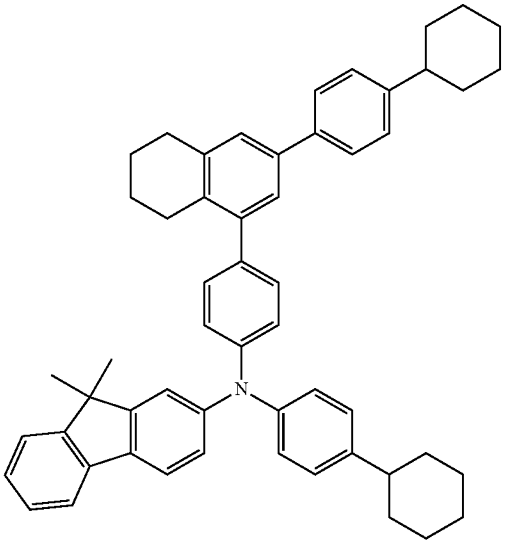

-continued
(257)
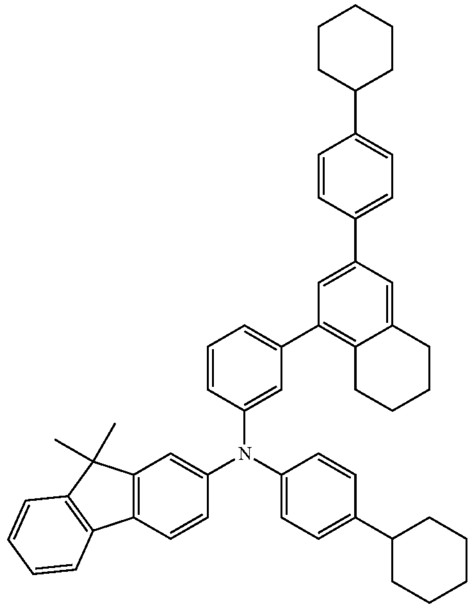
(258)
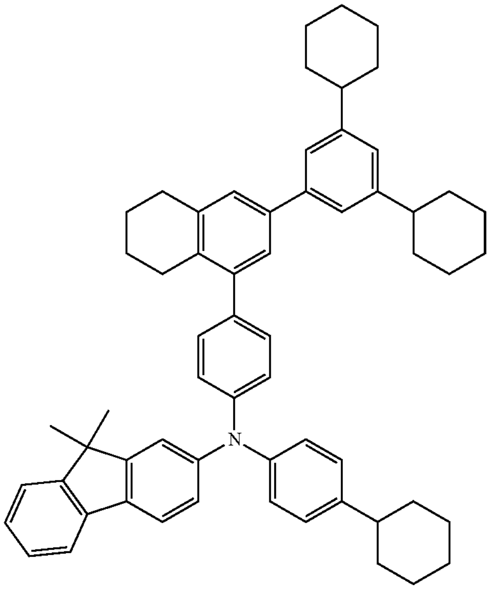
-continued
(259)
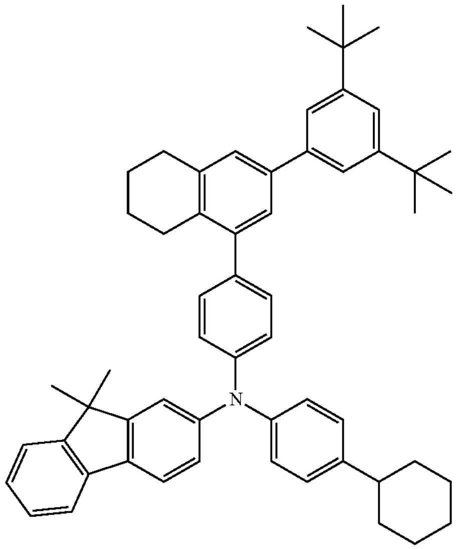
(260)
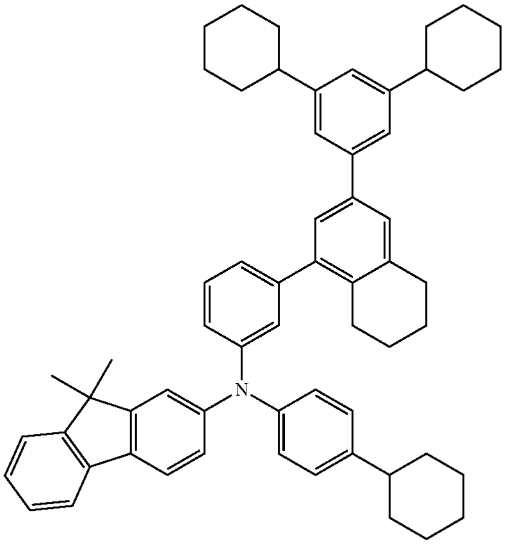

-continued
(261)
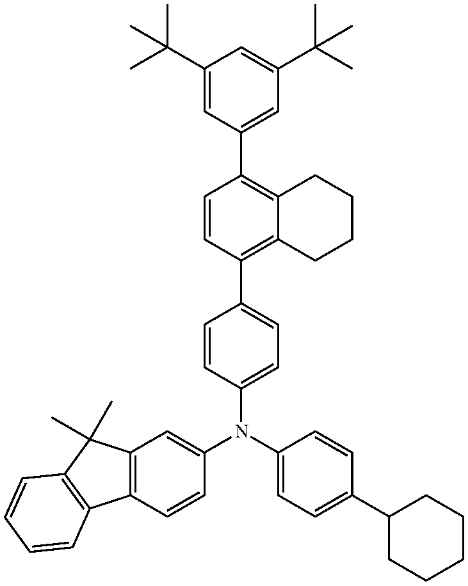
(262)
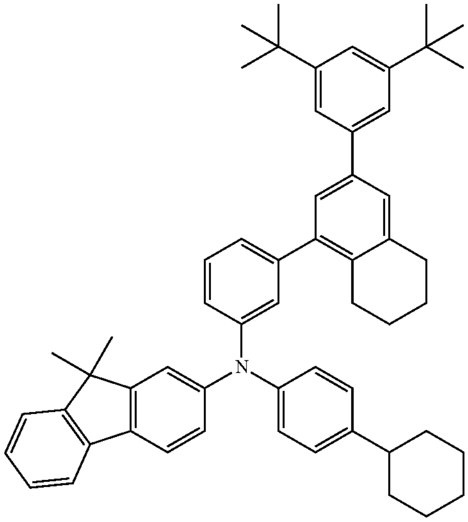
-continued
[Chemical Formula 27]
(263)
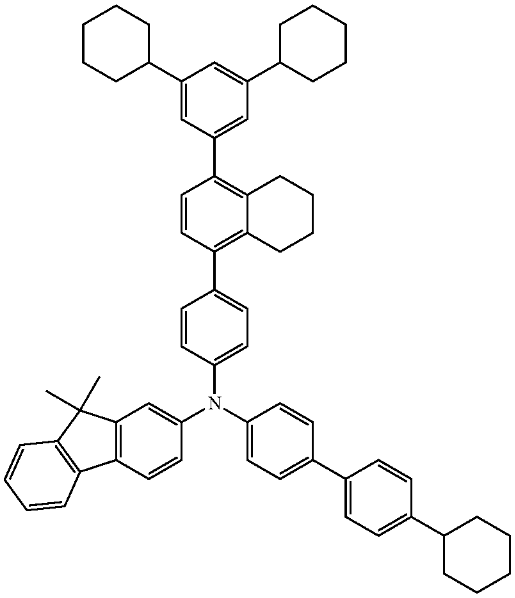
(264)
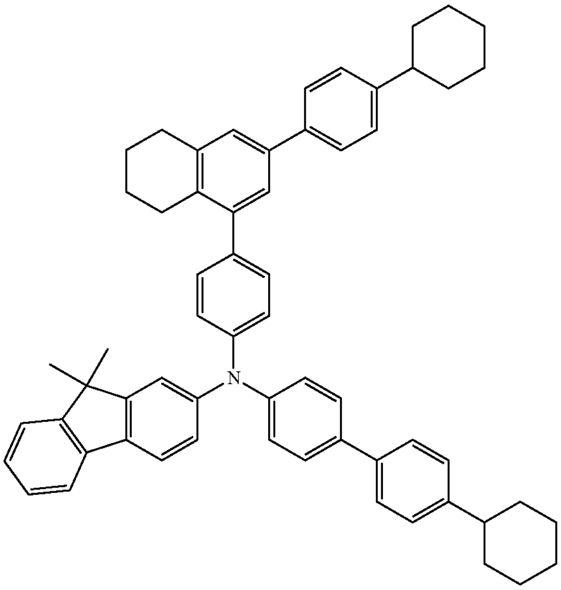

(265)
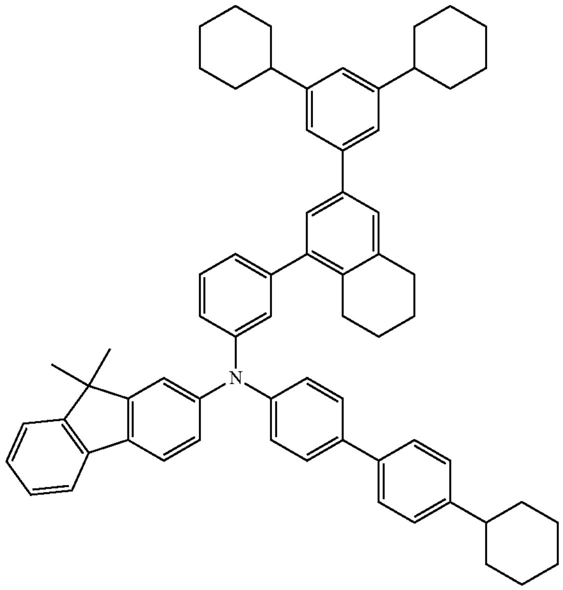
(266)
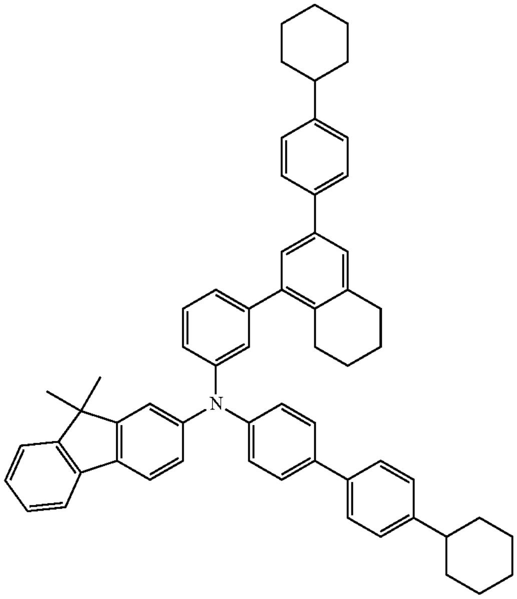
(267)
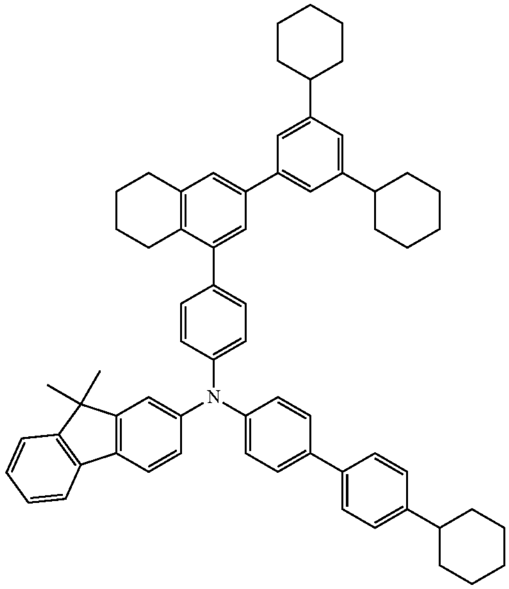
(268)
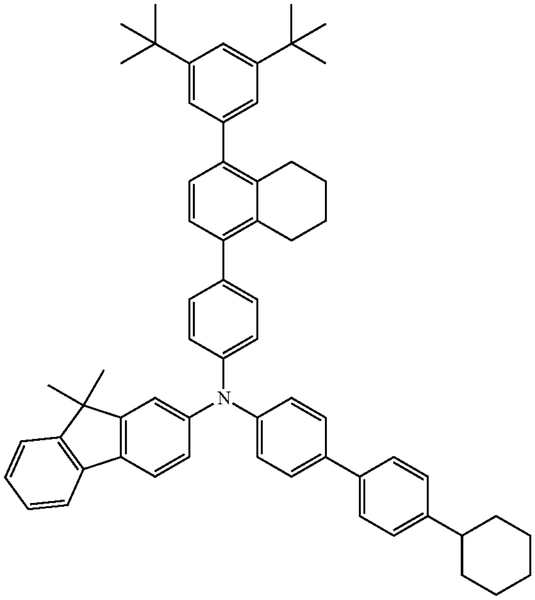

-continued
(269)
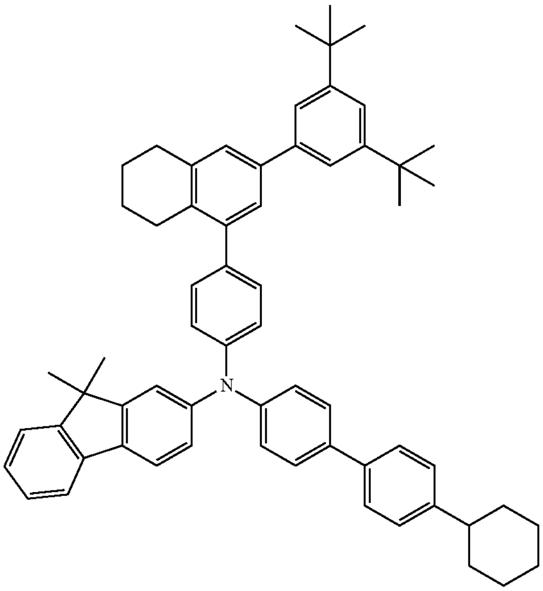
(270)
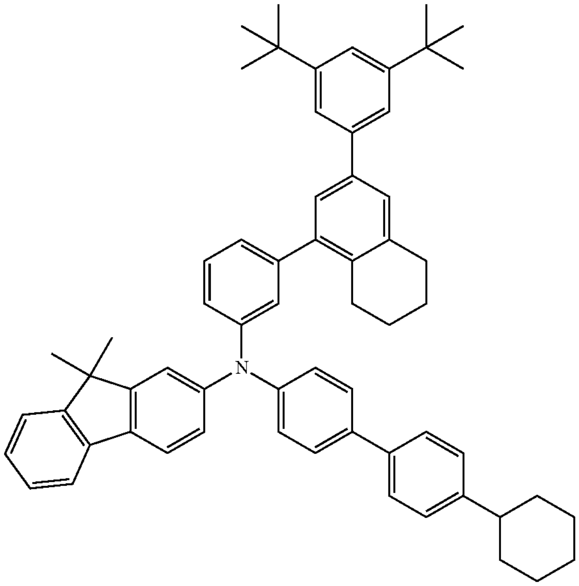
(271)
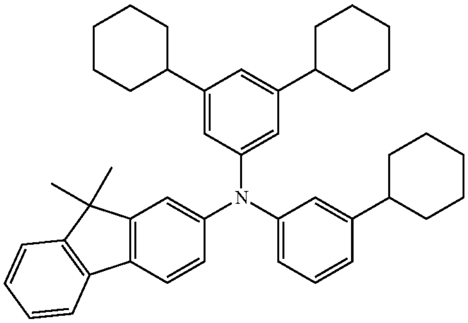
[Chemical Formula 28]
(272)
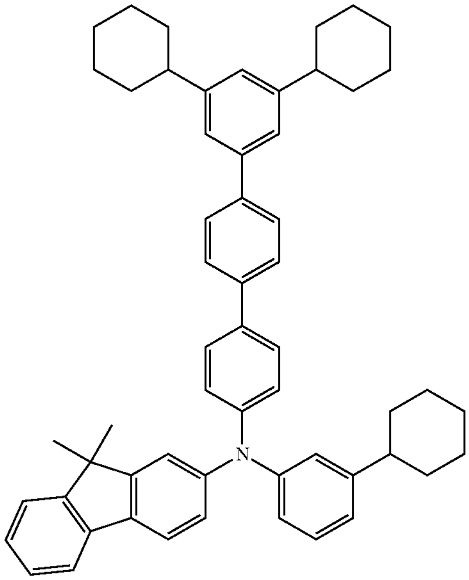
(273)
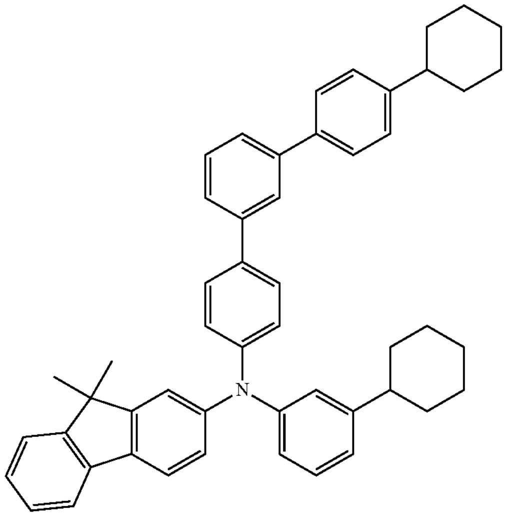

-continued
(274)
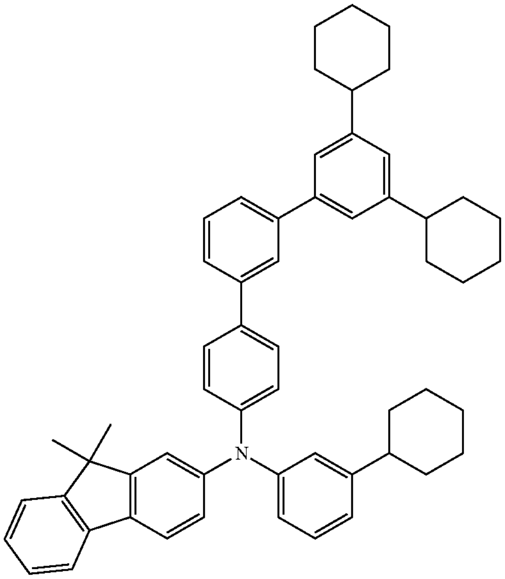
(275)
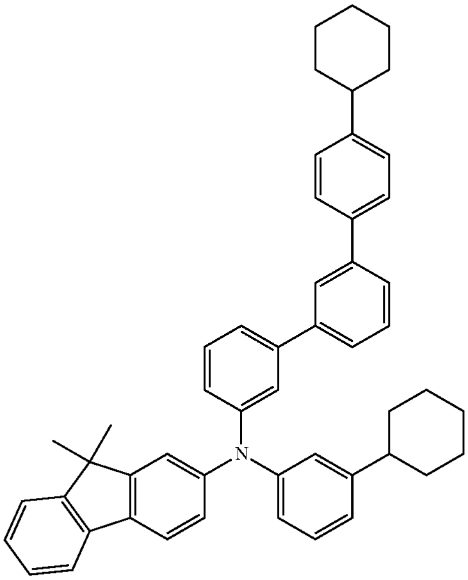
-continued
(276)
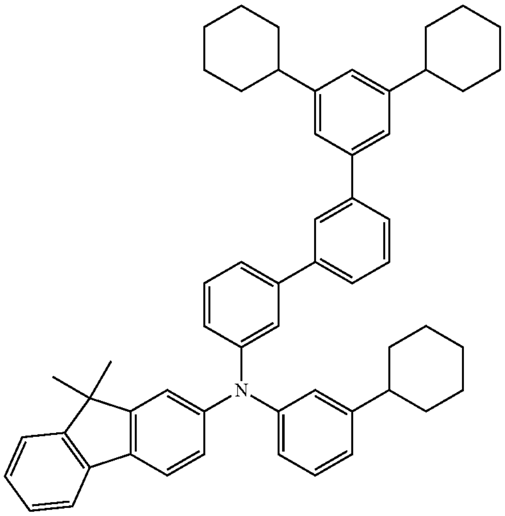
(277)
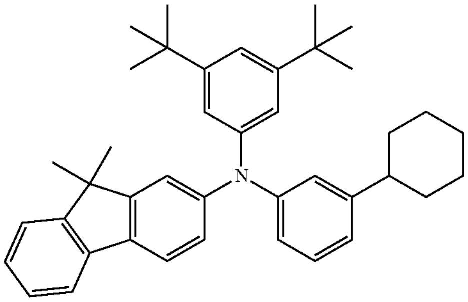
(278)
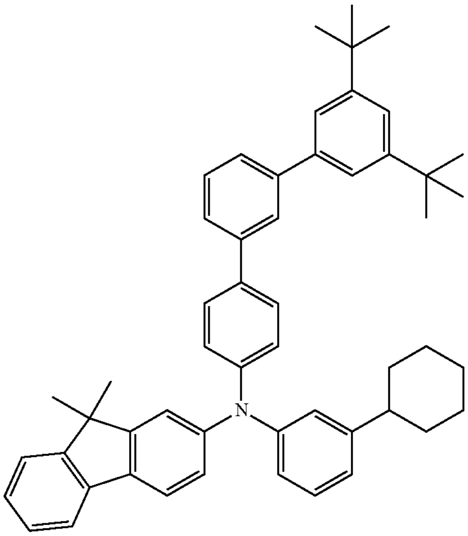

-continued
(279)
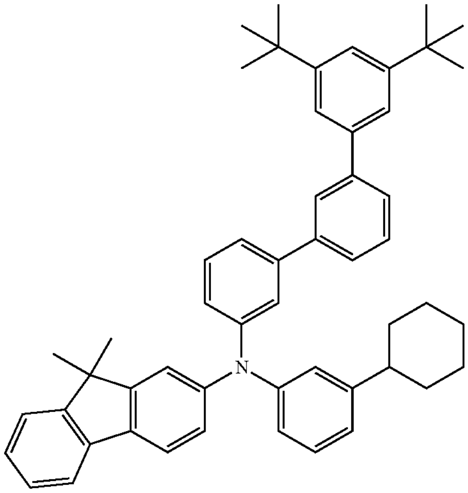
(280)
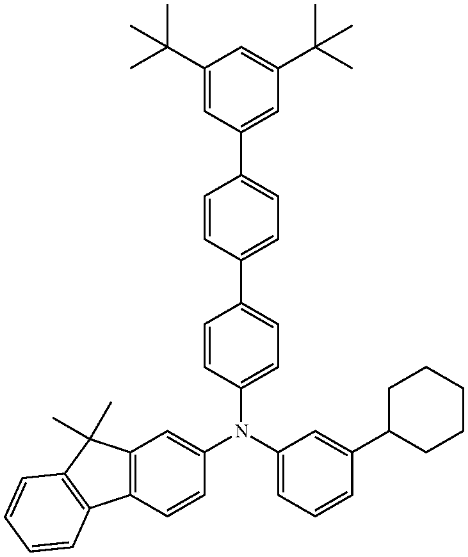
(281)
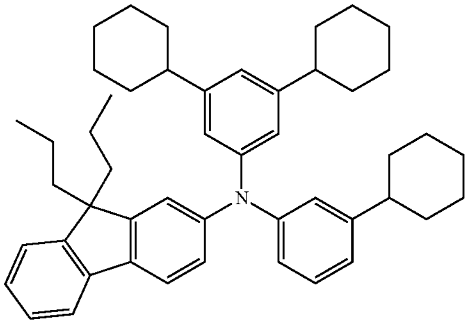
-continued
(282)
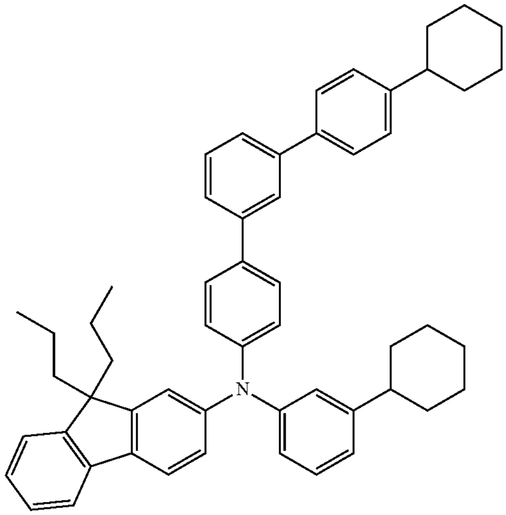
[Chemical Formula 29]
(283)
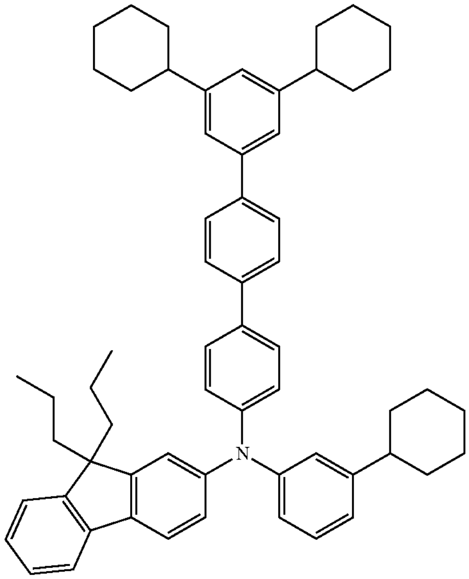

-continued
(284)
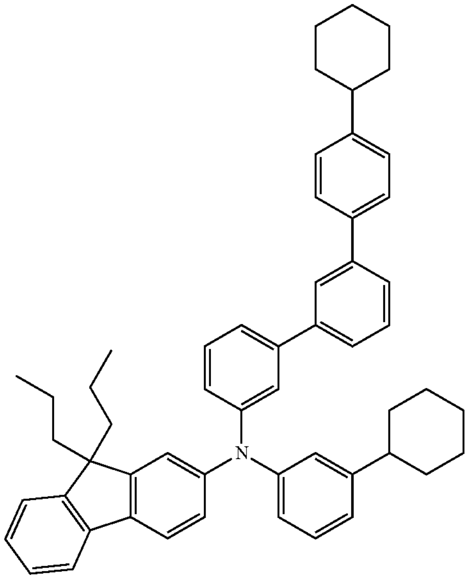
(285)
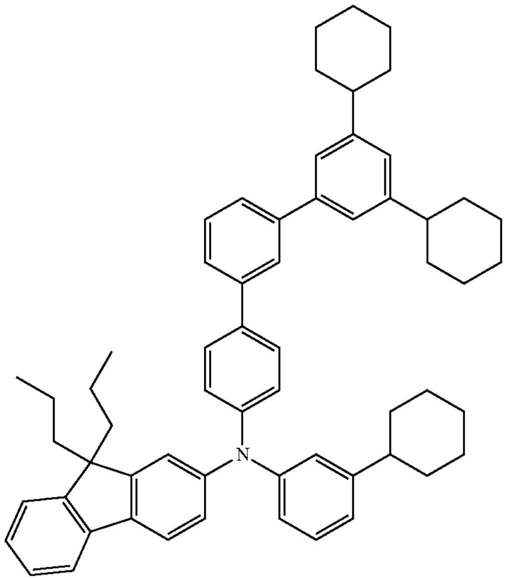
-continued
(286)
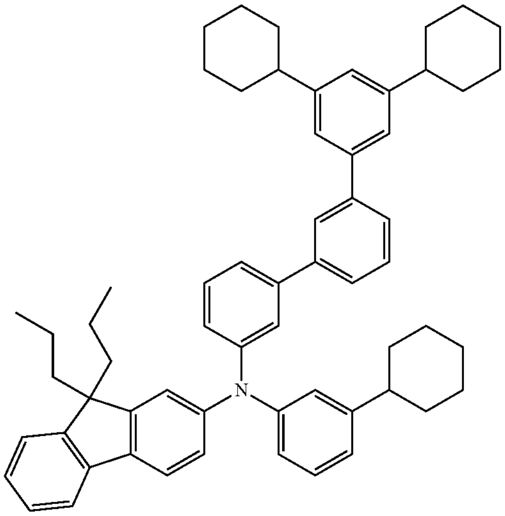
(287)
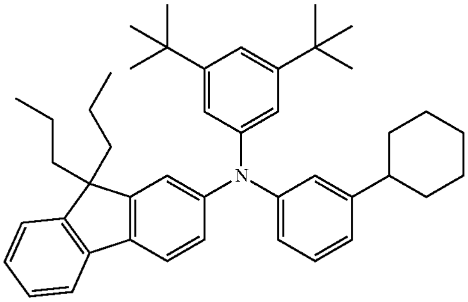
(288)
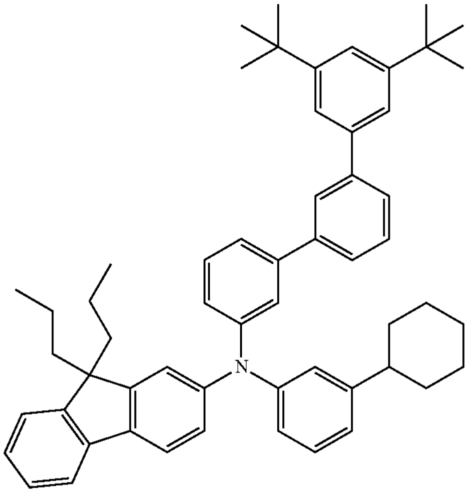

-continued
(289)
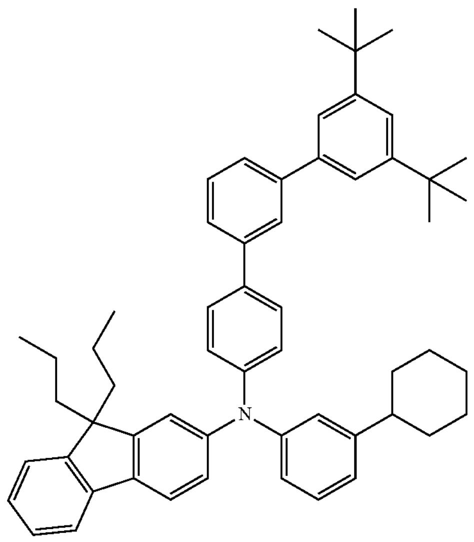
(290)
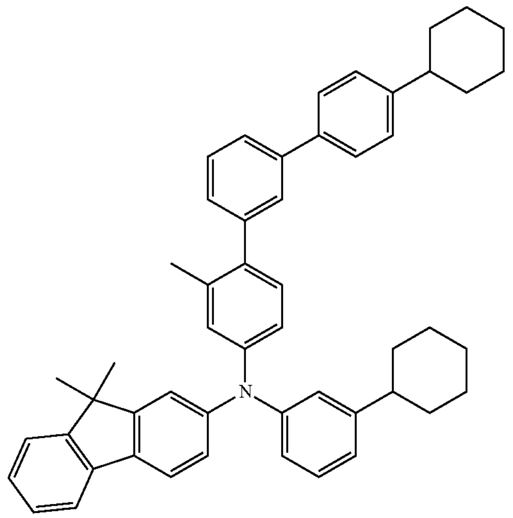
(291)
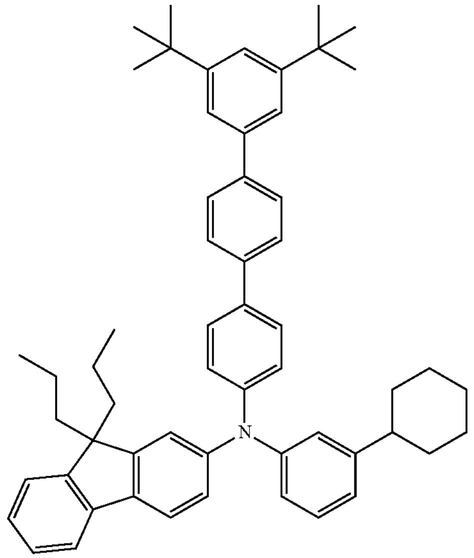
-continued
(292)
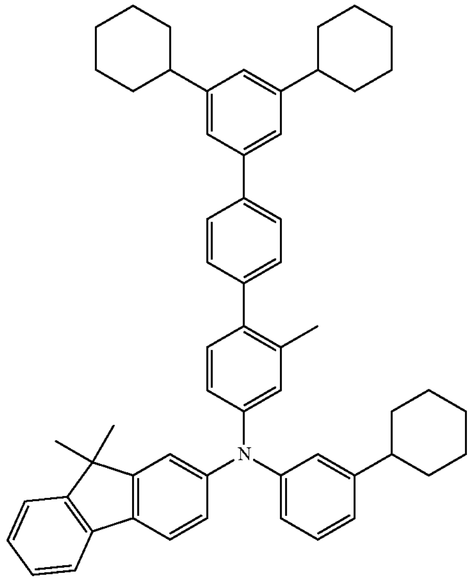
(293)
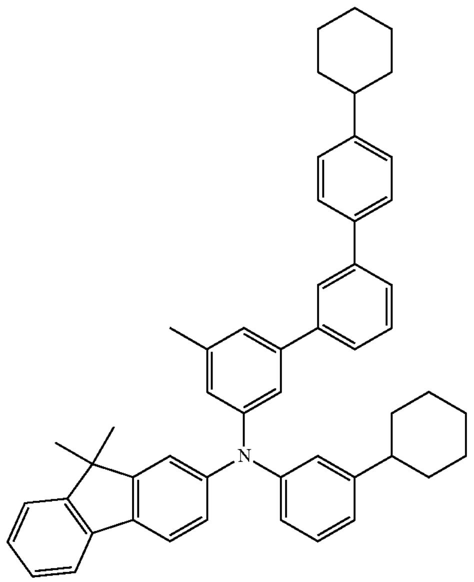

-continued
[Chemical Formula 30]
(294)
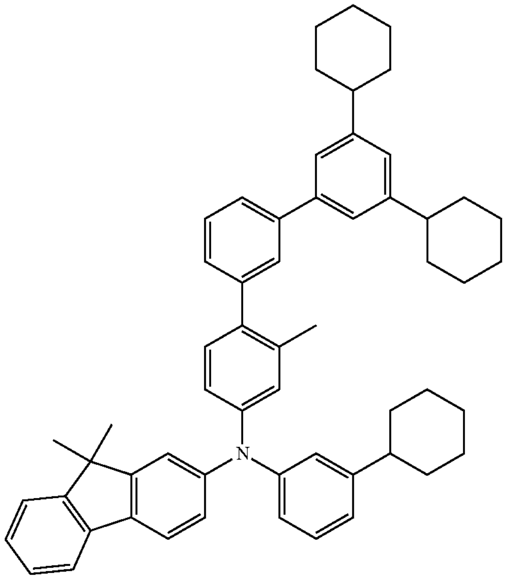
(295)
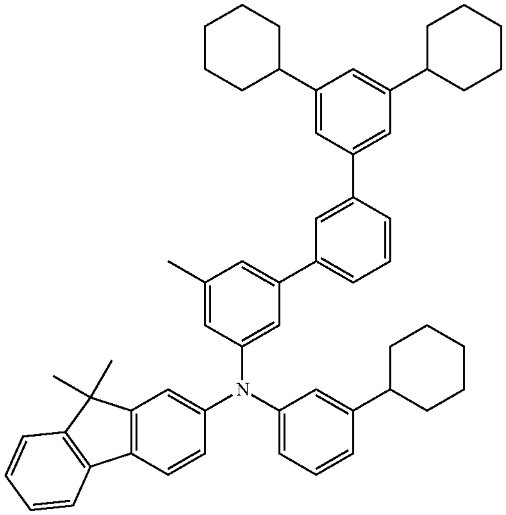
-continued
(296)
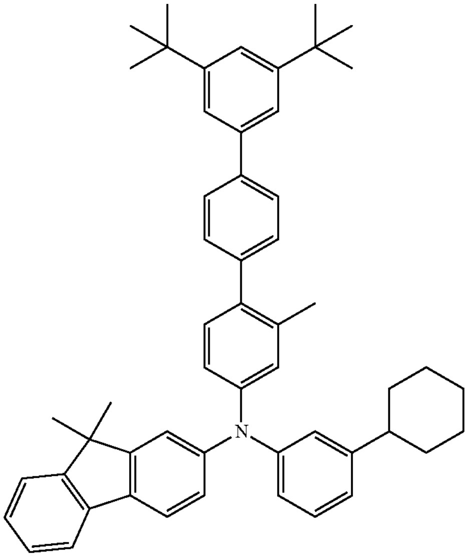
(297)
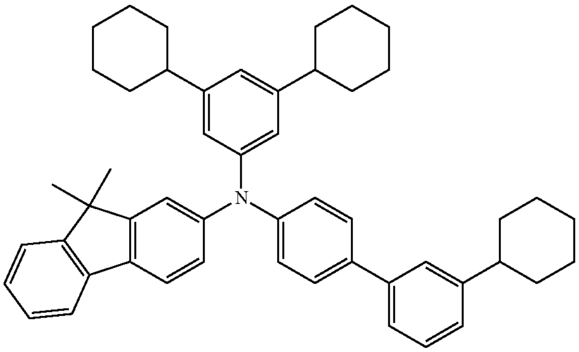
(298)
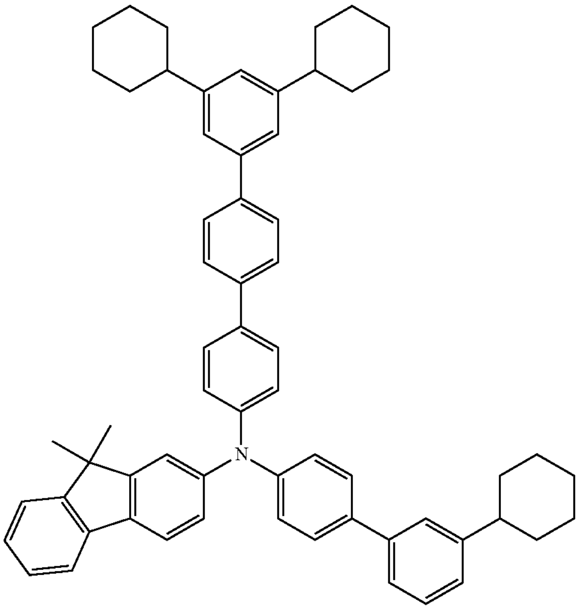

-continued
(299)
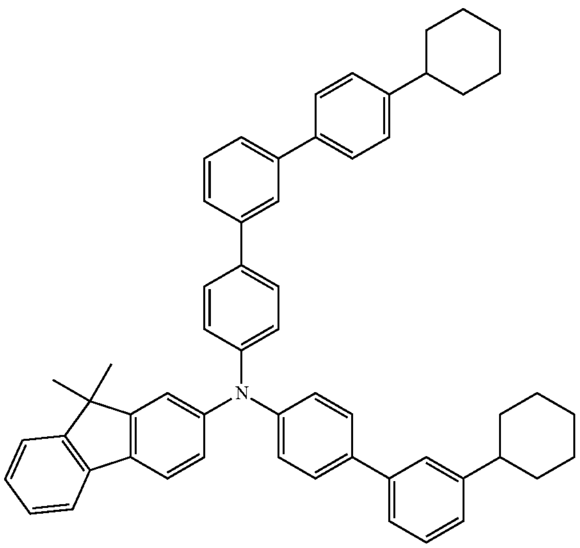
(300)
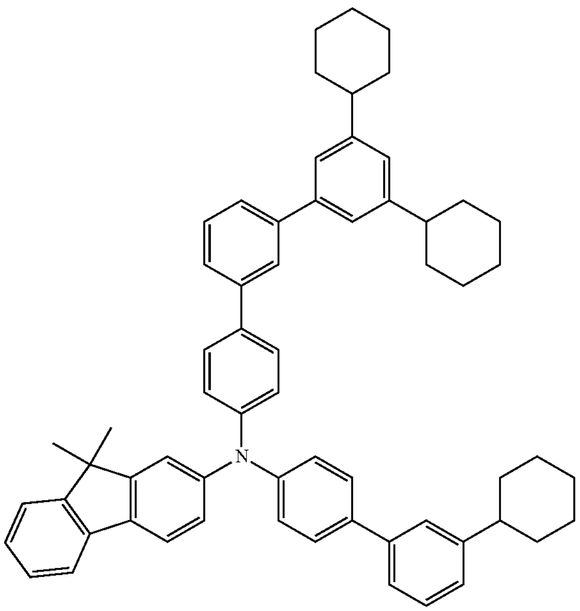
-continued
(301)
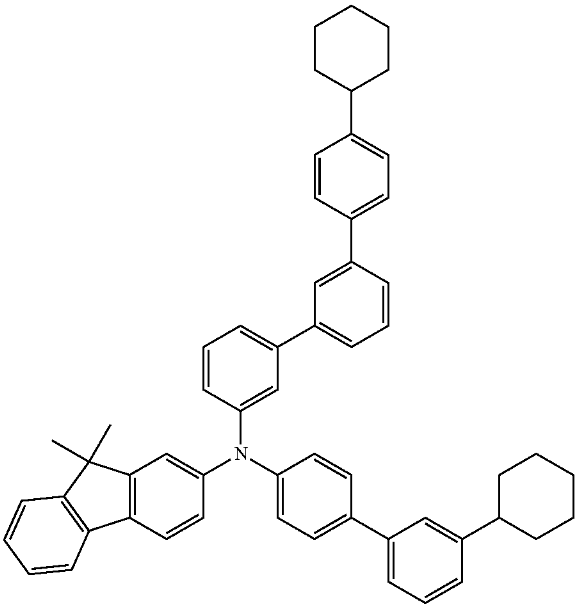
(302)
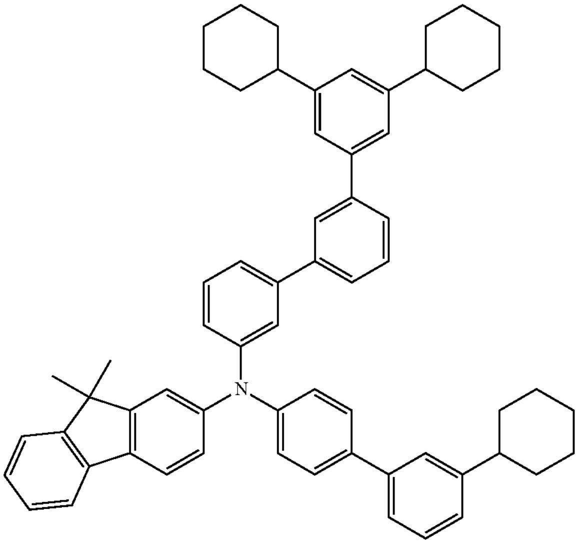
[Chemical Formula 31]
(303)
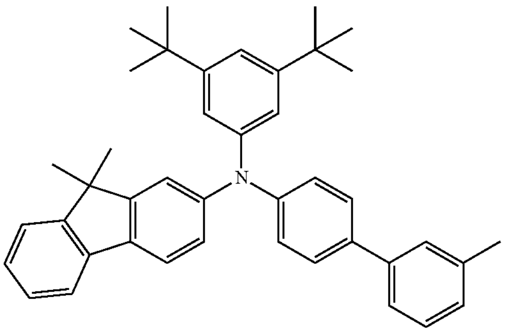

-continued
(304)
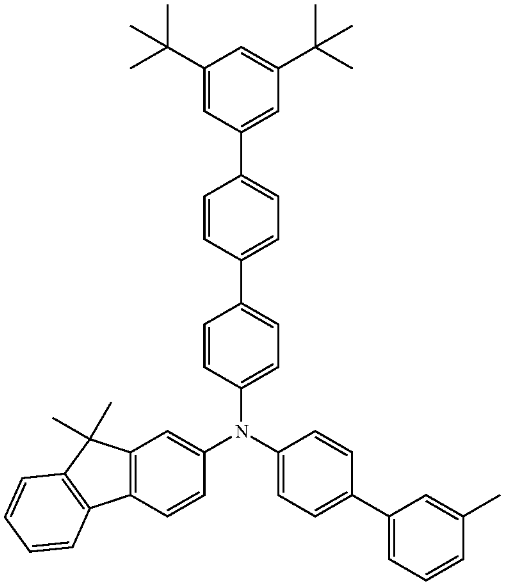
(305)
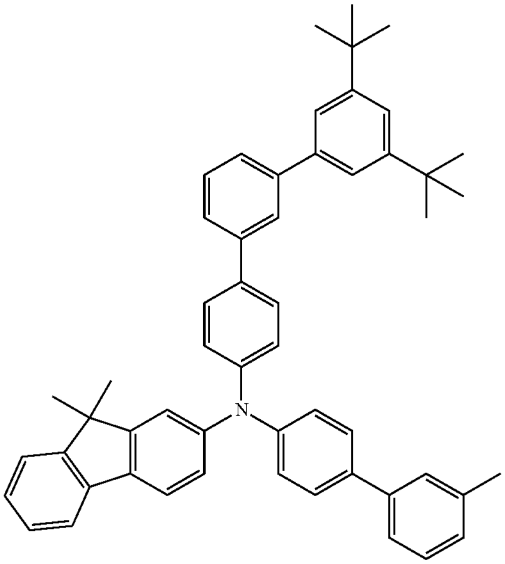
(306)
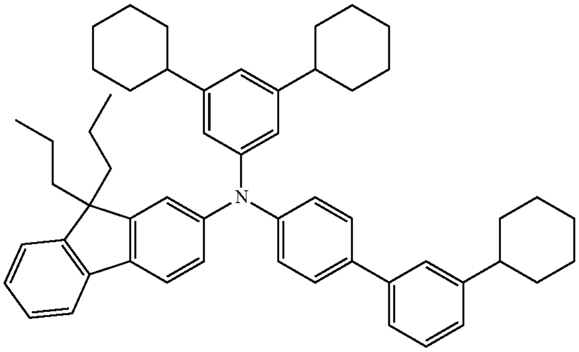
-continued
(307)
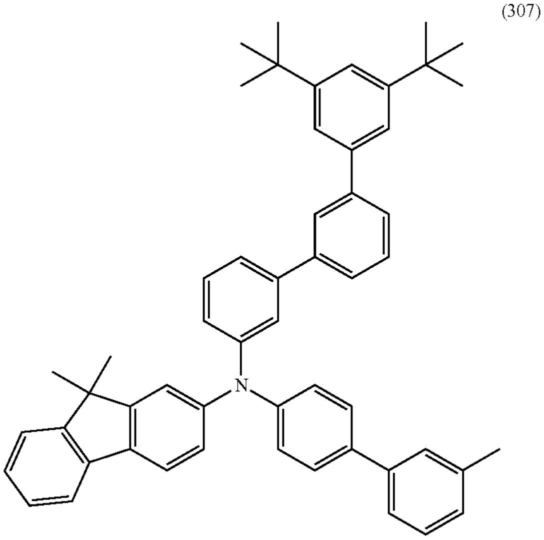
(308)
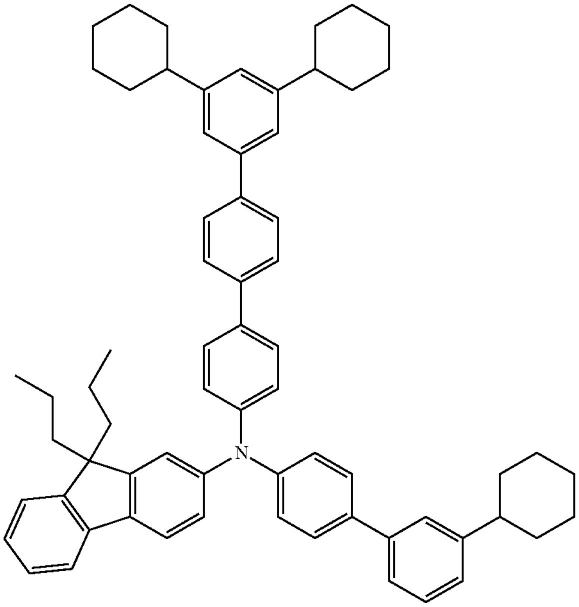

-continued
(309)
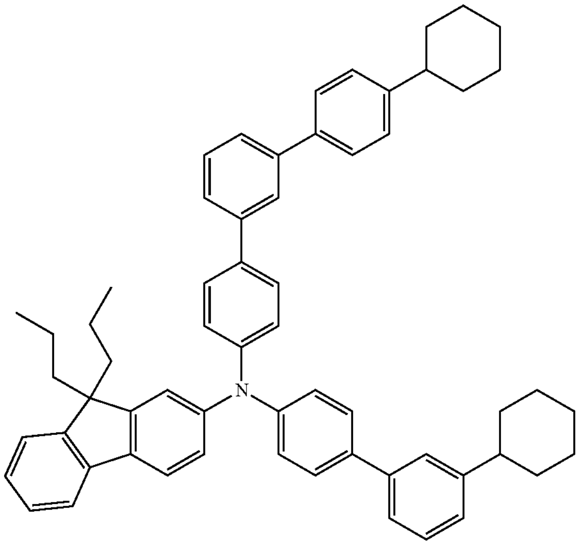
(310)
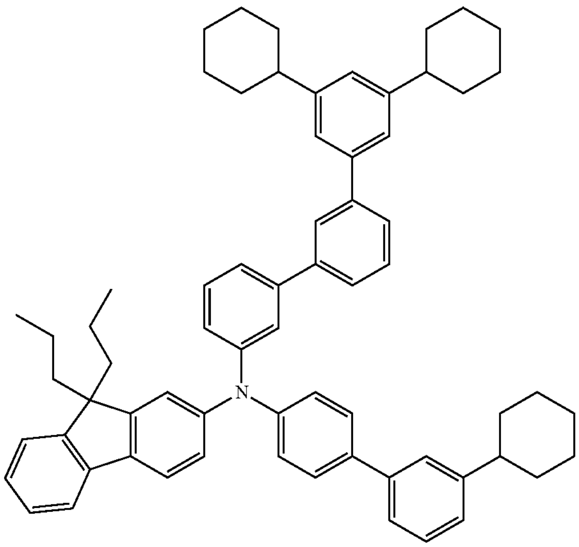
-continued
(311)
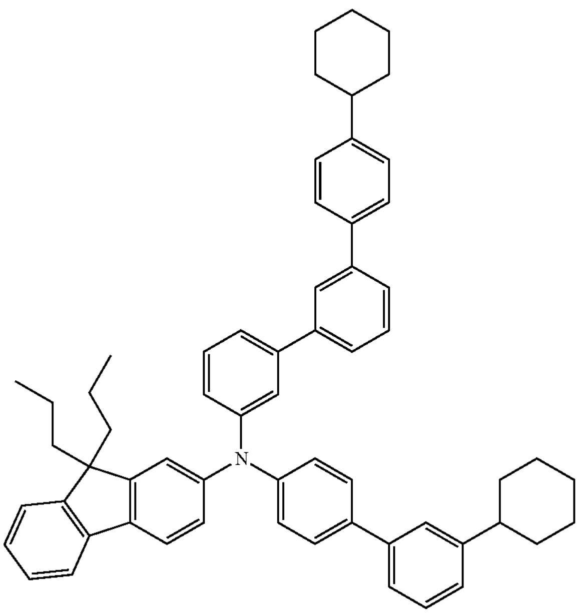
(312)
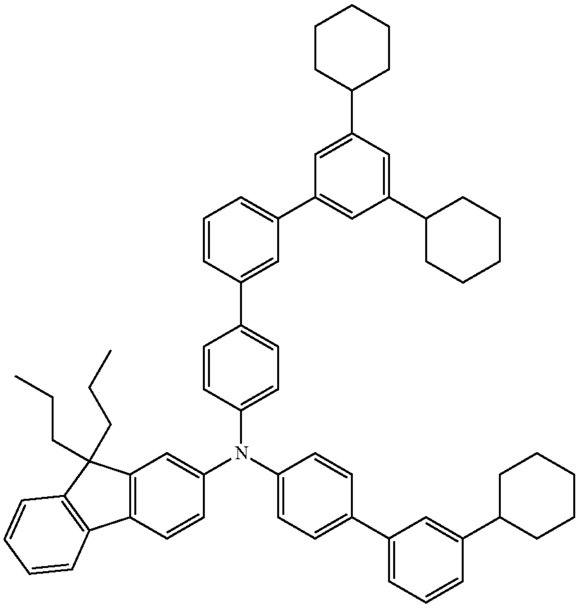
(313)
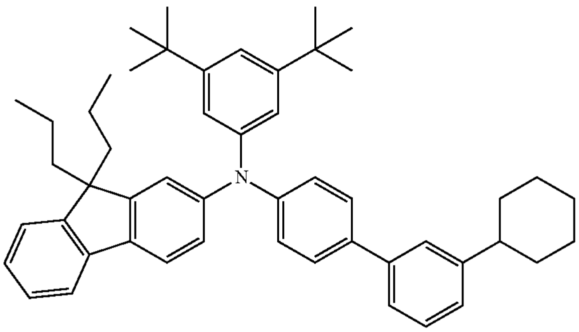

-continued
[Chemical Formula 32]
(314)
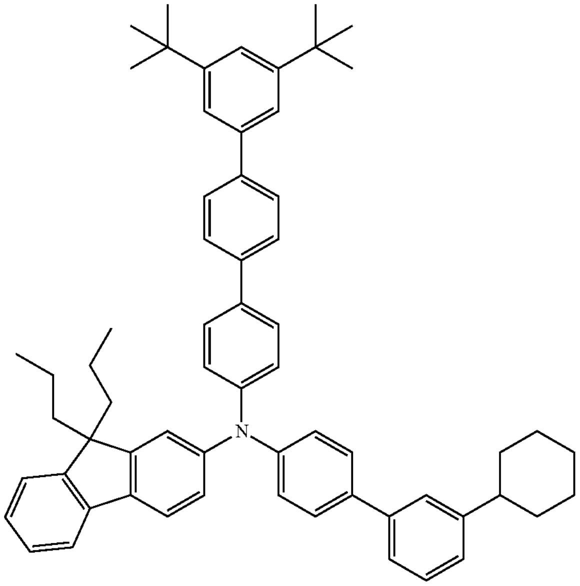
(315)
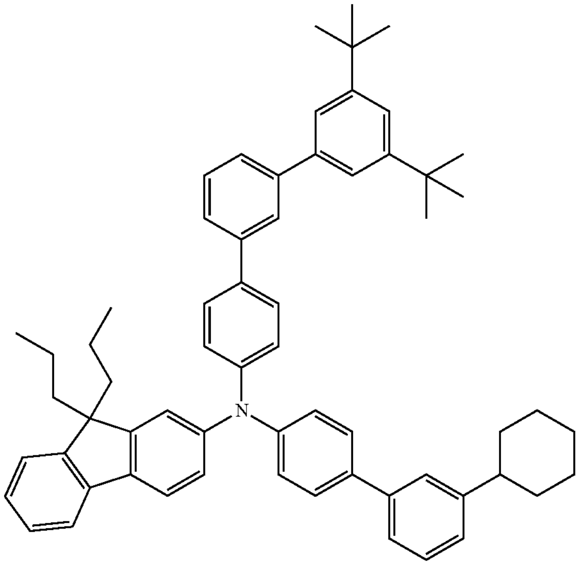
-continued
(316)
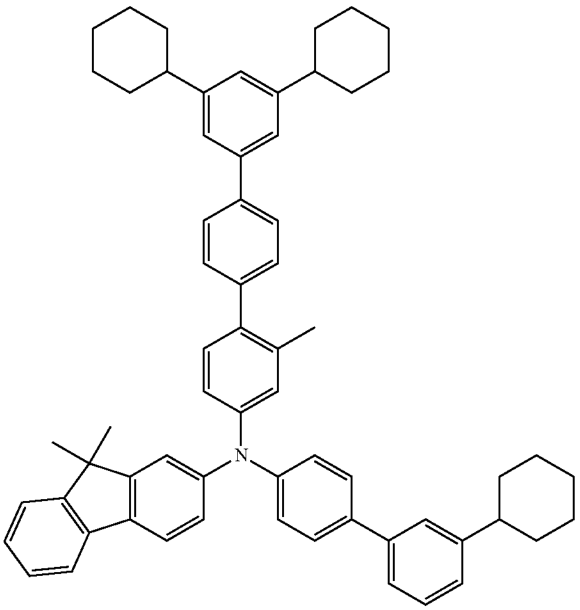
(317)
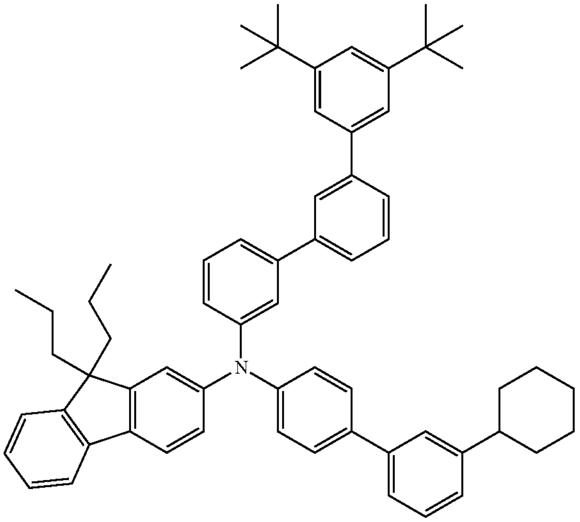

-continued
(318)
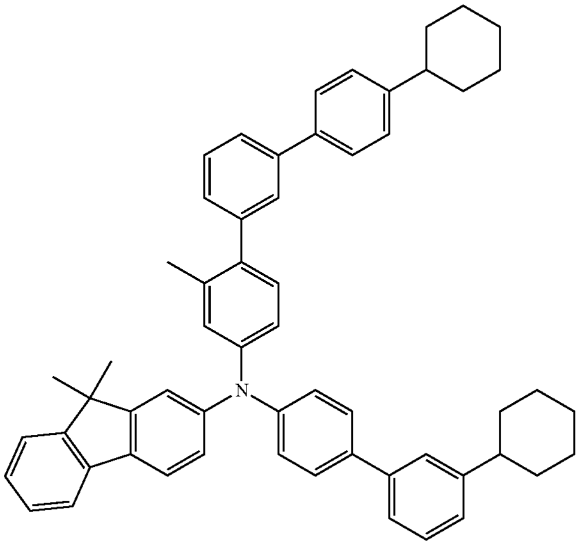
(319)
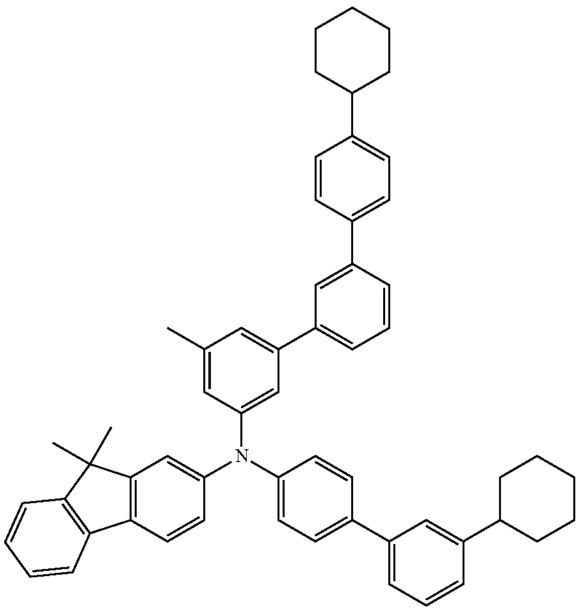
-continued
(320)
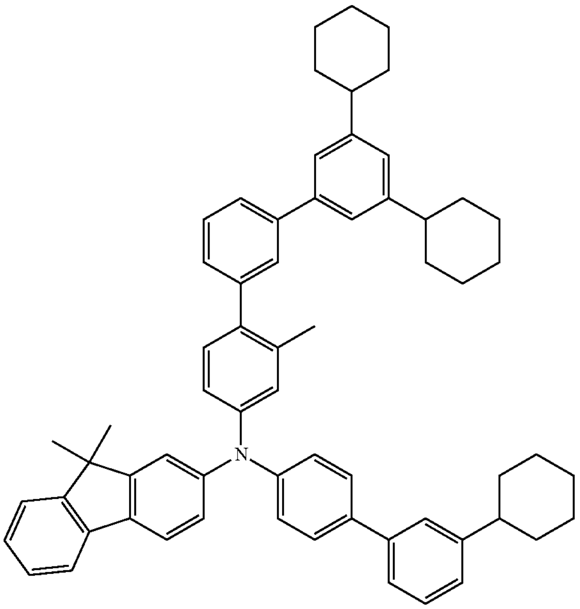
(321)
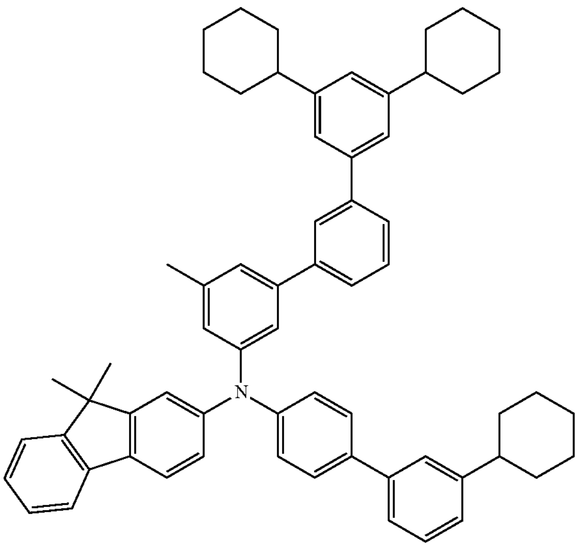

-continued
(322)
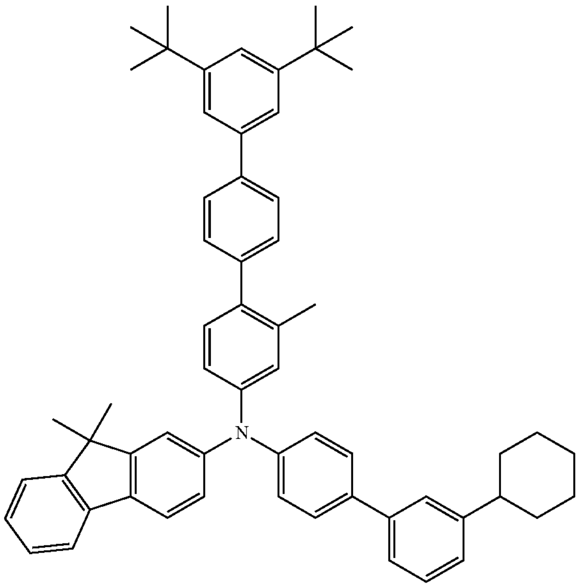
[Chemical Formula 33]
(323)
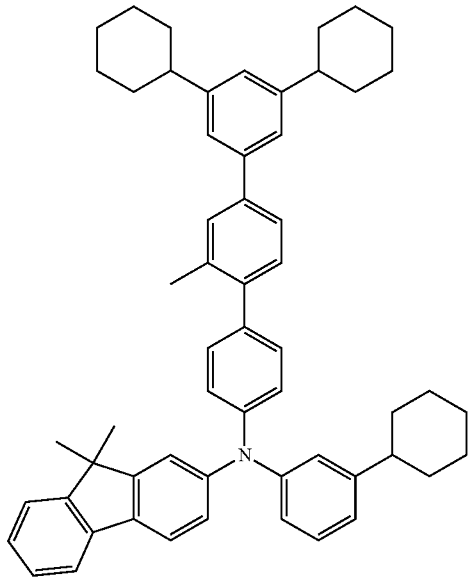
-continued
(324)
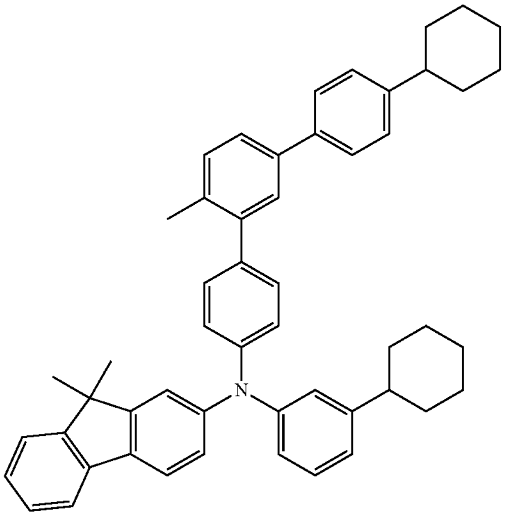
(325)
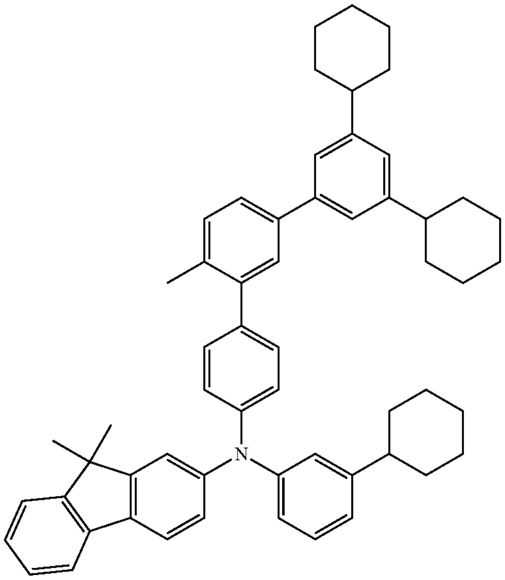

-continued
(326)
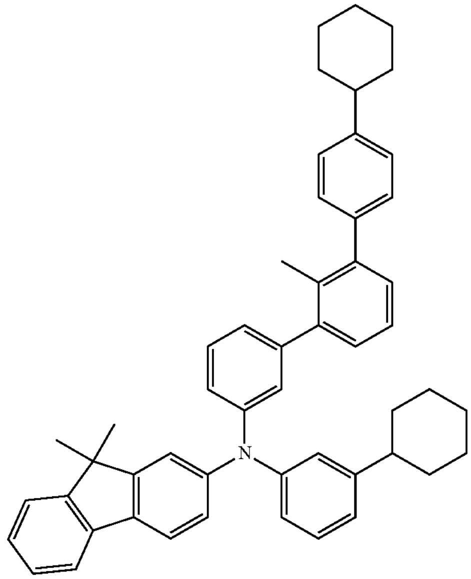
-continued
(328)
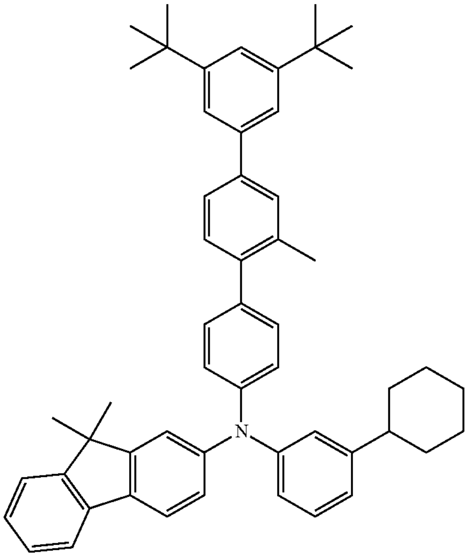
[Chemical Formula 34]
(327)
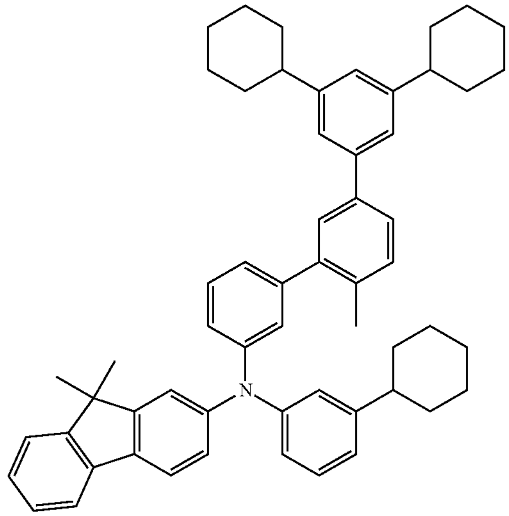
(329)
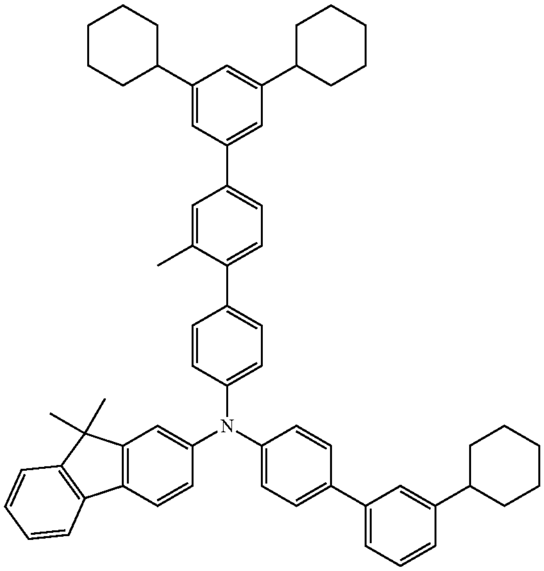

-continued
(330)
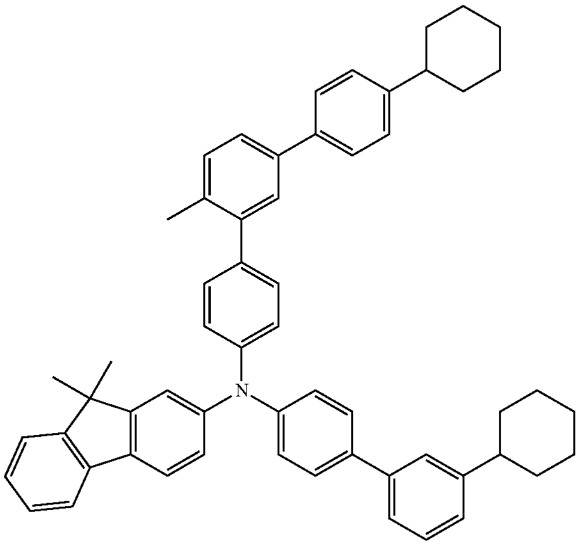
(331)
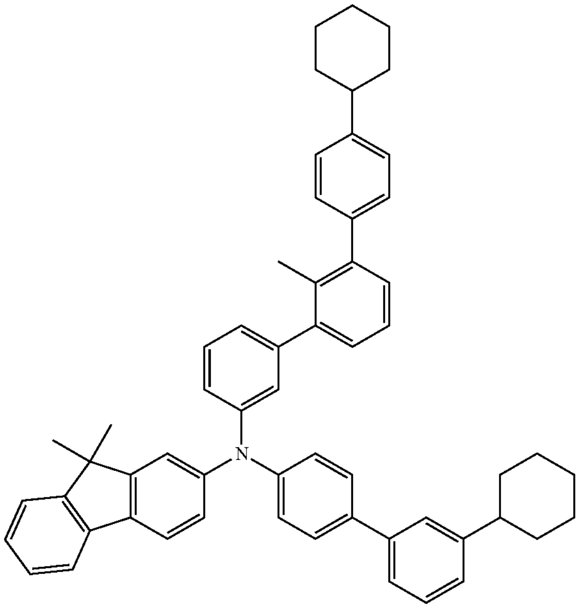
-continued
(332)
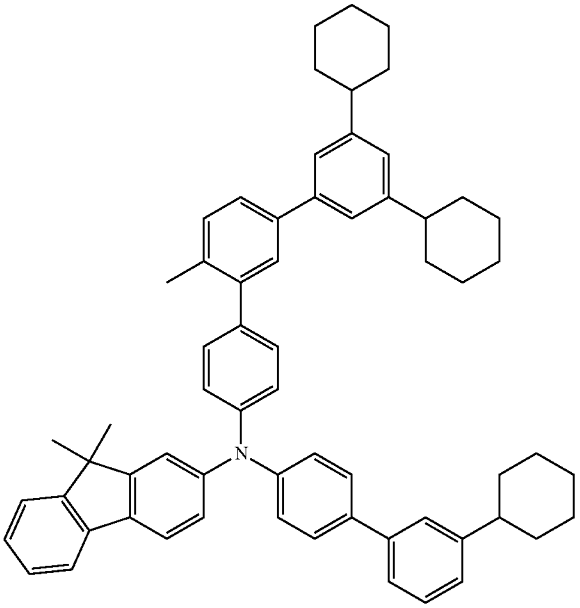
(333)
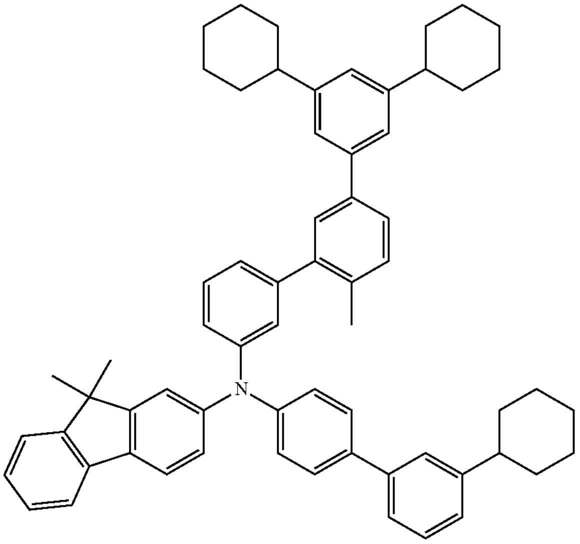

-continued
(334)
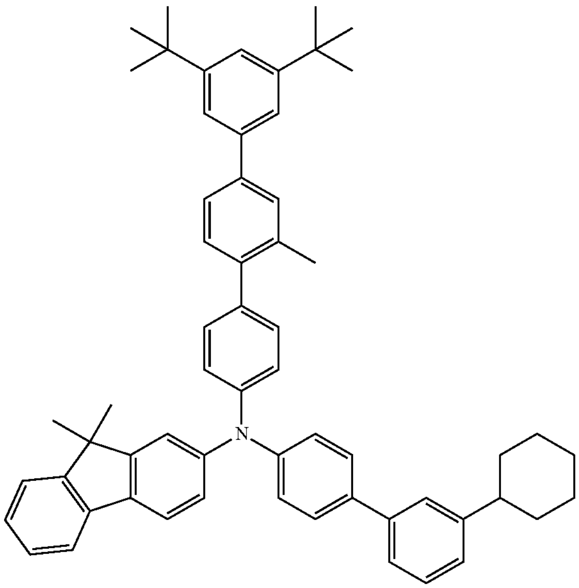
[Chemical Formula 35]
(335)
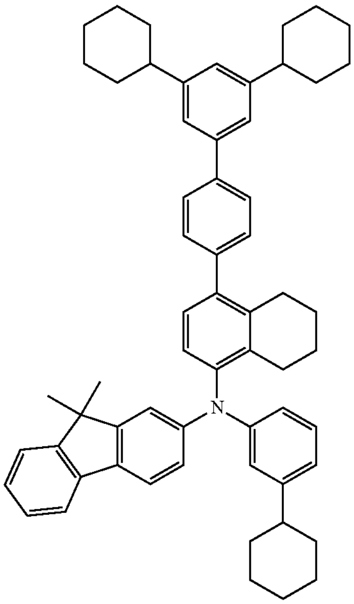
-continued
(336)
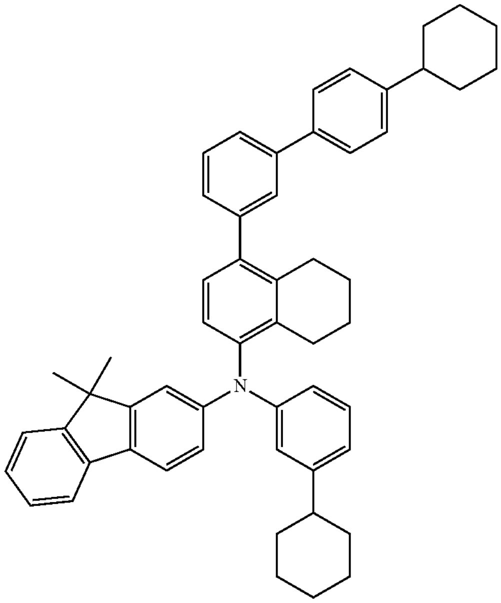
(337)
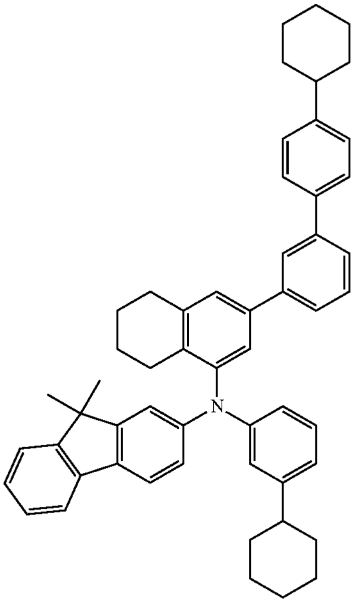

-continued
(338)
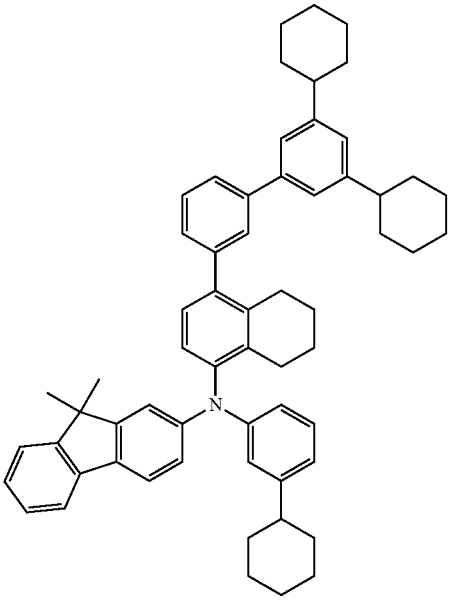
(339)
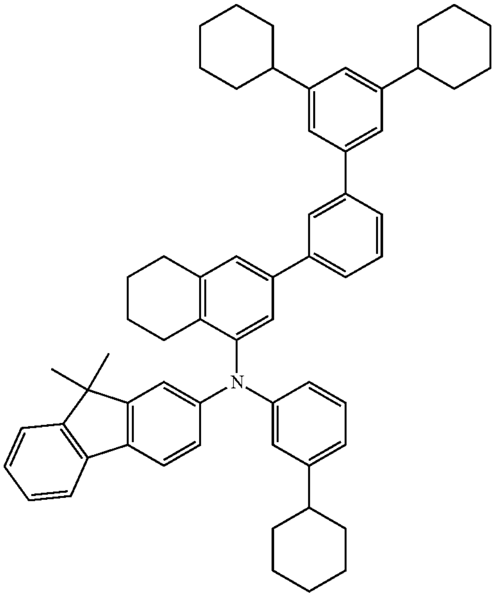
-continued
(340)
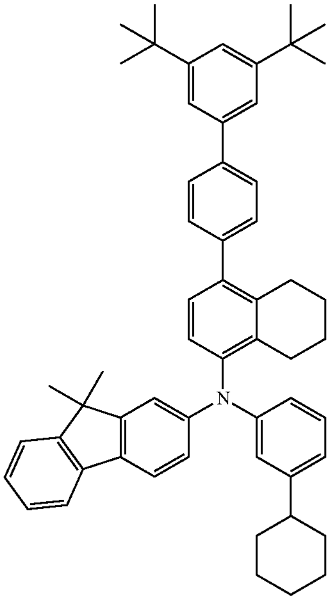
(341)
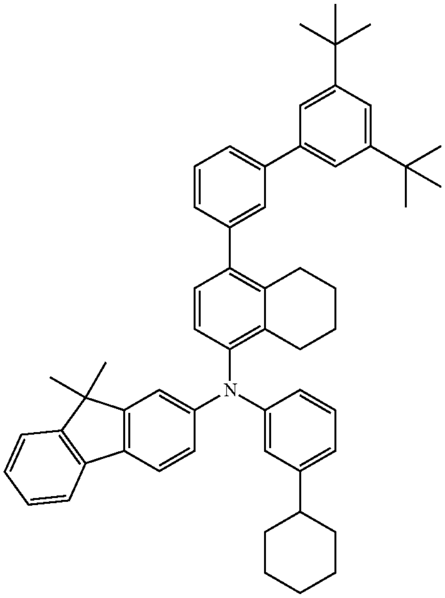

(342)
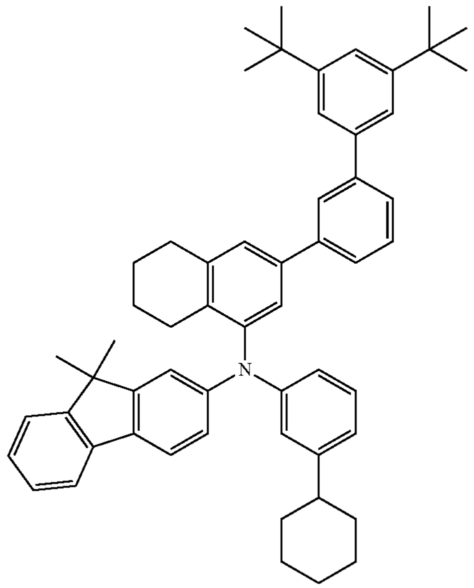
(343)
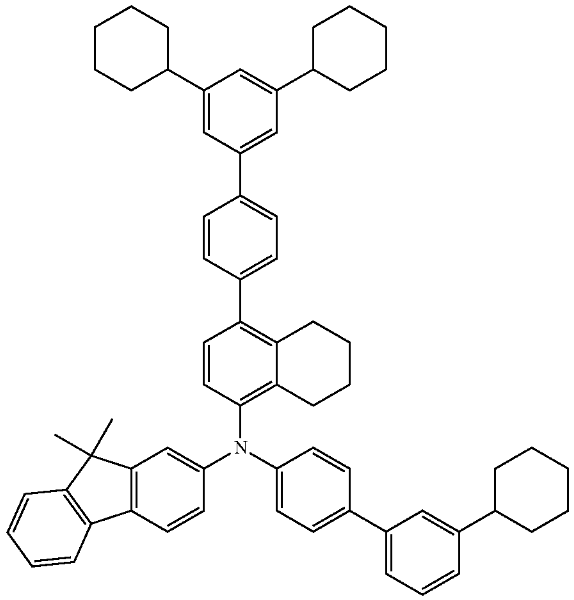
[Chemical Formula 36]
(344)
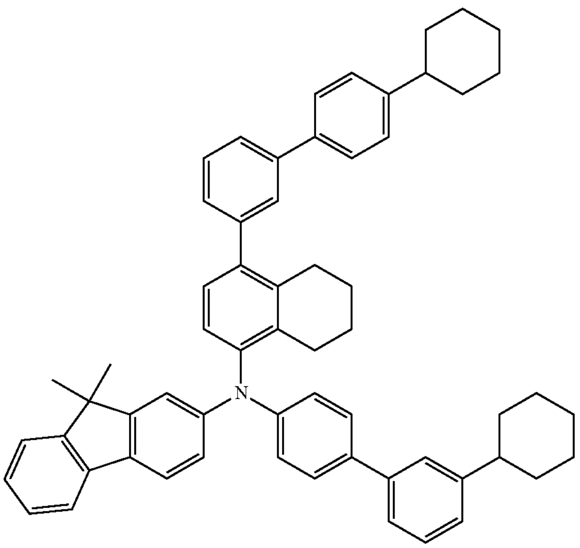
(345)
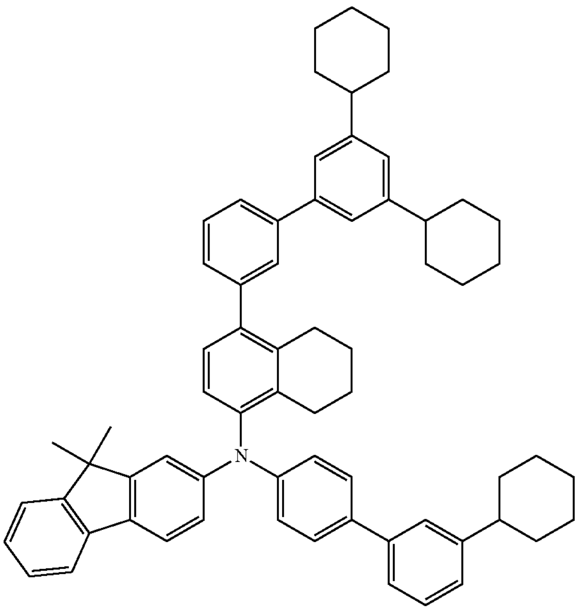

-continued
(346)
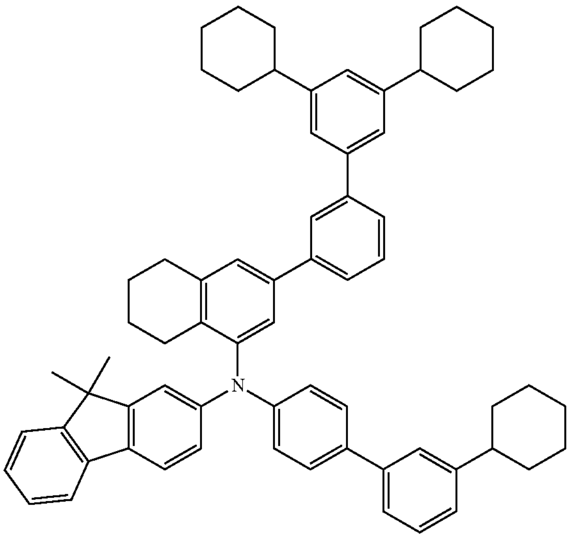
(347)
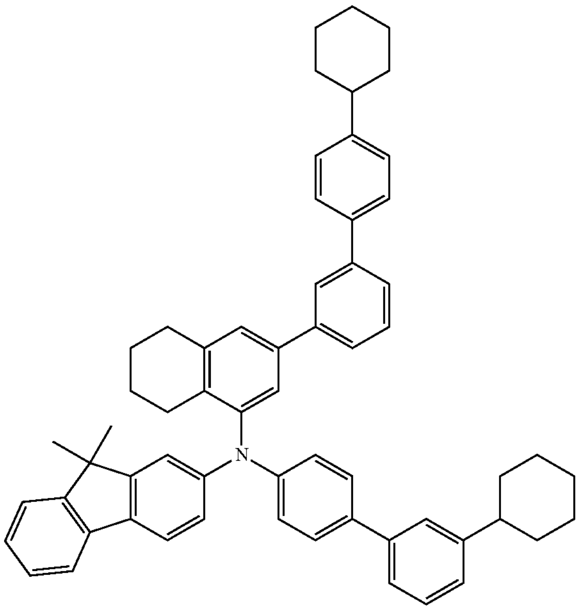
-continued
(348)
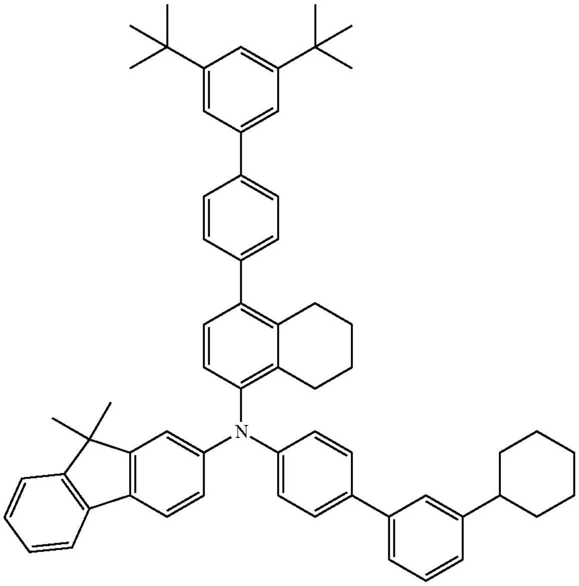
(349)
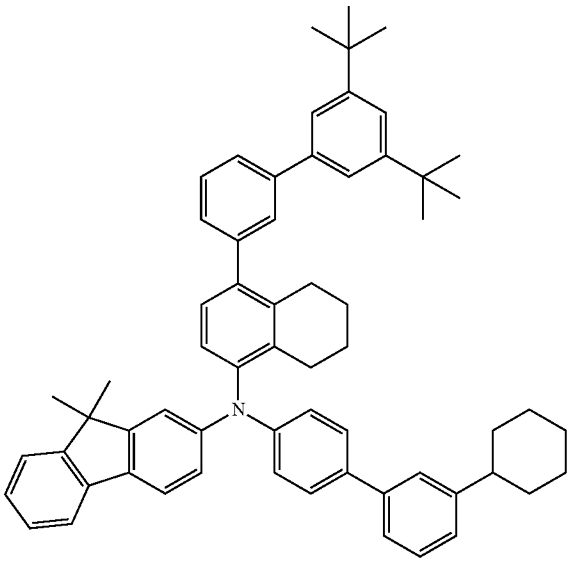

-continued
(350)
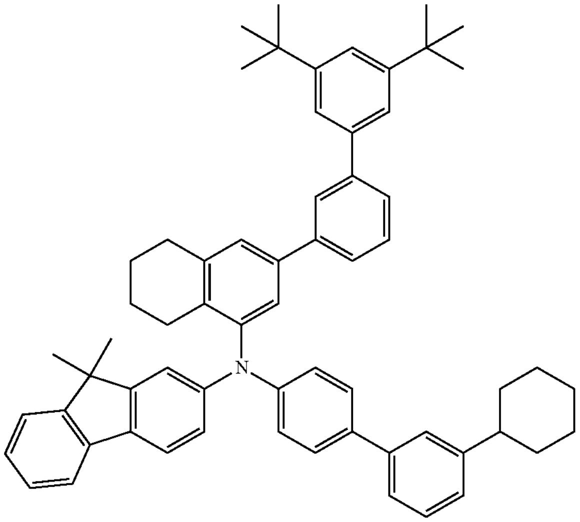
(351)
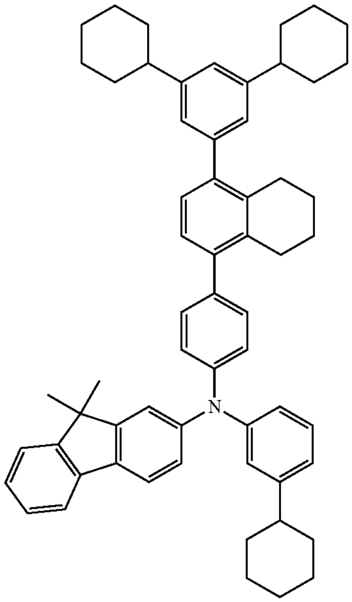
-continued
(352)
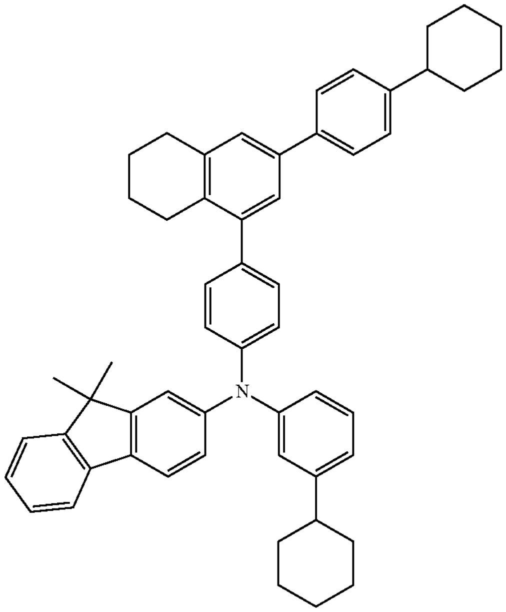
[Chemical Formula 37]
(353)
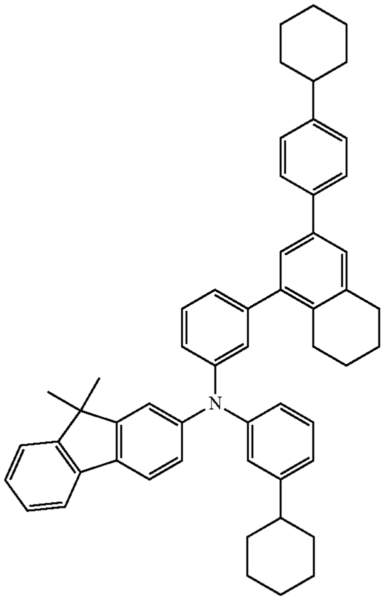

-continued
(354)
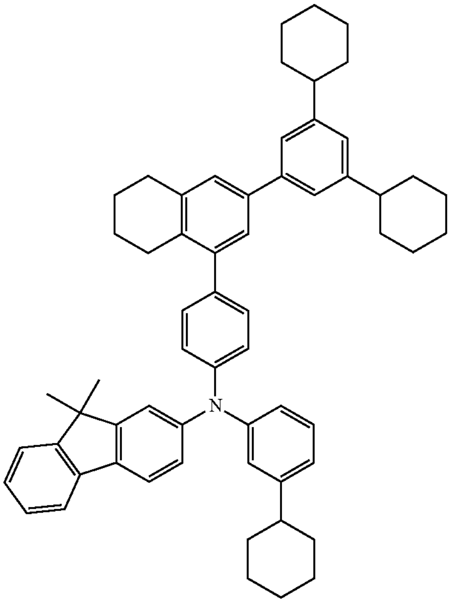
(355)
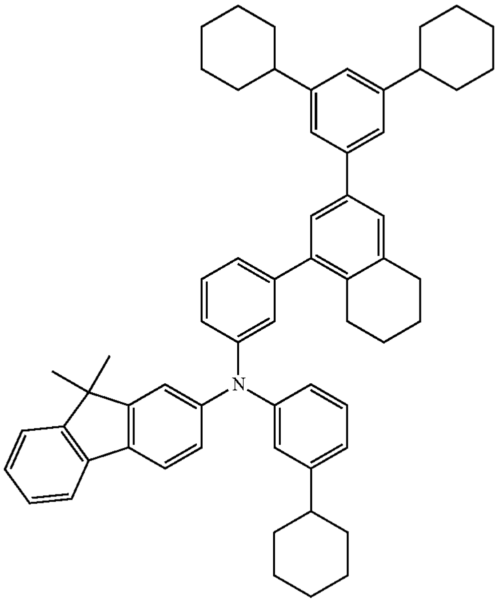
-continued
(356)
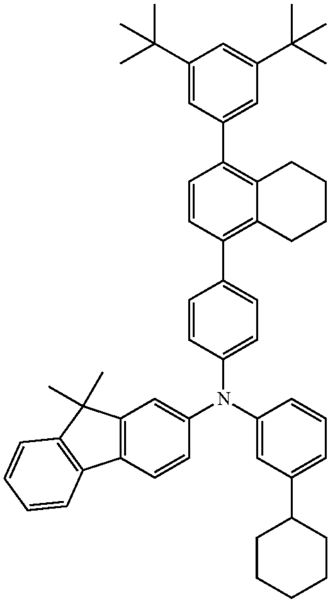
(357)
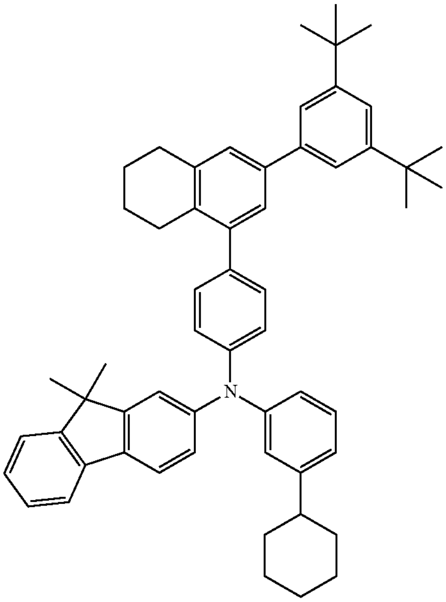

-continued
(358)
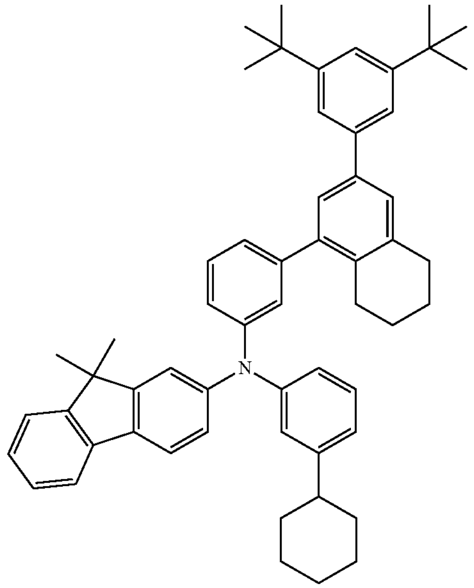
(359)
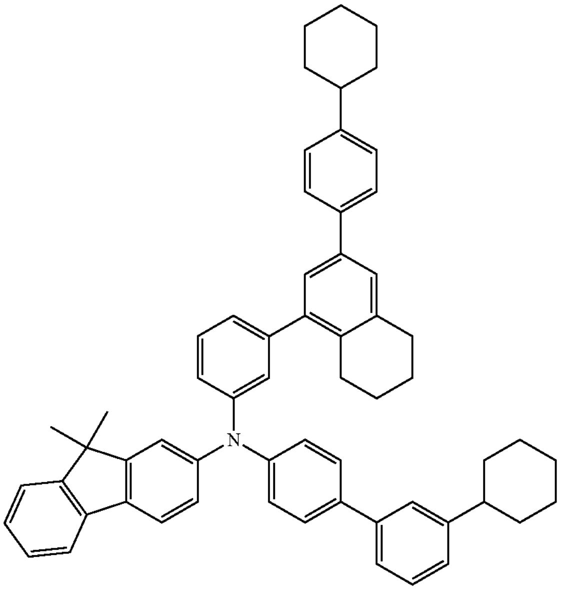
-continued
(360)
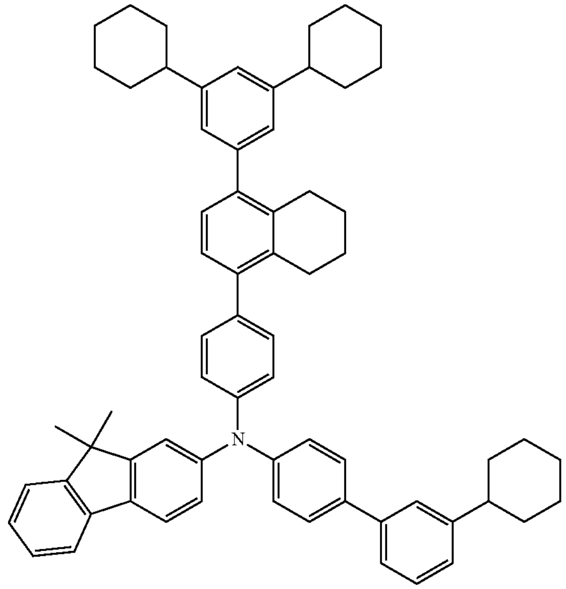
(361)
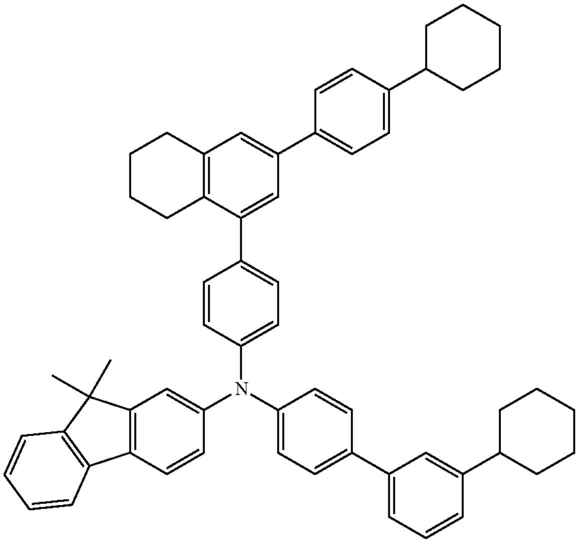

-continued
(362)
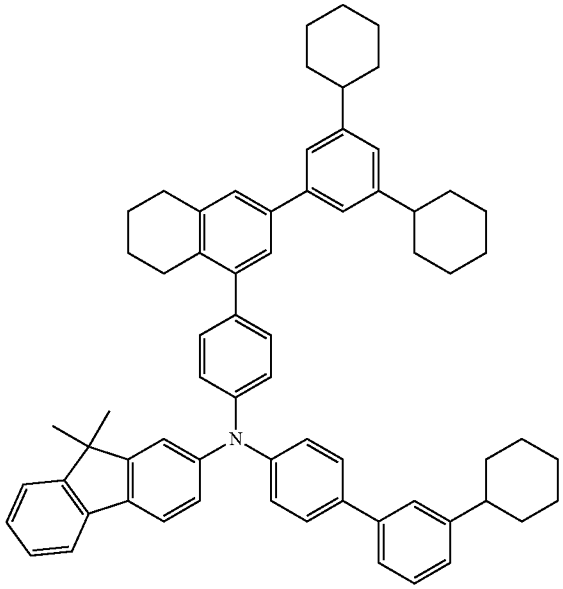
[Chemical Formula 38]
(363)
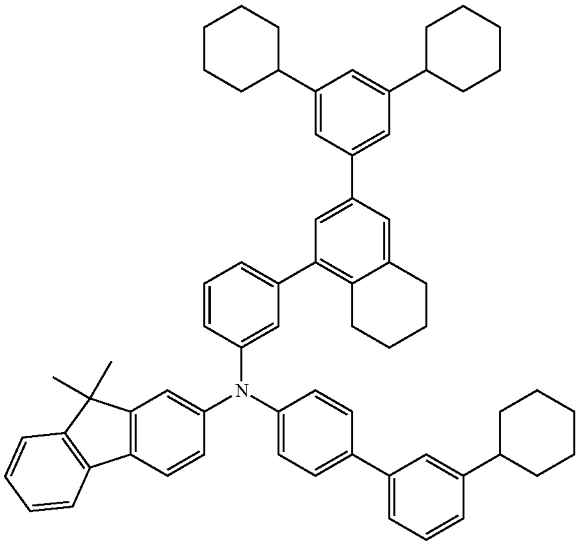
-continued
(364)
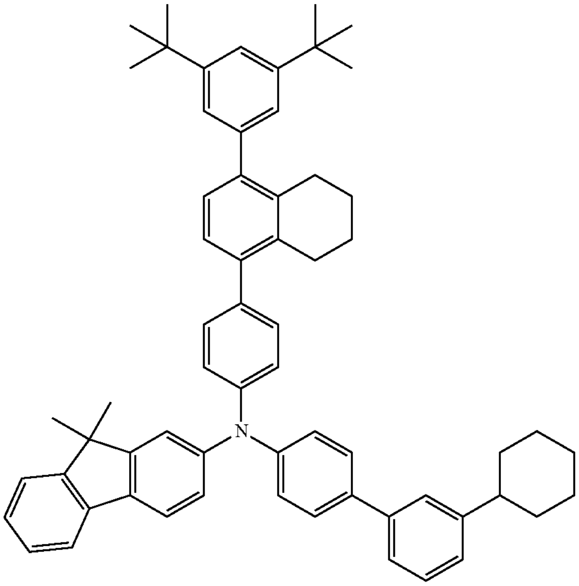
(365)
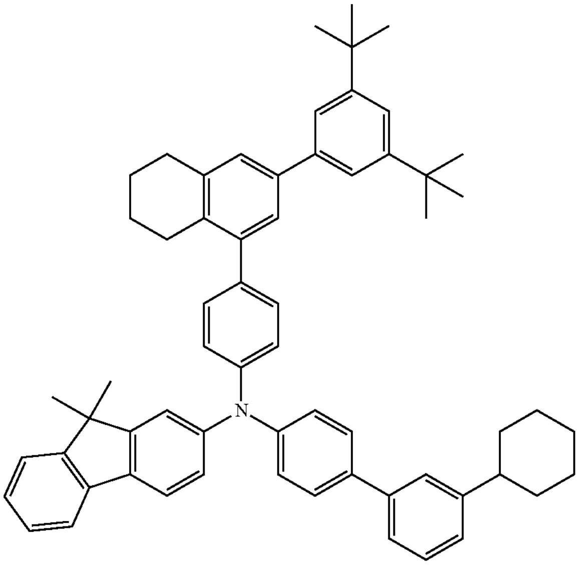

-continued
(366)
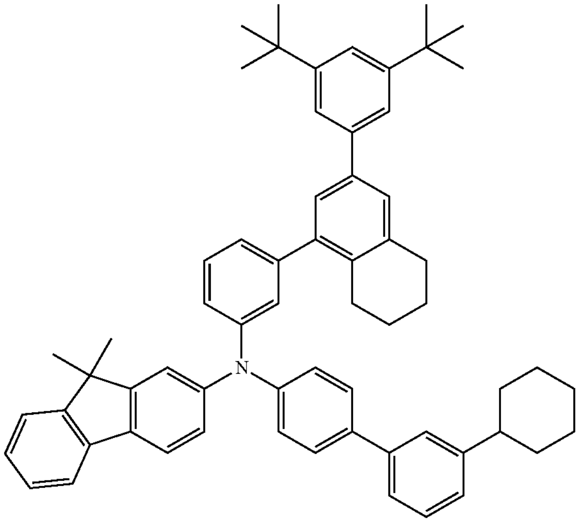
[Chemical Formula 39]
(367)
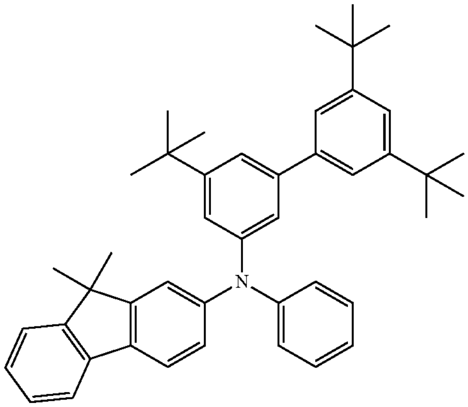
(368)
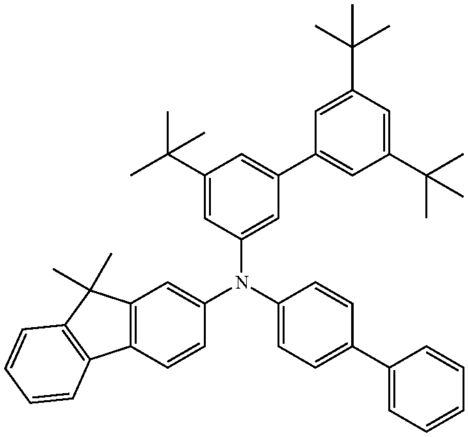
-continued
(369)
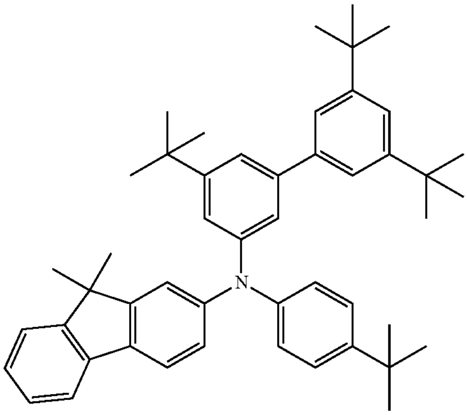
(370)
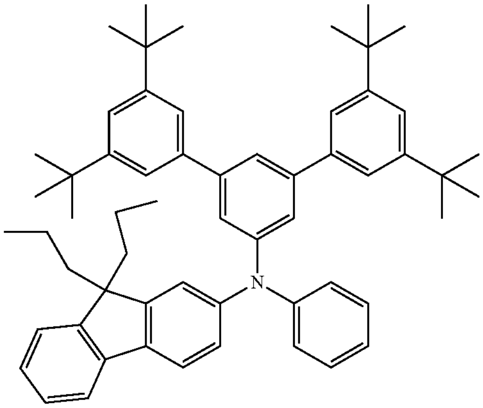
(371)
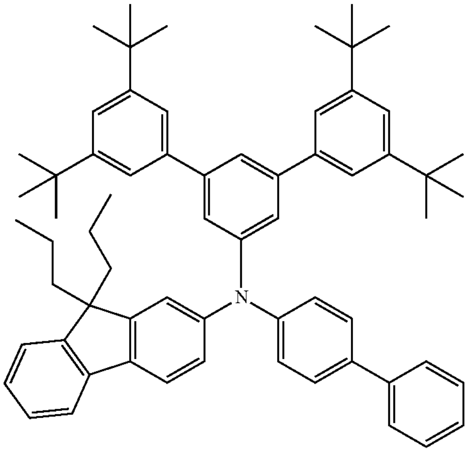

-continued
(372)
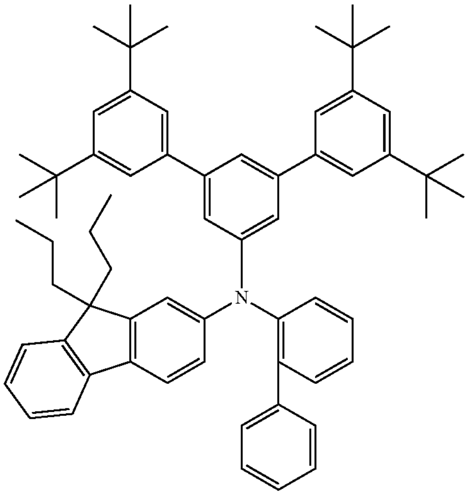
(373)
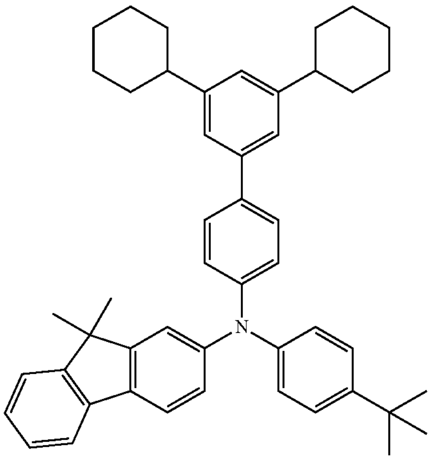
(374)
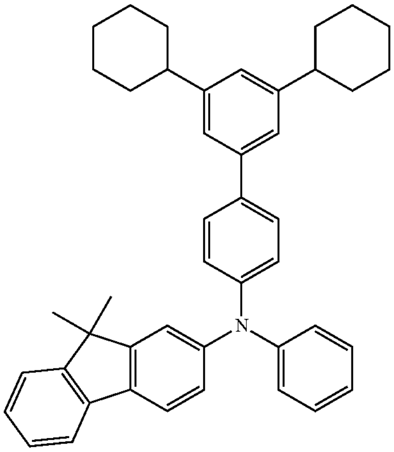
-continued
(375)
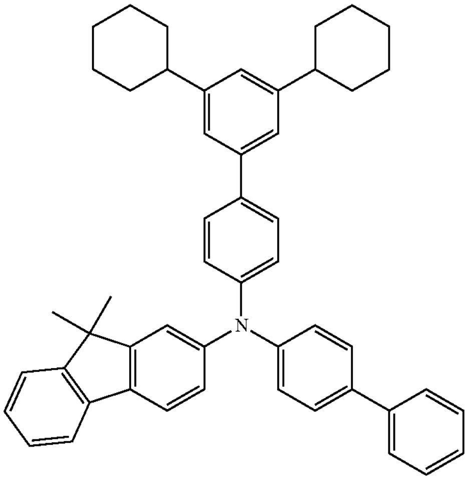
(376)
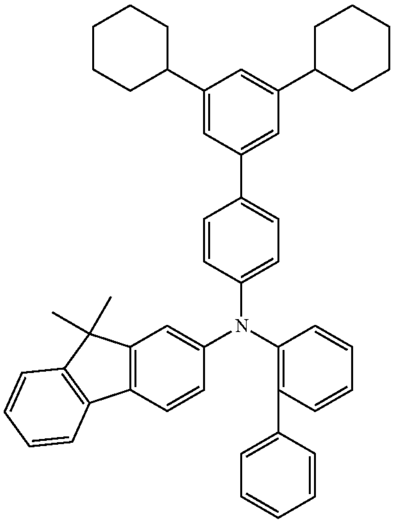
(377)
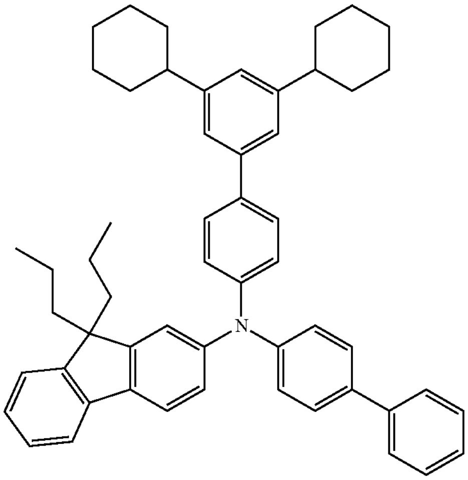

-continued
[Chemical Formula 40]
(378)
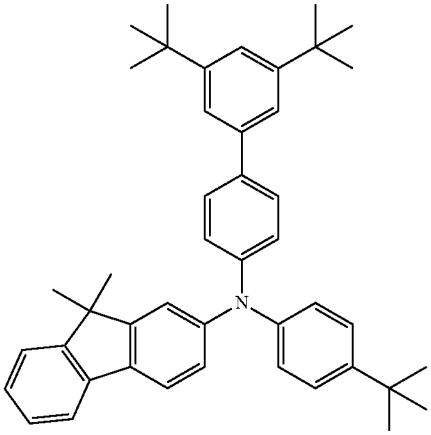
(379)
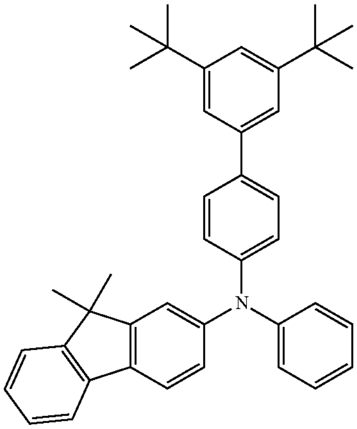
(380)
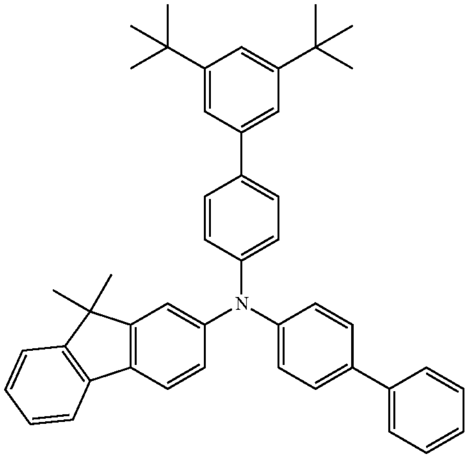
-continued
(381)
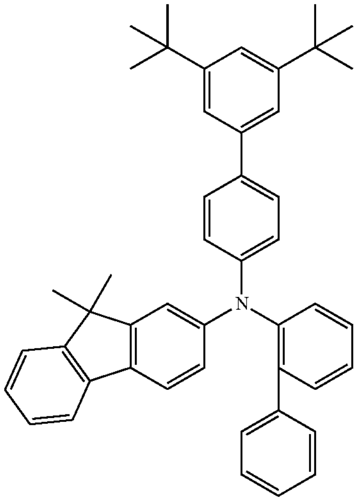
(382)
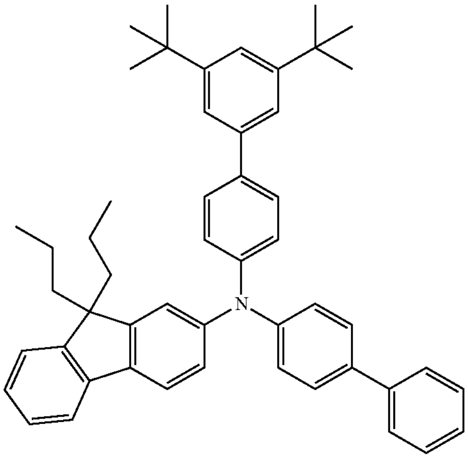
(383)
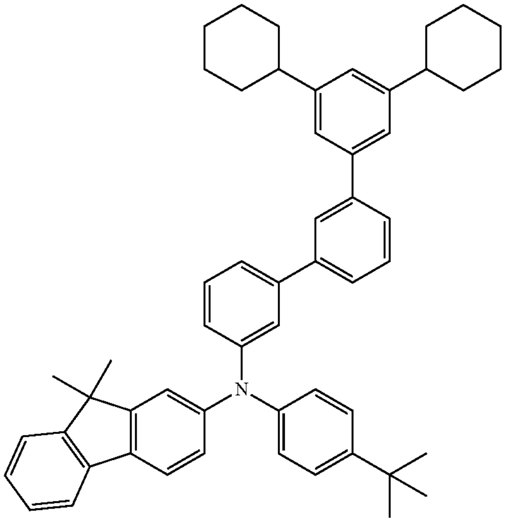

-continued
(384)
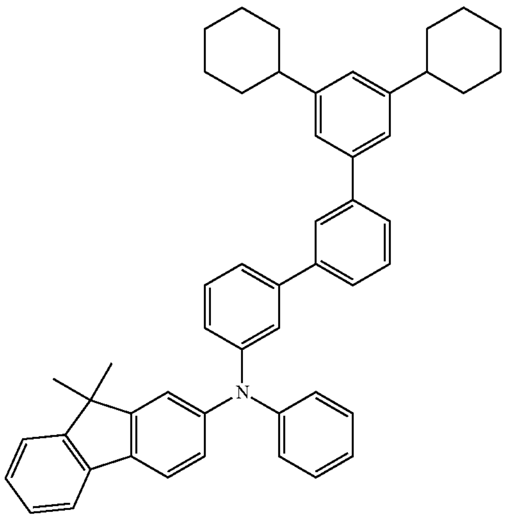
(385)
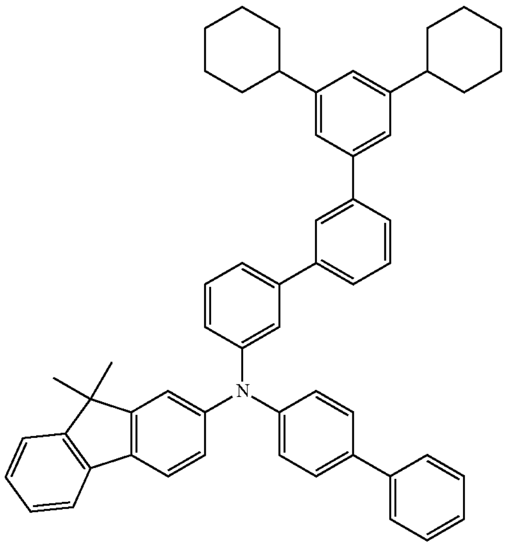
(386)
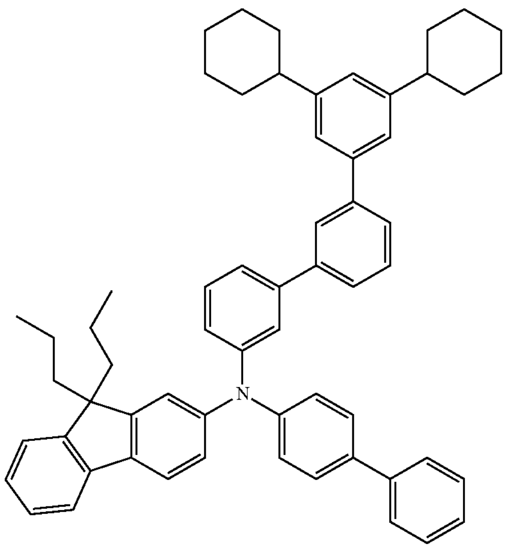
-continued
(387)
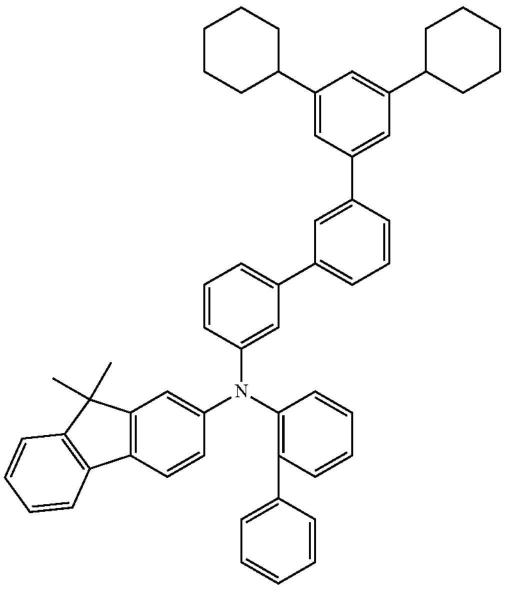
[Chemical Formula 41]
(388)
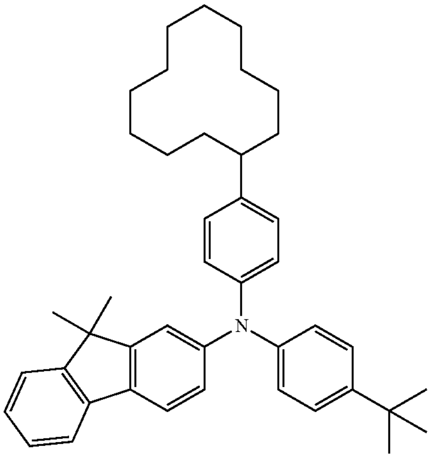
(389)
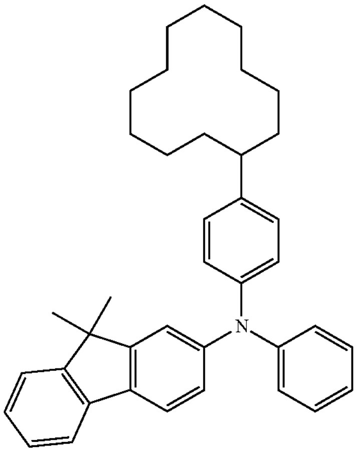

-continued
(390)
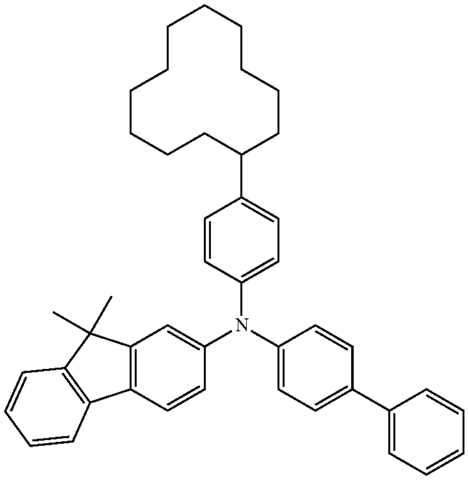
(391)
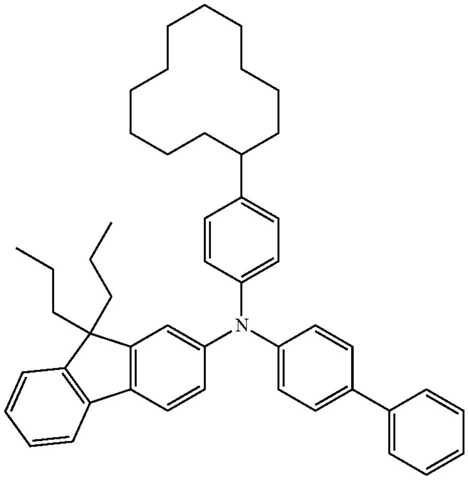
(392)
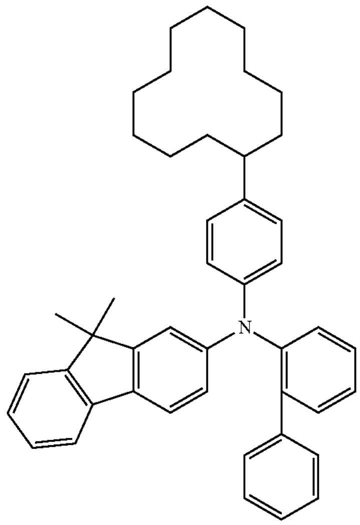
-continued
(393)
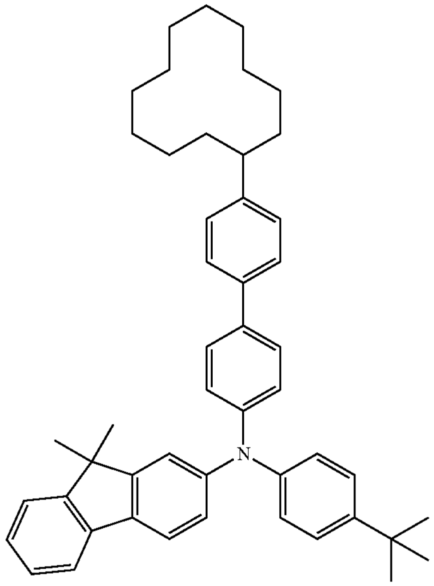
[Chemical Formula 42]
(394)
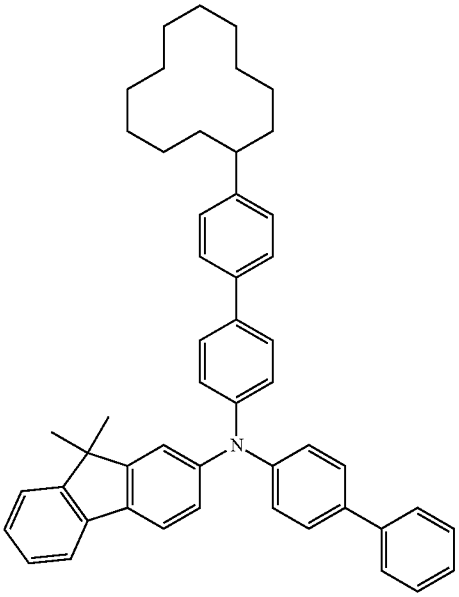

-continued
(395)
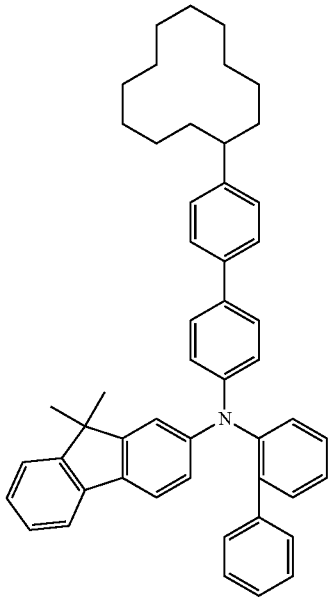
(396)
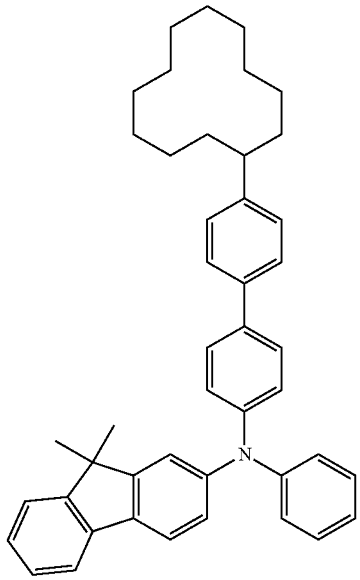
-continued
[Chemical Formula 43]
(397)
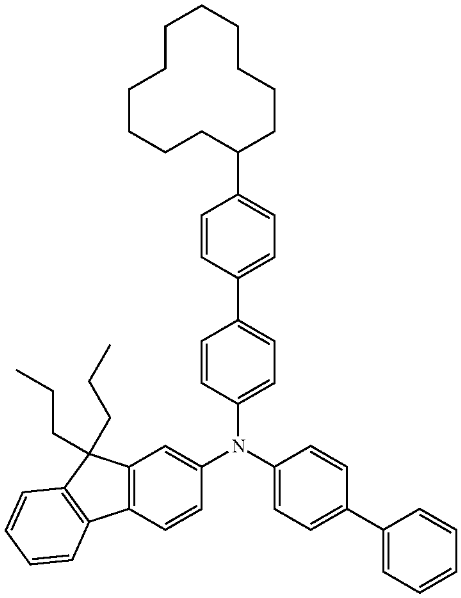
(398)
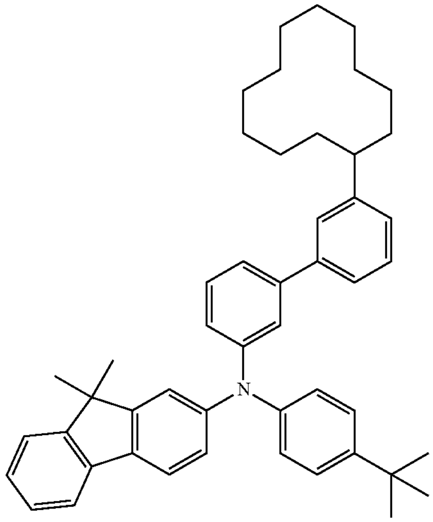
(399)
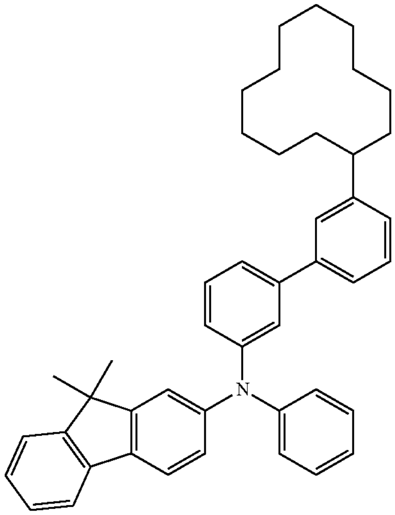

-continued (400)

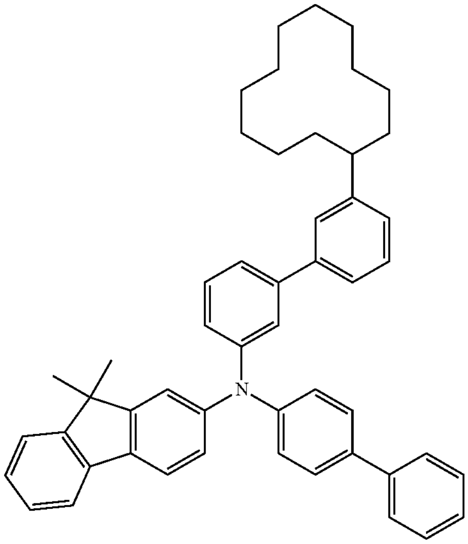

(401)

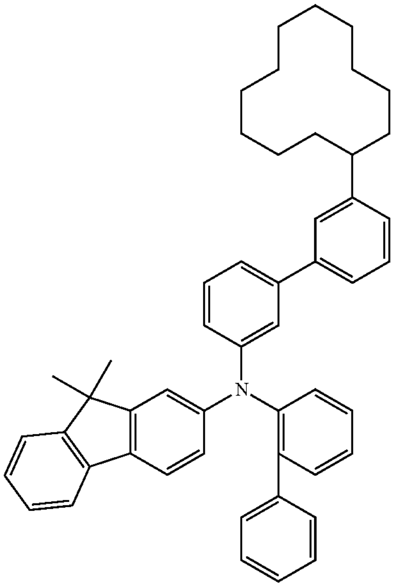

-continued (402)

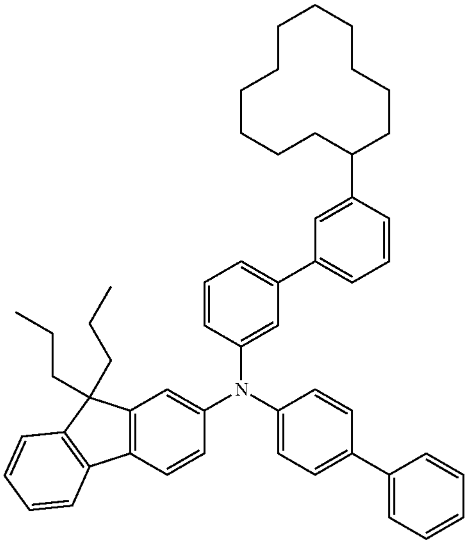

Next, an example of a synthesis method of the above-described monoamine compound is described. Note that the following method is just an example of a synthesis method of the present invention, and the synthesis method is not limited thereto.

[Chemical Formula 44]

(G1)

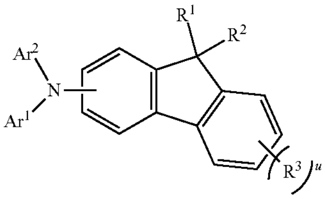

As shown in the following synthesis scheme, 9,9-disubstituted-9H-fluorenylamine (A) and organic halides (X1) and (X2) are coupled using a metal catalyst, a metal, or a metal compound in the presence of a base, so that the organic compound represented by the general formula (G1) can be obtained.

[Chemical Formula 45]

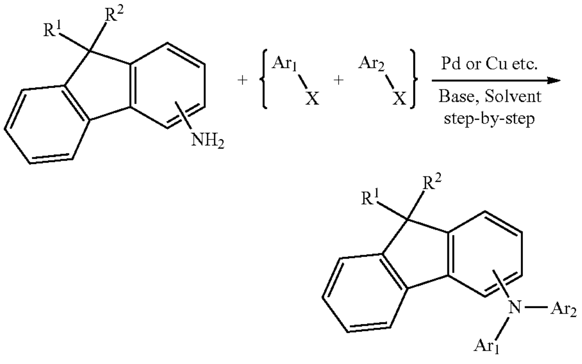

In the above synthesis scheme, $Ar^1$ and $Ar^2$ each independently represent a substituent with a substituted or unsubstituted benzene ring or a substituent in which two or three benzene rings are bonded to each other. Note that one or both of $Ar^1$ and $Ar^2$ have one or more hydrocarbon group(s) having 1 to 12 carbon atoms each forming a bond only by the $sp^3$ hybrid orbitals, the total number of the carbon atoms in the hydrocarbon group(s) in the hydrocarbon group(s) in $Ar^1$ and $Ar^2$ is 8 or more, and the total number of the carbon atoms in the hydrocarbon group(s) in $Ar^1$ or $Ar^2$ is 6 or more. Note that in the case where a plurality of straight-chain alkyl groups each having 1 or 2 carbon atoms are included as the hydrocarbon groups in $Ar^1$ and $Ar^2$, the straight-chain alkyl groups may be bonded to each other to form a ring. In addition, in the general formula (G1), $R^1$ and $R^2$ each independently represent an alkyl group having 1 to 4 carbon atoms. Note that $R^1$ and $R^2$ may be bonded to each other to form a ring. $R^3$ represents an alkyl group having 1 to 4 carbon atoms and u is an integer of 0 to 4. Furthermore, X represents either a halogen element or a triflate group.

In the case where the above synthesis reaction is performed using a Buchwald-Hartwig reaction, X represents a halogen element or a triflate group. As the halogen element, iodine, bromine, or chlorine is preferable. In this reaction, a palladium catalyst including a palladium complex or a palladium compound such as bis(dibenzylideneacetone)palladium(0) or allylpalladium(II) chloride dimer and a ligand that coordinates to the palladium complex or the palladium compound, such as tri(tert-butyl)phosphine, di-tert-butyl(1-methyl-2,2-diphenylcyclopropyl)phosphine, or tricyclohexylphosphine, is used. As the base, an organic base such as sodium tert-butoxide, an inorganic base such as cesium carbonate, and the like can be used. In the case where a solvent is used, toluene, xylene, 1,3,5-trimethylbenzene (mesitylene), or the like can be used. Furthermore, when the reaction temperature is set higher than or equal to 120° C., the reaction between the aryl group including a halogen element with a small periodic number such as chlorine and an amine proceeds in a short time in a high yield; thus, it is preferable to use xylene or 1,3,5-trimethylbenzene having high heat resistance.

When the above synthesis is performed by the Ullmann reaction, X represents a halogen element. As the halogen element, iodine, bromine, or chlorine is preferable. As a catalyst, copper or a copper compound is used. Note that copper(I) iodide or copper(II) acetate is preferably used. Examples of the base include an inorganic base such as potassium carbonate. As a solvent, 1,3-dimethyl-3,4,5,6-tetrahydro-2(1H)-pyrimidinone (DMPU), N-methyl-2-pyrrolidone (NMP), toluene, xylene, 1,3,5-trimethylbenzene, or the like. In the Ullmann reaction, when the reaction temperature is 100° C. or higher, an objective substance can be obtained in a shorter time in a higher yield; therefore, it is preferable to use DMPU, NMP, or 1,3,5-trimethylbenzene each having a high boiling point. In addition, since the reaction temperature is further preferably 150° C. or higher, DMPU is more preferably used.

In the above manner, the organic compound represented by the general formula (G1) can be synthesized.

Embodiment 2

Figure 1A:
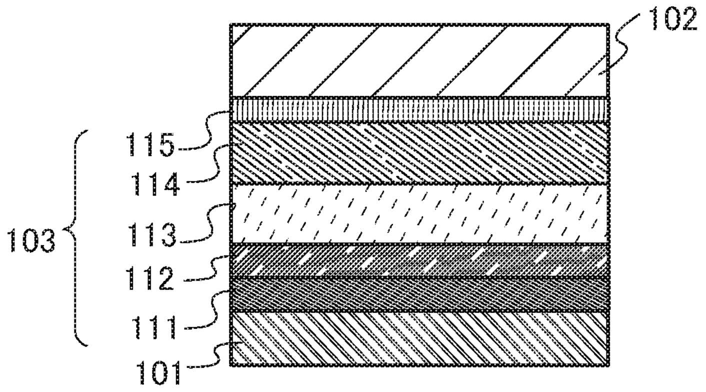
FIGS. 1A to 1C are schematic views of light-emitting devices.

FIG. 1A illustrates a light-emitting device of one embodiment of the present invention. The light-emitting device of one embodiment of the present invention includes a first electrode 101, a second electrode 102, and an EL layer 103, and the organic compound described in Embodiment 1 is used for the EL layer.

The EL layer 103 includes a light-emitting layer 113 and may also include a hole-injection layer 111 and/or a hole-transport layer 112. The light-emitting layer 113 includes a light-emitting material, and light is emitted from the light-emitting material in the light-emitting device of one embodiment of the present invention. The light-emitting layer 113 may include a host material and other materials. The organic compound of one embodiment of the present invention described in Embodiment 1 may be included in any of the light-emitting layer 113, the hole-transport layer 112, and the hole-injection layer 111; alternatively, the organic compound may be included in all of them.

Note that FIG. 1A additionally illustrates an electron-transport layer 114 and an electron-injection layer 115; however, the structure of the light-emitting device is not limited thereto.

The organic compound exhibits a good hole-transport property and thus is effectively used for the hole-transport layer 112. Furthermore, a mixed film of the organic compound of one embodiment of the present invention and an acceptor substance can be used as the hole-injection layer 111.

In addition, the organic compound of one embodiment of the present invention can be used as a host material. Furthermore, the hole-transport material and an electron-transport material may be deposited by co-evaporation so that an exciplex is formed of the electron-transport material and the hole-transport material. The exciplex having an appropriate emission wavelength allows efficient energy transfer to the light-emitting material, achieving a light-emitting device with a high efficiency and a long lifetime.

Since the organic compound of one embodiment of the present invention has a low refractive index, the light-emitting device using the organic compound in its EL layer can have high external quantum efficiency.

Next, examples of specific structures and materials of the above-described light-emitting device will be described. As described above, the light-emitting device of one embodiment of the present invention includes, between the pair of electrodes of the first electrode 101 and the second electrode 102, the EL layer 103 including a plurality of layers; the EL layer 103 includes the organic compound disclosed in Embodiment 1 in any of the layers.

The first electrode 101 is preferably formed using any of metals, alloys, and conductive compounds with a high work function (specifically, higher than or equal to 4.0 eV), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 wt % to 20 wt % of zinc oxide to indium oxide. Furthermore, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used. Graphene can also be used. Note that when a composite material described later is used for a layer that is in contact with the first electrode 101 in the EL layer 103, an electrode material can be selected regardless of its work function.

Although the EL layer 103 preferably has a stacked-layer structure, there is no particular limitation on the stacked-layer structure, and various layers such as a hole-injection layer, a hole-transport layer, an electron-transport layer, an electron-injection layer, a carrier-blocking layer, an exciton-blocking layer, and a charge-generation layer can be employed. Two kinds of stacked-layer structure of the EL layer 103 are described: the structure illustrated in FIG. 1A, which includes the electron-transport layer 114 and the electron-injection layer 115 in addition to the hole-injection layer 111, the hole-transport layer 112, and the light-emitting layer 113; and the structure illustrated in FIG. 1B, which includes the electron-transport layer 114, the electron-injection layer 115, and a charge-generation layer 116 in addition to the hole-injection layer 111, the hole-transport layer 112, and the light-emitting layer 113. Materials for forming each layer will be specifically described below.

The hole-injection layer 111 contains a substance having an acceptor property. Either an organic compound or an inorganic compound can be used as the substance having an acceptor property.

As the substance having an acceptor property, it is possible to use a compound having an electron-withdrawing group (a halogen group or a cyano group); for example, 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), or 2-(7-dicyanomethylene-1,3,4,5,6,8,9,10-octafluoro-7H-pyren-2-ylidene)malononitrile can be used. A compound in which electron-withdrawing groups are bonded to a condensed aromatic ring having a plurality of heteroatoms, such as HAT-CN, is particularly preferable because it is thermally stable. A [3]radialene derivative having an electron-withdrawing group (in particular, a cyano group or a halogen group such as a fluoro group) has a very high electron-accepting property and thus is preferable. Specific examples include α,α',α"-1,2,3-cyclopropanetriylidenetris[4-cyano-2,3,5,6-tetrafluorobenzeneacetonitrile], α,α'α"-1,2,3-cyclopropanetriylidenetris[2,6-dichloro-3,5-difluoro-4-(trifluoromethyl)benze neacetonitrile], and α,α'α"-1,2,3-cyclopropanetriylidenetris [2,3,4,5,6-pentafluorobenzeneacetonitrile]. As the substance having an acceptor property, molybdenum oxide, vanadium oxide, ruthenium oxide, tungsten oxide, manganese oxide, or the like can be used, other than the above-described organic compounds. Alternatively, the hole-injection layer 111 can be formed using a phthalocyanine-based complex compound such as phthalocyanine (abbreviation: $H_2Pc$) and copper phthalocyanine (CuPc), an aromatic amine compound such as 4,4'-bis[N-(4-diphenylaminophenyl)-N-phenylamino]biphenyl (abbreviation: DPAB) and N,N-bis{4-[bis(3-methylphenyl)amino]phenyl}-N,N-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS). The substance having an acceptor property can extract electrons from an adjacent hole-transport layer (or hole-transport material) by the application of an electric field.

Alternatively, a composite material in which a material having a hole-transport property contains any of the aforementioned substances having an acceptor property can be used for the hole-injection layer 111. By using a composite material in which a material having a hole-transport property contains an acceptor substance, a material used to form an electrode can be selected regardless of its work function. In other words, besides a material having a high work function, a material having a low work function can be used for the first electrode 101.

As the material having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the material having a hole-transport property used for the composite material preferably has a hole mobility of $1\times10^{-6}$ $cm^2/Vs$ or higher. Organic compounds which can be used as the material having a hole-transport property in the composite material are specifically given below.

Examples of the aromatic amine compounds that can be used for the composite material include N,N-di(p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenylanthracen-9-yl)phenyl]-9H-carbazole (abbreviation: CzPA), and 1,4-bis[4-(N-carbazolyl)phenyl]-2,3,5,6-tetraphenylbenzene.

Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples include pentacene and coronene. The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA). Note that the organic compound of one embodiment of the present invention can also be used.

Other examples include high molecular compounds such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl)methacrylamide] (abbreviation:

PTPDMA), and poly[N,N-bis(4-butylphenyl)-N,N-bis(phenyl)benzidine](abbreviation: poly-TPD).

The material having a hole-transport property that is used in the composite material further preferably has any of a carbazole skeleton, a dibenzofuran skeleton, a dibenzothiophene skeleton, and an anthracene skeleton. In particular, an aromatic amine having a substituent that includes a dibenzofuran ring or a dibenzothiophene ring, an aromatic monoamine that includes a naphthalene ring, or an aromatic monoamine in which a 9-fluorenyl group is bonded to nitrogen of amine through an arylene group may be used. Note that the second organic compound having an N,N-bis(4-biphenyl)amino group is preferable because a light-emitting device having a long lifetime can be fabricated. Specific examples of the second organic compound include N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4"-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II)(4)),N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4"-(6;1'-binaphthyl-2-yl)triphenylamine (abbreviation: BBAαNβNB), 4,4'-diphenyl-4"-(7;1'-binaphthyl-2-yl)triphenylamine (abbreviation: BBAαNβNB-03), 4,4'-diphenyl-4"-(7-phenyl)naphthyl-2-yltriphenylamine (abbreviation: BBAPβNB-03), 4,4'-diphenyl-4"-(6;2-binaphthyl-2-yl)triphenylamine (abbreviation: BBA(βN2)B), 4,4'-diphenyl-4"-(7;2'-binaphthyl-2-yl)triphenylamine (abbreviation: BBA(βN2)B-03), 4,4'-diphenyl-4"-(4;2'-binaphthyl-1-yl)triphenylamine (abbreviation: BBAβNαNB), 4,4'-diphenyl-4"-(5;2'-binaphthyl-1-yl)triphenylamine (abbreviation: BBAβNαNB-02), 4-(4-biphenylyl)-4'-(2-naphthyl)-4"-phenyltriphenylamine (abbreviation: TPBiAβNB), 4-(3-biphenylyl)-4'-[4-(2-naphthyl)phenyl]-4"-phenyltriphenylamine (abbreviation: mTPBiAβNBi), 4-(4-biphenylyl)-4'-[4-(2-naphthyl)phenyl]-4"-phenyltriphenylamine (abbreviation: TPBiAβNBi), 4-phenyl-4'-(1-naphthyl)triphenylamine (abbreviation: αNBA1BP), 4,4'-bis(1-naphthyl)triphenylamine (abbreviation: αNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBi1BP-02), 4-[4'-(carbazol-9-yl)biphenyl-4-yl]-4'-(2-naphthyl)-4"-phenyltriphenylamine (abbreviation: YGTBiβNB), N-[4-(9-phenyl-9H-carbazol-3-yl)phenyl]-N-[4-(1-naphthyl)phenyl]-9,9'-spirobi[9H-fluoren]-2-amine (abbreviation: PCBNBSF), N,N-bis ([1,1'-biphenyl]-4-yl)-9,9'-spirobi[9H-fluoren]-2-amine (abbreviation: BBASF), N,N-bis ([1,1'-biphenyl]-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi[9H-fluoren]-4-amine (abbreviation: oFBiSF), N-(4-biphenyl)-N-(9,9-dimethyl-9H-fluoren-2-yl)dibenzofuran-4-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), N-phenyl-N-[4-(9-phenyl-9H-carbazol-3-yl)phenyl]-9,9'-spirobi[9H-fluoren]-2-amine (abbreviation: PCBASF), N-(1,1'-biphenyl-4-yl)-9,9-dimethyl-N-[4-(9-phenyl-9H-carbazol-3-yl)phenyl]-9H-fluoren-2-amine (abbreviation: PCBBiF), N,N-bis(9,9-dimethyl-9H-fluoren-2-yl)-9,9'-spirobi-9H-fluoren-4-amine, N,N-bis(9,9-dimethyl-9H-fluoren-2-yl)-9,9'-spirobi-9H-fluoren-3-amine, N,N-bis(9,9-dimethyl-9H-fluoren-2-yl)9,9'-spirobi-9H-fluoren-2-amine, and N,N-bis(9,9-dimethyl-9H-fluoren-2-yl)-9,9'-spirobi-9H-fluoren-1-amine.

Note that it is further preferable that the material having a hole-transport property to be used in the composite material have a relatively deep HOMO level of greater than or equal to −5.7 eV and lower than or equal to −5.4 eV. Using the material with a hole-transport property which has a relatively deep HOMO level in the composite material makes it easy to inject holes into the hole-transport layer 112 and to obtain a light-emitting device having a long lifetime.

Note that the monoamine compound described in Embodiment 1 also has a hole-transport property, and thus can be suitably used as the material for a hole-injection layer used in the composite material. A layer with a low refractive index can be formed in the EL layer 103 with the use of the monoamine compound described in Embodiment 1, leading to higher external quantum efficiency of the light-emitting device.

Note that mixing the above composite material with a fluoride of an alkali metal or an alkaline earth metal (the proportion of fluorine atoms in a layer using the mixed material is preferably greater than or equal to 20%) can lower the refractive index of the layer. This also enables a layer with a low refractive index to be formed in the EL layer 103, leading to higher external quantum efficiency of the light-emitting device.

The formation of the hole-injection layer 111 can improve the hole-injection property, which allows the light-emitting device to be driven at a low voltage. In addition, the organic compound having an acceptor property is easy to use because it is easily deposited by vapor deposition.

The hole-transport layer 112 is formed using a material having a hole-transport property. The material having a hole-transport material preferably has a hole mobility higher than or equal to $1\times10^{-6}$ $cm^2/Vs$. The monoamine compound described in Embodiment 1 has a hole-transport property, and thus can be suitably used as a material for a hole-transport layer. Thus, the hole-transport layer 112 preferably includes the monoamine compound described in Embodiment 1, further preferably is formed using only the monoamine compound described in Embodiment 1. The hole-transport layer 112 including the monoamine compound described in Embodiment 1 can be a layer with a low refractive index in the EL layer 103, leading to higher external quantum efficiency of the light-emitting device.

Examples of the material having a hole-transport property, in the case of using a material other than the monoamine compound described in Embodiment 1 for the hole-transport layer 112, include compounds having an aromatic amine skeleton such as 4,4'-bis[N-(1-naphthyl)-N-phenylamino]biphenyl (abbreviation: NPB), N,N'-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]-9,9'-spirobi[9H-fluoren]-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage. Note that any of the substances given as examples of the material having a hole-transport property which is used in the composite material for the hole-injection layer 111 can also be suitably used as the material included in the hole-transport layer 112.

The light-emitting layer 113 includes a light-emitting substance and a host material. The light-emitting layer 113 may additionally include other materials. Alternatively, the light-emitting layer 113 may be a stack of two layers with different compositions.

As the light-emitting substance, fluorescent substances, phosphorescent substances, substances exhibiting thermally activated delayed fluorescence (TADF), or other light-emitting substances may be used. Note that one embodiment of the present invention is more suitably used in the case where the light-emitting layer 113 emits fluorescence, specifically, blue fluorescence.

Examples of the material that can be used as a fluorescent substance in the light-emitting layer 113 are as follows. Other fluorescent substances can also be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-diphenyl-N,N-bis[4-(9-phenyl-9H-fluoren-9-yl)phenyl]pyrene-1,6-diamine (abbreviation: 1,6FLPAPrn), N,N-bis(3-methylphenyl)-N,N-bis[3-(9-phenyl-9H-fluoren-9-yl)phenyl]pyrene-1,6-diamine (abbreviation: 1,6mMemFLPAPrn), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis[N,N,N-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N,N-triphenyl-1,4-phenylenediamine (abbreviation: 2DPAPPA), N,N,N',N',N",N",N"',N"'-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N,N-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), N,N'-diphenyl-N,N'-(1,6-pyrene-diyl)bis[(6-phenylbenzo[b]naphtho[1,2-d]furan)-8-amine](abbreviation: 1,6BnfAPrn-03), 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02), and 3,10-bis[N-(dibenzofuran-3-yl)-N-phenylamino]naphtho[2,3-b;6,7-b']bisbenzofuran (abbreviation: 3,10FrA2Nbf(IV)-02). Condensed aromatic diamine compounds typified by pyrenediamine compounds such as 1,6FLPAPrn, 1,6mMemFLPAPrn, and 1,6BnfAPrn-03 are particularly preferable because of their high hole-trapping properties, high emission efficiency, and high reliability. Furthermore, an organic compound having a naphthobisbenzofuran skeleton or a naphthobisbenzothiophene skeleton is preferable because it exhibits deep blue fluorescence and enables a favorable blue light-emitting device to be provided. An organic compound having a naphthobisbenzofuran skeleton or a naphthobisbenzothiophene skeleton including two or more arylamine skeletons, such as 3,10PCA2Nbf(IV)-02 and 3,10FrA2Nbf(IV)-02, is particularly preferable because of its high luminance quantum yield. An organic compound having a naphthobisbenzofuran skeleton or a naphthobisbenzothiophene skeleton in which any of a dibenzofuran skeleton, a dibenzothiophene skeleton, and a carbazole skeleton is bonded to the arylamine skeleton is further preferable because it improves outcoupling efficiency due to molecular orientation and has high reliability (especially at high temperature). Note that the organic compound having a naphthobisbenzofuran skeleton or a naphthobisbenzothiophene skeleton has an extremely narrow half-width, that is 30 nm or less, of the PL spectrum when it is in a toluene solution. Thus, it is preferable to use such a light-emitting substance with a narrow half-width in one embodiment of the present invention in which a layer with a low refractive index makes microcavity effect particularly effective.

Examples of the material that can be used when a phosphorescent substance is used as the light-emitting substance in the light-emitting layer 113 are as follows.

The examples are as follows: an organometallic iridium complex having a 4H-triazole skeleton, such as tris{2-[5-(2-methylphenyl)-4-(2,6-dimethylphenyl)-4H-1,2,4-triazol-3-yl-κN2]phenyl-KC}iridium(III) (abbreviation: $[Ir(mpptz-dmp)_3]$), tris(5-methyl-3,4-diphenyl-4H-1,2,4-triazolato)iridium(III) (abbreviation: $[Ir(Mptz)_3]$), and tris[4-(3-biphenyl)-5-isopropyl-3-phenyl-4H-1,2,4-triazolato]iridium(III) (abbreviation: $[Ir(iPrptz-3b)_3]$); an organometallic iridium complex having a 1H-triazole skeleton, such as tris[3-methyl-1-(2-methylphenyl)-5-phenyl-1H-1,2,4-triazolato]iridium(III) (abbreviation: $[Ir(Mptz1-mp)_3]$) and tris(1-methyl-5-phenyl-3-propyl-1H-1,2,4-triazolato)iridium(III) (abbreviation: $[Ir(Prptz1-Me)_3]$); an organometallic iridium complex having an imidazole skeleton, such as fac-tris[1-(2,6-diisopropylphenyl)-2-phenyl-H-imidazole]iridium(III) (abbreviation: $[Ir(iPrpmi)_3]$) and tris[3-(2,6-dimethylphenyl)-7-methylimidazo[1,2-f]phenanthridinato]iridium(III) (abbreviation: $[Ir(dmpimpt-Me)_3]$); and an organometallic iridium complex in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: $[Ir(CF_3ppy)_2(pic)]$), and bis[2-(4',6'-difluorophenyl)pyridinato-N,$C^{2'}$]iridium(III) acetylacetonate (abbreviation: FIr(acac)). These compounds emit blue phosphorescence and have an emission peak at 440 nm to 520 nm.

Other examples include organometallic iridium complexes having a pyrimidine skeleton, such as tris(4-methyl-6-phenylpyrimidinato)iridium(III) (abbreviation: $[Ir(mppm)_3]$), tris(4-t-butyl-6-phenylpyrimidinato)iridium(III)(abbreviation: $[Ir(tBuppm)_3]$), (acetylacetonato)bis(6-methyl-4-phenylpyrimidinato)iridium(III) (abbreviation: $[Ir(mppm)_2(acac)]$), (acetylacetonato)bis(6-tert-butyl-4-phenylpyrimidinato)iridium(III) (abbreviation: $[Ir(tBuppm)_2(acac)]$), (acetylacetonato)bis[6-(2-norbornyl)-4-phenylpyrimidinato]iridium(III) (abbreviation: $[Ir(nbppm)_2(acac)]$), (acetylacetonato)bis[5-methyl-6-(2-methylphenyl)-4-phenylpyrimidinato]iridium(III) (abbreviation: $[Ir(mpmppm)_2(acac)]$), and (acetylacetonato)bis(4,6-diphenylpyrimidinato)iridium(III) (abbreviation: $[Ir(dppm)_2(acac)]$); organometallic iridium complexes having a pyrazine skeleton, such as (acetylacetonato)bis(3,5-dimethyl-2-phenylpyrazinato)iridium(III) (abbreviation: $[Ir(mppr-Me)_2(acac)]$) and (acetylacetonato)bis(5-isopropyl-3-methyl-2-phenylpyrazinato)iridium(III) (abbreviation: $[Ir(mppr-iPr)_2(acac)]$); organometallic iridium complexes having a pyridine skeleton, such as tris(2-phenylpyridinato-N,$C^{2'}$)iridium(III) (abbreviation: $[Ir(ppy)_3]$), bis(2-phenylpyridinato-N,$C^{2'}$)iridium(III) acetylacetonate (abbreviation: $[Ir(ppy)_2(acac)]$), bis(benzo[h]quinolinato)iridium(III) acetylacetonate (abbreviation: $[Ir(bzq)_2(acac)]$), tris(benzo[h]quinolinato)iridium(III) (abbreviation: $[Ir(bzq)_3]$), tris(2-phenylquinolinato-N,$C^{2'}$)iridium(III) (abbreviation: $[Ir(pq)_3]$), and bis(2-phenylquinolinato-N,$C^{2'}$)iridium(III) acetylacetonate (abbreviation: $[Ir(pq)_2(acac)]$); and a rare earth metal complex such as tris(acetylacetonato) (monophenanthroline)terbium(III) (abbreviation: $[Tb(acac)_3(Phen)]$). These are mainly compounds that emit green phosphorescence and have an emission peak at 500 nm to 600 nm. Note that organometallic iridium complexes having a pyrimidine skeleton have distinctively high reliability and emission efficiency and thus are particularly preferable.

Other examples include organometallic iridium complexes having a pyrimidine skeleton, such as (diisobutyrylmethanato)bis[4,6-bis(3-methylphenyl)pyrimidinato]iridium(III) (abbreviation: $[Ir(5mdppm)_2(dibm)]$), bis[4,6-bis(3-methylphenyl)pyrimidinato](dipivaloylmethanato)iridium(III) (abbreviation: $[Ir(5mdppm)_2(dpm)]$), and bis[4,6-di(naphthalen-1-yl)pyrimidinato](dipivaloylmethanato)iridium(III) (abbreviation: $[Ir(dlnpm)_2(dpm)]$); organometallic iridium complexes having a pyrazine skeleton, such as (acetylacetonato)bis(2,3,5-triphenylpyrazinato)iridium(III) (abbreviation: $[Ir(tppr)_2(acac)]$), bis(2,3,5-triphenylpyrazinato)(dipivaloylmethanato)iridium(III) (abbreviation: $[Ir(tppr)_2(dpm)]$), and (acetylacetonato)bis[2,3-bis(4-fluorophenyl)quinoxalinato]iridium(III) (abbreviation: $[Ir(Fdpq)_2(acac)]$); organometallic iridium complexes having a pyridine skeleton, such as tris(1-phenylisoquinolinato-N,$C^{2'}$)iridium(III) (abbreviation: $[Ir(piq)_3]$) and bis(1-phenylisoquinolinato-N,$C^{2'}$)iridium(III) acetylacetonate (abbreviation: $[Ir(piq)_2(acac)]$); platinum complexes such as 2,3,7,8,12,13,17,18-octaethyl-21H,23H-porphyrinplatinum(II)(abbreviation: [PtOEP]); and rare earth metal complexes such as tris(1,3-diphenyl-1,3-propanedionato) (monophenanthroline)europium(III) (abbreviation: $[Eu(DBM)_3(Phen)]$) and tris[1-(2-thenoyl)-3,3,3-trifluoroacetonato(monophenanthroline)europium(III) (abbreviation: $[Eu(TTA)_3(Phen)]$). These compounds emit red phosphorescence having an emission peak at 600 nm to 700 nm. Furthermore, the organometallic iridium complexes having a pyrazine skeleton can provide red light emission with favorable chromaticity.

Besides the above phosphorescent compounds, known phosphorescent substances may be selected and used.

Examples of the TADF material include a fullerene, a derivative thereof, an acridine, a derivative thereof, and an eosin derivative. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2OEP$), which are represented by the following structural formulae.
[Chemical Formula 46]
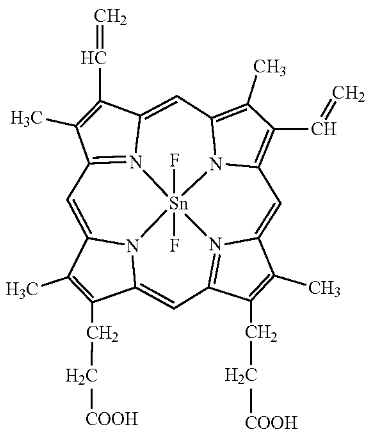
$SnF_2$(Proto IX)
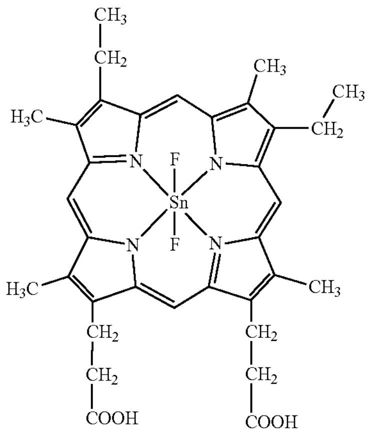
$SnF_2$(Meso IX)
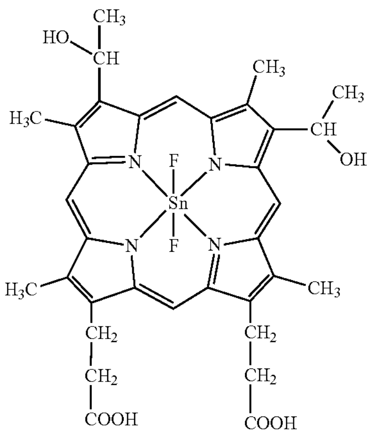
$SnF_2$(Hemato IX)
-continued
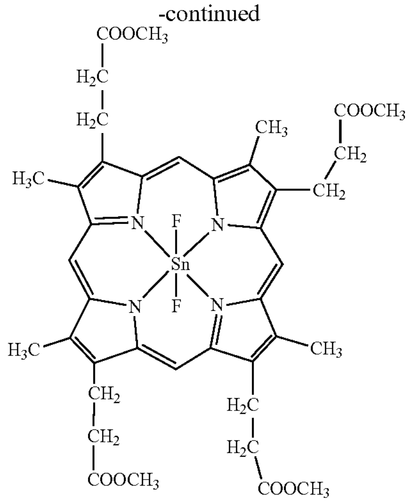
$SnF_2$(Copro III-4Me)
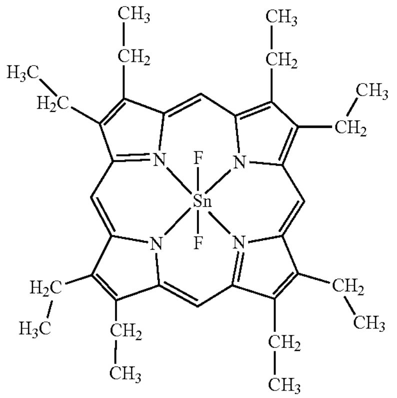
$SnF_2$(OEP)
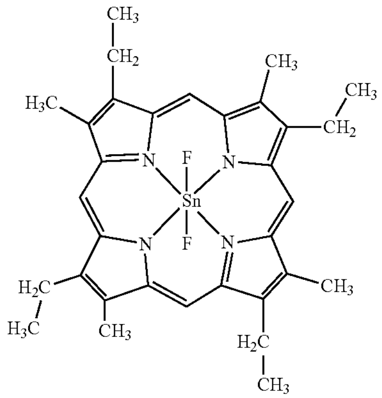
$SnF_2$(Etio I)

-continued

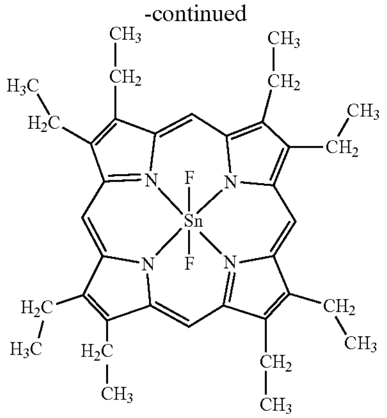

$PtCl_2OEP$

Alternatively, a heterocyclic compound having one or both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Such a heterocyclic compound is preferable because of having excellent electron-transport and hole-transport properties owing to a π-electron rich heteroaromatic ring and a π-electron deficient heteroaromatic ring. Among skeletons having the π-electron deficient heteroaromatic ring, a pyridine skeleton, a diazine skeleton (a pyrimidine skeleton, a pyrazine skeleton, and a pyridazine skeleton), and a triazine skeleton are preferred because of their high stability and reliability. In particular, a benzofuropyrimidine skeleton, a benzothienopyrimidine skeleton, a benzofuropyrazine skeleton, and a benzothienopyrazine skeleton are preferred because of their high accepting properties and high reliability. Among skeletons having the π-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. A dibenzofuran skeleton is preferable as a furan skeleton, and a dibenzothiophene skeleton is preferable as a thiophene skeleton. As a pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable. Note that a substance in which the π-electron rich heteroaromatic ring is directly bonded to the π-electron deficient heteroaromatic ring is particularly preferred because the electron-donating property of the π-electron rich heteroaromatic ring and the electron-accepting property of the π-electron deficient heteroaromatic ring are both improved, the energy difference between the S level and the T1 level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a skeleton containing boron such as phenylborane or boranthrene, an aromatic ring or a heteroaromatic ring having a cyano group or a nitrile group such as benzonitrile or cyanobenzene, a carbonyl skeleton such as benzophenone, a phosphine oxide skeleton, a sulfone skeleton, or the like can be used. As described above, a π-electron deficient skeleton and a π-electron rich skeleton can be used instead of at least one of the π-electron deficient heteroaromatic ring and the π-electron rich heteroaromatic ring.

[Chemical Formula 47]

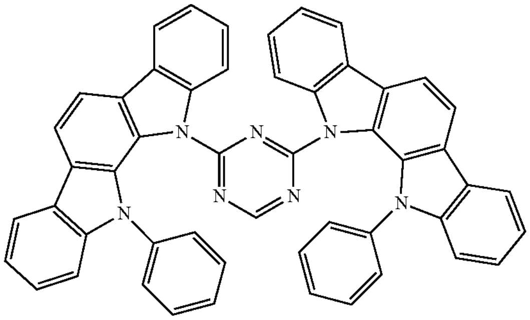

PIC-TRZ

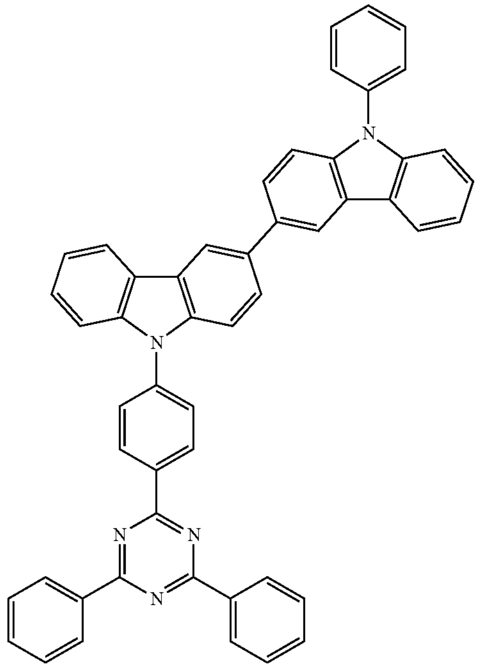

PCCzPTzn

-continued

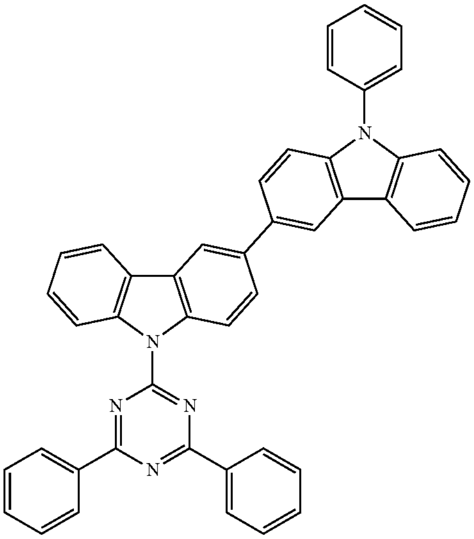

PCCzPTzn

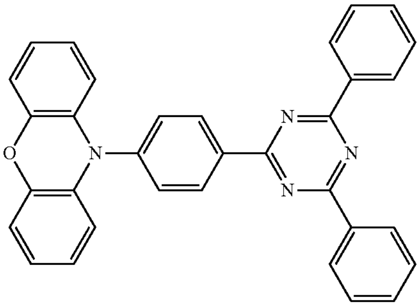

PIC-TRZ

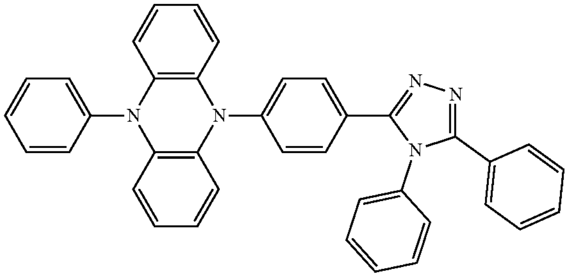

PPZ-3TPT

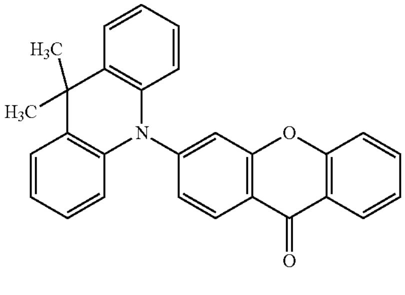

-continued

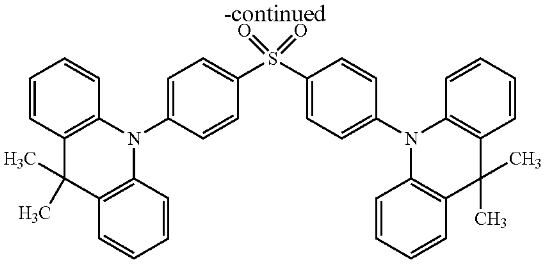

DMAC-DPS

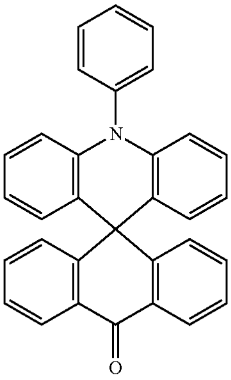

ACRSA

Note that a TADF material is a material having a small difference between the S1 level and the T1 level and a function of converting triplet excitation energy into singlet excitation energy by reverse intersystem crossing. Thus, a TADF material can upconvert triplet excitation energy into singlet excitation energy (i.e., reverse intersystem crossing) using a small amount of thermal energy and efficiently generate a singlet excited state. In addition, the triplet excitation energy can be converted into luminescence.

An exciplex whose excited state is formed of two kinds of substances has an extremely small difference between the S1 level and the T1 level and functions as a TADF material capable of converting triplet excitation energy into singlet excitation energy.

A phosphorescent spectrum observed at a low temperature (e.g., 77 K to 10 K) is used for an index of the T1 level. When the level of energy with a wavelength of the line obtained by extrapolating a tangent to the fluorescent spectrum at a tail on the short wavelength side is the S1 level and the level of energy with a wavelength of the line obtained by extrapolating a tangent to the phosphorescent spectrum at a tail on the short wavelength side is the T1 level, the difference between the S1 level and the T1 level of the TADF material is preferably smaller than or equal to 0.3 eV, further preferably smaller than or equal to 0.2 eV.

When a TADF material is used as the light-emitting substance, the S1 level of the host material is preferably higher than that of the TADF material. In addition, the T1 level of the host material is preferably higher than that of the TADF material.

As the host material in the light-emitting layer, various carrier-transport materials such as materials having an electron-transport property, materials having a hole-transport property, and the TADF materials can be used.

The material having a hole-transport property is preferably an organic compound having an aromatic amine skeleton or a π-electron rich heteroaromatic ring skeleton. Examples of the substance include compounds having an aromatic amine skeleton such as 4,4'-bis[N-(1-naphthyl)-N-phenylamino]biphenyl (abbreviation: NPB), N,N-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage. In addition, the organic compounds given as examples of the material having a hole-transport property can also be used.

As the material having an electron-transport property, metal complexes such as bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); or an organic compound having a π-electron deficient heteroaromatic ring skeleton is preferable. Examples of the organic compound having a π-electron deficient heteroaromatic ring skeleton include 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); heterocyclic compounds having a triazine skeleton such as 2-[3'-(9,9-dimethyl-9e-fluoren-2-yl)-1,1'-biphenyl-3-yl]-4,6-diphenyl-1,3,5-triazine (abbreviation: mFBPTzn), 2-[(1,1'-Biphenyl)-4-yl]-4-phenyl-6-[9,9'-spirobi(9H-fluoren)-2-yl]-1,3,5-triazine (abbreviation: BP-SFTzn), 2-{3-[3-(Benzo[b]naphtho[1,2-d]furan-8-yl)phenyl]phenyl}-4,6-diphenyl-1,3,5-triazine (abbreviation: mBnfBPTzn), and 2-{3-[3-(Benzo[b]naphtho[1,2-d]furan-6-yl)phenyl]phenyl}-4,6-diphenyl-1,3,5-triazine (abbreviation: mBnfBPTzn-02); and heterocyclic compounds having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compound having a diazine skeleton, the heterocyclic compound having a triazine skeleton, and the heterocyclic compound having a pyridine skeleton have high reliability and thus are preferable. In particular, the heterocyclic compound having a diazine (pyrimidine or pyrazine) skeleton has a high electron-transport property to contribute to a reduction in driving voltage.

As the TADF material that can be used as the host material, the above materials mentioned as the TADF material can also be used. When the TADF material is used as the host material, triplet excitation energy generated in the TADF material is converted into singlet excitation energy by reverse intersystem crossing and transferred to the light-emitting substance, whereby the emission efficiency of the light-emitting device can be increased. Here, the TADF material functions as an energy donor, and the light-emitting substance functions as an energy acceptor.

This is very effective in the case where the light-emitting substance is a fluorescent substance. In that case, the S1 level of the TADF material is preferably higher than that of the fluorescent substance in order that high emission efficiency be achieved. Furthermore, the T1 level of the TADF material is preferably higher than the S level of the fluorescent substance. Therefore, the T1 level of the TADF material is preferably higher than that of the fluorescent substance.

It is also preferable to use a TADF material that emits light whose wavelength overlaps with the wavelength on a lowest-energy-side absorption band of the fluorescent substance. This enables smooth transfer of excitation energy from the TADF material to the fluorescent substance and accordingly enables efficient light emission, which is preferable.

In addition, in order to efficiently generate singlet excitation energy from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protective group around a luminophore (a skeleton which causes light emission) of the fluorescent substance. As the protective group, a substituent having no 7 bond and a saturated hydrocarbon are preferably used. Specific examples include an alkyl group having 3 to 10 carbon atoms, a substituted or unsubstituted cycloalkyl group having 3 to 10 carbon atoms, and a trialkylsilyl group having 3 to 10 carbon atoms. It is further preferable that the fluorescent substance have a plurality of protective groups. The substituents having no 7 bond are poor in carrier transport performance, whereby the TADF material and the luminophore of the fluorescent substance can be made away from each other with little influence on carrier transportation or carrier recombination. Here, the luminophore refers to an atomic group (skeleton) that causes light emission in a fluorescent substance. The luminophore is preferably a skeleton having a 7 bond, further preferably includes an aromatic ring, and still further preferably includes a condensed aromatic ring or a condensed heteroaromatic ring. Examples of the condensed aromatic ring or the condensed heteroaromatic ring include a phenanthrene skeleton, a stilbene skeleton, an acridone skeleton, a phenoxazine skeleton, and a phenothiazine skeleton. Specifically, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferred because of its high fluorescence quantum yield.

In the case where a fluorescent substance is used as the light-emitting substance, a material having an anthracene skeleton is favorably used as the host material. The use of a substance having an anthracene skeleton as the host material for the fluorescent substance makes it possible to obtain a light-emitting layer with high emission efficiency and high durability. Among the substances having an anthracene skeleton, a substance having a diphenylanthracene skeleton, in particular, a substance having a 9,10-diphenylanthracene skeleton, is chemically stable and thus is preferably used as the host material. The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material preferably has a dibenzocarbazole skeleton because the HOMO level thereof is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole or dibenzocarbazole skeleton) is further preferable as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), and 9-(1-naphthyl)-10-[4-(2-naphthyl)phenyl]anthracene (abbreviation: αN-βNPAnth). Note that CzPA, cgDBCzPA, 2mBnfPPA, and PCzPA have excellent characteristics and thus are preferably selected.

Note that the host material may be a mixture of a plurality of kinds of substances; in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The weight ratio of the content of the material having a hole-transport property to the content of the material having an electron-transport property may be 1:19 to 19:1.

Note that a phosphorescent substance can be used as part of the mixed material. When a fluorescent substance is used as the light-emitting substance, a phosphorescent substance can be used as an energy donor for supplying excitation energy to the fluorescent substance.

An exciplex may be formed of these mixed materials. When these mixed materials are selected so as to form an exciplex that exhibits light emission whose wavelength overlaps with the wavelength on a lowest-energy-side absorption band of the light-emitting substance, energy can be transferred smoothly and light emission can be obtained efficiently, which is preferable. The use of such a structure is preferable because the driving voltage can also be reduced.

Note that at least one of the materials forming an exciplex may be a phosphorescent substance. In this case, triplet excitation energy can be efficiently converted into singlet excitation energy by reverse intersystem crossing.

Combination of a material having an electron-transport property and a material having a hole-transport property whose HOMO level is higher than or equal to that of the material having an electron-transport property is preferable for forming an exciplex efficiently. In addition, the LUMO level of the material having a hole-transport property is preferably higher than or equal to the LUMO level of the material having an electron-transport property. Note that the LUMO levels and the HOMO levels of the materials can be derived from the electrochemical characteristics (the reduction potentials and the oxidation potentials) of the materials that are measured by cyclic voltammetry (CV).

The formation of an exciplex can be confirmed by a phenomenon in which the emission spectrum of the mixed film in which the material having a hole-transport property and the material having an electron-transport property are mixed is shifted to the longer wavelength side than the emission spectra of each of the materials (or has another peak on the longer wavelength side) observed by comparison of the emission spectra of the material having a hole-transport property, the material having an electron-transport property, and the mixed film of these materials, for example. Alternatively, the formation of an exciplex can be confirmed by a difference in transient response, such as a phenomenon in which the transient PL lifetime of the mixed film has more long lifetime components or has a larger proportion of delayed components than that of each of the materials, observed by comparison of transient photoluminescence (PL) of the material having a hole-transport property, the material having an electron-transport property, and the mixed film of the materials. The transient PL can be rephrased as transient electroluminescence (EL). That is, the formation of an exciplex can also be confirmed by a difference in transient response observed by comparison of the transient EL of the material having a hole-transport property, the material having an electron-transport property, and the mixed film of the materials.

An electron-transport layer 114 contains a substance having an electron-transport property. As the substance having an electron-transport property, it is possible to use any of the above-listed substances having electron-transport properties that can be used as the host material.

Note that the electron-transport layer preferably includes a material having an electron-transport property and an alkali metal, an alkaline earth metal, a compound thereof or a complex thereof. The electron mobility of the material included in the electron-transport layer 114 in the case where the square root of the electric field strength [V/cm] is 600 is preferably higher than or equal to $1\times10^{-7}$ $cm^2/Vs$ and lower than or equal to $5\times10^{-5}$ $cm^2/Vs$. The amount of electrons injected into the light-emitting layer can be controlled by the reduction in the electron-transport property of the electron-transport layer 114, whereby the light-emitting layer can be prevented from having excess electrons. It is particularly preferable that this structure be employed when the hole-injection layer is formed using a composite material that includes a material having a hole-transport property with a relatively deep HOMO level of −5.7 eV or higher and −5.4 eV or lower, in which case the light-emitting device can have a long lifetime. In this case, the material having an electron-transport property preferably has a HOMO level of −6.0 eV or higher. The material having an electron-transport property is preferably an organic compound having an anthracene skeleton and further preferably an organic compound having both an anthracene skeleton and a heterocyclic skeleton. The heterocyclic skeleton is preferably a nitrogen-containing five-membered ring skeleton or a nitrogen-containing six-membered ring skeleton, and particularly preferably a nitrogen-containing five-membered ring skeleton or a nitrogen-containing six-membered ring skeleton including two heteroatoms in the ring, such as a pyrazole ring, an imidazole ring, an oxazole ring, a thiazole ring, a pyrazine ring, a pyrimidine ring, or a pyridazine ring. In addition, it is preferable that the alkali metal, the alkaline earth metal, the compound thereof, or the complex thereof have a 8-hydroxyquinolinato structure. Specific examples include 8-hydroxyquinolinato-lithium (abbreviation: Liq) and 8-hydroxyquinolinato-sodium (abbreviation: Naq). In particular, a complex of a monovalent metal ion, especially a complex of lithium is preferable, and Liq is further preferable. Note that in the case where the 8-hydroxyquinolinato structure is included, a methyl-substituted product (e.g., a 2-methyl-substituted product or a 5-methyl-substituted product) of the alkali metal, the alkaline earth metal, the compound, or the complex can also be used. There is preferably a difference in the concentration (including 0) of the alkali metal, the alkaline earth metal, the compound thereof, or the complex thereof in the electron-transport layer in the thickness direction.

A layer containing an alkali metal, an alkaline earth metal, or a compound thereof such as lithium fluoride (LiF), cesium fluoride (CsF), calcium fluoride ($CaF_2$), or 8-hydroxyquinolinatolithium (Liq) may be provided as the electron-injection layer 115 between the electron-transport layer 114 and the second electrode 102. For example, an electride or a layer that is formed using a substance having an electron-transport property and that includes an alkali metal, an alkaline earth metal, or a compound thereof can be used as the electron-injection layer 115. Examples of the electride include a substance in which electrons are added at high concentration to calcium oxide-aluminum oxide.

Note that as the electron-injection layer 115, it is possible to use a layer containing a substance that has an electron-transport property (preferably an organic compound having a bipyridine skeleton) and contains a fluoride of the alkali metal or the alkaline earth metal at a concentration higher than that at which the electron-injection layer 115 becomes in a microcrystalline state (50 wt % or higher). Since the layer has a low refractive index, a light-emitting device including the layer can have high external quantum efficiency.

Instead of the electron-injection layer 115, a charge-generation layer 116 may be provided (FIG. 1). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a hole-transport material. When a potential is applied to the p-type layer 117, electrons are injected into the electron-transport layer 114 and holes are injected into the second electrode 102 serving as a cathode; thus, the light-emitting device operates. Since the organic compound of one embodiment of the present invention has a low refractive index, using the organic compound for the p-type layer 117 enables the light-emitting device to have high external quantum efficiency.

Note that the charge-generation layer 116 preferably includes an electron-relay layer 118 and/or an electron-injection buffer layer 119 in addition to the p-type layer 117.

The electron-relay layer 118 includes at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the acceptor substance in the p-type layer 117 and the LUMO level of a substance contained in a layer of the electron-transport layer 114 that is in contact with the charge-generation layer 116. As a specific value of the energy level, the LUMO level of the substance having an electron-transport property in the electron-relay layer 118 is preferably higher than or equal to −5.0 eV, more preferably higher than or equal to −5.0 eV and lower than or equal to −3.0 eV Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)). As the substance having an electron-transport property, a material similar to the above-described material for the electron-transport layer 114 can be used.

For the second electrode 102, a metal, an alloy, an electrically conductive compound, or a mixture thereof each having a low work function (specifically, lower than or equal to 3.8 eV) or the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys containing these elements (e.g., MgAg and AlLi), rare earth metals such as europium (Eu) and ytterbium (Yb), and alloys containing these rare earth metals. However, when the electron-injection layer is provided between the second electrode 102 and the electron-transport layer, for the second electrode 102, a variety of conductive materials such as Al, Ag, ITO, or indium oxide-tin oxide containing silicon or silicon oxide can be used regardless of the work function. Films of these conductive materials can be formed by a dry process such as a vacuum evaporation method or a sputtering method, an ink-jet method, a spin coating method, or the like. Alternatively, a wet process using a sol-gel method or a wet process using a paste of a metal material may be employed.

Furthermore, any of a variety of methods can be used for forming the EL layer 103, regardless of a dry method or a wet method. For example, a vacuum evaporation method, a gravure printing method, an offset printing method, a screen printing method, an ink-jet method, a spin coating method, or the like may be used.

Different methods may be used to form the electrodes or the layers described above.

The structure of the layers provided between the first electrode 101 and the second electrode 102 is not limited to the above-described structure. Preferably, a light-emitting region where holes and electrons recombine is positioned away from the first electrode 101 and the second electrode 102 so as to prevent quenching due to the proximity of the light-emitting region and a metal used for electrodes and carrier-injection layers.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer closer to the recombination region in the light-emitting layer 113, are formed using a substance having a wider band gap than the light-emitting material of the light-emitting layer or the light-emitting material included in the light-emitting layer.

Next, an embodiment of a light-emitting device with a structure in which a plurality of light-emitting units are stacked (this type of light-emitting device is also referred to as a stacked or tandem light-emitting device) is described with reference to FIG. 1C. This light-emitting device includes a plurality of light-emitting units between an anode and a cathode. One light-emitting unit has substantially the same structure as the EL layer 103 illustrated in FIG. 1A. In other words, the light-emitting device illustrated in FIG. 1A or 1B includes a single light-emitting unit, and the light-emitting device illustrated in FIG. 1C includes a plurality of light-emitting units.

Figure 1B:
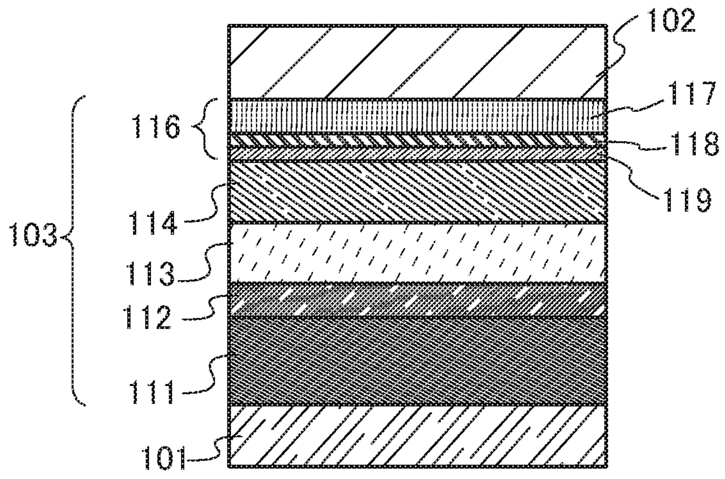
Figure 1C:
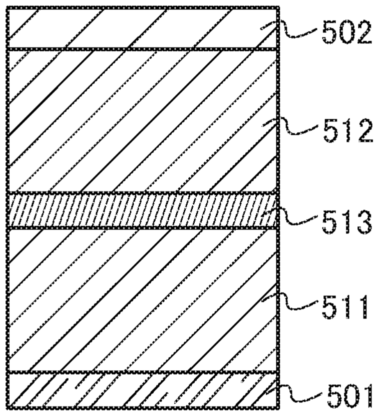

In FIG. 1C, a first light-emitting unit 511 and a second light-emitting unit 512 are stacked between an anode 501 and a cathode 502, and a charge-generation layer 513 is provided between the first light-emitting unit 511 and the second light-emitting unit 512. The anode 501 and the cathode 502 correspond, respectively, to the first electrode 101 and the second electrode 102 illustrated in FIG. 1A, and the materials given in the description for FIG. 1A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the anode 501 and the cathode 502. That is, in FIG. 1C, the charge-generation layer 513 injects electrons into the first light-emitting unit 511 and holes into the second light-emitting unit 512 when a voltage is applied so that the potential of the anode becomes higher than the potential of the cathode.

The charge-generation layer 513 preferably has a structure similar to that of the charge-generation layer 116 described with reference to FIG. 1B. A composite material of an organic compound and a metal oxide has an excellent carrier-injection property and an excellent carrier-transport property; thus, low-voltage driving and low-current driving can be achieved. In the case where the anode-side surface of a light-emitting unit is in contact with the charge-generation layer 513, the charge-generation layer 513 can also function as a hole-injection layer of the light-emitting unit; therefore, a hole-injection layer is not necessarily provided in the light-emitting unit.

In the case where the charge-generation layer 513 includes the electron-injection buffer layer 119, the electron-injection buffer layer 119 functions as the electron-injection layer in the light-emitting unit on the anode side and thus, an electron-injection layer is not necessarily formed in the light-emitting unit on the anode side.

The light-emitting device having two light-emitting units is described with reference to FIG. 1C; however, one embodiment of the present invention can also be applied to a light-emitting device in which three or more light-emitting units are stacked. With a plurality of light-emitting units partitioned by the charge-generation layer 513 between a pair of electrodes as in the light-emitting device of this embodiment, it is possible to provide a long-life element which can emit light with high luminance at a low current density. A light-emitting apparatus which can be driven at a low voltage and has low power consumption can be provided.

When the emission colors of the light-emitting units are different, light emission of a desired color can be obtained from the light-emitting device as a whole. For example, in a light-emitting device having two light-emitting units, the emission colors of the first light-emitting unit may be red and green and the emission color of the second light-emitting unit may be blue, so that the light-emitting device can emit white light as the whole.

The above-described layers and electrodes such as the EL layer 103, the first light-emitting unit 511, the second light-emitting unit 512, and the charge-generation layer can be formed by a method such as an evaporation method (including a vacuum evaporation method), a droplet discharge method (also referred to as an ink-jet method), a coating method, or a gravure printing method. A low molecular material, a middle molecular material (including an oligomer and a dendrimer), or a high molecular material may be included in the layers and electrodes.

Embodiment 3

In this embodiment, a light-emitting apparatus including the light-emitting device described in Embodiment 2 is described.

Figure 2A:
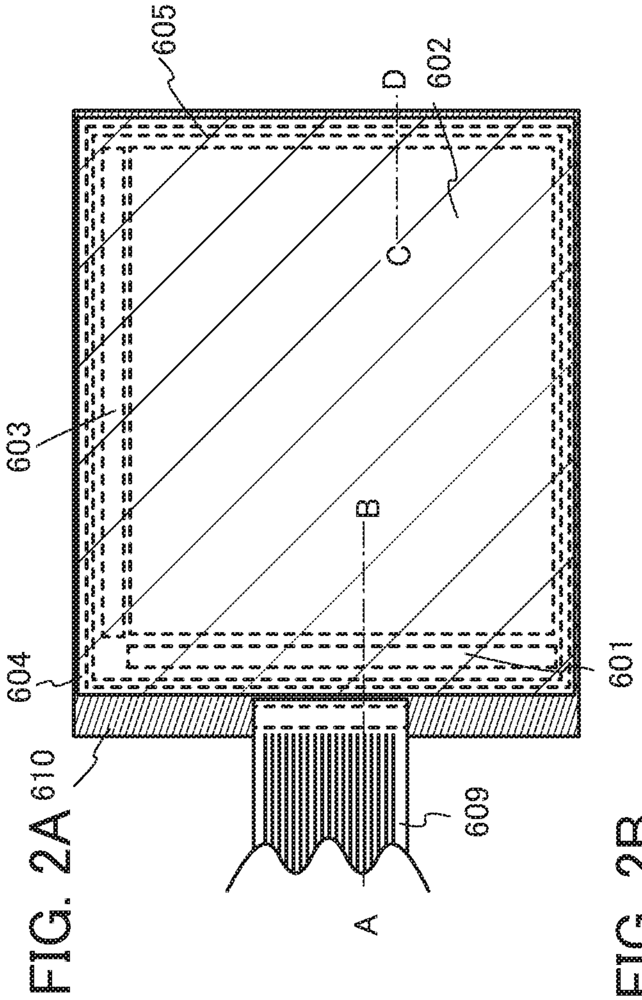
FIGS. 2A and 2B are conceptual views of an active matrix light-emitting apparatus.
Figure 2B:
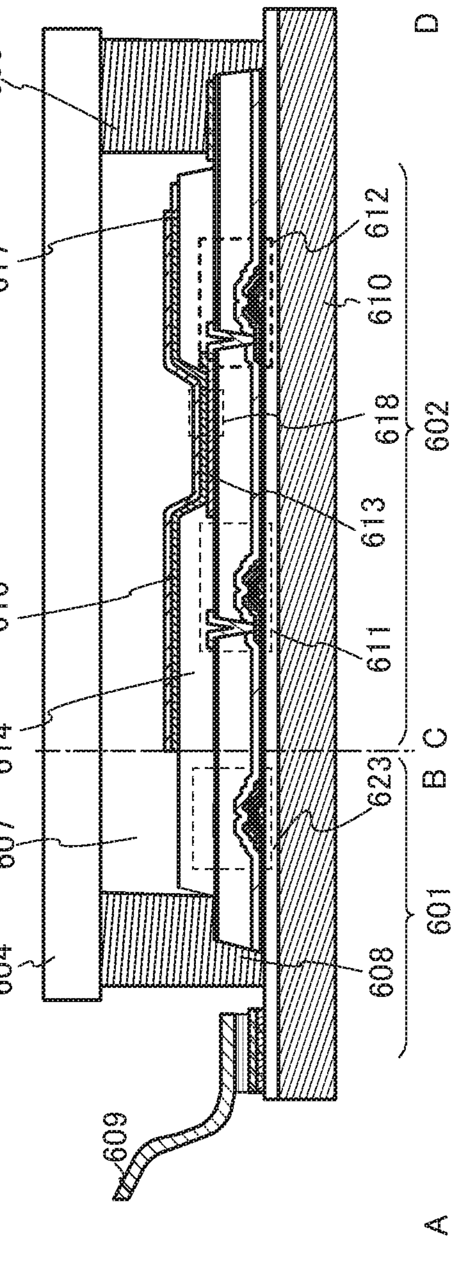

In this embodiment, the light-emitting apparatus manufactured using the light-emitting device described in Embodiment 2 is described with reference to FIGS. 2A and 2B. Note that FIG. 2A is a top view of the light-emitting apparatus and FIG. 2B is a cross-sectional view taken along the lines A-B and C-D in FIG. 2A. This light-emitting apparatus includes a driver circuit portion (source line driver circuit) 601, a pixel portion 602, and a driver circuit portion (gate line driver circuit) 603, which are to control light emission of a light-emitting device and illustrated with dotted lines. Reference numeral 604 denotes a sealing substrate; 605, a sealing material; and 607, a space surrounded by the sealing material 605.

Reference numeral 608 denotes a lead wiring for transmitting signals to be input to the source line driver circuit 601 and the gate line driver circuit 603 and receiving signals such as a video signal, a clock signal, a start signal, and a reset signal from a flexible printed circuit (FPC) 609 serving as an external input terminal. Although only the FPC is illustrated here, a printed wiring board (PWB) may be attached to the FPC. The light-emitting apparatus in the present specification includes, in its category, not only the light-emitting apparatus itself but also the light-emitting apparatus provided with the FPC or the PWB.

Next, a cross-sectional structure is described with reference to FIG. 2B. The driver circuit portions and the pixel portion are formed over an element substrate 610; FIG. 2B shows the source line driver circuit 601, which is a driver circuit portion, and one pixel in the pixel portion 602.

The element substrate 610 may be a substrate containing glass, quartz, an organic resin, a metal, an alloy, or a semiconductor or a plastic substrate formed of fiber reinforced plastic (FRP), poly(vinyl fluoride) (PVF), polyester, or acrylic resin.

The structure of transistors used in pixels and driver circuits is not particularly limited. For example, inverted staggered transistors may be used, or staggered transistors may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as an In—Ga—Zn-based metal oxide, may be used.

There is no particular limitation on the crystallinity of a semiconductor material used for the transistors, and an amorphous semiconductor or a semiconductor having crystallinity (a microcrystalline semiconductor, a polycrystalline semiconductor, a single crystal semiconductor, or a semiconductor partly including crystal regions) may be used. It is preferable that a semiconductor having crystallinity be used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. When an oxide semiconductor having a wider band gap than silicon is used, off-state current of the transistors can be reduced.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such materials for the semiconductor layer makes it possible to provide a highly reliable transistor in which a change in the electrical characteristics is suppressed.

Charge accumulated in a capacitor through a transistor including the above-described semiconductor layer can be held for a long time because of the low off-state current of the transistor. When such a transistor is used in a pixel, operation of a driver circuit can be stopped while a gray scale of an image displayed in each display region is maintained. As a result, an electronic device with extremely low power consumption can be obtained.

For stable characteristics of the transistor, a base film is preferably provided. The base film can be formed with a single-layer structure or a stacked-layer structure using an inorganic insulating film such as a silicon oxide film, a silicon nitride film, a silicon oxynitride film, or a silicon nitride oxide film. The base film can be formed by a sputtering method, a chemical vapor deposition (CVD) method (e.g., a plasma CVD method, a thermal CVD method, or a metal organic CVD (MOCVD) method), an atomic layer deposition (ALD) method, a coating method, a printing method, or the like. Note that the base film is not necessarily provided.

Note that an FET 623 is illustrated as a transistor formed in the driver circuit portion 601. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit is not necessarily formed over the substrate, and the driver circuit can be formed outside, not over the substrate.

The pixel portion 602 includes a plurality of pixels including a switching FET 611, a current controlling FET 612, and a first electrode 613 electrically connected to a drain of the current controlling FET 612. One embodiment of the present invention is not limited to the structure. The pixel portion 602 may include three or more FETs and a capacitor in combination.

Note that to cover an end portion of the first electrode 613, an insulator 614 is formed, for which a positive photosensitive acrylic resin film is used here.

In order to improve coverage with an EL layer or the like which is formed later, the insulator 614 is formed to have a curved surface with curvature at its upper or lower end portion. For example, in the case where positive photosensitive acrylic resin is used as a material of the insulator 614, only the upper end portion of the insulator 614 preferably has a curved surface with a curvature radius (0.2 μm to 3 μm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. The stacked-layer structure enables low wiring resistance, favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 2. As another material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, and Ca, or an alloy or a compound thereof, such as MgAg, MgIn, and AlLi) is preferably used. In the case where light generated in the EL layer 616 is transmitted through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting device is formed with the first electrode 613, the EL layer 616, and the second electrode 617. The light-emitting device is the light-emitting device described in Embodiment 2. In the light-emitting apparatus of this embodiment, the pixel portion, which includes a plurality of light-emitting devices, may include both the light-emitting device described in Embodiment 2 and a light-emitting device having a different structure.

The sealing substrate 604 is attached to the element substrate 610 with the sealing material 605, so that a light-emitting device 618 is provided in the space 607 surrounded by the element substrate 610, the sealing substrate 604, and the sealing material 605. The space 607 may be filled with a filler, or may be filled with an inert gas (such as nitrogen or argon), or the sealing material. It is preferable that the sealing substrate be provided with a recessed portion and a drying agent be provided in the recessed portion, in which case deterioration due to influence of moisture can be suppressed.

An epoxy-based resin or glass frit is preferably used for the sealing material 605. It is preferable that such a material not be permeable to moisture or oxygen as much as possible. As the sealing substrate 604, a glass substrate, a quartz substrate, or a plastic substrate formed of fiber reinforced plastic (FRP), poly(vinyl fluoride) (PVF), polyester, and acrylic resin can be used.

Although not illustrated in FIGS. 2A and 2B, a protective film may be provided over the second electrode. As the protective film, an organic resin film or an inorganic insulating film may be formed. The protective film may be formed so as to cover an exposed portion of the sealing material 605. The protective film may be provided so as to cover surfaces and side surfaces of the pair of substrates and exposed side surfaces of a sealing layer, an insulating layer, and the like.

The protective film can be formed using a material through which an impurity such as water does not permeate easily. Thus, diffusion of an impurity such as water from the outside into the inside can be effectively suppressed.

As a material of the protective film, an oxide, a nitride, a fluoride, a sulfide, a ternary compound, a metal, a polymer, or the like can be used. For example, the material may contain aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, aluminum nitride, hafnium nitride, silicon nitride, tantalum nitride, titanium nitride, niobium nitride, molybdenum nitride, zirconium nitride, gallium nitride, a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method with favorable step coverage. One such method is an atomic layer deposition (ALD) method. A material that can be deposited by an ALD method is preferably used for the protective film. A dense protective film having reduced defects such as cracks or pinholes or a uniform thickness can be formed by an ALD method. Furthermore, damage caused to a process member in forming the protective film can be reduced.

By an ALD method, a uniform protective film with few defects can be formed even on, for example, a surface with a complex uneven shape or upper, side, and lower surfaces of a touch panel.

As described above, the light-emitting apparatus manufactured using the light-emitting device described in Embodiment 2 can be obtained.

The light-emitting apparatus in this embodiment is manufactured using the light-emitting device described in Embodiment 2 and thus can have favorable characteristics. Specifically, since the light-emitting device described in Embodiment 2 has high emission efficiency, the light-emitting apparatus can achieve low power consumption.

Figure 3A:
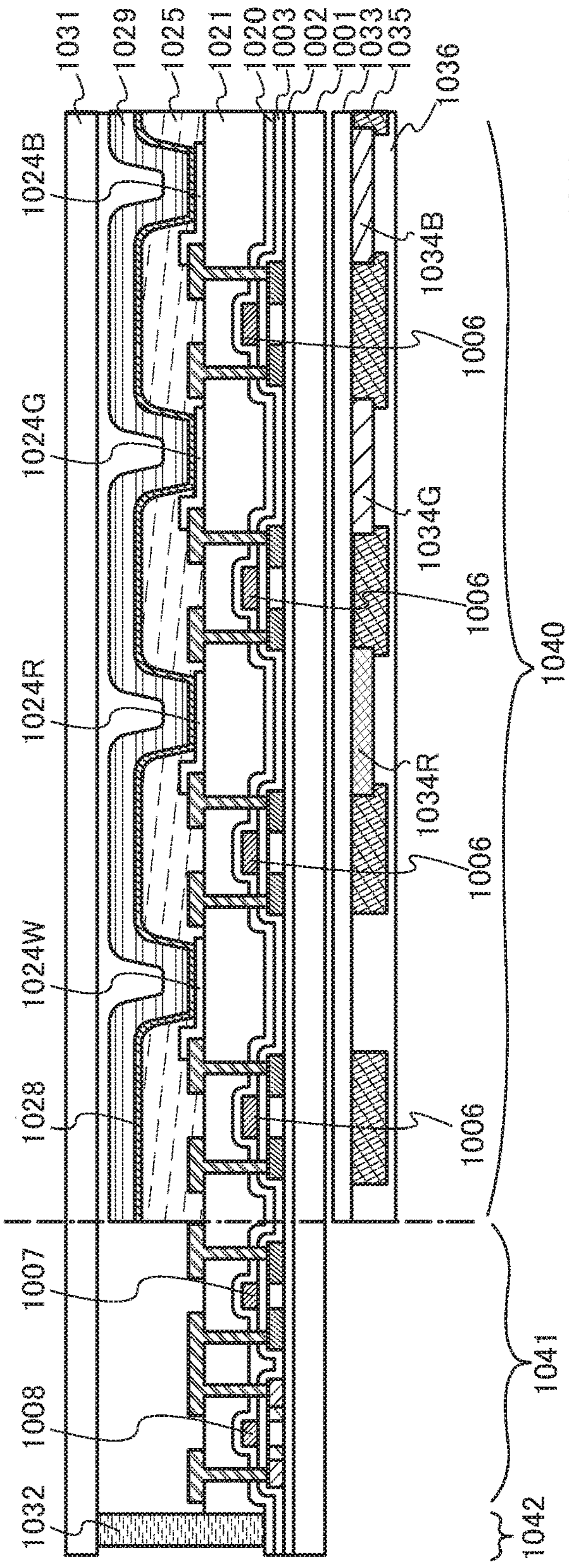
FIGS. 3A and 3B are conceptual views of an active matrix light-emitting apparatus.
Figure 3B:
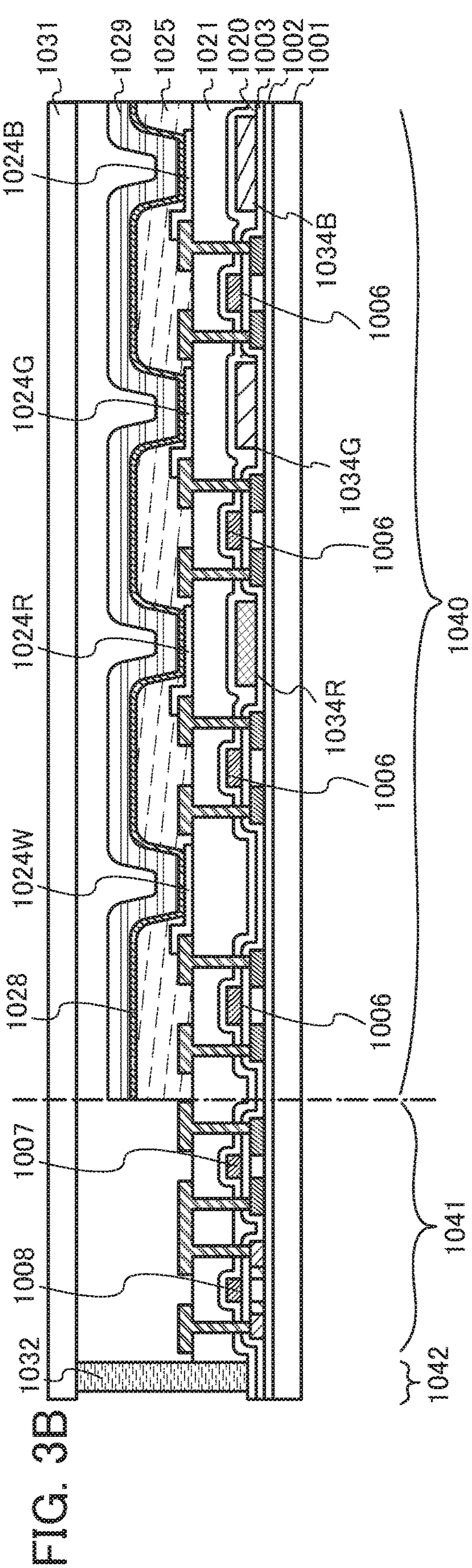

FIGS. 3A and 3B each illustrate an example of a light-emitting apparatus in which full color display is achieved by formation of a light-emitting device exhibiting white light emission and with the use of coloring layers (color filters) and the like. In FIG. 3A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting devices, a partition 1025, an EL layer 1028, a second electrode 1029 of the light-emitting devices, a sealing substrate 1031, a sealing material 1032, and the like are illustrated.

In FIG. 3A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is aligned and fixed to the substrate 1001. Note that the coloring layers and the black matrix 1035 are covered with an overcoat layer 1036. In FIG. 3A, light emitted from part of the light-emitting layer does not pass through the coloring layers, while light emitted from the other part of the light-emitting layer passes through the coloring layers. Since light which does not pass through the coloring layers is white and light which passes through any one of the coloring layers is red, green, or blue, an image can be displayed using pixels of the four colors.

FIG. 3B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 4:
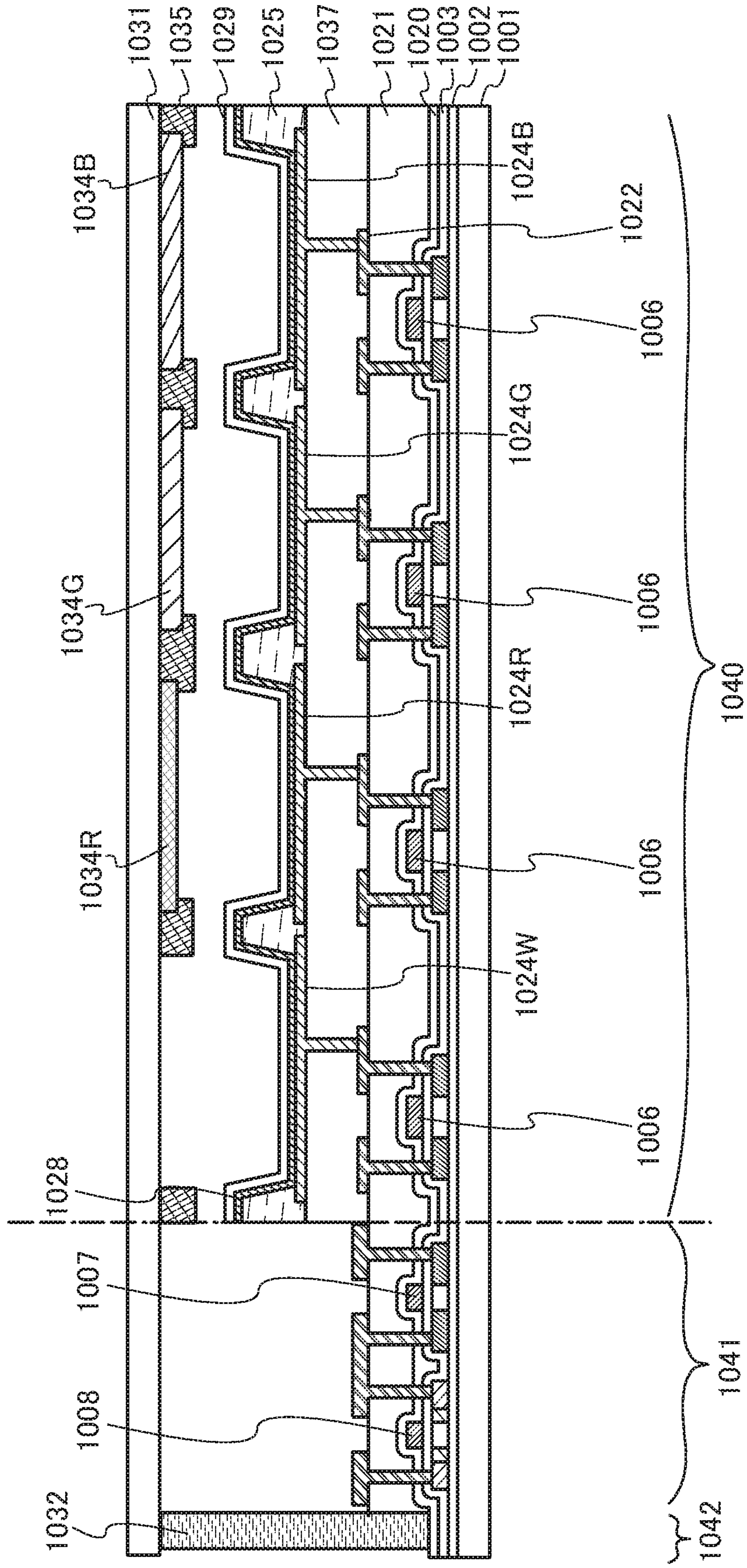
FIG. 4 is a conceptual view of an active matrix light-emitting apparatus.

The above-described light-emitting apparatus is a light-emitting apparatus having a structure in which light is extracted from the substrate 1001 side where FETs are formed (a bottom emission structure), but may be a light-emitting apparatus having a structure in which light is extracted from the sealing substrate 1031 side (a top emission structure). FIG. 4 is a cross-sectional view of a light-emitting apparatus having a top emission structure. In this case, a substrate which does not transmit light can be used as the substrate 1001. The process up to the step of forming a connection electrode which connects the FET and the anode of the light-emitting device is performed in a manner similar to that of the light-emitting apparatus having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any of other known materials.

The first electrodes 1024W, 1024R, 1024G, and 1024B of the light-emitting devices each serve as an anode here, but may serve as a cathode. Furthermore, in the case of a light-emitting apparatus having a top emission structure as illustrated in FIG. 4, the first electrodes are preferably reflective electrodes. The EL layer 1028 is formed to have a structure similar to the structure of the EL layer 103, which is described in Embodiment 2, with which white light emission can be obtained.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031. Although an example in which full color display is performed using four colors of red, green, blue, and white is shown here, there is no particular limitation and full color display using four colors of red, yellow, green, and blue or three colors of red, green, and blue may be performed.

In the light-emitting apparatus having a top emission structure, a microcavity structure can be favorably employed. A light-emitting device with a microcavity structure is formed with the use of a reflective electrode as the first electrode and a semi-transmissive and semi-reflective electrode as the second electrode. The light-emitting device with a microcavity structure includes at least an EL layer between the reflective electrode and the semi-transmissive and semi-reflective electrode, which includes at least a light-emitting layer serving as a light-emitting region.

Note that the reflective electrode has a visible light reflectivity of 40% to 10000, preferably 70% to 100%, and a resistivity of $1\times10^{-2}$ Ωcm or lower. In addition, the semi-transmissive and semi-reflective electrode has a visible light reflectivity of 20% to 80%, preferably 40% to 70%, and a resistivity of $1\times10^{-2}$ Ωcm or lower.

Light emitted from the light-emitting layer included in the EL layer is reflected and resonated by the reflective electrode and the semi-transmissive and semi-reflective electrode.

In the light-emitting device, by changing thicknesses of the transparent conductive film, the composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light). For this reason, the optical path length between the reflective electrode and the light-emitting layer is preferably adjusted to $(2n-1)\lambda/4$ (n is a natural number of 1 or larger and λ is a wavelength of color to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer. The tandem light-emitting device described above may be combined with a plurality of EL layers; for example, a light-emitting device may have a structure in which a plurality of EL layers are provided, a charge-generation layer is provided between the EL layers, and each EL layer includes a plurality of light-emitting layers or a single light-emitting layer.

With the microcavity structure, emission intensity with a specific wavelength in the front direction can be increased, whereby power consumption can be reduced. Note that in the case of a light-emitting apparatus which displays images with subpixels of four colors, red, yellow, green, and blue, the light-emitting apparatus can have favorable characteristics because the luminance can be increased owing to yellow light emission and each subpixel can employ a microcavity structure suitable for wavelengths of the corresponding color.

The light-emitting apparatus in this embodiment is manufactured using the light-emitting device described in Embodiment 2 and thus can have favorable characteristics. Specifically, since the light-emitting device described in Embodiment 2 has high emission efficiency, the light-emitting apparatus can achieve low power consumption.

Figure 5A:
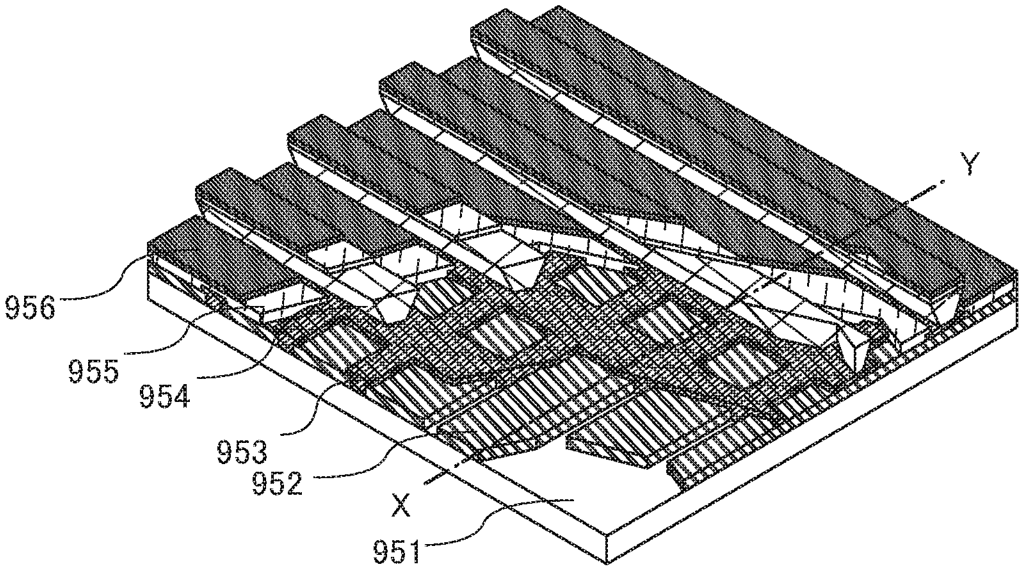
FIGS. 5A and 5B are conceptual views of a passive matrix light-emitting apparatus.
Figure 5B:
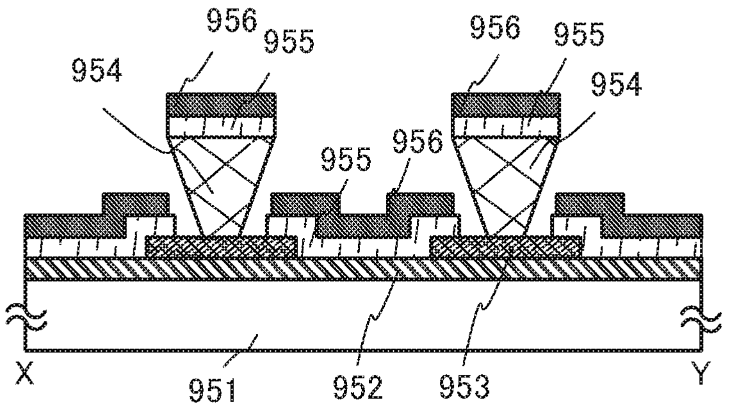

An active matrix light-emitting apparatus is described above, whereas a passive matrix light-emitting apparatus is described below. FIGS. 5A and 5B illustrate a passive matrix light-emitting apparatus manufactured using the present invention. Note that FIG. 5A is a perspective view of the light-emitting apparatus, and FIG. 5B is a cross-sectional view taken along the line X-Y in FIG. 5A. In FIGS. 5A and 5B, over a substrate 951, an EL layer 955 is provided between an electrode 952 and an electrode 956. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition layer 954 is trapezoidal, and the lower side (a side of the trapezoid which is parallel to the surface of the insulating layer 953 and is in contact with the insulating layer 953) is shorter than the upper side (a side of the trapezoid which is parallel to the surface of the insulating layer 953 and is not in contact with the insulating layer 953). The partition layer 954 thus provided can prevent defects in the light-emitting device due to static electricity or others. The passive-matrix light-emitting apparatus also includes the light-emitting device described in Embodiment 2; thus, the light-emitting apparatus can have high reliability or low power consumption.

Since many minute light-emitting devices arranged in a matrix in the light-emitting apparatus described above can each be controlled, the light-emitting apparatus can be suitably used as a display device for displaying images.

This embodiment can be freely combined with any of the other embodiments.

Embodiment 4

Figure 6A:
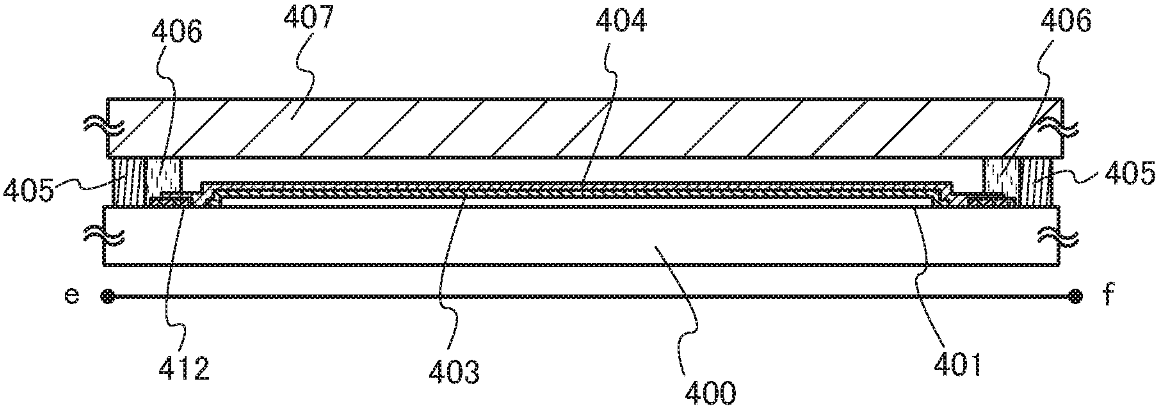
FIGS. 6A and 6B illustrate a lighting device.
Figure 6B:
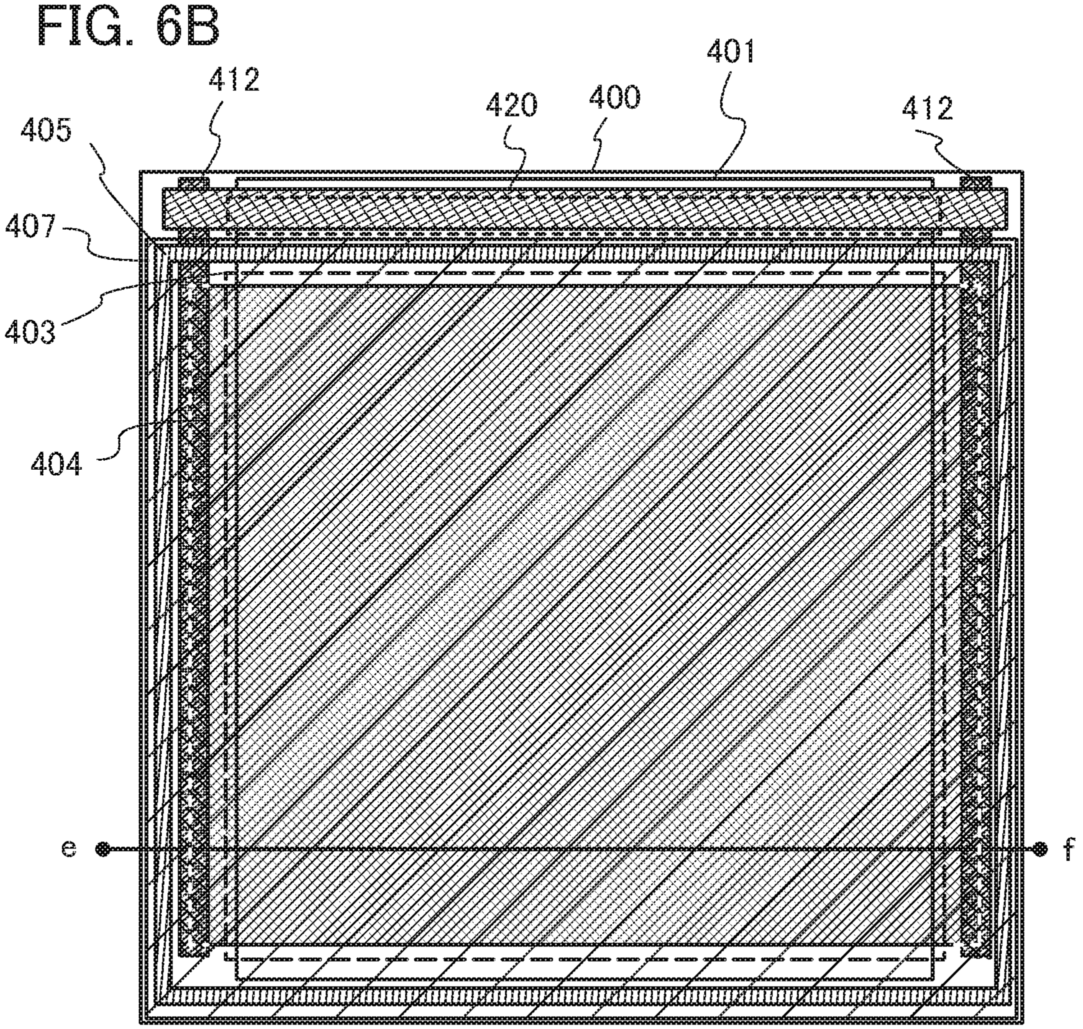

In this embodiment, an example in which the light-emitting device described in Embodiment 2 is used for a lighting device will be described with reference to FIGS. 6A and 6B. FIG. 6B is a top view of the lighting device, and FIG. 6A is a cross-sectional view taken along the line e-f in FIG. 6B.

In the lighting device in this embodiment, a first electrode 401 is formed over a substrate 400 which is a support and has a light-transmitting property. The first electrode 401 corresponds to the first electrode 101 in Embodiment 1. When light is extracted through the first electrode 401 side, the first electrode 401 is formed using a material having a light-transmitting property.

A pad 412 for applying voltage to a second electrode 404 is provided over the substrate 400.

An EL layer 403 is formed over the first electrode 401. The structure of the EL layer 403 corresponds to, for example, the structure of the EL layer 103 in Embodiment 1, or the structure in which the light-emitting units 511 and 512 and the charge-generation layer 513 are combined. Refer to the descriptions for the structure.

The second electrode 404 is formed to cover the EL layer 403. The second electrode 404 corresponds to the second electrode 102 in Embodiment 1. The second electrode 404 is formed using a material having high reflectance when light is extracted through the first electrode 401 side. The second electrode 404 is connected to the pad 412, whereby voltage is applied.

As described above, the lighting device described in this embodiment includes a light-emitting device including the first electrode 401, the EL layer 403, and the second electrode 404. Since the light-emitting device is a light-emitting device with high emission efficiency, the lighting device in this embodiment can be a lighting device having low power consumption.

The substrate 400 provided with the light-emitting device having the above structure is fixed to a sealing substrate 407 with sealing materials 405 and 406 and sealing is performed, whereby the lighting device is completed. It is possible to use only either the sealing material 405 or the sealing material 406. The inner sealing material 406 (not shown in FIG. 6B) can be mixed with a desiccant which enables moisture to be adsorbed, increasing reliability.

When parts of the pad 412 and the first electrode 401 are extended to the outside of the sealing materials 405 and 406, the extended parts can serve as external input terminals. An IC chip 420 mounted with a converter or the like may be provided over the external input terminals.

The lighting device described in this embodiment includes as an EL element the light-emitting device described in Embodiment 2; thus, the light-emitting apparatus can consume less power.

Embodiment 5

In this embodiment, examples of electronic devices each including the light-emitting device described in Embodiment 2 will be described. The light-emitting device described in Embodiment 2 has high emission efficiency and low power consumption. As a result, the electronic devices described in this embodiment can each include a light-emitting portion having low power consumption.

Examples of the electronic device including the above light-emitting device include television devices (also referred to as TV or television receivers), monitors for computers and the like, digital cameras, digital video cameras, digital photo frames, cellular phones (also referred to as mobile phones or mobile phone devices), portable game machines, portable information terminals, audio playback devices, and large game machines such as pachinko machines. Specific examples of these electronic devices are shown below.

Figure 7A:
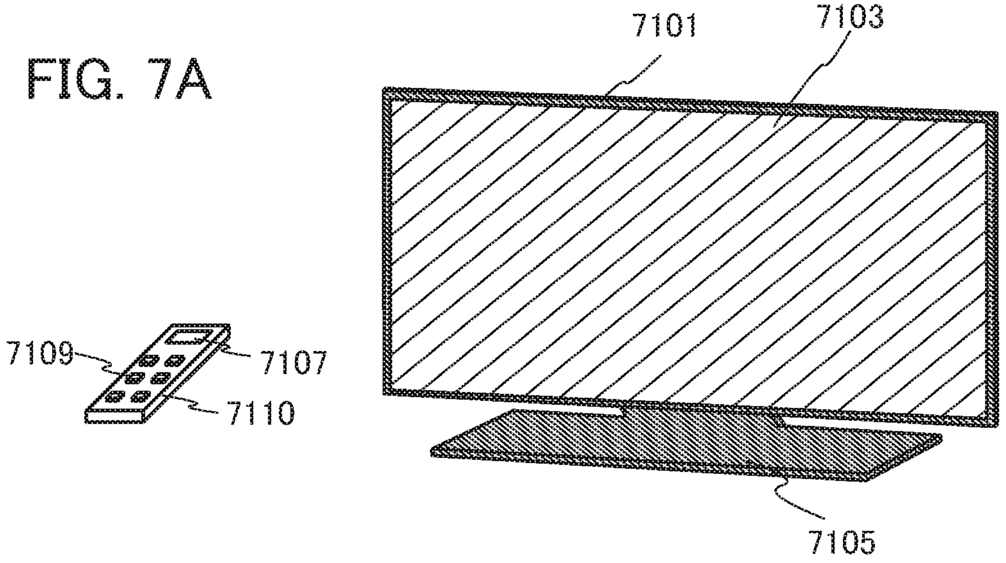
Figure 7A:
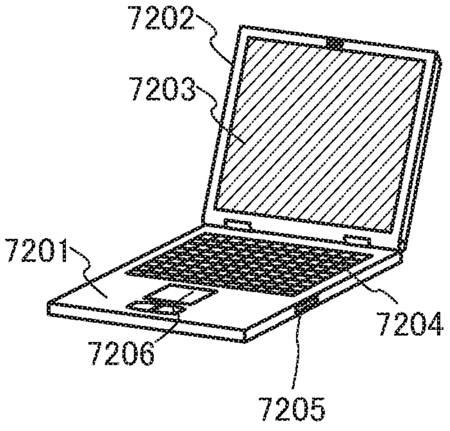
Figure 7A:
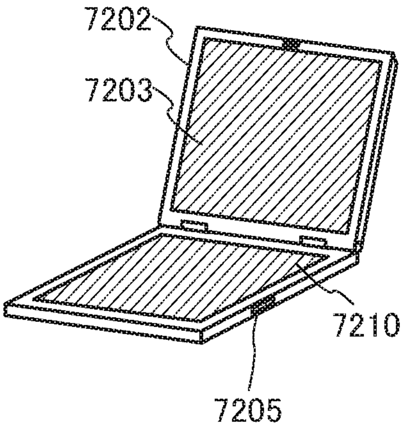

FIG. 7A illustrates an example of a television device. In the television device, a display portion 7103 is incorporated in a housing 7101. Here, the housing 7101 is supported by a stand 7105. Images can be displayed on the display portion 7103, and in the display portion 7103, the light-emitting devices described in Embodiment 2 are arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, a general television broadcast can be received. Moreover, when the television device is connected to a communication network with or without wires via the modem, one-way (from a sender to a receiver) or two-way (between a sender and a receiver or between receivers) data communication can be performed.

FIG. 7B1 illustrates a computer, which includes a main body 7201, a housing 7202, a display portion 7203, a keyboard 7204, an external connection port 7205, a pointing device 7206, and the like. Note that this computer is manufactured using the light-emitting devices described in Embodiment 2 and arranged in a matrix in the display portion 7203. The computer illustrated in FIG. 7B1 may have a structure illustrated in FIG. 7B2. A computer illustrated in FIG. 7B2 is provided with a second display portion 7210 instead of the keyboard 7204 and the pointing device 7206. The second display portion 7210 is a touch panel, and input operation can be performed by touching display for input on the second display portion 7210 with a finger or a dedicated pen. The second display portion 7210 can also display images other than the display for input. The display portion 7203 may also be a touch panel. Connecting the two screens with a hinge can prevent troubles; for example, the screens can be prevented from being cracked or broken while the computer is being stored or carried.

Figure 7C:
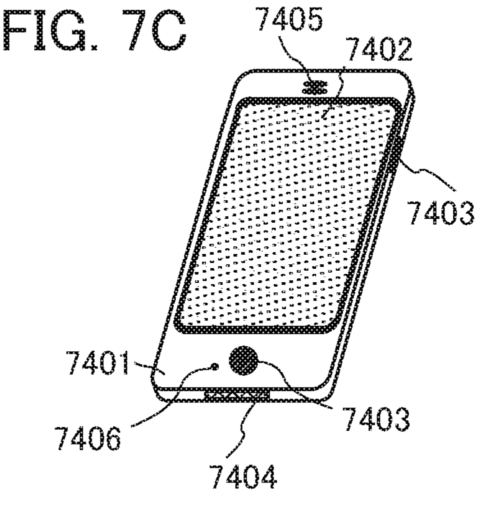

FIG. 7C illustrates an example of a portable terminal. A cellular phone is provided with a display portion 7402 incorporated in a housing 7401, operation buttons 7403, an external connection port 7404, a speaker 7405, a microphone 7406, and the like. Note that the cellular phone has the display portion 7402 including the light-emitting devices described in Embodiment 2 and arranged in a matrix.

When the display portion 7402 of the portable terminal illustrated in FIG. 7C is touched with a finger or the like, data can be input into the portable terminal. In this case, operations such as making a call and creating an e-mail can be performed by touching the display portion 7402 with a finger or the like.

The display portion 7402 has mainly three screen modes. The first mode is a display mode mainly for displaying images. The second mode is an input mode mainly for inputting information such as text. The third mode is a display-and-input mode in which the two modes, the display mode and the input mode, are combined.

For example, in the case of making a call or creating an e-mail, a text input mode mainly for inputting text is selected for the display portion 7402 so that text displayed on the screen can be input. In this case, it is preferable to display a keyboard or number buttons on almost the entire screen of the display portion 7402.

When a sensing device including a sensor such as a gyroscope or an acceleration sensor for detecting inclination is provided inside the portable terminal, display on the screen of the display portion 7402 can be automatically changed in direction by determining the orientation of the portable terminal (whether the portable terminal is placed horizontally or vertically).

The screen modes are switched by touching the display portion 7402 or operating the operation buttons 7403 of the housing 7401. Alternatively, the screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal sensed by an optical sensor in the display portion 7402 is sensed, the screen mode may be controlled so as to be switched from the input mode to the display mode.

The display portion 7402 may also function as an image sensor. For example, an image of a palm print, a fingerprint, or the like is taken when the display portion 7402 is touched with the palm or the finger, whereby personal authentication can be performed. Furthermore, by providing a backlight or a sensing light source which emits near-infrared light in the display portion, an image of a finger vein, a palm vein, or the like can be taken.

Note that the structure described in this embodiment can be combined with any of the structures described in Embodiments 1 to 4 as appropriate.

As described above, the application range of the light-emitting apparatus having the light-emitting device described in Embodiment 2 is wide so that this light-emitting apparatus can be applied to electronic devices in a variety of fields. By using the light-emitting device described in Embodiment 2, an electronic device with low power consumption can be obtained.

Figure 8A:
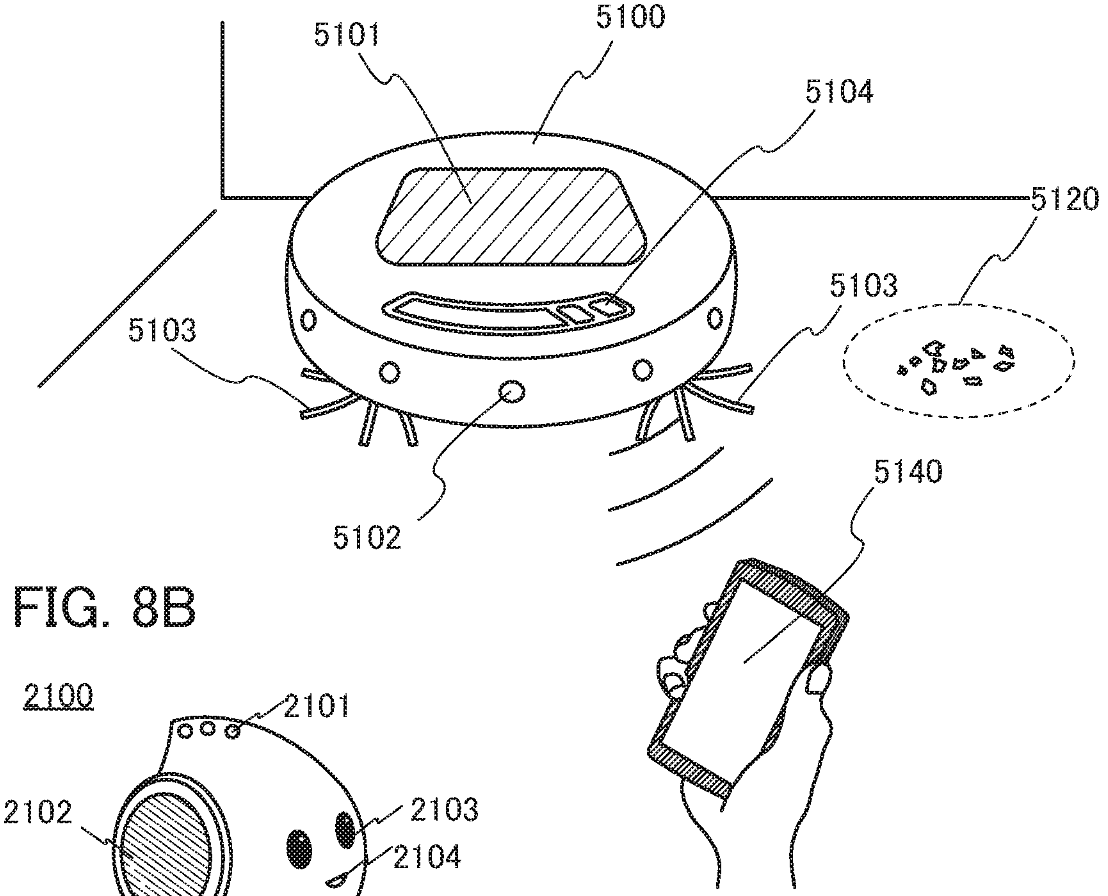
FIGS. 8A to 8C illustrate electronic devices.

FIG. 8A is a schematic view illustrating an example of a cleaning robot.

A cleaning robot 5100 includes a display 5101 on its top surface, a plurality of cameras 5102 on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. The cleaning robot 5100 has a wireless communication means.

The cleaning robot 5100 is self-propelled, detects dust 5120, and sucks up the dust through the inlet provided on the bottom surface.

The cleaning robot 5100 can determine whether there is an obstacle such as a wall, furniture, or a step by analyzing images taken by the cameras 5102. When the cleaning robot 5100 detects an object that is likely to be caught in the brush 5103 (e.g., a wire) by image analysis, the rotation of the brush 5103 can be stopped.

The display 5101 can display the remaining capacity of a battery, the amount of collected dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic device 5140 such as a smartphone. The portable electronic device 5140 can display images taken by the cameras 5102. Accordingly, an owner of the cleaning robot 5100 can monitor his/her room even when the owner is not at home. The owner can also check the display on the display 5101 by the portable electronic device 5140 such as a smartphone.

The light-emitting apparatus of one embodiment of the present invention can be used for the display 5101.

Figure 8B:
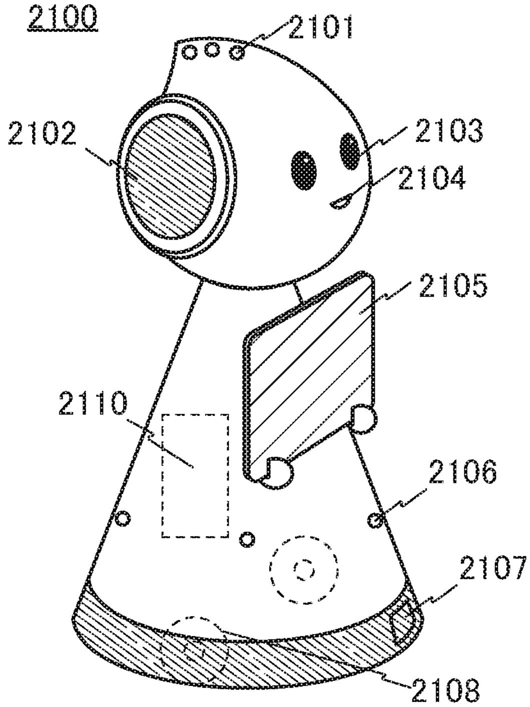

A robot 2100 illustrated in FIG. 8B includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus of one embodiment of the present invention can be used for the display 2105.

Figure 8C:
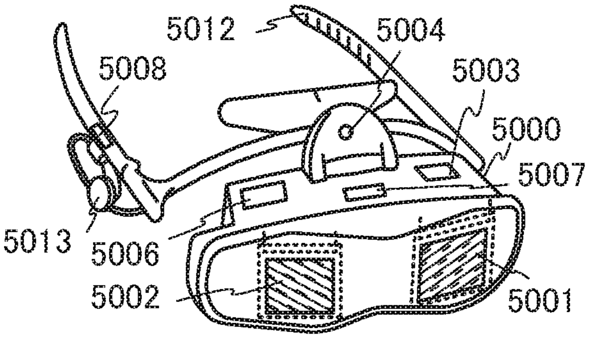

FIG. 8C illustrates an example of a goggle-type display. The goggle-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 5008, a display portion 5002, a support 5012, and an earphone 5013.

The light-emitting apparatus of one embodiment of the present invention can be used for the display portion 5001 and the display portion 5002.

Figure 9:
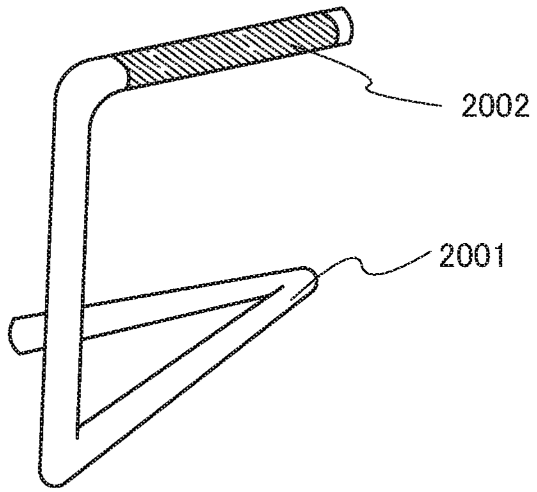
FIG. 9 illustrates a lighting device.

FIG. 9 illustrates an example in which the light-emitting device described in Embodiment 2 is used for a table lamp which is a lighting device. The table lamp illustrated in FIG. 9 includes a housing 2001 and a light source 2002, and the lighting device described in Embodiment 3 may be used for the light source 2002.

Figure 10:
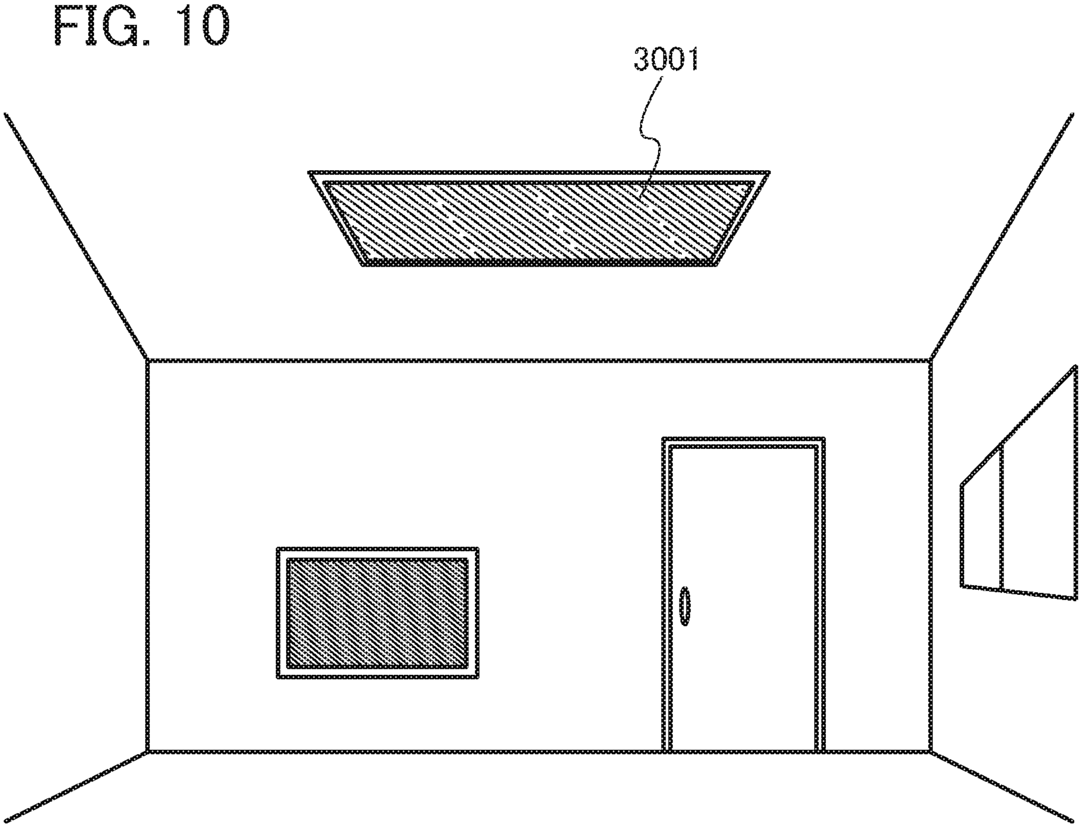
FIG. 10 illustrates alighting device.

FIG. 10 illustrates an example in which the light-emitting device described in Embodiment 2 is used for an indoor lighting device 3001. Since the light-emitting device described in Embodiment 2 has high emission efficiency, the lighting device can have low power consumption. Furthermore, since the light-emitting device described in Embodiment 2 can have a large area, the light-emitting device can be used for a large-area lighting device. Furthermore, since the light-emitting device described in Embodiment 2 is thin, the light-emitting device can be used for a lighting device having a reduced thickness.

Figure 11:
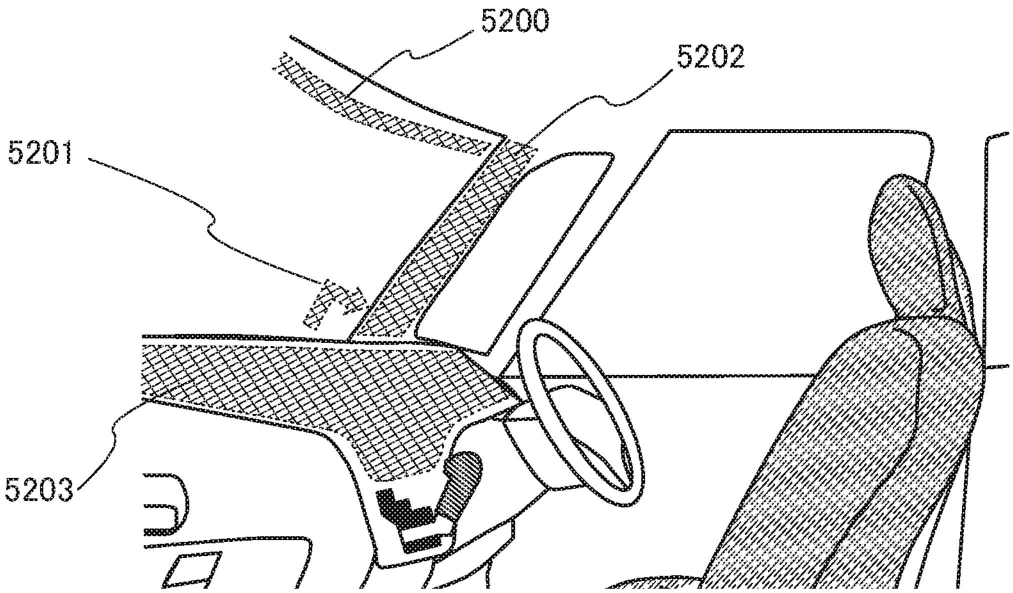
FIG. 11 illustrates in-vehicle display devices and lighting devices.

The light-emitting device described in Embodiment 2 can also be used for an automobile windshield or an automobile dashboard. FIG. 11 illustrates one mode in which the light-emitting devices described in Embodiment 2 are used for an automobile windshield and an automobile dashboard. Display regions 5200 to 5203 each include the light-emitting device described in Embodiment 2.

The display regions 5200 and 5201 are display devices which are provided in the automobile windshield and in which light-emitting devices each of which is described in Embodiment 2 are incorporated. The light-emitting devices described in Embodiment 2 can be formed into what is called a see-through display device, through which the opposite side can be seen, by including a first electrode and a second electrode formed of electrodes having a light-transmitting property. Such see-through display devices can be provided even in the automobile windshield without hindering the view. In the case where a driving transistor or the like is provided, a transistor having a light-transmitting property, such as an organic transistor including an organic semiconductor material or a transistor including an oxide semiconductor, is preferably used.

A display device incorporating the light-emitting device described in Embodiment 2 is provided in the display region 5202 in a pillar portion. The display region 5202 can compensate for the view hindered by the pillar by displaying an image taken by an imaging unit provided in the car body. Similarly, the display region 5203 provided in the dashboard portion can compensate for the view hindered by the car body by displaying an image taken by an imaging unit provided on the outside of the automobile. Thus, blind areas can be eliminated to enhance the safety. Images that compensate for the areas which a driver cannot see enable the driver to ensure safety easily and comfortably.

The display region 5203 can provide a variety of kinds of information by displaying navigation data, a speedometer, a tachometer, air-condition setting, and the like. The content or layout of the display can be changed freely by a user as appropriate. Note that such information can also be displayed on the display regions 5200 to 5203. The display regions 5200 to 5203 can also be used as lighting devices.

Figure 12A:
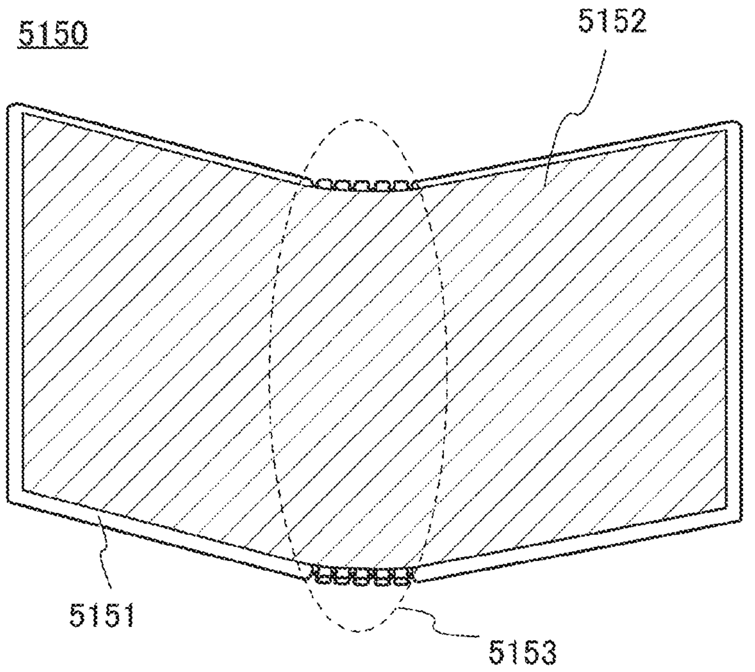
FIGS. 12A and 12B illustrate an electronic device.
Figure 12B:
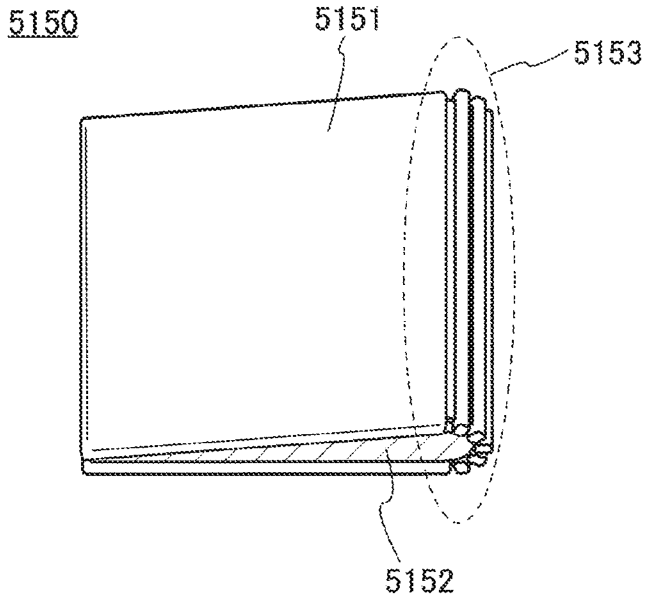

FIGS. 12A and 12B illustrate a foldable portable information terminal 5150. The foldable portable information terminal 5150 includes a housing 5151, a display region

5152, and a bend portion 5153. FIG. 12A illustrates the portable information terminal 5150 that is opened. FIG. 12B illustrates the portable information terminal 5150 that is folded. Despite its large display region 5152, the portable information terminal 5150 is compact in size and has excellent portability when folded.

The display region 5152 can be folded in half with the bend portion 5153. The bend portion 5153 includes a flexible member and a plurality of supporting members. When the display region is folded, the flexible member expands and the bend portion 5153 has a radius of curvature of greater than or equal to 2 mm, preferably greater than or equal to 3 mm.

Note that the display region 5152 may be a touch panel (an input/output device) including a touch sensor (an input device). The light-emitting apparatus of one embodiment of the present invention can be used for the display region 5152.

Figure 13A:
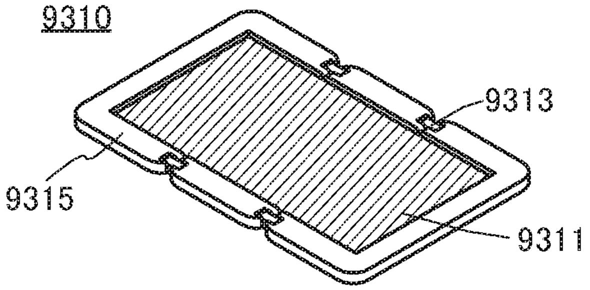
FIGS. 13A to 13C illustrate an electronic device.
Figure 13B:
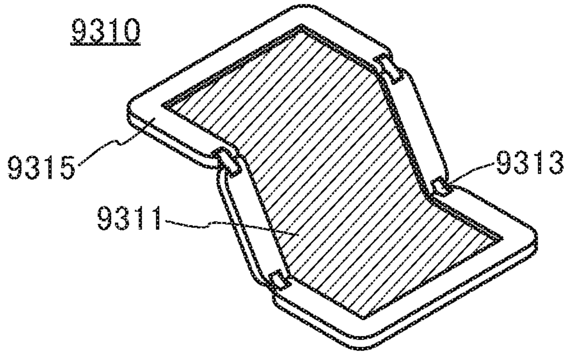
Figure 13C:
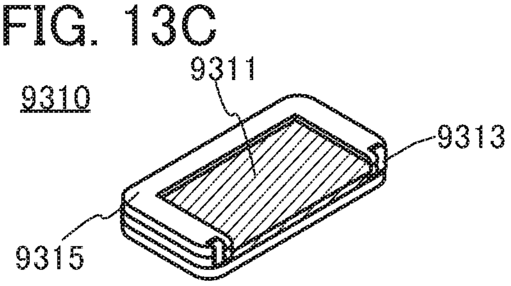

FIGS. 13A to 13C illustrate a foldable portable information terminal 9310. FIG. 13A illustrates the portable information terminal 9310 that is opened. FIG. 13B illustrates the portable information terminal 9310 that is being opened or being folded. FIG. 13C illustrates the portable information terminal 9310 that is folded. The portable information terminal 9310 is highly portable when folded. The portable information terminal 9310 is highly browsable when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. The light-emitting apparatus of one embodiment of the present invention can be used for the display panel 9311.

Example 1

<Synthesis Example 1

In this example, a synthesis method of N,N-bis(4-cyclohexylphenyl)-9,9, -dimethyl-9H-fluoren-2-amine (abbreviation: dchPAF), which is the organic compound represented by the structural formula (100) in Embodiment 1, is described. A structure of dchPAF is shown below.

[Chemical Formula 48]

(100)

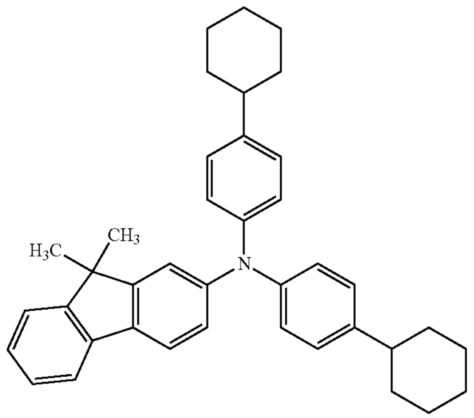

Step 1: Synthesis of N,N-bis(4-cyclohexylphenyl)-9,9, -dimethyl-9H-fluoren-2-amine (Abbreviation: dchPAF)

In a three-neck flask were put 10.6 g (51 mmol) of 9,9-dimethyl-9H-fluoren-2-amine, 18.2 g (76 mmol) of 4-cyclohexyl-1-bromobenzene, 21.9 g (228 mmol) of sodium-tert-butoxide, and 255 mL of xylene. This mixture was degassed under reduced pressure, and then the air in the flask was replaced with nitrogen. The mixture was stirred while being heated to approximately 50° C. Then, 370 mg (1.0 mmol) of allylpalladium(II) chloride dimer (abbreviation: $[(Allyl)PdCl]_2$) and 1660 mg (4.0 mmol) of di-tert-butyl(1-methyl-2,2-diphenylcyclopropyl)phosphine (abbreviation: cBRIDP (registered trademark)) were added, and the mixture was heated at 120° C. for approximately 5 hours. After that, the temperature of the flask was lowered to approximately 60° C., and approximately 4 mL of water was added to the mixture, so that a solid was precipitated. The precipitated solid was separated by filtration. The filtrate was concentrated, and the obtained solution was purified by silica gel column chromatography. The obtained solution was concentrated to give a concentrated toluene solution. The toluene solution was dropped into ethanol for reprecipitation. The precipitate was collected by filtration at approximately 10° C. and the obtained solid was dried at approximately 80° C. under reduced pressure, whereby 10.1 g of a target white solid was obtained in a yield of 40%. The synthesis scheme of dchPAF in Step 1 is shown below.

[Chemical Formula 49]

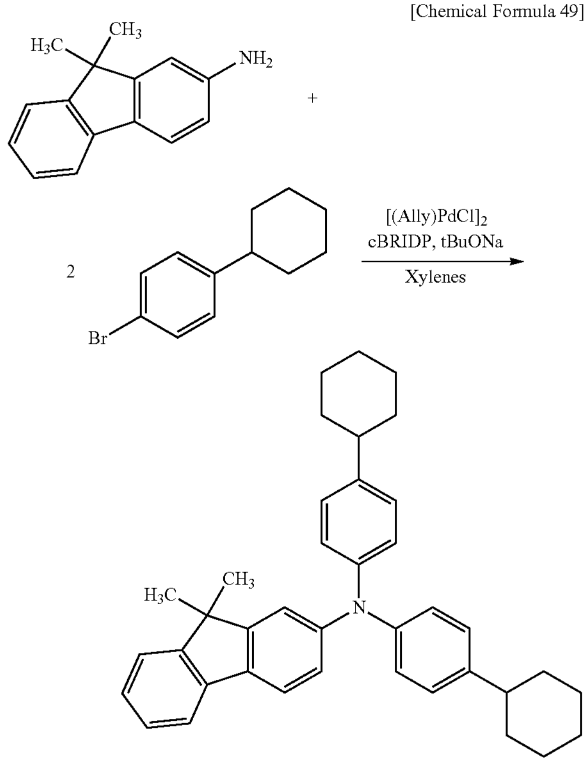

(100)

Figure 14:
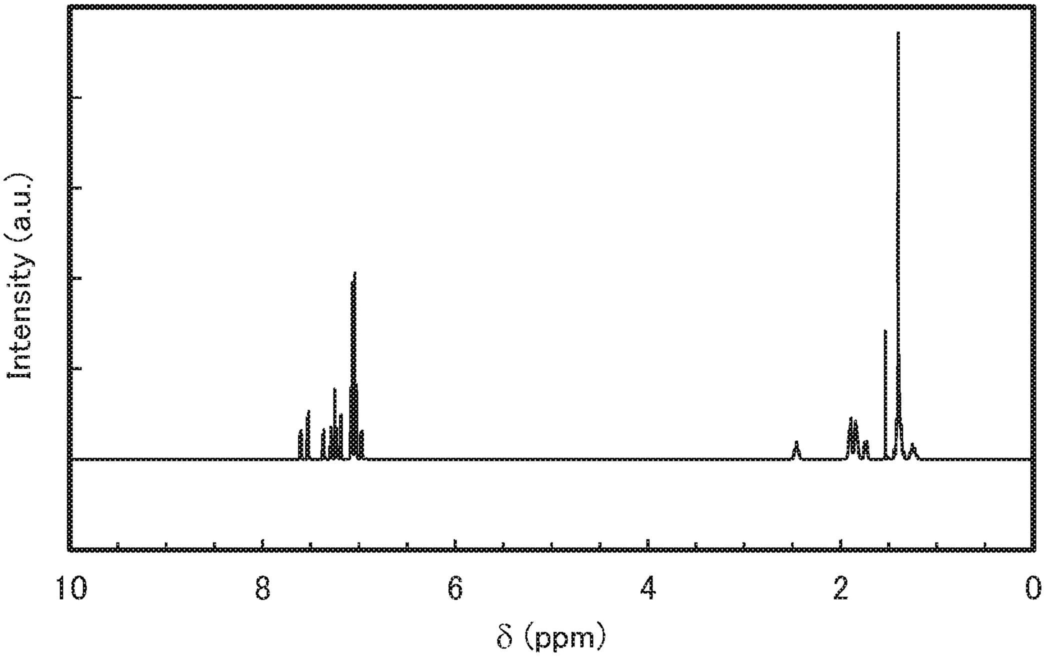
FIG. 14 is a $^{1}$H-NMR chart of dchPAF.

Analysis results by nuclear magnetic resonance spectroscopy ($^1$H-NMR) of the white solid obtained in Step 1 are shown below. FIG. 14 show the $^1$H-NMR chart. The results show that dchPAF was synthesized in this synthesis example.

$^1$H-NMR. δ ($CDCl_3$): 7.60 (d, 1H, J=7.5 Hz), 7.53 (d, 1H, J=8.0 Hz), 7.37 (d, 2H, J=7.5 Hz), 7.29 (td, 1H, J=7.5 Hz, 1.0 Hz), 7.23 (td, 1H, J=7.5 Hz, 1.0 Hz), 7.19 (d, 1H, J=1.5 Hz), 7.06 (m, 8H), 6.97 (dd, 1H, J=8.0 Hz, 1.5 Hz), 2.41-2.51 (brm, 2H), 1.79-1.95 (m, 8H), 1.70-1.77 (m, 2H), 1.33-1.45 (brm, 14H), 1.19-1.30 (brm, 2H).

Then, 5.6 g of the obtained solid was purified by a train sublimation method. The purification by sublimation was conducted by heating at 215° C. under a pressure of 3.0 Pa with the argon flow rate of 12.0 mL/min. After the purification by sublimation, 5.2 g of a pale yellowish white solid was obtained at a collection rate of 94%.

Figure 15:
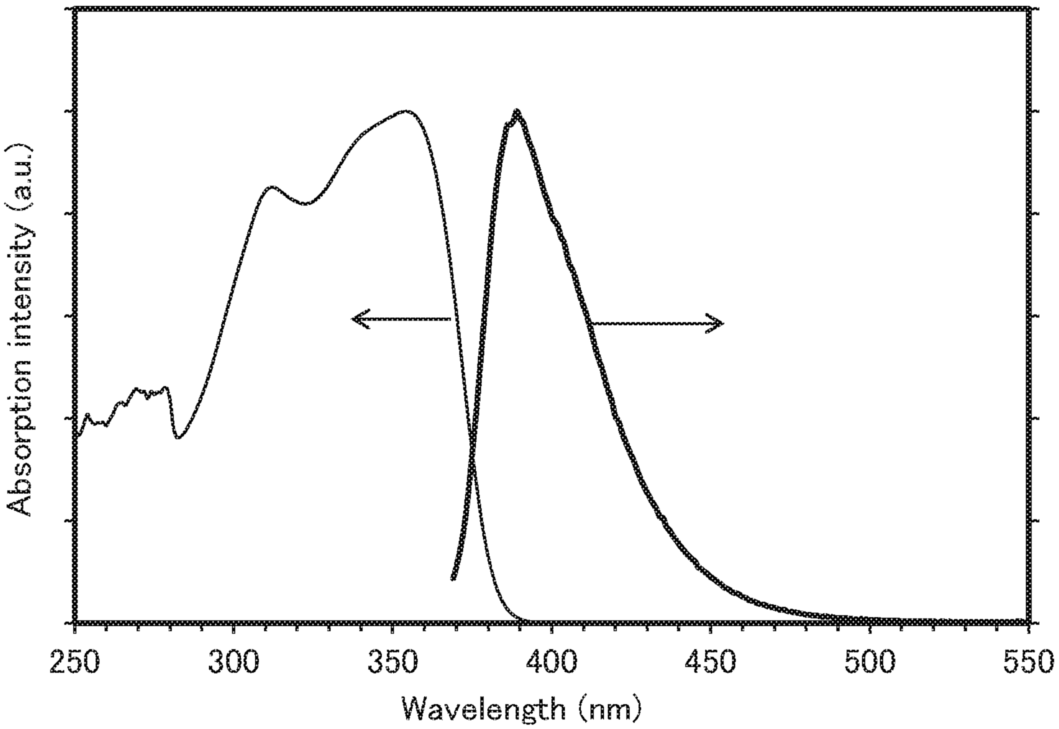
FIG. 15 shows an absorption spectrum and an emission spectrum of dchPAF in a toluene solution.

Next, an ultraviolet-visible absorption spectrum (hereinafter, simply referred to as an absorption spectrum) of dchPAF in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FS920, manufactured by Hamamatsu Photonics K.K.), both of which were measured at room temperature. A quartz cell was used for the measurement cell. FIG. 15 shows measurement results of the absorption spectrum and emission spectrum. The horizontal axis represents the wavelength and the vertical axes represent the absorption intensity and emission intensity. The absorption intensity shown in FIG. 15 is a result obtained by subtraction of an absorption spectrum of only toluene in a quartz cell from the measured absorption spectrum of the toluene solution in the quartz cell.

As shown in FIG. 15, the organic compound dchPAF has an emission peak at 354 nm.

Next, the organic compound dchPAF was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C8 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Furthermore, a sample was prepared in such a manner that dchPAF was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 525 underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500. The detection result of the dissociated product ions by time-of-flight (TOF) MS are shown in FIG. 16.

Figure 16:
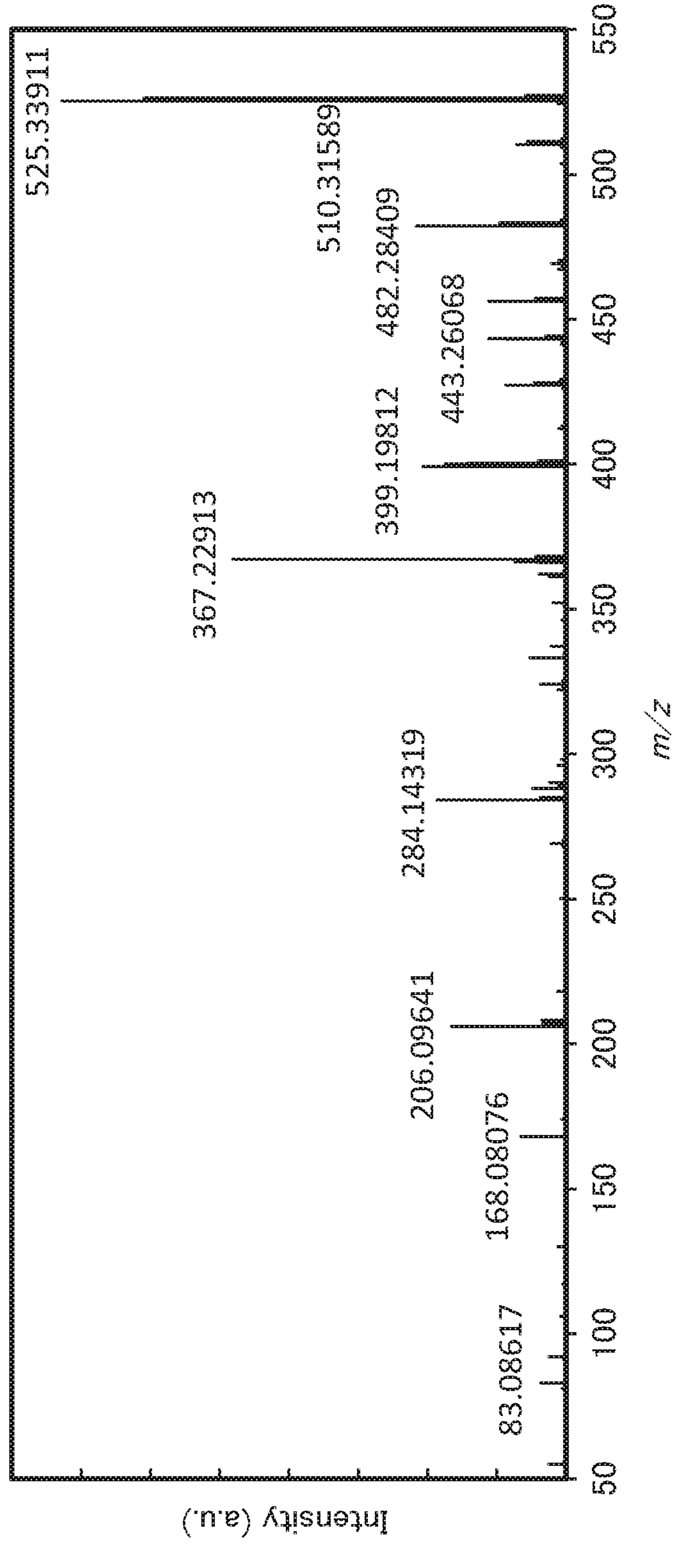
FIG. 16 shows an MS spectrum of dchPAF.

FIG. 16 shows that product ions of dchPAF are mainly detected at m/z of around 525. Note that the result in FIG.

16 shows characteristics derived from dchPAF and therefore can be regarded as important data for identifying dchPAF contained in a mixture.

Note that a fragment ion at m/z of 367, which was observed in measurement with a collision energy of 50 eV, is estimated to be derived from N-(4-cyclohexylphenyl)-N-(9,9-dimethyl-9H-fluoren-2yl)amine generated in such a manner that a C—N bond of dchPAF was cut, and this is the characteristics of dchPAF.

Figure 82:
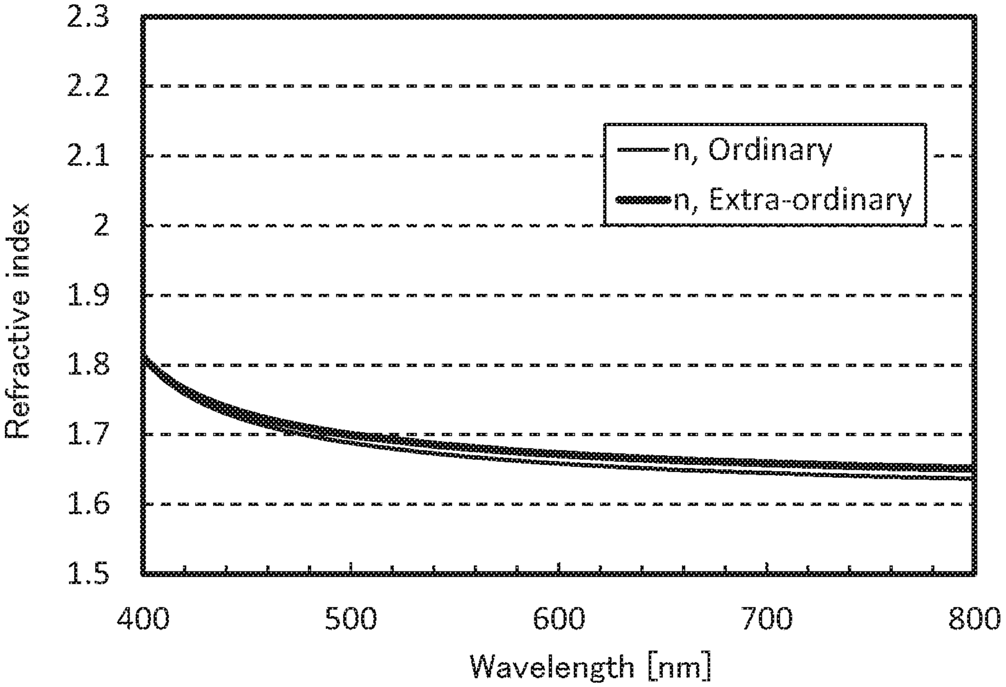
FIG. 82 shows measurement data of a refractive index of dchPAF.

FIG. 82 shows the results of measuring the refractive index of dchPAF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 82.

FIG. 82 shows that dchPAF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Example 2

Synthesis Example 2

In this example, a synthesis method of N-[(4'-cyclohexyl)-1,1'-biphenyl-4yl]-N-(4-cyclohexylphenyl)-9,9-dimethyl-9H-fluoren-2-amine (abbreviation: chBichPAF), which is the organic compound represented by the structural formula (101) in Embodiment 1, is described. A structure of chBichPAF is shown below.

[Chemical Formula 50]

(101)

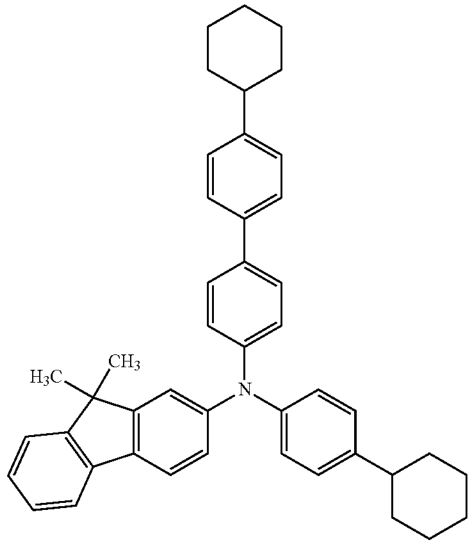

Step 1: Synthesis of N-(4-cycrohexylphenyl)-N-(9,9-dimethyl-9H-fluoren-2yl)amine In a three-neck flask were put 10.5 g (50 mmol) of 9,9-dimethyl-9H-fluoren-2-amine, 12.0 g (50 mmol) of 4-cyclohexyl-1-bromobenzene, 14.4 g (150 mmol) of sodium-tert-butoxide, and 250 mL of xylene. This mixture was degassed under reduced pressure, and then the air in the flask was replaced with nitrogen. The mixture was heated while being stirred at approximately 50° C. Then, 183 mg (0.50 mmol) of allylpalladium(II) chloride dimer (abbreviation: $[(Allyl)PdCl]_2$) and 821 mg (2.0 mmol) of di-tert-butyl (1-methyl-2,2-diphenylcyclopropyl)phosphine (abbreviation: cBRIDP (registered trademark)) were added, and the mixture was heated at 90° C. for approximately 6 hours. After that, the temperature of the flask was lowered to approximately 60° C., approximately 4 mL of water was added to the mixture, and a precipitated solid was separated by filtration. The filtrate was concentrated, and the obtained solution was purified by silica gel column chromatography. The obtained solution was concentrated to give a condensed toluene solution. This toluene solution was dried at approximately 60° C. in a vacuum, whereby a 17.3 g of a target brown oily substance was obtained in a yield of 92%. The synthesis scheme of Step 1 is shown below.

[Chemical Formula 51]

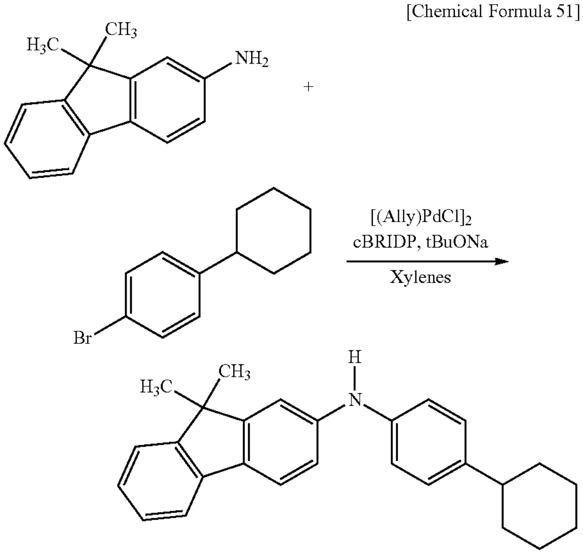

Step 2: Synthesis of N-[(4'-cyclohexyl)-1,1'-biphenyl-4yl]-N-(4-cyclohexylphenyl)-9,9-dimethyl-9H-fluoren-2-amine (Abbreviation: chBichPAF)

In a three-neck flask were put 4.7 g (12.8 mmol) of N-(4-cycrohexylphenyl)-N-(9,9-dimethyl-9H-fluoren-2yl) amine obtained in Step 1, 3.5 g (12.8 mmol) of 4'-cyclohexyl-4-chloro-1,1'-biphenyl, 3.7 g (38.5 mmol) of sodium-tert-butoxide, and 65 mL of xylene. This mixture was degassed under reduced pressure, and then the air in the flask was replaced with nitrogen. The mixture was stirred while being heated to approximately 50° C. Then, 47 mg (0.13 mmol) of allylpalladium(II) chloride dimer (abbreviation: $[(Allyl)PdCl]_2$) and 180 mg (0.51 mmol) of di-tert-butyl(1-methyl-2,2-diphenylcyclopropyl)phosphine (abbreviation: cBRIDP (registered trademark)) were added, and the mixture was heated at 110° C. for approximately 5 hours. After that, the temperature of the flask was lowered to approximately 60° C., approximately 1 mL of water was added to the mixture, and a precipitated solid was separated by filtration. The filtrate was concentrated, and the obtained solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 5.3 g of a white solid was obtained in a yield of 69%. The synthesis scheme of Step 2 is shown below.

[Chemical Formula 52]

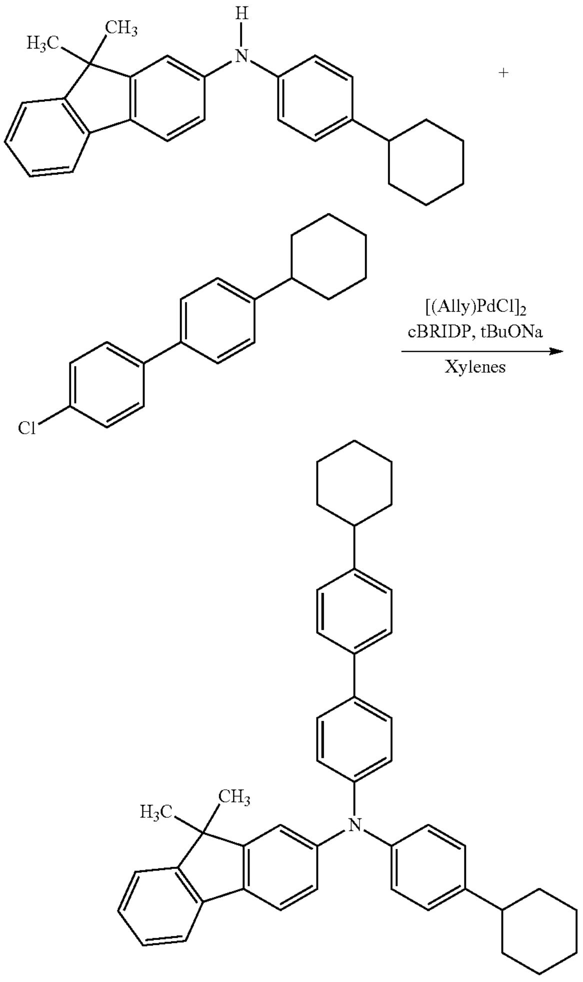

(101)

Figure 17:
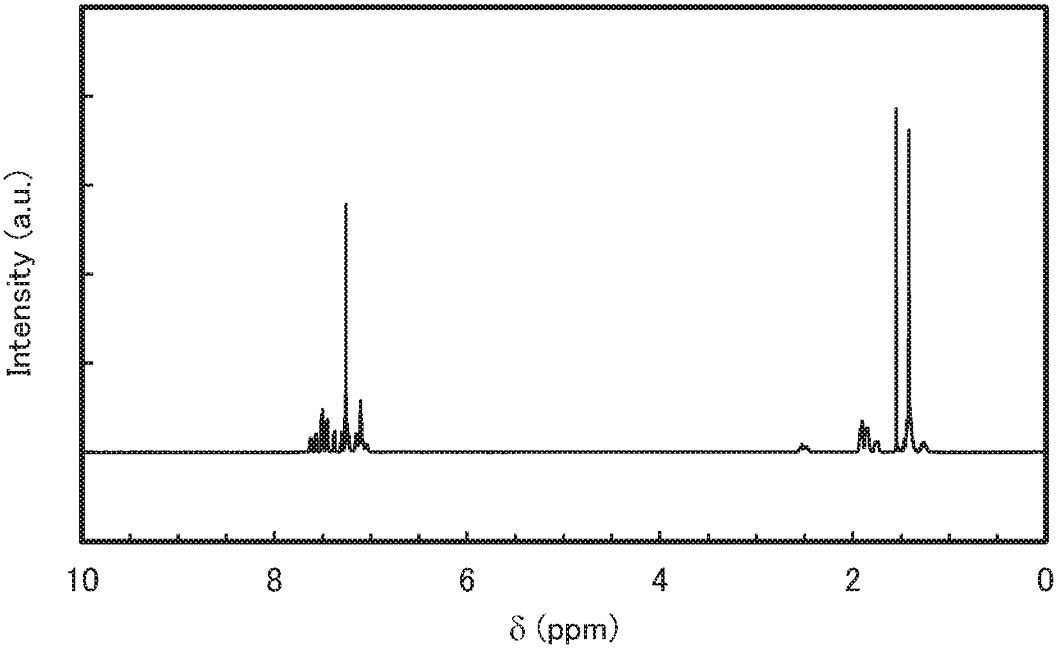
FIG. 17 is a $^{1}$H-NMR chart of chBichPAF.

Analysis results by nuclear magnetic resonance spectroscopy ($^1$H-NMR) of the white solid obtained in Step 2 are shown below. FIG. 17 shows the $^1$H-NMR chart. The results show that chBichPAF was synthesized in this synthesis example.

$^1$H-NMR. δ ($CDCl_3$): 7.63 (d, 1H, J=7.5 Hz), 7.57 (d, 1H, J=7.5 Hz), 7.51 (d, 2H, J=8.0 Hz), 7.46 (d, 2H, J=7.5 Hz), 7.38 (d, 1H, J=7.5 Hz), 7.30 (td, 1H, J=7.0 Hz, 1.5 Hz), 7.20-7.28 (m, 6H), 7.01-7.18 (m, 7H), 2.43-2.57 (brm, 2H), 1.81-1.96 (m, 8H), 1.71-1.79 (brm, 2H), 1.34-1.50 (brm, 14H), 1.20-1.32 (brm, 2H).

Then, 3.5 g of the obtained solid was purified by a train sublimation method. The purification by sublimation was conducted by heating at 270° C. under a pressure of 3.0 Pa with the argon flow rate of 12.3 mL/min. After the purification by sublimation, 3.1 g of a pale yellowish white solid was obtained at a collection rate of 88%.

Figure 18:
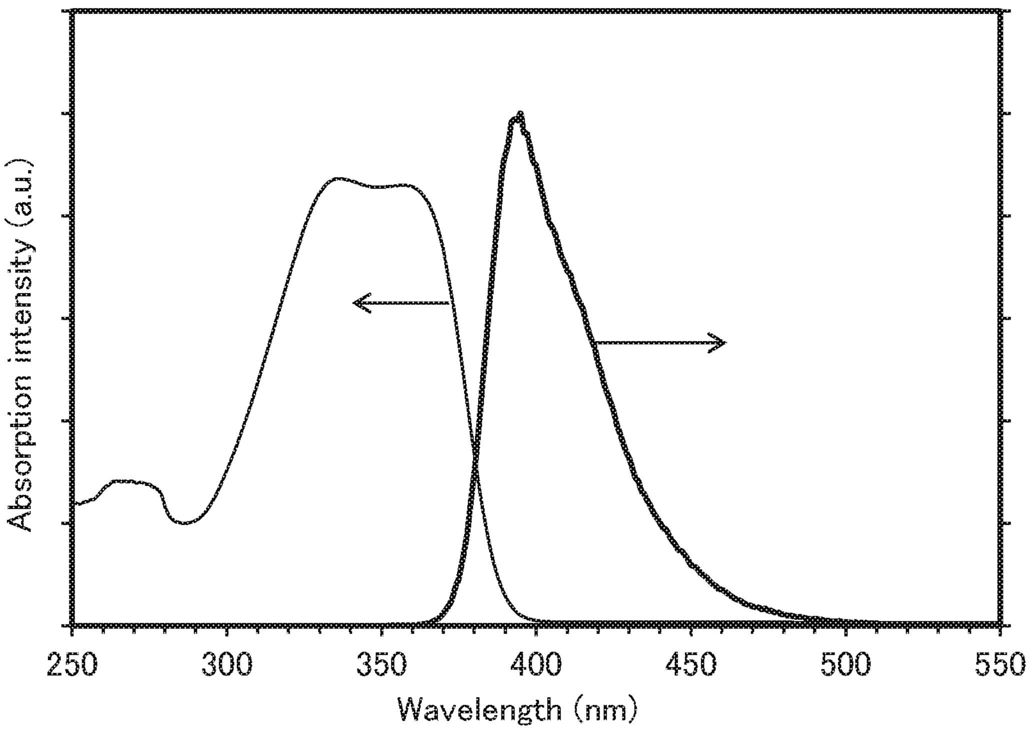
FIG. 18 shows an absorption spectrum and an emission spectrum of chBichPAF in a toluene solution.

Next, an ultraviolet-visible absorption spectrum (hereinafter, simply referred to as an absorption spectrum) of chBichPAF in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FS920, manufactured by Hamamatsu Photonics K.K.), both of which were measured at room temperature. A quartz cell was used for the measurement cell. FIG. 18 shows measurement results of the absorption spectrum and the emission spectrum. The horizontal axis represents the wavelength and the vertical axes represent the absorption intensity and emission intensity. The absorption intensity shown in FIG. 18 is a result obtained by subtraction of an absorption spectrum of only toluene in a quartz cell from the measured absorption spectrum of the toluene solution in the quartz cell.

As shown in FIG. 18, the organic compound chBichPAF has an emission peak at 357 nm.

Next, the organic compound chBichPAF was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C8 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that chBichPAF was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 601 which underwent the ionization under the above-described conditions was collided with an argon gas in a collision cell to dissociate into product ions. Energy (collision energy) for the collision with argon was 60 eV The measurement mass range was set to m/z (mass-to-charge ratio)=100 to 1500. The detection results of the dissociated product ions by time-of-flight (TOF) MS are shown in FIG. 19.

Figure 19:
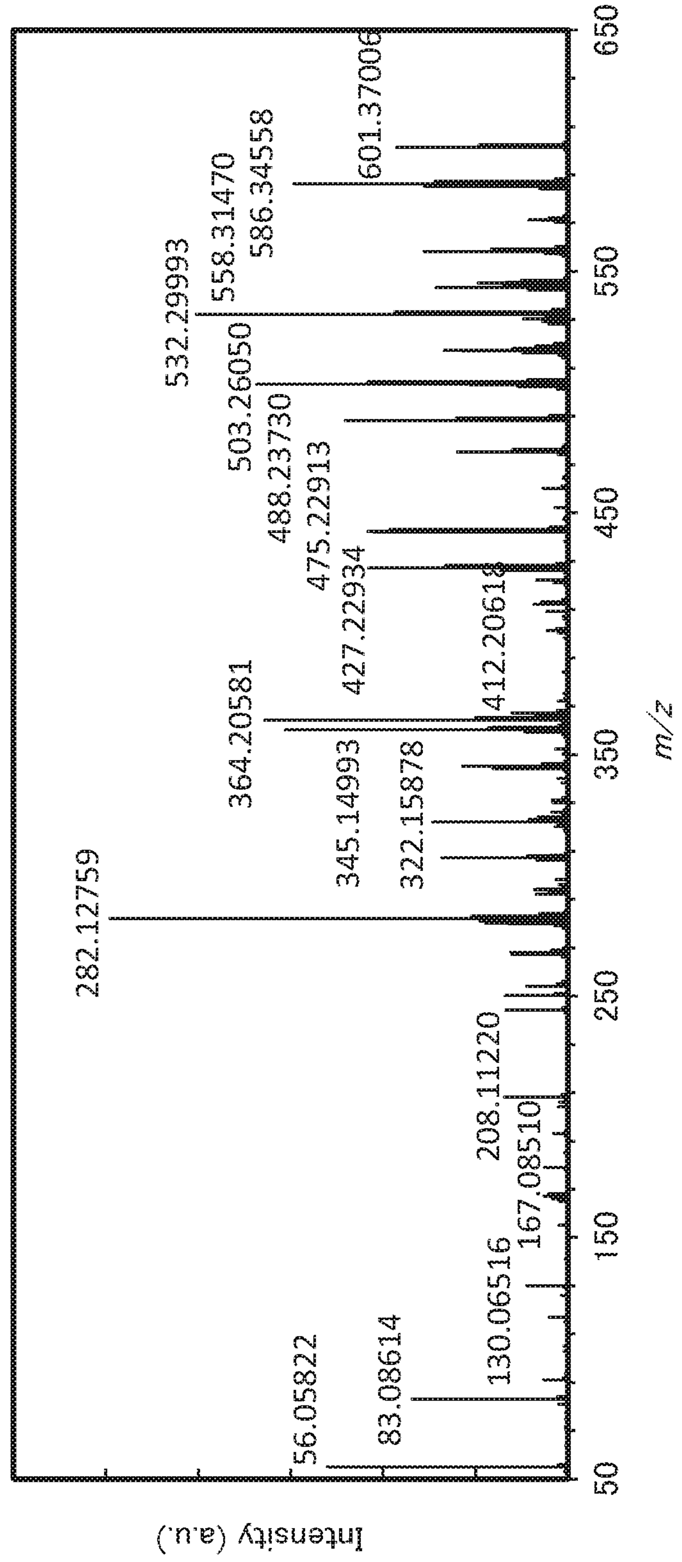
FIG. 19 shows an MS spectrum of chBichPAF.

FIG. 19 shows that product ions of chBichPAF are mainly detected at m/z of around 601. Note that the result in FIG. 19 shows characteristics derived from chBichPAF and therefore can be regarded as important data for identifying chBichPAF contained in a mixture.

Note that a fragment ion at m/z of 442, which was observed in measurement with a collision energy of 70 eV, is estimated to be derived from N-(4'-cyclohexyl-1,1'-biphenyl-4-yl]-N-(9,9-dimethyl-9H-fluoren-2yl)amine generated in such a manner that a C—N bond of chBichPAF was cut, and this is the characteristics of chBichPAF.

Figure 83:
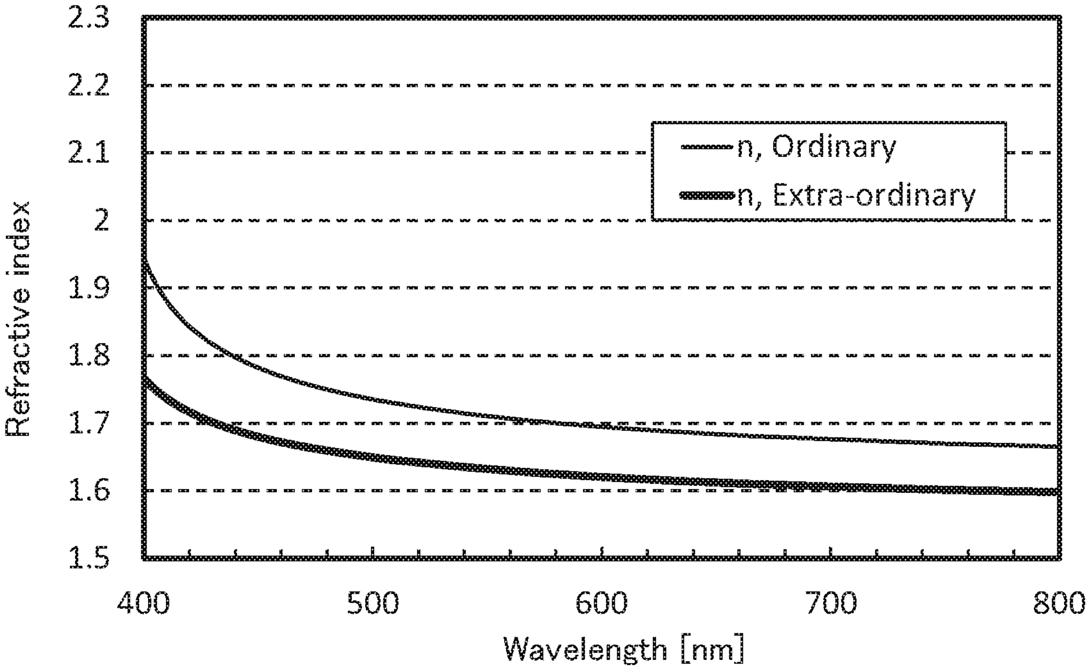
FIG. 83 shows measurement data of a refractive index of chBichPAF.

FIG. 83 shows the results of measuring the refractive index of chBichPAF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 83.

FIG. 83 shows that chBichPAF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, the glass transition temperature (hereinafter referred to as "Tg") of chBichPAF was measured. Tg was measured using a differential scanning calorimeter (a Perkin-Elmer Co., Ltd. Pyris 1 DSC) in a state where a powder was put on an aluminum cell. As a result, Tg of chBichPAF was 96° C.

Example 3

Synthesis Example 3

In this example, a synthesis method of N,N-bis(4-cyclohexylphenyl)-N-(spiro[cyclohexane-1,9'-[9H]fluoren]-2'yl) amine (abbreviation: dchPASchF), which is the organic compound represented by the structural formula (102) in Embodiment 1, is described. A structure of dchPASchF is shown below.

[Chemical Formula 53]

(102)

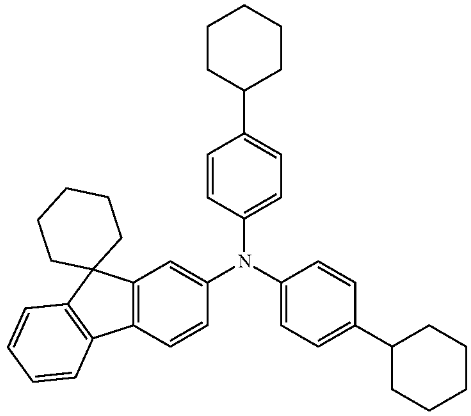

Step 1: Synthesis of 4-cyclohexylaniline

In a three-neck flask were put 21.5 g (90 mmol) of 4-cyclohexyl-1-bromobenzene and 450 mL of toluene. This mixture was degassed under reduced pressure, and then the air in the flask was replaced with nitrogen. The mixture was stirred while being cooled down to approximately −20° C. Then, 823 mg (2.25 mmol) of allylpalladium(II) chloride dimer (abbreviation: $[(Allyl)PdCl]_2$) and 3690 mg (9.0 mmol) of di-tert-butyl(1-methyl-2,2-diphenylcyclopropyl) phosphine (abbreviation: cBRIDP (registered trademark)) were added. To this solution, 100 mL of the toluene solution of 1.0 mol/L of lithium bis(hexamethyldisilazide) was dropped. After that, the temperature of the flask was increased to approximately 120° C. so that the mixture was reacted for approximately 2 hours. After the flask was cooled down, approximately 200 mL of water was added to the mixture and the mixture was left to be separated into an organic layer and an aqueous layer. Then, approximately 100 mL of toluene was added to the obtained aqueous layer to extract a reaction product. The obtained organic layer was mixed with the organic layer that was separated in the previous step, and the mixed organic layer was washed with saturated saline. Magnesium sulfate was put into this solution for drying, and filtration was performed. The obtained toluene solution was concentrated and purified by silica gel column chromatography. The obtained solution was concentrated to give a condensed toluene solution. The toluene solution was dried at approximately 60° C. in a vacuum, whereby a 14.5 g of a target brown oily substance was obtained in a yield of 92%. The synthesis scheme of Step 1 is shown below.

[Chemical Formula 54]

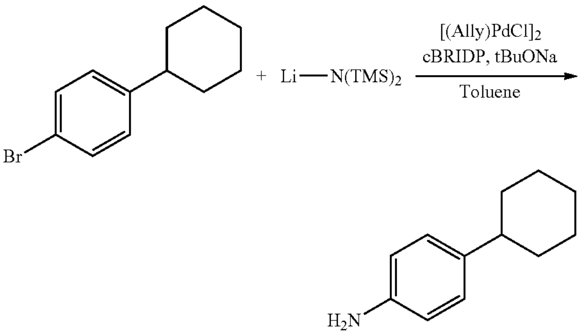

Step 2: Synthesis of N-(4-cyclohexylphenyl)-N-(spiro[cyclohexane-1,9'[9H]fluoren]-2'-yl)amine In a three-neck flask were put 3.0 g (16.9 mmol) of 4-cyclohexylaniline, 5.3 g (16.9 mmol) of 2'-bromo(spiro [cyclohexane-1,9'[9H]fluoren]), 4.9 g (50.7 mmol) of sodium-tert-butoxide, and 85 mL of xylene. This mixture was degassed under reduced pressure, and then the air in the flask was replaced with nitrogen. The mixture was stirred while being heated to 60° C. Then, 62 mg (0.17 mmol) of allylpalladium(II) chloride dimer (abbreviation: $[(Allyl)PdCl]_2$) and 280 mg (0.67 mmol) of di-tert-butyl(1-methyl-2,2-diphenylcyclopropyl)phosphine (abbreviation: cBRIDP (registered trademark)) were added. The mixture was heated at 90° C. and reacted for approximately 7 hours. After that, the temperature of the flask was lowered to approximately 60° C., approximately 1 mL of water was added to the mixture, and a precipitated solid was separated by filtration. The filtrate was concentrated, and the obtained solution was purified by silica gel column chromatography. The obtained solution was concentrated to give a condensed toluene solution. The toluene solution was dried at approximately 60° C. in a vacuum, whereby 5.1 g of a target brown oily substance was obtained in a yield of 73%. The synthesis scheme of N-(4-cyclohexylphenyl)-N-(spiro[cyclohexane-1,9'[9H]fluoren]-2'-yl)amine in Step 2 is shown below.

[Chemical Formula 55]

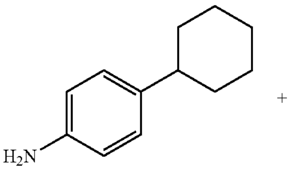

-continued

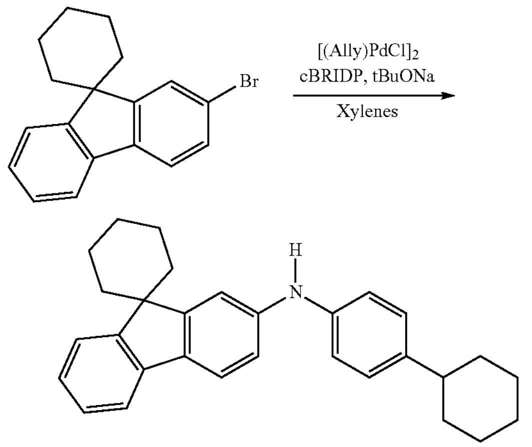

Step 3: Synthesis of N,N-bis(4-cyclohexylphenyl)-N-(spiro[cyclohexane-1,9'-[9H]fluoren]-2'yl)amine (Abbreviation: dchPASchF)

In a three-neck flask were put 2.5 g (6.2 mmol) of N-(4-cyclohexylphenyl)-N-(spiro[cyclohexane-1,9'[9H]fluoren]-2'yl)amine obtained in Step 2, 1.5 g (6.2 mmol) of 4-cyclohexyl-1-bromobenzene, 1.8 g (18.6 mmol) of sodium-tert-butoxide, and 31 mL of xylene. This mixture was degassed under reduced pressure, and then the air in the flask was replaced with nitrogen. The mixture was stirred while being heated to 50° C. Then, 23 mg (0.062 mmol) of allylpalladium(II) chloride dimer (abbreviation: [(Allyl)PdCl]$_2$) and 88 mg (0.248 mmol) of di-tert-butyl(1-methyl-2,2-diphenylcyclopropyl)phosphine (abbreviation: cBRIDP (registered trademark)) were added, and the mixture was heated at 90° C. for approximately 5 hours. After that, the temperature of the flask was lowered to approximately 60° C., approximately 1 mL of water was added to the mixture, and a precipitated solid was separated by filtration. The filtrate was concentrated, and the obtained solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 3.1 g of a target white solid was obtained in a yield of 88%. The synthesis scheme of dchPASchF in Step 3 is shown below.

[Chemical Formula 56]

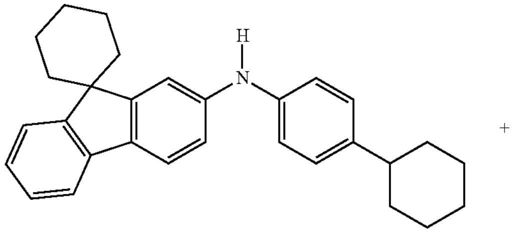

-continued

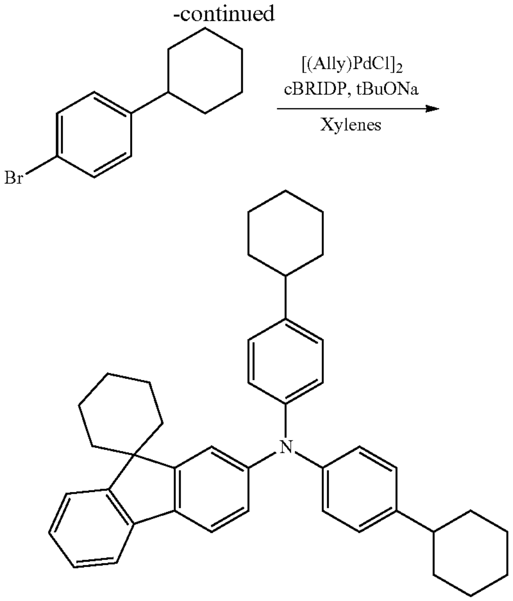

(102)

Figure 20:
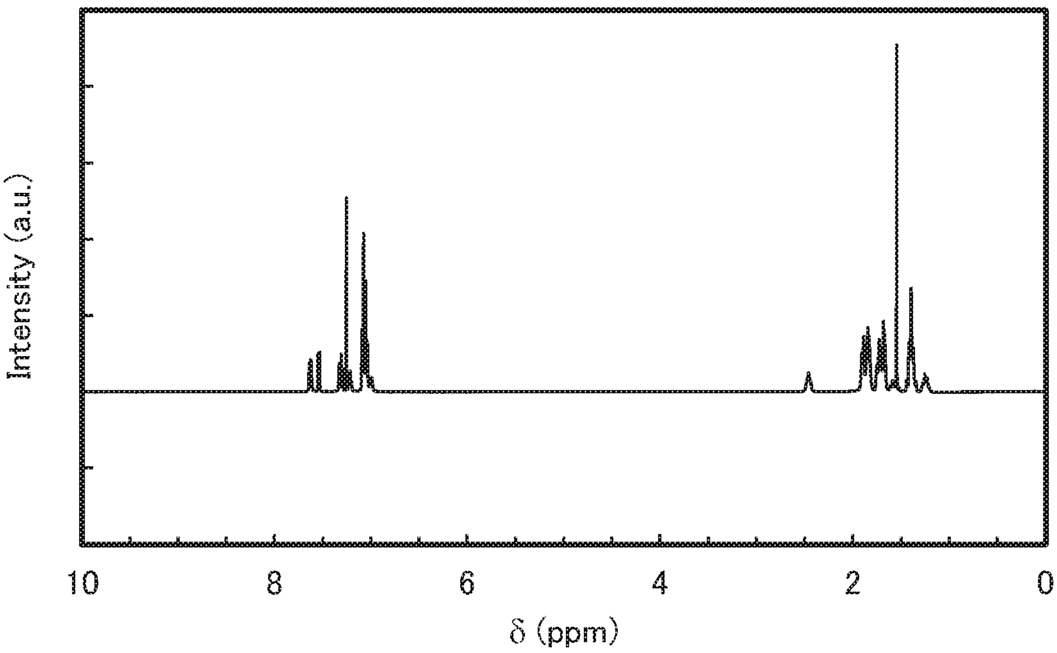
FIG. 20 is a $^{1}$H-NMR chart of dchPASchF.

Analysis results by nuclear magnetic resonance spectroscopy ($^1$H-NMR) of the white solid obtained in Step 3 are shown below. FIG. 20 shows the $^1$H-NMR chart. The results show that N,N-bis(4-cyclohexylphenyl)-N-(spiro[cyclohexane-1,9'-[9H]fluoren]-2'yl)amine (abbreviation: dchPASchF) was synthesized in this example.

$^1$H-NMR. δ ($CDCl_3$): 7.60-7.65 (m, 2H), 7.54 (d, 1H, J=8.0 Hz), 7.28-7.35 (m, 2H), 7.19-7.24 (t, 1H, J=7.5 Hz), 7.02-7.12 (m, 8H), 6.97-7.22 (d, 1H, J=8.0 Hz), 2.40-2.52 (brm, 2H), 1.79-1.95 (m, 10H), 1.63-1.78 (m, 9H), 1.55-1.63 (m, 1H), 1.32-1.46 (m, 8H), 1.18-1.30 (brm, 2H).

Then, 3.1 g of the obtained solid was purified by a train sublimation method. The purification by sublimation was conducted by heating at 235° C. under a pressure of 3.0 Pa with the argon flow rate of 12.3 mL/min. After the purification by sublimation, 2.8 g of a pale yellowish white solid was obtained at a collection rate of 92%.

Figure 21:
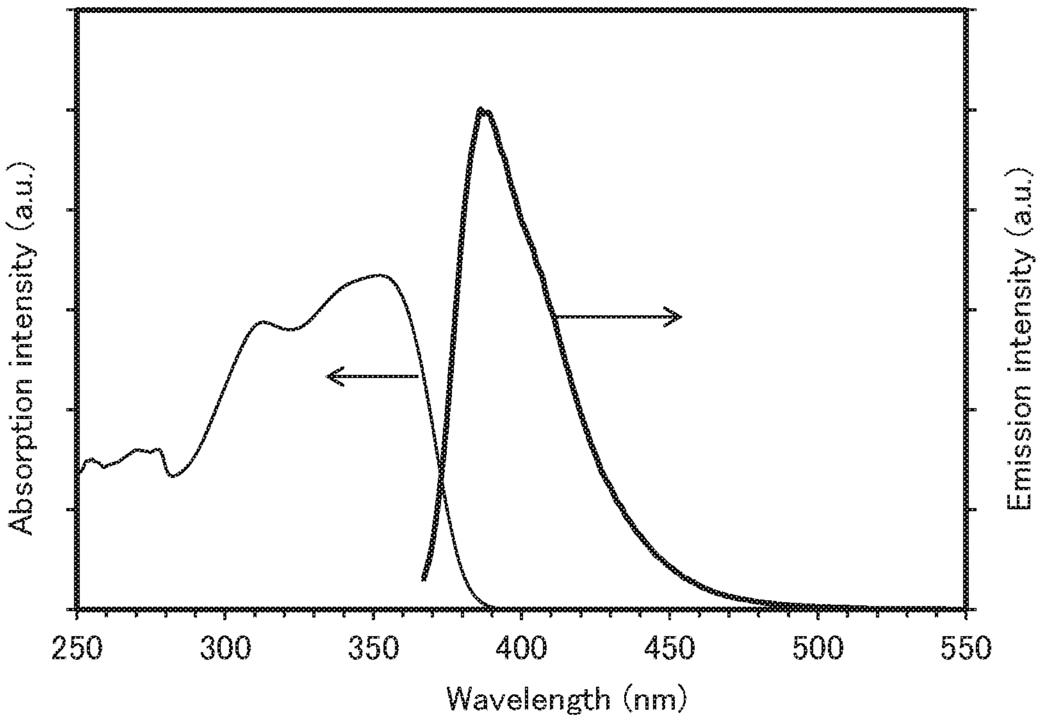
FIG. 21 shows an absorption spectrum and an emission spectrum of dchPASchF in a toluene solution.

Next, an ultraviolet-visible absorption spectrum (hereinafter, simply referred to as an absorption spectrum) of dchPASchF in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FS920, manufactured by Hamamatsu Photonics K.K.), both of which were measured at room temperature. A quartz cell was used for the measurement cell. FIG. 21 shows measurement results of the absorption spectrum and the emission spectrum. The horizontal axis represents the wavelength and the vertical axes represent the absorption intensity and emission intensity. The absorption intensity shown in FIG. 21 is a result obtained by subtraction of an absorption spectrum of only toluene in a quartz cell from the measured absorption spectrum of the toluene solution in the quartz cell.

As shown in FIG. 21, the organic compound dchPASchF has an emission peak at 352 nm.

Next, the organic compound dchPASchF was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C8 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that dchPASchF was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 565 which underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500. The detection results of the dissociated product ions by time-of-flight (TOF) MS are shown in FIG. 22.

Figure 22:
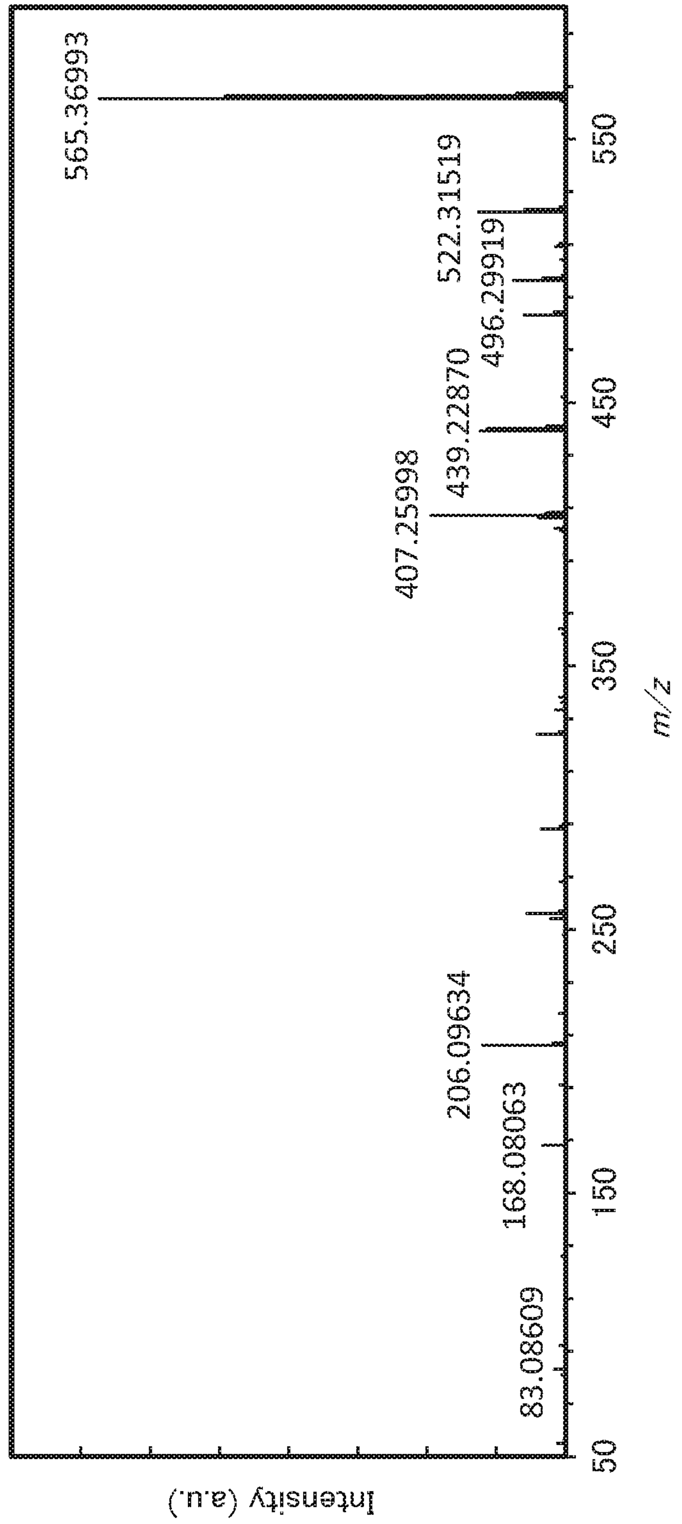
FIG. 22 shows an MS spectrum of dchPASchF.

FIG. 22 shows that product ions of dchPASchF are mainly detected at m/z of around 565. Note that the result in FIG. 22 shows characteristics derived from dchPASchF and therefore can be regarded as important data for identifying dchPASchF contained in a mixture.

Note that a fragment ion at m/z of 407, which was observed in measurement with a collision energy of 50 eV, is estimated to be derived from N-(4-cyclohexylphenyl)-N-(spiro[cyclohexane-1,9'[9H]fluoren]-2'yl)amine generated in such a manner that a C—N bond of dchPASchF was cut, and this is the characteristics of dchPASchF.

Figure 84:
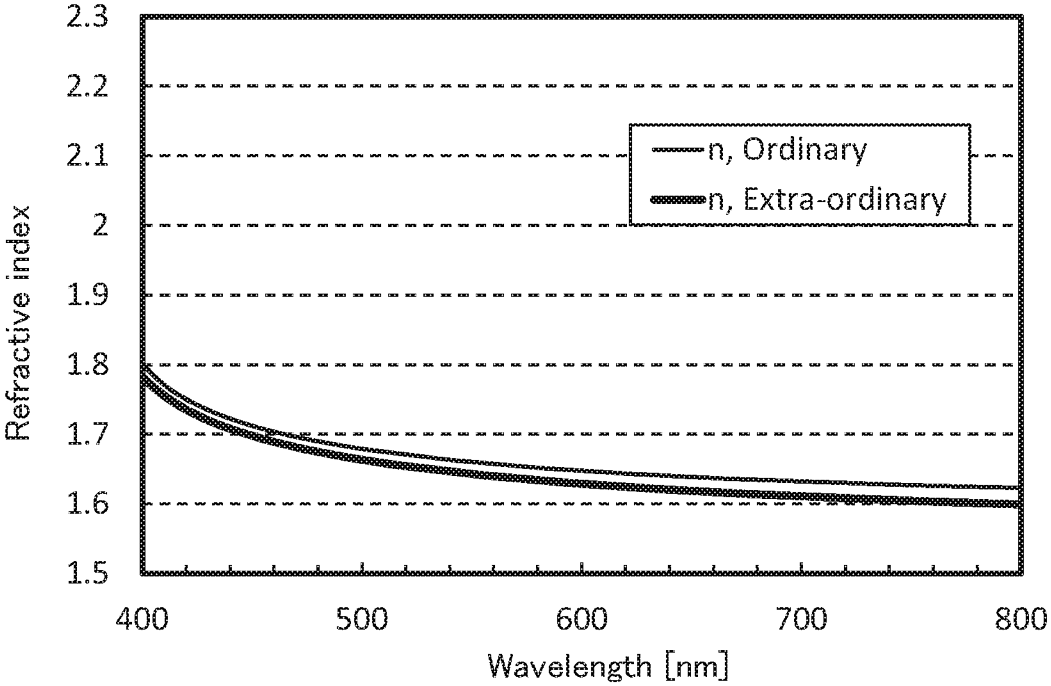
FIG. 84 shows measurement data of a refractive index of dchPASchF.

FIG. 84 shows the results of measuring the refractive index of dchPASchF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 84.

FIG. 84 shows that dchPASchF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Example 4

Synthesis Example 4

In this example, a synthesis method of N-(4'-cyclohexyl)-1,1'-biphenyl-4yl]-N-(4-cyclohexylphenyl)-N-(spiro[cyclohexane-1,9'-[9H]fluoren]-2'yl)amine (abbreviation: chBichPASchF), which is the organic compound represented by the structural formula (103) in Embodiment 1, is described. A structure of chBichPASchF is shown below.

[Chemical Formula 57]

(103)

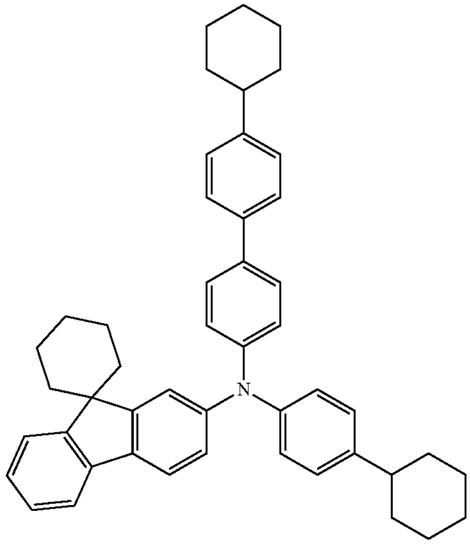

Step 1: Synthesis of 4-cyclohexylaniline

The synthesis was performed in a manner similar to Step 1 of the synthesis example 3 in Example 3.

Step 2: Synthesis of N-(4-cyclohexylphenyl)-N-(spiro[cyclohexane-1,9'[9H]fluoren]-2'-yl)amine The synthesis was performed in a manner similar to Step 2 of the synthesis example 3 in Example 3.

Step 3: Synthesis of N-[(4'-cyclohexyl)-1,1'-biphenyl-4yl]-N-(4-cyclohexylphenyl)-N-(spiro[cyclohexane-1,9'-[9H]fluoren]-2'yl)amine (Abbreviation: chBichPASchF)

In a three-neck flask were put 2.5 g (6.2 mmol) of N-(4-cyclohexylphenyl)-N-(spiro[cyclohexane-1,9'[9H]fluoren]-2'-yl)amine obtained in Step 2, 1.7 g (6.2 mmol) of 4'-cyclohexyl-4-chloro-1,1'-biphenyl, 1.8 g (18.6 mmol) of sodium-tert-butoxide, and 31 mL of xylene. This mixture was degassed under reduced pressure, and then the air in the flask was replaced with nitrogen. The mixture was stirred while being heated to 50° C. Then, 23 mg (0.062 mmol) of allylpalladium(II) chloride dimer (abbreviation: [(Allyl)$PdCl]_2$) and 88 mg (0.248 mmol) of di-tert-butyl(1-methyl-2,2-diphenylcyclopropyl)phosphine (abbreviation: cBRIDP (registered trademark)) were added, and the mixture was heated at 110° C. for approximately 5 hours. After that, the temperature of the flask was lowered to approximately 60° C., approximately 1 mL of water was added to the mixture, and a precipitated solid was separated by filtration. The filtrate was concentrated, and the obtained solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 2.7 g of a target white solid was obtained in a yield of 68%. The synthesis scheme of Step 3 is shown below.

[Chemical Formula 58]

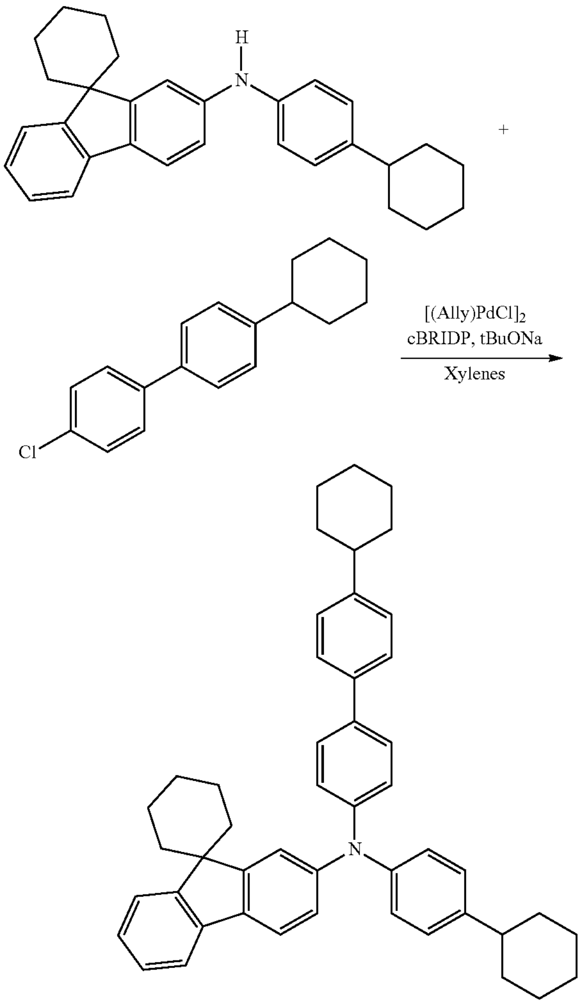

(103)

Figure 23:
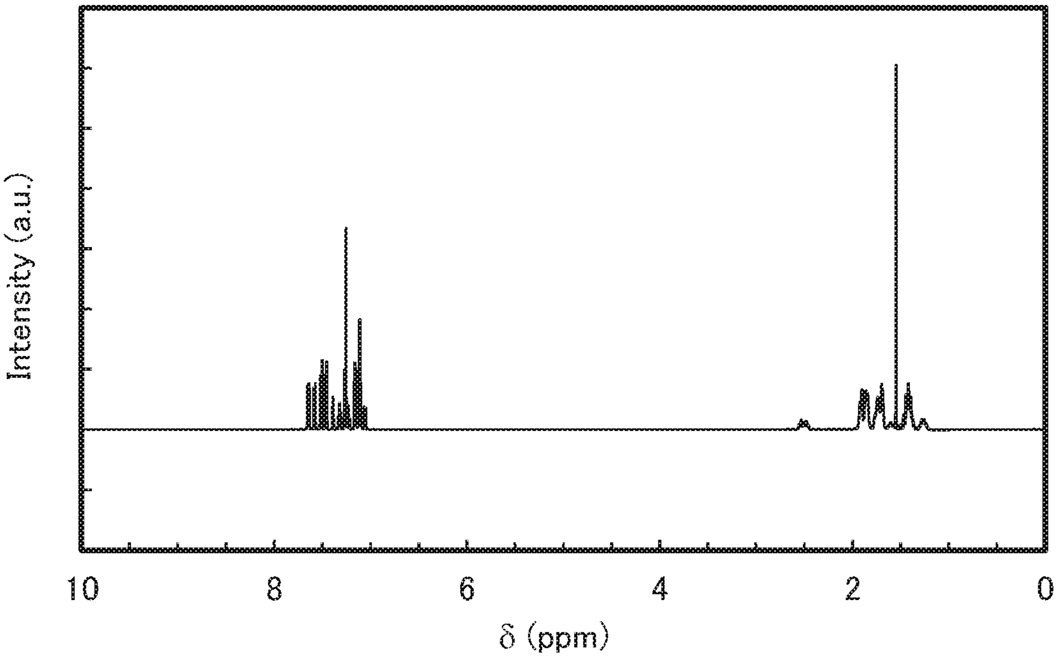
FIG. 23 is a $^{1}$H-NMR chart of chBichPASchF.

Analysis results by nuclear magnetic resonance spectroscopy ($^1$H-NMR) of the white solid obtained in Step 3 are shown below. FIG. 23 shows the $^1$H-NMR chart. The results show that N-[(4'-cyclohexyl)-1,1'-biphenyl-4yl]-N-(4-cyclohexylphenyl)-N-(spiro[cyclohexane-1,9'-[9H]fluoren]-2'yl)amine (abbreviation: chBichPASchF) was synthesized in this synthesis example.

$^1$H-NMR. δ ($CDCl_3$): 7.65 (d, 2H, J=8.0 Hz), 7.58 (d, 1H, J=8.0 Hz), 7.51 (d, 2H, J=8.5 Hz), 7.46 (m, 2H), 7.39 (d, 1H, 1.5 Hz), 7.32 (t, 1H, J=8.0 Hz), 7.21-7.38 (m, 3H), 7.14-7.18 (m, 2H), 7.08-7.14 (m, 4H), 7.06 (dd, 1H, J=8.0 Hz, 1.5 Hz), 2.43-2.57 (brm, 2H), 1.80-1.97 (m, 10H), 1.64-1.80 (m, 9H), 1.56-1.64 (m, 1H), 1.34-1.53 (m, 8H), 1.20-1.32 (brm, 2H).

Then, 2.6 g of the obtained solid was purified by a train sublimation method. The purification by sublimation was conducted by heating at 275° C. under a pressure of 3.0 Pa with the argon flow rate of 12.3 mL/min. After the purification by sublimation, 2.3 g of a pale yellowish white solid was obtained at a collection rate of 89%.

Figure 24:
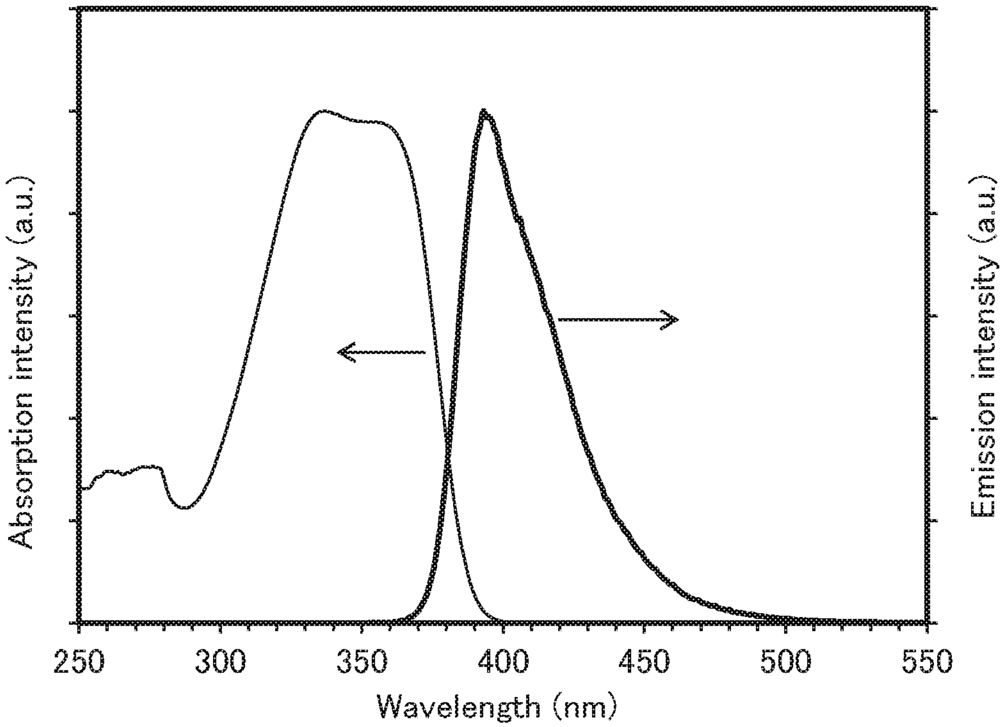
FIG. 24 shows an absorption spectrum and an emission spectrum of chBichPASchF in a toluene solution.

Next, an ultraviolet-visible absorption spectrum (hereinafter, simply referred to as an absorption spectrum) of chBichPASchF in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FS920, manufactured by Hamamatsu Photonics K.K.), both of which were measured at room temperature. A quartz cell was used for the measurement cell. FIG. 24 shows measurement results of the absorption spectrum and the emission spectrum. The horizontal axis represents the wavelength and the vertical axes represent the absorption intensity and emission intensity. The absorption intensity shown in FIG. 24 is a result obtained by subtraction of an absorption spectrum of only toluene in a quartz cell from the measured absorption spectrum of the toluene solution in the quartz cell.

As shown in FIG. 24, the organic compound chBichPASchF has an emission peak at 357 nm.

Next, the organic compound chBichPASchF was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C8 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that chBichPASchF was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 641 which underwent the ionization under the above-described conditions was collided with an argon gas in a collision cell to dissociate into product ions. Energy (collision energy) for the collision with argon was 60 eV The measurement mass range was set to m/z (mass-to-charge ratio)=100 to 1500. The detection results of the dissociated product ions by time-of-flight (TOF) MS are shown in FIG. 25.

Figure 25:
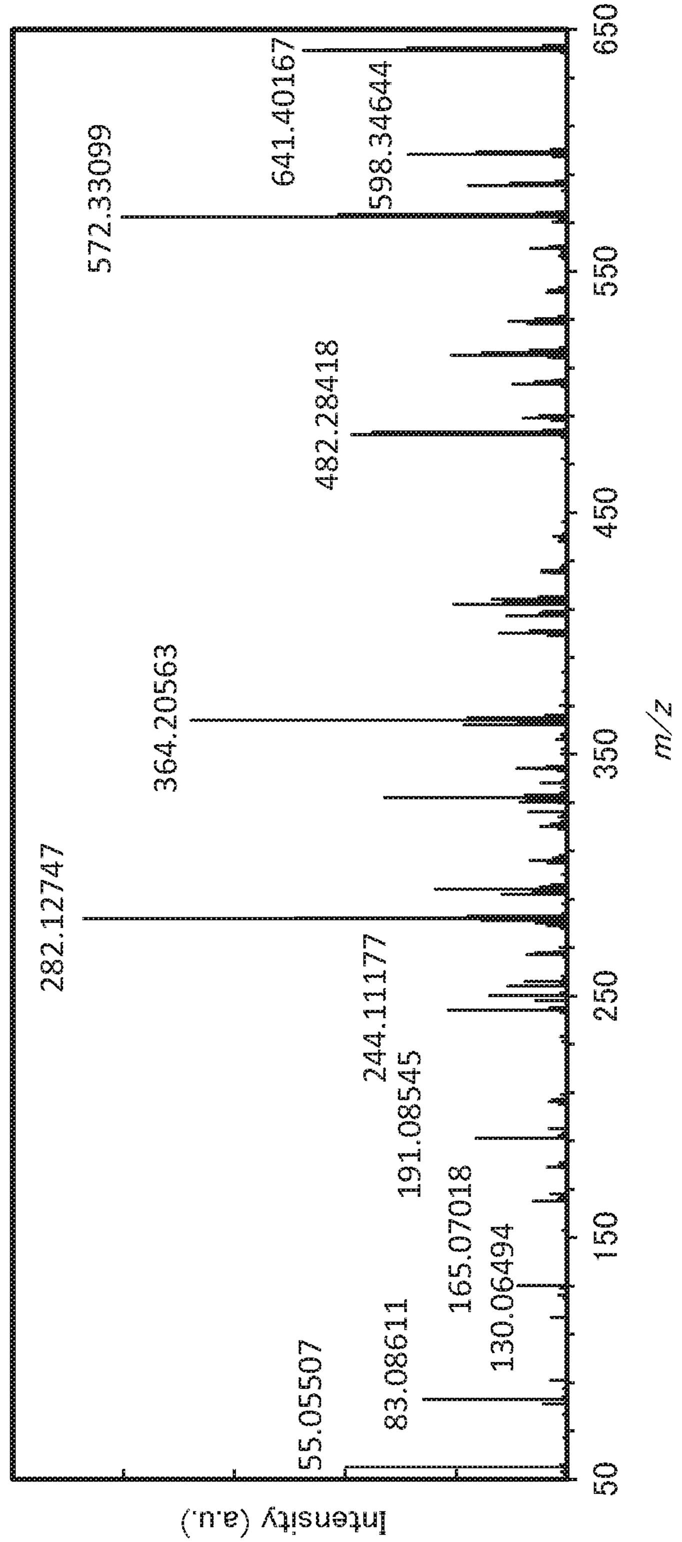
FIG. 25 shows an MS spectrum of chBichPASchF.

FIG. 25 shows that product ions of chBichPASchF are mainly detected at m/z of around 641. Note that the result in FIG. 25 shows characteristics derived from chBichPASchF and therefore can be regarded as important data for identifying chBichPASchF contained in a mixture.

Note that a fragment ion at m/z of 482, which was observed in measurement with a collision energy of 60 eV, is estimated to be derived from N-[(4'-cyclohexyl)-1,1'-biphenyl-4-yl]-N-(spiro[cyclohexane-1,9'-[9H]-fluoren]-2'-yl)-amine generated in such a manner that a C—N bond of chBichPASchF was cut, and this is the characteristics of chBichPASchF.

Figure 85:
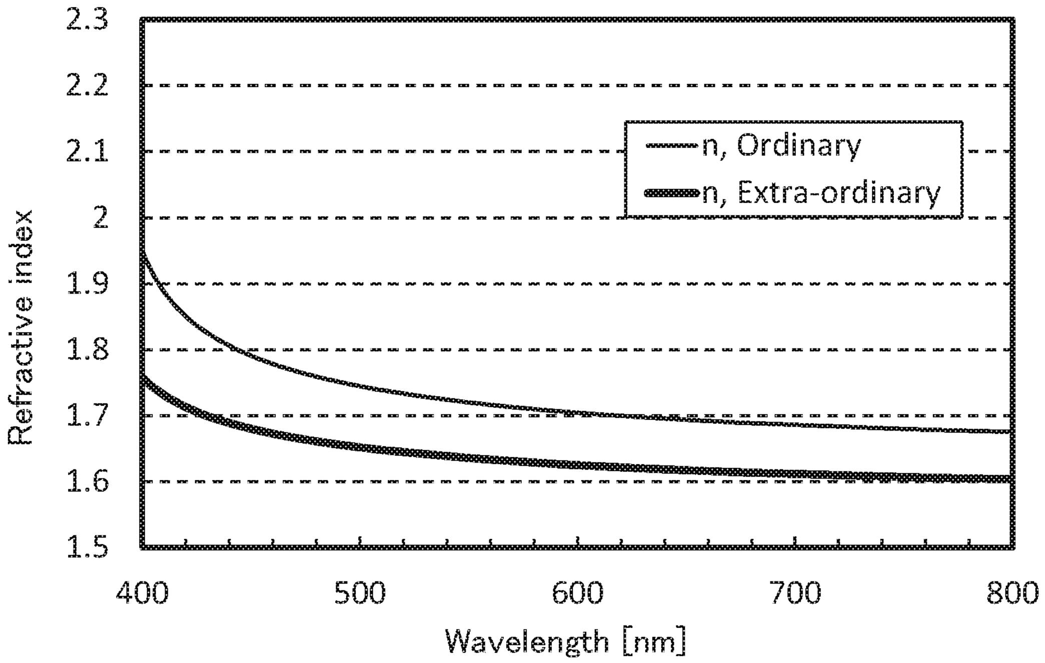
FIG. 85 shows measurement data of a refractive index of chBichPASchF.

FIG. 85 shows the results of measuring the refractive index of chBichPASchF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 85.

FIG. 85 shows that chBichPASchF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of chBichPASchF was measured. Tg was measured using a differential scanning calorimeter (a Perkin-Elmer Co., Ltd. Pyris 1 DSC) in a state where a powder was put on an aluminum cell. As a result, Tg of chBichPASchF was 102° C.

Example 5

Synthesis Example 5

In this example, a synthesis method of N-(4-cyclohexylphenyl)-bis(spiro[cyclohexane-1,9'-[9H]fluoren]-2'-yl) amine (abbreviation: SchFB1chP), which is the organic compound represented by the structural formula (104) in Embodiment 1, is described. A structure of SchFB1chP is shown below.

[Chemical Formula 59]

(104)

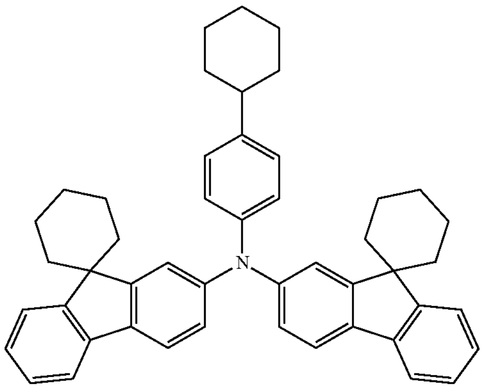

Step 1: Synthesis of 4-cyclohexylaniline

The synthesis was performed in a manner similar to Step 1 of the synthesis example 3 in Example 3.

Step 2: Synthesis of N-(4-cyclohexylphenyl)-N-(spiro[cyclohexane-1,9'[9H]fluoren]-2'-yl)amine The synthesis was performed in a manner similar to Step 2 of the synthesis example 3 in Example 3.

Step 3: Synthesis of N-(4-cyclohexylphenyl)-bis (spiro[cyclohexane-1,9'-[9H]fluoren]-2'-yl)amine (Abbreviation: SchFB1chP)

In a three-neck flask were put 3.0 g (16.9 mmol) of 4-cyclohexylaniline, the synthesis method thereof is described in Step 2, 5.3 g (16.9 mmol) of 2'-bromo(spiro [cyclohexane-1,9'[9H]fluoren]), 4.9 g (50.7 mmol) of sodium-tert-butoxide, and 85 mL of xylene. This mixture was degassed under reduced pressure, and then the air in the flask was replaced with nitrogen. The mixture was stirred while being heated to 60° C. Then, 62 mg (0.17 mmol) of allylpalladium(II) chloride dimer (abbreviation: [(Allyl) $PdCl]_2$) and 280 mg (0.67 mmol) of di-tert-butyl(1-methyl-2,2-diphenylcyclopropyl)phosphine (abbreviation: cBRIDP (registered trademark)) were added. This mixture was heated at 90° C. and reacted for approximately 7 hours. After that, the temperature of the flask was lowered to approximately 60° C., approximately 1 mL of water was added to the mixture, and a precipitated solid was separated by filtration. The filtrate was concentrated, and the obtained solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 0.95 g of a target white solid was obtained in a yield of 8.8%. The synthesis scheme of Step 3 is shown below.

[Chemical Formula 60]

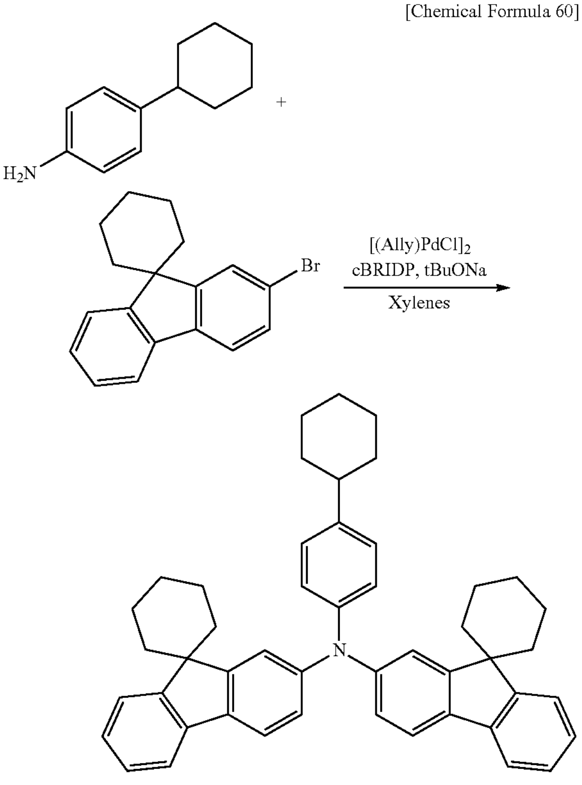

(104)

Figure 26:
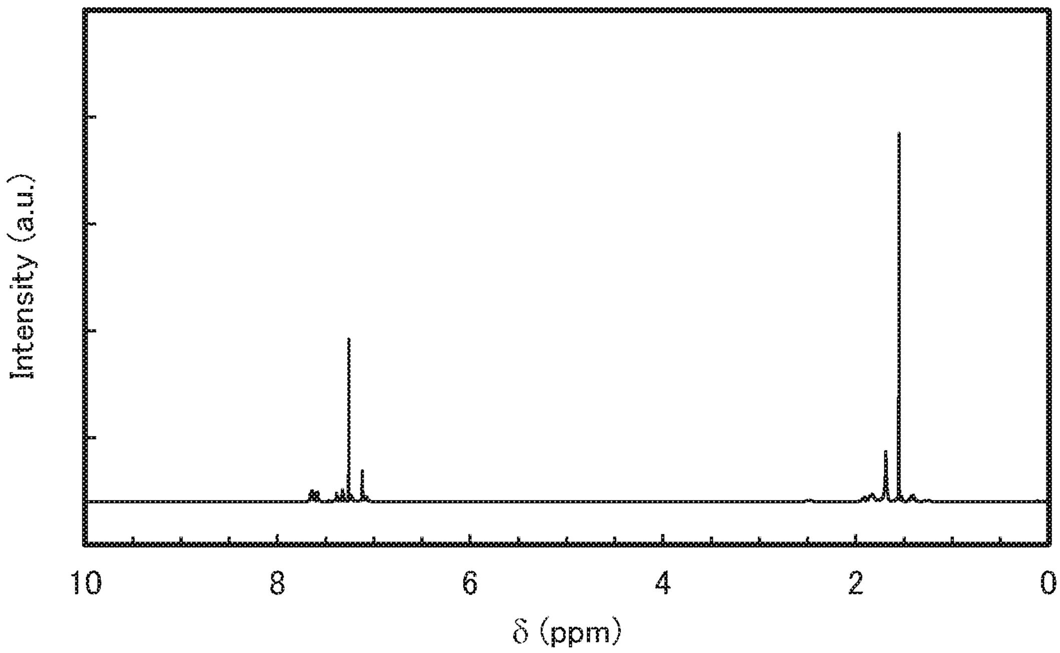
FIG. 26 is a $^{1}$H-NMR chart of SchFB1chP.

Analysis results by nuclear magnetic resonance spectroscopy ($^1$H-NMR) of the white solid obtained in Step 3 are shown below. FIG. 26 shows the H-NMR chart. These results show that N-(4-cyclohexylphenyl)-bis(spiro[cyclohexane-1,9'-[9H]fluoren]-2'-yl)amine (abbreviation: SchFB1chP) was synthesized in this synthesis example.

$^1$H-NMR. δ ($CDCl_3$): 7.64 (t, 4H, J=8.0 Hz), 7.59 (d, 2H, J=8.5 Hz), 7.39 (brs, 2H), 7.33 (t, 2H, J=7.5 Hz), 7.20-7.25 (m, 2H), 7.12 (brs, 4H), 7.08 (d, 2H, J=8.0 Hz), 2.44-2.52 (brm, 1H), 1.63-1.97 (m, 23H), 1.50-1.61 (m, 2H), 1.34-1.48 (m, 4H), 1.20-1.32 (brm, 1H).

Then, 0.93 g of the obtained solid was purified by a train sublimation method. The purification by sublimation was conducted by heating at 250° C. under a pressure of 3.0 Pa with the argon flow rate of 13.3 mL/min. After the purification by sublimation, 0.64 g of a pale yellowish white solid was obtained at a collection rate of 69%.

Figure 27:
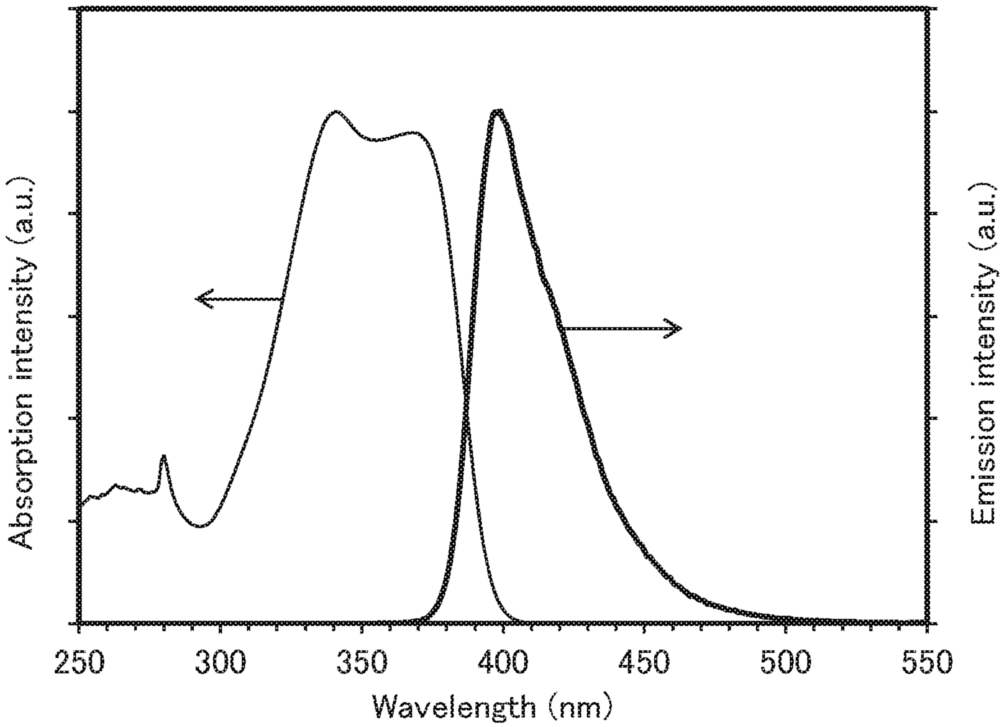
FIG. 27 shows an absorption spectrum and an emission spectrum of SchFB1chP in a toluene solution.

Next, an ultraviolet-visible absorption spectrum (hereinafter, simply referred to as an absorption spectrum) of SchFB1chP in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FS920, manufactured by Hamamatsu Photonics K.K.), both of which were measured at room temperature. A quartz cell was used for the measurement cell. FIG. 27 shows measurement results of the absorption spectrum and the emission spectrum. The horizontal axis represents the wavelength and the vertical axes represent the absorption intensity and emission intensity. The absorption intensity shown in FIG. 27 is a result obtained by subtraction of an absorption spectrum of only toluene in a quartz cell from the measured absorption spectrum of the toluene solution in the quartz cell.

As shown in FIG. 27, the organic compound SchFB1chP has an emission peak at 368 nm.

Next, the organic compound SchFB1chP was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C8 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that SchFB1chP was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 639 which underwent the ionization under the above-described conditions was collided with an argon gas in a collision cell to dissociate into product ions. Energy (collision energy) for the collision with argon was 60 eV The measurement mass range was set to m/z (mass-to-charge ratio)=100 to 1500. The detection results of the dissociated product ions by time-of-flight (TOF) MS are shown in FIG. 28.

Figure 28:
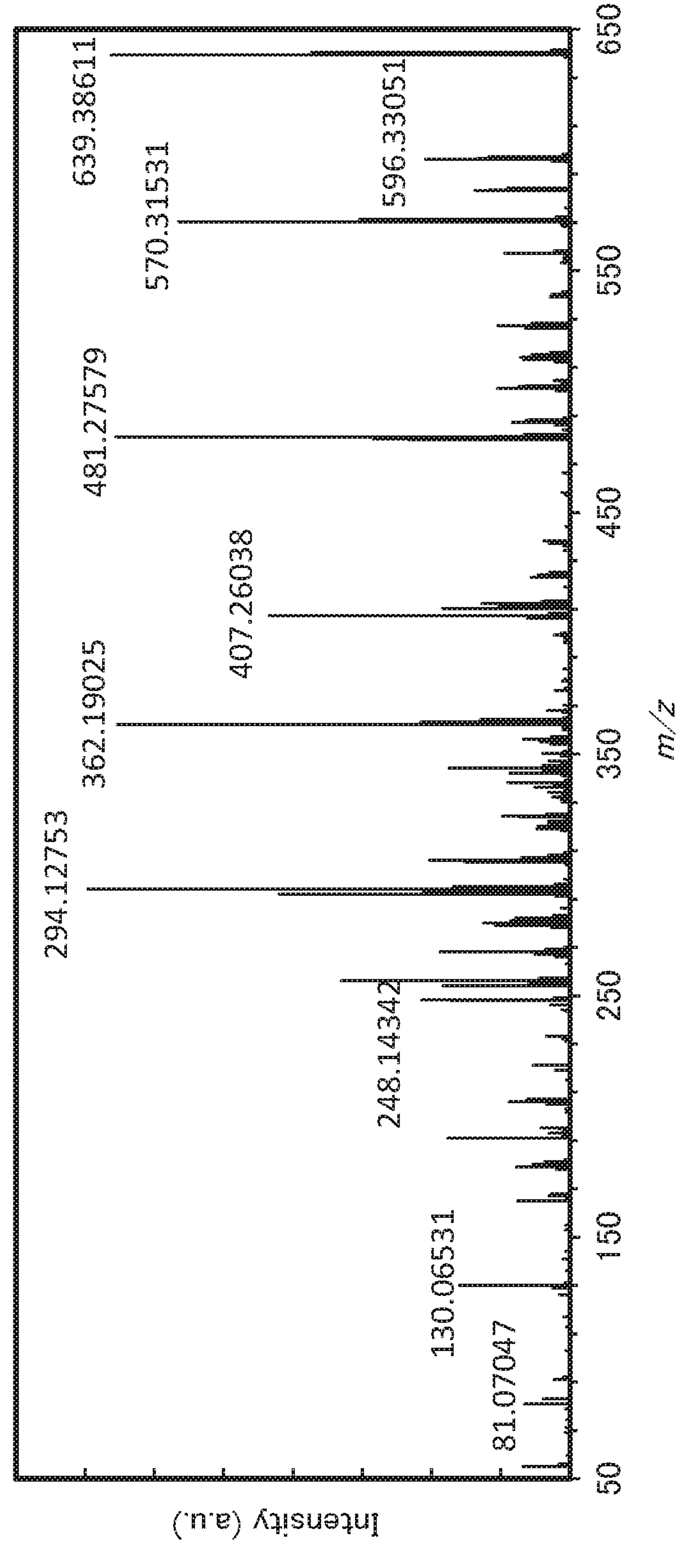
FIG. 28 shows an MS spectrum of SchFB1chP.

FIG. 28 shows that product ions of SchFB1chP are mainly detected at m/z of around 639. Note that the result in FIG. 28 shows characteristics derived from SchFB1chP and therefore can be regarded as important data for identifying SchFB1chP contained in a mixture.

Note that a fragment ion at m/z of 481, which was observed in measurement with a collision energy of 60 eV, is estimated to be derived from N,N-bis(spiro[cyclohexane-1,9'-[9H]fluoren]-2'-yl)amine generated in such a manner that a C—N bond of SchFB1chP was cut, and this is the characteristics of SchFB1chP.

Figure 86:
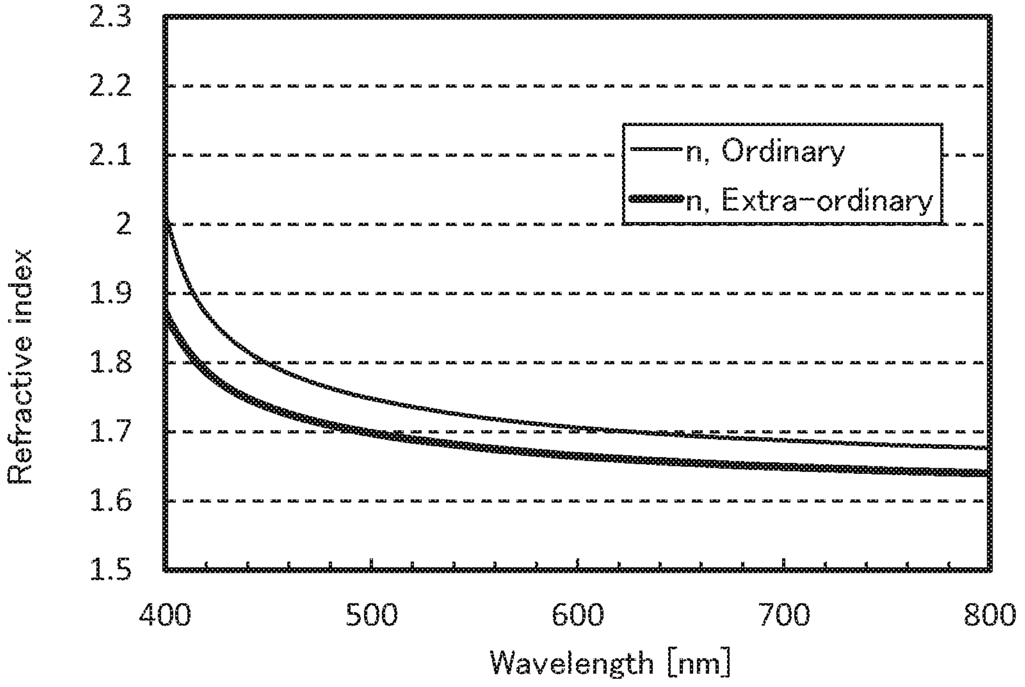
FIG. 86 shows measurement data of a refractive index of SchFB1chP.

FIG. 86 shows the results of measuring the refractive index of SchFB1chP by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 86.

FIG. 86 shows that SchFB1chP is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of SchFB1chP was measured. Tg was measured using a differential scanning calorimeter (a Perkin-Elmer Co., Ltd. Pyris 1 DSC) in a state where a powder was put on an aluminum cell. As a result, Tg of SchFB1chP was 112° C.

Example 6

Synthesis Example 6

In this example, a synthesis method of N-[(3',5'-ditertiarybutyl)-1,1'-biphenyl-4-yl]-N-(4-cyclohexylphenyl)-9,9-dimethyl-9H-fluor en-2-amine (abbreviation: mmtBuBichPAF), which is the organic compound represented by the structural formula (105) in Embodiment 1, is described. A structure of mmtBuBichPAF is shown below.

[Chemical Formula 61]

(105)

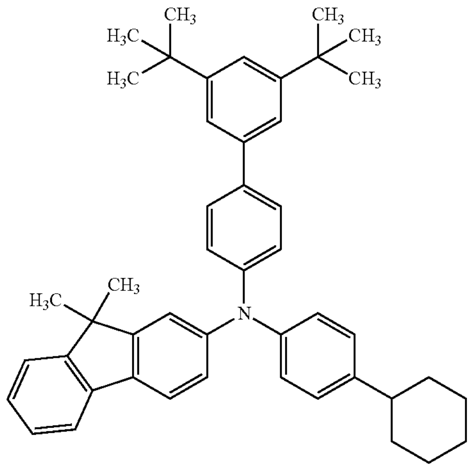

Step 1: Synthesis of 3',5'-ditertiarybutyl-4-chloro-1,1'-biphenyl

In a three-neck flask were put 13.5 g (50 mmol) of 3,5-ditertiarybutyl-1-bromobenzene, 8.2 g (52.5 mmol) of 4-chlorophenylboronic acid, 21.8 g (158 mmol) of potassium carbonate, 125 mL of toluene, 31 mL of ethanol, and 40 mL of water. This mixture was degassed under reduced pressure, and then the air in the flask was replaced with nitrogen. To this mixture, 225 mg (1.0 mmol) of palladium acetate and 680 mg (2.0 mmol) of tris(2,6-methylphenyl) phosphine were added, and the mixture was heated and refluxed at 80° C. for approximately 3 hours. After that, the temperature of the flask was lowered to room temperature, and the mixture was separated into an organic layer and an aqueous layer. Magnesium sulfate was added to this solution for drying to be concentrated. The obtained solution was purified by silica gel column chromatography. The obtained solution was concentrated and dried for hardening. After that, hexane was added for recrystallization. The mixed solution in which a white solid was precipitated was cooled with ice and filtrated. The obtained solid was dried at approximately 60° C. in a vacuum, whereby 9.5 g of a target white solid was obtained in a yield of 63%. The synthesis scheme of Step 1 is shown below.

[Chemical Formula 62]

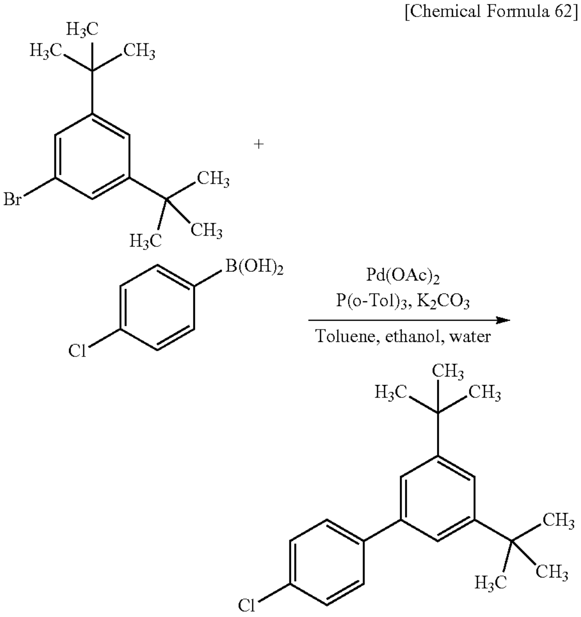

Step 2: Synthesis of N-(4-cycrohexylphenyl)-N-(9,9-dimethyl-9H-fluoren-2yl)amine The synthesis was performed in a manner similar to Step 1 of the synthesis example 2 in Example 2.

<Step 3: Synthesis of N-[(3',5'-ditertiarybutyl)-1,1'-biphenyl-4-yl]-N-(4-cyclohexylphenyl)-9,9-dimethyl-9H-fluor en-2-amine (Abbreviation: mmtBuBichPAF)

In a three-neck flask were put 3.2 g (10.6 mmol) of 3',5'-ditertiarybutyl-4-chloro-1,1'-biphenyl obtained in Step 1, 3.9 g (10.6 mmol) of N-(4-cycrohexylphenyl)-N-(9,9-dimethyl-9H-fluoren-2yl)amine obtained in Step 2, 3.1 g (31.8 mmol) of sodium-tert-butoxide, and 53 mL of xylene. This mixture was degassed under reduced pressure, and then the air in the flask was replaced with nitrogen. The mixture was stirred while being heated to 50° C. Then, 39 mg (0.11 mmol) of allylpalladium(II) chloride dimer (abbreviation: $[(Allyl)PdCl]_2$) and 150 mg (0.42 mmol) of di-tert-butyl(1-methyl-2,2-diphenylcyclopropyl)phosphine (abbreviation: cBRIDP (registered trademark)) were added, and this mixture was heated at 120° C. for approximately 3 hours. After that, the temperature of the flask was lowered to approximately 60° C., approximately 1 mL of water was added to the mixture, and a precipitated solid was separated by filtration. The filtrate was concentrated, and the obtained solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 5.8 g of a target white solid was obtained in a yield of 87%. The synthesis scheme of Step 3 is shown below.

[Chemical Formula 63]

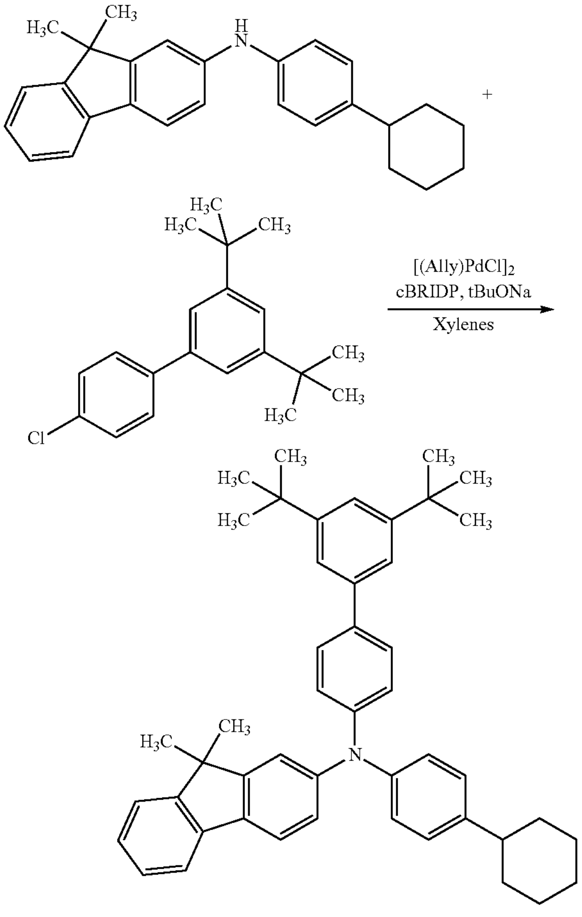

(105)

Figure 29:
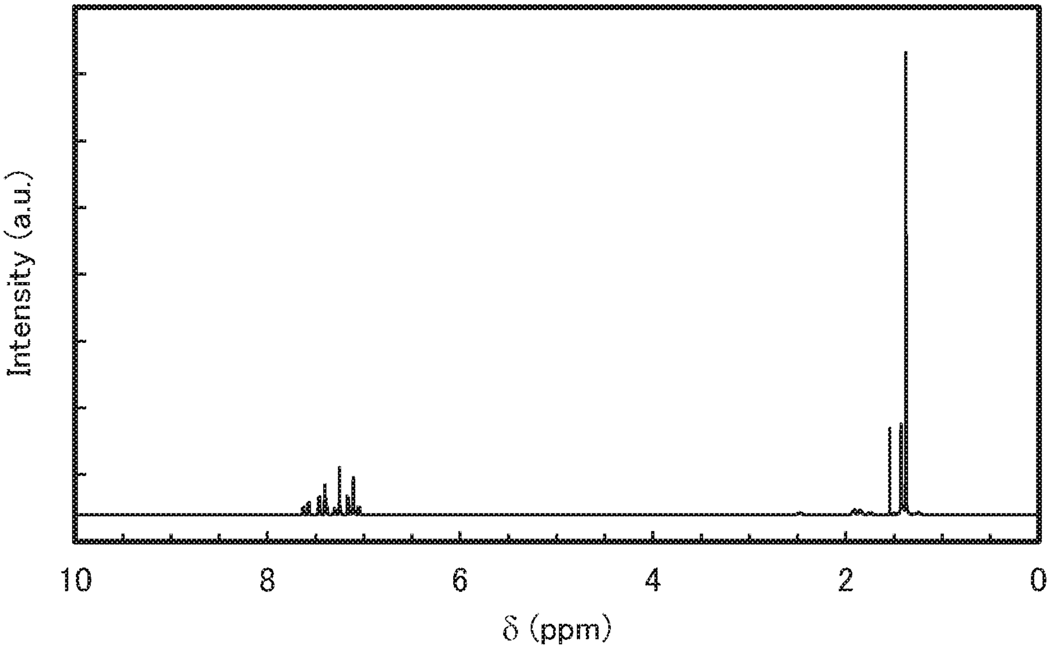
FIG. 29 is a $^{1}$H-NMR chart of mmtBuBichPAF.

Analysis results by nuclear magnetic resonance spectroscopy ($^1$H-NMR) of the white solid obtained in Step 3 are shown below. FIG. 29 shows the $^1$H-NMR chart. The results show that N-[(3',5'-ditertiarybutyl)-1,1'-biphenyl-4-yl]-N-(4-cyclohexylphenyl)-9,9-dimethyl-9H-fluor en-2-amine (abbreviation: mmtBuBichPAF) was synthesized in this synthesis example.

$^1$H-NMR. δ ($CDCl_3$): 7.63 (d, 1H, J=7.5 Hz), 7.57 (d, 1H, J=8.0 Hz), 7.44-7.49 (m, 2H), 7.37-7.42 (m, 4H), 7.31 (td, 1H, J=7.5 Hz, 2.0 Hz), 7.23-7.27 (m, 2H), 7.15-7.19 (m, 2H), 7.08-7.14 (m, 4H), 7.05 (dd, 1H, J=8.0 Hz, 2.0 Hz), 2.43-2.53 (brm, 1H), 1.81-1.96 (m, 4H), 1.75 (d, 1H, J=12.5 Hz), 1.32-1.48 (m, 28H), 1.20-1.31 (brm, 1H).

Then, 3.5 g of the obtained solid was purified by a train sublimation method. The purification by sublimation was conducted by heating at 255° C. under a pressure of 3.0 Pa with the argon flow rate of 11.8 mL/min. After the purification by sublimation, 3.1 g of a pale yellowish white solid was obtained at a collection rate of 89%.

Figure 30:
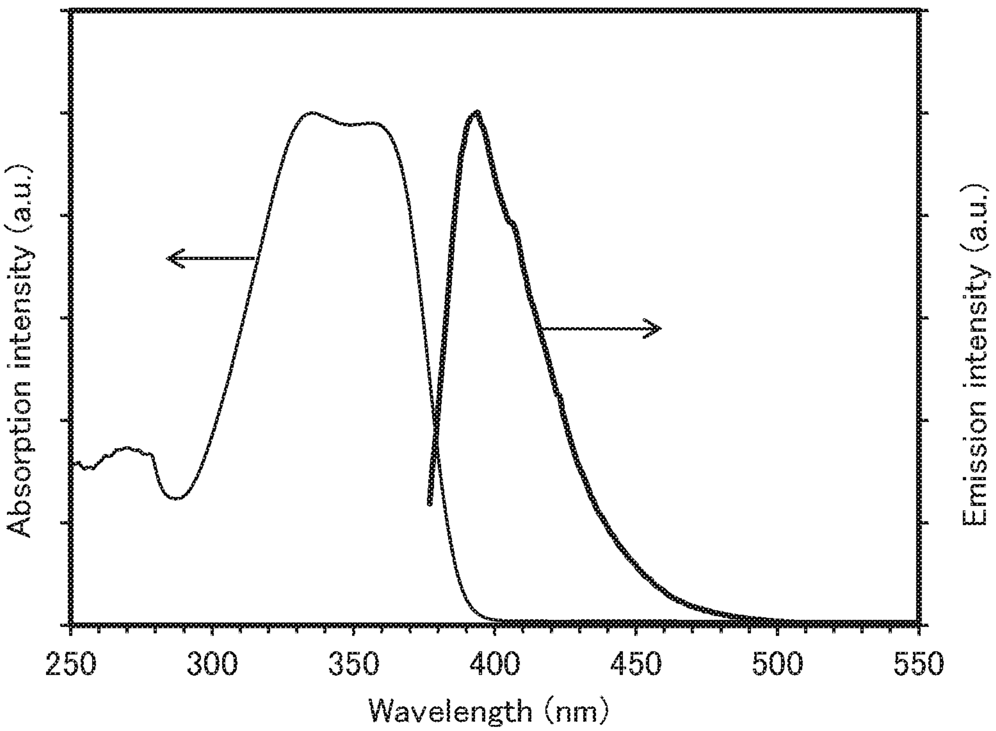
FIG. 30 shows an absorption spectrum and an emission spectrum of mmtBuBichPAF in a toluene solution.

Next, an ultraviolet-visible absorption spectrum (hereinafter, simply referred to as an absorption spectrum) of mmtBuBichPAF in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FS920, manufactured by Hamamatsu Photonics K.K.), both of which were measured at room temperature. A quartz cell was used for the measurement cell. FIG. 30 shows measurement results of the absorption spectrum and the emission spectrum. The horizontal axis represents the wavelength and the vertical axes represent the absorption intensity and emission intensity. The absorption intensity shown in FIG. 30 is a result obtained by subtraction of an absorption spectrum of only toluene in a quartz cell from the measured absorption spectrum of the toluene solution in the quartz cell.

As shown in FIG. 30, the organic compound mmtBuBichPAF has an emission peak at 360 nm.

Next, the organic compound mmtBuBichPAF was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C8 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that mmtBuBichPAF was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 631 which underwent the ionization under the above-described conditions was collided with an argon gas in a collision cell to dissociate into product ions. Energy (collision energy) for the collision with argon was 60 eV The measurement mass range was set to m/z (mass-to-charge ratio)=100 to 1500. The detection results of the dissociated product ions by time-of-flight (TOF) MS are shown in FIG. 31.

Figure 31:
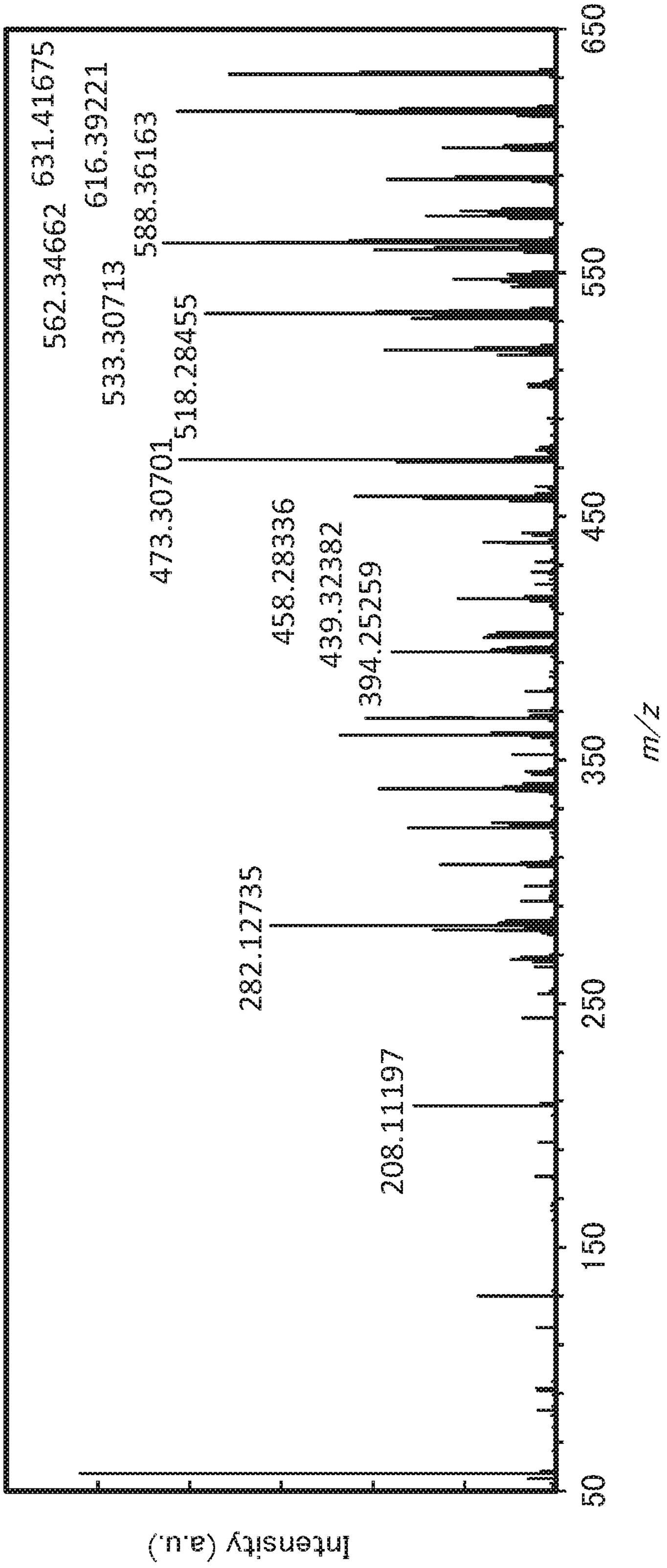
FIG. 31 shows an MS spectrum of a mass spectrum of mmtBuBichPAF.

FIG. 31 shows that product ions of mmtBuBichPAF are mainly detected at m/z of around 631. Note that the result in FIG. 31 shows characteristics derived from mmtBuBichPAF and therefore can be regarded as important data for identifying mmtBuBichPAF contained in a mixture.

Note that a fragment ion at m/z of 473, which was observed in measurement with a collision energy of 60 eV, is estimated to be derived from N-(3',5'-ditertiarybutyl-1,1'-biphenyl-4-yl)-N-(9,9-dimethyl-9H-fluoren-2yl)amine generated in such a manner that a C—N bond of mmtBuBichPAF was cut, and this is the characteristics of mmtBuBichPAF.

Figure 87:
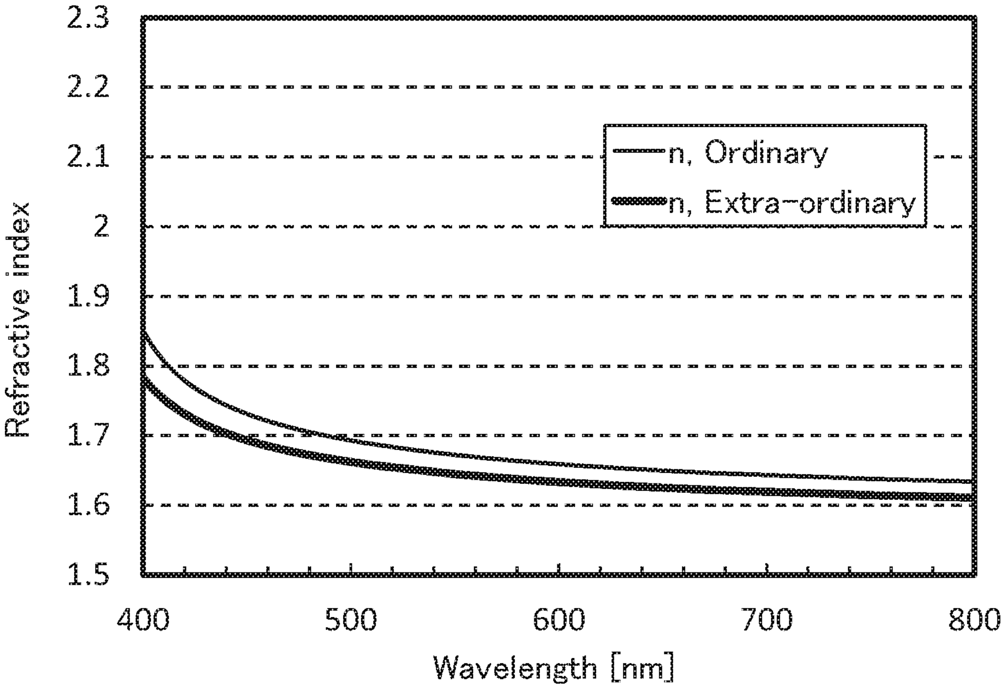
FIG. 87 shows measurement data of a refractive index of mmtBuBichPAF.

FIG. 87 shows the results of measuring the refractive index of mmtBuBichPAF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 87.

FIG. 87 shows that mmtBuBichPAF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of mmtBuBichPAF was measured. Tg was measured using a differential scanning calorimeter (a Perkin-Elmer Co., Ltd. Pyris 1 DSC) in a state where a powder was put on an aluminum cell. As a result, Tg of mmtBuBichPAF was 102° C.

Example 7

Synthesis Example 7

In this example, a synthesis method of N,N-bis(3',5'-ditertiarybutyl-1,1'-biphenyl-4-yl)-9,9, -dimethyl-9H-fluoren-2-amine (abbreviation: dmmtBuBiAF), which is the organic compound represented by the structural formula (106) in Embodiment 1, is described. A structure of dmmtBuBiAF is shown below.

[Chemical Formula 64]

(106)

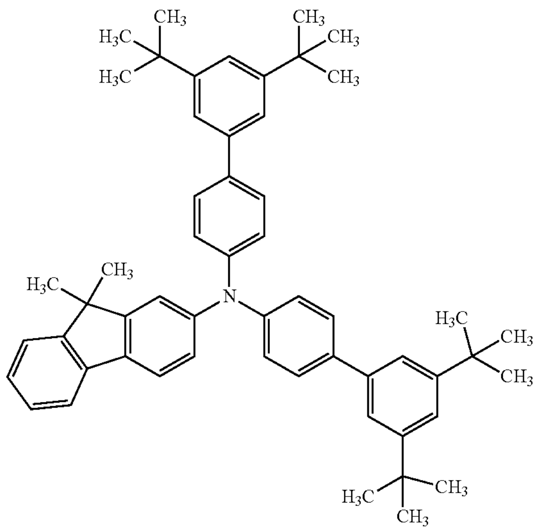

Step 1: Synthesis of 3',5'-ditertiarybutyl-4-chloro-1,1'-biphenyl

The synthesis was performed in a manner similar to Step 1 of the synthesis example 6 in Example 6.

<Step 2: Synthesis of N,N-bis(3',5'-ditertiarybutyl-1,1'-biphenyl-4-yl)-9,9, -dimethyl-9H-fluoren-2-amine (Abbreviation: dmmtBuBiAF)

In a three-neck flask were put 2.8 g (13.5 mmol) of 9,9-dimethyl-9H-fluoren-2-amine, 6.1 g (20.3 mmol) of 3',5'-ditertiarybutyl-4-chloro-1,1'-biphenyl obtained in Step 1, 5.8 g (60.8 mmol) of sodium-tert-butoxide, and 70 mL of xylene. This mixture was degassed under reduced pressure, and then the air in the flask was replaced with nitrogen. The mixture was stirred while being heated to 50° C. Then, 100 mg (0.27 mmol) of allylpalladium(II) chloride dimer (abbreviation: $[(Allyl)PdCl]_2$) and 381 mg (1.08 mmol) of di-tert-butyl(1-methyl-2,2-diphenylcyclopropyl)phosphine (abbreviation: cBRIDP (registered trademark)) were added, and the mixture was heated at 120° C. for approximately 3 hours. After that, the temperature of the flask was lowered to approximately 60° C., approximately 1 mL of water was added to the mixture, and a precipitated solid was separated by filtration. The filtrate was concentrated, and the obtained solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 4.2 g of a target white solid was obtained in a yield of 42%. The synthesis scheme of Step 2 is shown below.

[Chemical Formula 65]

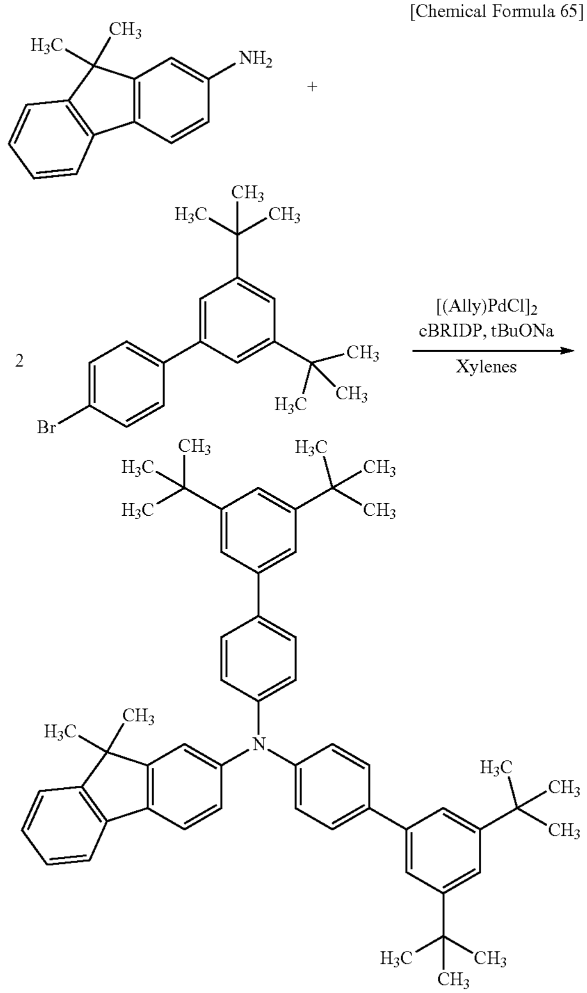

(106)

Figure 32:
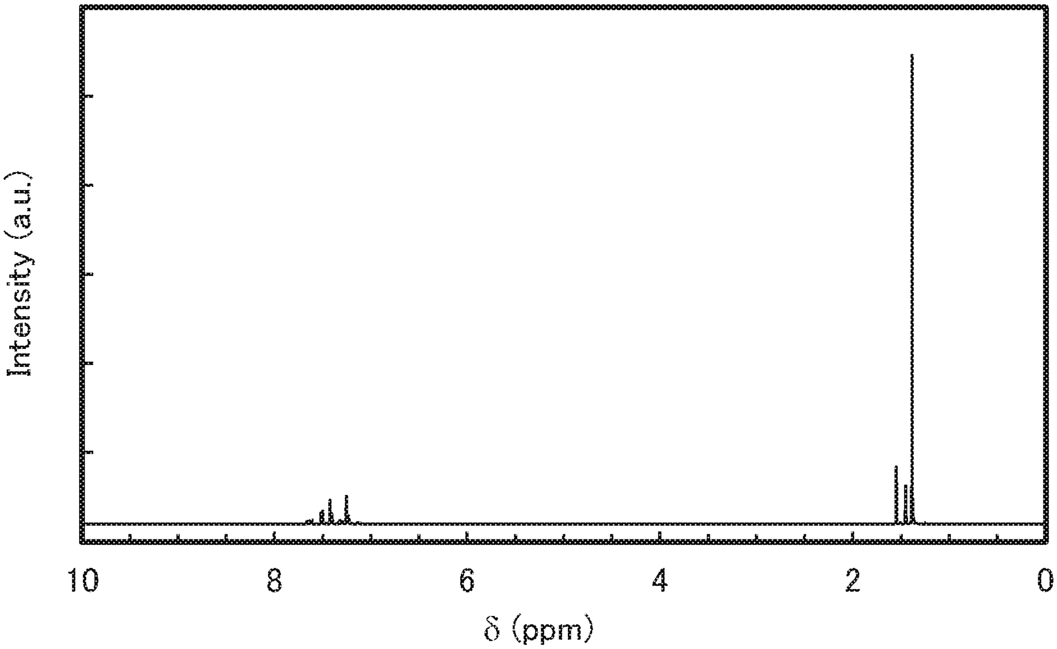
FIG. 32 is a $^{1}$H-NMR chart of dmmtBuBiAF.

Analysis results by nuclear magnetic resonance spectroscopy ($^1$H-NMR) of the white solid obtained in Step 2 are shown below. FIG. 32 shows the $^1$H-NMR chart. The results show that N,N-bis(3',5'-ditertiarybutyl-1,1'-biphenyl-4-yl)-9,9, -dimethyl-9H-fluoren-2-amine (abbreviation: dmmtBuBiAF) was synthesized in this synthesis example.

$^1$H-NMR. δ ($CDCl_3$): 7.66 (d, 1H, J=7.5 Hz), 7.62 (d, 1H, J=8.0 Hz), 7.51 (d, 4H, J=8.5 Hz), 7.38-7.44 (m, 7H), 7.26-7.35 (m, 3H), 7.20-7.25 (m, 4H), 7.13 (dd, 1H, J=8.0 Hz, 1.5 Hz), 1.45 (s, 6H), 1.39 (s, 36H).

Then, 4.0 g of the obtained solid was purified by a train sublimation method. The purification by sublimation was conducted by heating at 260° C. under a pressure of 3.0 Pa with the argon flow rate of 18.8 mL/min. After the purification by sublimation, 2.8 g of a pale yellowish white solid was obtained at a collection rate of 70%.

Figure 33:
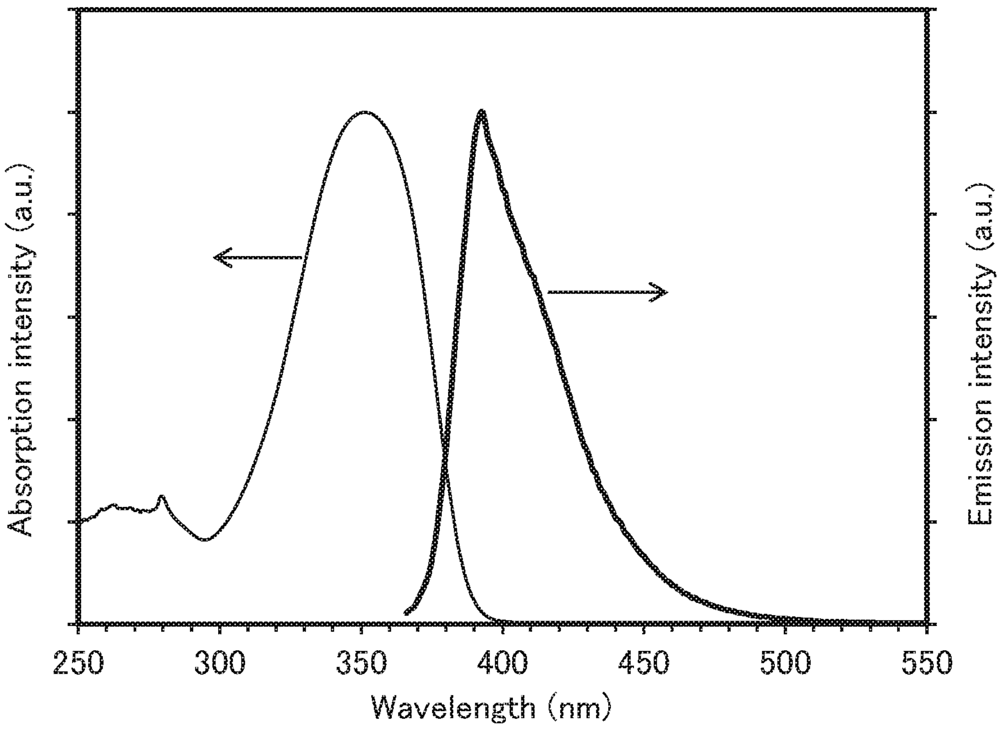
FIG. 33 shows an absorption spectrum and an emission spectrum of dmmtBuBiAF in a toluene solution.

Next, an ultraviolet-visible absorption spectrum (hereinafter, simply referred to as an absorption spectrum) of dmmtBuBiAF in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FS920, manufactured by Hamamatsu Photonics K.K.), both of which were measured at room temperature. A quartz cell was used for the measurement cell. FIG. 33 shows measurement results of the absorption spectrum and the emission spectrum. The horizontal axis represents the wavelength and the vertical axes represent the absorption intensity and emission intensity. The absorption intensity shown in FIG. 33 is a result obtained by subtraction of an absorption spectrum of only toluene in a quartz cell from the measured absorption spectrum of the toluene solution in the quartz cell.

As shown in FIG. 33, the organic compound dmmtBuBiAF has an emission peak at 351 nm.

Next, the organic compound dmmtBuBiAF was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C4 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that dmmtBuBiAF was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 737 which underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500. The detection results of the dissociated product ions by time-of-flight (TOF) MS are shown in FIG. 34.

Figure 34:
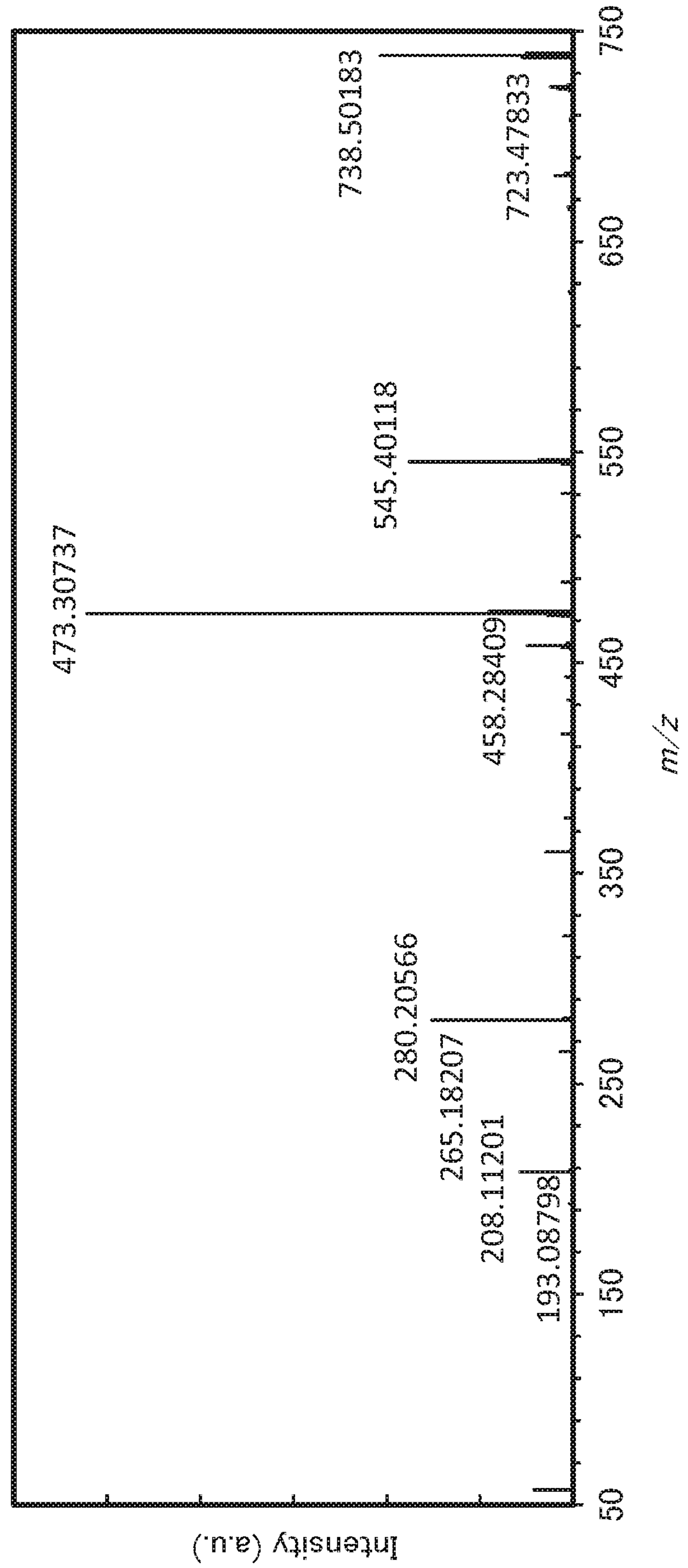
FIG. 34 shows an MS spectrum of dmmtBuBiAF.

FIG. 34 shows that product ions of dmmtBuBiAF are mainly detected at m/z of around 738. Note that the result in FIG. 34 shows characteristics derived from dmmtBuBiAF and therefore can be regarded as important data for identifying dmmtBuBiAF contained in a mixture.

Note that a fragment ion at m/z of 473, which was observed in measurement with a collision energy of 50 eV, is estimated to be derived from N-(3',5'-ditertiarybutyl-1,1'-biphenyl-4-yl)-N-(9,9, -dimethyl-9H-fluoren-2-yl)amine generated in such a manner that a C—N bond of dmmtBuBiAF was cut, and this is the characteristics of dmmtBuBiAF.

Figure 88:
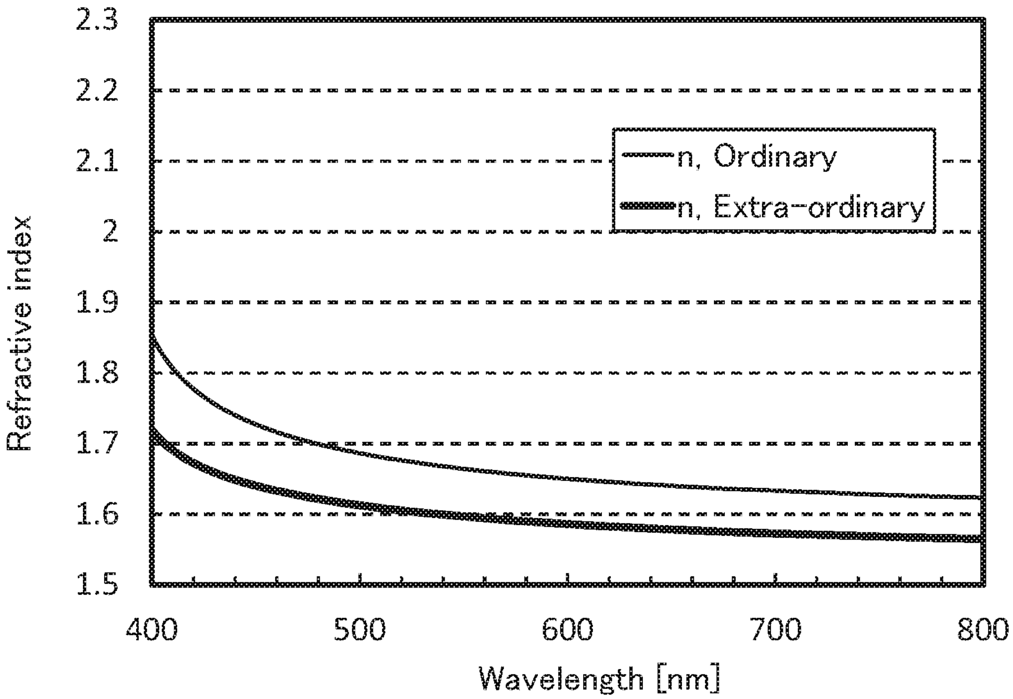
FIG. 88 shows measurement data of a refractive index of dmmtBuBiAF.

FIG. 88 shows the results of measuring the refractive index of dmmtBuBiAF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 88.

FIG. 88 shows that dmmtBuBiAF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of dmmtBuBiAF was measured. Tg was measured using a differential scanning calorimeter (a Perkin-Elmer Co., Ltd. Pyris 1 DSC) in a state where a powder was put on an aluminum cell. As a result, Tg of dmmtBuBiAF was 120° C.

Example 8

Synthesis Example 8

In this example, a synthesis method of N-(3,5-ditertiarybutylphenyl)-N-(3',5', -ditertiarybutyl-1,1'-biphenyl-4-yl)-9,9, -dimethyl-9H-fluoren-2-amine (abbreviation: mmtBuBimmtBuPAF), which is the organic compound represented by the structural formula (107) in Embodiment 1, is described. A structure of mmtBuBimmtBuPAF is shown below.

[Chemical Formula 66]

(107)

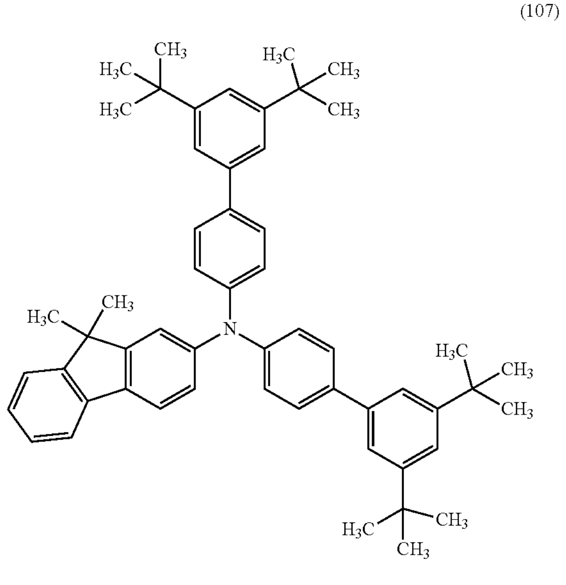

Step 1: Synthesis of 3',5'-ditertiarybutyl-4-chloro-1,1'-biphenyl

The synthesis was performed in a manner similar to Step 1 of the synthesis example 6 in Example 6.

Step 2: Synthesis of N-(3',5'-ditertiarybutyl-1,1'-biphenyl-4-yl)-N-(9,9, -dimethyl-9H-fluoren-2-yl)amine In a three-neck flask were put 2.8 g (13.5 mmol) of 9,9-dimethyl-9H-fluoren-2-amine, 6.1 g (20.3 mmol) of 3',5'-ditertiarybutyl-4-chloro-1,1'-biphenyl obtained in Step 1, 5.8 g (60.8 mmol) of sodium-tert-butoxide, and 70 mL of xylene. This mixture was degassed under reduced pressure, and then the air in the flask was replaced with nitrogen. The mixture was stirred while being heated to 50° C. Then, 100 mg (0.27 mmol) of allylpalladium(II) chloride dimer (abbreviation: $[(Allyl)PdCl]_2$) and 381 mg (1.08 mmol) of di-tert-butyl(1-methyl-2,2-diphenylcyclopropyl)phosphine (abbreviation: cBRIDP (registered trademark)) were added, and the mixture was heated at 120° C. for approximately 3 hours. After that, the temperature of the flask was lowered to approximately 60° C., approximately 1 mL of water was added to the mixture, and a precipitated solid was separated by filtration. The filtrate was concentrated, and the obtained solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 2.9 g of a brown oily substance N-(3',5'-ditertiarybutyl-1,1'-biphenyl-4-yl)-N-(9,9, -dimethyl-9H-fluoren-2-yl)amine was obtained in a yield of 46%. The synthesis scheme of Step 2 is shown below.

[Chemical Formula 67]

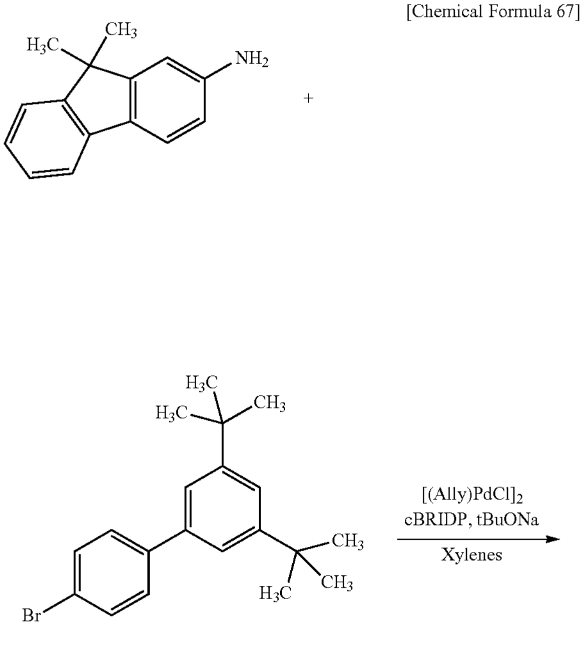

-continued

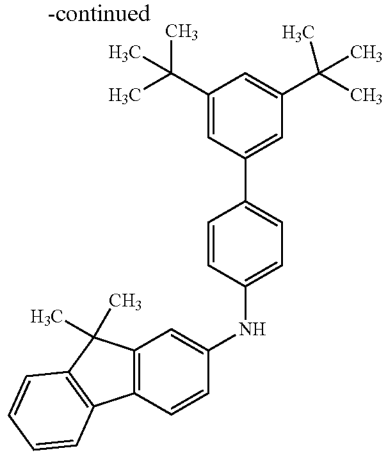

Step 3: Synthesis of N-(3,5-ditertiarybutylphenyl)-N-(3',5', -ditertiarybutyl-1,1'-biphenyl-4-yl)-9,9, -dimethyl-9H-fluoren-2-amine (Abbreviation: mmtBuBimmtBuPAF)

In a three-neck flask were put 2.7 g (5.7 mmol) of N-(3',5'-ditertiarybutyl-1,1'-biphenyl-4-yl)-N-(9,9, -dimethyl-9H-fluoren-2-yl)amine obtained in Step 2, 1.5 g (5.7 mmol) of 3,5-ditertiarybutyl-1-bromobenzene, 1.6 g (17.0 mmol) of sodium-tert-butoxide, and 30 mL of xylene. This mixture was degassed under reduced pressure, and then the air in the flask was replaced with nitrogen. The mixture was stirred while being heated to 50° C. Then, 21 mg (0.057 mmol) of allylpalladium(II) chloride dimer (abbreviation: $[(Allyl)PdCl]_2$) and 73 mg (0.208 mmol) of di-tert-butyl(1-methyl-2,2-diphenylcyclopropyl)phosphine (abbreviation: cBRIDP (registered trademark)) were added, and the mixture was heated at 120° C. for approximately 7 hours. After that, the temperature of the flask was lowered to approximately 60° C., approximately 1 mL of water was added to the mixture, and a precipitated solid was separated by filtration. The filtrate was concentrated, and the obtained solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 3.6 g of a target white solid was obtained in a yield of 95%. The synthesis scheme of Step 3 is shown below.

[Chemical Formula 68]

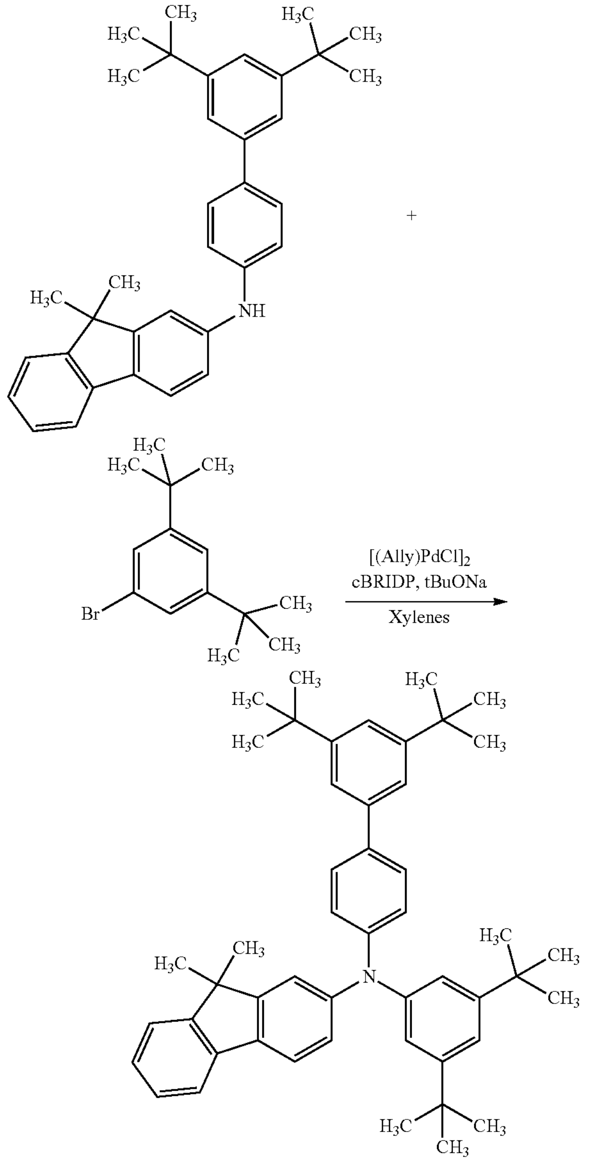

(107)

Figure 35:
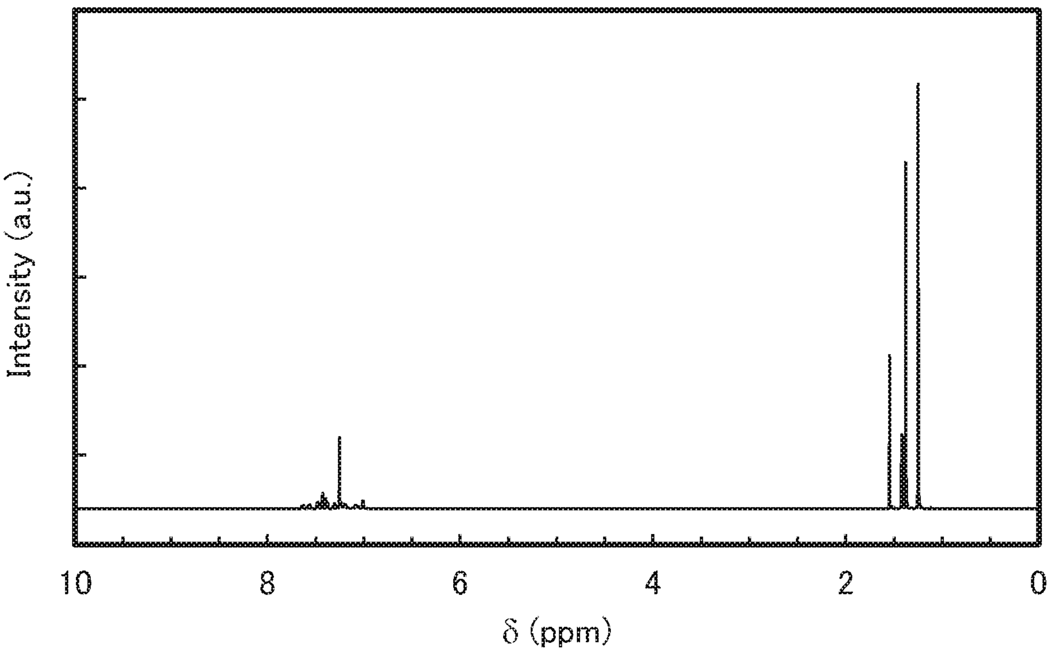
FIG. 35 is $^{1}$H-NMR chart of mmtBuBimmtBuPAF.

Analysis results by nuclear magnetic resonance spectroscopy ($^1$H-NMR) of the white solid obtained in Step 3 are shown below. FIG. 35 shows the $^1$H-NMR chart. The results show that N-(3,5-ditertiarybutylphenyl)-N-(3',5', -ditertiarybutyl-1,1'-biphenyl-4-yl)-9,9, -dimethyl-9H-fluoren-2-amine (abbreviation: mmtBuBimmtBuPAF) was synthesized in this synthesis example.

$^1$H-NMR. δ ($CDCl_3$): 7.64 (d, 1H, J=7.5 Hz), 7.57 (d, 1H, J=8.0 Hz), 7.48 (d, 2H, J=8.0 Hz), 7.43 (m, 2H), 7.39 (m, 2H), 7.31 (td, 1H, J=6.0 Hz, 1.5 Hz), 7.15-7.25 (m, 4H), 6.97-7.02 (m, 4H), 1.42 (s, 6H), 1.38 (s, 18H), 1.25 (s, 18H).

Then, 3.2 g of the obtained solid was purified by a train sublimation method. The purification by sublimation was conducted by heating at 210° C. under a pressure of 3.0 Pa with the argon flow rate of 19.3 mL/min. After the purification by sublimation, 3.0 g of a pale yellowish white solid was obtained at a collection rate of 94%.

Figure 36:
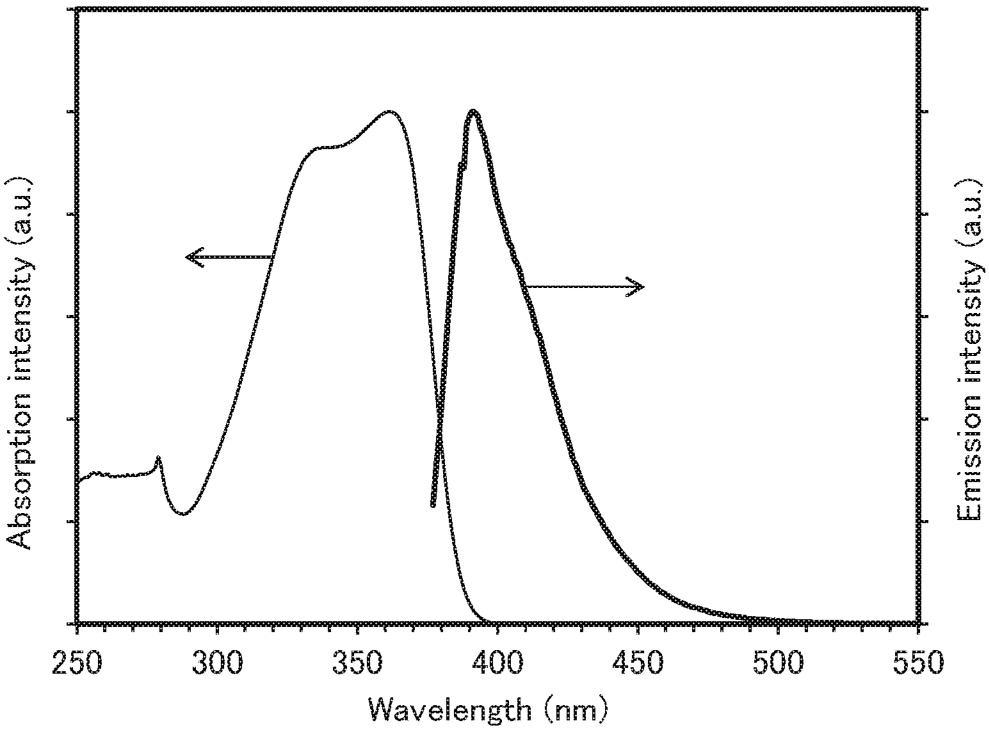
FIG. 36 shows an absorption spectrum and an emission spectrum of mmtBuBimmtBuPAF in a toluene solution.

Next, an ultraviolet-visible absorption spectrum (hereinafter, simply referred to as an absorption spectrum) of mmtBuBimmtBuPAF in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FS920, manufactured by Hamamatsu Photonics K.K.), both of which were measured at room temperature. A quartz cell was used for the measurement cell. FIG. 36 shows measurement results of the absorption spectrum and the emission spectrum. The horizontal axis represents the wavelength and the vertical axes represent the absorption intensity and emission intensity. The absorption intensity shown in FIG. 36 is a result obtained by subtraction of an absorption spectrum of only toluene in a quartz cell from the measured absorption spectrum of the toluene solution in the quartz cell.

As shown in FIG. 36, the organic compound mmtBuBimmtBuPAF has an emission peak at 362 nm.

Next, the organic compound mmtBuBimmtBuPAF was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C4 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that mmtBuBimmtBuPAF was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 661 which underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500. The detection results of the dissociated product ions by time-of-flight (TOF) MS are shown in FIG. 37.

Figure 37:
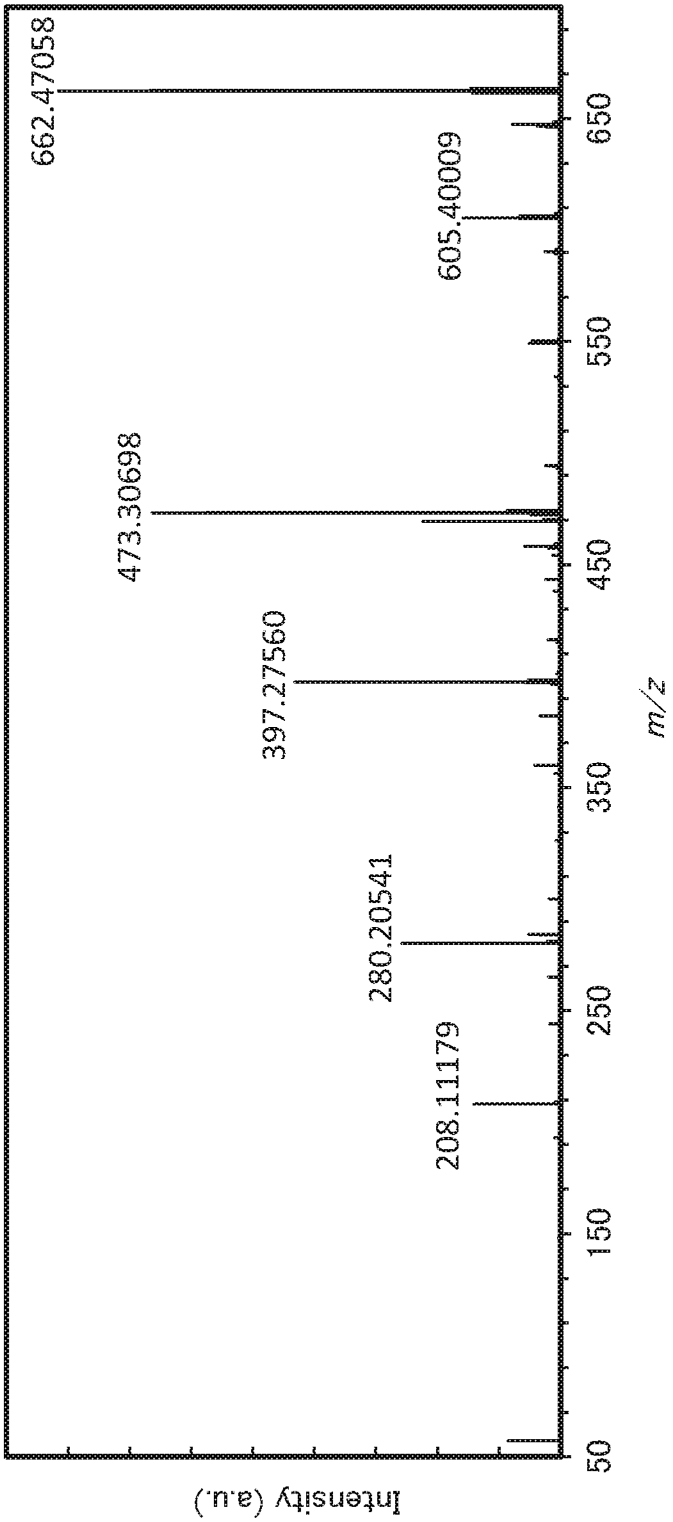
FIG. 37 shows an MS spectrum of mmtBuBimmtBuPAF.

FIG. 37 shows that product ions of mmtBuBimmtBuPAF are mainly detected at m/z of around 662. Note that the result in FIG. 37 shows characteristics derived from mmtBuBimmtBuPAF and therefore can be regarded as important data for identifying mmtBuBimmtBuPAF contained in a mixture.

Note that a fragment ion at m/z of 397, which was observed in measurement with a collision energy of 50 eV, is estimated to be derived from N-(3,5, -ditertiarybutylbenzene-1-yl)-N-(9,9, -dimethyl-9H-fluoren-2-yl)amine generated in such a manner that a C—N bond of mmtBuBimmtBuPAF was cut, and this is the characteristics of mmtBuBimmtBuPAF.

Figure 89:
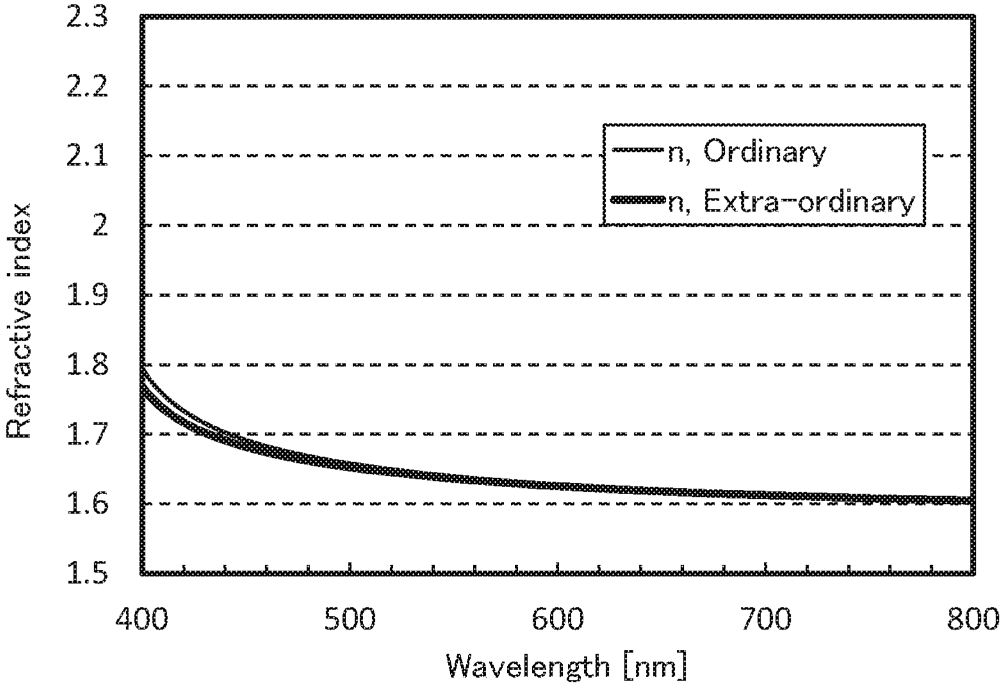
FIG. 89 shows measurement data of a refractive index of mmtBuBimmtBuPAF.

FIG. 89 shows the results of measuring the refractive index of mmtBuBimmtBuPAF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 89.

FIG. 89 shows that mmtBuBimmtBuPAF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of mmtBuBimmtBuPAF was measured. Tg was measured using a differential scanning calorimeter (a Perkin-Elmer Co., Ltd. Pyris 1 DSC) in a state where a powder was put on an aluminum cell. As a result, Tg of mmtBuBimmtBuPAF was 101° C.

Example 9

Synthesis Example 9

In this example, a synthesis method of N,N-bis(4-cyclohexylphenyl)-9,9-dipropyl-9H-fluoren-2-amine (abbreviation: dchPAPrF), which is the organic compound represented by the structural formula (108) in Embodiment 1, is described. A structure of dchPAPrF is shown below.

[Chemical Formula 69]

(108)

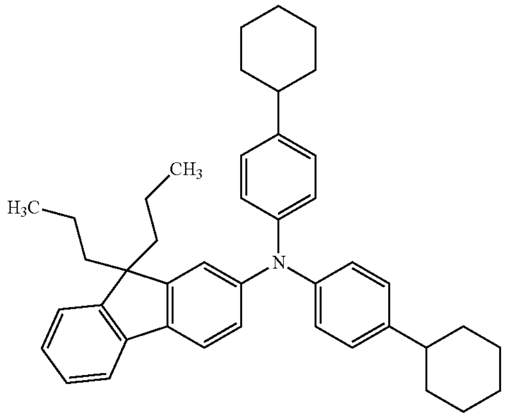

Step 1: Synthesis of 2-bromo-9,9-dipropyl-9H-fluoren

In a three-neck flask was put 24.5 g (100 mmol) of 2-bromo-9H-fluorene, the pressure in the flask was reduced, and then the air in the flask was replaced with nitrogen. To this flask, 28.8 g (300 mmol) of sodium-tert-butoxide and 500 mL of dehydrated dimethyl sulfoxide were added, and the mixture was stirred. Then, the flask was heated to approximately 95° C. To this mixture, 37.4 g (220 mmol) of 1-iodopropane was added dropwise for reaction. This mixture was air-cooled while being stirred for approximately 14 hours. After the cooling, 500 mL of toluene and 500 mL of water were added to this mixture, and the mixture was stirred. This mixture was separated into an organic layer and an aqueous layer. Approximately 500 mL of toluene was added to the obtained aqueous layer to separate the mixture into an organic layer and an aqueous layer. These separations were repeated twice. The obtained organic layer and the solution of the extract were combined and washed with water, and then separated. This step was repeated twice. Magnesium sulfate was added to the obtained organic layer for drying and the solution was concentrated. The obtained solution was purified by silica gel column chromatography. The obtained solution was concentrated and dried in a vacuum. As a result, 23.8 g of a target white solid was obtained in a yield of 72%. The synthesis scheme of Step 1 is shown below.

[Chemical Formula 70]

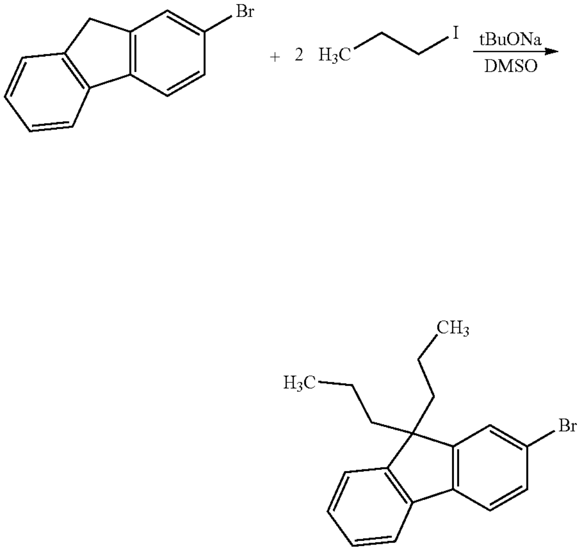

Step 2: Synthesis of 4-cyclohexylaniline

The synthesis was performed in a manner similar to Step 1 of the synthesis example 3 in Example 3.

Step 3: Synthesis of N-(4-cyclohexylphenyl)-N-(9,9-dipropyl-9H-fluoren-2-yl)amine In a three-neck flask were put 11.0 g (33.3 mmol) of 2-bromo-9,9-diproryl-9H-fluorene obtained in Step 1, 5.8 g (33.3 mmol) of 4-cyclohexylaniline obtained in Step 2, and 9.6 g (100 mmol) of sodium-tert-butoxide. The pressure in the flask was reduced, and then the air in the flask was replaced with nitrogen. In the flask was put 170 mL of xylene, the mixture was degassed under reduced pressure, and then the air in the flask was replaced with nitrogen. The mixture was stirred while being heated to approximately 50° C. Then, 122 mg (0.33 mmol) of allylpalladium(II) chloride dimer (abbreviation: $[(Allyl)PdCl]_2$) and 547 mg (1.33 mmol) of di-tert-butyl(1-methyl-2,2-diphenylcyclopropyl) phosphine (abbreviation: cBRIDP (registered trademark)) were added, and the mixture was heated at 90° C. for approximately 3 hours. After that, the temperature of the flask was lowered to approximately 60° C., approximately 2 mL of water was added to the mixture, and a precipitated solid was separated by filtration. The filtrate was concentrated, and the obtained solution was purified by silica gel column chromatography. The obtained solution was concentrated to give a condensed toluene solution. The toluene solution was dried at approximately 40° C. in a vacuum under reduced pressure, whereby 9.1 g of a target brown oily substance was obtained in a yield of 64%. The synthesis scheme of Step 3 is shown below.

[Chemical Formula 71]

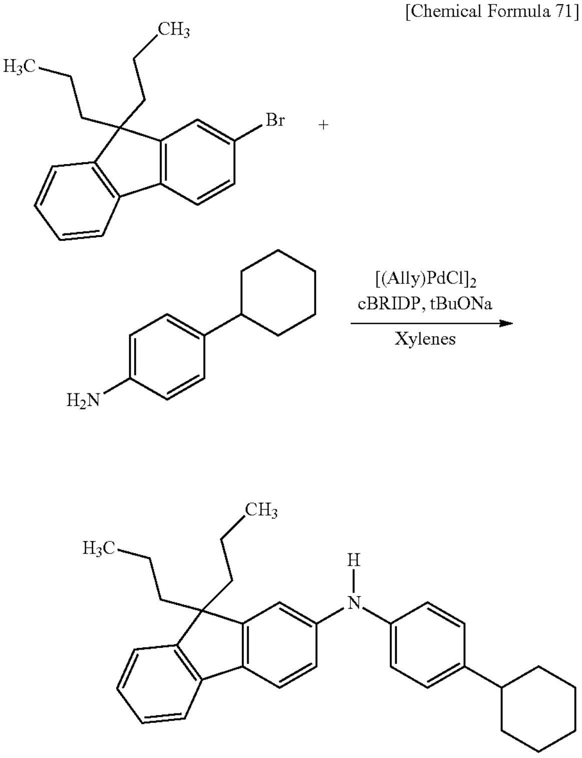

Step 4: Synthesis of N,N-bis(4-cyclohexylphenyl)-9,9-dipropyl-9H-fluoren-2-amine (Abbreviation: dchPAPrF)

In a three-neck flask were put 4.2 g (10 mmol) of N-(4-cyclohexylphenyl)-N-(9,9-dipropyl-9H-fluoren-2-yl) amine obtained in Step 3, 2.4 g (10 mmol) of 1-bromo-4-cyclohexylbenzene, 2.9 g (30 mmol) of sodium-tert-butoxide, and 50 mL of xylene. This mixture was degassed under reduced pressure, and then the air in the flask was replaced with nitrogen. The mixture was stirred while being heated to 50° C. Then, 37 mg (0.10 mmol) of allylpalladium(II) chloride dimer (abbreviation: $[(Allyl)PdCl]_2$) and 141 mg (0.40 mmol) of di-tert-butyl(1-methyl-2,2-diphenylcyclopropyl)phosphine (abbreviation: cBRIDP (registered trademark)) were added, and the mixture was heated at 100° C. for approximately 3 hours. After that, the temperature of the flask was lowered to approximately 60° C., approximately 2 mL of water was added to the mixture, and a precipitated solid was separated by filtration. The filtrate was concentrated, and the obtained solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 4.7 g of a target white solid was obtained in a yield of 81%. The synthesis scheme of Step 4 is shown below.

[Chemical Formula 72]

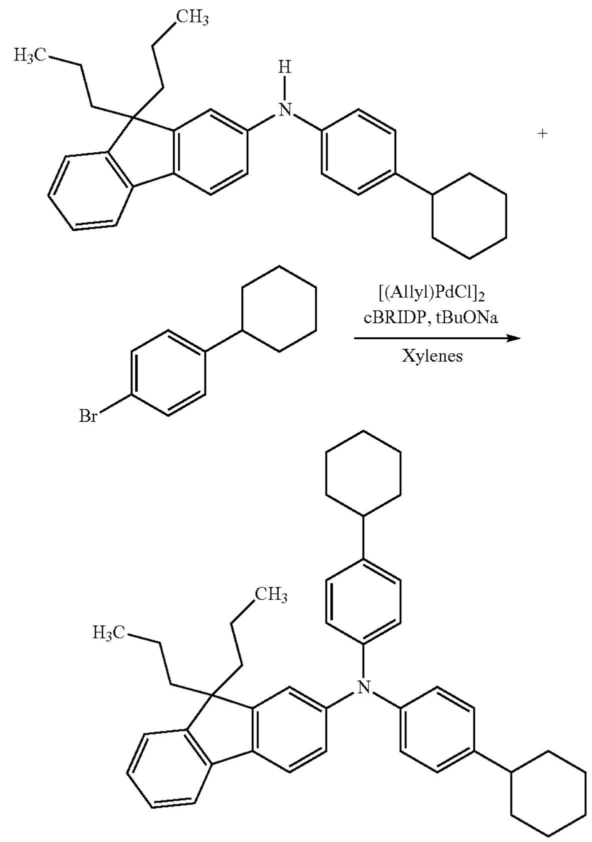

(108)

Figure 38:
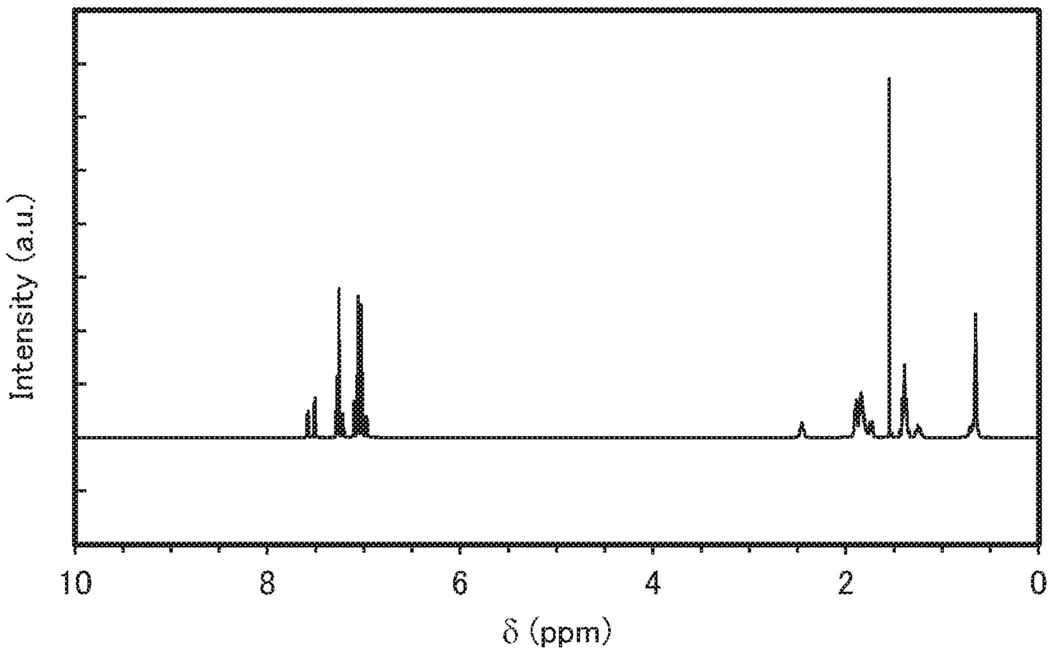
FIG. 38 is a $^{1}$H-NMR chart of dchPAPrF.

Analysis results by nuclear magnetic resonance spectroscopy ($^1$H-NMR) of the white solid obtained in Step 4 are shown below. FIG. 38 shows the $^1$H-NMR chart. The results show that N,N-bis(4-cyclohexylphenyl)-9,9-dipropyl-9H-fluoren-2-amine (abbreviation: dchPAPrF) was synthesized in this synthesis example.

$^1$H-NMR. δ ($CDCl_3$): 7.58 (m, 1H), 7.51 (d, 1H, J=8.0 Hz), 7.28 (t, 2H, J=7.5 Hz), 7.19-7.24 (m, 1H), 7.11 (d, 1H, J=1.5 Hz), 7.00-7.19 (m, 8H), 6.97 (dd, 1H, J=8.0 Hz, 1.5 Hz), 2.40-2.50 (brm, 2H), 1.70-1.94 (m, 14H), 1.33-1.46 (m, 8H), 1.18-1.30 (brm, 2H), 0.60-0.78 (m, 10H).

Then, 4.0 g of the obtained solid was purified by a train sublimation method. The purification by sublimation was conducted by heating at 225° C. under a pressure of 3.0 Pa with the argon flow rate of 19.0 mL/min. After the purification by sublimation, 3.1 g of a pale yellowish white solid was obtained at a collection rate of 77%.

Figure 39:
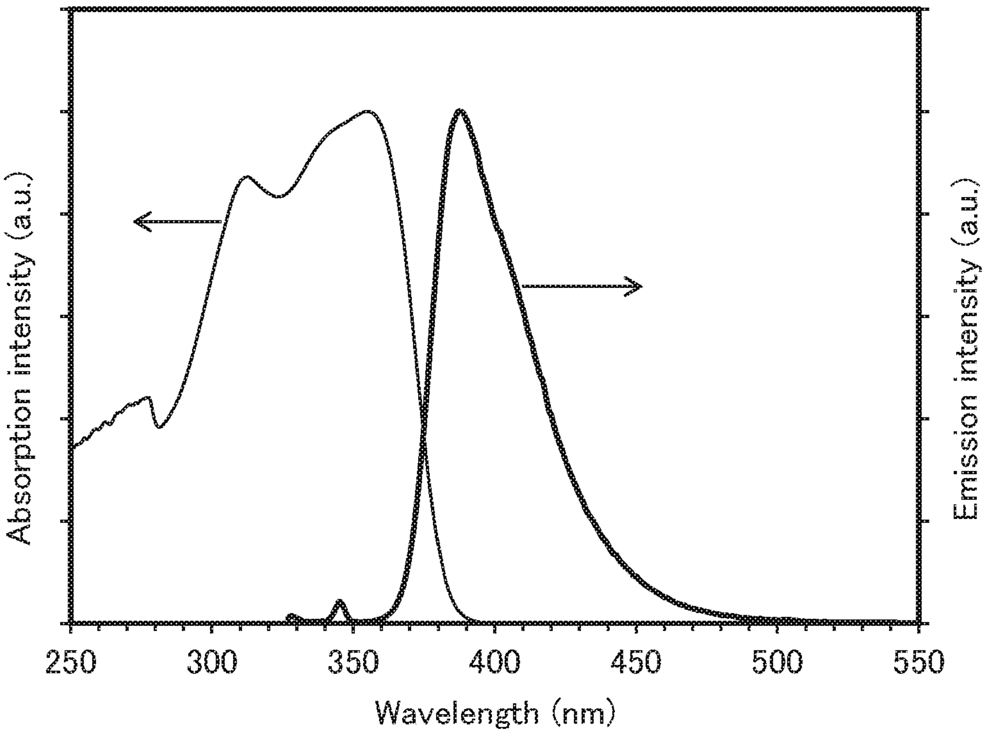
FIG. 39 shows an absorption spectrum and an emission spectrum of dchPAPrF in a toluene solution.

Next, an ultraviolet-visible absorption spectrum (hereinafter, simply referred to as an absorption spectrum) of dchPAPrF in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FS920, manufactured by Hamamatsu Photonics K.K.), both of which were measured at room temperature. A quartz cell was used for the measurement cell. FIG. 39 shows measurement results of the absorption spectrum and the emission spectrum. The horizontal axis represents the wavelength and the vertical axes represent the absorption intensity and emission intensity. The absorption intensity shown in FIG. 39 is a result obtained by subtraction of an absorption spectrum of only toluene in a quartz cell from the measured absorption spectrum of the toluene solution in the quartz cell.

As shown in FIG. 39, the organic compound dchPAPrF has an emission peak at 355 nm.

Next, the organic compound dchPAPrF was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C4 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that dchPAPrF was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 581 which underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500. The detection results of the dissociated product ions by time-of-flight (TOF) MS are shown in FIG. 40.

Figure 40:
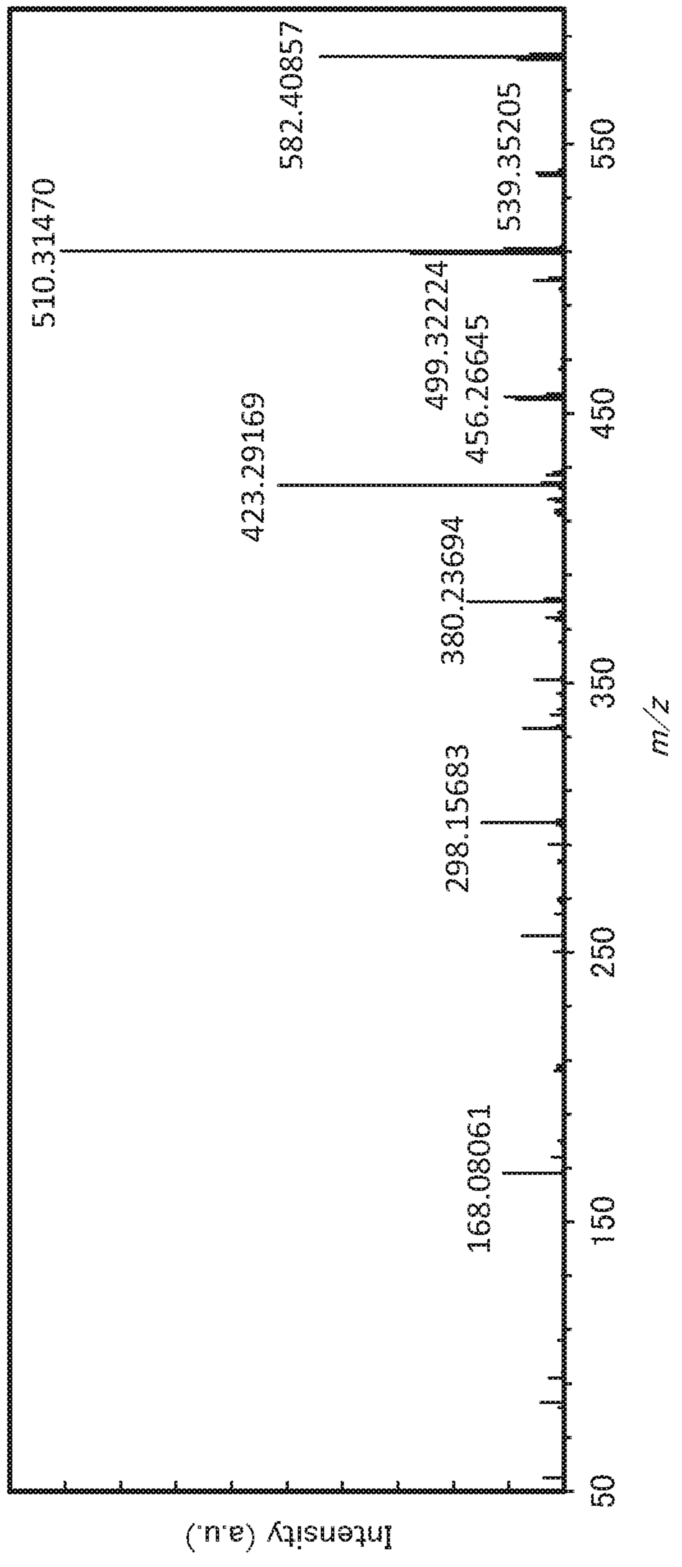
FIG. 40 shows an MS spectrum of dchPAPrF.

FIG. 40 shows that product ions of dchPAPrF are mainly detected at m/z of around 582. Note that the result in FIG. 40 shows characteristics derived from dchPAPrF and therefore can be regarded as important data for identifying dchPAPrF contained in a mixture.

Note that a fragment ion at m/z of 423, which was observed in measurement with a collision energy of 50 eV, is estimated to be derived from N-(4-cyclohexylphenyl)-N-(9,9-dipropyl-9H-fluoren-2-yl)amine generated in such a manner that a C—N bond of dchPAPrF was cut, and this is the characteristics of dchPAPrF.

Figure 90:
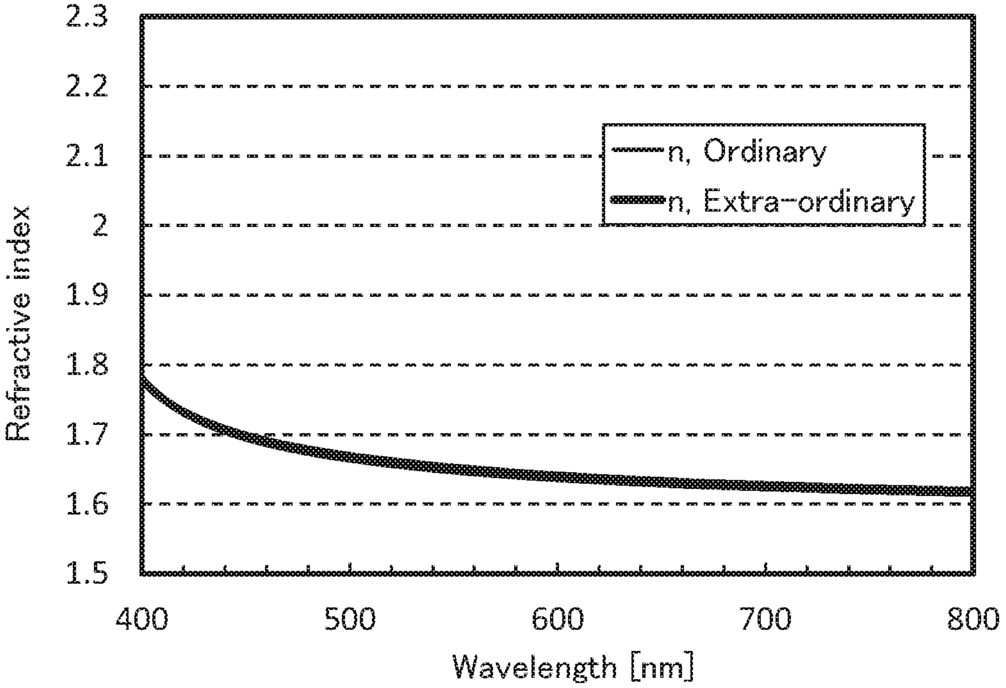
FIG. 90 shows measurement data of a refractive index of dchPAPrF.

FIG. 90 shows the results of measuring the refractive index of dchPAPrF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 90.

FIG. 90 shows that dchPAPrF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Example 10

Synthesis Example 10

In this example, a synthesis method of N-[(3',5'-dicyclohexyl)-1,1'-biphenyl-4-yl]-N-(4-cyclohexylphenyl)-9,9-dimethyl-9H-fluoren-2-amine (abbreviation: mmchBichPAF), which is the organic compound represented by the structural formula (109) in Embodiment 1, is described. A structure of mmchBichPAF is shown below.

[Chemical Formula 73]

(109)

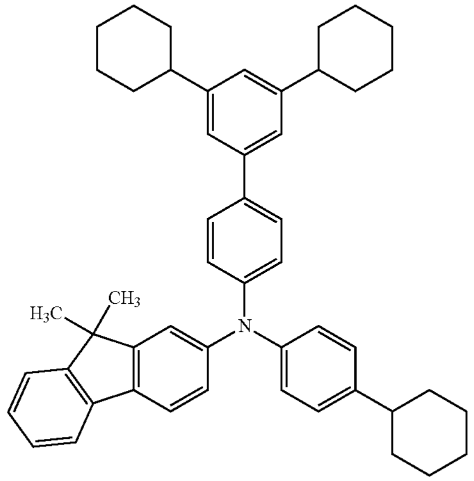

Step 1: Synthesis of 3,5-dicyclohexyl-1-methoxybenzene

In a three-neck flask was put 36.3 g (137 mmol) of 3,5-dibromo-1-methoxybenzene, the pressure in the flask was reduced, and then the air in the flask was replaced with nitrogen. To this flask, 1000 mL of tetrahydrofuran, 1.88 g (2.05 mmol) of tris(dibenzylideneacetone)dipalladium(0), and 1.95 g (4.10 mmol) of 2-dicyclohexylphosphino-2',4',6'-triisopropylbiphenyl (abbreviation: XPhos) were added, and the mixture was heated at approximately 65° C. To this mixture, 300 mL of 1.0M solution of cyclohexylmagnesium bromide was added dropwise for reaction. After cooled down, the mixture was stirred at room temperature for approximately 14 hours. After that, 200 mL of water was added dropwise to separate the mixture into an organic layer and an aqueous layer. Approximately 500 mL of ethyl acetate was added to the obtained aqueous layer to separate the mixture into an aqueous layer and an organic layer. These separations were repeated twice. The obtained organic layer and the solution of the extract were combined and washed with a saturated aqueous solution of sodium hydrogen carbonate, and then separated into an aqueous layer and an organic layer. Magnesium sulfate was added to the obtained organic layer for drying and concentration. The obtained solution was purified by silica gel column chromatography. The obtained solution was concentrated and dried in a vacuum. As a result, 32.9 g of a target colorless oily substance was obtained in a yield of 88%. The synthesis scheme of Step 1 is shown below.

[Chemical Formula 74]

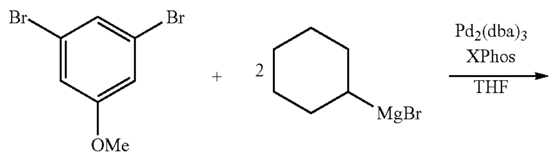

-continued

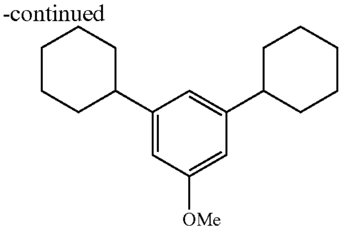

Step 2: Synthesis of 3,5-dicyclohexylphenol

In a three-neck flask was put 32.0 g (117.5 mmol) of 3,5-dicyclohexyl-1-methoxybenzene obtained in Step 1, the pressure in the flask was reduced, and then the air in the flask was replaced with nitrogen. To this flask, 400 mL of dichloromethane was added, and the mixture was cooled down to −20° C. To this solution, 123 mL (123 mmol) of 1.0M dichloromethane solution of boron tribromide was added dropwise. The temperature of the mixture was increased to room temperature and the mixture was stirred at room temperature for approximately 14 hours. Approximately 200 mL of tap water was added to the mixture to separate the mixture into an organic layer and an aqueous layer. Approximately 200 mL of dichloromethane was added to the obtained aqueous layer for separation. Two organic layers obtained by the separations were mixed, washed with a saturated aqueous solution of sodium hydrogen carbonate, and then separated. Magnesium sulfate was added to the obtained organic layer for drying, and the organic layer was filtrated. The obtained dichloromethane solution was concentrated and purified by silica gel column chromatography. The obtained solution was concentrated, whereby a colorless oily substance was obtained. The oily substance was dried at approximately 40° C. in a vacuum, whereby 26.0 g of a colorless oily substance was obtained in a yield of 86%. The synthesis scheme of Step 2 is shown below.

[Chemical Formula 75]

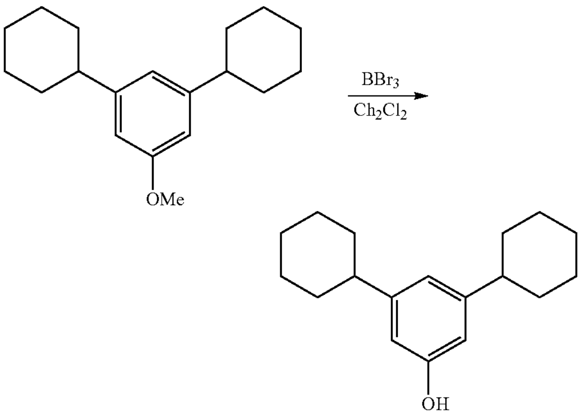

Step 3: Synthesis of trifluoromethanesulfonate-3,5-dicyclohexylbenzene

In a three-neck flask was put 32.0 g (117.5 mmol) of 3,5-dicyclohexyl-1-methoxybenzene obtained in Step 1. The pressure in the flask was reduced, and then the air in the flask was replaced with nitrogen. In the flask was put 400 mL of dichloromethane and cooled down to −20° C. To this solution, 37.0 g (131 mmol) of trifluoromethanesulfonic anhydride was added dropwise. The temperature of the mixture was increased to room temperature and the mixture was stirred at room temperature for approximately 14 hours. To the mixture was added approximately 200 mL of water and separated into an organic layer and an aqueous layer. Approximately 200 mL of dichloromethane was added to the obtained aqueous layer for separation. Two organic layers obtained by the separations were mixed, washed with saturated aqueous solution of sodium hydrogen carbonate, and then separated. Magnesium sulfate was added to the obtained organic layer for drying, and the organic layer was filtrated. The obtained dichloromethane solution was concentrated and purified by silica gel column chromatography. The obtained solution was concentrated, whereby a colorless oily substance was obtained. The oily substance was dried at approximately 60° C. in a vacuum, whereby 33.4 g of a colorless oily substance was obtained in a yield of 85%. The synthesis scheme of Step 3 is shown below.

[Chemical Formula 76]

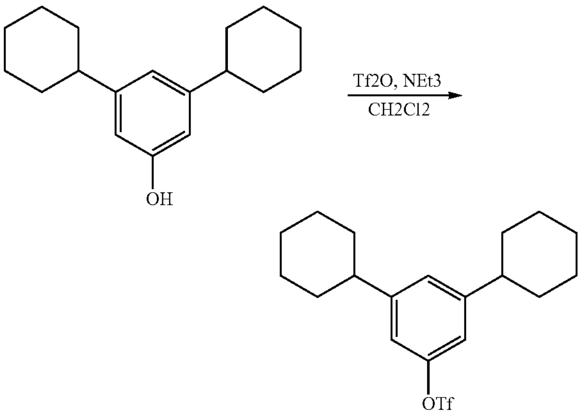

Step 4: Synthesis of 3',5'-dicyclohexyl-4-chloro-1,1'-biphenyl

In a three-neck flask were put 9.8 g (25 mmol) of trifluoromethanesulfonate-3,5-dicyclohexylbenzene obtained in Step 1, 4.3 g (27.5 mmol) of 4-chlorophenylboronic acid, 8.8 g (82.5 mmol) of sodium carbonate, 125 mL of 1,4-dioxane, and 41 mL of tap water. This mixture was degassed under reduced pressure, and then the air in the flask was replaced with nitrogen. Then, 112 mg (0.50 mmol) of palladium(II) acetate and 266 mg (1.0 mmol) of triphenylphosphine were added to this mixture, and the mixture was heated at 50° C. for approximately 4 hours. After that, the temperature of the flask was lowered to room temperature and the mixture was separated into an organic layer and an aqueous layer. Magnesium sulfate was added to the solution for drying and concentration. The obtained toluene solution was purified by silica gel column chromatography. The obtained solution was concentrated and dried for hardening. After that, hexane was added for recrystallization. The precipitated white solid was cooled with ice, and then filtrated. The solid was dried at approximately 60° C. in a vacuum, whereby 9.5 g of a target white solid was obtained in a yield of 63%. The synthesis scheme of Step 4 is shown below.

[Chemical Formula 77]

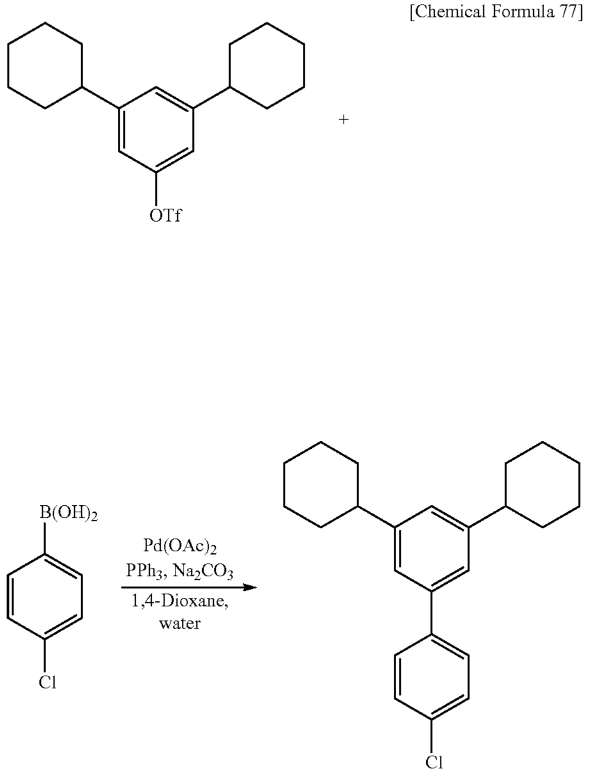

Step 5: Synthesis of N-[(3',5'-dicyclohexyl)-1,1'-biphenyl-4-yl]-N-(4-cyclohexylphenyl)-9,9-dimethyl-9H-fluoren-2-amine (Abbreviation: mmchBichPAF)

In a three-neck flask were put 3.5 g (10.0 mmol) of 3',5'-dicyclohexyl-4-chloro-1,1'-biphenyl obtained in Step 4, 3.7 g (10.0 mmol) of 3,5-dicyclohexylphenol synthesized in Step 2, 2.9 g (30.0 mmol) of sodium-tert-butoxide, and 50 mL of xylene. This mixture was degassed under reduced pressure, and then the air in the flask was replaced with nitrogen. The mixture was stirred while being heated to 50° C. Then, 37 mg (0.10 mmol) of allylpalladium(II) chloride dimer (abbreviation: $[(Allyl)PdCl]_2$) and 141 mg (0.40 mmol) of di-tert-butyl(1-methyl-2,2-diphenylcyclopropyl) phosphine (abbreviation: cBRIDP (registered trademark)) were added, and the mixture was heated at 100° C. for approximately 3 hours. After that, the temperature of the flask was lowered to approximately 60° C., approximately 2 mL of water was added to the mixture, and a precipitated solid was separated by filtration. The filtrate was concentrated, and the obtained solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at 20° C., and the obtained solid was dried at approximately 80° C. under reduced pressure, whereby 6.0 g of a target white solid was obtained in a yield of 88%. The synthesis scheme of mmchBichPAF in Step 5 is shown below.

[Chemical Formula 78]

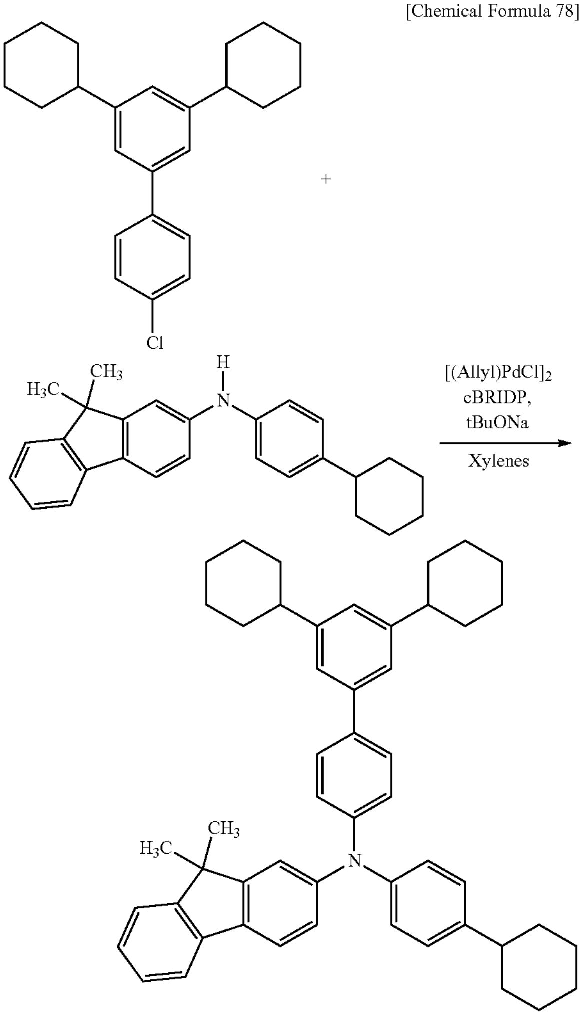

(109)

Figure 41:
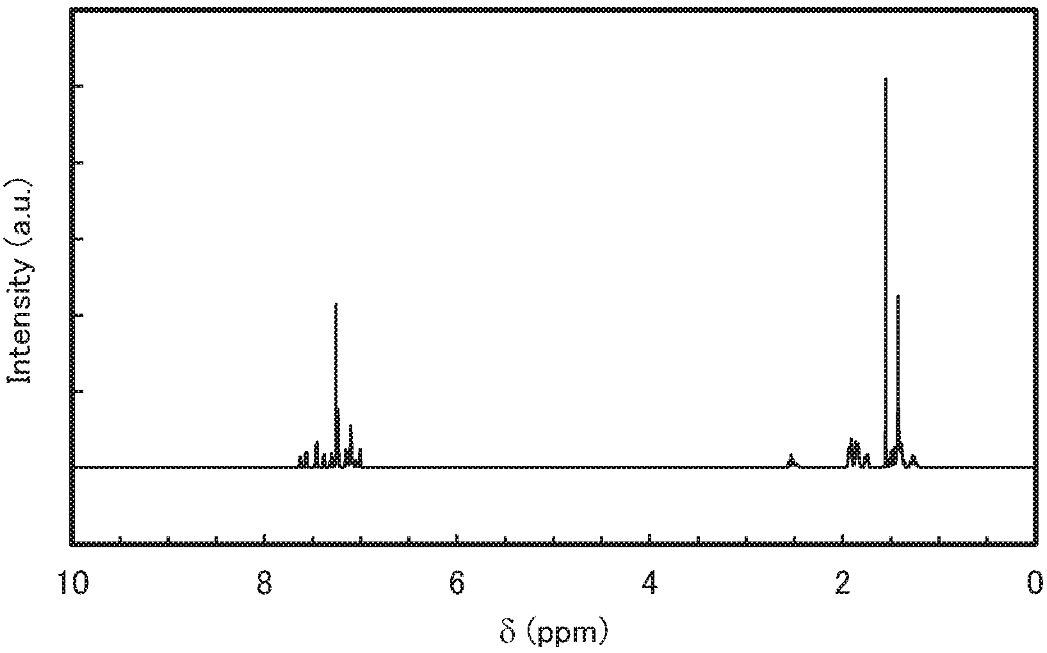
FIG. 41 is $^{1}$H-NMR chart of mmchBichPAF.

Analysis results by nuclear magnetic resonance spectroscopy ($^1$H-NMR) of the white solid obtained in Step 5 are shown below. FIG. 41 shows the H-NMR chart. These results show that N-[(3',5'-dicyclohexyl)-1,1'-biphenyl-4-yl]-N-(4-cyclohexylphenyl)-9,9-dimethyl-9H-fluoren-2-amine (abbreviation: mmchBichPAF) was synthesized in this synthesis example.

$^1$H-NMR. δ ($CDCl_3$): 7.63 (d, 1H, J=7.5 Hz), 7.57 (d, 1H, J=8.5 Hz), 7.46 (d, 2H, J=8.5 Hz), 7.39 (d, 1H, J=7.5 Hz), 7.31 (td, 1H, J=7.5 Hz, 1.5 Hz), 7.21-7.28 (m, 4H), 7.07-7.18 (m, 6H), 7.02-7.06 (m, 1H), 7.01 (s, 1H), 2.44-2.57 (brm, 3H), 1.89-1.96 (m, 6H), 1.81-1.88 (m, 6H), 1.71-1.78 (m, 3H), 1.34-1.53 (m, 18H), 1.20-1.32 (m, 3H).

Then, 5.0 g of the obtained solid was purified by a train sublimation method. The purification by sublimation was conducted by heating at 270° C. under a pressure of 3.0 Pa with the argon flow rate of 19.8 mL/min. After the purification by sublimation, 3.5 g of a pale yellowish white solid was obtained at a collection rate of 70%.

Figure 42:
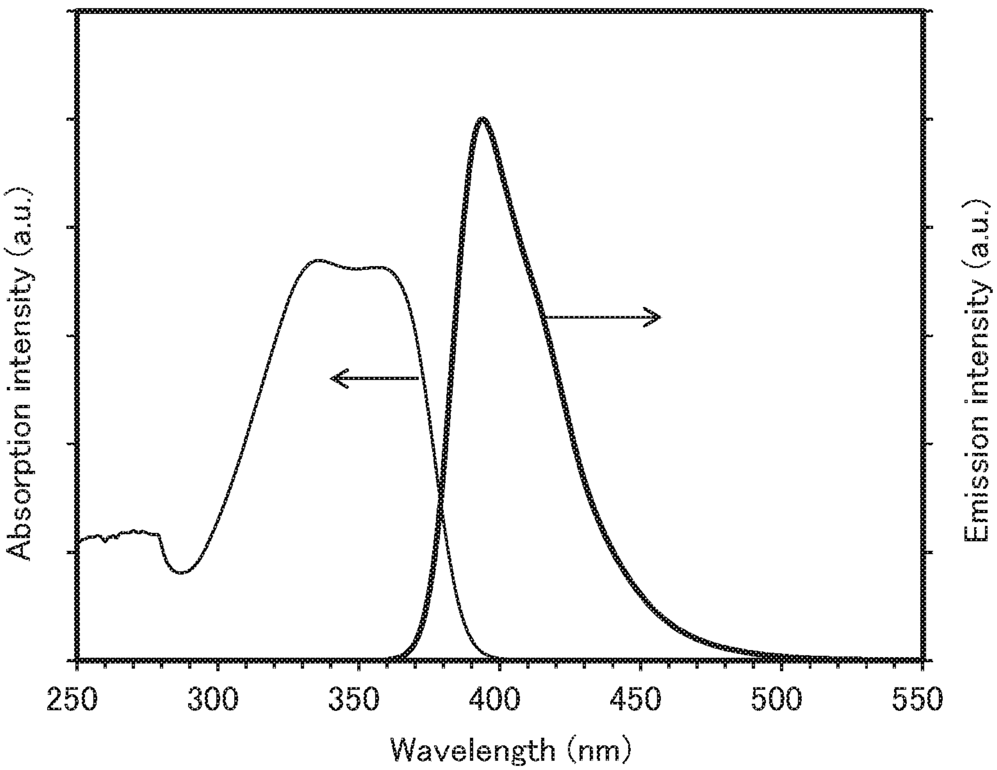
FIG. 42 shows an absorption spectrum and an emission spectrum of mmchBichPAF in a toluene solution.

Next, an ultraviolet-visible absorption spectrum (hereinafter, simply referred to as an absorption spectrum) of mmchBichPAF in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FS920, manufactured by Hamamatsu Photonics K.K.), both of which were measured at room temperature. A quartz cell was used for the measurement cell. FIG. 42 shows measurement results of the absorption spectrum and the emission spectrum. The horizontal axis represents the wavelength and the vertical axes represent the absorption intensity and emission intensity. The absorption intensity shown in FIG. 42 is a result obtained by subtraction of an absorption spectrum of only toluene in a quartz cell from the measured absorption spectrum of the toluene solution in the quartz cell.

As shown in FIG. 42, the organic compound mmchBichPAF has an emission peak at 362 nm.

Next, the organic compound mmchBichPAF was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C4 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that mmchBichPAF was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 683 which underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500. The detection results of the dissociated product ions by time-of-flight (TOF) MS are shown in FIG. 43.

Figure 43:
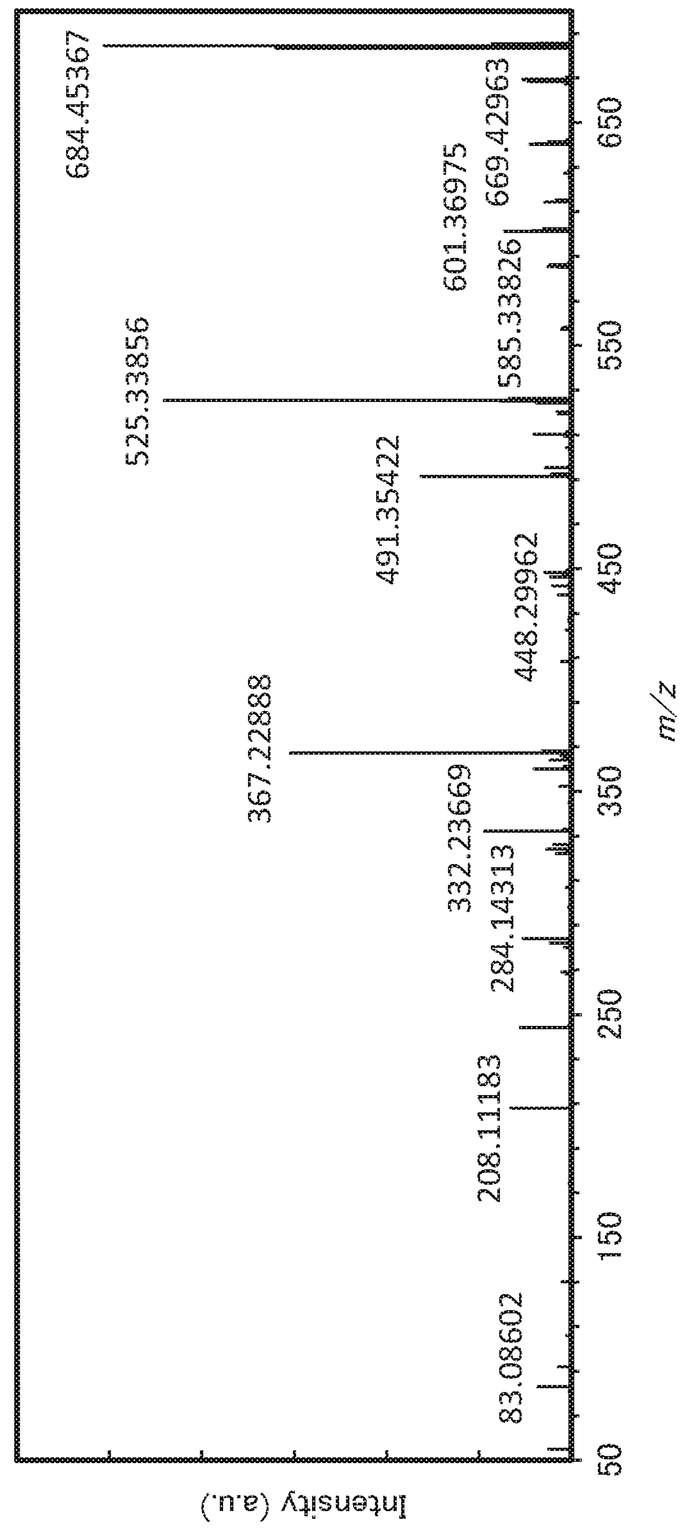
FIG. 43 shows an MS spectrum of mmchBichPAF.

FIG. 43 shows that product ions of mmchBichPAF are mainly detected at m/z of around 684. Note that the result in FIG. 43 shows characteristics derived from mmchBichPAF and therefore can be regarded as important data for identifying mmchBichPAF contained in a mixture.

Note that a fragment ion at m/z of 525, which was observed in measurement with a collision energy of 50 eV, is estimated to be derived from N-[(3',5'-dicyclohexyl)-1,1'-biphenyl-4-yl]-N-9,9-dimethyl-9H-fluoren-2-amine generated in such a manner that a C—N bond of mmchBichPAF was cut, and this is the characteristics of mmchBichPAF.

Figure 91:
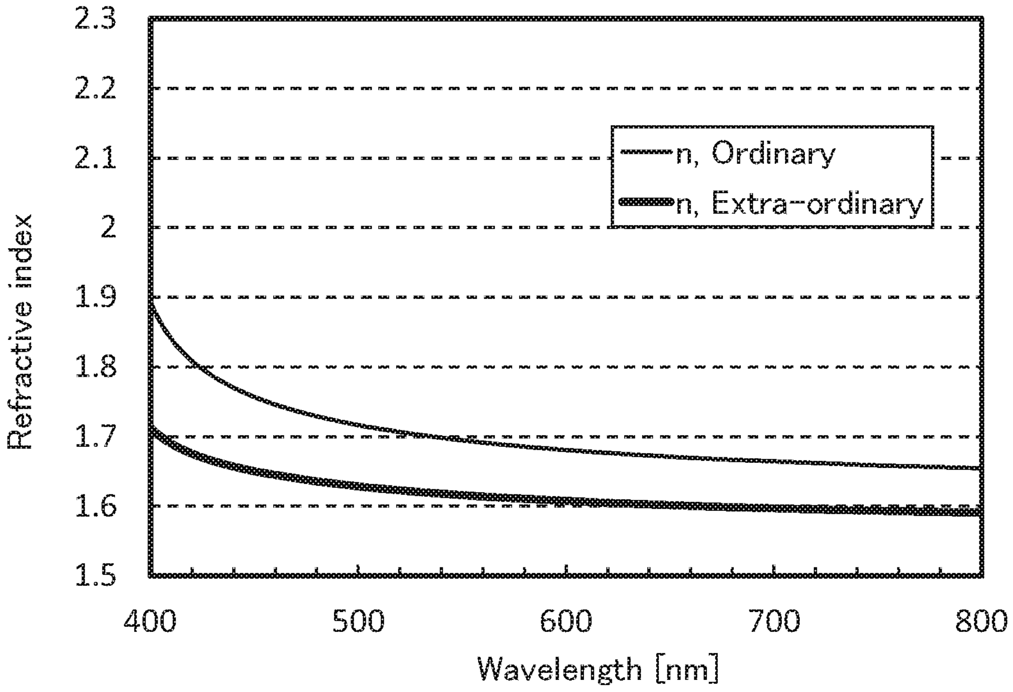
FIG. 91 shows measurement data of a refractive index of mmchBichPAF.

FIG. 91 shows the results of measuring the refractive index of mmchBichPAF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 91.

FIG. 91 shows that mmchBichPAF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of mmchBichPAF was measured. Tg was measured using a differential scanning calorimeter (a Perkin-Elmer Co., Ltd. Pyris 1 DSC) in a state where a powder was put on an aluminum cell. As a result, Tg of mmchBichPAF was 102° C.

Example 11

Synthesis Example 11

In this example, a synthesis method of N-(3,3",5,5"-tetra-t-butyl-1,1':3',1"-terphenyl-5'-yl)-N-(4-cyclohexylphenyl)-9,9-dimethyl-9H-fluoren-2-amine (abbreviation: mmtBumTPchPAF), which is the organic compound represented by the structural formula (110) in Embodiment 1, is described. A structure of mmtBumTPchPAF is shown below.

[Chemical Formula 79]

(110)

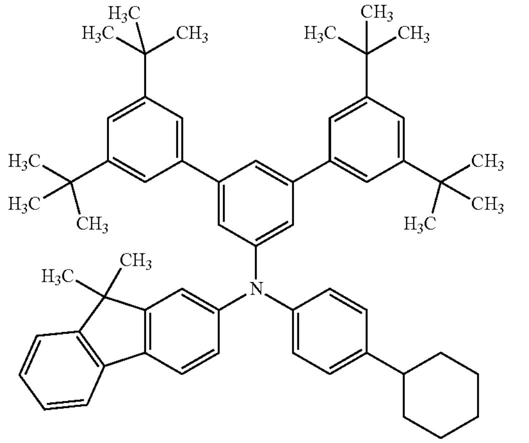

Step 1: Synthesis of 3,3",5,5"-tetra-t-butyl-5'-chloro-1,1':3',1"-terphenyl

In a three-neck flask were put 1.66 g (6.14 mmol) of 1,3-dibromo-5-chlorobenzene, 4.27 g (13.5 mmol) of 2-(3,5-di-t-butylphenyl)-4,4,5,5-tetramethyl-1,3,2-dioxaborolane, 187 mg (0.614 mmol) of tris(2-methylphenyl)phosphine, 13.5 mL of a 2M aqueous solution of potassium carbonate, 20 mL of toluene, and 10 mL of ethanol. The mixture was degassed by being stirred under reduced pressure, and then the air in the flask was replaced with nitrogen. To the mixture, 27.5 mg (0.122 mmol) of palladium acetate was added, and the mixture was stirred at 80° C. under a nitrogen stream for approximately 4 hours. After the stirring, water was added to this mixture to separate the mixture into an organic layer and an aqueous layer. Then, an aqueous layer was subjected to extraction with toluene. The obtained extracted solution and the organic layer were combined, and the mixture was washed with water and saturated saline. Then, the mixture was dried with magnesium sulfate. The mixture was separated by gravity filtration, and the obtained filtrate was concentrated to give a yellow oily substance. This oily substance was purified by silica gel column chromatography. The obtained fraction was concentrated, whereby 2.98 g of a target white solid was obtained in a yield of 99%. The synthesis scheme of Step 1 is shown below.

[Chemical Formula 80]

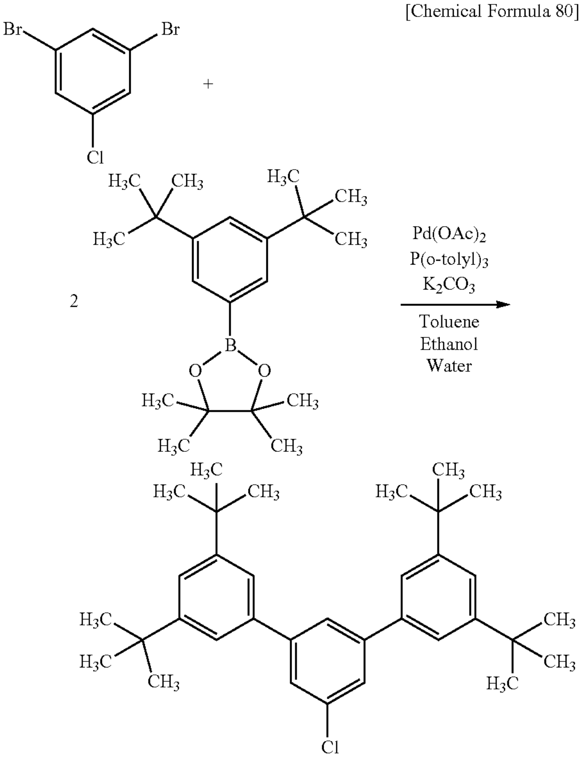

Analysis results by nuclear magnetic resonance spectroscopy ($^1$H-NMR) of the white solid obtained in Step 1 are shown below. The results show that the organic compound 3,3",5,5"-tetra-t-butyl-5'-chloro-1,1':3',1"-terphenyl was synthesized in this synthesis example.

$^1$H-NMR. δ ($CDCl_3$): 7.63-7.64 (m, 1H), 7.52-7.47 (m, 4H), 7.44-7.40 (m, 4H), 1.38 (s, 36H).

Step 2: Synthesis of N-(4-cycrohexylphenyl)-N-(9,9-dimethyl-9H-fluoren-2yl)amine The synthesis was performed in a manner similar to Step 1 of the synthesis example 2 in Example 2.

Step 3: Synthesis of N-(3,3",5,5"-tetra-t-butyl-1,1':3',1"-terphenyl-5'-yl)-N-(4-cyclohexylphenyl)-9,9-dimethyl-9H-fluoren-2-amine (Abbreviation: mmtBumTPchPAF)

In a three-neck flask were put 2.69 g (7.32 mmol) of N-(4-cycrohexylphenyl)-N-(9,9-dimethyl-9H-fluoren-2yl)amine obtained in Step 2, 2.98 g (6.09 mmol) of 3,3",5,5"-tetra-t-butyl-5'-chloro-1,1':3',1"-terphenyl obtained in Step 1, 0.103 g (0.292 mmol) of di-tert-butyl(1-methyl-2,2-diphenylcyclopropyl)phosphine (abbreviation: cBRIDP (registered trademark)), 1.76 g (18.3 mmol) of sodium-tert-butoxide, and 30 mL of xylene. This mixture was degassed by being stirred under reduced pressure, and then the air in the flask was replaced with nitrogen. Then, 26.7 mg (0.0730 mmol) of allylpalladium(II) chloride dimer (abbreviation:

$[(Allyl)PdCl]_2$) was added to this mixture, and the mixture was stirred at 120° C. under a nitrogen stream for approximately 10 hours. After the stirring, water was added to the mixture to separate the mixture into an organic layer and an aqueous layer. The obtained aqueous layer was subjected to extraction with toluene. The obtained extracts solution and the organic layer were combined, and the mixture was washed with water and saturated saline. Then, the mixture was dried with magnesium sulfate. The mixture was separated by gravity filtration, and the obtained filtrate was concentrated to give a black oily substance. This oily substance was purified by silica gel column chromatography. The obtained fraction was concentrated to give a pale yellow oily substance. This oily substance was purified by high performance liquid column chromatography (developing solvent: chloroform). The obtained fraction was concentrated to give a white solid. Ethanol was added to this solid, followed by irradiation with ultrasonic waves. The solid was collected by suction filtration, whereby 3.36 g of a target white solid was obtained in a yield of 67%. The synthesis scheme of Step 3 is shown below.

[Chemical Formula 81]

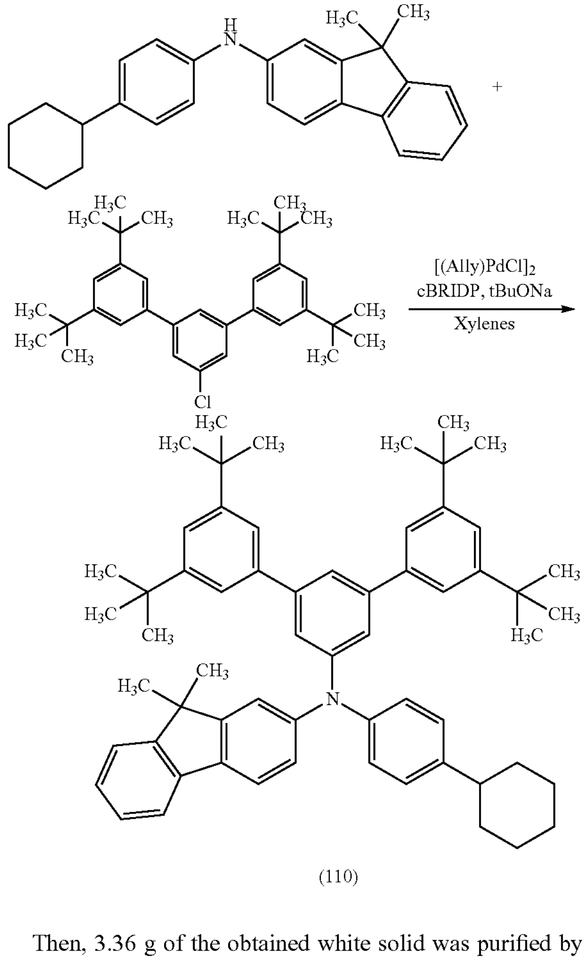

(110)

Then, 3.36 g of the obtained white solid was purified by a train sublimation method. The purification by sublimation was conducted by heating at 240° C. under a pressure of 5.0 Pa with the argon flow rate of 10 mL/min. After the purification by sublimation, 1.75 g of a colorless transparent glassy solid was obtained at a collection rate of 52%.

Figure 44:
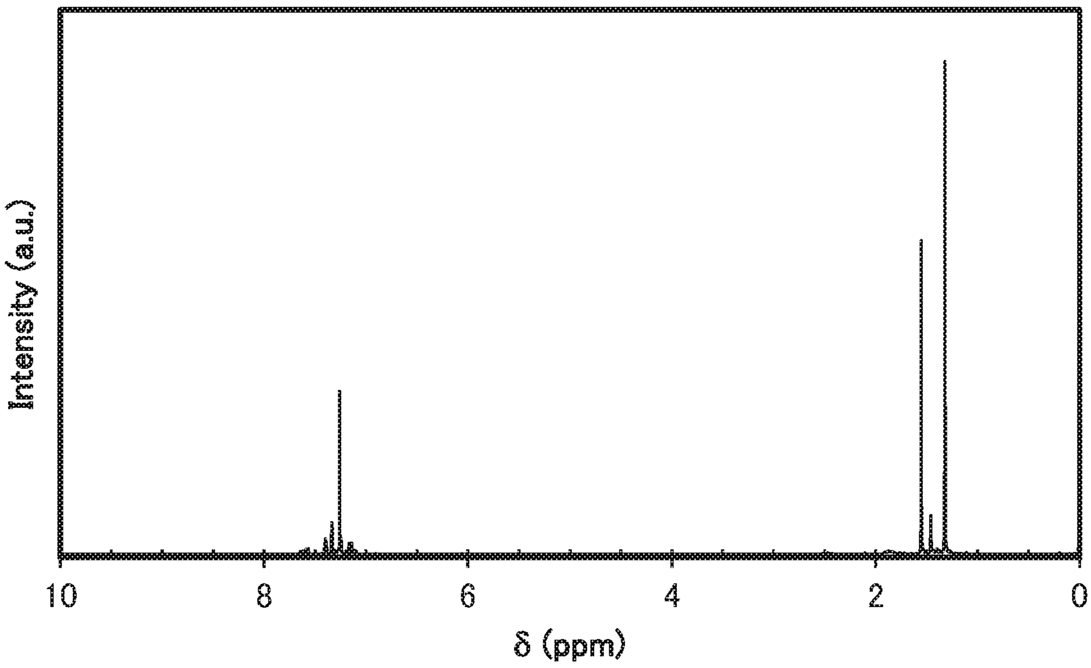
FIG. 44 is $^{1}$H-NMR chart of mmtBumTPchPAF.

Analysis results by nuclear magnetic resonance ($^1$H-NMR) spectroscopy of the white solid obtained in Step 3 are shown below. FIG. 44 is the $^1$H-NMR chart. The results show that N-(3,3",5,5"-tetra-t-butyl-1,1':3',1"-terphenyl-5'-yl)-N-(4-cyclohexylphenyl)-9,9-dimethyl-9H-fluoren-2-amine (abbreviation: mmtBumTPchPAF) was synthesized in this synthesis example.

$^1$H-NMR (300 MHz, $CDCl_3$): δ=7.63 (d, J=6.6 Hz, 1H), 7.58 (d, J=8.1 Hz, 1H), 7.42-7.37 (m, 4H), 7.36-7.09 (m, 14H), 2.55-2.39 (m, 1H), 1.98-1.20 (m, 51H).

Figure 45:
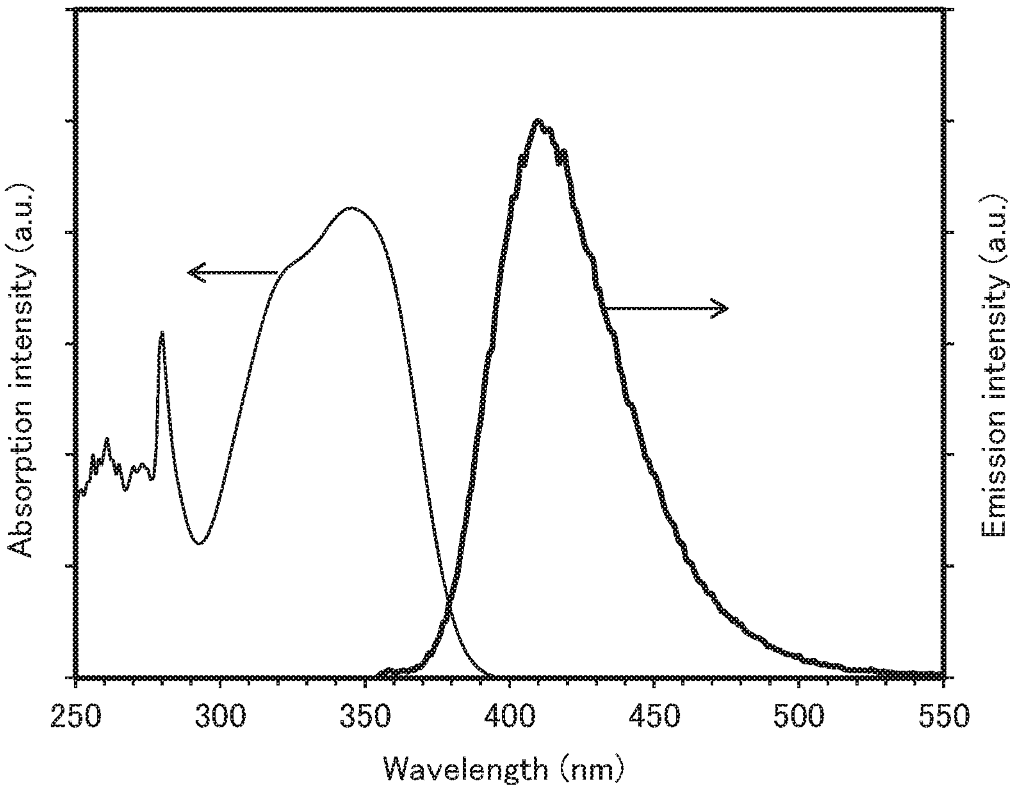
FIG. 45 shows an absorption spectrum and an emission spectrum of mmtBumTPchPAF in a toluene solution.

Next, an ultraviolet-visible absorption spectrum (hereinafter, simply referred to as an absorption spectrum) of mmtBumTPchPAF in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FS920, manufactured by Hamamatsu Photonics K.K.), both of which were measured at room temperature. A quartz cell was used for the measurement cell. FIG. 45 shows measurement results of the absorption spectrum and the emission spectrum. The horizontal axis represents the wavelength and the vertical axes represent the absorption intensity and emission intensity. The absorption intensity shown in FIG. 45 is a result obtained by subtraction of an absorption spectrum of only toluene in a quartz cell from the measured absorption spectrum of the toluene solution in the quartz cell.

As shown in FIG. 45, the organic compound mmtBumTPchPAF has an emission peak at 346 nm.

Next, the organic compound mmtBumTPchPAF was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C4 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that mmtBumTPchPAF was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 819 which underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500. The detection results of the dissociated product ions by time-of-flight (TOF) MS are shown in FIG. 46.

Figure 46:
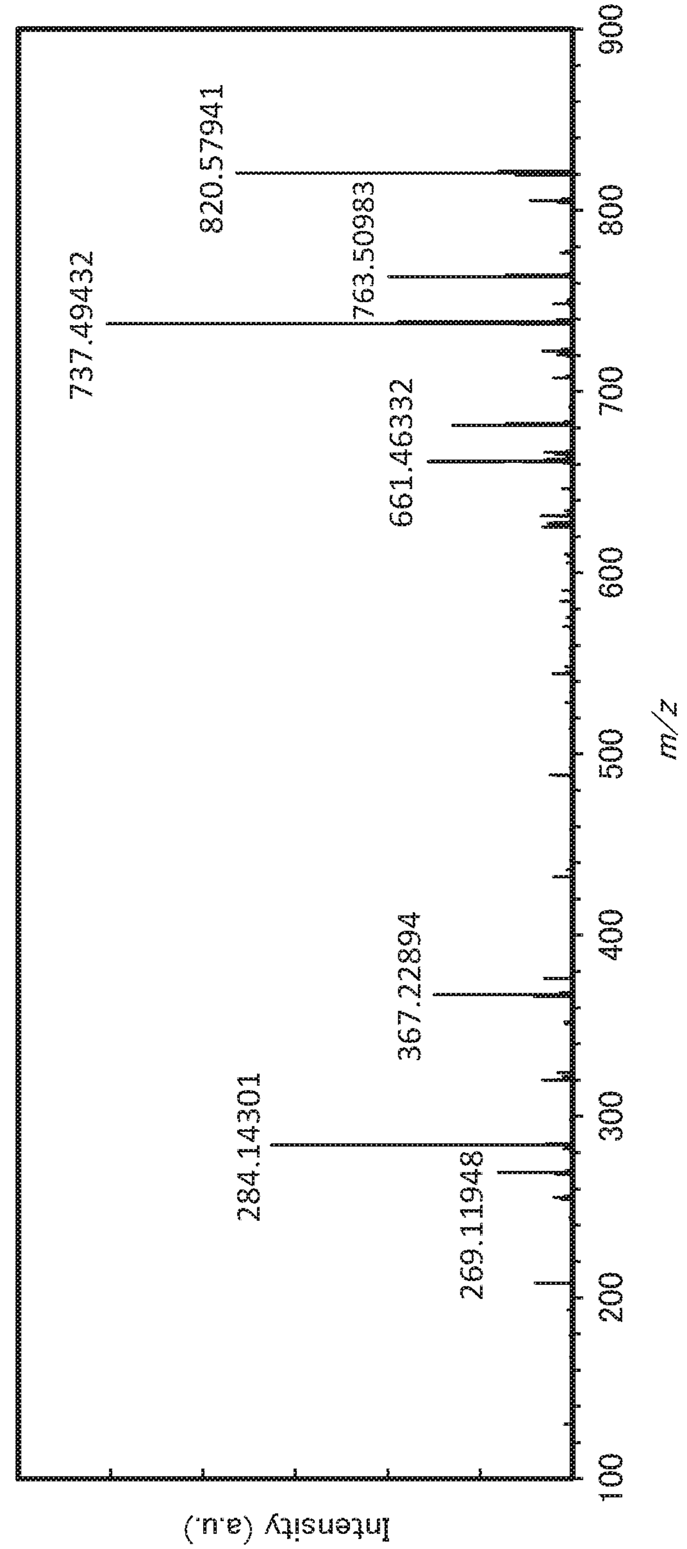
FIG. 46 shows an MS spectrum of mmtBumTPchPAF.

FIG. 46 shows that product ions of mmtBumTPchPAF are mainly detected at m/z of around 820. Note that the result in FIG. 46 shows characteristics derived from mmtBumTPch-PAF and therefore can be regarded as important data for identifying mmtBumTPchPAF contained in a mixture.

Note that a fragment ion at m/z of 661, which was observed in measurement with a collision energy of 50 eV, is estimated to be derived from N-(3,3",5,5"-tetra-t-butyl-1, 1':3,1"-terphenyl-5'-yl)-N-(9,9-dimethyl-9H-fluoren-2-yl) amine generated in such a manner that a C—N bond of mmtBumTPchPAF was cut, and this is the characteristics of mmtBumTPchPAF.

Figure 92:
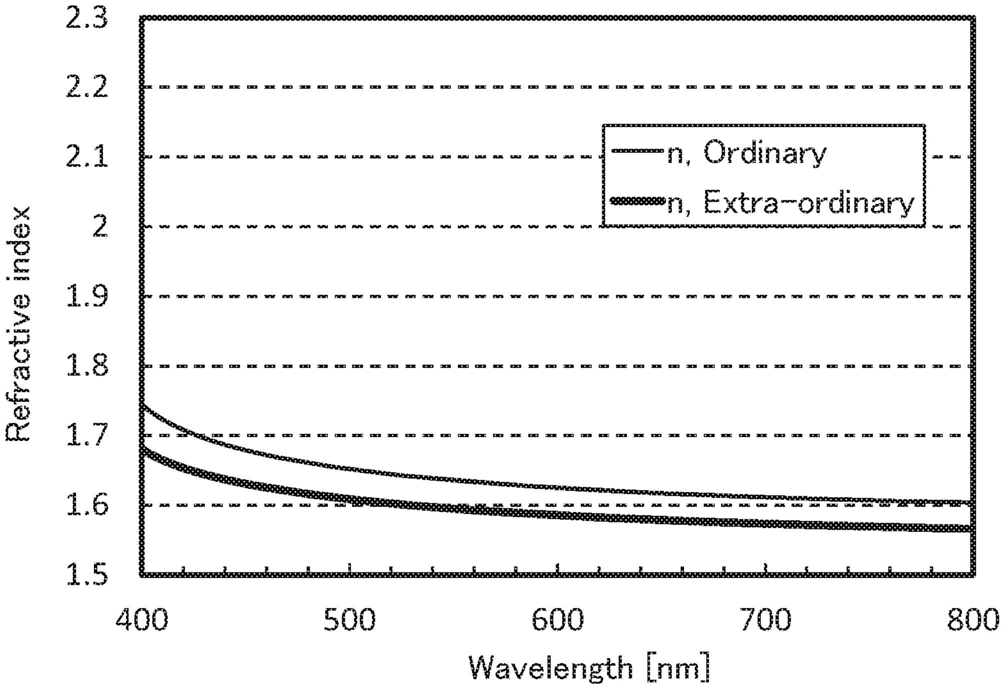
FIG. 92 shows measurement data of a refractive index of mmtBumTPchPAF.

FIG. 92 shows the results of measuring the refractive index of mmtBumTPchPAF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 92.

FIG. 92 shows that mmtBumTPchPAF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of mmtBumTPchPAF was measured. Tg was measured using a differential scanning calorimeter (a Perkin-Elmer Co., Ltd. Pyris 1 DSC) in a state where a powder was put on an aluminum cell. As a result, Tg of mmtBumTPchPAF was 124° C.

Example 12

Synthesis Example 12

In this example, a synthesis method of N-(4-cyclododecylphenyl)-N-(4-cyclohexylphenyl)-9,9-dimethyl-9H-fluoren-2-amine (abbreviation: CdoPchPAF), which is the organic compound represented by the structural formula (111) in Embodiment 1, is described. A structure of CdoPchPAF is shown below.

[Chemical Formula 82]

(111)

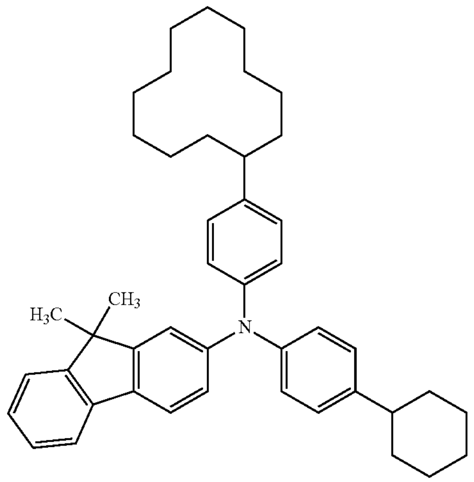

Step 1: Synthesis of 1-(4-chlorophenyl)-1-cyclododecanol

In a 500 mL three-neck flask was put 5.00 g (27.4 mmol) of 1-bromo-4-chlorobenzene. The pressure in the flask was reduced, and then the air in the flask was replaced with nitrogen. To this mixture, 137 mL of dehydrated tetrahydrofuran was added and the mixture was cooled down to −78° C. To the mixture, 18.9 mL (30.2 mmol) of a 1.6M hexane solution of n-butyllithium was added and the mixture was stirred at −78° C. under a nitrogen stream for 2 hours. After a certain period of time, 5.78 g (30.2 mmol) of cyclododecanone was added to the mixture, the temperature of the mixture was increased to room temperature, and then the mixture was stirred for 17 hours. After the stirring, water and ethyl acetate were added to this mixture and an aqueous layer was subjected to extraction with ethyl acetate. The obtained extracted solution and the organic layer were combined, and the mixture was washed with water and saturated saline. Then, the mixture was dried with magnesium sulfate. The mixture was separated by gravity filtration and the obtained filtrate was concentrated to give a yellow solid. Hexane was added to this solid, followed by irradiation with ultrasonic waves. The solid was collected by suction filtration, whereby 6.48 g of a target white solid was obtained in a yield of 80.1%. The synthesis scheme of Step 1 is shown below.

[Chemical Formula 83]

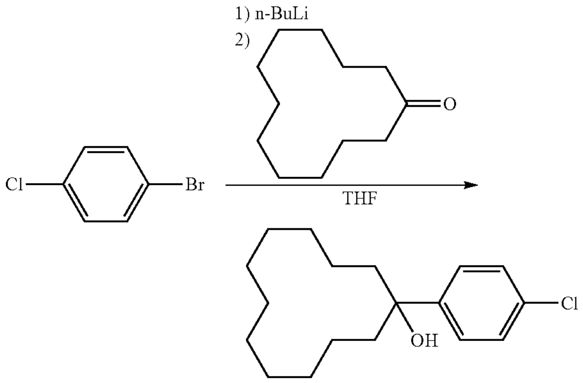

Analysis results by nuclear magnetic resonance spectroscopy ($^1$H-NMR) of the white solid obtained in Step 1 are shown below. The results show that the organic compound 1-(4-chlorophenyl)-1-cyclododecanol was synthesized in this synthesis example.

$^1$H-NMR (300 MHz, $CDCl_3$): δ=7.44-7.38 (m, 2H), 7.32-7.25 (m, 2H), 1.90-1.78 (m, 4H), 1.63 (s, 1H), 1.49-1.11 (m, 18H).

Step 2: Synthesis of 1-chloro-4-cyclododecylbenzene

In a 500 mL three-neck flask was put 6.48 g (22.0 mmol) of 1-(4-chlorophenyl)-1-cyclododecanol obtained in Step 1. The pressure in the flask was reduced, and then the air in the flask was replaced with nitrogen. To this mixture, 220 mL of dehydrated dichloromethane was added and the mixture was cooled down to 0° C. under a nitrogen stream. To the mixture was added 11.0 mL (69.1 mmol) of triethylsilane and the mixture was stirred at 0° C. Then, 16.6 mL (132 mmol) of boron trifluoride ethyl ether was added to the mixture from a dropping funnel, the temperature of the mixture was increased to room temperature, and then the mixture was stirred for approximately 72 hours. After the stirring, the mixture was added to a saturated aqueous solution of sodium hydrogen carbonate, and stirred for 24 hours. After the stirring, the mixture was separated into an organic layer and an aqueous layer, and the aqueous layer was subjected to extraction with dichloromethane. The obtained solution of the extract and an organic layer were combined, and the mixture was washed with water and saturated saline. Then, the mixture was dried with magnesium sulfate. The mixture was separated by gravity filtration and the obtained filtrate was concentrated to give a white solid. The solid was purified by silica gel column chromatography. The obtained fraction was concentrated, whereby 5.85 g of a target white solid was obtained in a yield of 95%. The synthesis scheme of Step 2 is shown below.

[Chemical Formula 84]

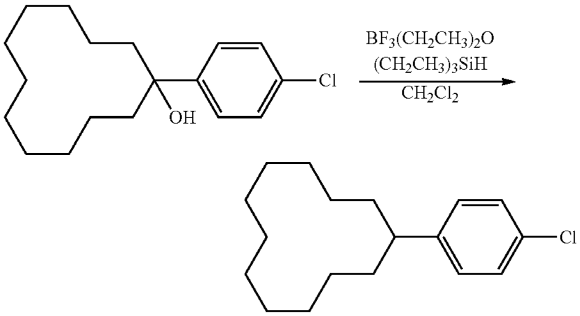

Analysis results by nuclear magnetic resonance spectroscopy ($^1$H-NMR) of the white solid obtained in Step 2 are shown below. The results show that the organic compound 1-chloro-4-cyclododecylbenzene was synthesized in this synthesis example.

$^1$H-NMR (300 MHz, CDC1$_{13}$: 6=7.26-7.21 (m, 2H), 7.14-7.08 (m, 2H), 2.78-2.66 (m, 1H), 1.84-1.70 (m, 2H), 1.52-1.19 (m, 20H).

Step 3: Synthesis of N-(4-cycrohexylphenyl)-N-(9,9-dimethyl-9H-fluoren-2yl)amine The synthesis was performed in a manner similar to Step 1 of the synthesis example 2 in Example 2.

Step 4: Synthesis of N-(4-cyclododecylphenyl)-N-(4-cyclohexylphenyl)-9,9-dimethyl-9H-fluoren-2-amine (Abbreviation: CdoPchPAF)

In a three-neck flask were put 2.89 g (7.86 mmol) of N-(4-cycrohexylphenyl)-N-(9,9-dimethyl-9H-fluoren-2yl) amine obtained in Step 3, 1.83 g (6.56 mmol) of 1-chloro-4-cyclododecylbenzene, 0.111 g (0.315 mmol) of di-tert-butyl(1-methyl-2,2-diphenylcyclopropyl)phosphine (abbreviation: cBRIDP (registered trademark)), 1.89 g (19.7 mmol) of sodium-tert-butoxide, and 33 mL of xylene. This mixture was degassed by being stirred under reduced pressure, and then the air in the flask was replaced with nitrogen. Then, 28.8 mg (0.0787 mmol) of allylpalladium(II) chloride dimer (abbreviation: $[(Allyl)PdCl]_2$) was added to this mixture, and the mixture was stirred at 120° C. under a nitrogen stream for 4 hours. After the stirring, water was added to the mixture to separate an organic layer and an aqueous layer, and the obtained aqueous layer was subjected to extraction with toluene. The obtained extracted solution and the organic layer were combined, and the mixture was washed with water and saturated saline. Then, the mixture was dried with magnesium sulfate. The mixture was separated by gravity filtration, and the obtained filtrate was concentrated to give a black oily substance. This oily substance was purified by silica gel column chromatography. The obtained fraction was concentrated to give a colorless transparent oily substance. This oily substance was purified by high performance liquid column chromatography (developing solvent: chloroform). The obtained fraction was concentrated to give a colorless transparent oily substance. Methanol was added to this oily substance, followed by irradiation with ultrasonic waves. The precipitated solid was collected by suction filtration, so that 3.08 g of a target white solid was obtained in a yield of 77%. The synthesis scheme of Step 4 is shown below.

[Chemical Formula 85]

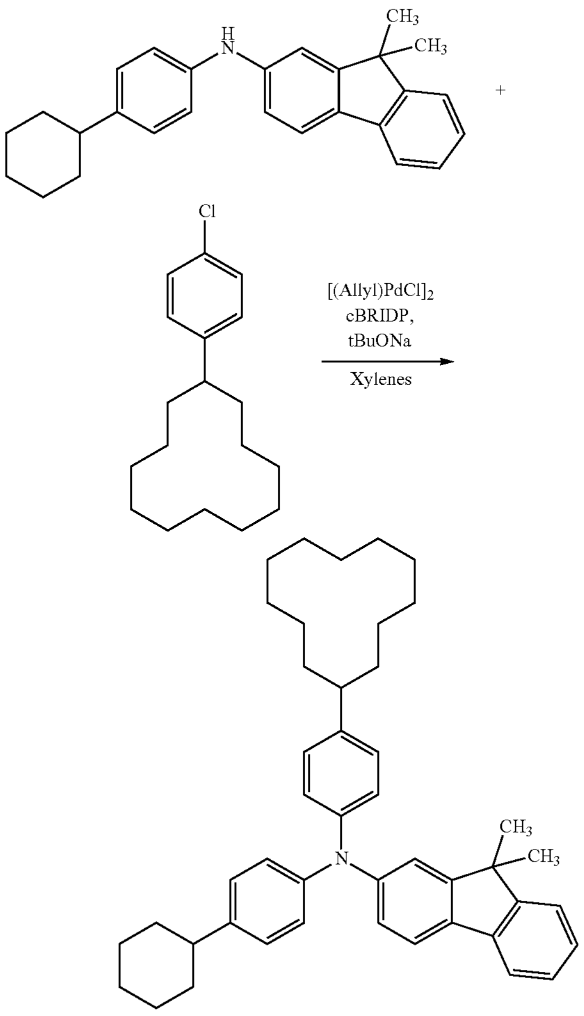

(111)

Then, 3.08 g of the obtained white solid was purified by a train sublimation method. The purification by sublimation was conducted by heating at 230° C. under a pressure of 5.5 Pa with the argon flow rate of 10 mL/min. After the purification by sublimation, 2.58 g of a pale yellow glassy solid was obtained at a collection rate of 84%.

Figure 47:
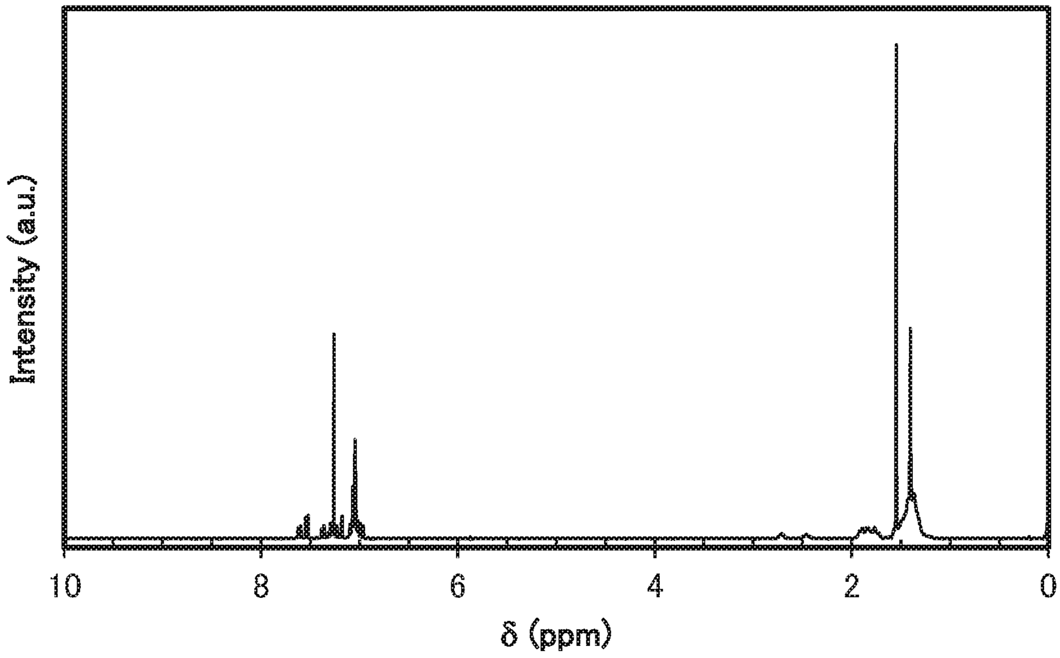
FIG. 47 is $^{1}$H-NMR chart of CdoPchPAF.

Analysis results by nuclear magnetic resonance ($^1$H-NMR) spectroscopy of the white solid obtained in Step 4 are shown below. FIG. 47 is the $^1$H-NMR chart. The results show that N-(4-cyclododecylphenyl)-N-(4-cyclohexylphenyl)-9,9-dimethyl-9H-fluoren-2-amine (abbreviation: CdoPchPAF) was synthesized in this synthesis example.

$^1$H-NMR (300 MHz, $CDCl_3$): δ=7.61 (d, J=6.6 Hz, 1H), 7.53 (d, J=8.1 Hz, 1H), 7.37 (d, J=7.5 Hz, 1H), 7.33-7.17 (m, 3H), 7.12-6.95 (m, 9H), 2.77-2.66 (m, 1H), 2.52-2.39 (m, 1H), 1.96-1.26 (m, 37H).

Figure 48:
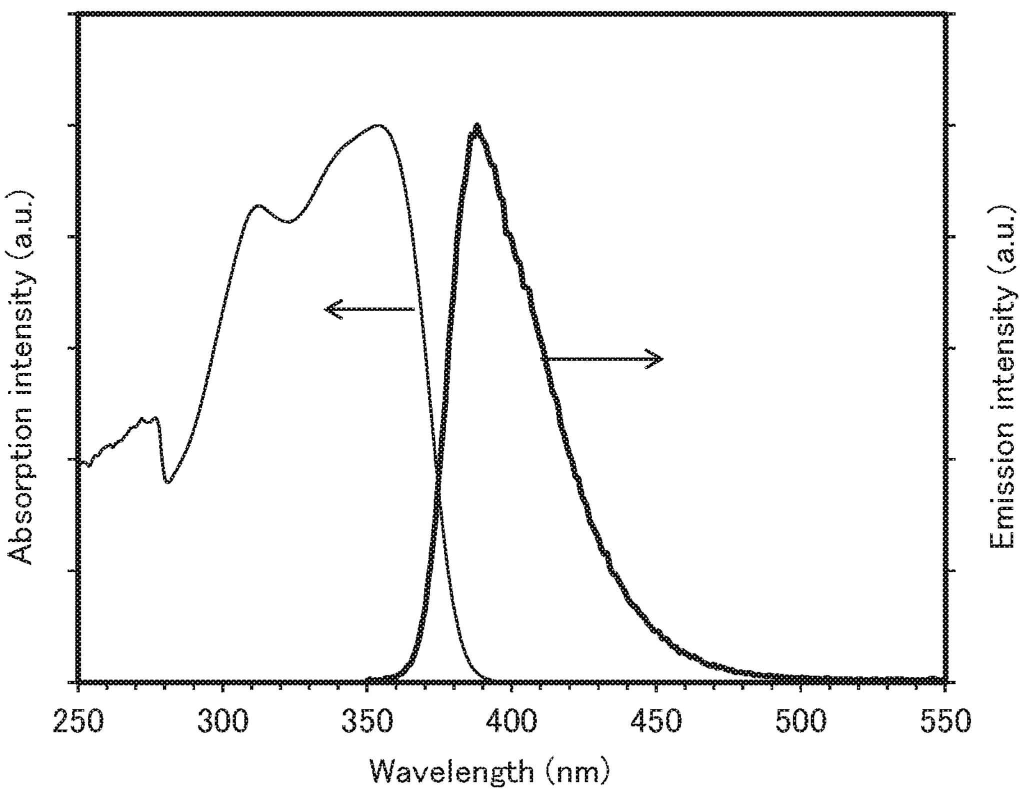
FIG. 48 shows an absorption spectrum and an emission spectrum of CdoPchPAF in a toluene solution.

Next, an ultraviolet-visible absorption spectrum (hereinafter, simply referred to as an absorption spectrum) of CdoPchPAF in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FS920, manufactured by Hamamatsu Photonics K.K.), both of which were measured at room temperature. A quartz cell was used for the measurement cell. FIG. 48 shows measurement results of the absorption spectrum and the emission spectrum. The horizontal axis represents the wavelength and the vertical axes represent the absorption intensity and emission intensity. The absorption intensity shown in FIG. 48 is a result obtained by subtraction of an absorption spectrum of only toluene in a quartz cell from the measured absorption spectrum of the toluene solution in the quartz cell.

As shown in FIG. 48, the organic compound CdoPchPAF has an emission peak at 356 nm.

Next, the organic compound CdoPchPAF was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C8 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that CdoPchPAF was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 609 which underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500. The detection results of the dissociated product ions by time-of-flight (TOF) MS are shown in FIG. 49.

Figure 49:
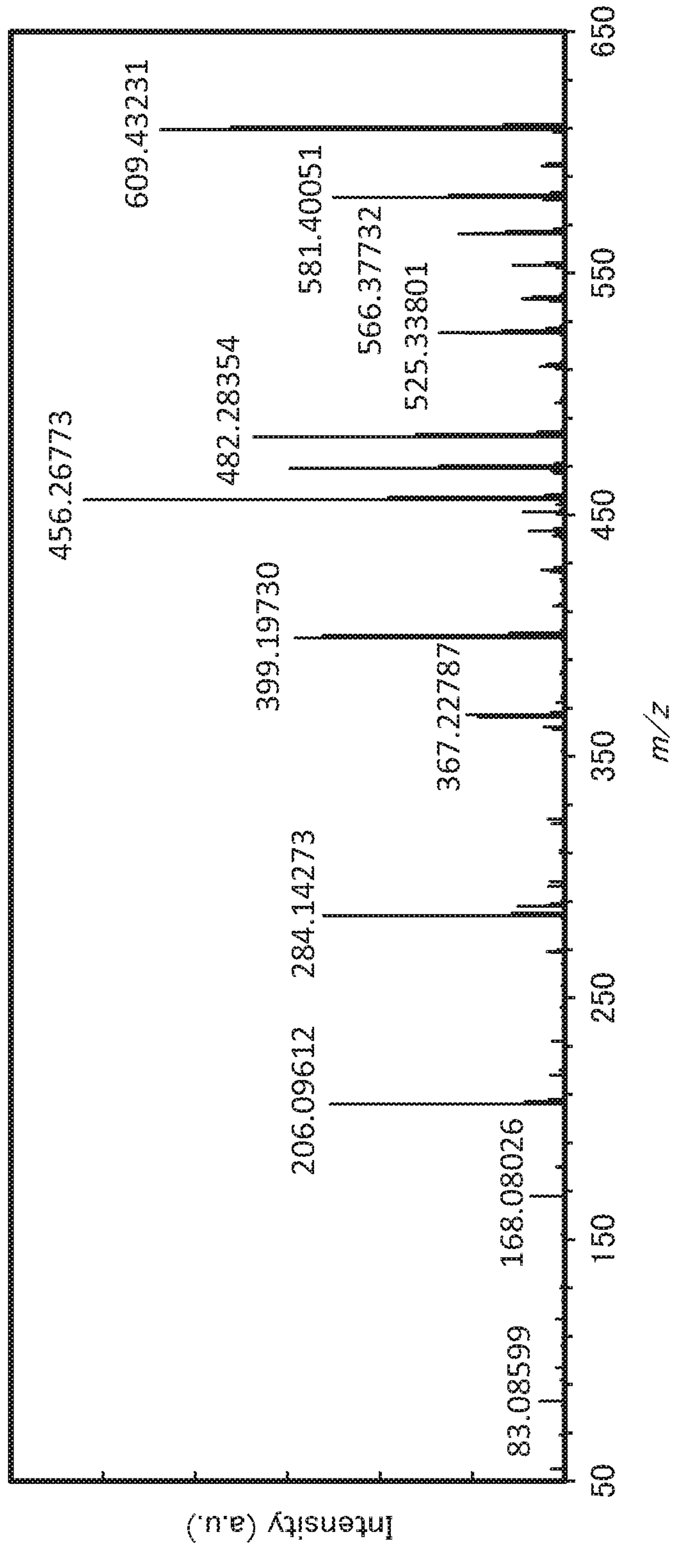
FIG. 49 shows an MS spectrum of CdoPchPAF.

FIG. 49 shows that product ions of CdoPchPAF are mainly detected at m/z of around 609. Note that the result in FIG. 49 shows characteristics derived from CdoPchPAF and therefore can be regarded as important data for identifying CdoPchPAF contained in a mixture.

Note that a fragment ion at m/z of 540, which was observed in measurement with a collision energy of 50 eV, is estimated to be derived from N-(4-cyclododecylphenyl)-N-(9,9-dimethyl-9H-fluoren-2-yl)amine generated in such a manner that a C—N bond of CdoPchPAF was cut, and this is the characteristics of CdoPchPAF.

Figure 93:
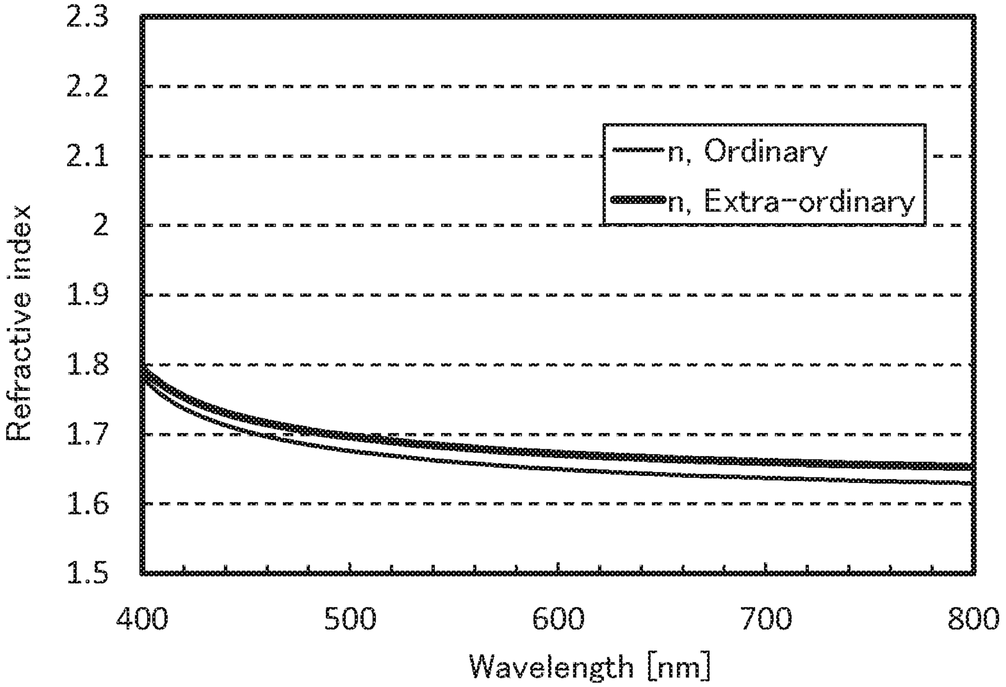
FIG. 93 shows measurement data of a refractive index of CdoPchPAF.

FIG. 93 shows the results of measuring the refractive index of CdoPchPAF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 93.

FIG. 93 shows that CdoPchPAF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Example 13

In this example, light-emitting devices of one embodiment of the present invention described in the above embodiments and comparative light-emitting devices are described. Structural formulae of organic compounds used in this example are shown below.

[Chemical Formula 86]

(i)

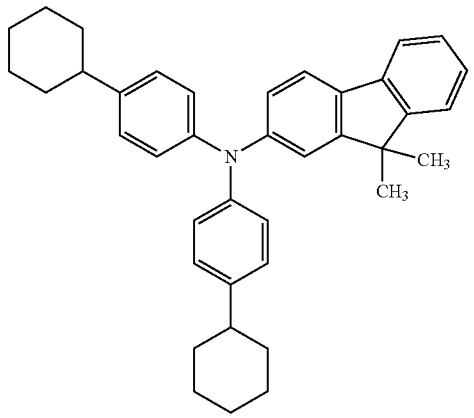

dchPAF (ii)

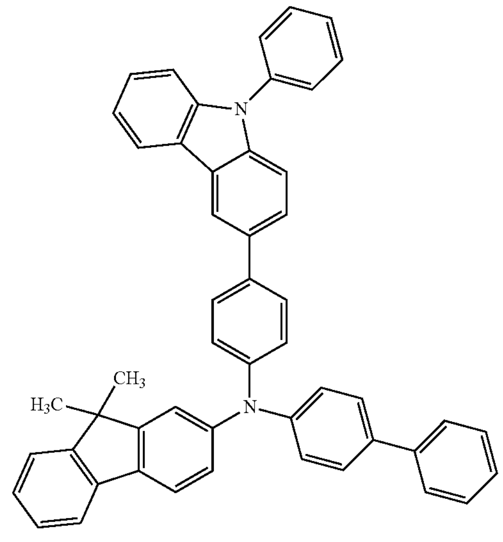

PCBBiF

-continued (iii)

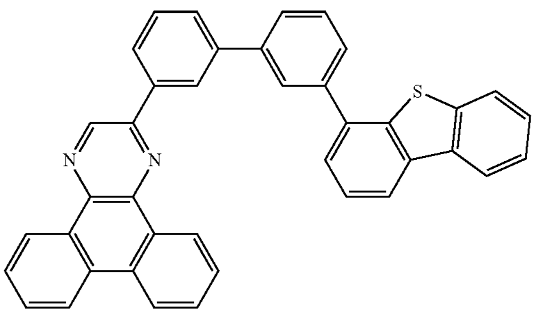

2mDBTBPDBq-II (iv)

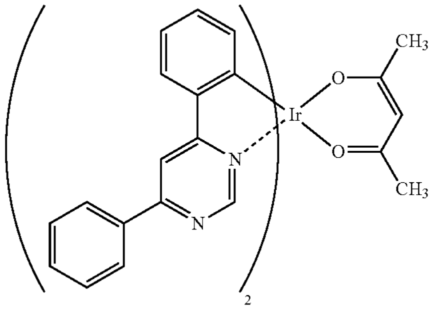

[Ir(dppm)2(acac)]

(v)

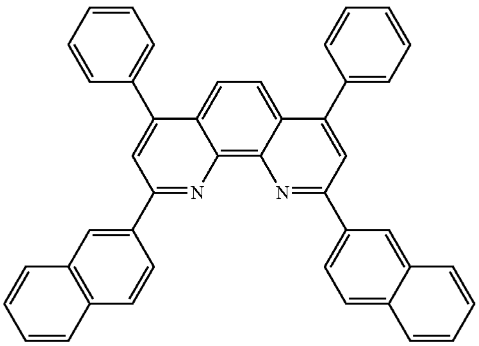

NBPhen (vi)

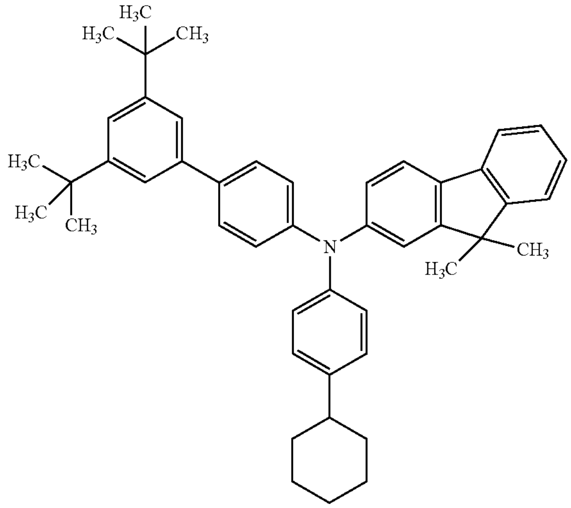

mmtBuBichPAF

-continued (vii)

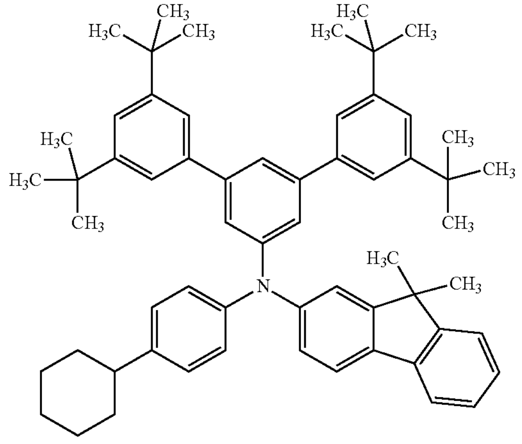

mmtBumTPchPAF (Fabrication Method of Light-Emitting Device 1-1)

First, indium tin oxide containing silicon oxide (ITSO) was deposited over a glass substrate by a sputtering method to form the first electrode 101. The thickness of the first electrode 101 was 70 nm and the electrode area was 2 mm×2 mm.

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N,N-bis(4-cyclohexylphenyl)-9,9, -dimethyl-9H-fluoren-2-amine (abbreviation: dchPAF) represented by the structural formula (i) and ALD-MP001Q (produced by Analysis Atelier Corporation, material serial No. 1S20180314) were deposited by co-evaporation to a thickness of 10 nm on the first electrode 101 using a resistance-heating method such that the weight ratio of dchPAF to ALD-MP001Q was 1:0.1, whereby the hole-injection layer 111 was formed. Note that ALD-MP001Q is an organic compound having an acceptor property.

Subsequently, over the hole-injection layer 111, dchPAF was deposited by evaporation to a thickness of 50 nm to form the hole-transport layer 112.

Then, 2-[3'-(dibenzothiophen-4-yl)biphenyl-3-yl]dibenzo[f,h]quinoxaline (abbreviation: 2mDBTBPDBq-II) represented by the structural formula (iii), N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by the structural formula (ii), and (acetylacetonato)bis(4,6-diphenylpyrimidinato)iridium(III) (abbreviation: $[Ir(dppm)_2(acac)]$) represented by the structural formula (iv) were deposited by co-evaporation to a thickness of 20 nm such that the weight ratio of 2mDBTBPDBq-II to PCBBiF and $[Ir(dppm)_2(acac)]$ was 0.7:0.3:0.075, and then 2mDBTBPDBq-II, PCBBiF, and $[Ir(dppm)_2(acac)]$ were deposited by co-evaporation to a thickness of 20 nm such that the weight ratio of 2mDBTBPDBq-II to PCBBiF and $[Ir(dppm)_2(acac)]$ was 0.8:0.2:0.075, whereby the light-emitting layer 113 was formed.

After that, over the light-emitting layer 113, 2mDBTBPDBq-II was deposited by evaporation to a thickness of 20 nm and 2,9-di(2-naphthyl)-4,7-diphenyl-1,10-phenanthroline (abbreviation: NBPhen) represented by the structural formula (v) was deposited by evaporation to a thickness of 25 nm, whereby the electron-transport layer 114 was formed.

After the formation of the electron-transport layer 114, lithium fluoride (LiF) was deposited by evaporation to a thickness of 1 nm to form the electron-injection layer 115. Then, aluminum was deposited by evaporation to a thickness of 200 nm to form the second electrode 102. Thus, the light-emitting device 1-1 of this example was fabricated.

(Fabrication Method of Light-Emitting Devices 1-2 to 1-4)

The light-emitting devices 1-2 to 1-4 were fabricated in a manner similar to that for the light-emitting device 1-1 except that in the formation of the hole transport layer 112, PCBBiF was deposited by evaporation to a thickness of 5 nm in the light-emitting device 1-2, 10 nm in the light-emitting device 1-3, and 15 nm in the light-emitting device 1-4 after dchPAF was deposited by evaporation to a thickness of 50 nm.

(Fabrication Method of Light-Emitting Devices 2-1 to 2-4)

The light-emitting device 2-1 was fabricated in a manner similar to that for the light-emitting device 1-1 except that dchPAF was replaced with N-[(3',5'-ditertiarybutyl)-1,1'-biphenyl-4-yl]-N-(4-cyclohexylphenyl)-9,9-dimethyl-9H-fluor en-2-amine (abbreviation: mmtBuBichPAF) represented by the structural formula (vi). The light-emitting devices 2-2 to 2-4 were fabricated in a manner similar to that for the light-emitting device 2-1 except that in the formation of the hole-transport layer 112, PCBBiF was deposited by evaporation to a thickness of 5 nm in the light-emitting device 2-2, 10 nm in the light-emitting device 2-3, and 15 nm in the light-emitting device 2-4, after mmtBuBichPAF was deposited by evaporation to a thickness of 50 nm.

(Fabrication Method of Light-Emitting Devices 3-1 to 3-4)

The light-emitting device 3-1 was fabricated in a manner similar to that for the light-emitting device 1-1 except that dchPAF was replaced with N-(3,3",5,5"-tetra-t-butyl-1,1':3',1"-terphenyl-5'-yl)-N-(4-cyclohexylphenyl)-9,9-dimethyl-9H-fluoren-2-amine (abbreviation: mmtBumTPchPAF) represented by the structural formula (vii). The light-emitting devices 3-2 to 3-4 were fabricated in a manner similar to that for the light-emitting device 3-1 except that in the formation of the hole-transport layer 112, PCBBiF was deposited by evaporation to a thickness of 5 nm in the light-emitting device 3-2, 10 nm in the light-emitting device 3-3, and 15 nm in the light-emitting device 3-4, after mmtBumTPchPAF was deposited by evaporation to a thickness of 50 nm.

(Fabrication of Comparative Light-Emitting Devices 1-1 to 1-4)

The comparative light-emitting device 1-1 was fabricated in a manner similar to that for the light-emitting device 1-1 except that dchPAF was replaced with PCBBiF. The comparative light-emitting devices 1-2 to 1-4 were fabricated in a manner similar to that for the comparative light-emitting device 1-1 except that in the formation of the hole-transport layer 112, PCBBiF was deposited by evaporation to a thickness of 55 nm in the comparative light-emitting device 1-2, 60 nm in the comparative light-emitting device 1-3, and 65 nm in the comparative light-emitting device 1-4.

The device structures of the light-emitting devices and the comparative light-emitting devices are listed in the following table.

TABLE 1

| | | Light-emitting device 1-X | Light-emitting device 2-X | Light-emitting device 3-X | Comparative light-emitting device 1-X |
|---|---|---|---|---|---|
| Electron-injection layer | 1 nm | Lif | | | |
| Electron-transport layer | 25 nm | NBPhen | | | |
| | 20 nm | 2mDBTBPDBq-II | | | |
| Light-emitting layer | 20 nm | 2mDBTBPDBq-II:PCBBiF:$Ir(dppm)_2(acac)$ (0.8:0.2:0.075) | | | |
| | 20 nm | 2mDBTBPDBq-II:PCBBiF:$Ir(dppm)_2(acac)$ (0.7:0.3:0.075) | | | |
| Hole-transport layer | *2 | PCBBiF | | | |
| | 50 nm | *1 | | | |
| Hole-injection layer | 10 nm | *1: ALD-MP001Q (1:0.1) | | | |

Figure 94:
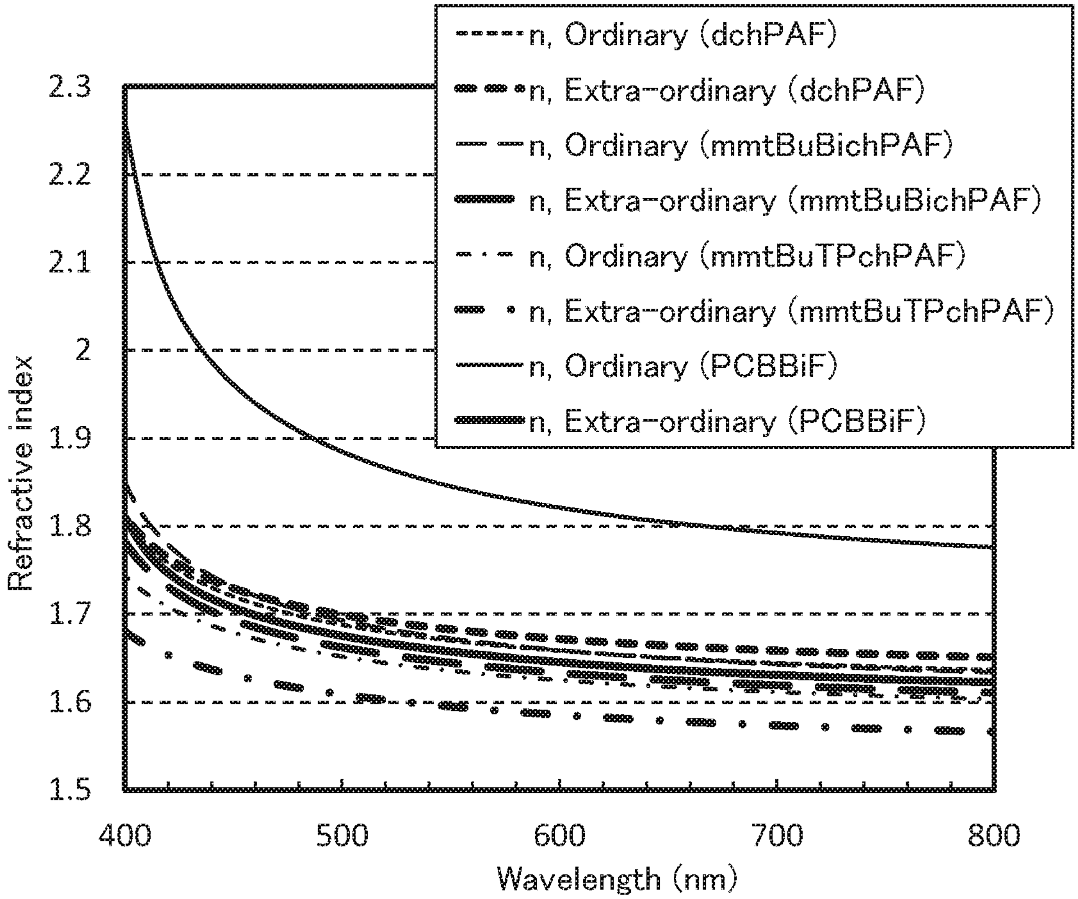
FIG. 94 shows measurement data of refractive indices of dchPAF, mmtBuBichPAF, mmtBumTPchPAF, and PCBBiF.

*1 Light-emitting device 1-X: dchPAF
Light-emitting device 2-X: mmtBuBichPAF
Light-emitting device 3-X: mmtBuTPchPAF
Comparative light-emitting device 1-X: PCBBiF
*2 X = 1: 0 nm
X = 2: 5 nm
X = 3: 10 nm
X = 4: 15 nm The refractive indices of PCBBiF as a reference and the materials with a low refractive index used for the hole-injection layer and part of the hole-transport layer are shown in FIG. 94, and the refractive indices at a wavelength of 585 nm are shown in the following table.

TABLE 2

| | Refractive index |
|---|---|
| dchPAF | 1.66 |
| mmtBuBichPAF | 1.66 |
| mmtBumTPchPAF | 1.63 |
| PCBBif | 1.83 |

The light-emitting devices and the comparative light-emitting devices were sealed using a glass substrate in a glove box containing a nitrogen atmosphere so as not to be exposed to the air (a sealing material was applied to surround the element and UV treatment and heat treatment at 80° C. for 1 hour were performed at the time of sealing). Then, the initial characteristics and reliability of the light-emitting devices were measured. Note that the glass substrate over which the light-emitting device was formed was not subjected to particular treatment for improving the outcoupling efficiency.

Figure 50:
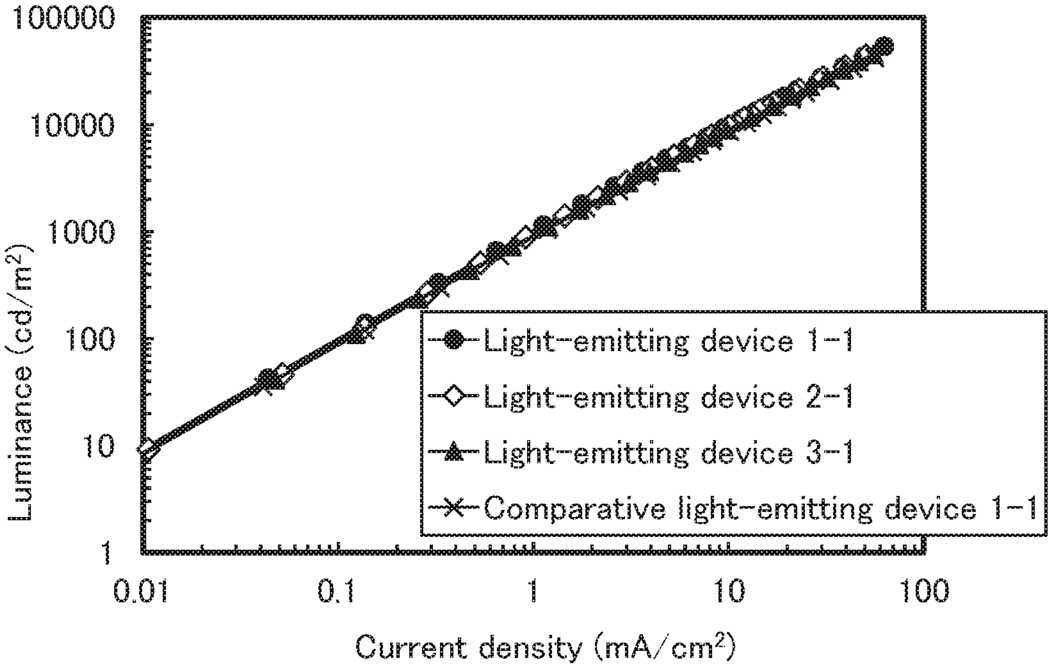
FIG. 50 shows the luminance-current density characteristics of light-emitting devices 1-1, 2-1, 3-1, and a comparative light-emitting device 1-1.
Figure 51:
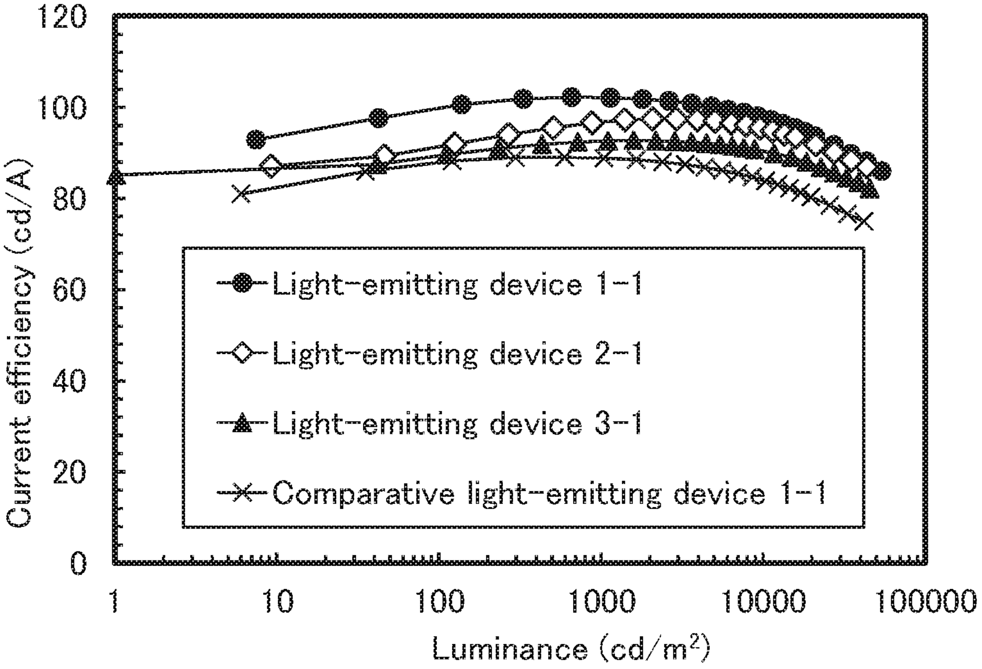
FIG. 51 shows the current efficiency-luminance characteristics of the light-emitting devices 1-1, 2-1, 3-1, and the comparative light-emitting device 1-1.
Figure 52:
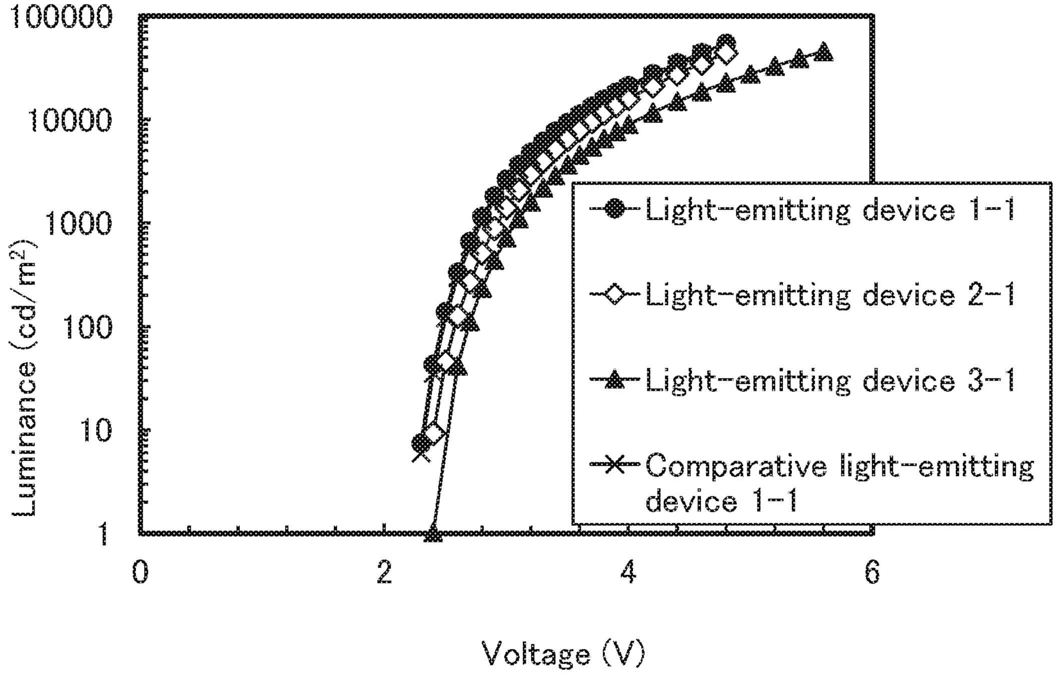
FIG. 52 shows the luminance-voltage characteristics of the light-emitting devices 1-1, 2-1, 3-1, and the comparative light-emitting device 1-1.
Figure 53:
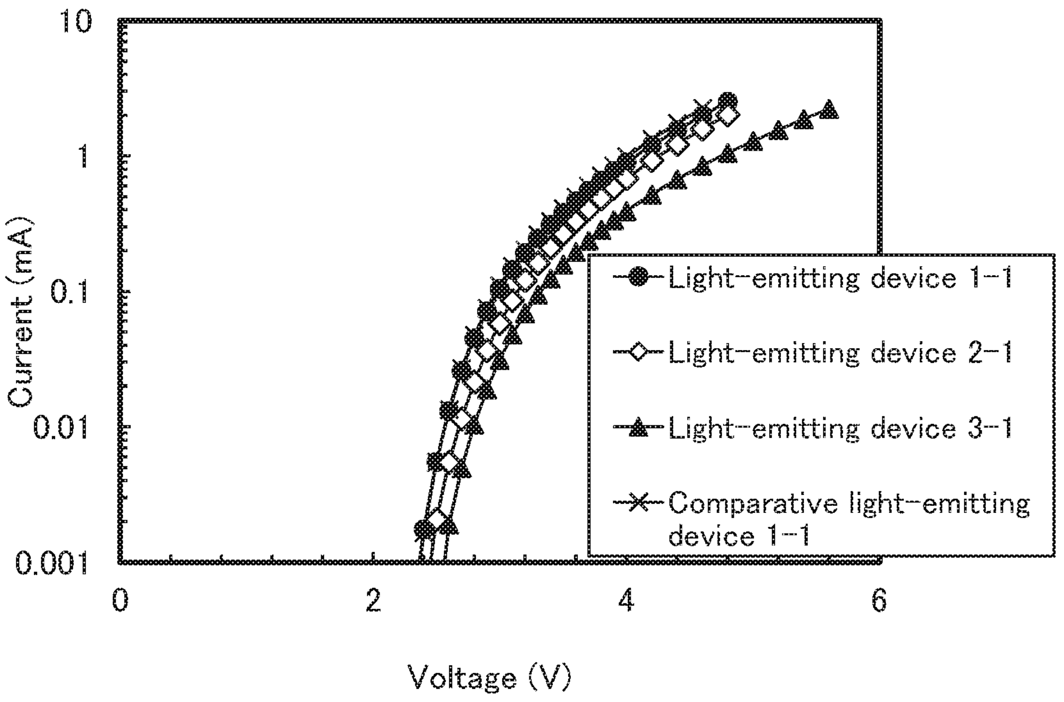
FIG. 53 shows the current-voltage characteristics of the light-emitting devices 1-1, 2-1, 3-1, and the comparative light-emitting device 1-1.
Figure 54:
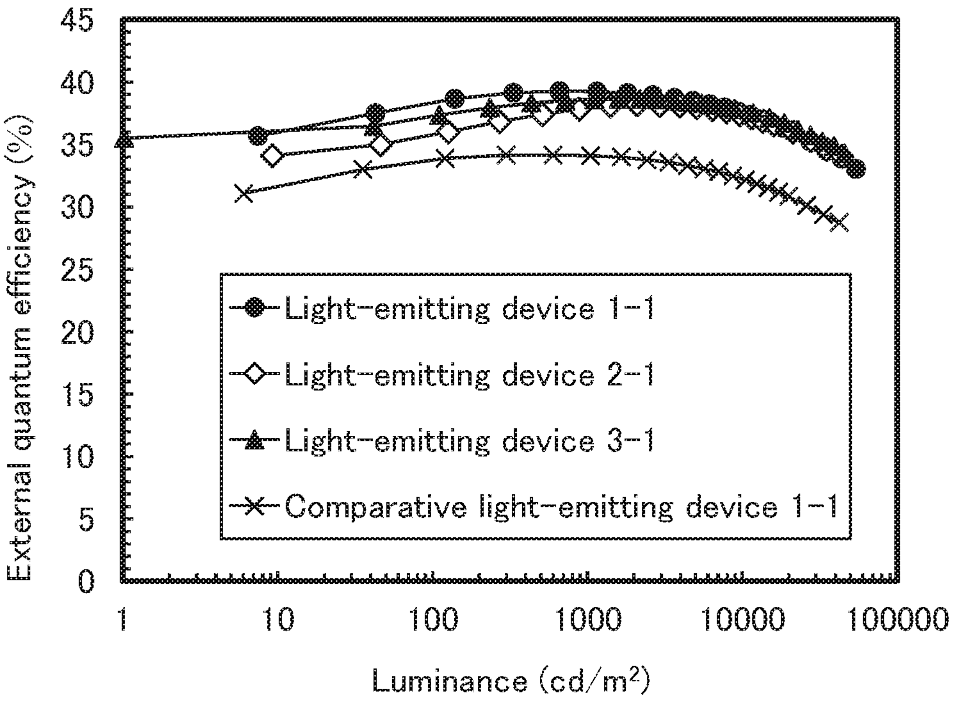
FIG. 54 shows the external quantum efficiency-luminance characteristics of the light-emitting devices 1-1, 2-1, 3-1, and the comparative light-emitting device 1-1.
Figure 55:
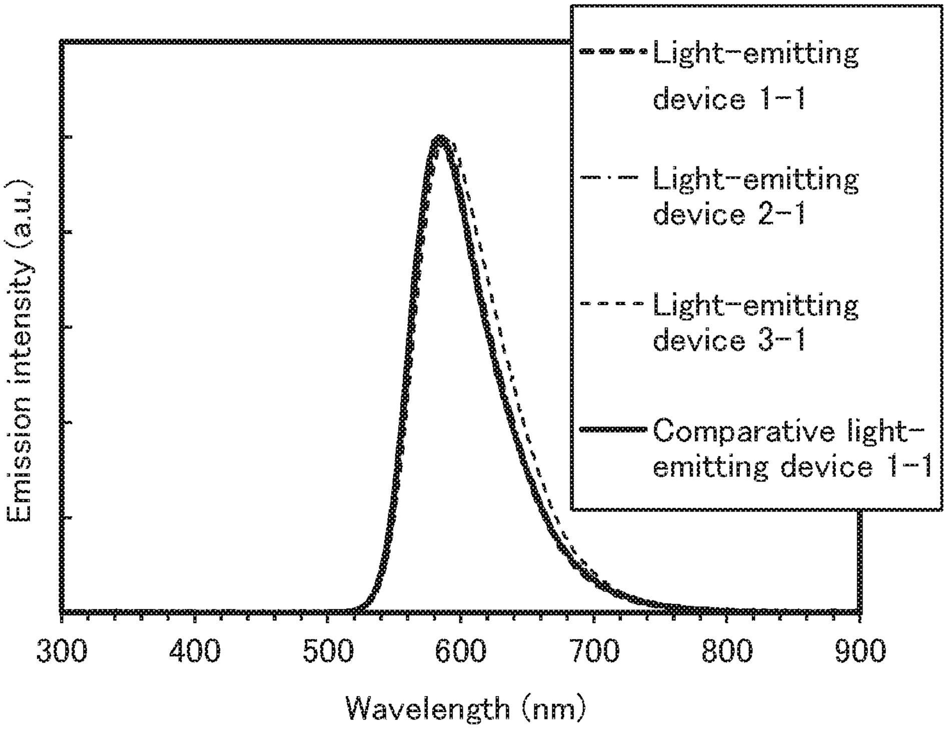
FIG. 55 shows the emission spectra of the light-emitting devices 1-1, 2-1, 3-1, and the comparative light-emitting device 1-1.

FIG. 50 shows the luminance-current density characteristics of the light-emitting devices 1-1, 2-1, and 3-1, and the comparative light-emitting device 1-1. FIG. 51 shows the current efficiency-luminance characteristics thereof. FIG. 52 shows the luminance-voltage characteristics thereof. FIG. 53 shows the current-voltage characteristics thereof. FIG. 54 shows the external quantum efficiency-luminance characteristics thereof. FIG. 55 shows the emission spectra thereof. Table 3 shows the main characteristics of the light-emitting devices at a luminance of about 1000 $cd/m^2$. Luminance, CIE chromaticity, and emission spectra were measured with a spectroradiometer (UR-UL1R manufactured by TOPCON TECHNOHOUSE CORPORATION). The external quantum efficiency was calculated from the luminance and the emission spectrum measured with the spectroradiometer, on the assumption that the light-emitting devices had Lambertian light-distribution characteristics.

TABLE 3

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting device 1-1 | 2.8 | 0.04 | 1.1 | 0.555 | 0.444 | 102.1 | 39.2 |
| Light-emitting device 1-2 | 2.8 | 0.04 | 1.0 | 0.559 | 0.440 | 98.6 | 38.7 |
| Light-emitting device 1-3 | 2.8 | 0.04 | 1.0 | 0.563 | 0.435 | 94.5 | 38.1 |
| Light-emitting device 1-4 | 2.8 | 0.04 | 1.0 | 0.567 | 0.432 | 88.7 | 36.8 |
| Light-emitting device 2-1 | 2.9 | 0.04 | 0.9 | 0.558 | 0.441 | 96.6 | 37.8 |
| Light-emitting device 2-2 | 3.0 | 0.04 | 1.1 | 0.561 | 0.437 | 94.2 | 37.7 |
| Light-emitting device 2-3 | 3.1 | 0.05 | 1.2 | 0.566 | 0.433 | 88.5 | 36.6 |
| Light-emitting device 2-4 | 3.1 | 0.04 | 1.0 | 0.569 | 0.429 | 82.7 | 35.2 |
| Light-emitting device 3-1 | 3.1 | 0.05 | 1.2 | 0.567 | 0.431 | 92.6 | 38.6 |
| Light-emitting device 3-2 | 3.1 | 0.04 | 1.0 | 0.571 | 0.428 | 86.5 | 37.2 |
| Light-emitting device 3-3 | 3.2 | 0.04 | 1.1 | 0.574 | 0.425 | 80.5 | 35.7 |
| Light-emitting device 3-4 | 3.3 | 0.06 | 1.4 | 0.576 | 0.423 | 74.4 | 34.0 |
| Comparative light-emitting device 1-1 | 2.8 | 0.05 | 1.2 | 0.552 | 0.447 | 88.9 | 34.1 |
| Comparative light-emitting device 1-2 | 2.8 | 0.05 | 1.2 | 0.554 | 0.444 | 88.7 | 34.5 |
| Comparative light-emitting device 1-3 | 2.8 | 0.05 | 1.2 | 0.558 | 0.441 | 87.3 | 34.5 |
| Comparative light-emitting device 1-4 | 2.8 | 0.05 | 1.2 | 0.560 | 0.438 | 85.1 | 34.3 |

FIGS. 50 to 55 show that the light-emitting devices of one embodiment of the present invention are EL devices having higher emission efficiency than the comparative light-emitting devices.

Note that in the case where a plurality of light-emitting devices are fabricated using materials with different refractive indices, even when the thicknesses of the corresponding functional layers are equal among the light-emitting devices, the optical distance between electrodes differs depending on the refractive indices of the materials that are used. Furthermore, deposition by evaporation sometimes has difficulty in precise control of the thicknesses; thus, a light-emitting device fabricated in such a manner might be fabricated to an undesired thickness in some cases.

The light-emitting device of this example has a structure in which light is amplified or attenuated by interference caused by the following: a large amount of light reflected on the cathode where aluminum is used, and a certain amount of light reflected due to a difference in refractive index between the electrode material of the anode and the organic compound. The wavelength of light that is amplified or attenuated by the interference depends on the optical distance between electrodes in principle. Although substances have specific emission spectra, light with a wavelength with high emission intensity in the emission spectrum is amplified efficiently, whereas light with a wavelength with low emission intensity is amplified inefficiently; thus, the emission efficiency depends on the wavelength of light that is amplified, i.e., the optical distance between electrodes.

As described above, the light-emitting device in this example is fabricated using materials with different refractive indices. Furthermore, since it is difficult to precisely control the thickness during deposition by evaporation, the optical distances between electrodes are different among the light-emitting devices even when the thicknesses of the corresponding functional layers are equal among the light-emitting devices. The wavelengths of light that is amplified are also different, and thus the emission efficiency cannot be accurately compared in FIG. 55.

Figure 56:
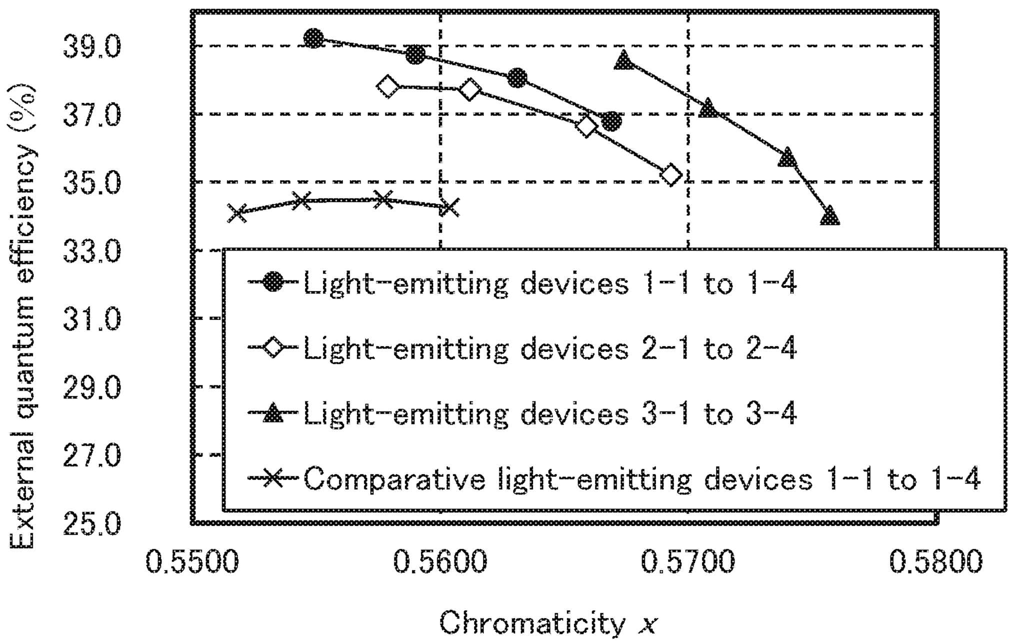
FIG. 56 shows relationships between chromaticity x and external quantum efficiency of light-emitting devices 1-1 to 1-4, light-emitting devices 2-1 to 2-4, light-emitting devices 3-1 to 3-4, and comparative light-emitting devices 1-1 to 1-4.

FIG. 56 shows the relationship between chromaticity x and external quantum efficiency, at a luminance of about 1000 cd/m$^2$, of the light-emitting devices 1-1 to 1-4, the light-emitting devices 2-1 to 2-4, the light-emitting devices 3-1 to 3-4, and the comparative light-emitting devices 1-1 to 1-4. The light-emitting devices 1-1 to 1-4, the light-emitting devices 2-1 to 2-4, the light-emitting devices 3-1 to 3-4, and the comparative light-emitting devices 1-1 to 1-4 differ in the thickness of the EL layer, that is, differ in the optical distance between electrodes and wavelength of amplified light.

The reason why the horizontal axis of FIG. 56 represents the chromaticity x is as follows: the interference effect depends on the optical distance between electrodes, and lights emitted using similar light-emitting substances and subjected to similar interference effects show similar emission spectra; thus, lights with the same chromaticity can be regarded as being subjected to the same interference effect, which indicate the optical distances between the electrodes are the same. In other words, with reference to FIG. 56, the improvement in emission efficiency owing to the layer with a low refractive index can be simply examined, without considering the difference in refractive index of the materials and the difference in optical distances derived from deposition.

In FIG. 56, the light-emitting devices 1-1 to 1-4, the light-emitting devices 2-1 to 2-4, and the light-emitting devices 3-1 to 3-4, which use dchPAF, mmtBuBichPAF, and mmtBumTPchPAF, respectively, as a material with a low refractive index, show higher emission efficiency than the comparative light-emitting devices 1-1 to 1-4, which use PCBBiF with a normal refractive index as the organic compound used for the light-emitting device. This shows that using dchPAF, mmtBuBichPAF, and mmtBumTPchPAF enables the light-emitting device to have extremely high emission efficiency.

As shown in Table 3, the light-emitting devices of one embodiment of the present invention are EL devices having favorable driving characteristics with no significant deterioration of driving voltage and the like.

Figure 57:
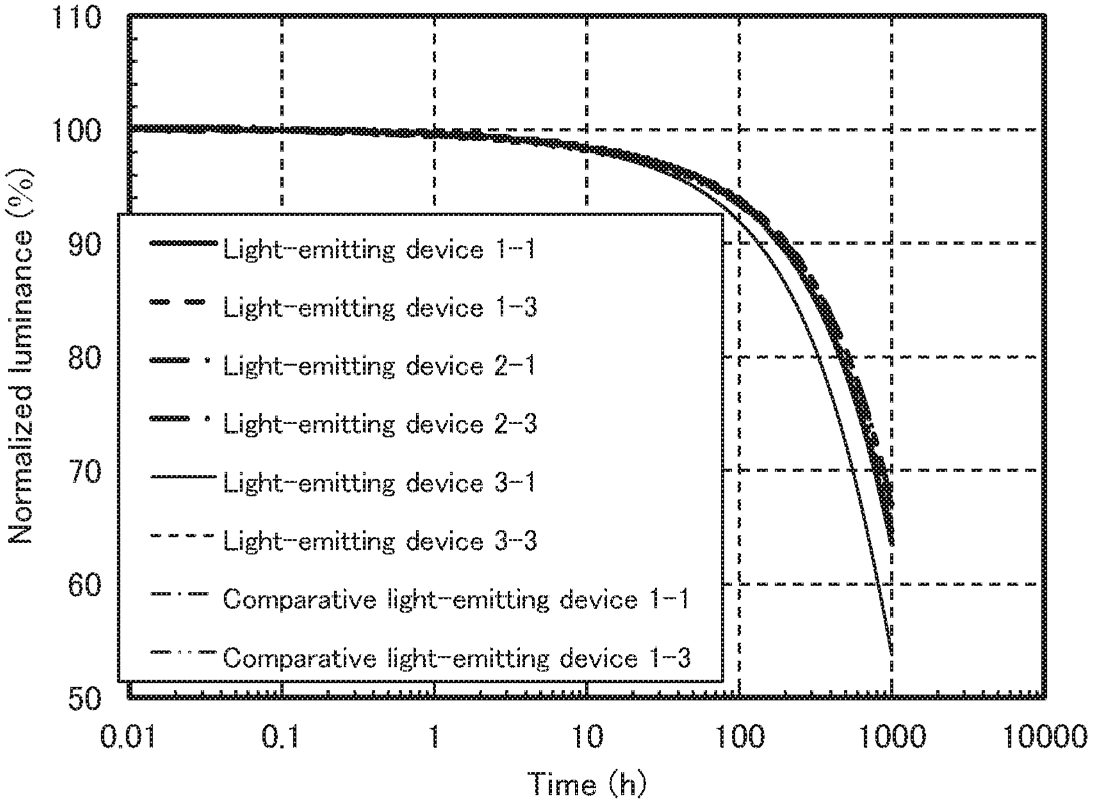
FIG. 57 shows a luminance change with respect to driving time of the light-emitting devices 1-1 and 1-3, the light-emitting devices 2-1 and 2-3, the light-emitting devices 3-1 and 3-3, and the comparative light-emitting devices 1-1 and 1-3.

FIG. 57 shows luminance change with respect to driving time when the light-emitting devices 1-1, 1-3, 2-1, 2-3, 3-1, and 3-3, and the comparative light-emitting devices 1-1 and 1-3 are driven at a constant current of 2 mA (50 mA/cm$^2$). FIG. 57 shows no big difference in luminance change among the EL devices, which reveals that the light-emitting devices of one embodiment of the present invention have high emission efficiency while keeping a long lifetime.

Example 14

In this example, light-emitting devices of one embodiment of the present invention described in the above embodiments and comparative light-emitting devices are described. Structural formulae of organic compounds used in this example are shown below.

[Chemical Formula 87]

(i)

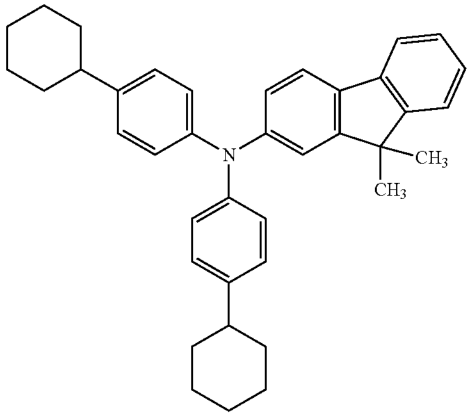

dchPAF

-continued (viii)

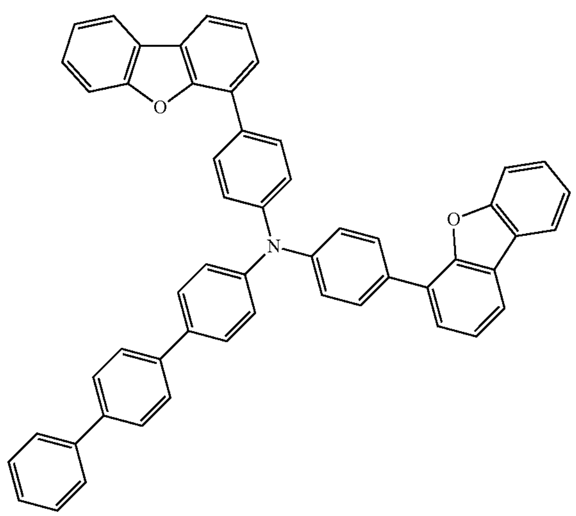

DBfBB1TP (ix)

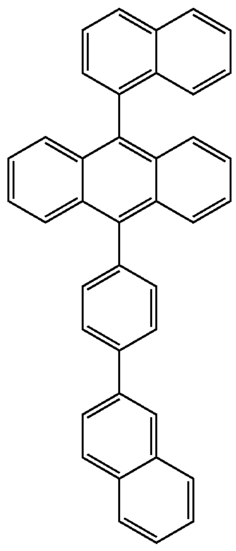

αN-βNPAnth

-continued
(x)
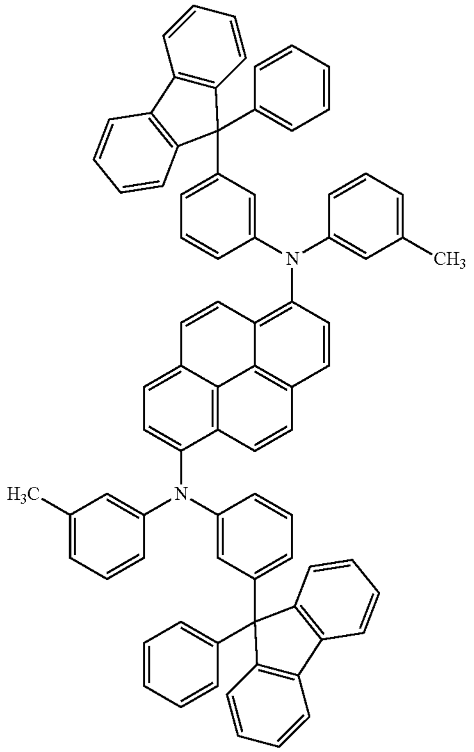
1,6mMemFLPAPrn
(xi)
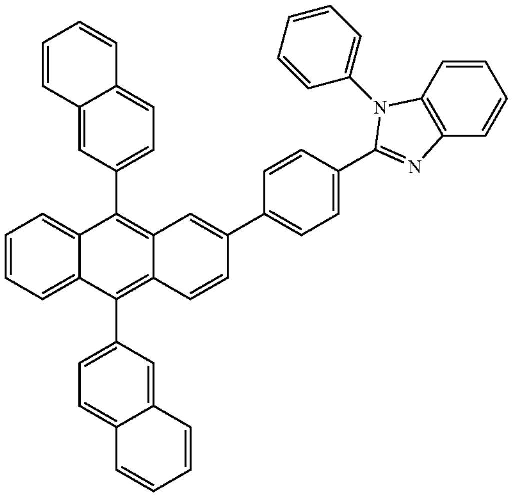
ZADN
(xii)
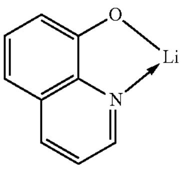
Liq
-continued
(vi)
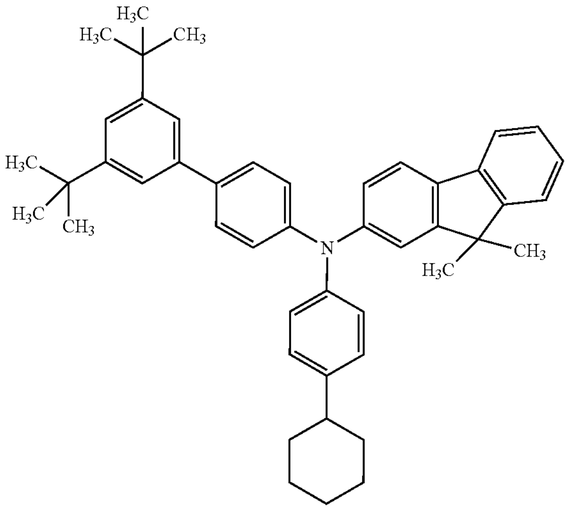
mmtBuBichPAF
(vii)
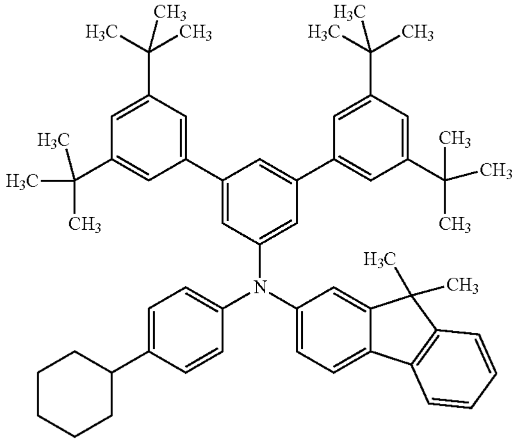
mmtBumTPchPAF
(ii)
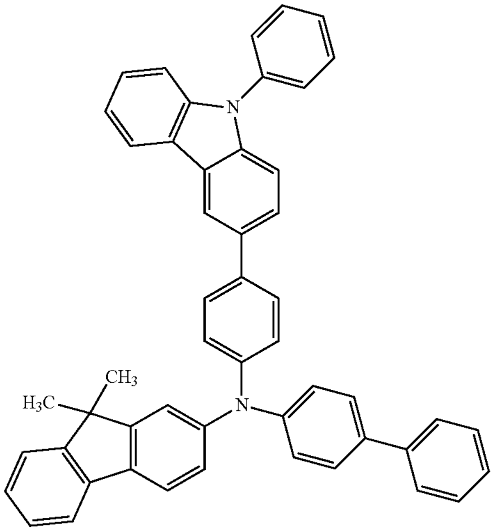
PCBBiF (Fabrication Method of Light-Emitting Device 4-1)

First, indium tin oxide containing silicon oxide (ITSO) was deposited over a glass substrate by a sputtering method to form the first electrode 101. The thickness of the first electrode 101 was 55 nm and the electrode area was 2 mm×2 mm.

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N,N-bis(4-cyclohexylphenyl)-9,9, -dimethyl-9H-fluoren-2-amine (abbreviation: dchPAF) represented by the structural formula (i) and ALD-MP001Q (produced by Analysis Atelier Corporation, material serial No. 1S20180314) were deposited by co-evaporation to a thickness of 10 nm on the first electrode 101 using a resistance-heating method such that the weight ratio of dchPAF to ALD-MP001Q was 1:0.1, whereby the hole-injection layer 111 was formed. Note that ALD-MP001Q is an organic compound having an acceptor property.

Subsequently, over the hole-injection layer 111, dchPAF was deposited by evaporation to a thickness of 35 nm and N,N-bis[4-(dibenzofurane-4-yl)phenyl]-4-amino-p-terphenyl (abbreviation: DBfBB1TP) was deposited by evaporation to a thickness of 10 nm, whereby the hole-transport layer 112 was formed.

Then, 9-(1-naphthyl)-10-[4-(2-naphthyl)phenyl]anthracene (abbreviation: αN-βNPAnth) represented by the structural formula (ix) and N,N-bis(3-methylphenyl)-N,N-bis[3-(9-phenyl-9H-fluoren-9-yl)phenyl]pyrene-1,6-diamine (abbreviation: 1,6mMemFLPAPrn) represented by the structural formula (x) were deposited by co-evaporation to a thickness of 25 nm such that the weight ratio of αN-βNPAnth to 1,6mMemFLPAPrn was 1:0.03, where by the light-emitting layer 113 was formed.

After that, over the light-emitting layer 113, 2-{4-[9,10-di(naphthalen-2-yl)-2-anthryl]phenyl}-1-phenyl-1H-benzimidazole (abbreviation: ZADN) represented by the structural formula (xi) and 8-hydroxyquinolinatolithium (abbreviation: Liq) represented by the structural formula (xii) (manufactured by Chemipro Kasei Kaisha, Ltd., Serial No. 181201) was deposited by co-evaporation such that the weight ratio of ZADN to Liq was 1:1, whereby the electron-transport layer 114 was formed.

After the formation of the electron-transport layer 114, Liq was deposited by evaporation to a thickness of 1 nm to form the electron-injection layer 115. Then, aluminum was deposited by evaporation to a thickness of 200 nm to form the second electrode 102. Thus, the light-emitting device 4-1 of this example was fabricated.

(Fabrication Method of Light-Emitting Devices 4-2 to 4-4)

The light-emitting devices 4-2 to 4-4 were fabricated in a manner similar to that for the light-emitting device 4-1 except that in the formation of the hole transport layer 112, DBfBB1TP was deposited by evaporation to a thickness of 15 nm in the light-emitting device 4-2, 20 nm in the light-emitting device 4-3, and 25 nm in the light-emitting device 4-4, after dchPAF was deposited by evaporation to a thickness of 35 nm.

(Fabrication Method of Light-Emitting Devices 5-1 to 5-4)

The light-emitting device 5-1 was fabricated in a manner similar to that for the light-emitting device 4-1 except that dchPAF was replaced with N-[(3',5'-ditertiarybutyl)-1,1'-biphenyl-4-yl]-N-(4-cyclohexylphenyl)-9,9-dimethyl-9H-fluor en-2-amine (abbreviation: mmtBuBichPAF) represented by the structural formula (vi). The light-emitting devices 5-2 to 5-4 were fabricated in a manner similar to that for the light-emitting device 5-1 except that in the formation of the hole-transport layer 112, DBfBB1TP was deposited by evaporation to a thickness of 15 nm in the light-emitting device 5-2, 20 nm in the light-emitting device 5-3, and 25 nm in the light-emitting device 5-4, after mmtBuBichPAF was deposited by evaporation to a thickness of 35 nm.

(Fabrication Method of Light-Emitting Devices 6-1 to 6-4)

The light-emitting device 6-1 was fabricated in a manner similar to that for the light-emitting device 4-1 except that dchPAF was replaced with N-(3,3",5,5"-tetra-t-butyl-1,1':3',1"-terphenyl-5'-yl)-N-(4-cyclohexylphenyl)-9,9-dimethyl-9H-fluoren-2-amine (abbreviation: mmtBumTPchPAF) represented by the structural formula (vii). The light-emitting devices 6-2 to 6-4 were fabricated in a manner similar to that for the light-emitting device 6-1 except that in the formation of the hole-transport layer 112, DBfBB1TP was deposited by evaporation to a thickness of 15 nm in the light-emitting device 6-2, 20 nm in the light-emitting device 6-3, and 25 nm in the light-emitting device 6-4, after mmtBumTPchPAF was deposited by evaporation to a thickness of 35 nm.

(Fabrication of Comparative Light-Emitting Devices 2-1 to 2-4)

The comparative light-emitting device 2-1 was fabricated in a manner similar to that for the light-emitting device 4-1 except that dchPAF was replaced with N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by the structural formula (ii). The comparative light-emitting devices 2-2 to 2-4 were fabricated in a manner similar to that for the light-emitting device 4-1 except that in the formation of the hole-transport layer 112, DBfBB1TP was deposited by evaporation to a thickness of 15 nm in the comparative light-emitting device 2-2, 20 nm in the comparative light-emitting device 2-3, and 25 nm in the comparative light-emitting device 2-4, after PCBBiF was deposited by evaporation to a thickness of 35 nm.

The device structures of the light-emitting devices and the comparative light-emitting devices are listed in the following table.

TABLE 4

| | | Light-emitting device 4-X | Light-emitting device 5-X | Light-emitting device 6-X | Comparative light-emitting device 2-X |
|---|---|---|---|---|---|
| Electron-injection layer | 1 nm | Liq | | | |
| Electron-transport layer | 25 nm | ZADN:Liq (1:1) | | | |
| Light-emitting layer | 25 nm | αN-βNPAnth:1,6mMemFLPAPrn (1:00.3) | | | |

TABLE 4-continued

| | Light-emitting device 4-X | Light-emitting device 5-X | Light-emitting device 6-X | Comparative light-emitting device 2-X |
|---|---|---|---|---|
| Hole-transport layer | *4 | DBfBB1TP | | |
| | 35 nm | *3 | | |
| Hole-injection layer | 10 nm | *3:ALD-MP001Q (1:0.1) | | |

*3 Light-emitting device 4-X: dchPAF
Light-emitting device 5-X: mmtBuBichPAF
Light-emitting device 6-X: mmtBuTPchPAF
Comparative light-emitting device 2-X: PCBBiF
*4 X = 1: 10 nm
X = 2: 15 nm
X = 3: 20 nm
X = 4: 25 nm The refractive indices of PCBBiF as a reference and the materials with a low refractive index used for the hole-injection layer and part of the hole-transport layer are shown in FIG. 94, and the refractive indices at a wavelength of 465 nm are shown in the following table.

TABLE 5

| | Refractive index |
|---|---|
| dchPAF | 1.71 |
| mmtBuBichPAF | 1.72 |
| mmtBumTPchPAF | 1.67 |
| PCBBiF | 1.93 |

The light-emitting devices and the comparative light-emitting devices were sealed using a glass substrate in a glove box containing a nitrogen atmosphere so as not to be exposed to the air (a sealing material was applied to surround the element and UV treatment was performed at the time of sealing). Then, the initial characteristics and reliability of the light-emitting devices were measured. Note that the glass substrate over which the light-emitting device was formed was not subjected to particular treatment for improving outcoupling efficiency.

Figure 58:
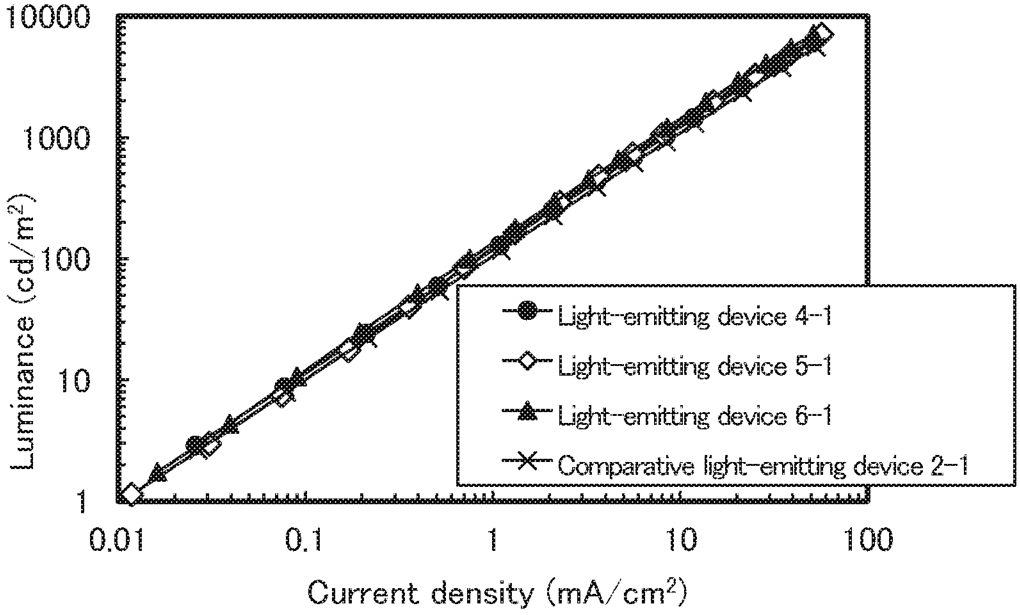
FIG. 58 shows the luminance-current density characteristics of light emitting devices 4-1, 5-1, and 6-1, and a comparative light-emitting device 2-1.
Figure 59:
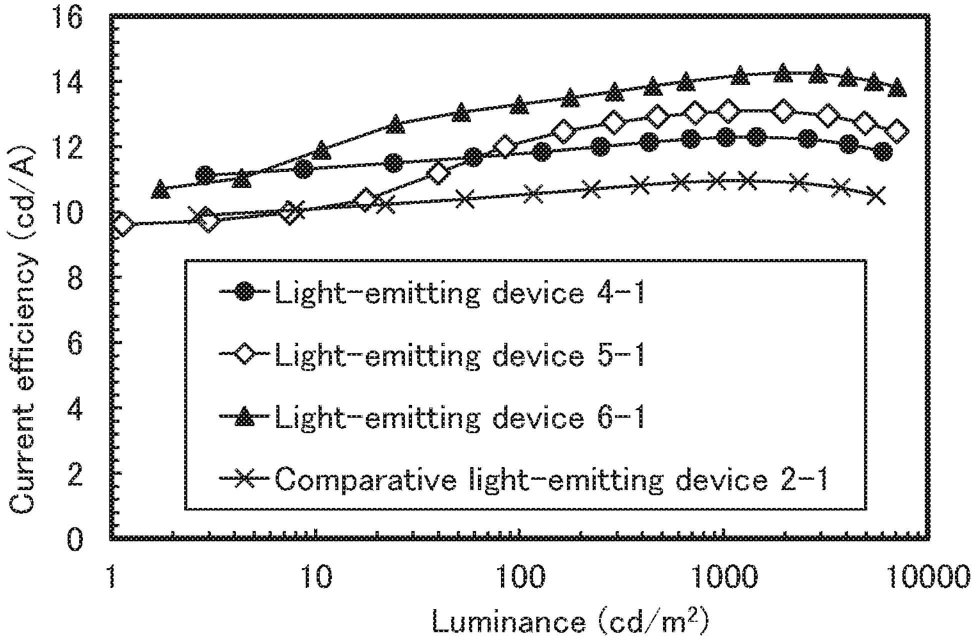
FIG. 59 shows the current efficiency-luminance characteristics of the light emitting devices 4-1, 5-1, and 6-1, and the comparative light-emitting device 2-1.
Figure 60:
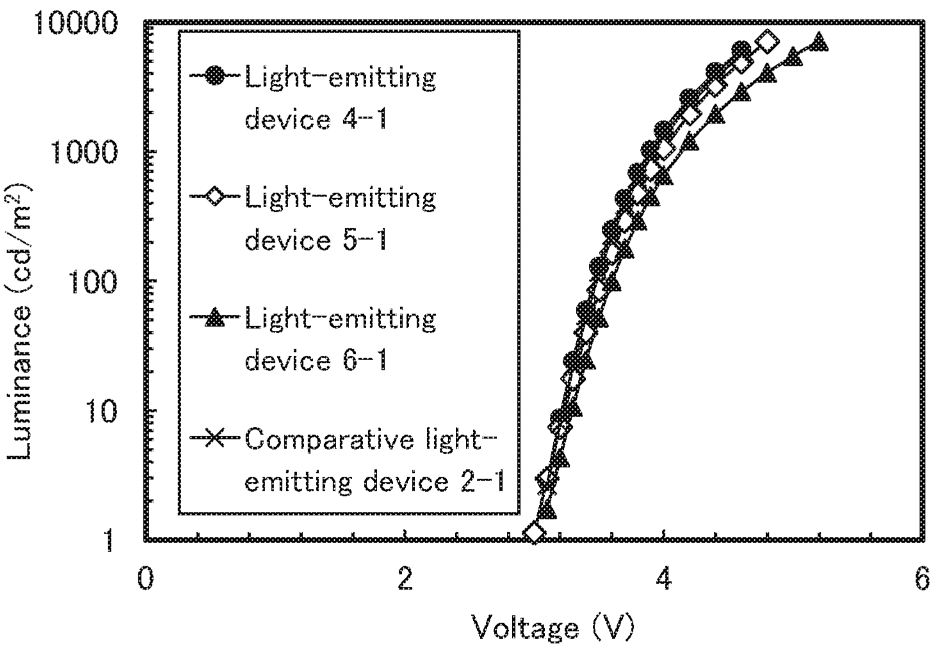
FIG. 60 shows the luminance-voltage characteristics of the light emitting devices 4-1, 5-1, and 6-1, and the comparative light-emitting device 2-1.
Figure 61:
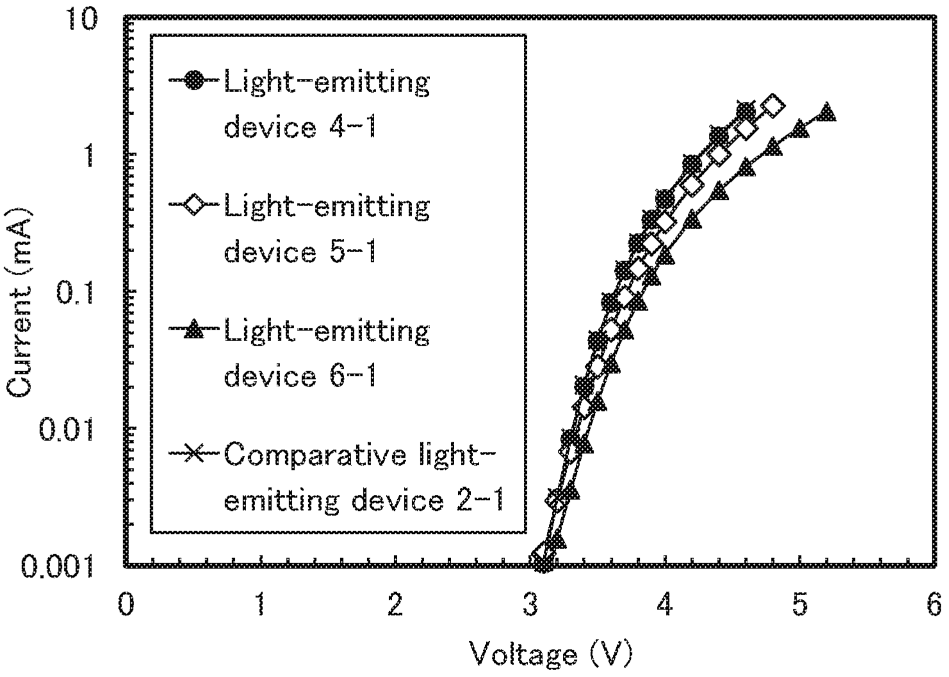
FIG. 61 shows the current-voltage characteristics of the light emitting devices 4-1, 5-1, and 6-1, and the comparative light-emitting device 2-1.
Figure 62:
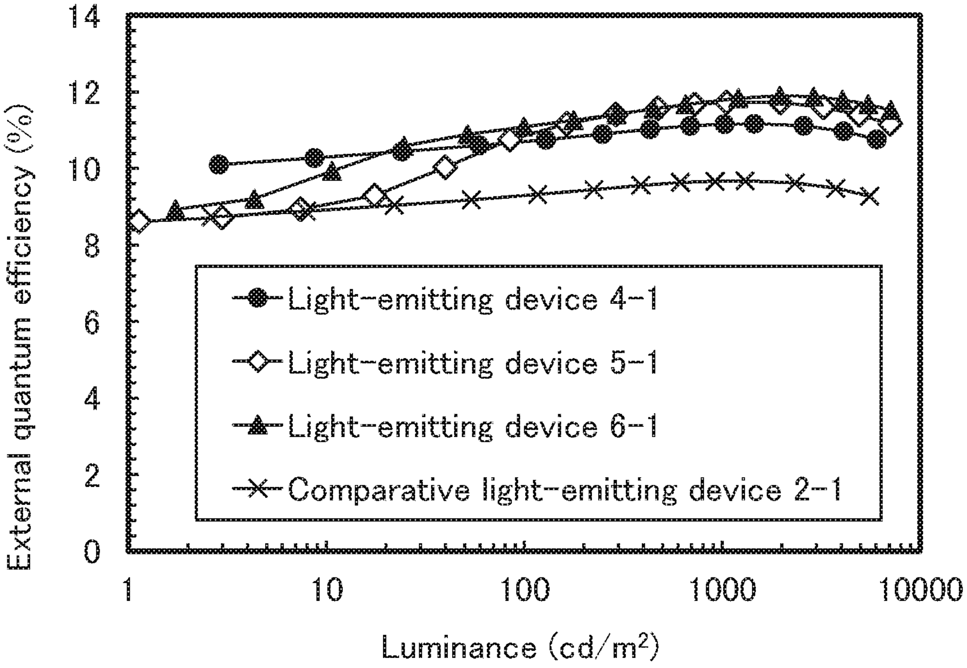
FIG. 62 shows the external quantum efficiency-luminance characteristics of the light emitting devices 4-1, 5-1, and 6-1, and the comparative light-emitting device 2-1.
Figure 63:
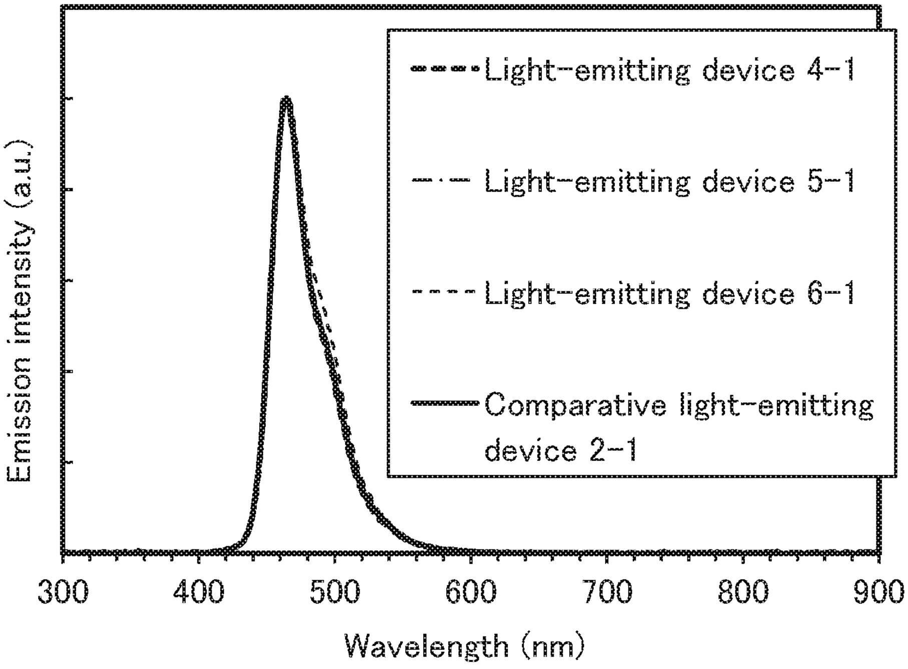
FIG. 63 shows the emission spectra of the light emitting devices 4-1, 5-1, and 6-1, and the comparative light-emitting device 2-1.

FIG. 58 shows the luminance-current density characteristics of the light-emitting devices 4-1, 5-1, and 6-1 and the comparative light-emitting device 2-1. FIG. 59 shows the current efficiency-luminance characteristics thereof. FIG. 60 shows the luminance-voltage characteristics thereof. FIG. 61 shows the current-voltage characteristics thereof. FIG. 62 shows the external quantum efficiency-luminance characteristics thereof. FIG. 63 shows the emission spectra thereof. Table 6 shows the main characteristics of the light-emitting devices at a luminance of about 1000 cd/$m^2$. Luminance, CIE chromaticity, and emission spectra were measured with a spectroradiometer (UR-UL1R manufactured by TOPCON TECHNOHOUSE CORPORATION). The external quantum efficiency was calculated from the luminance and the emission spectrum measured with the spectroradiometer, on the assumption that the light-emitting devices had Lambertian light-distribution characteristics.

TABLE 6

| | Voltage (V) | Current (mA) | Current density (mA/$cm^2$) | Chromaticity x | Chromaticity y | Current efficiency (cd/A) | External quantum efficiency (%) |
|---|---|---|---|---|---|---|---|
| Light-emitting device 4-1 | 3.9 | 0.34 | 8.4 | 0.129 | 0.141 | 12.3 | 11.2 |
| Light-emitting device 4-2 | 4.0 | 0.41 | 10.1 | 0.128 | 0.157 | 10.4 | 8.8 |
| Light-emitting device 4-3 | 4.0 | 0.32 | 8.0 | 0.127 | 0.169 | 11.9 | 9.5 |
| Light-emitting device 4-4 | 4.0 | 0.24 | 5.9 | 0.127 | 0.194 | 11.8 | 8.7 |
| Light-emitting device 5-1 | 4.0 | 0.32 | 8.1 | 0.129 | 0.142 | 13.1 | 11.7 |
| Light-emitting device 5-2 | 4.0 | 0.21 | 5.3 | 0.128 | 0.158 | 12.6 | 10.6 |
| Light-emitting device 5-3 | 4.2 | 0.27 | 6.8 | 0.127 | 0.174 | 13.2 | 10.3 |
| Light-emitting device 5-4 | 4.4 | 0.33 | 8.2 | 0.127 | 0.194 | 12.7 | 9.1 |
| Light-emitting device 6-1 | 4.2 | 0.34 | 8.5 | 0.127 | 0.158 | 14.2 | 11.8 |
| Light-emitting device 6-2 | 4.2 | 0.22 | 5.5 | 0.126 | 0.181 | 13.7 | 10.5 |
| Light-emitting device 6-3 | 4.4 | 0.30 | 7.6 | 0.127 | 0.197 | 13.5 | 9.8 |
| Light-emitting device 6-4 | 4.6 | 0.37 | 9.1 | 0.129 | 0.215 | 12.6 | 8.4 |
| Comparative light-emitting device 2-1 | 3.9 | 0.34 | 8.4 | 0.130 | 0.145 | 10.9 | 9.7 |
| Comparative light-emitting device 2-2 | 4.0 | 0.36 | 9.1 | 0.129 | 0.155 | 11.2 | 9.5 |
| Comparative light-emitting device 2-3 | 4.0 | 0.28 | 7.0 | 0.128 | 0.166 | 11.4 | 9.2 |

TABLE 6-continued

| | Voltage (V) | Current (mA) | Current density ($mA/cm^2$) | Chromaticity x | Chromaticity y | Current efficiency (cd/A) | External quantum efficiency (%) |
|---|---|---|---|---|---|---|---|
| Comparative light-emitting device 2-4 | 4.2 | 0.39 | 9.8 | 9.128 | 0.179 | 11.4 | 8.7 |

FIGS. 58 to 63 show that the light-emitting devices of one embodiment of the present invention are EL devices having higher emission efficiency than the comparative light-emitting devices.

Note that in the case where a plurality of light-emitting devices are fabricated using materials with different refractive indices, even when the thicknesses of the corresponding functional layers are equal among the light-emitting devices, the light-emitting device have different optical distances between electrodes depending on the refractive indices of the materials that are used. Furthermore, deposition by evaporation sometimes has difficulty in precise control of the thicknesses; thus, a light-emitting device fabricated in such a manner might be fabricated to an undesired thickness.

The light-emitting device of this example has a structure in which light is amplified or attenuated by interference caused by the following: a large amount of light reflected on the cathode where aluminum is used, and a certain amount of light reflected due to a difference in refractive index between the electrode material of the anode and the organic compound. The wavelength of light that is amplified or attenuated by the interference depends on the optical distance between electrodes in principle. Although substances have specific emission spectra, light with a wavelength with high emission intensity in the emission spectrum is amplified efficiently, whereas light with a wavelength with low emission intensity is amplified inefficiently; thus, the emission efficiency depends on the wavelength of light that is amplified, i.e., the optical distance between electrodes.

As described above, the light-emitting device in this example is fabricated using materials with different refractive indices. Furthermore, since it is difficult to precisely control the thickness during deposition by evaporation, the optical distances between electrodes are different among the light-emitting devices even when the thicknesses of the corresponding functional layers are equal among the light-emitting devices. The wavelengths of light that is amplified are also different, and thus the emission efficiency cannot be accurately compared in FIG. 63.

Figure 64:
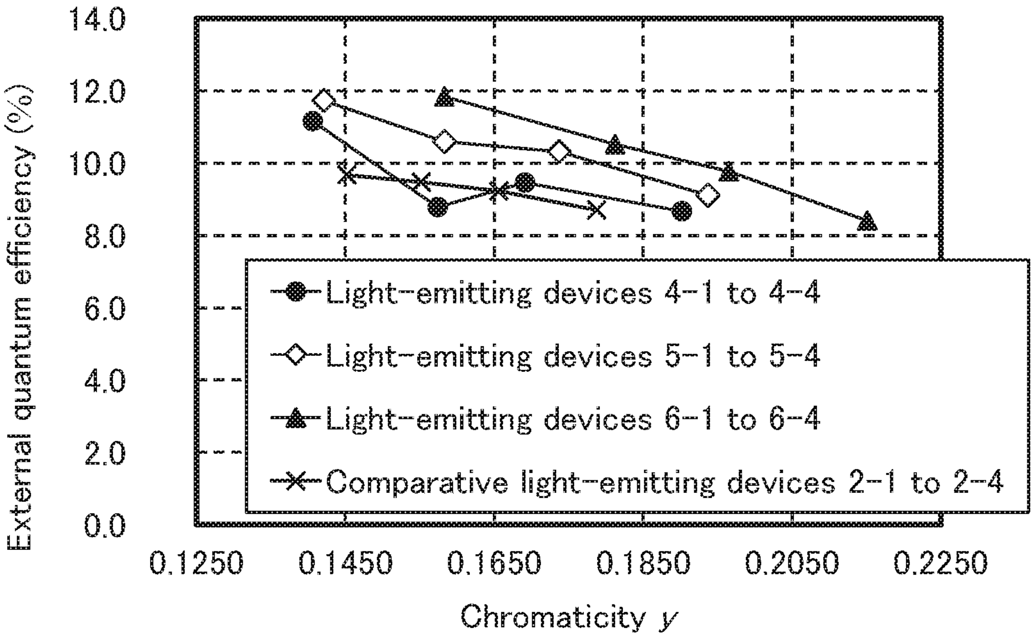
FIG. 64 shows relationships between chromaticity x and external quantum efficiency of light-emitting devices 4-1 to 4-4, light-emitting devices 5-1 to 5-4, light-emitting devices 6-1 to 6-4, and comparative light-emitting devices 2-1 to 2-4.

FIG. 64 shows the relationship between chromaticity y and external quantum efficiency, at a luminance of about 1000 $cd/m^2$, of the light-emitting devices 4-1 to 4-4, the light-emitting devices 5-1 to 5-4, the light-emitting devices 6-1 to 6-4, and the comparative light-emitting devices 2-1 to 2-4. The light-emitting devices 4-1 to 4-4, the light-emitting devices 5-1 to 5-4, the light-emitting devices 6-1 to 6-4, and the comparative light-emitting devices 2-1 to 2-4 differ in the thickness of the EL layer, that is, differ in the optical distance between electrodes and wavelength of amplified light.

The reason why the horizontal axis of FIG. 64 represents the chromaticity y is as follows: the interference effect depends on the optical distance between electrodes, and lights emitted using similar light-emitting substances and subjected to similar interference effects show similar emission spectra; thus, lights with the same chromaticity can be regarded as being subjected to the same interference effect, which indicate the optical distances between the electrodes are the same. In other words, with reference FIG. 64, the improvement in emission efficiency owing to the layer with a low refractive index can be simply examined, without considering the difference in refractive index of the materials and the difference in optical distances derived from deposition.

In FIG. 64, the light-emitting devices 4-1 to 4-4, the light-emitting devices 5-1 to 5-4, and the light-emitting devices 6-1 to 6-4, which use dchPAF, mmtBuBichPAF, and mmtBumTPchPAF, respectively, as a material with a low refractive index, show higher emission efficiency than the comparative light-emitting devices 2-1 to 2-4, which use PCBBiF with a normal refractive index as the organic compound used for the light-emitting device. This shows that using dchPAF, mmtBuBichPAF, and mmtBumTPchPAF enables the light-emitting device to have extremely high emission efficiency.

As shown in Table 6, the light-emitting devices of one embodiment of the present invention are EL devices having favorable driving characteristics with no significant deterioration of driving voltage and the like.

Figure 65:
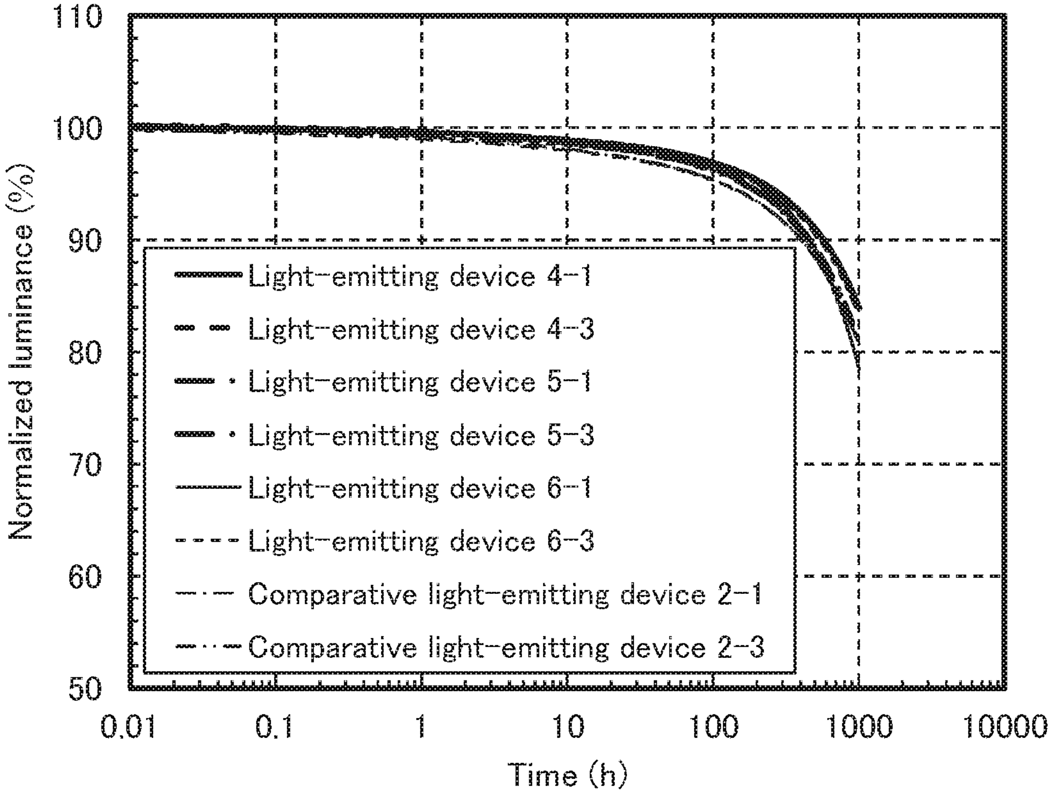
FIG. 65 shows a luminance change with respect to driving time of the light-emitting devices 4-1 and 4-3, the light-emitting devices 5-1 and 5-3, the light-emitting devices 6-1 and 6-3, and the comparative light-emitting devices 2-1 and 2-3.

FIG. 65 shows luminance change with respect to driving time when the light-emitting devices 4-1, 4-3, 5-1, 5-3, 6-1, and 6-3, and the comparative light-emitting devices 2-1 and 2-3 are driven at a constant current of 2 mA (50 $mA/cm^2$). FIG. 65 shows no big difference in luminance change among the EL devices, which reveals that the light-emitting devices of one embodiment of the present invention have high emission efficiency while keeping a long lifetime.

Example 15

In this example, light-emitting devices of one embodiment of the present invention described in the above embodiments and comparative light-emitting devices are described. Structural formulae of organic compounds used in this example are shown below.

[Chemical Formula 88]
(i)
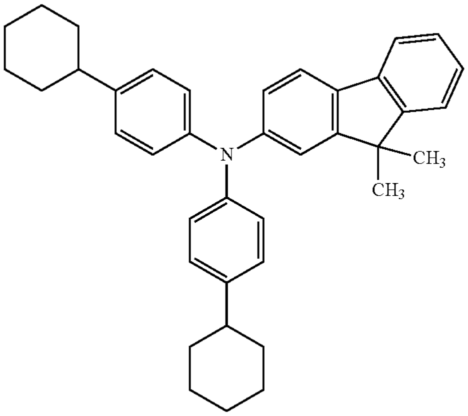
dchPAF
(viii)
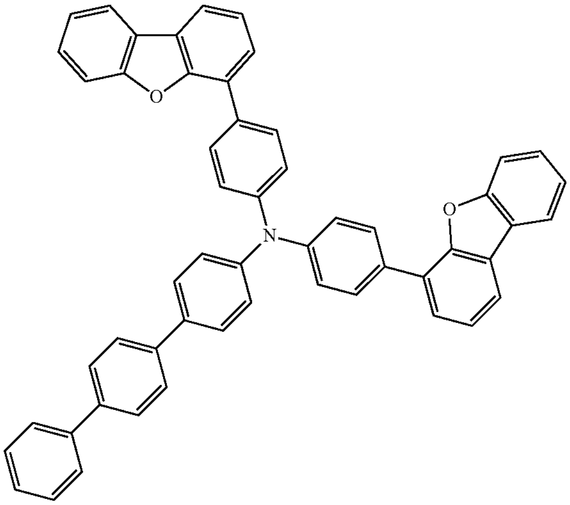
DBfBB1TP
(ix)
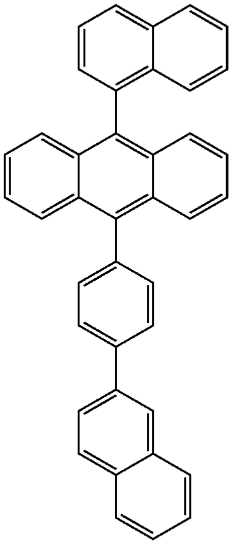
αN-βNPAnth
(xiii)
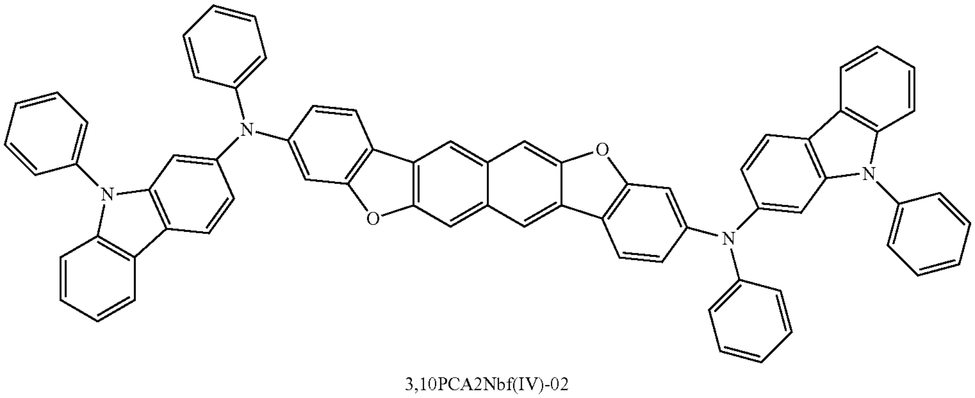
3,10PCA2Nbf(IV)-02

-continued (iii)

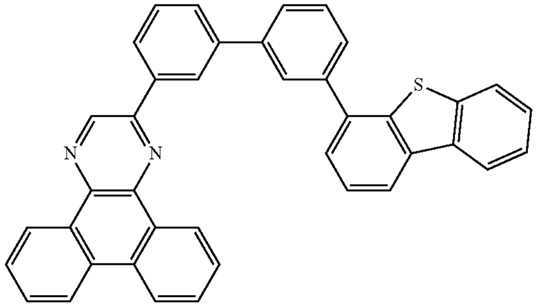

2mDBTBPDBq-II (v)

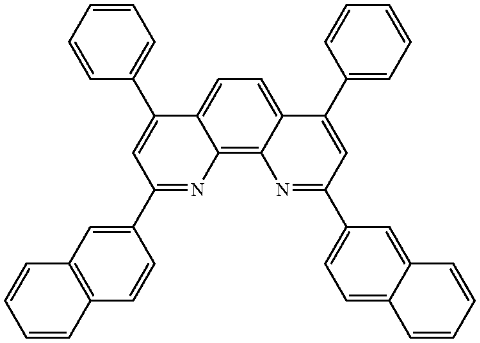

NBPhen (ii)

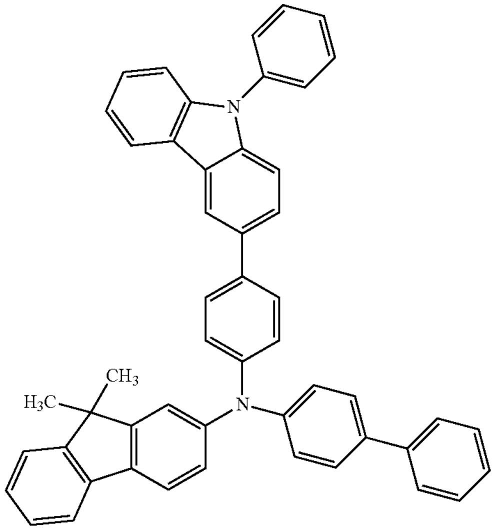

PCBBiF (xiv)

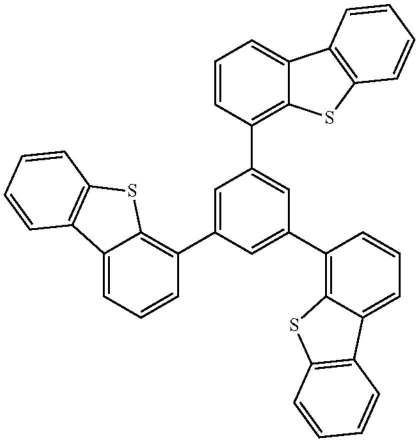

DBT3P-II (Fabrication Method of Light-Emitting Device 7-0)

First, as a reflective electrode, an alloy film of silver (Ag), palladium (Pd), and copper (Cu), i.e., an Ag—Pd—Cu (APC) film, was formed over a glass substrate to a thickness of 100 nm by a sputtering method, and then, as a transparent electrode, indium tin oxide containing silicon oxide (ITSO) was formed to a thickness of 85 nm by a sputtering method, whereby the first electrode 101 was formed. The electrode area was to 4 $mm^2$ (2 mm×2 mm).

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N,N-bis(4-cyclohexylphenyl)-9,9, -dimethyl-9H-fluoren-2-amine (abbreviation: dchPAF) represented by the structural formula (i) and ALD-MP001Q (produced by Analysis Atelier Corporation, material serial No. 1S20180314) were deposited to a thickness of 10 nm by co-evaporation over the first electrode 101 using a resistance-heating method such that the weight ratio of dchPAF to ALD-MP001Q was 1:0.1, whereby the hole-injection layer 111 was formed. Note that ALD-MP001Q is an organic compound having an acceptor property.

Subsequently, over the hole-injection layer 111, dchPAF was deposited to a thickness of 30 nm by evaporation, and then N,N-bis[4-(dibenzofuran-4-yl)phenyl]-4-amino-p-terphenyl (abbreviation: DBfBB1TP) represented by the structural formula (viii) was deposited to a thickness of 10 nm by evaporation, whereby the hole-transport layer 112 was formed.

Then, 9-(1-naphthyl)-10-[4-(2-naphthyl)phenyl]anthracene (abbreviation: αN-βNPAnth) represented by the structural formula (ix) and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by the structural formula (xiii) were deposited to a thickness of 25 nm by co-evaporation such that the weight ratio of αN-βNPAnth to 3,10PCA2Nbf(IV)-02 was 1:0.015, whereby the light-emitting layer 113 was formed.

Then, over the light-emitting layer 113, 2-[3'-(dibenzothiophen-4-yl)biphenyl-3-yl]dibenzo[f,h]quinoxaline (abbreviation: 2mDBTBPDBq-II) represented by the structural formula (iii) was deposited to a thickness of 5 nm by evaporation, and then 2,9-di(2-naphthyl)-4,7-diphenyl-1,10-phenanthroline (abbreviation: NBPhen) represented by the structural formula (v) was deposited to a thickness of 15 nm by evaporation, whereby the electron-transport layer 114 was formed.

After the electron-transport layer 114 was formed, lithium fluoride (LiF) was deposited to a thickness of 1 nm by evaporation to form the electron-injection layer 115, and then silver (Ag) and magnesium (Mg) were deposited to a thickness of 15 nm by evaporation such that the volume ratio of Ag to Mg was 1:0.1 to form the second electrode 102, whereby the light-emitting device 7-0 was fabricated. The second electrode 102 is a transflective electrode having a function of reflecting light and a function of transmitting light; thus, the light-emitting device of this example is a top-emission device in which light is extracted through the second electrode 102. Over the second electrode 102, 1,3,5-tri(dibenzothiophen-4-yl)-benzene (abbreviation: DBT3P-II) represented by the structural formula (xiv) was deposited to a thickness of 70 nm by evaporation so that outcoupling efficiency can be improved.

(Fabrication Method of Light-Emitting Devices 7-1 to 7-12)

The light-emitting device 7-1 was fabricated in a manner similar to that for the light-emitting device 7-0 except that the thickness of dchPAF in the hole-transport layer 112 was 20 nm. The light-emitting device 7-2 was fabricated in a manner similar to that for the light-emitting device 7-1 except that the thickness of NBPhen in the electron-transport layer 114 was 20 nm. The light-emitting device 7-3 was fabricated in a manner similar to that for the light-emitting device 7-1 except that the thickness of NBPhen in the electron-transport layer 114 was 25 nm. The light-emitting device 7-4 was fabricated in a manner similar to that for the light-emitting device 7-0 except that the thickness of dchPAF in the hole-transport layer 112 was 25 nm. The light-emitting device 7-5 was fabricated in a manner similar to that for the light-emitting device 7-4 except that the thickness of NBPhen in the electron-transport layer 114 was 20 nm. The light-emitting device 7-6 was fabricated in a manner similar to that for the light-emitting device 7-4 except that the thickness of NBPhen in the electron-transport layer 114 was 25 nm. The light-emitting device 7-7 was fabricated in a manner similar to that for the light-emitting device 7-0. The light-emitting device 7-8 was fabricated in a manner similar to that for the light-emitting device 7-7 except that the thickness of NBPhen in the electron-transport layer 114 was 20 nm. The light-emitting device 7-9 was fabricated in a manner similar to that for the light-emitting device 7-7 except that the thickness of NBPhen in the electron-transport layer 114 was 25 nm. The light-emitting device 7-10 was fabricated in a manner similar to that for the light-emitting device 7-0 except that the thickness of dchPAF in the hole-transport layer 112 was 35 nm. The light-emitting device 7-11 was fabricated in a manner similar to that for the light-emitting device 7-10 except that the thickness of NBPhen in the electron-transport layer 114 was 20 nm. The light-emitting device 7-12 was fabricated in a manner similar to that for the light-emitting device 7-10 except that the thickness of NBPhen in the electron-transport layer 114 was 25 nm.

(Fabrication Method of Comparative Light-Emitting Devices 3-0 to 3-12)

The comparative light-emitting device 3-0 was fabricated in a manner similar to that for the light-emitting device 7-0 except that dchPAF used in the hole-injection layer 111 and the hole-transport layer 112 was replaced with N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by the structural formula (ii). The comparative light-emitting device 3-1 was fabricated in a manner similar to that for the comparative light-emitting device 3-0 except that the thickness of PCBBiF in the hole-transport layer 112 was 20 nm. The comparative light-emitting device 3-2 was fabricated in a manner similar to that for the comparative light-emitting device 3-1 except that the thickness of NBPhen in the electron-transport layer 114 was 20 nm. The comparative light-emitting device 3-3 was fabricated in a manner similar to that for the comparative light-emitting device 3-1 except that the thickness of NBPhen in the electron-transport layer 114 was 25 nm. The comparative light-emitting device 3-4 was fabricated in a manner similar to that for the comparative light-emitting device 3-0 except that the thickness of PCBBiF in the hole-transport layer 112 was 25 nm. The comparative light-emitting device 3-5 was fabricated in a manner similar to that for the comparative light-emitting device 3-4 except that the thickness of NBPhen in the electron-transport layer 114 was 20 nm. The comparative light-emitting device 3-6 was fabricated in a manner similar to that for the comparative light-emitting device 3-4 except that the thickness of NBPhen in the electron-transport layer 114 was 25 nm. The comparative light-emitting device 3-7 was fabricated in a manner similar to that for the comparative light-emitting device 3-0. The comparative light-emitting device 3-8 was fabricated in a manner similar to that for the comparative light-emitting device 3-7 except that the thickness of NBPhen in the electron-transport layer 114 was 20 nm. The comparative light-emitting device 3-9 was fabricated in a manner similar to that for the comparative light-emitting device 3-7 except that the thickness of NBPhen in the electron-transport layer 114 was 25 nm. The comparative light-emitting device 3-10 was fabricated in a manner similar to that for the comparative light-emitting device 3-0 except that the thickness of PCBBiF in the hole-transport layer 112 was 35 nm. The comparative light-emitting device 3-11 was fabricated in a manner similar to that for the comparative light-emitting device 3-10 except that the thickness of NBPhen in the electron-transport layer 114 was 20 nm. The comparative light-emitting device 3-12 was fabricated in a manner similar to that for the comparative light-emitting device 3-10 except that the thickness of NBPhen in the electron-transport layer 114 was 25 nm.

The device structures of the light-emitting devices 7-0 to 7-12 and the comparative light-emitting devices 3-0 to 3-12 are listed in the following table.

TABLE 7

| | | Light-emitting device 7-X | Comparative light-emitting device 3-X |
|---|---|---|---|
| Electron-injection layer | 1 nm | Lif | |
| Electron-transport layer | *6 | NBPhen | |
| | 5 nm | 2mDBTBPDBq-II | |
| Light-emitting layer | 25 nm | αN-βNPAnth:3,10PCA2Nbf(IV)-02 (1:0.015) | |
| Hole-transport layer | 10 nm | DBfBB1TP | |
| | *5 | dchPAF | PCBBiF |
| Hole-injection layer | 10 nm | dchPAF:ALD-MP001Q (1:0.1) | PCBBif: ALD-MP001Q (1:0.1) |

*5 X = 1 to 3: 20 nm
X = 4 to 6: 25 nm
X = 0, 7 to 9: 30 nm
X = 10 to 12: 35 nm
*6 X = 0, 1, 4, 7, 10: 15 nm
X = 2, 5, 8, 11: 20 nm
X = 3, 6, 9, 12: 25 nm

The light-emitting devices and the comparative light-emitting devices were sealed using a glass substrate in a glove box containing a nitrogen atmosphere so as not to be exposed to the air (a sealing material was applied to surround the element and UV treatment was performed at the time of sealing). Then, the initial characteristics and reliability of the light-emitting devices were measured. Note that the sealed glass substrate was not subjected to particular treatment for improving outcoupling efficiency.

Figure 66:
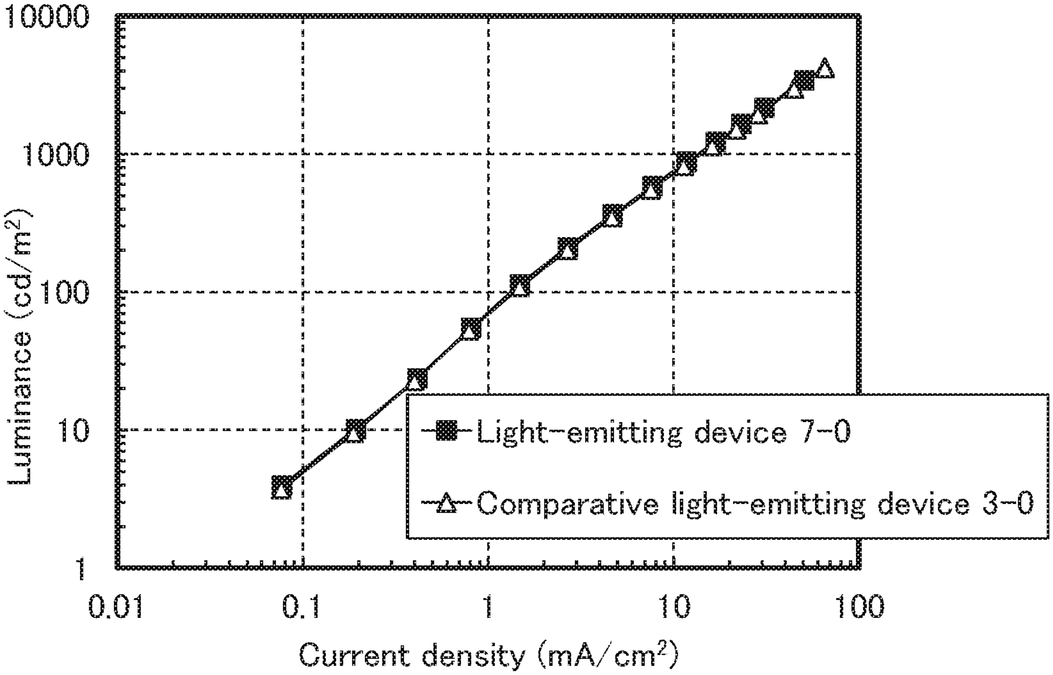
FIG. 66 shows the luminance-current density characteristics of a light-emitting device 7-0 and a comparative light-emitting device 3-0.
Figure 67:
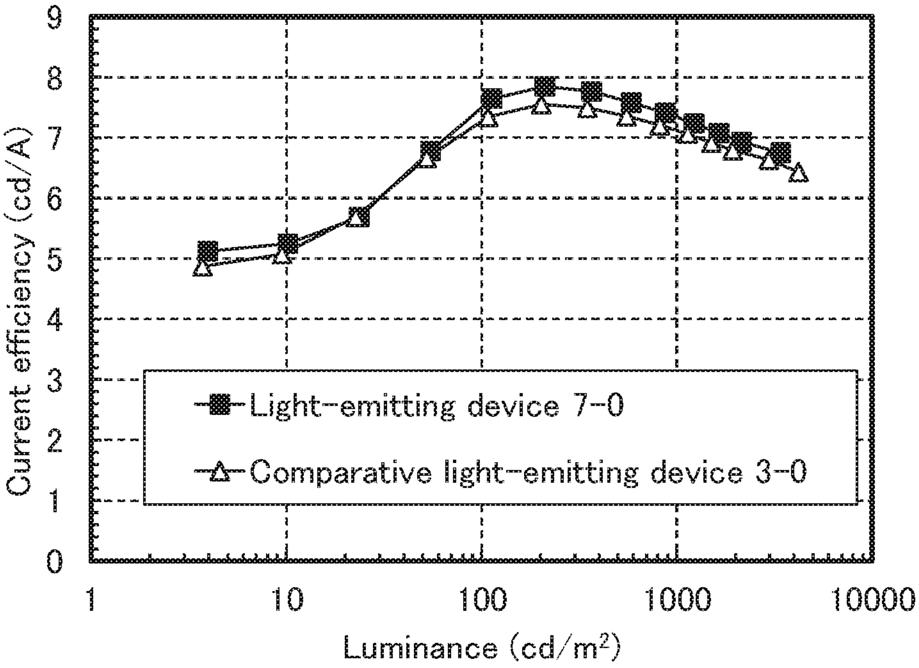
FIG. 67 shows the current efficiency-luminance characteristics of the light-emitting device 7-0 and the comparative light-emitting device 3-0.
Figure 68:
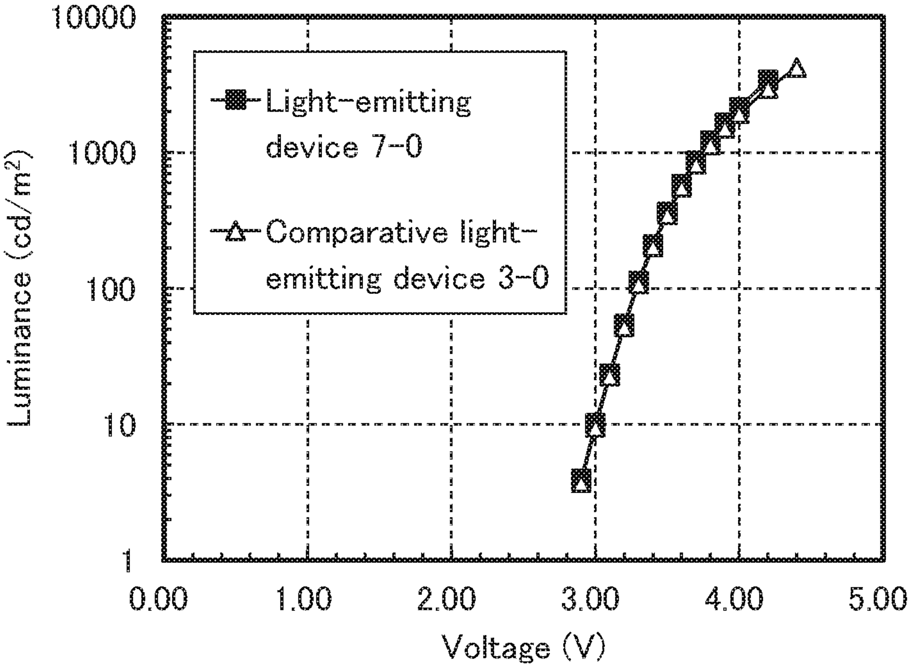
FIG. 68 shows the luminance-voltage characteristics of the light-emitting device 7-0 and the comparative light-emitting device 3-0.
Figure 69:
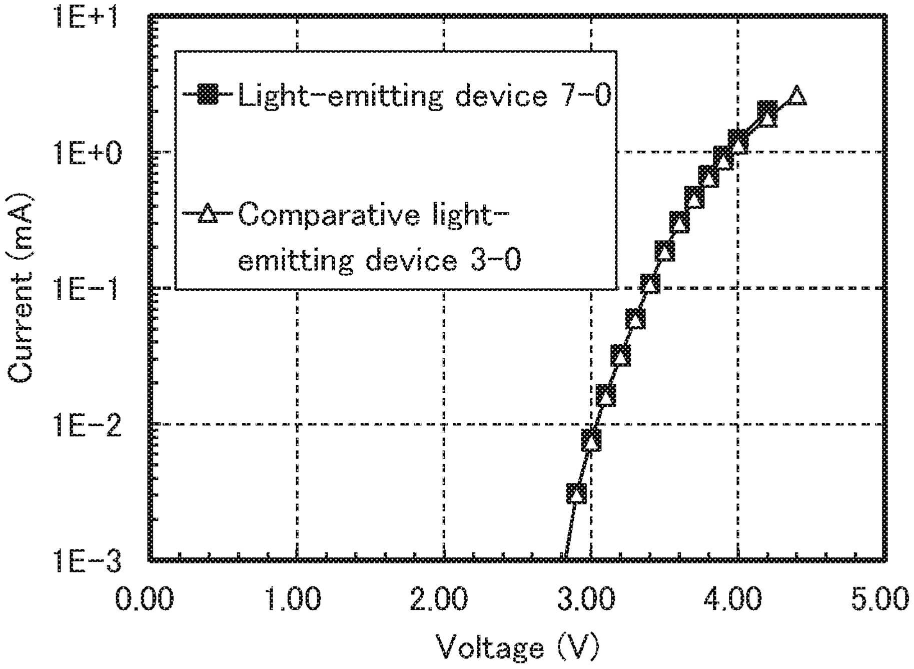
FIG. 69 shows the current-voltage characteristics of the light-emitting device 7-0 and the comparative light-emitting device 3-0.
Figure 70:
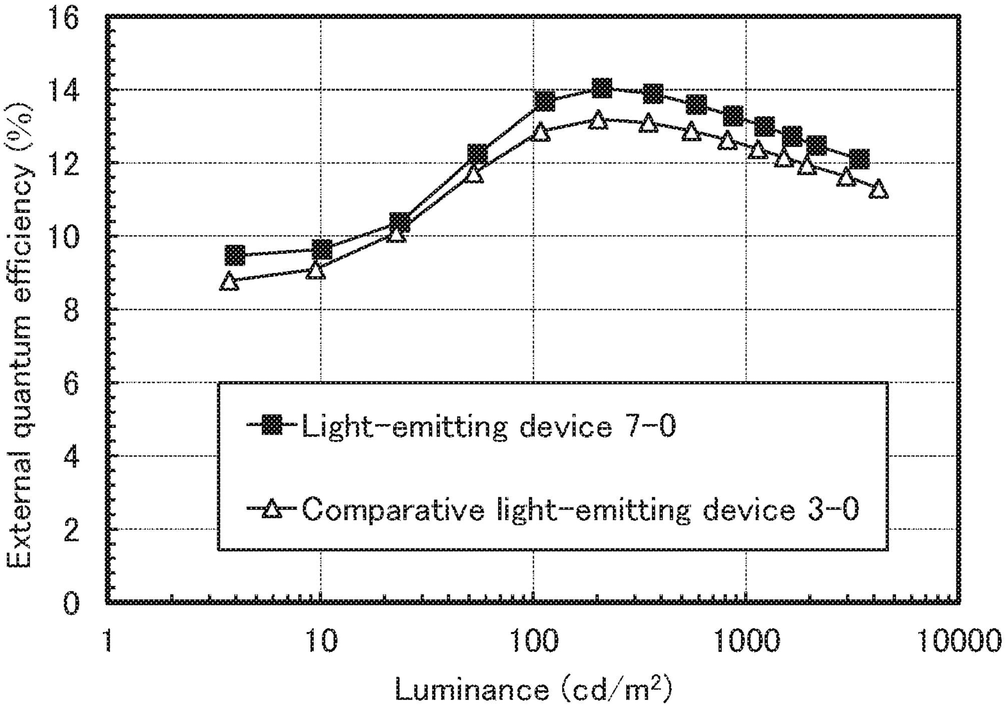
FIG. 70 shows the external quantum efficiency-luminance characteristics of the light-emitting device 7-0 and the comparative light-emitting device 3-0.
Figure 71:
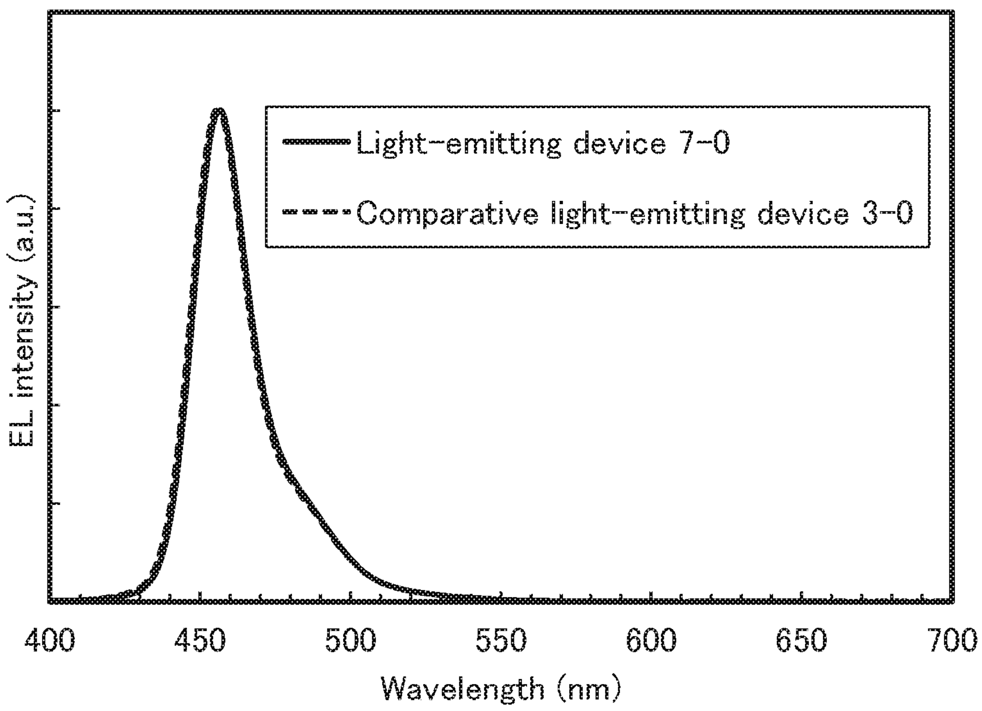
FIG. 71 shows the emission spectra of the light-emitting device 7-0 and the comparative light-emitting device 3-0.

FIG. 66 shows the luminance-current density characteristics of the light-emitting device 7-0 and the comparative light-emitting device 3-0. FIG. 67 shows the current efficiency-luminance characteristics thereof. FIG. 68 shows the luminance-voltage characteristics thereof. FIG. 69 shows the current-voltage characteristics thereof. FIG. 70 shows the external quantum efficiency-luminance characteristics thereof. FIG. 71 shows the emission spectra thereof. Table 8 shows the main characteristics of the light-emitting device 7-0 and the comparative light-emitting device 3-0 at a luminance of about 1000 cd/m$^2$. Luminance, CIE chromaticity, and emission spectra were measured with a spectroradiometer (UR-UL1R manufactured by TOPCON TECHNOHOUSE CORPORATION). The external quantum efficiency was calculated from the luminance and the emission spectrum measured with the spectroradiometer, on the assumption that the light-emitting devices had Lambertian light-distribution characteristics.

TABLE 8

| | Voltage (V) | Current (mA) | Current density (mA/cm$^2$) | Chromaticity x | Chromaticity y | Current efficiency (cd/A) | External quantum efficiency (%) | BI (cd/A/y) |
|---|---|---|---|---|---|---|---|---|
| Light-emitting device 7-0 | 3.7 | 0.47 | 11.8 | 0.141 | 0.055 | 7.4 | 13.3 | 135 |
| Comparative light-emitting device 3-0 | 3.8 | 0.65 | 16.1 | 0.141 | 0.057 | 7.1 | 12.4 | 125 |

FIGS. 66 to 71 and Table 8 show that the light-emitting devices of one embodiment of the present invention, which use a material with a low refractive index, are EL devices with higher external light-emission efficiency and a more favorable blue index (BI) than the comparative light-emitting devices.

Note that the blue index (BI) is a value obtained by dividing current efficiency (cd/A) by chromaticity y, and is one of the indicators of characteristics of blue light emission. As the chromaticity y is smaller, the color purity of blue light emission tends to be higher. With high color purity, a wide range of blue can be expressed even with a small number of luminance components; thus, using blue light emission with high color purity reduces the luminance needed for expressing blue, leading to lower power consumption. Thus, BI that is based on chromaticity y, which is one of the indicators of color purity of blue, is suitably used as a mean for showing efficiency of blue light emission. The light-emitting device with higher BI can be regarded as a blue light emitting device having more favorable characteristics for a display.

Table 9 shows the characteristics of the light-emitting devices 7-1 to 7-12 and Table 10 shows the characteristics of the comparative light-emitting devices 3-1 to 3-12. The characteristics were obtained when a current of 0.2 mA (5 mA/cm$^2$) was applied. The light-emitting devices 7-1 to 7-12 and the comparative light-emitting devices 3-1 to 3-12 are different in the thickness of the hole-transport layer 112 or the electron-transport layer 114, that is, optical distance between electrodes, and thus have difference also in wavelength of light that is amplified.

TABLE 9

| Light-emitting devices | | | | | | | | |
|---|---|---|---|---|---|---|---|---|
| | Voltage (V) | Current (mA) | Current density (mA/cm$^2$) | Chromaticity x | Chromaticity y | External quantum efficiency (%) | Current efficiency (cd/A) | BI (cd/A/y) |
| 7-1 | 3.5 | 0.20 | 5.0 | 0.144 | 0.049 | 8.7 | 4.5 | 91 |
| 7-2 | 3.5 | 0.20 | 5.0 | 0.144 | 0.049 | 10.9 | 5.5 | 114 |
| 7-3 | 3.6 | 0.20 | 5.0 | 0.142 | 0.050 | 12.4 | 6.4 | 129 |
| 7-4 | 3.5 | 0.20 | 5.0 | 0.143 | 0.051 | 11.6 | 6.2 | 121 |
| 7-5 | 3.5 | 0.20 | 5.0 | 0.142 | 0.053 | 13.6 | 7.4 | 140 |
| 7-6 | 3.6 | 0.20 | 5.0 | 0.139 | 0.057 | 14.5 | 8.3 | 145 |
| 7-7 | 3.5 | 0.20 | 5.0 | 0.141 | 0.055 | 13.8 | 7.7 | 141 |
| 7-8 | 3.6 | 0.20 | 5.0 | 0.139 | 0.060 | 15.3 | 9.0 | 151 |
| 7-9 | 3.6 | 0.20 | 5.0 | 0.136 | 0.068 | 15.4 | 9.9 | 146 |
| 7-10 | 3.5 | 0.20 | 5.0 | 0.139 | 0.061 | 15.1 | 9.1 | 150 |
| 7-11 | 3.6 | 0.20 | 5.0 | 0.135 | 0.070 | 15.8 | 10.4 | 149 |
| 7-12 | 3.6 | 0.20 | 5.0 | 0.131 | 0.083 | 15.3 | 11.2 | 135 |

TABLE 10

| Comparative light-emitting devices | | | | | | | | |
|---|---|---|---|---|---|---|---|---|
| | Voltage (V) | Current (mA) | Current density (mA/cm$^2$) | Chromaticity x | Chromaticity y | External quantum efficiency (%) | Current efficiency (cd/A) | BI (cd/A/y) |
| 3-1 | 3.5 | 0.20 | 5.0 | 0.144 | 0.049 | 8.7 | 4.5 | 91 |
| 3-2 | 3.5 | 0.20 | 5.0 | 0.143 | 0.049 | 10.9 | 5.6 | 113 |
| 3-3 | 3.6 | 0.20 | 5.0 | 0.142 | 0.051 | 12.3 | 6.5 | 126 |
| 3-4 | 3.5 | 0.20 | 5.0 | 0.143 | 0.052 | 11.5 | 6.1 | 119 |
| 3-5 | 3.5 | 0.20 | 5.0 | 0.141 | 0.055 | 13.3 | 7.4 | 135 |
| 3-6 | 3.6 | 0.20 | 5.0 | 0.138 | 0.060 | 14.0 | 8.3 | 137 |
| 3-7 | 3.5 | 0.20 | 5.0 | 0.140 | 0.057 | 13.0 | 7.5 | 132 |
| 3-8 | 3.5 | 0.20 | 5.0 | 0.137 | 0.063 | 14.2 | 8.7 | 138 |
| 3-9 | 3.6 | 0.20 | 5.0 | 0.133 | 0.074 | 14.1 | 9.6 | 130 |
| 3-10 | 3.5 | 0.20 | 5.0 | 0.137 | 0.066 | 13.8 | 8.7 | 133 |
| 3-11 | 3.5 | 0.20 | 5.0 | 0.133 | 0.077 | 14.2 | 9.9 | 129 |
| 3-12 | 3.6 | 0.20 | 5.0 | 0.128 | 0.093 | 13.6 | 10.7 | 115 |

Figure 72:
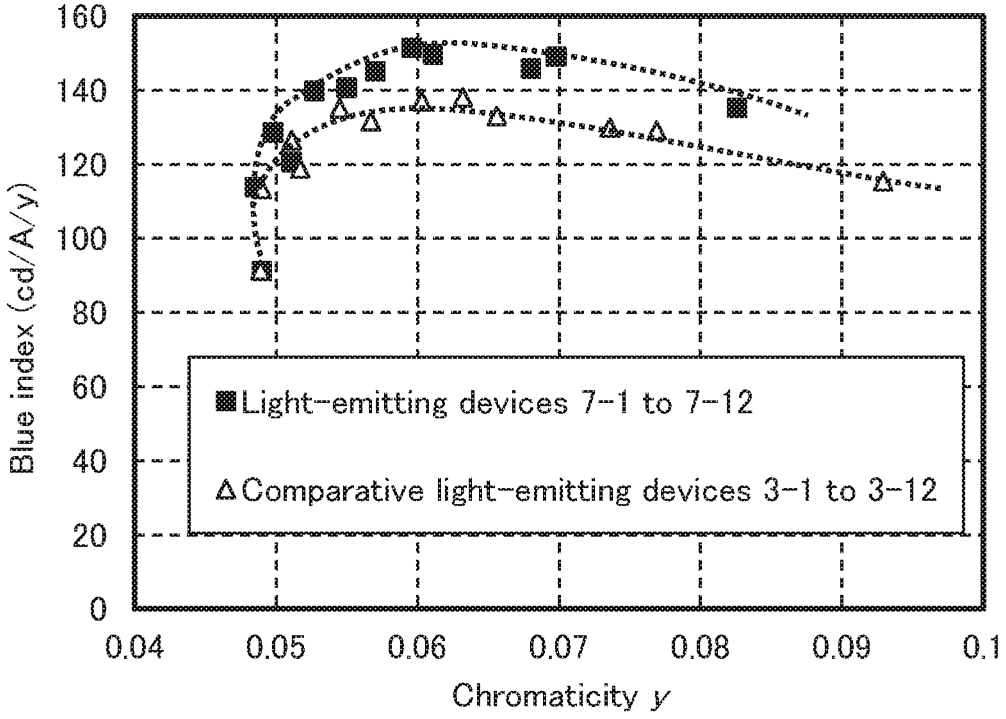
FIG. 72 shows the relationship between chromaticity y and BI of light-emitting devices 7-1 to 7-12 and comparative light-emitting devices 3-1 to 3-12.

Table 9 and Table 10 show that the light-emitting devices of one embodiment of the present invention, which use a material with a low refractive index, have higher external quantum efficiency and a more favorable blue index (BI) than the comparative light-emitting devices, which use a material with a normal refractive index. In addition, each table show that the efficiency and BI change depending on the optical distance (i.e., wavelength of light that is amplified and chromaticity) of the light-emitting device. Since the intensity of blue light emission required for a display depends on the chromaticity, comparison of BI at the same chromaticity is effective. FIG. 72 shows a change in BI with respect to the chromaticity y.

FIG. 72 shows that the light-emitting devices of one embodiment of the present invention have more favorable BI than the comparative light-emitting devices that exhibit the same chromaticity.

Figure 73:
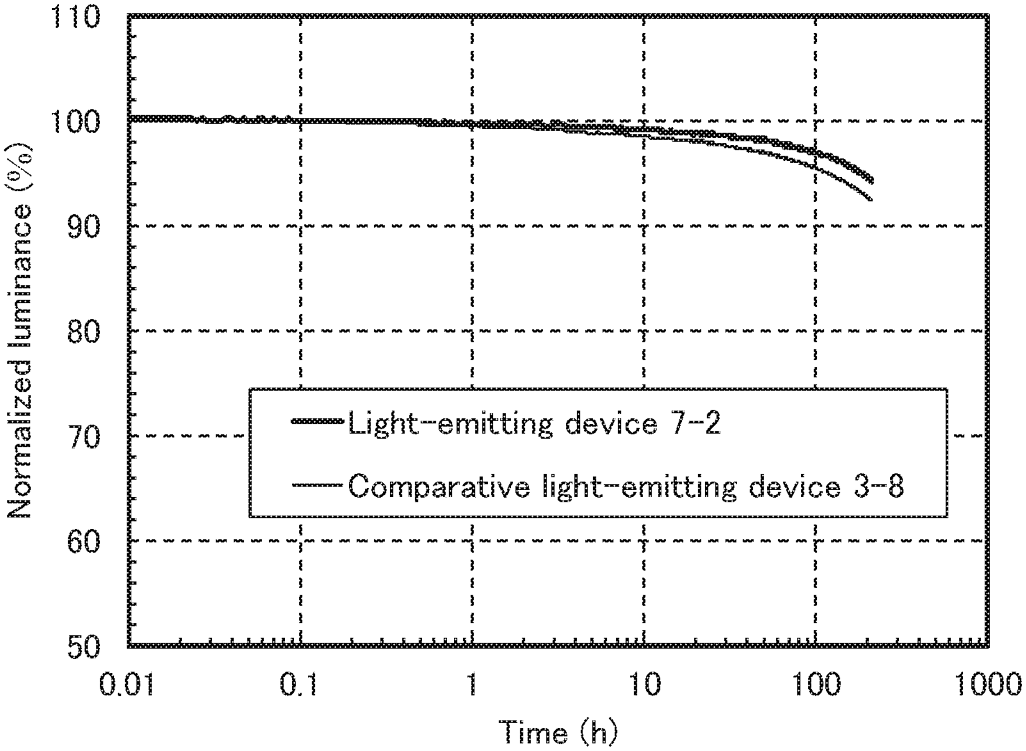
FIG. 73 shows a luminance change with respect to driving time of the light-emitting device 7-2 and the comparative light-emitting device 3-8.

Next, FIG. 73 shows luminance change with respect to driving time when the light-emitting device 7-2 and the comparative light-emitting device 3-8 are driven at a constant current with a current density of 50 mA/cm$^2$. FIG. 73 shows that the light-emitting device of one embodiment of the present invention has high emission efficiency while keeping a long lifetime.

Example 16

In this example, light-emitting devices of one embodiment of the present invention described in the above embodiments and comparative light-emitting devices are described. Structural formulae of organic compounds used in this example are shown below.

[Chemical Formula 89]

(i)

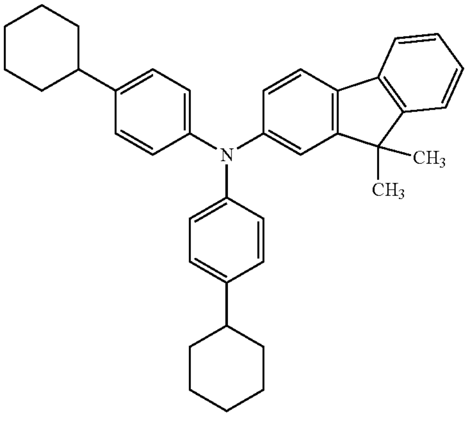

dchPAF (viii)

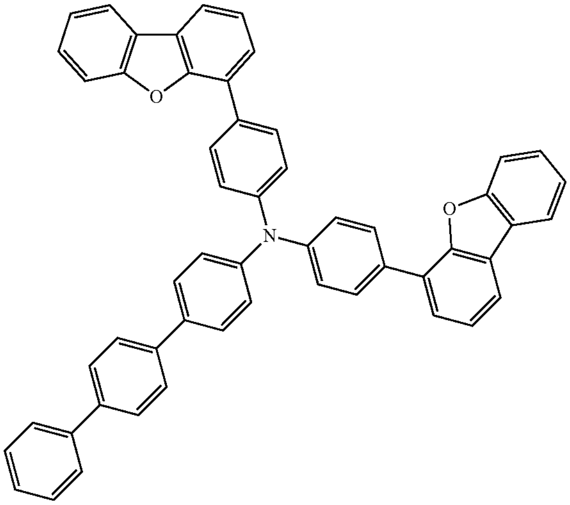

DBfBB1TP (ix)

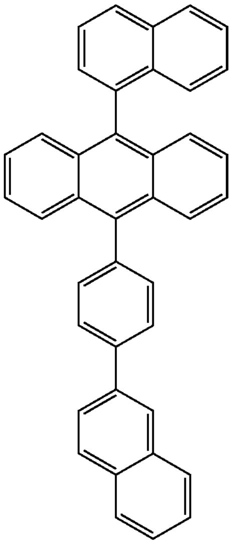

αN-βNPAnth

-continued (xiii)

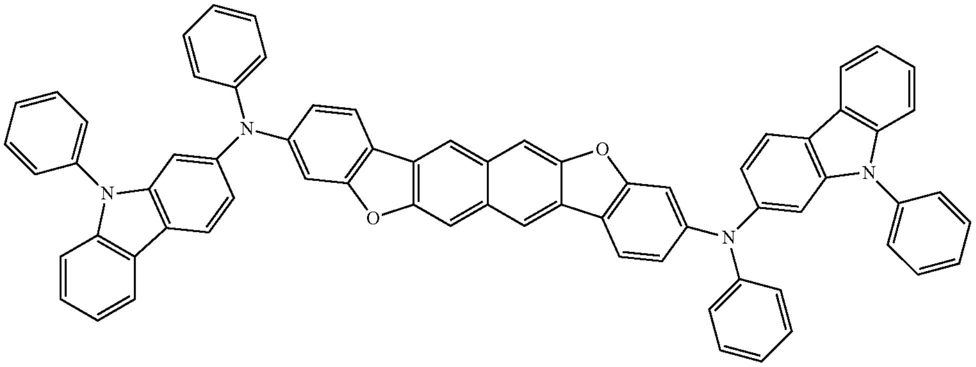

3,10PCA2Nbf(IV)-02

(iii)

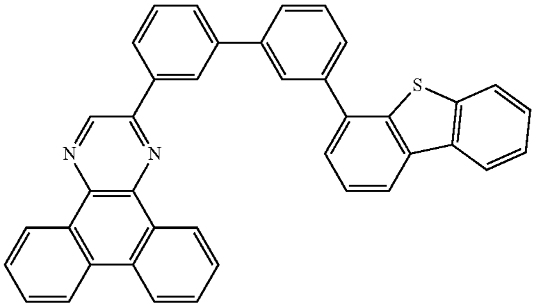

2mDBTBPDBq-II (xv)

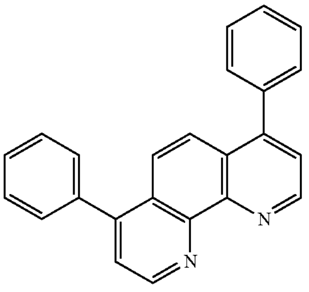

BPhen (ii)

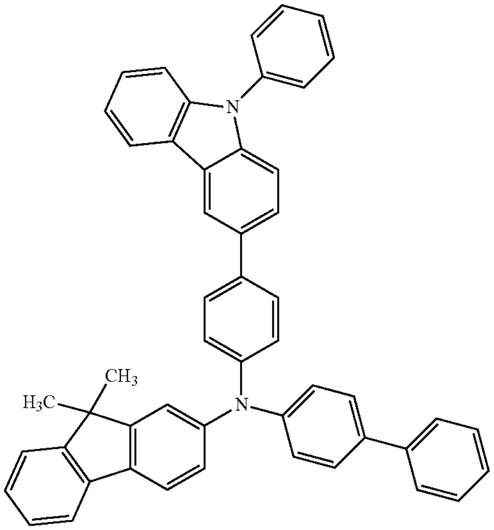

PCBBiF (xiv)

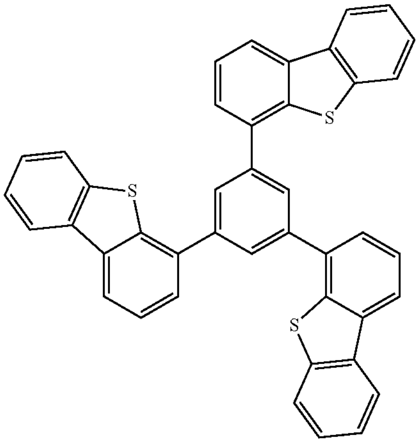

DBT3P-II (Fabrication Method of a Light-Emitting Device 8-0)

First, as a reflective electrode, an alloy film of silver (Ag), palladium (Pd), and copper (Cu), i.e., an Ag—Pd—Cu (APC) film, was formed over a glass substrate to a thickness of 100 nm by a sputtering method, and then, as a transparent electrode, indium tin oxide containing silicon oxide (ITSO) was formed to a thickness of 85 nm by a sputtering method, whereby the first electrode 101 was formed. The electrode area was 4 $mm^2$ (2 mm×2 mm).

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N,N-bis(4-cyclohexylphenyl)-9,9, -dimethyl-9H-fluoren-2-amine (abbreviation: dchPAF) represented by the structural formula (i) and ALD-MP001Q (produced by Analysis Atelier Corporation, material serial No. 1S20180314) were deposited by co-evaporation to a thickness of 10 nm over the first electrode 101 using a resistance-heating method such that the weight ratio of dchPAF to ALD-MP001Q was 1:0.1, whereby the hole-injection layer 111 was formed. Note that ALD-MP001Q is an organic compound having an acceptor property.

Subsequently, over the hole-injection layer 111, dchPAF was deposited to a thickness of 30 nm by evaporation, and then N,N-bis[4-(dibenzofuran-4-yl)phenyl]-4-amino-p-terphenyl (abbreviation: DBfBB1TP) represented by the structural formula (viii) was deposited to a thickness of 10 nm by evaporation, whereby the hole-transport layer 112 was formed.

Then, 9-(1-naphthyl)-10-[4-(2-naphthyl)phenyl]anthracene (abbreviation: αN-βNPAnth) represented by the structural formula (ix) and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by the structural formula (xiii) were deposited to a thickness of 25 nm by co-evaporation such that the weight ratio of αN-βNPAnth to 3,10PCA2Nbf(IV)-02 was 1:0.015, whereby the light-emitting layer 113 was formed.

Then, over the light-emitting layer 113, 2-[3'-(dibenzothiophen-4-yl)biphenyl-3-yl]dibenzo[f,h]quinoxaline (abbreviation: 2mDBTBPDBq-II) represented by the structural formula (iii) was deposited by evaporation to a thickness of 5 nm, and then 2,9-di(2-naphthyl)-4,7-diphenyl-1,10-phenanthroline (abbreviation: NBPhen) represented by the structural formula (v) was deposited by evaporation to a thickness of 5 nm, whereby the electron-transport layer 114 was formed.

After the electron-transport layer 114 was formed, bathophenanthroline (abbreviation: BPhen) represented by the structural formula (xv) and lithium fluoride (LiF) were deposited by co-evaporation to a thickness of 15 nm such that the volume ratio of BPhen to LiF was 0.25:0.75, whereby the electron-injection layer 115 was formed.

Lastly, silver (Ag) and magnesium (Mg) were deposited by evaporation to a thickness of 15 nm such that the volume ratio of Ag to Mg was 1:0.1 to form the second electrode 102, whereby the light-emitting device 8-0 was fabricated. The second electrode 102 is a transflective electrode having a function of reflecting light and a function of transmitting light; thus, the light-emitting device of this example is a top-emission device in which light is extracted through the second electrode 102. Over the second electrode 102, 1,3,5-tri(dibenzothiophen-4-yl)-benzene (abbreviation: DBT3P-II) represented by the structural formula (xiv) was deposited by evaporation to a thickness of 70 nm so that outcoupling efficiency can be improved.

Note that a co-evaporation film in which BPhen and LiF were mixed such that the volume ratio of BPhen to LiF was 0.25:0.75 was used as the electron-injection layer 115 of the light-emitting device 8-0, and the co-evaporation film has an extremely low refractive index because of a large amount of LiF contained therein. That is, it can be said that the light-emitting device 8-0 has the EL layer 103 including layers with a low refractive index on both the anode side and the cathode side.

(Fabrication Method of Light-Emitting Devices 8-1 to 8-12)

The light-emitting device 8-1 was fabricated in a manner similar to that for the light-emitting device 8-0 except that the thickness of dchPAF in the hole-transport layer 112 was 20 nm. The light-emitting device 8-2 was fabricated in a manner similar to that for the light-emitting device 8-1 except that the thickness of the co-evaporation film of BPhen and LiF in the electron-transport layer 114 was 20 nm. The light-emitting device 8-3 was fabricated in a manner similar to that for the light-emitting device 8-1 except that the thickness of the co-evaporation film of BPhen and LiF in the electron-transport layer 114 was 25 nm. The light-emitting device 8-4 was fabricated in a manner similar to that for the light-emitting device 8-0 except that the thickness of dchPAF in the hole-transport layer 112 was 25 nm. The light-emitting device 8-5 was fabricated in a manner similar to that for the light-emitting device 8-4 except that the thickness of the co-evaporation film of BPhen and LiF in the electron-transport layer 114 was 20 nm. The light-emitting device 8-6 was fabricated in a manner similar to that for the light-emitting device 8-4 except that the thickness of the co-evaporation film of BPhen and LiF in the electron-transport layer 114 was 25 nm. The light-emitting device 8-7 was fabricated in a manner similar to that for the light-emitting device 8-0. The light-emitting device 8-8 was fabricated in a manner similar to that for the light-emitting device 8-7 except that the thickness of the co-evaporation film of BPhen and LiF in the electron-transport layer 114 was 20 nm. The light-emitting device 8-9 was fabricated in a manner similar to that for the light-emitting device 8-7 except that the thickness of the co-evaporation film of BPhen and LiF in the electron-transport layer 114 was 25 nm. The light-emitting device 8-10 was fabricated in a manner similar to that for the light-emitting device 8-0 of except that the thickness of dchPAF in the hole-transport layer 112 was 35 nm. The light-emitting device 8-11 was fabricated in a manner similar to that for the light-emitting device 8-10 except that the thickness of the co-evaporation film of BPhen and LiF in the electron-transport layer 114 was 20 nm. The light-emitting device 8-12 was fabricated in a manner similar to that for the light-emitting device 8-10 except that the thickness of the co-evaporation film of BPhen and LiF in the electron-transport layer 114 was 25 nm.

(Fabrication Method of Comparative Light-Emitting Devices 3-0 to 3-12)

The comparative light-emitting device 3-0 was fabricated in a manner similar to that for the light-emitting device 8-0 except that dchPAF in the hole-injection layer 111 and the hole-transport layer 112 was replaced with N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by the structural formula (ii), the thickness of NBPhen of the electron-transport layer 114 was 15 nm, and LiF was deposited to a thickness of 1 nm to form the electron-injection layer 115. That is, the comparative light-emitting device 3-0 does not include a layer with a low refractive index. The comparative light-emitting device 3-1 was fabricated in a manner similar to that for the comparative light-emitting device 3-0 except that the thickness of PCBBiF in the hole-transport layer 112 was 20 nm. The comparative light-emitting device 3-2 was fabricated in a manner similar to that for the comparative light-emitting device 3-1 except that the thickness of NBPhen in the electron-transport layer 114 was 20 nm. The comparative light-emitting device 3-3 was fabricated in a manner similar to that for the comparative light-emitting device 3-1 except that the thickness of NBPhen in the electron-transport layer 114 was 25 nm. The comparative light-emitting device 3-4 was fabricated in a manner similar to that for the comparative light-emitting device 3-0 except that the thickness of PCBBiF in the hole-transport layer 112 was 25 nm. The comparative light-emitting device 3-5 was fabricated in a manner similar to that for the comparative light-emitting device 3-4 except that the thickness of NBPhen in the electron-transport layer 114 was 20 nm. The comparative light-emitting device 3-6 was fabricated in a manner similar to that for the comparative light-emitting device 3-4 except that the thickness of NBPhen in the electron-transport layer 114 was 25 nm. The comparative light-emitting device 3-7 was fabricated in a manner similar to that for the comparative light-emitting device 3-0. The comparative light-emitting device 3-8 was fabricated in a manner similar to that for the comparative light-emitting device 3-7 except that the thickness of NBPhen in the electron-transport layer 114 was 20 nm. The comparative light-emitting device 3-9 was fabricated in a manner similar to that for the comparative light-emitting device 3-7 except that the thickness of NBPhen in the electron-transport layer 114 was 25 nm. The comparative light-emitting device 3-10 was fabricated in a manner similar to that for the comparative light-emitting device 3-0 except that the thickness of PCBBiF in the hole-transport layer 112 was 35 nm. The comparative light-emitting device 3-11 was fabricated in a manner similar to that for the comparative light-emitting device 3-10 except that the thickness of NBPhen in the electron-transport layer 114 was 20 nm. The comparative light-emitting device 3-12 was fabricated in a manner similar to that for the comparative light-emitting device 3-10 except that the thickness of NBPhen in the electron-transport layer 114 was 25 nm.

The device structures of the light-emitting devices 8-0 to 8-12 and the comparative light-emitting devices 3-0 to 3-12 are listed in the following table.

TABLE 11

| | | Light-emitting device 8-Y | Comparative light-emitting device 3-X |
|---|---|---|---|
| Electron-injection layer | *9 | Lif:BPhen (0.75:0.25 [vol %]) | Lif |
| Electron-transport layer | *8 | NBphen | |
| | 5 nm | 2mDBTBPDBq-II | |
| Light-emitting layer | 25 nm | αN-βNPAnth:3,10PCA2Nbf(IV)-02 (1:0.015) | |
| Hole-transport layer | 10 nm | DBfBB1TP | |
| | *7 | dchPAF | PCBBiF |
| Hole-injection layer | 10 nm | dchPAF:ALD-MP001Q (1:0.1) | PCBBif: ALD-MP001Q (1:0.1) |

*7 X, Y = 1 to 3: 20 nm
X, Y = 4 to 6: 25 nm
X, Y = 0, 7 to 9: 30 nm
X, Y = 10 to 12: 35 nm
*8 X = 0, 1, 4, 7, 10: 15 nm
X = 2, 5, 8, 11: 20 nm
X = 3, 6, 9, 12: 25 nm
Y= 0 to 12: 5 nm
*9 X = 0 to 12: 1 nm
Y = 0, 1, 4, 7, 10: 15 nm
Y = 2, 5, 8, 11: 20 nm
Y = 3, 6, 9, 12: 25 nm

The light-emitting devices and the comparative light-emitting devices were sealed using a glass substrate in a glove box containing a nitrogen atmosphere so as not to be exposed to the air (a sealing material was applied to surround the element and UV treatment and heat treatment at 80° C. for 1 hour were performed at the time of sealing). Then, the initial characteristics and reliability of the light-emitting devices were measured. Note that the sealed glass substrate was not subjected to particular treatment for improving outcoupling efficiency.

Figure 74:
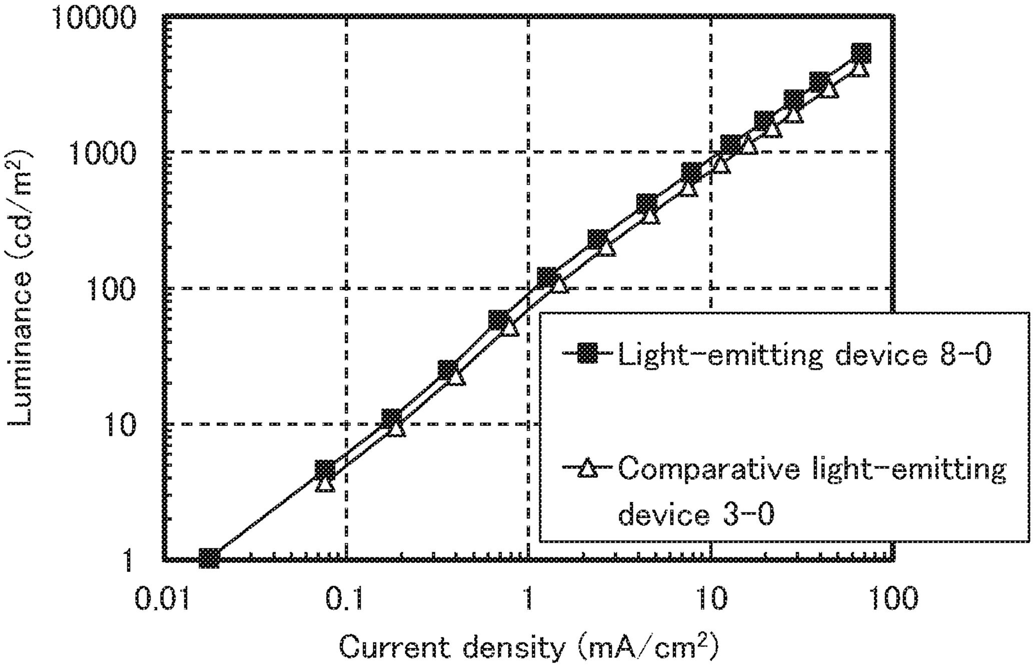
FIG. 74 shows the luminance-current density characteristics of a light-emitting device 8-0 and a comparative light-emitting device 3-0.
Figure 75:
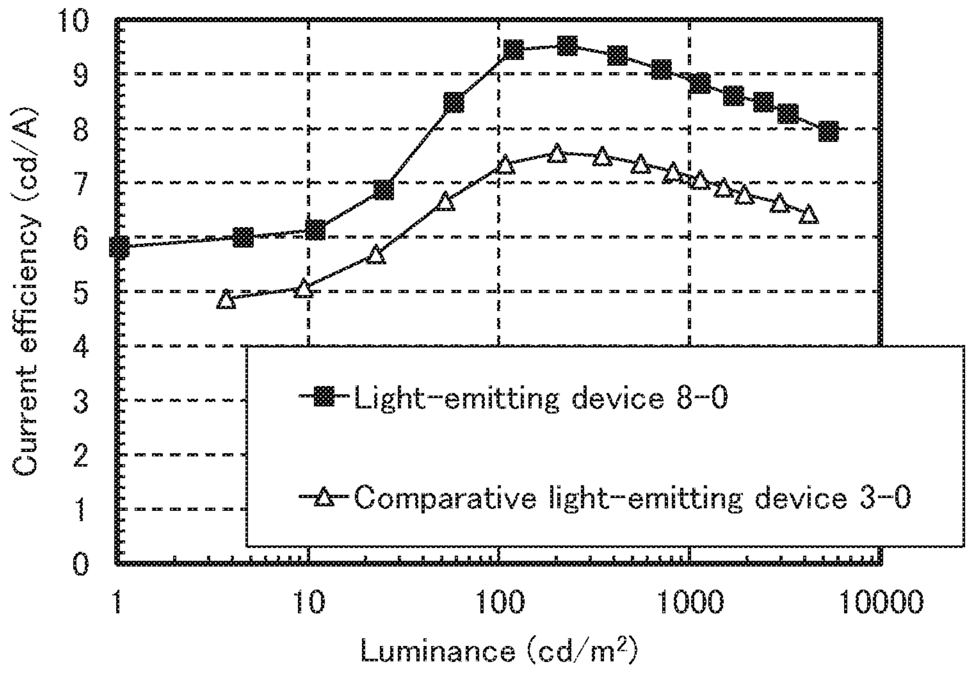
FIG. 75 shows the current efficiency-luminance characteristics of the light-emitting device 8-0 and the comparative light-emitting device 3-0.
Figure 76:
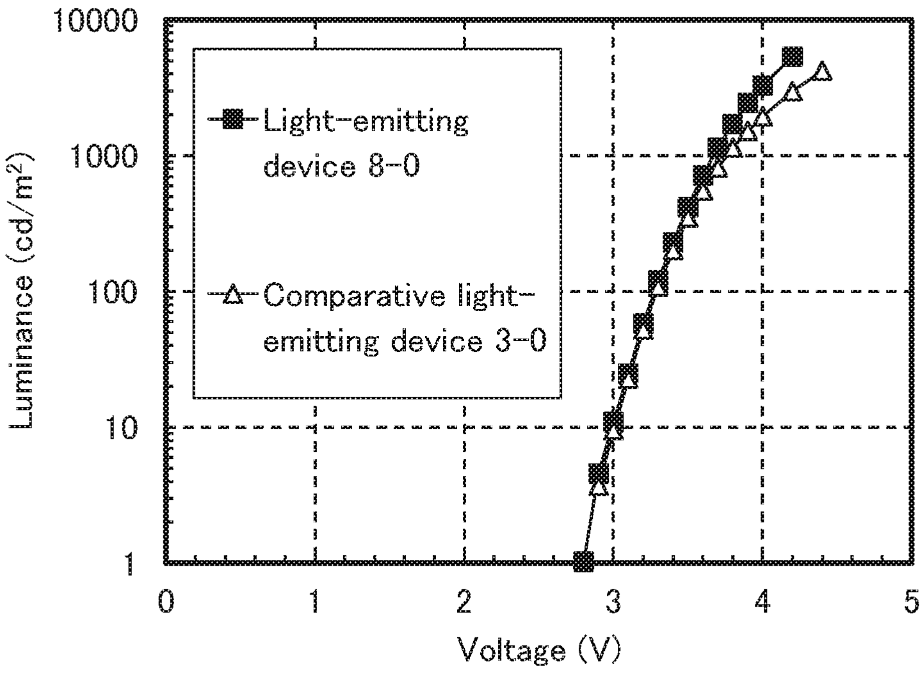
FIG. 76 shows the luminance-voltage characteristics of the light-emitting device 8-0 and the comparative light-emitting device 3-0.
Figure 77:
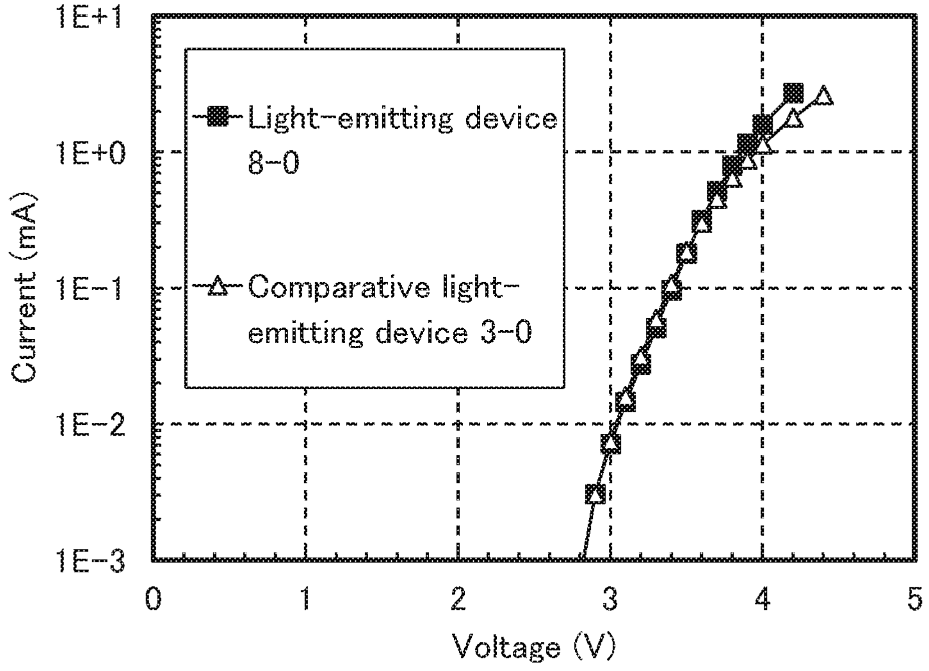
FIG. 77 shows the current-voltage characteristics of the light-emitting device 8-0 and the comparative light-emitting device 3-0.
Figure 78:
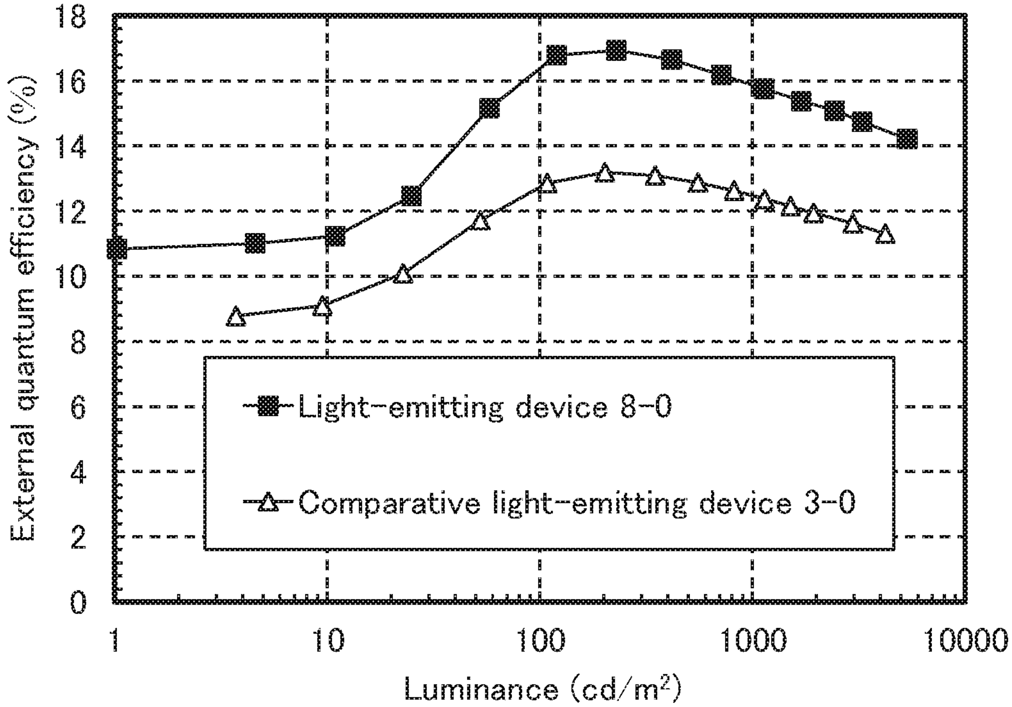
FIG. 78 shows the external quantum efficiency-luminance characteristics of the light-emitting device 8-0 and the comparative light-emitting device 3-0.
Figure 79:
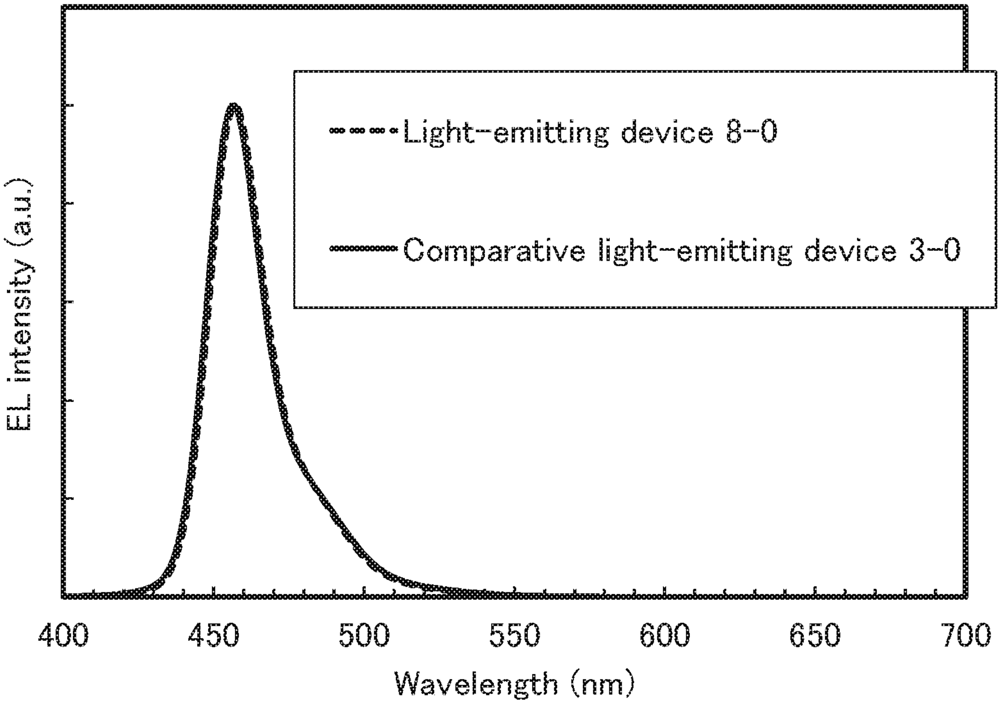
FIG. 79 shows the emission spectra of the light-emitting device 8-0 and the comparative light-emitting device 3-0.

FIG. 74 shows the luminance-current density characteristics of the light-emitting device 8-0 and the comparative light-emitting device 3-0. FIG. 75 shows the current efficiency-luminance characteristics thereof. FIG. 76 shows the luminance-voltage characteristics thereof. FIG. 77 shows the current-voltage characteristics thereof. FIG. 78 shows the external quantum efficiency-luminance characteristics thereof. FIG. 79 shows the emission spectra thereof. Table 12 shows the main characteristics of the light-emitting device 8-0 and the comparative light-emitting device 3-0 at a luminance of about 1000 cd/$m^2$. Luminance, CIE chromaticity, and emission spectra were measured with a spectroradiometer (UR-UL1R manufactured by TOPCON TECHNOHOUSE CORPORATION). The external quantum efficiency was calculated from the luminance measured with the spectroradiometer, on the assumption that the light-emitting devices had Lambertian light-distribution characteristics.

TABLE 12

| | Voltage (V) | Current (mA) | Current density (mA/cm$^2$) | Chromaticity x | Chromaticity y | Current efficiency (cd/A) | External quantum efficiency (%) | BI (cd/A/y) |
|---|---|---|---|---|---|---|---|---|
| Light-emitting device 8-0 | 3.7 | 0.52 | 12.9 | 0.140 | 0.056 | 8.8 | 15.8 | 159 |
| Comparative light-emitting device 3-0 | 3.8 | 0.65 | 16.1 | 0.141 | 0.057 | 7.1 | 12.4 | 125 |

FIGS. 74 to 79 and Table 12 show that the light emitting devices of one embodiment of the present invention, which use a material with a low refractive index, are EL devices with higher external light-emission efficiency and a more favorable blue index (BI) than the comparative light-emitting devices.

Table 13 shows the characteristics of the light-emitting devices 8-1 to 8-12 and Table 14 shows the characteristics of the comparative light-emitting devices 3-1 to 3-12. The characteristics were obtained when a current of 0.2 mA (5 mA/cm$^2$) was applied. The light-emitting device 8-1 to 8-12 and the comparative light-emitting devices 3-1 to 3-12 are different in the thickness of the hole-transport layer 112 and the electron-transport layer 114, that is, optical distance between electrodes, and thus have difference also in wavelength of light that is amplified.

TABLE 13

| Light-emitting devices | Voltage (V) | Current (mA) | Current density (mA/cm$^2$) | Chromaticity x | Chromaticity y | External quantum efficiency (%) | Current efficiency (cd/A) | BI (cd/A/y) |
|---|---|---|---|---|---|---|---|---|
| 8-1 | 3.6 | 0.20 | 5.0 | 0.145 | 0.047 | 8.9 | 4.4 | 94 |
| 8-2 | 3.5 | 9.20 | 5.0 | 0.145 | 0.046 | 11.1 | 5.4 | 118 |
| 8-3 | 3.5 | 0.20 | 5.0 | 0.144 | 0.046 | 12.8 | 6.2 | 136 |
| 8-4 | 3.6 | 0.20 | 5.0 | 0.144 | 0.049 | 12.0 | 6.1 | 126 |
| 8-5 | 3.5 | 0.20 | 5.0 | 0.143 | 0.049 | 14.4 | 7.4 | 150 |
| 8-6 | 3.5 | 0.20 | 5.0 | 0.141 | 0.051 | 15.7 | 8.3 | 162 |
| 8-7 | 3.6 | 0.20 | 5.0 | 0.142 | 0.053 | 14.6 | 7.9 | 151 |
| 8-8 | 3.5 | 0.20 | 5.0 | 0.140 | 0.056 | 16.6 | 9.3 | 167 |
| 8-9 | 3.5 | 0.20 | 5.0 | 0.137 | 0.061 | 17.1 | 10.2 | 167 |
| 8-10 | 3.6 | 0.20 | 5.0 | 0.139 | 0.059 | 15.9 | 9.4 | 158 |
| 8-11 | 3.5 | 0.20 | 5.0 | 0.136 | 0.066 | 17.1 | 10.8 | 163 |
| 8-12 | 3.5 | 0.20 | 5.0 | 0.132 | 0.075 | 16.9 | 11.5 | 153 |

TABLE 14

| Comparative light-emitting devices | Voltage (V) | Current (mA) | Current density (mA/cm$^2$) | Chromaticity x | Chromaticity y | External quantum efficiency (%) | Current efficiency (cd/A) | BI (cd/A/y) |
|---|---|---|---|---|---|---|---|---|
| 3-1 | 3.5 | 0.20 | 5.0 | 0.144 | 0.049 | 8.7 | 4.5 | 91 |
| 3-2 | 3.5 | 0.20 | 5.0 | 0.143 | 0.049 | 10.9 | 5.6 | 113 |
| 3-3 | 3.6 | 0.20 | 5.0 | 0.142 | 0.051 | 12.3 | 6.5 | 126 |
| 3-4 | 3.5 | 0.20 | 5.0 | 0.143 | 0.052 | 11.5 | 6.1 | 119 |
| 3-5 | 3.5 | 0.20 | 5.0 | 0.141 | 0.055 | 13.3 | 7.4 | 135 |
| 3-6 | 3.6 | 0.20 | 5.0 | 0.138 | 0.060 | 14.0 | 8.3 | 137 |
| 3-7 | 3.5 | 0.20 | 5.0 | 0.140 | 0.057 | 13.0 | 7.5 | 132 |
| 3-8 | 3.5 | 0.20 | 5.0 | 0.137 | 0.063 | 14.2 | 8.7 | 138 |
| 3-9 | 3.6 | 0.20 | 5.0 | 0.133 | 0.074 | 14.1 | 9.6 | 130 |
| 3-10 | 3.5 | 0.20 | 5.0 | 0.137 | 0.066 | 13.8 | 8.7 | 133 |
| 3-11 | 3.5 | 0.20 | 5.0 | 0.133 | 0.077 | 14.2 | 9.9 | 129 |
| 3-12 | 3.6 | 0.20 | 5.0 | 0.128 | 0.093 | 13.6 | 10.7 | 115 |

Figure 80:
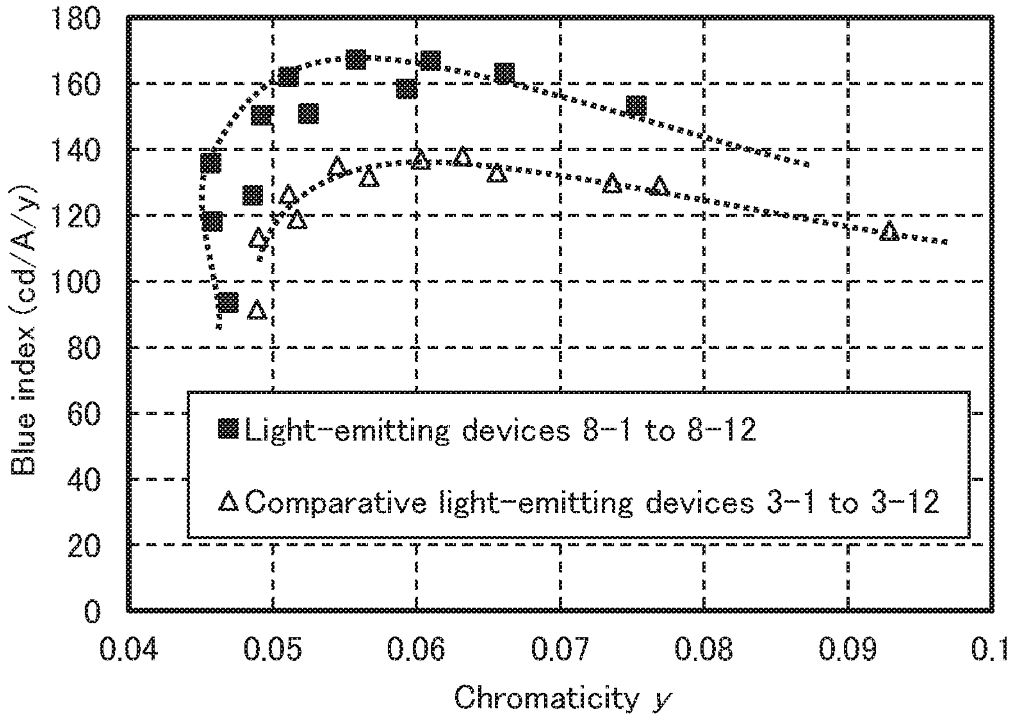
FIG. 80 shows the relationship between chromaticity y and BI of light-emitting devices 8-1 to 8-12 and the comparative light-emitting devices 3-1 to 3-12.

Table 13 and Table 14 show that the light-emitting devices of one embodiment of the present invention, which use a material with a low refractive index, have higher external quantum efficiency and a more favorable blue index (BI) than the comparative light-emitting devices, which use a material with a normal refractive index. In addition, each table show that the efficiency and BI change depending on the optical distance (i.e., wavelength of light that is amplified and chromaticity) of the light-emitting device. Since the intensity of blue light emission required for a display depends on the chromaticity, comparison of BI at the same chromaticity is effective. FIG. 80 shows a change in BI with respect to the chromaticity y.

FIG. 80 shows that the light-emitting devices of one embodiment of the present invention have more favorable BI than the comparative light-emitting devices that exhibit the same chromaticity.

Figure 81:
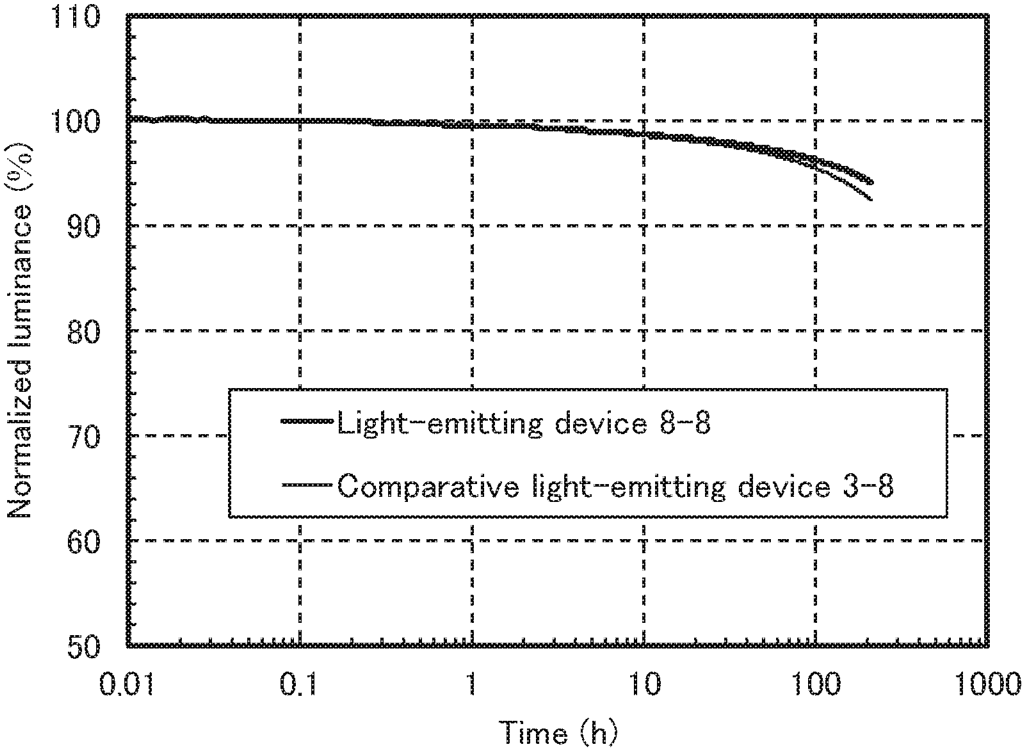
FIG. 81 shows a luminance change with respect to driving time of the light-emitting device 8-8 and the comparative light-emitting device 3-8.

FIG. 81 shows luminance change with respect to driving time when the light-emitting device 8-8 and the comparative light-emitting device 3-8 are driven at a constant current with a current density of 50 mA/$cm^2$. FIG. 81 shows that the light-emitting device of one embodiment of the present invention has high emission efficiency while keeping a long lifetime.

Example 17

In this example, light-emitting devices of one embodiment of the present invention described in the above embodiment and comparative light-emitting devices are described. Structural formulae of organic compounds used in this example are shown below.

[Chemical Formula 90]

(vi)

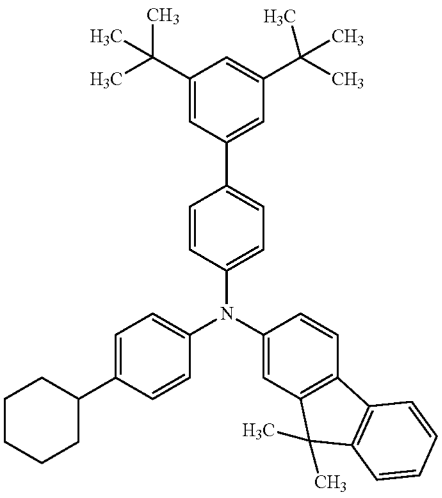

mmtBuBichPAF (viii)

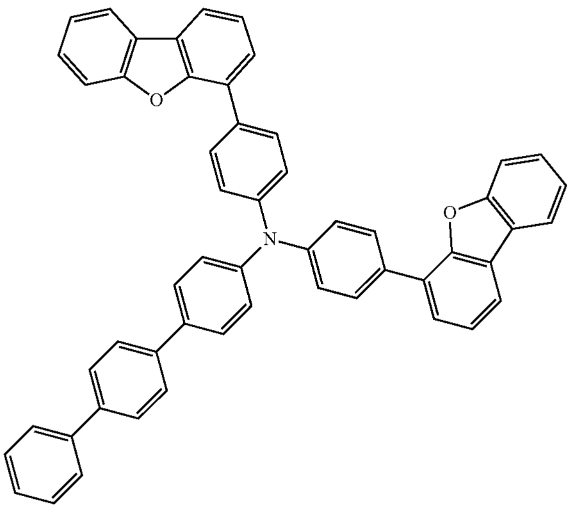

DBfBB1TP (ix)

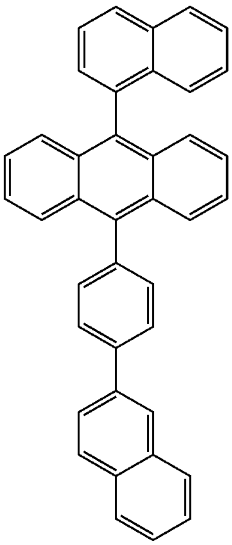

αN-βNPAnth

-continued
(xiii)
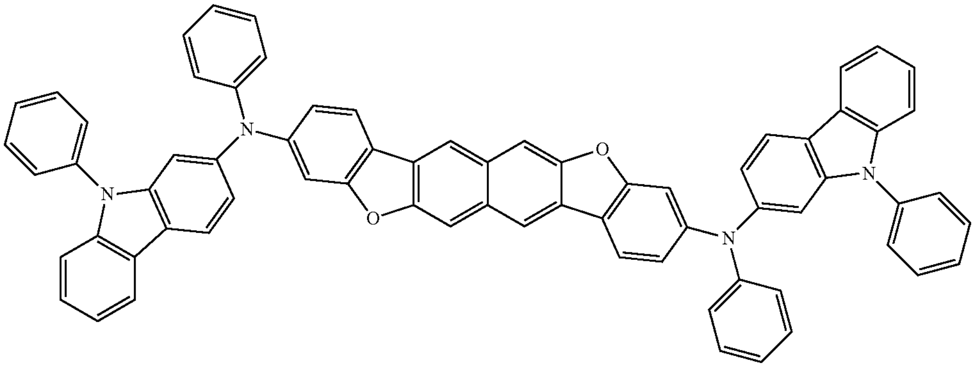
3,10PCA2Nbf(IV)-02
(xii)
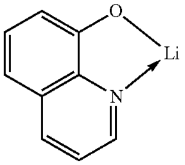
Liq
(xi)
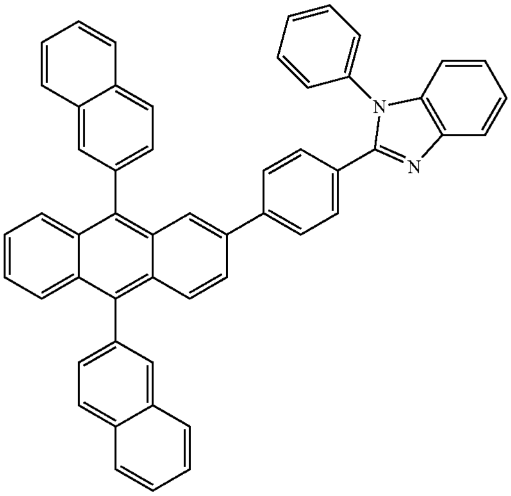
ZADN
(vii)
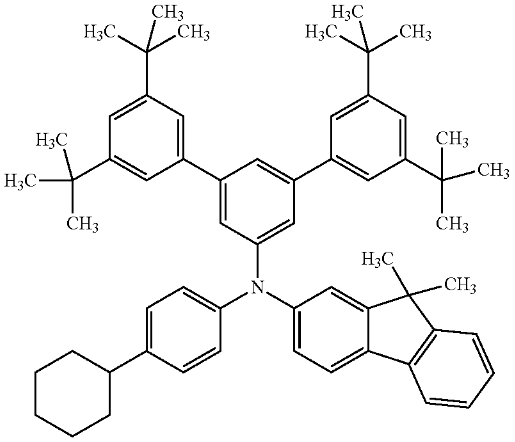
mmtBumTPchPAF
(ii)
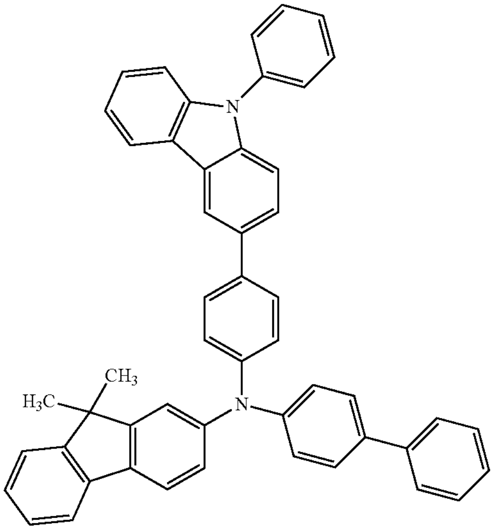
PCBBiF (Fabrication Method of Light-Emitting Device 9)

First, indium tin oxide containing silicon oxide (ITSO) was formed over a glass substrate by a sputtering method, whereby the first electrode 101 was formed. The thickness of the first electrode 101 was 55 nm and the electrode area was 2 mm×2 mm.

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N-[(3',5'-ditertiarybutyl)-1,1'-biphenyl-4-yl]-N-(4-cyclohexylphenyl)-9,9-dimethyl-9H-fluor en-2-amine (abbreviation: mmtBuBichPAF) represented by the structural formula (vi) and ALD-MP001Q (produced by Analysis Atelier Corporation, material serial No. 1S20180314) were deposited by co-evaporation to a thickness of 10 nm over the first electrode 101 using a resistance-heating method such that the weight ratio of mmtBuBichPAF to ALD-MP001Q was 1:0.1, whereby the hole-injection layer 111 was formed. Note that ALD-MP001Q is an organic compound having an acceptor property.

Subsequently, over the hole-injection layer 111, mmtBuBichPAF was deposited to a thickness of 30 nm by evaporation, and then N,N-bis[4-(dibenzofuran-4-yl)phenyl]-4-amino-p-terphenyl (abbreviation: DBfBB1TP) represented by the structural formula (viii) was deposited to a thickness of 10 nm by evaporation, whereby the hole-transport layer 112 was formed.

Then, 9-(1-naphthyl)-10-[4-(2-naphthyl)phenyl]anthracene (abbreviation: αN-βNPAnth) represented by the structural formula (ix) and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by the structural formula (xiii) were deposited to a thickness of 25 nm by co-evaporation such that the weight ratio of αN-βNPAnth to 3,10PCA2Nbf(IV)-02 was 1:0.015, whereby the light-emitting layer 113 was formed.

Then, over the light-emitting layer 113, 2-{4-[9,10-di(naphthalen-2-yl)-2-anthryl]phenyl}-1-phenyl-1H-benzimidazole (abbreviation: ZADN) represented by the structural formula (xi) and 8-hydroxyquinolinatolithium (abbreviation: Liq) represented by the structural formula (xii) was deposited to a thickness of 25 nm by co-evaporation such that the weight ratio of ZADN to Liq was 1:1, whereby the electron-transport layer 114 was formed.

After the electron-transport layer 114 was formed, Liq was deposited to a thickness of 1 nm by evaporation to form the electron-injection layer 115. Then, aluminum was deposited to a thickness of 200 nm by evaporation to form the second electrode 102. Thus, the light-emitting device 9 of this example was fabricated.

(Fabrication Method of Light-Emitting Device 10)

The light-emitting device 10 was fabricated in a manner similar to that for the light-emitting device 9 except that mmtBuBichPAF was replaced with N-(3,3",5,5"-tetra-t-butyl-1,1':3',1"-terphenyl-5'-yl)-N-(4-cyclohexylphenyl)-9,9-dimethyl-9H-fluoren-2-amine (abbreviation: mmtBumTPchPAF) represented by the structural formula (vii).

(Fabrication Method of Comparative Light-Emitting Device 4)

The comparative light-emitting device 4 was fabricated in a manner similar to that for the light-emitting device 9 except that mmtBuBichPAF was replaced with N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by the structural formula (ii).

The device structures of the light-emitting devices 9 and 10 and the comparative light-emitting device 4 are listed in the following table.

TABLE 15

| | Thickness | Light-emitting device 9 | Light-emitting device 10 | Comparative light-emitting device 4 |
|---|---|---|---|---|
| Electron-injection layer | 1 nm | | Liq | |
| Electron-transport layer | 25 nm | | ZADN:Liq (1:1) | |
| Light-emitting layer | 25 nm | | αN-βNPAnth:3,10PCA2Nbf(IV)-02 (1:0.015) | |
| Hole-transport layer | 10 nm | | DBfBB1TP | |
| | 30 nm | mmtBuBichPAF | mmtBumTPchPAF | PCBBiF |
| Hole-injection layer | 10 nm | mmtBuBichPAF:ALD-MP001Q (1:0.1) | mmtBumTPchPAF:ALD-MP001Q (1:0.1) | PCBBiF:ALD-MP001Q (1:0.1) |

Figure 95:
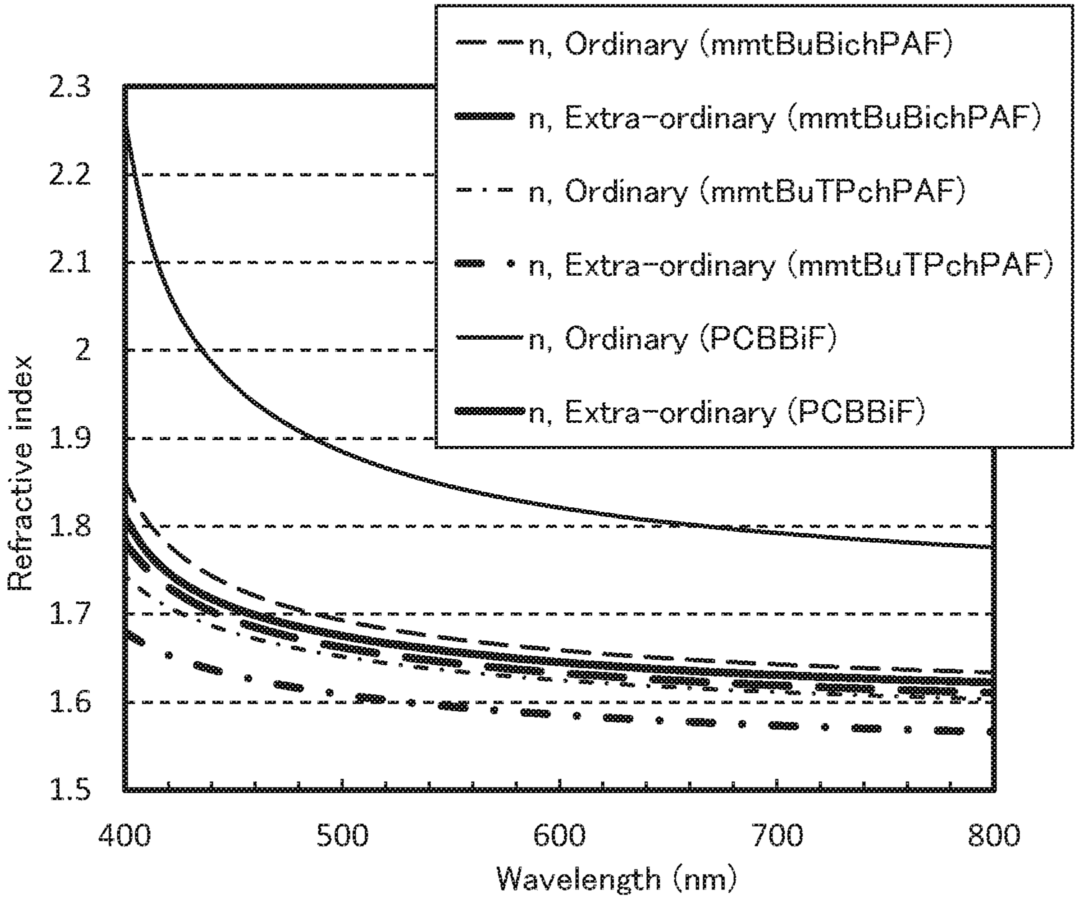
FIG. 95 shows measurement data of refractive indices of mmtBuBichPAF, mmtBumTPchPAF, and PCBBiF.

The refractive indices of PCBBiF as a reference and the materials with a low refractive index (mmtBuBichPAF and mmtBumTPchPAF) used for the hole-injection layer and part of the hole-transport layer are shown in FIG. 95, and the refractive indices at a wavelength of 458 nm are shown in the following table.

TABLE 16

| | Refractive index |
|---|---|
| mmtBuBichPAF | 1.66 |
| mmtBumTPchPAF | 1.63 |
| PCBBiF | 1.94 |

The light-emitting devices and the comparative light-emitting device were sealed using a glass substrate in a glove box containing a nitrogen atmosphere so as not to be exposed to the air (a sealing material was applied to surround the element and UV treatment and heat treatment at 80° C. for 1 hour were performed at the time of sealing). Then, the initial characteristics and reliability of the light-emitting devices were measured. Note that the glass substrate over which the light-emitting device was formed was not subjected to particular treatment for improving outcoupling efficiency.

Figure 96:
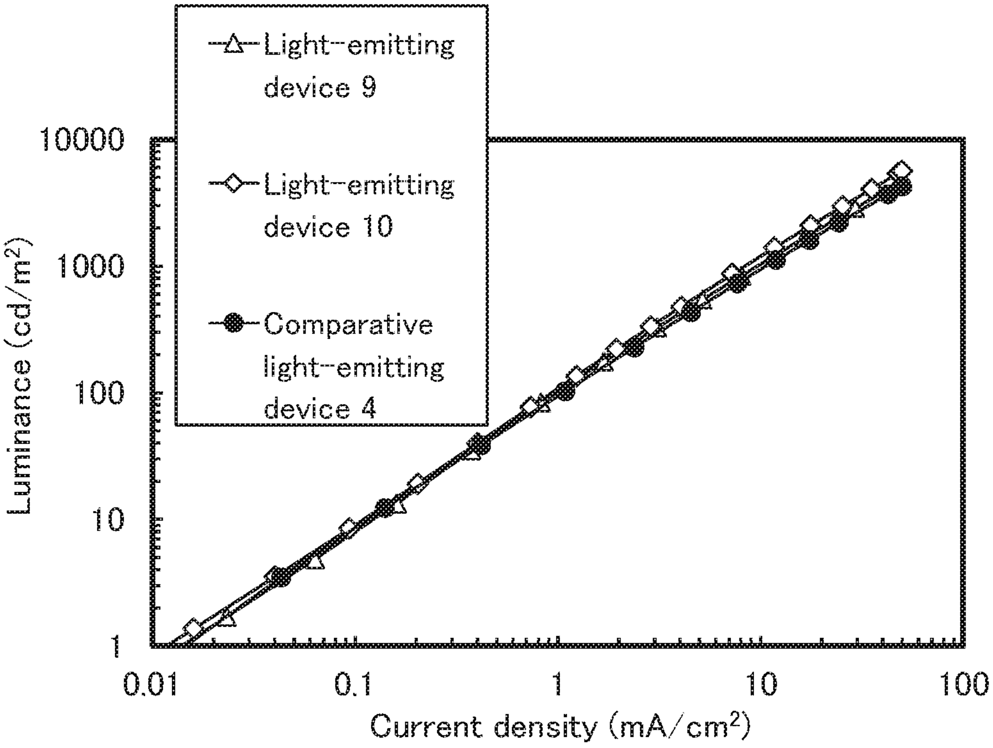
FIG. 96 shows the luminance-current density characteristics of a light-emitting device 9, a light-emitting device 10, and a comparative light-emitting device 4.
Figure 97:
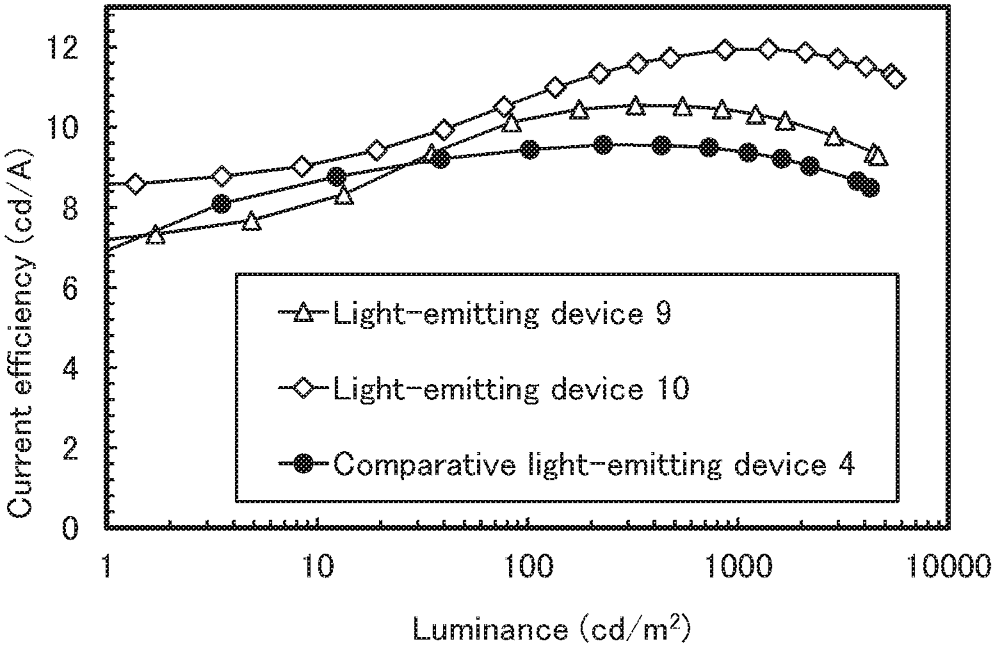
FIG. 97 shows the current efficiency-luminance characteristics of the light-emitting device 9, the light-emitting device 10, and the comparative light-emitting device 4.
Figure 98:
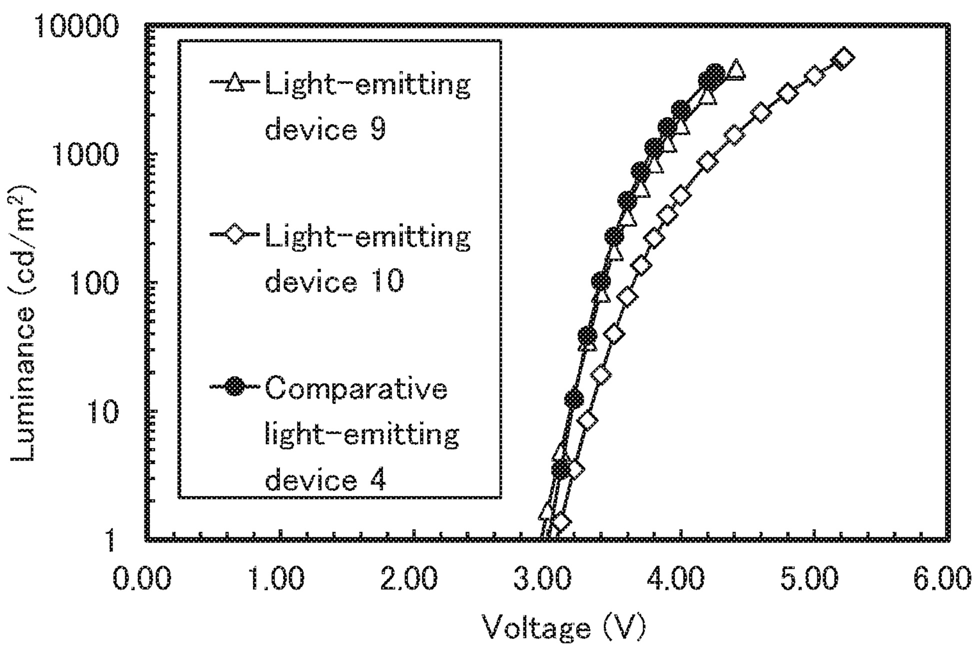
FIG. 98 shows the luminance-voltage characteristics of the light-emitting device 9, the light-emitting device 10, and the comparative light-emitting device 4.
Figure 99:
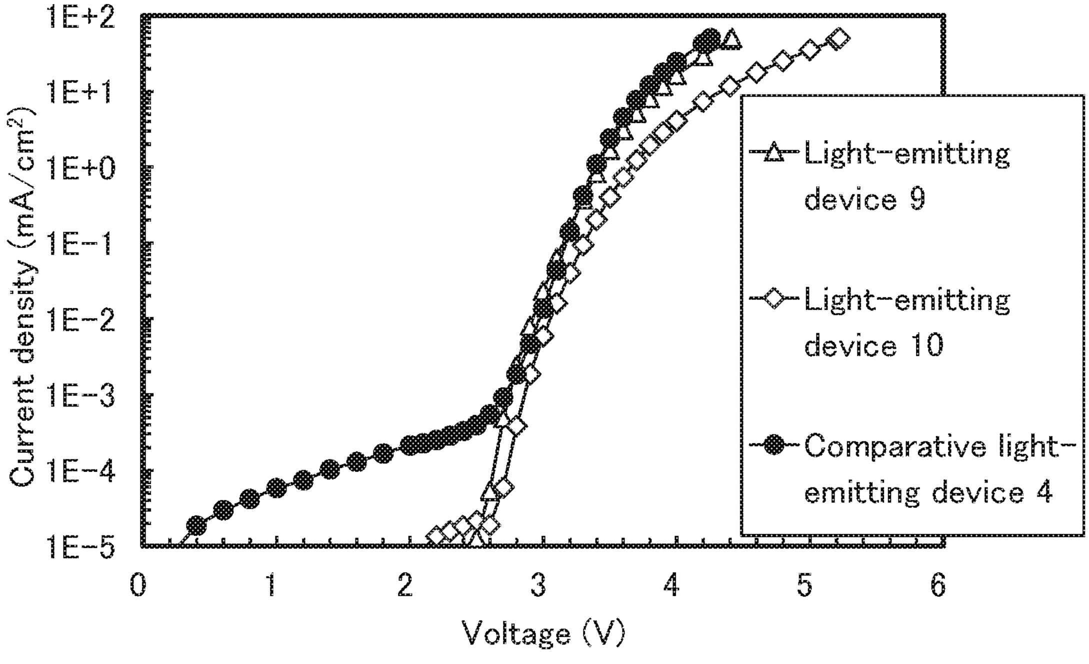
FIG. 99 shows the current-voltage characteristics of the light-emitting device 9, the light-emitting device 10, and the comparative light-emitting device 4.
Figure 100:
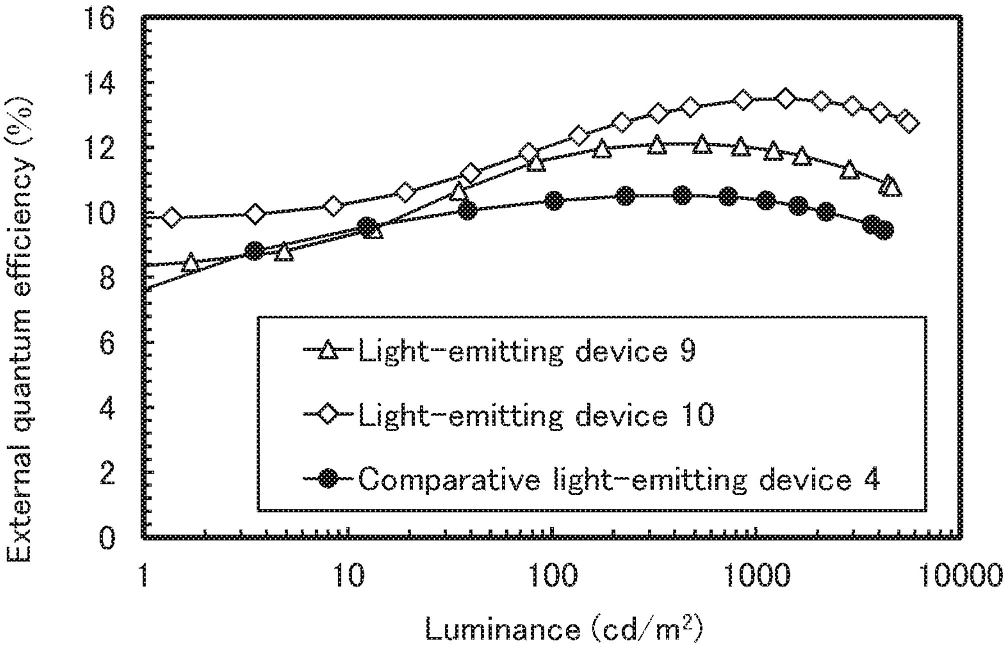
FIG. 100 shows the external quantum efficiency-luminance density characteristics of the light-emitting device 9, the light-emitting device 10, and the comparative light-emitting device 4.
Figure 101:
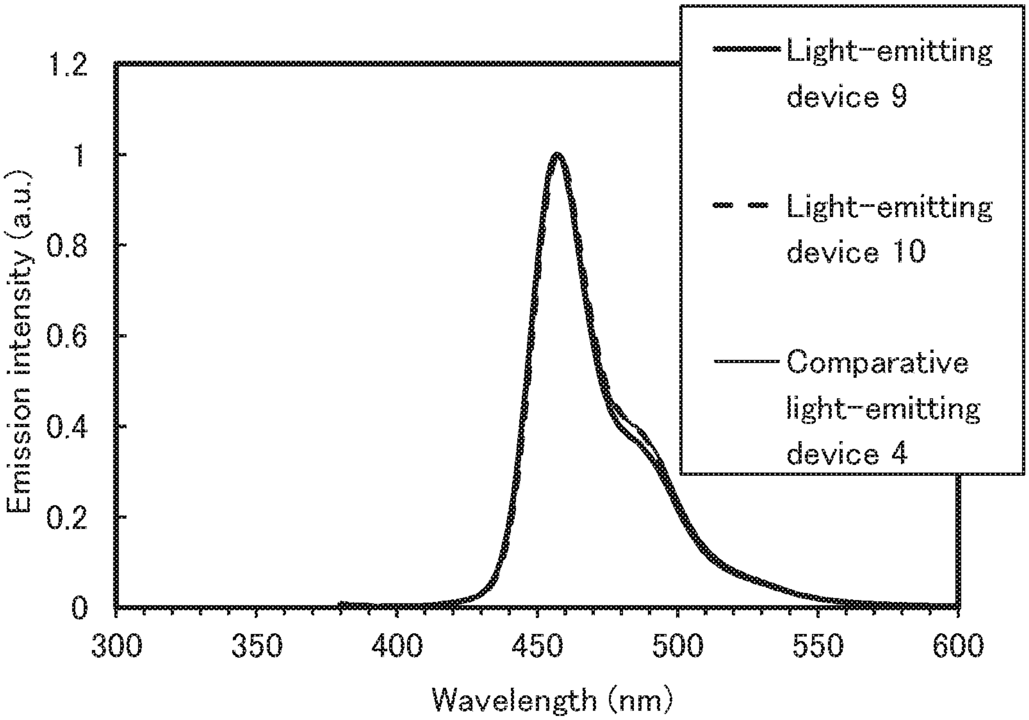
FIG. 101 shows the emission spectra of the light-emitting device 9, the light-emitting device 10, and the comparative light-emitting device 4.

FIG. 96 shows the luminance-current density characteristics of the light-emitting devices 9 and 10 and the comparative light-emitting device 4. FIG. 97 shows the current efficiency-luminance characteristics thereof. FIG. 98 shows the luminance-voltage characteristics thereof. FIG. 99 shows the current density-voltage characteristics thereof. FIG. 100 shows the external quantum efficiency-luminance characteristics thereof. FIG. 101 shows the emission spectra thereof. Table 17 shows the main characteristics of the light-emitting devices at a luminance of about 1000 cd/m$^2$. Luminance, CIE chromaticity, and emission spectra were measured with a spectroradiometer (UR-UL1R manufactured by TOPCON TECHNOHOUSE CORPORATION). The external quantum efficiency was calculated from the luminance and emission spectra measured with the spectroradiometer, on the assumption that the light-emitting devices had Lambertian light-distribution characteristics.

TABLE 17

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting device 9 | 3.8 | 0.32 | 8.0 | 0.14 | 0.10 | 10.5 | 12.0 |
| Light-emitting device 10 | 4.2 | 0.29 | 7.3 | 0.14 | 0.10 | 11.9 | 13.5 |
| Comparative light-emitting device 4 | 3.8 | 0.48 | 12.0 | 0.14 | 0.10 | 9.4 | 10.4 |

FIGS. 96 to 101 and Table 17 show that the light-emitting devices of one embodiment of the present invention, which each include a layer using a material with a low refractive index, are favorable EL devices having the same shape of the emission spectra as and higher emission efficiency than the comparative light-emitting devices.

Example 18

In this example, results of measuring the hole mobility of the organic compounds of one embodiment of the present invention are described. The hole mobility was measured with devices fabricated for the measurement. The fabrication methods of the devices are described below.

(Fabrication Method of Device 1)

As an electrode, an alloy film of silver (Ag), palladium (Pd), and copper (Cu), i.e., an Ag—Pd—Cu (APC) film, was formed over a glass substrate to a thickness of 100 nm by a sputtering method, and then, indium tin oxide containing silicon oxide (ITSO) was formed to a thickness of 50 nm by a sputtering method, whereby the first electrode 101 was formed. The electrode area was 4 mm$^2$ (2 mm×2 mm).

Next, in pretreatment for forming the device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, dchPAF and molybdenum oxide were deposited by evaporation to a thickness of 5 nm over the first electrode 101 such that the weight ratio of dchPAF to molybdenum oxide was 1:1, whereby the hole-injection layer 111 was formed.

Over the hole-injection layer 111, dchPAF was deposited as the hole-transport layer 112 by evaporation to a thickness of 491.5 nm.

Then, dchPAF and molybdenum oxide were deposited by evaporation to a thickness of 5 nm such that the weight ratio of dchPAF to molybdenum oxide was 1:1, whereby a buffer layer was formed.

Then, aluminum (Al) was deposited by evaporation to a thickness of 200 nm to form the second electrode 102, whereby the device 1 that is a hole-only device was fabricated.

(Fabrication Method of Device 2)

The device 2 was fabricated in a manner similar to that for the device 1 except that dchPAF was replaced with mmtBuBichPAF and the thickness of the hole-transport layer 112 was 478 nm.

(Fabrication Method of Device 3)

The device 3 was fabricated in a manner similar to that for the device 1 except that dchPAF was replaced with mmtBumTPchPAF and the thickness of the hole-transport layer 112 was 457 nm.

The device structures of the devices 1, 2, and 3 are listed below.

TABLE 18

| | Thickness | Device 1 | Device 2 | Device 3 |
|---|---|---|---|---|
| Buffer layer | 5 nm | dchPAF: molybdenum oxide (1:1) | mmtBuBichPAF: molybdenum oxide (1:1) | mmtBuTPchPAF: molybdenum oxide (1:1) |
| Hole-transport layer | *10 | dchPAF | mmtBuBichPAF | mmtBuTPchPAF |
| Hole-injection layer | 5 nm | dchPAF: molybdenum oxide (1:1) | mmtBuBichPAF: molybdenum oxide (1:1) | mmtBuTPchPAF: molybdenum oxide (1:1) |

*10 Device 1: 491.5 nm, Device 2: 478 nm, Device 3: 457 mn

The devices were sealed using a glass substrate in a glove box containing a nitrogen atmosphere so as not to be exposed to the air (a sealing material was applied to surround the element and UV treatment was performed at the time of sealing), and then measured.

Figure 102:
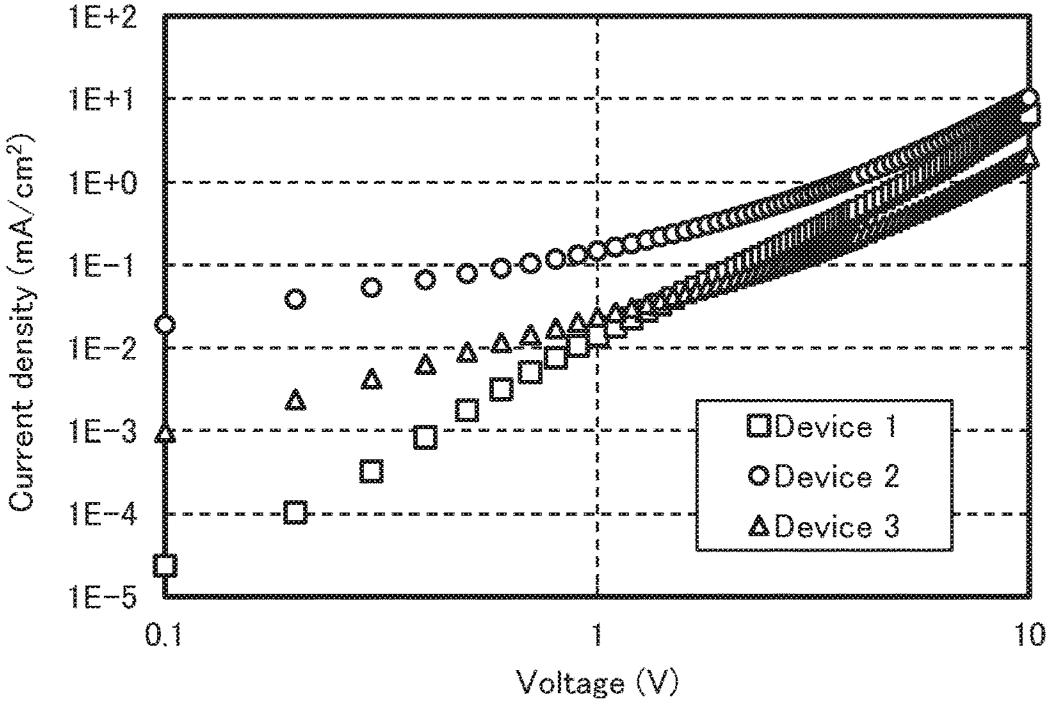
FIG. 102 shows the current density-voltage characteristics of a device 1, a device 2, and a device 3.

The current density-voltage characteristics of the devices 1, 2, and 3 are shown in FIG. 102. Note that the measurement was performed at room temperature.

The hole mobility of the organic compounds were calculated from the electrical characteristics shown in FIG. 102 using device simulation. For the simulation, Setfos (drift-diffusion module manufactured by CYBERNET SYSTEMS Co., Ltd.) was used. The simulation parameters are as follows: the work function of ITSO of the first electrode 101 was 5.36 eV, the work function of Al of the second electrode 102 was 4.2 eV, the HOMO level of dchPAF was −5.36 eV, the HOMO level of mmtBuBichPAF was −5.38 eV, the HOMO level of mmtBumTPchPAF was −5.42 eV, and the charge density of the hole-transport layer 112 was $1.0\times10^{18}$ $cm^{-3}$.

The work functions of the electrodes were measured by photoelectron spectroscopy using "AC-2" manufactured by Riken Keiki Co., Ltd. in the air.

The HOMO levels of the organic compounds were measured by cyclic voltammetry (CV) measurement. Note that for the measurement, an electrochemical analyzer (ALS 600A or 600C, produced by BAS Inc.) was used, and the measurement was performed on a solution obtained by dissolving each compound in N,N-dimethylformamide (abbreviation: DMF). In the measurement, the potential of a working electrode with respect to a reference electrode was changed within an appropriate range, so that the oxidation peak potential and the reduction peak potential were obtained. In addition, the HOMO levels of the compounds were obtained from the estimated redox potential of the reference electrode of −4.94 eV and the obtained peak potentials.

Figure 103:
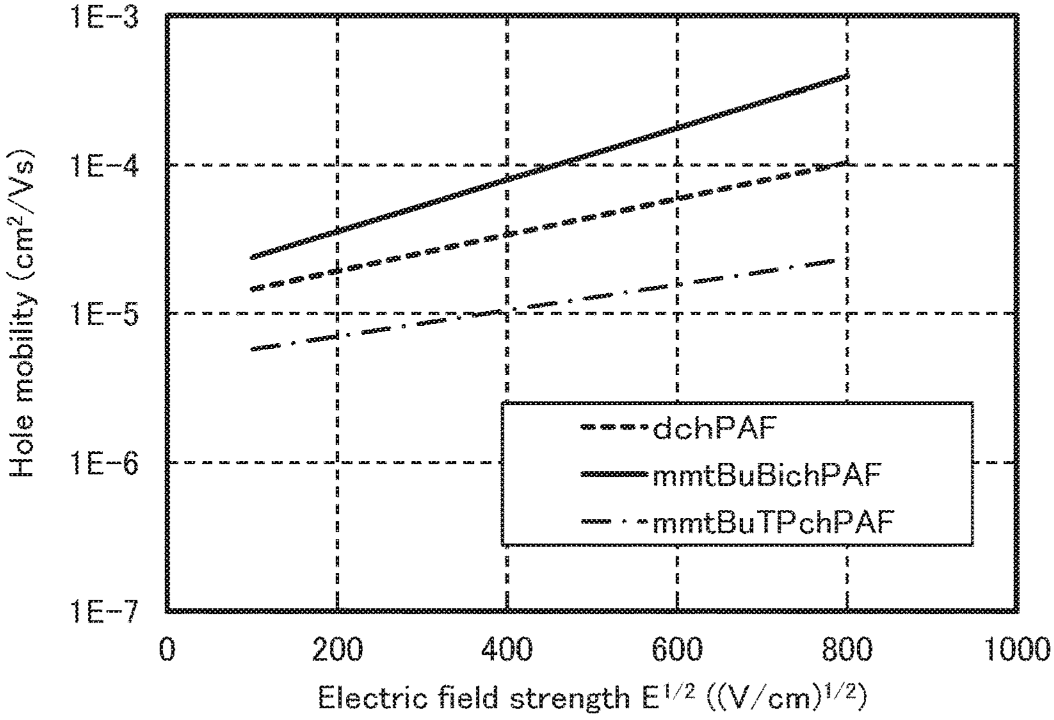
FIG. 103 shows the electric field strength dependence of the hole mobility of an organic compound of one embodiment of the present invention.

The electric field strength dependence of the hole mobility of the organic compounds obtained by the simulation is shown in FIG. 103. Note that the horizontal axis of FIG. 103 represents the one-half power of electric field strength calculated from voltage. In addition, the hole mobility at an electric field strength of 300 $(V/cm)^{1/2}$ is shown in the following table.

TABLE 19

| | Hole mobility *11 ($cm^2/Vs$) |
|---|---|
| dchPAF | $2.6\times10^{-5}$ |
| mmtBuBichPAF | $5.3\times10^{-5}$ |
| mmtBuTPchPAF | $8.6\times10^{-6}$ |

*11 At an electric field strength of 300 $(V/cm)^{1/2}$

As described above, the organic compound of one embodiment of the present invention is a substance having hole mobility of higher than or equal to $1\times10^{-6}$ $cm^2/Vs$, and thus is suitable for a hole-transport layer of a light-emitting device.

Example 19

Synthesis Example 13

In this example, a synthesis method of N-(3,3",5,5"-tetra-t-butyl-1,1':3',1"-terphenyl-5'-yl)-N-phenyl-9,9-dimethyl-9H-fluoren-2-amine (abbreviation: mmtBumTPFA), which is the organic compound represented by the structural formula (246) in Embodiment 1, is described. A structure of mmtBumTPFA is shown below.

[Chemical Formula 91]

(246)

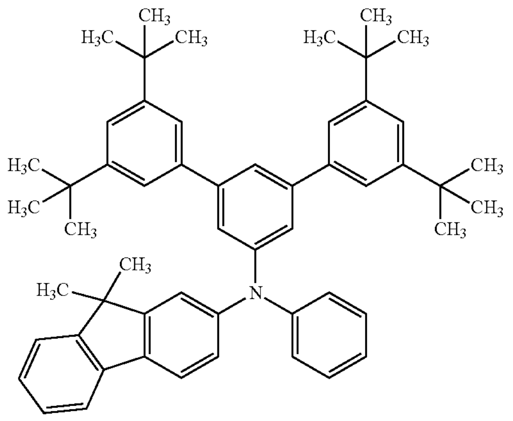

Step 1: Synthesis of 3,3",5,5"-tetra-t-butyl-5'-chloro-1,1':3',1"-terphenyl

The synthesis was performed in a manner similar to Step 1 of the synthesis example 11 in Example 11.

Step 2: Synthesis of N-(3,3",5,5"-tetra-t-butyl-1,1':3',1"-terphenyl-5'-yl)-N-phenyl-9,9-dimethyl-9H-fluoren-2-amine (Abbreviation: mmtBumTPFA)

In a three-neck flask were put 4.89 g (10 mmol) of 3,3",5,5"-tetra-t-butyl-5'-chloro-1,1':3',1"-terphenyl, 2.85 g (10 mmol) of N-phenyl-9,9-dimethyl-9H-fluoren-2-amine, 2.88 g (30 mmol) of sodium-tert-butoxide, and 50 mL of xylene. The mixture was degassed under reduced pressure, and then the air in the flask was replaced with nitrogen. Then, 37 mg (0.10 mmol) of allylpalladium(II) chloride dimer (abbreviation: $[(Allyl)PdCl]_2$) and 164 mg (0.40 mmol) of di-tert-butyl(1-methyl-2,2-diphenylcyclopropyl)

phosphine (abbreviation: cBRIDP (trademark)) were added to this mixture, and the mixture was stirred at 120° C. under a nitrogen stream for 4 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained fraction was concentrated to give a condensed toluene solution. Ethanol was added to this toluene solution and the toluene solution was concentrated under reduced pressure, whereby an ethanol suspension was obtained. The precipitate was filtrated at approximately 20° C. and the obtained solid was dried at approximately 80° C. under reduced pressure, so that 6.86 g of a target white solid was obtained in a yield of 93%. The synthesis scheme of Step 2 is shown below.

[Chemical Formula 92]

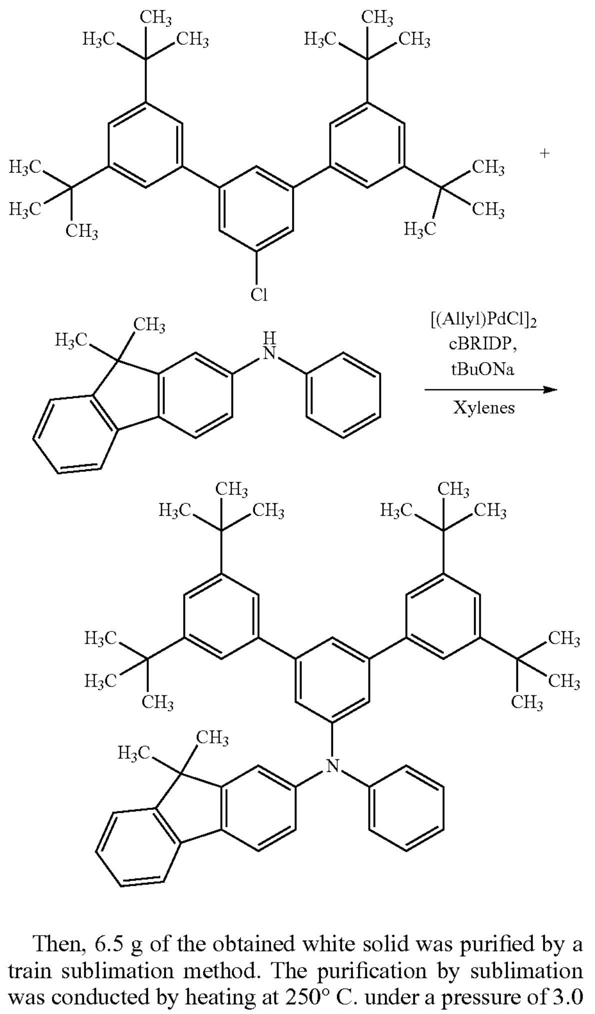

Then, 6.5 g of the obtained white solid was purified by a train sublimation method. The purification by sublimation was conducted by heating at 250° C. under a pressure of 3.0 Pa with the argon flow rate of 12.2 mL/min. After the purification by sublimation, 6.0 g of a pale yellowish white solid was obtained at a collection rate of 92%.

Figure 104A:
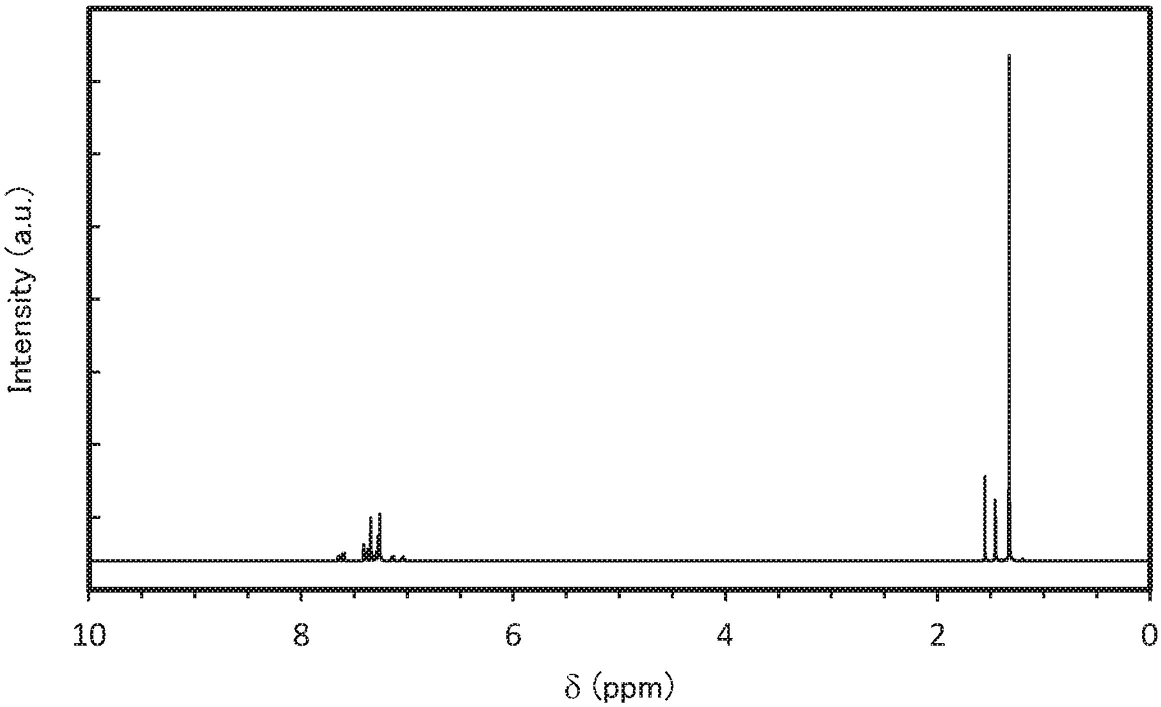
FIGS. 104A and 104B are $^1$H-NMR charts of mmtBumTPFA.
Figure 104B:
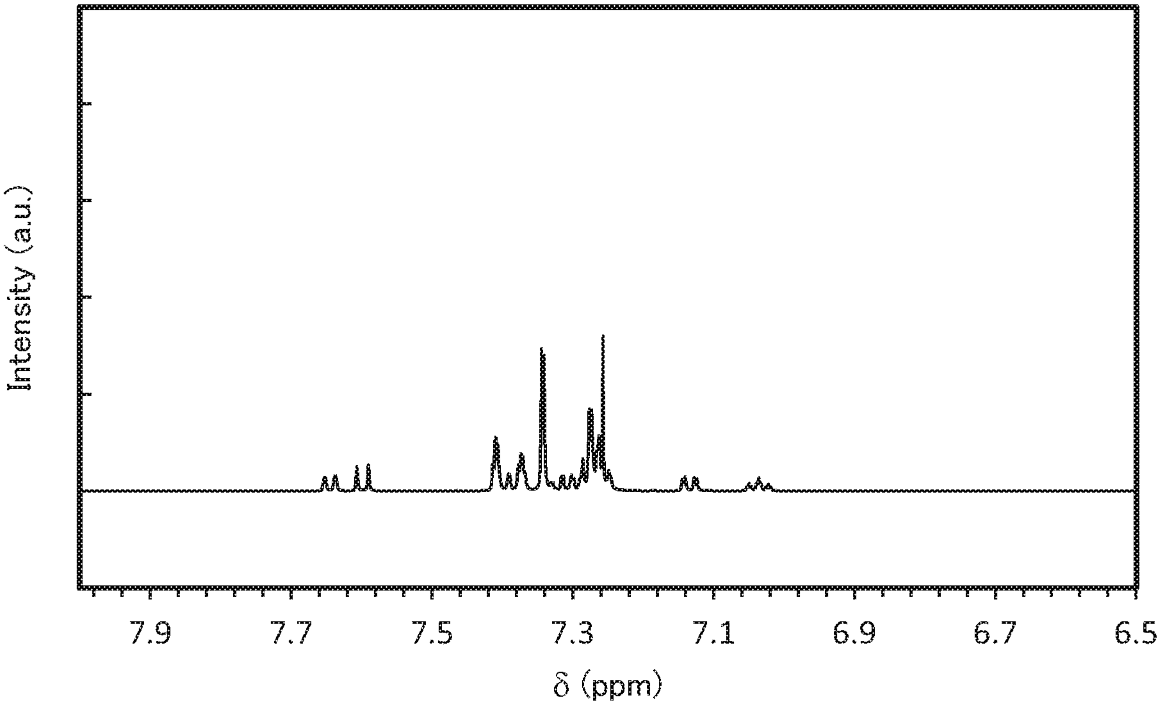

Analysis results by nuclear magnetic resonance spectroscopy ($^1$H-NMR) of the white solid obtained in Step 2 are shown below. FIGS. 104A and 104B are the $^1$H-NMR charts. The results show that the organic compound N-(3,3",5,5"-tetra-t-butyl-1,1':3,1"-terphenyl-5'-yl)-N-phenyl-9,9-dimethyl-9H-fluoren-2-amine (abbreviation: mmtBumTPFA) was synthesized in this synthesis example.

$^1$H-NMR. δ ($CDCl_3$): 7.65 (d, 1H, J=7.5 Hz), 7.60 (d, 1H, J=8.0 Hz), 7.38-7.42 (m, 3H), 7.34 (d, 4H, J=1.5 Hz), 7.23-7.33 (m, 8H), 7.13 (dd, 1H, J=2.0 Hz, 8.0 Hz), 7.04 (tt, 1H, J=1.5 Hz, 7.0 Hz), 1.45 (s, 6H), 1.33 (s, 36H).

Figure 105:
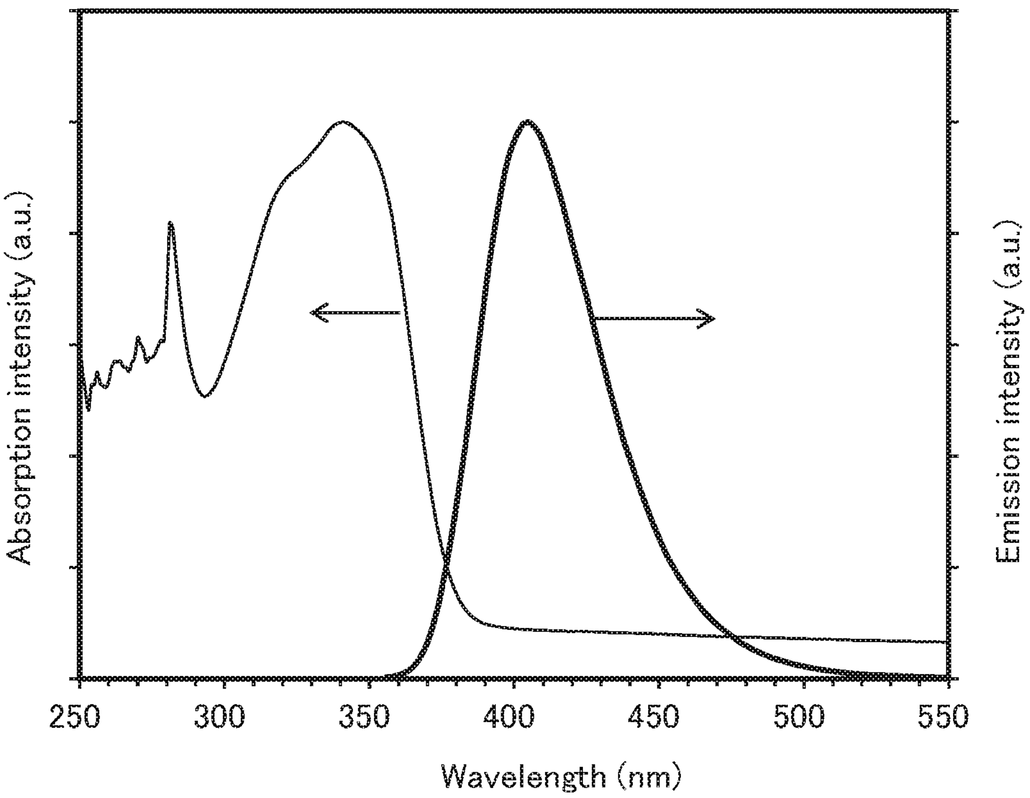
FIG. 105 shows an absorption spectrum and an emission spectrum of mmtBumTPFA in a toluene solution.

Next, an ultraviolet-visible absorption spectrum (hereinafter, simply referred to as an absorption spectrum) of mmtBumTPFA in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FP-8600, manufactured by JASCO Corporation), both of which were measured at room temperature. A quartz cell was used for the measurement cell. FIG. 105 shows measurement results of the absorption spectrum and the emission spectrum. The horizontal axis represents the wavelength and the vertical axes represent the absorption intensity and emission intensity. The absorption intensity shown in FIG. 105 is a result obtained by subtraction of an absorption spectrum of only toluene in a quartz cell from the measured absorption spectrum of the toluene solution in the quartz cell.

As shown in FIG. 105, the organic compound mmtBumTPFA has an emission peak at 405 nm.

Next, the organic compound mmtBumTPFA was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C4 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that mmtBumTPFA was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 737 which underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500. The detection results of the dissociated product ions by time-of-flight (TOF) MS are shown in FIG. 106.

Figure 106:
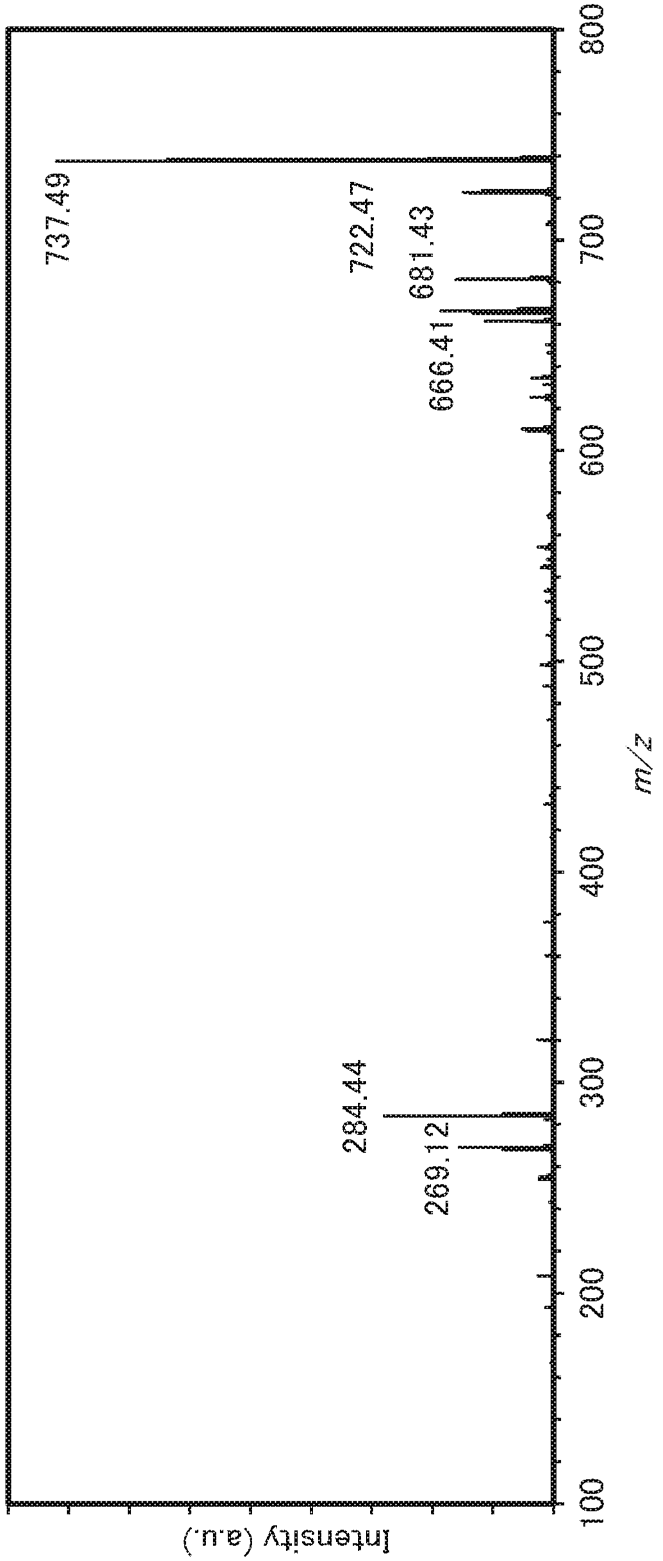
FIG. 106 shows an MS spectrum of mmtBumTPFA.

FIG. 106 shows that product ions of mmtBumTPFA are mainly detected at m/z of around 737. Note that the result in FIG. 106 shows characteristics derived from mmtBumTPFA and therefore can be regarded as important data for identifying mmtBumTPFA contained in a mixture.

FIG. 127 shows the results of measuring the refractive index of mmtBumTPFA by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 127.

FIG. 127 shows that mmtBumTPFA is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of mmtBumTPFA was measured. Tg was measured using a differential scanning calorimeter (a Perkin-Elmer Co., Ltd. Pyris 1 DSC) in a state where a powder was put on an aluminum cell. As a result, Tg of mmtBumTPFA was 110° C.

Example 20

Synthesis Example 14

In this example, a synthesis method of N-(1,1'-biphenyl-4-yl)-N-(3,3",5,5"-tetra-t-butyl-1,1':3',1"-terphenyl-5'-yl)-9,9-dimethyl-9H-fluoren-2-amine (abbreviation: mmtBumTPFBi), which is the organic compound represented by the structural formula (247) in Embodiment 1, is described. A structure of mmtBumTPFBi is shown below.

[Chemical Formula 93]

(247)

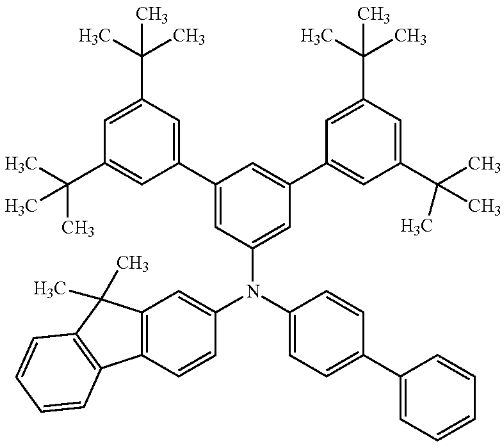

Step 1: Synthesis of 3,3",5,5"-tetra-t-butyl-5'-chloro-1,1':3',1"-terphenyl

The synthesis was performed in a manner similar to Step 1 of the synthesis example 11 in Example 11.

Step 2: Synthesis of N-(1,1'-biphenyl-4-yl)-N-(3,3",5,5"-tetra-t-butyl-1,1':3',1"-terphenyl-5'-yl)-9,9-dimethyl-9H-fluoren-2-amine (Abbreviation: mmtBumTPFBi)

In a three-neck flask were put 4.89 g (10 mmol) of 3,3",5,5"-tetra-t-butyl-5'-chloro-1,1':3',1"-terphenyl, 3.61 g (10 mmol) of N-(1,1'-biphenyl-4-yl)-9,9-dimethyl-9H-fluoren-2-amine, 2.88 g (30 mmol) of sodium-tert-butoxide, and 50 mL of xylene. The mixture was degassed under reduced pressure, and then the air in the flask was replaced with nitrogen. Then, 37 mg (0.10 mmol) of allylpalladium(II) chloride dimer (abbreviation: $[(Allyl)PdCl]_2$) and 164 mg (0.40 mmol) of di-tert-butyl(1-methyl-2,2-diphenylcyclopropyl)phosphine (abbreviation: cBRIDP (trademark)) were added to this mixture, and the mixture was stirred at 120° C. under a nitrogen stream for approximately 3 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at approximately 20° C. and the obtained solid was dried at approximately 80° C. under reduced pressure, so that 7.0 g of a target white solid was obtained in a yield of 86%. The synthesis scheme of Step 2 is shown below.

[Chemical Formula 94]

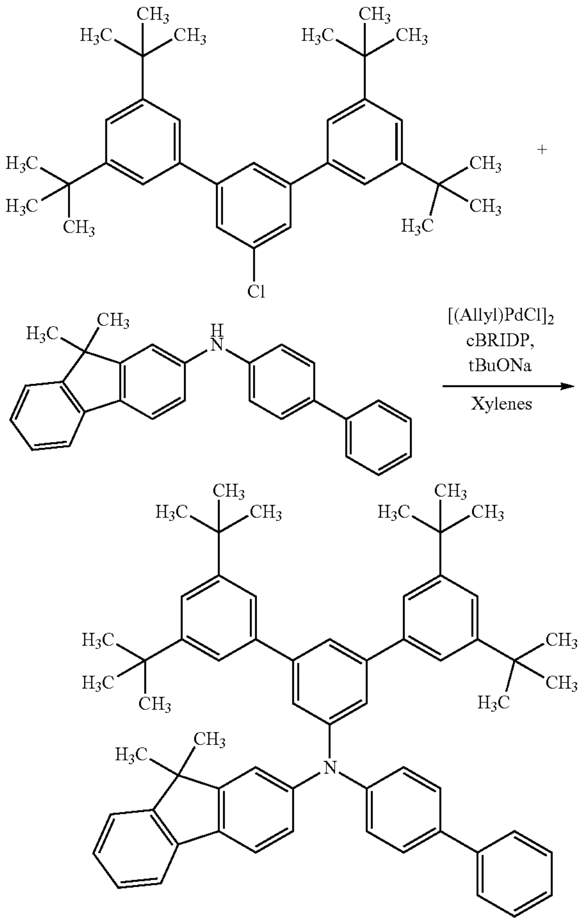

Then, 6.8 g of the obtained white solid was purified by a train sublimation method. The purification by sublimation was conducted by heating at 265° C. under a pressure of 3.0 Pa with the argon flow rate of 12.2 mL/min. After the purification by sublimation, 5.9 g of a pale yellowish white solid was obtained at a collection rate of 87%.

Figure 107A:
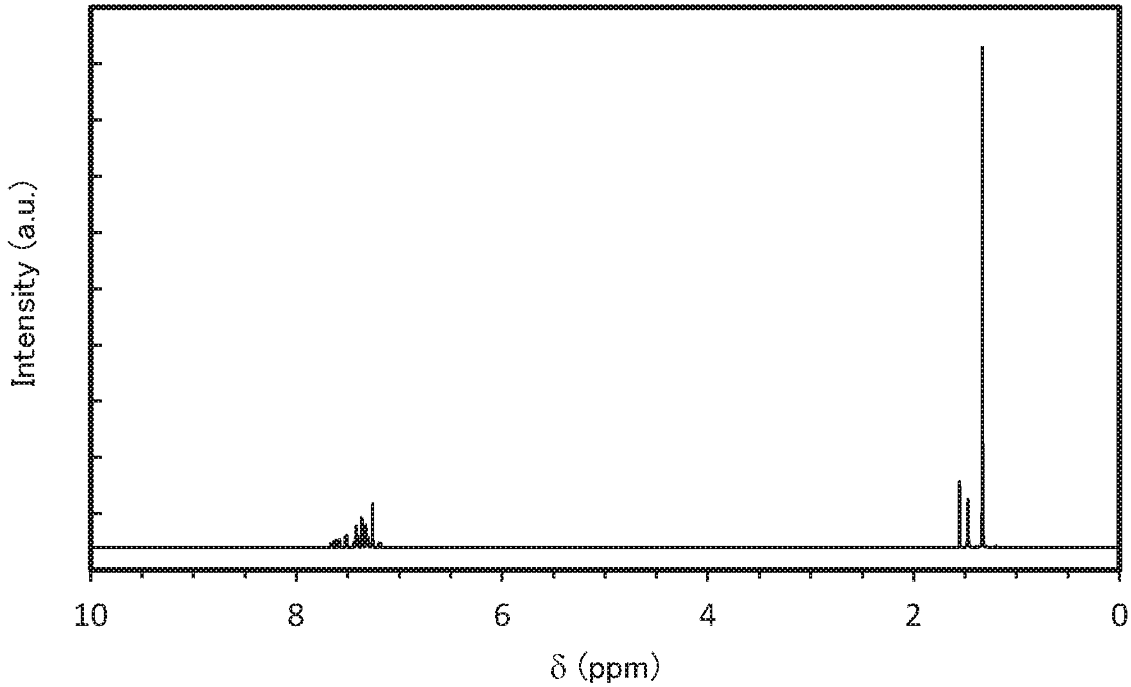
FIGS. 107A and 107B are $^1$H-NMR charts of mmtBumTPFBi.
Figure 107B:
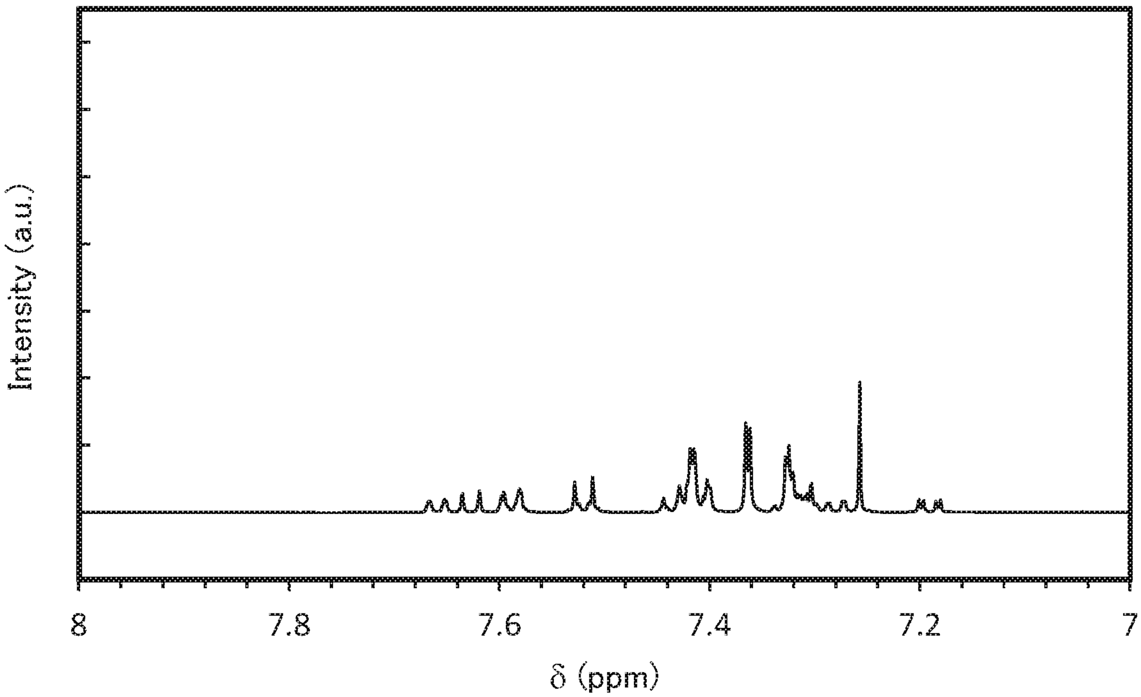

Analysis results by nuclear magnetic resonance spectroscopy ($^1H$-NMR) of the white solid obtained in Step 2 are shown below. FIGS. 107A and 107B are the $^1$H-NMR charts. The results show that the organic compound N-(1, 1'-biphenyl-4-yl)-N-(3,3",5,5"-tetra-t-butyl-1,1':3',1"-terphenyl-5'-yl)-9,9-dimethyl-9H-fluoren-2-amine (abbreviation: mmtBumTPFBi) was synthesized in this synthesis example.

$^1$H-NMR. δ ($CDCl_3$): 7.66 (d, 1H, J=7.5 Hz), 7.63 (d, 1H, J=8.0 Hz), 7.59 (d, 2H, J=7.5 Hz), 7.52 (dt, 2H, J=2.0 Hz, 8.5 Hz), 7.39-7.45 (m, 7H), 7.36 (d, 4H, J=2.5 Hz), 7.29-7.34 (m, 6H), 7.26-7.29 (m, 1H), 7.19 (dd, 1H, J=2.5 Hz, 8.0 Hz), 1.47 (s, 6H), 1.33 (s, 36H).

Figure 108:
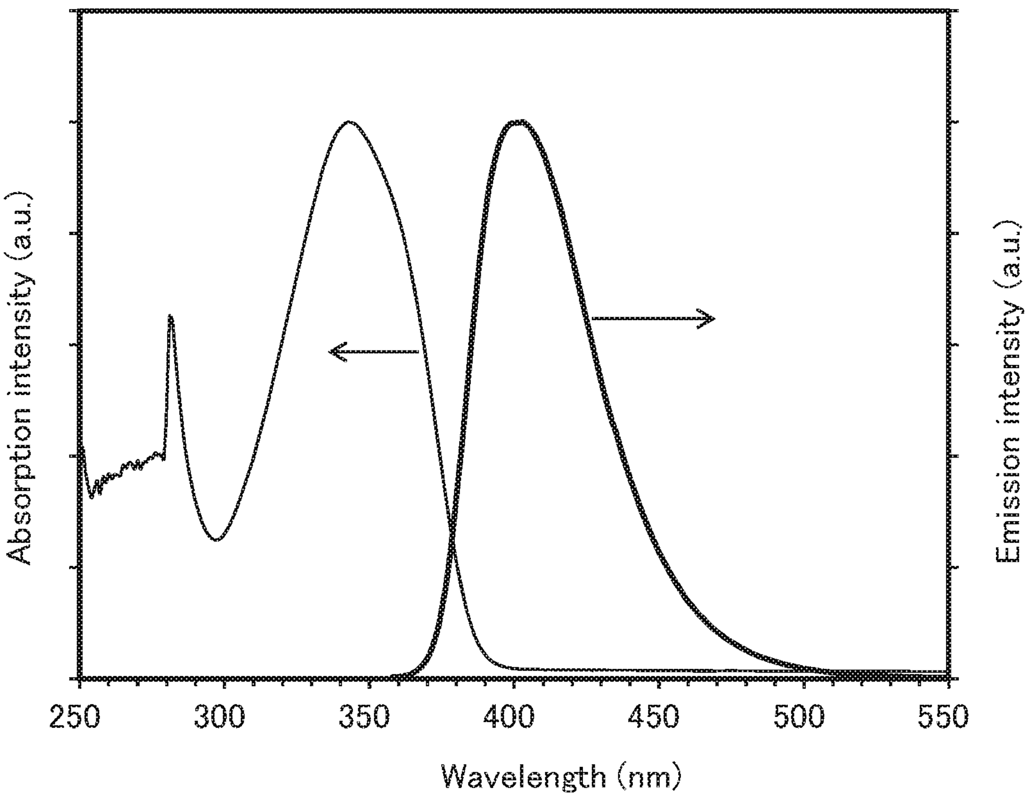
FIG. 108 shows an absorption spectrum and an emission spectrum of mmtBumTPFBi in a toluene solution.

Next, an ultraviolet-visible absorption spectrum (hereinafter, simply referred to as an absorption spectrum) of mmtBumTPFBi in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FP-8600, manufactured by JASCO Corporation), both of which were measured at room temperature. A quartz cell was used for the measurement cell. FIG. 108 shows measurement results of the absorption spectrum and the emission spectrum. The horizontal axis represents the wavelength and the vertical axes represent the absorption intensity and emission intensity. The absorption intensity shown in FIG. 108 is a result obtained by subtraction of an absorption spectrum of only toluene in a quartz cell from the measured absorption spectrum of the toluene solution in the quartz cell.

As shown in FIG. 108, the organic compound mmtBumTPFBi has an emission peak at 403 nm.

Next, the organic compound mmtBumTPFBi was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C4 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that mmtBumTPFBi was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 814 which underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500. The detection results of the dissociated product ions by time-of-flight (TOF) MS are shown in FIG. 109.

Figure 109:
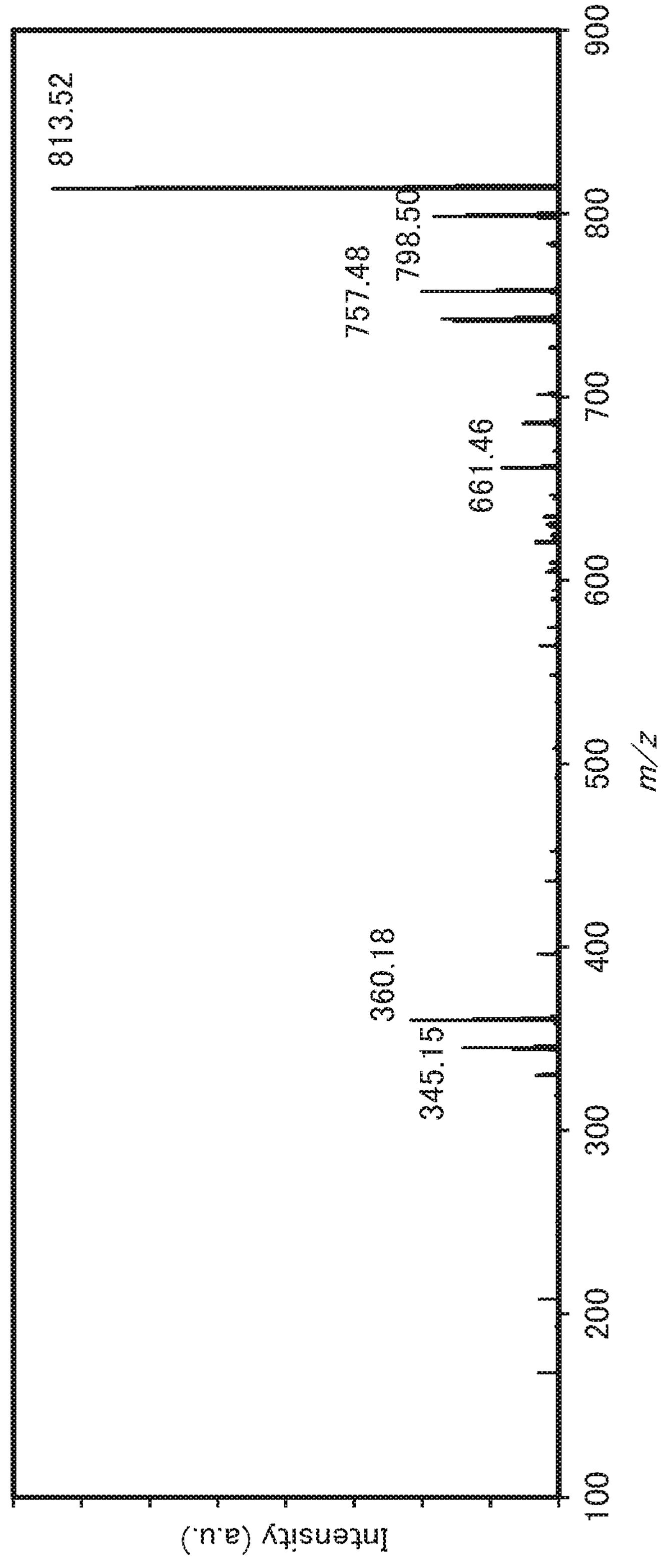
FIG. 109 shows an MS spectrum of mmtBumTPFBi.

FIG. 109 shows that product ions of mmtBumTPFBi are mainly detected at m/z of around 814. Note that the result in FIG. 109 shows characteristics derived from mmtBumTPFBi and therefore can be regarded as important data for identifying mmtBumTPFBi contained in a mixture.

FIG. 128 shows the results of measuring the refractive index of mmtBumTPFBi by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 128.

FIG. 128 shows that mmtBumTPFBi is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of mmtBumTPFBi was measured. Tg was measured using a differential scanning calorimeter (a Perkin-Elmer Co., Ltd. Pyris 1 DSC) in a state where a powder was put on an aluminum cell. As a result, Tg of mmtBumTPFBi was 126° C.

Example 21

Synthesis Example 15

In this example, a synthesis method of N-(1,1'-biphenyl-2-yl)-N-(3,3",5,5"-Tetra-t-butyl-1,1':3',1"-terphenyl-5'-yl)-9,9-dimethyl-9H-fluoren-2-amine (abbreviation: mmtBumTPoFBi), which is the organic compound represented by the structural formula (248) in Embodiment 1, is described. A structure of mmtBumTPoFBi is shown below.

[Chemical Formula 95]

(248)

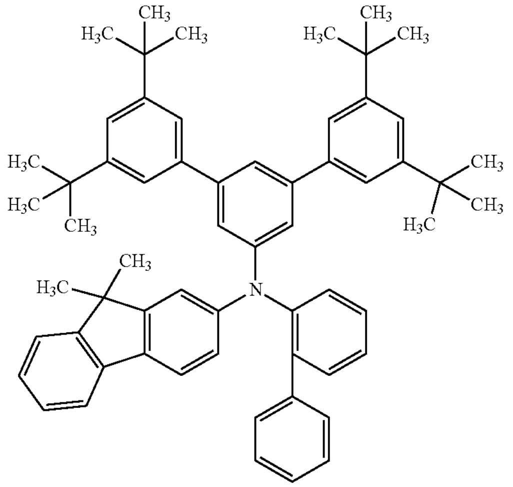

Step 1: Synthesis of 3,3",5,5"-tetra-t-butyl-5'-chloro-1,1':3,1"-terphenyl

The synthesis was performed in a manner similar to Step 1 of the synthesis example 11 in Example 11.

Step 2: Synthesis of N-(1,1'-biphenyl-2-yl)-N-(3,3", 5,5"-Tetra-t-butyl-1,1':3',1"-terphenyl-5'-yl)-9,9-dimethyl-9H-fluoren-2-amine (Abbreviation: mmtBumTPoFBi)

In a three-neck flask were put 4.89 g (10 mmol) of 13,3",5,5"-tetra-t-butyl-5'-chloro-1,1:3',1"-terphenyl, 3.61 g (10 mmol) of N-(1,1'-biphenyl-2-yl)-9,9-dimethyl-9H-fluoren-2-amine, 2.88 g (30 mmol) of sodium-tert-butoxide, and 50 mL of xylene. The mixture was degassed under reduced pressure, and then the air in the flask was replaced with nitrogen. Then, 37 mg (0.10 mmol) of allylpalladium(II) chloride dimer (abbreviation: $[(Allyl)PdCl]_2$) and 164 mg (0.40 mmol) of di-ter-butyl(1-methyl-2,2-diphenylcyclopropyl)phosphine (abbreviation: cBRIDP (registered trademark)) were added to this mixture, and the mixture was stirred at 120° C. under a nitrogen stream for approximately 7 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained fraction was concentrated to give a condensed toluene solution. Ethanol was added to this toluene solution and the toluene solution was concentrated under reduced pressure, whereby an ethanol suspension was obtained. The precipitate was filtrated at approximately 20° C. and the obtained solid was dried at approximately 80° C. under reduced pressure, so that 6.86 g of a target white solid was obtained in a yield of 93%. The synthesis scheme of Step 2 is shown below.

[Chemical Formula 96]

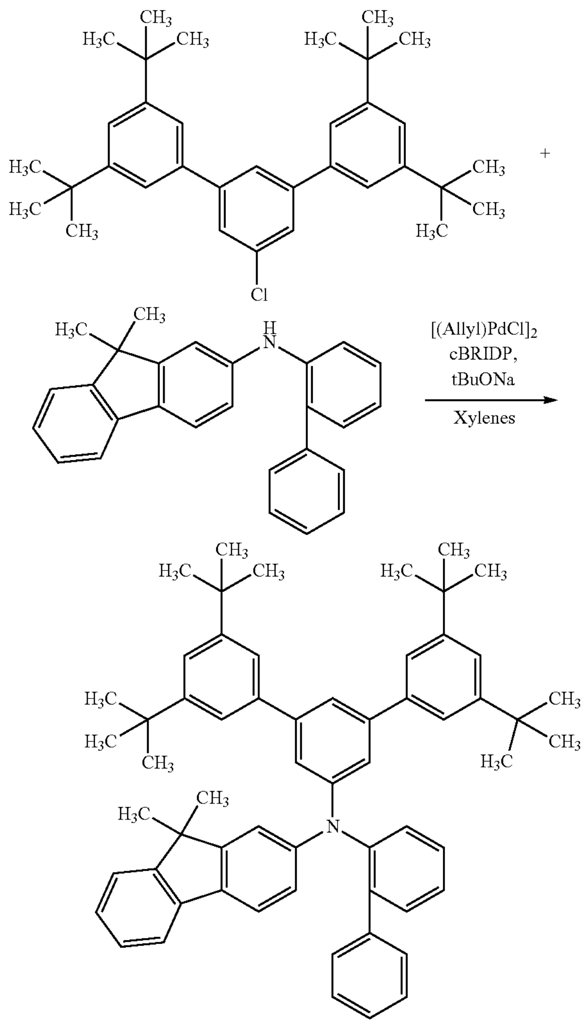

Then, 4.0 g of the obtained white solid was purified by a train sublimation method. The purification by sublimation was conducted by heating at 245° C. under a pressure of 3.0 Pa with the argon flow rate of 20.1 mL/min. After the purification by sublimation, 3.8 g of a pale yellowish white solid was obtained at a collection rate of 94%.

Figure 110A:
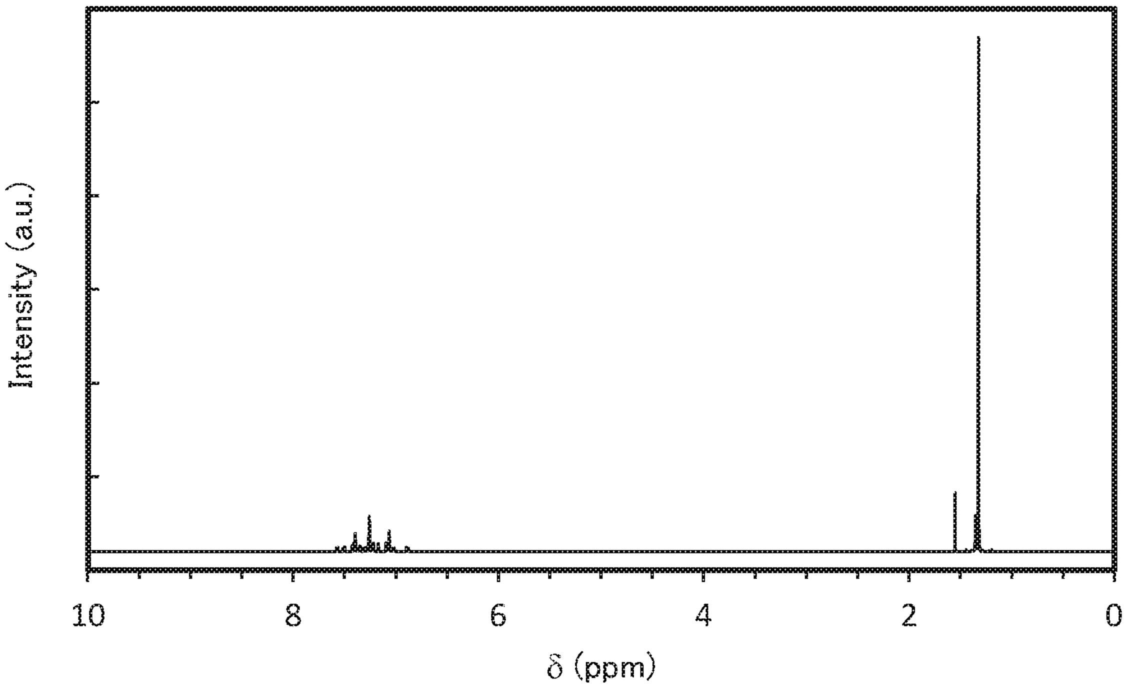
FIGS. 110A and 110B are $^1$H-NMR charts of mmtBumTPoFBi.
Figure 110B:
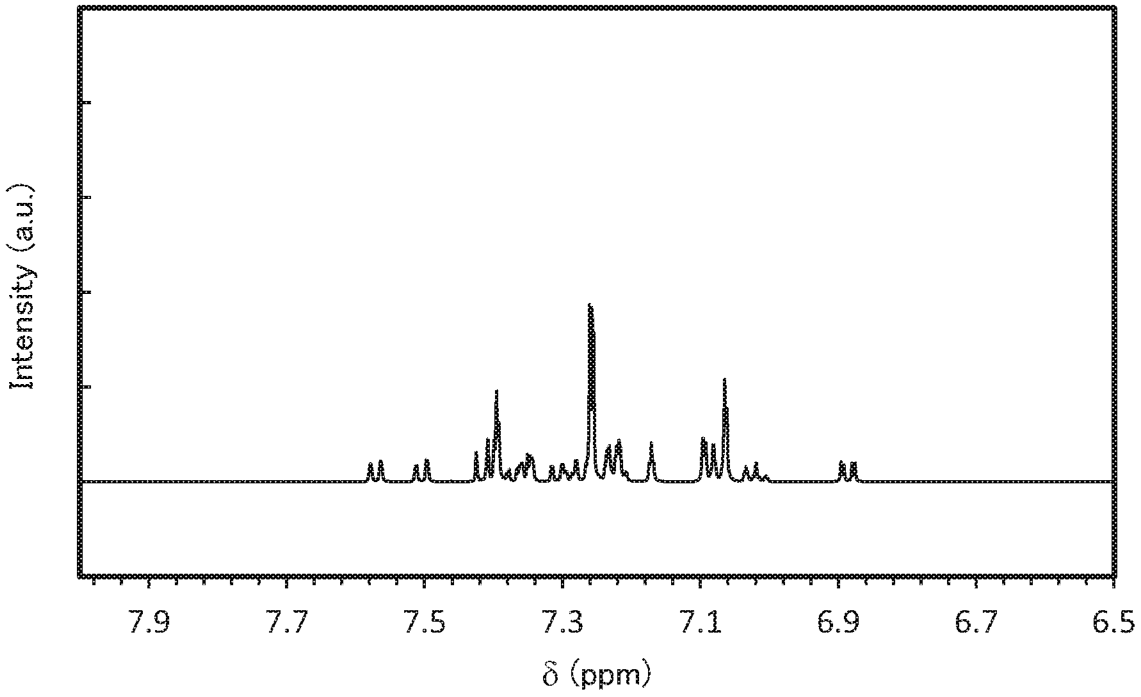

Analysis results by nuclear magnetic resonance spectroscopy ($^1$H-NMR) of the white solid obtained in Step 2 are shown below. FIGS. 110A and 110B are the $^1$H-NMR charts. The results show that the organic compound N-(1,1'-biphenyl-2-yl)-N-(3,3",5,5"-Tetra-t-butyl-1,1':3',1"-terphenyl-5'-yl)-9,9-dimethyl-9H-fluoren-2-amine (abbreviation: mmtBumTPoFBi) was synthesized in this synthesis example.

$^1$H-NMR. δ ($CDCl_3$): 7.57 (d, 1H, J=7.5 Hz), 7.50 (dd, 1H, J=1.5 Hz, 8.0 Hz), 7.33-7.44 (m, 6H), 7.27-7.32 (m, 2H), 7.26 (d, 4H, J=1.0 Hz), 7.20-7.24 (m, 3H), 7.17 (t, 1H, J=1.5 Hz), 7.05-7.11 (m, 5H), 6.99-7.04 (m, 1H), 6.89 (dd, 1H, J=2.0 Hz, 8.0 Hz), 1.35 (s, 6H), 1.32 (s, 26H).

Figure 111:
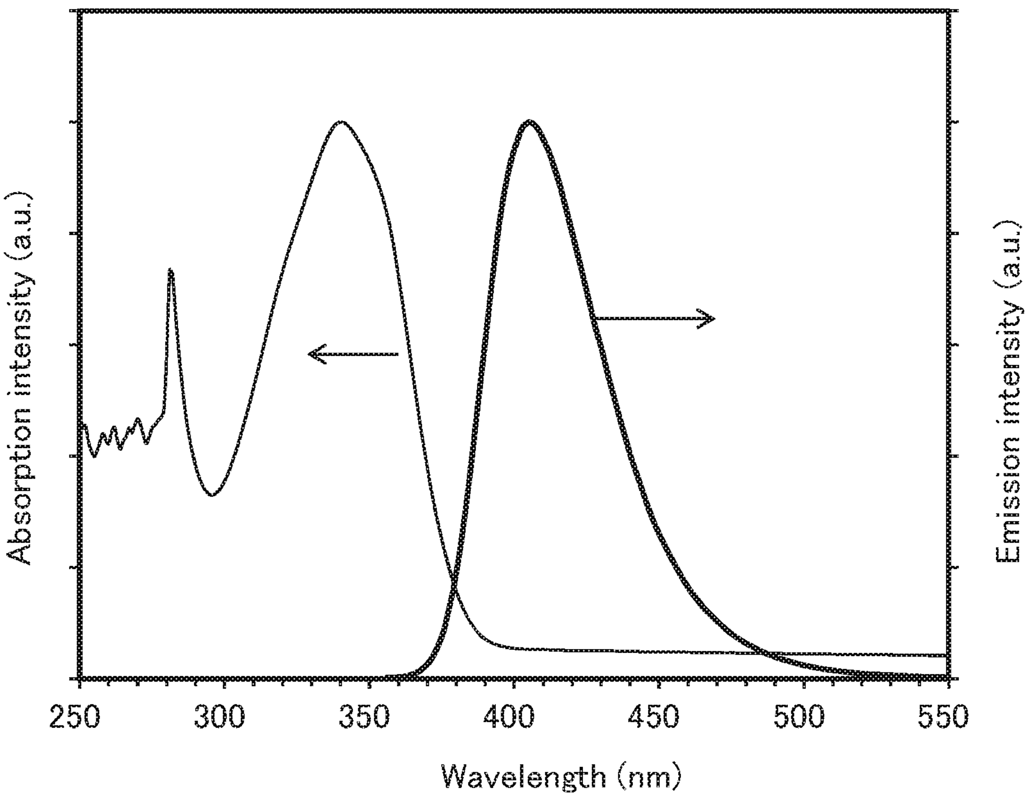
FIG. 111 shows an absorption spectrum and an emission spectrum of mmtBumTPoFBi in a toluene solution.

Next, an ultraviolet-visible absorption spectrum (hereinafter, simply referred to as an absorption spectrum) of mmtBumTPoFBi in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FP-8600, manufactured by JASCO Corporation), both of which were measured at room temperature. A quartz cell was used for the measurement cell. FIG. 111 shows measurement results of the absorption spectrum and the emission spectrum. The horizontal axis represents the wavelength and the vertical axes represent the absorption intensity and emission intensity. The absorption intensity shown in FIG. 111 is a result obtained by subtraction of an absorption spectrum of only toluene in a quartz cell from the measured absorption spectrum of the toluene solution in the quartz cell.

As shown in FIG. 111, the organic compound mmtBumTPoFBi has an emission peak at 405 nm.

Next, the organic compound mmtBumTPoFBi was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C4 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that mmtBumTPoFBi was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 814 which underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500.

Figure 112:
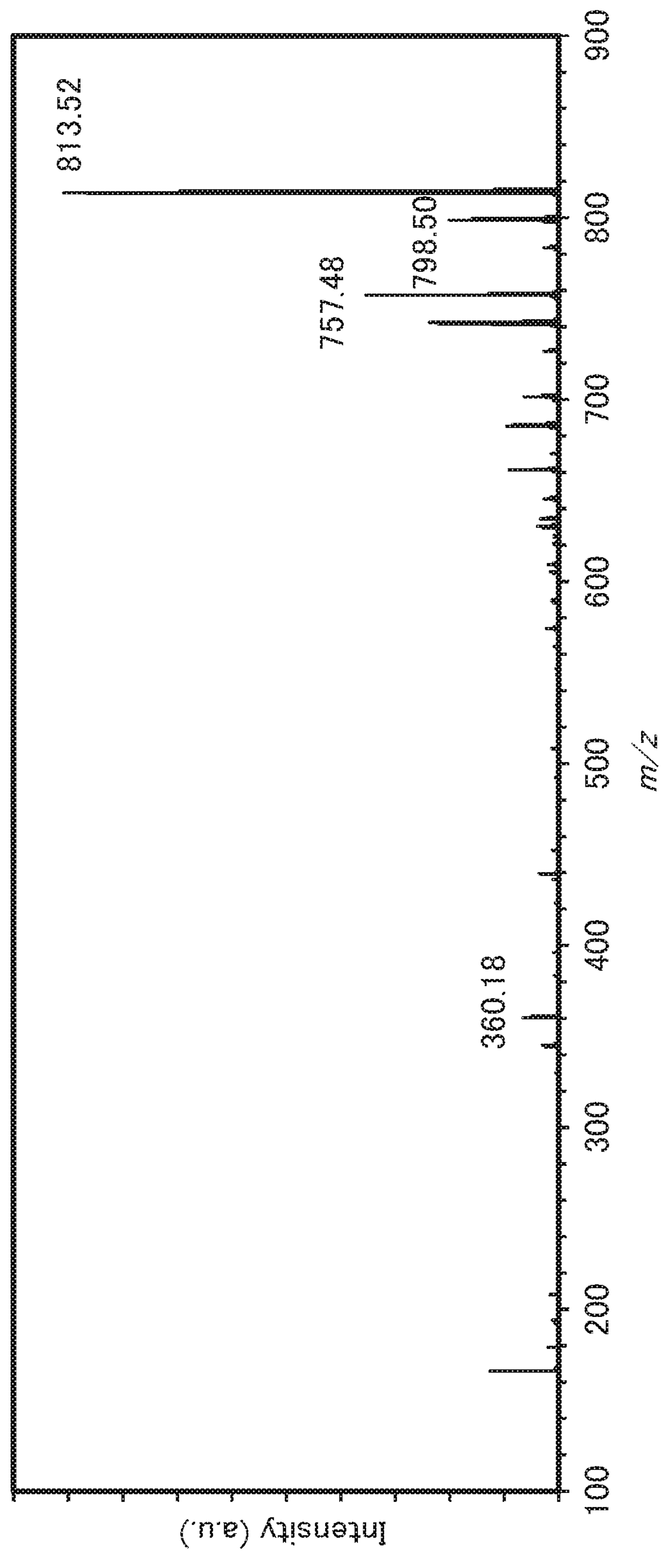
FIG. 112 shows an MS spectrum of mmtBumTPoFBi.

The detection results of the dissociated product ions by time-of-flight (TOF) MS are shown in FIG. 112.

FIG. 112 shows that product ions of mmtBumTPoFBi are mainly detected at m/z of around 814. Note that the result in FIG. 112 shows characteristics derived from mmtBumTPoFBi and therefore can be regarded as important data for identifying mmtBumTPoFBi contained in a mixture.

FIG. 129 shows the results of measuring the refractive index of mmtBumTPoFBi by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 129.

FIG. 129 shows that mmtBumTPoFBi is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of mmtBumTPoFBi was measured. Tg was measured using a differential scanning calorimeter (a Perkin-Elmer Co., Ltd. Pyris 1 DSC) in a state where a powder was put on an aluminum cell. As a result, Tg of mmtBumTPoFBi was 120° C.

Example 22

Synthesis Example 16

In this example, a synthesis method of N-[(3,3',5'-tri-t-butyl)-1,1'-biphenyl-5-yl]-N-(4-cyclohexylphenyl)-9,9-dimethyl-9H-fluoren-2-amine (abbreviation: mmtBumBichPAF), which is the organic compound of one embodiment of the present invention, is described. A structure of mmtBumBichPAF is shown below.

[Chemical Formula 97]

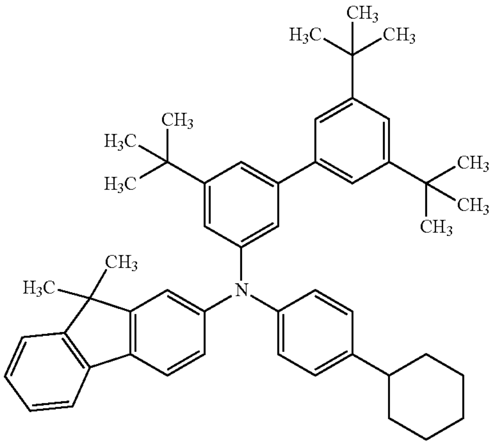

Step 1: Synthesis of 3-bromo-3',5,5'-tri-tert-butylbiphenyl

In a three-neck flask were put 37.2 g (128 mmol) of 1,3-dibromo-5-tert-butylbenzene, 20.0 g (85 mmol) of 3,5-di-tert-butylphenylboronic acid, 35.0 g (255 mmol) of potassium carbonate, 570 mL of toluene, 170 mL of ethanol, and 130 mL of tap water. The mixture was degassed under reduced pressure, and then the air in the flask was replaced with nitrogen. Then, 382 mg (1.7 mmol) of palladium acetate and 901 mg (3.4 mmol) of triphenylphosphine were added, and the mixture was heated at 40° C. for approximately 5 hours. After that, the temperature of the flask was lowered to room temperature and the mixture was separated into an organic layer and an aqueous layer. Magnesium sulfate was added to the solution for drying and concentration. The obtained hexane solution was purified by silica gel column chromatography, whereby 21.5 g of a target colorless oily substance was obtained in a yield of 63%. The synthesis scheme of 3-bromo-3',5,5'-tri-tert-butylbiphenyl in Step 1 is shown below.

[Chemical Formula 98]

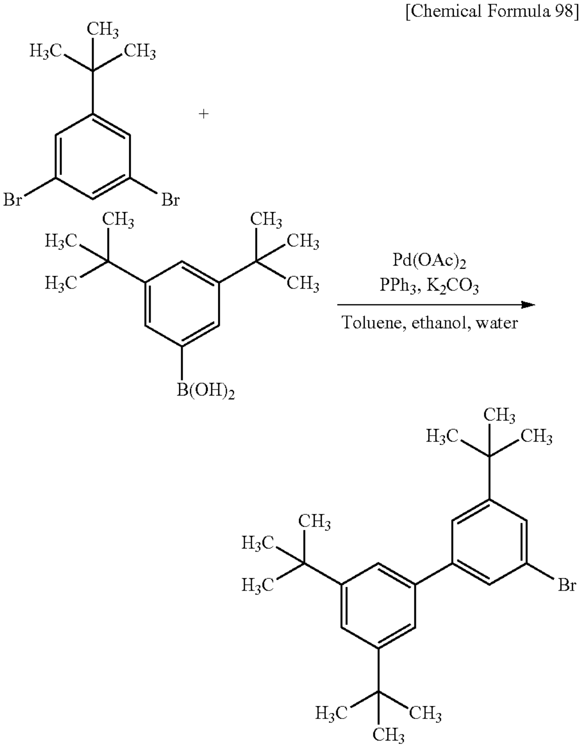

Step 2: Synthesis of N-[(3,3',5'-tri-t-butyl)-1,1'-biphenyl-5-yl]-N-(4-cyclohexylphenyl)-9,9-dimethyl-9H-fluoren-2-amine (Abbreviation: mmtBumBichPAF)

In a three-neck flask were put 2.6 g (6.5 mmol) of 3-bromo-3',5,5'-tri-tert-butylbiphenyl obtained in Step 1, 2.4 g (6.5 mmol) of N-(4-cyclohexylphenyl)-9,9-dimethyl-9H-fluoren-2-amine, 2.0 g (20 mmol) of sodium-tert-butoxide, and 40 mL of xylene. The mixture was degassed under reduced pressure, and then the air in the flask was replaced with nitrogen. Then, 75 mg (0.13 mmol) of bis(dibenzylideneacetone)palladium(0) and 165 mg (0.39 mmol) of 2-dicyclohexylphosphino-2',6'-dimethoxybiphenyl (abbreviation: Sphos (registered trademark)) were added to this mixture, and the mixture was stirred at 120° C. under a nitrogen stream for approximately 7 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained fraction was concentrated to give a condensed toluene solution. Ethanol was added to this toluene solution and the toluene solution was concentrated under reduced pressure, whereby an ethanol suspension was obtained. The precipitate was filtrated at approximately 20° C. and the obtained solid was dried at approximately 80° C. under reduced pressure, whereby 3.9 g of a target white solid was obtained in a yield of 87%. The synthesis scheme of Step 2 is shown below.

[Chemical Formula 99]

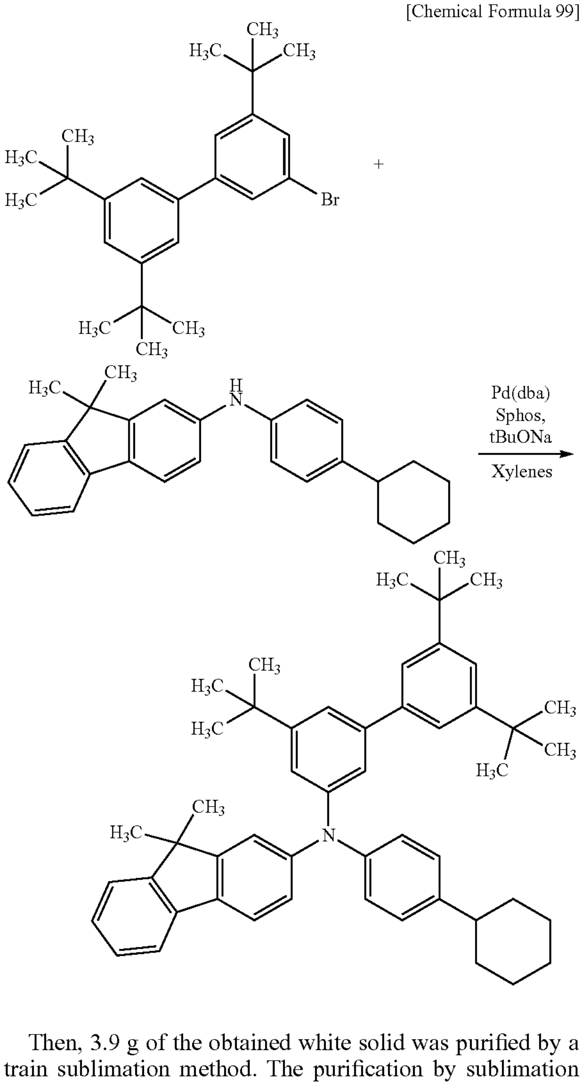

Then, 3.9 g of the obtained white solid was purified by a train sublimation method. The purification by sublimation was conducted by heating at 235° C. under a pressure of 3.6 Pa with the argon flow rate of 15 mL/min. After the purification by sublimation, 2.7 g of a white solid was obtained at a collection rate of 65%.

Figure 113A:
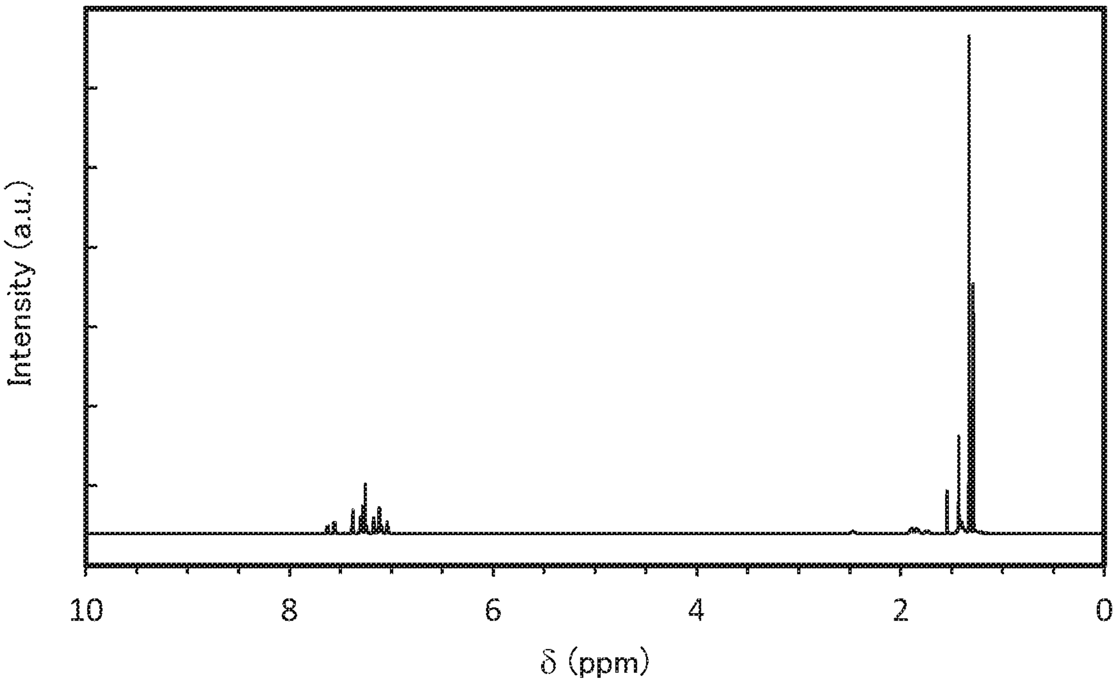
FIGS. 113A and 113B are $^1$H-NMR charts of mmtBumBichPAF.
Figure 113B:
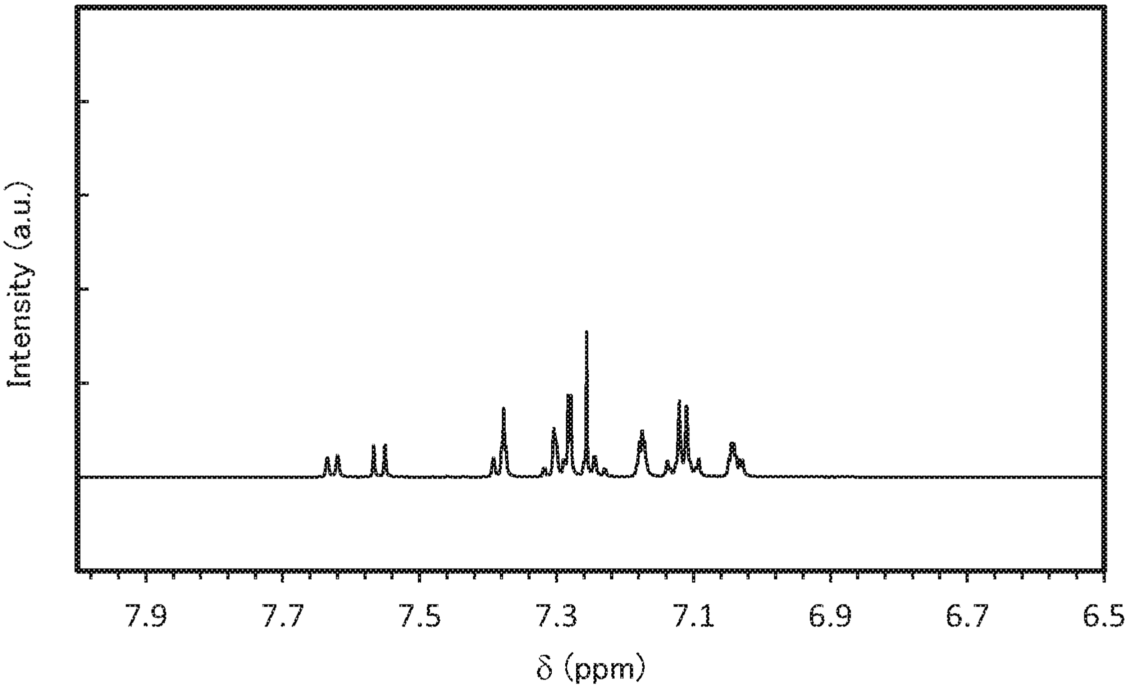

Analysis results by nuclear magnetic resonance spectroscopy (H-NMR) of the white solid obtained in Step 2 are shown below. FIGS. 113A and 113B are the $^1$H-NMR charts. The results show that the organic compound N-[(3,3',5'-tri-t-butyl)-1,1'-biphenyl-5-yl]-N-(4-cyclohexylphenyl)-9,9-dimethyl-9H-fluoren-2-amine (abbreviation: mmtBumBichPAF was synthesized in this synthesis example.

$^1$H-NMR. δ ($CDCl_3$): 7.63 (d, 1H, J=7.5 Hz), 7.56 (d, 1H, J=8.5 Hz), 7.37-40 (m, 2H), 7.27-7.32 (m, 4H), 7.22-7.25 (m, 1H), 7.16-7.19 (brm, 2H), 7.08-7.15 (m, 4H), 7.02-7.06 (m, 2H), 2.43-2.51 (brm, 1H), 1.80-1.93 (brm, 4H), 1.71-1.77 (brm, 1H), 1.36-1.46 (brm, 10H), 1.33 (s, 18H), 1.22-1.30 (brm, 10H).

Figure 114:
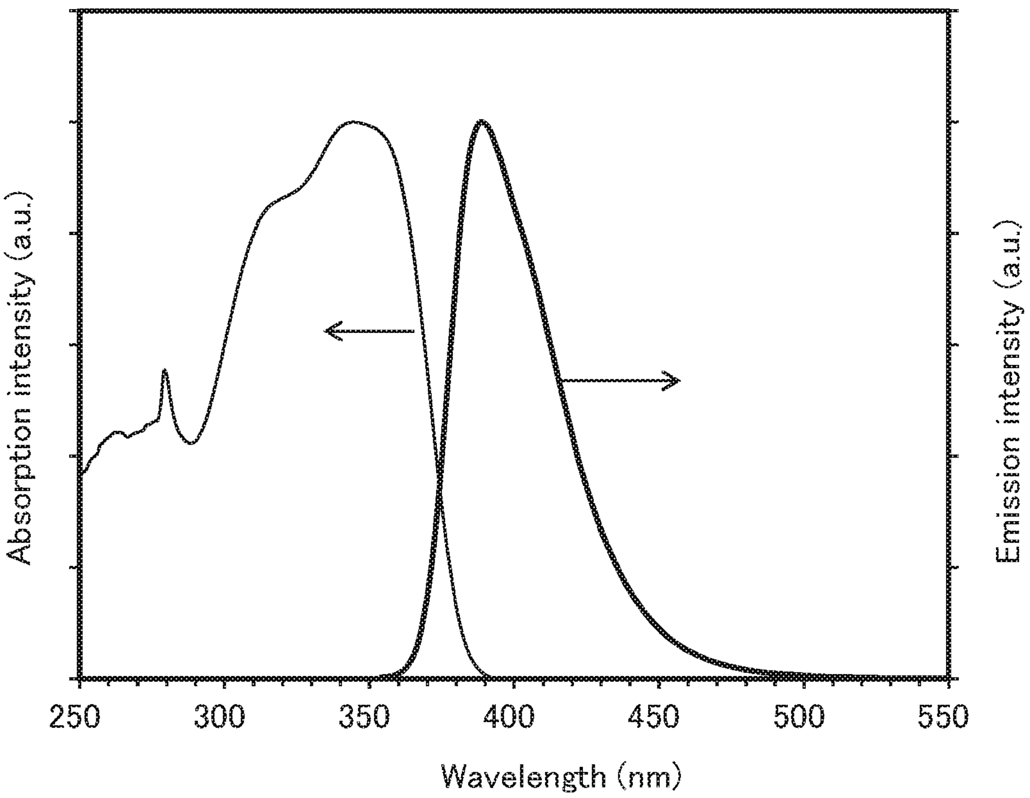
FIG. 114 shows an absorption spectrum and an emission spectrum of mmtBumBichPAF in a toluene solution.

Next, an ultraviolet-visible absorption spectrum (hereinafter, simply referred to as an absorption spectrum) of mmtBumBichPAF in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FP-8600, manufactured by JASCO Corporation), both of which were measured at room temperature. A quartz cell was used for the measurement cell. FIG. 114 shows measurement results of the absorption spectrum and the emission spectrum. The horizontal axis represents the wavelength and the vertical axes represent the absorption intensity and emission intensity. The absorption intensity shown in FIG. 114 is a result obtained by subtraction of an absorption spectrum of only toluene in a quartz cell from the measured absorption spectrum of the toluene solution in the quartz cell.

As shown in FIG. 114, the organic compound mmtBumBichPAF has an emission peak at 391 nm.

Next, the organic compound mmtBumBichPAF was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C4 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that mmtBumBichPAF was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 688 which underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500. The detection results of the dissociated product ions by time-of-flight (TOF) MS are shown in FIG. 115.

Figure 115:
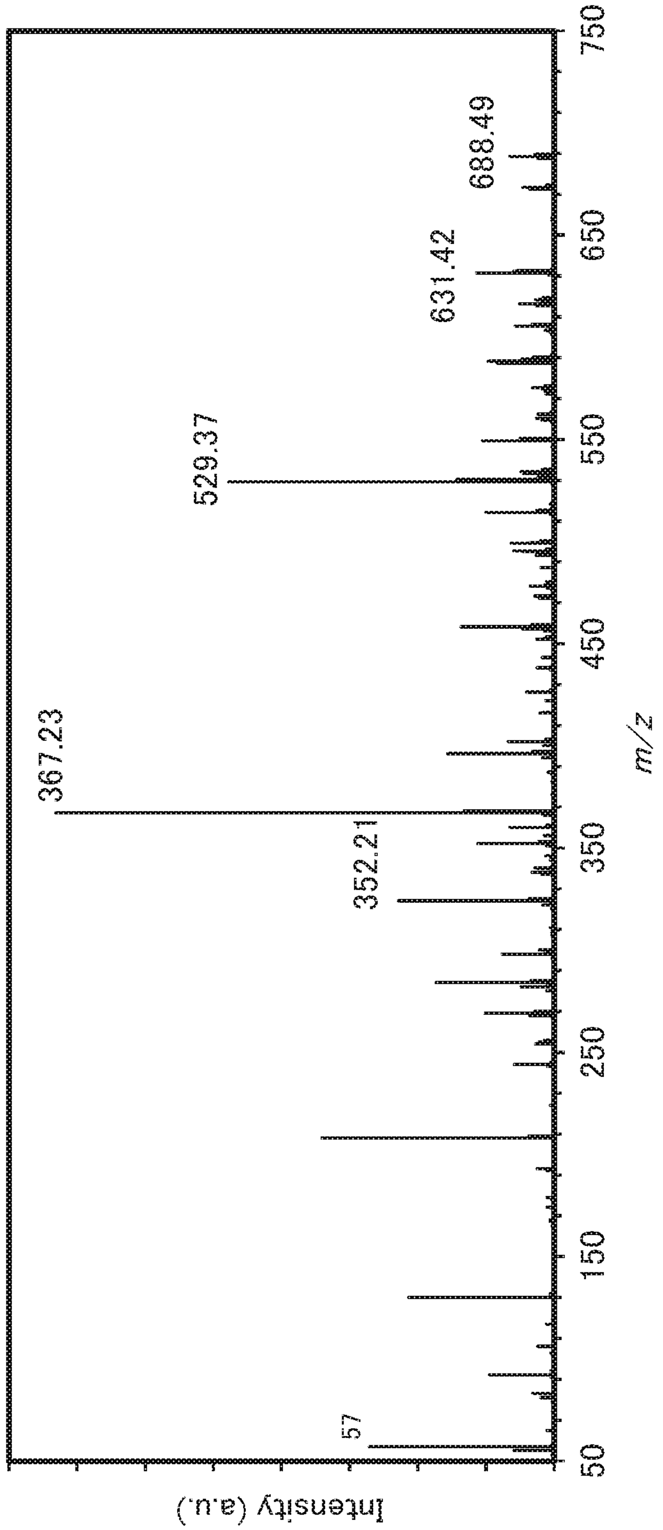
FIG. 115 shows an MS spectrum of mmtBumBichPAF.

FIG. 115 shows that product ions of mmtBumBichPAF are mainly detected at m/z of around 688. Note that the result in FIG. 115 shows characteristics derived from mmtBumBichPAF and therefore can be regarded as important data for identifying mmtBumBichPAF contained in a mixture.

FIG. 130 shows the results of measuring the refractive index of mmtBumBichPAF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 130.

FIG. 130 shows that mmtBumBichPAF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of mmtBumBichPAF was measured. Tg was measured using a differential scanning calorimeter (a Perkin-Elmer Co., Ltd. Pyris 1 DSC) in a state where a powder was put on an aluminum cell. As a result, Tg of mmtBumBichPAF was 103° C.

Example 23

Synthesis Example 17

In this example, a synthesis method of N-(1,1'-biphenyl-2-yl)-N-[(3,3',5'-tri-t-butyl)-1,1'-biphenyl-5-yl)-9,9-dimethyl-9H-fluoren-2-amine (abbreviation: mmtBumBioFBi), which is the organic compound of one embodiment of the present invention, is described. A structure of mmtBumBioFBi is shown below.

[Chemical Formula 100]

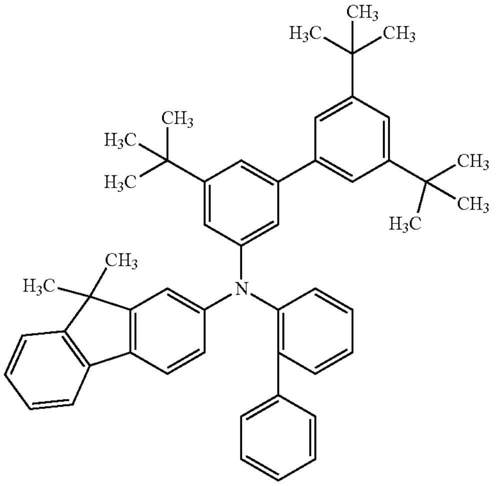

Step 1: Synthesis of 3-bromo-3',5,5'-tri-tert-butylbiphenyl

The synthesis was performed in a manner similar to Step 1 of the synthesis example 16 in Example 22.

Step 2: Synthesis of N-(1,1'-biphenyl-2-yl)-N-[(3,3',5'-tri-t-butyl)-1,1'-biphenyl-5-yl)-9,9-dimethyl-9H-fluoren-2-amine (Abbreviation: mmtBumBioFBi)

In a three-neck flask were put 3.0 g (7.5 mmol) of 3-bromo-3',5,5'-tri-tert-butylbiphenyl obtained in Step 1, 2.7 g (7.5 mmol) of N-(1,1'-biphenyl-2-yl)-9,9-dimethyl-9H-fluoren-2-amine, 2.2 g (23 mmol) of sodium-tert-butoxide, and 40 mL of xylene. The mixture was degassed under reduced pressure, and then the air in the flask was replaced with nitrogen. Then, 86 mg (0.15 mmol) of bis(dibenzylideneacetone)palladium(0) and 184 mg (0.45 mmol) of 2-dicyclohexylphosphino-2',6'-dimethoxybiphenyl (abbreviation: Sphos (registered trademark)) were added to this mixture, and the mixture was stirred at 120° C. under a nitrogen stream for approximately 7 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained fraction was concentrated to give a condensed toluene solution. Ethanol was added to this toluene solution and the toluene solution was concentrated under reduced pressure, whereby an ethanol suspension was obtained. The precipitate was filtrated at approximately 20° C. and the obtained solid was dried at approximately 80° C. under reduced pressure, whereby 4.0 g of a target white solid was obtained in a yield of 78%. The synthesis scheme of Step 2 is shown below.

[Chemical Formula 101]

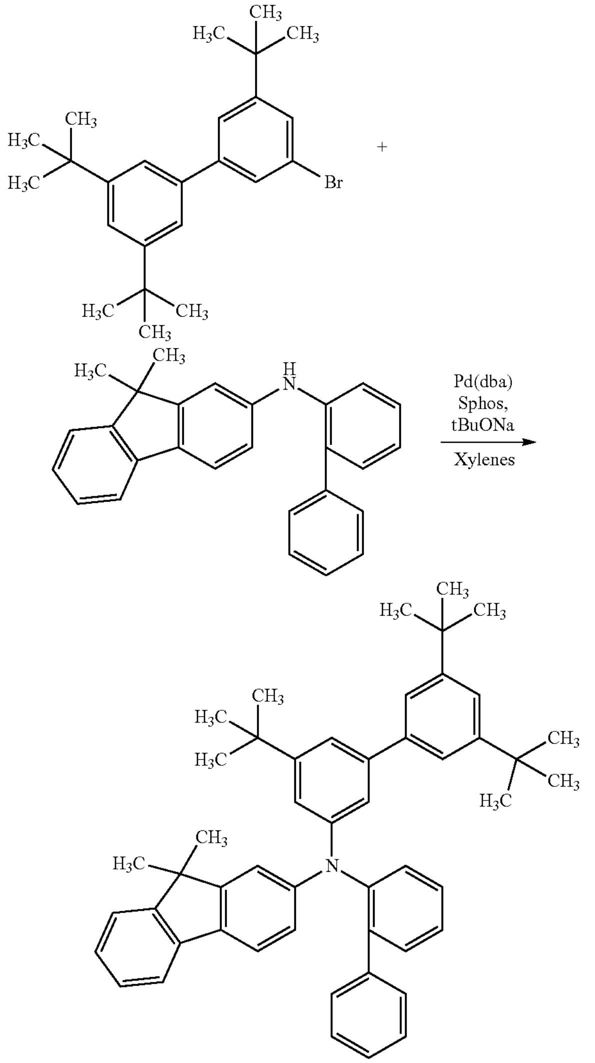

Then, 4.0 g of the obtained white solid was purified by a train sublimation method. The purification by sublimation was conducted by heating at 245° C. under a pressure of 4.0 Pa with the argon flow rate of 15 mL/min. After the purification by sublimation, 2.8 g of a white solid was obtained at a collection rate of 70%.

Figure 116A:
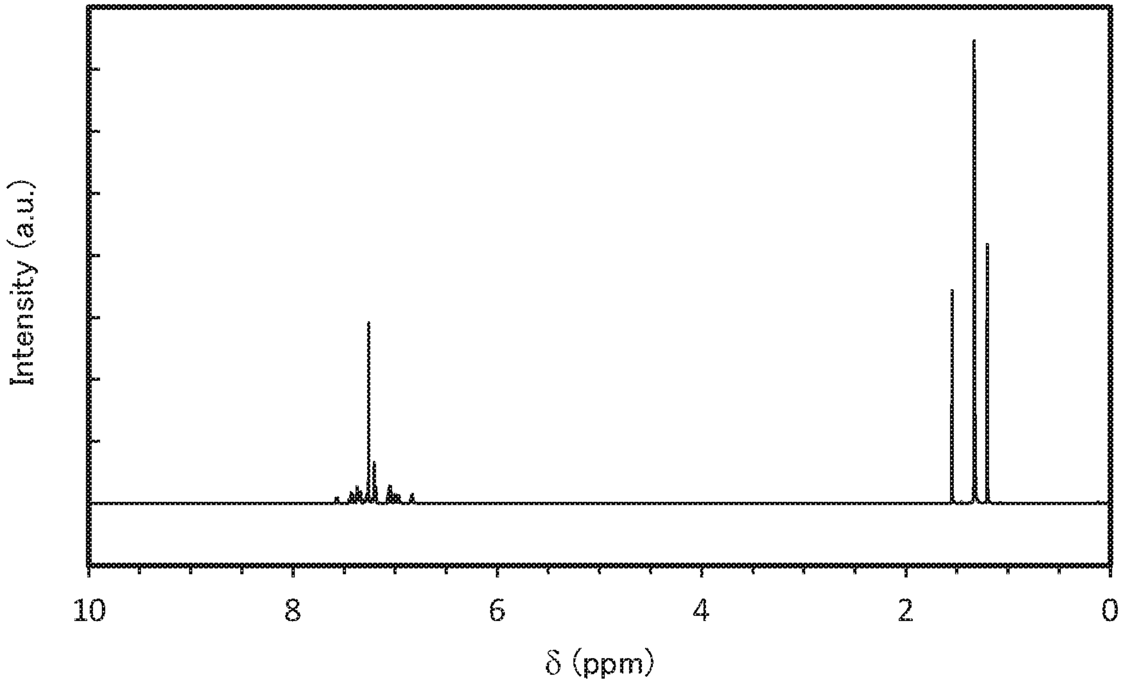
FIGS. 116A and 116B are $^1$H-NMR charts of mmtBumBioFBi.
Figure 116B:
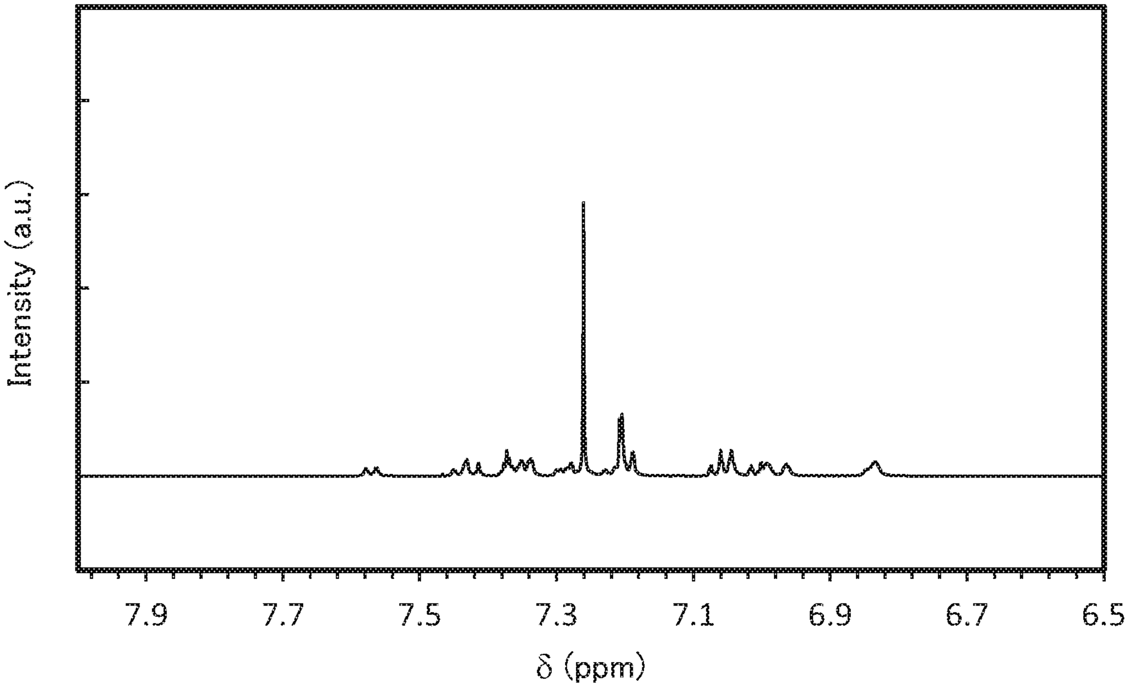

Analysis results by nuclear magnetic resonance spectroscopy ($^1$H-NMR) of the white solid obtained in Step 2 are shown below. FIGS. 116A and 116B are the $^1$H-NMR charts. The results show that the organic compound N-(1,1'-biphenyl-2-yl)-N-[(3,3',5'-tri-t-butyl)-1,1'-biphenyl-5-yl)-9,9-dimethyl-9H-fluoren-2-amine (abbreviation: mmtBumBioFBi) was synthesized in this synthesis example.

$^1$H-NMR. δ ($CDCl_3$): 7.57 (d, 1H, J=7.5 Hz), 7.40-7.47 (m, 2H), 7.32-7.39 (m, 4H), 7.27-7.31 (m, 2H), 7.27-7.24 (m, 5H), 6.94-7.09 (m, 6H), 6.83 (brs, 2H), 1.33 (s, 18H), 1.32 (s, 6H), 1.20 (s, 9H).

Figure 117:
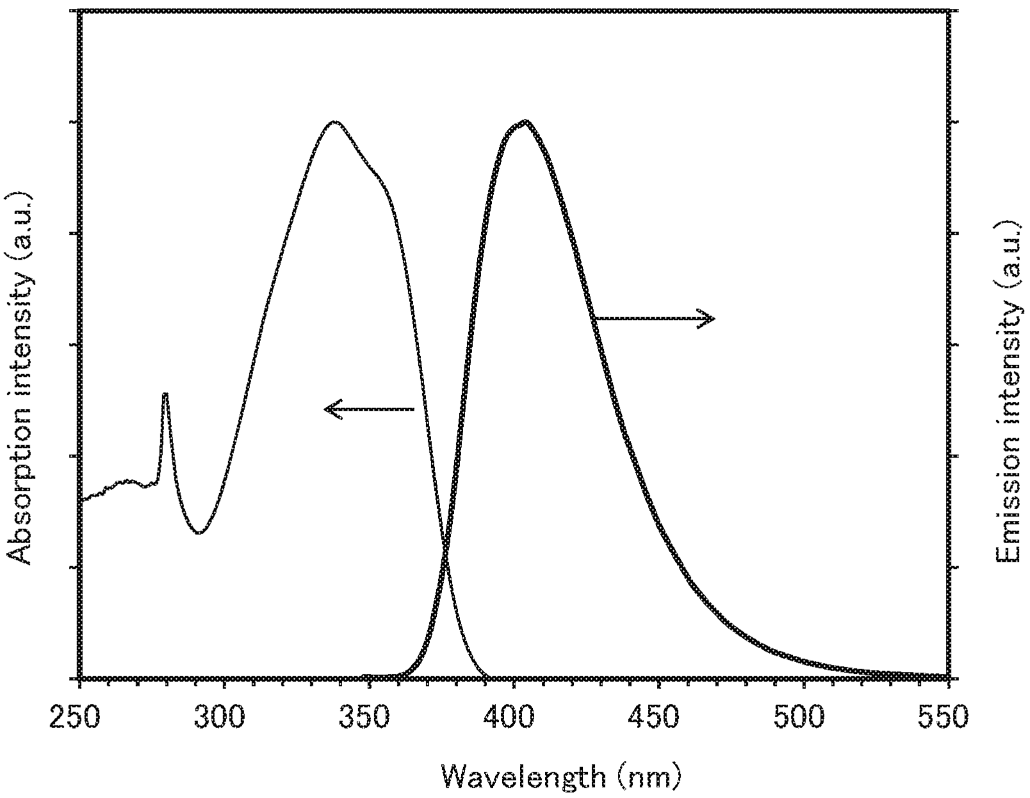
FIG. 117 shows an absorption spectrum and an emission spectrum of mmtBumBioFBi in a toluene solution.

Next, an ultraviolet-visible absorption spectrum (hereinafter, simply referred to as an absorption spectrum) of mmtBumBioFBi in a toluene solution and an emission spectrum thereof were measured. The absorption spectrum was measured with an ultraviolet-visible light spectrophotometer (V-550, manufactured by JASCO Corporation), and the emission spectrum was measured with a fluorescence spectrophotometer (FP-8600, manufactured by JASCO Corporation), both of which were measured at room temperature. A quartz cell was used for the measurement cell. FIG. 117 shows measurement results of the absorption spectrum and the emission spectrum. The horizontal axis represents the wavelength and the vertical axes represent the absorption intensity and emission intensity. The absorption intensity shown in FIG. 117 is a result obtained by subtraction of an absorption spectrum of only toluene in a quartz cell from the measured absorption spectrum of the toluene solution in the quartz cell.

As shown in FIG. 117, the organic compound mmtBumBioFBi has an emission peak at 404 nm.

Next, the organic compound mmtBumBioFBi was subjected to a mass spectrometry (MS) analysis by liquid chromatography-mass spectrometry (LC-MS).

In the LC-MS analysis, liquid chromatography (LC) separation was carried out with ACQUITY UPLC (registered trademark) manufactured by Waters Corporation, and MS analysis (mass spectrometry) was carried out with Xevo G2 Tof MS manufactured by Waters Corporation. Acquity UPLC BEH C4 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Further, a sample was prepared in such a manner that mmtBumBioFBi was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 681 which underwent the ionization under the above-described conditions was collided with an argon gas in a collision cell to dissociate into product ions. Energy (collision energy) for the collision with argon was 50 eV The measurement mass range was set to m/z (mass-to-charge ratio)=100 to 1500. The detection results of the dissociated product ions by time-of-flight (TOF) MS are shown in FIG. 118.

Figure 118:
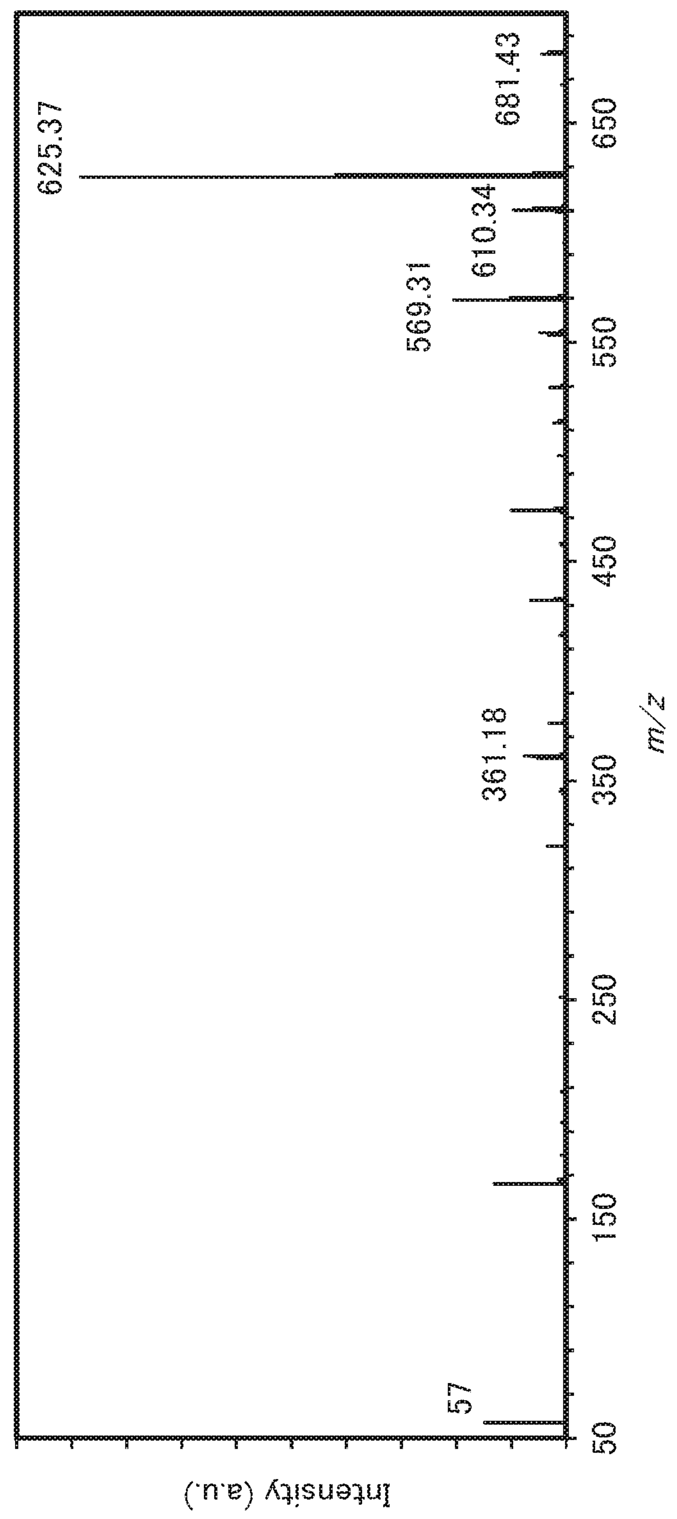
FIG. 118 shows an MS spectrum of mmtBumBioFBi.

FIG. 118 that product ions of mmtBumBioFBi are mainly detected at m/z of around 681. Note that the result in FIG. 118 shows characteristics derived from mmtBumBioFBi and therefore can be regarded as important data for identifying mmtBumBioFBi contained in a mixture.

FIG. 131 shows the results of measuring the refractive index of mmtBumBioFBi by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 131.

FIG. 131 shows that mmtBumBioFBi is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of mmtBumBioFBi was measured. Tg was measured using a differential scanning calorimeter (a Perkin-Elmer Co., Ltd. Pyris 1 DSC) in a state where a powder was put on an aluminum cell. As a result, Tg of mmtBumBioFBi was 102° C.

Example 24

Synthesis Example 18

In this example, a synthesis method of N-(4-tert-butylphenyl)-N-(3,3",5,5"-tetra-tert-butyl-1,1':3',1"-terphenyl-5'-yl)-9,9-dimethyl-9H-fluoren-2-amine (abbreviation: mmtBumTPtBuPAF), which is the organic compound of one embodiment of the present invention, is described. A structure of mmtBumTPtBuPAF is shown below.

[Chemical Formula 102]

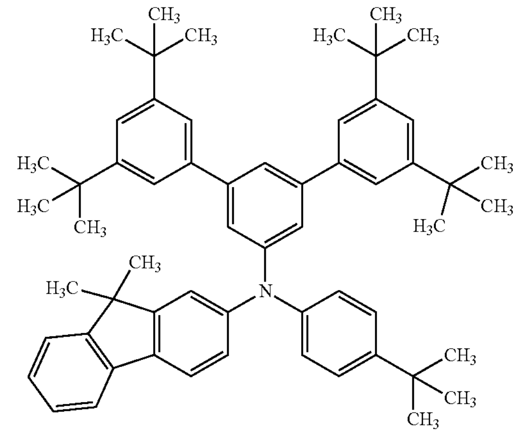

Step 1: Synthesis of N-(4-t-butyl)-9,9-dimethyl-9H-fluoren-2-amine

In a three-neck flask were put 11.5 g (55 mmol) of 9,9-dimethyl-9H-fluoren-2-amine, 11.7 g (55 mmol) of 4-t-butylaniline, 15.9 g (165 mmol) of sodium-tert-butoxide, and 180 mL of xylene. The mixture was degassed under reduced pressure, and then the air in the flask was replaced with nitrogen. Then, 200 mg (0.55 mmol) of allylpalladium (II) chloride dimer (abbreviation: $[(Allyl)PdCl]_2$) and 900 mg (2.20 mmol) of 2-dicyclohexylphosphino-2',6'-dimethoxybiphenyl (abbreviation: Sphos (registered trademark)) were added to this mixture, and the mixture was stirred at 120° C. under a nitrogen stream for approximately 4 hours. After that, the temperature of the flask was lowered to approximately 60° C., approximately 3 mL of water was added, a precipitated solid was separated by filtration, and the solid was washed with toluene. The filtrate was concentrated, and the obtained toluene solution was purified by silica gel column chromatography. The obtained fraction was concentrated and dried under reduced pressure, whereby 16.4 g of a target brown oily substance was obtained in a yield of 87%. The synthesis scheme of N-(4-t-butyl)-9,9-dimethyl-9H-fluoren-2-amine in Step 1 is shown below.

[Chemical Formula 103]

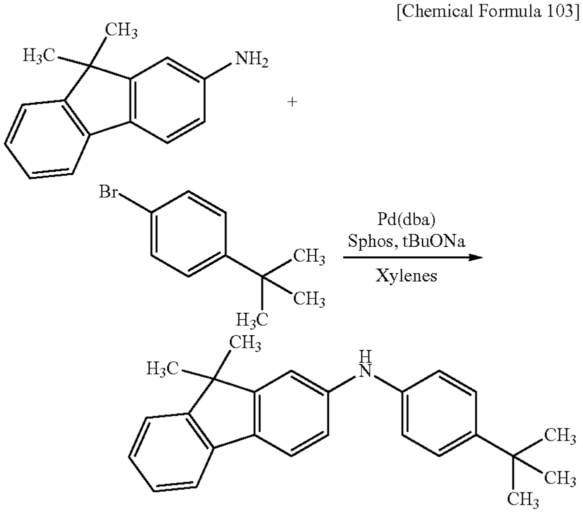

Step 2: Synthesis of 13,3",5,5"-tetra-t-butyl-5'-chloro-1,1':3',1"-terphenyl

The synthesis was performed in a manner similar to Step 1 of the synthesis example 11 in Example 11.

Step 3: Synthesis of N-(4-tert-butylphenyl)-N-(3,3",5,5"-tetra-tert-butyl-1,1':3',1"-terphenyl-5'-yl)-9,9-dimethyl-9H-fluoren-2-amine (Abbreviation: mmtBumTPtBuPAF)

In a three-neck flask were put 3.8 g (8.6 mmol) of 13,3",5,5"-tetra-t-butyl-5'-chloro-1,1':3',1"-terphenyl synthesized in Step 2, 3.0 g (8.6 mmol) of N-(4-t-butyl)-9,9-dimethyl-9H-fluoren-2-amine synthesized in Step 1, 2.5 g (25.9 mmol) of sodium-tert-butoxide, and 45 mL of xylene. The mixture was degassed under reduced pressure, and then the air in the flask was replaced with nitrogen. Then, 35 mg (0.086 mmol) of allylpalladium(II) chloride dimer (abbreviation: $[(Allyl)PdCl]_2$) and 122 mg (0.346 mmol) of di-tert-butyl(1-methyl-2,2-diphenylcyclopropyl)phosphine (abbreviation: cBRIDP (registered trademark)) were added to this mixture, and the mixture was stirred at 120° C. under a nitrogen stream for approximately 5 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The filtrate was concentrated to give a condensed toluene solution. Ethanol was added to this toluene solution and the toluene solution was concentrated under reduced pressure, whereby an ethanol suspension was obtained. The precipitate was filtrated at approximately 20° C., the obtained solid was dried at approximately 80° C. under reduced pressure, whereby 4.8 g of a target white solid was obtained in a yield of 70%. The synthesis scheme of mmtBumTPtBuPAF in Step 3 is shown below.

[Chemical Formula 104]

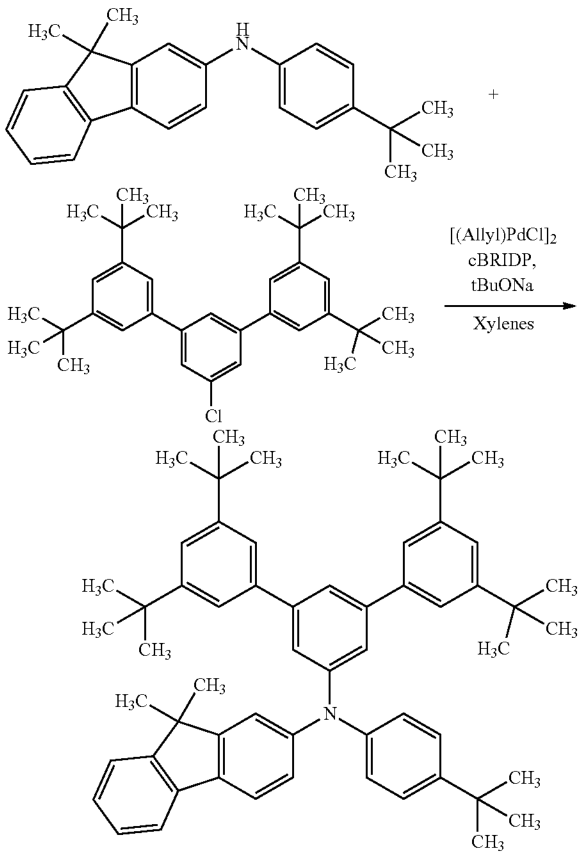

Figure 119A:
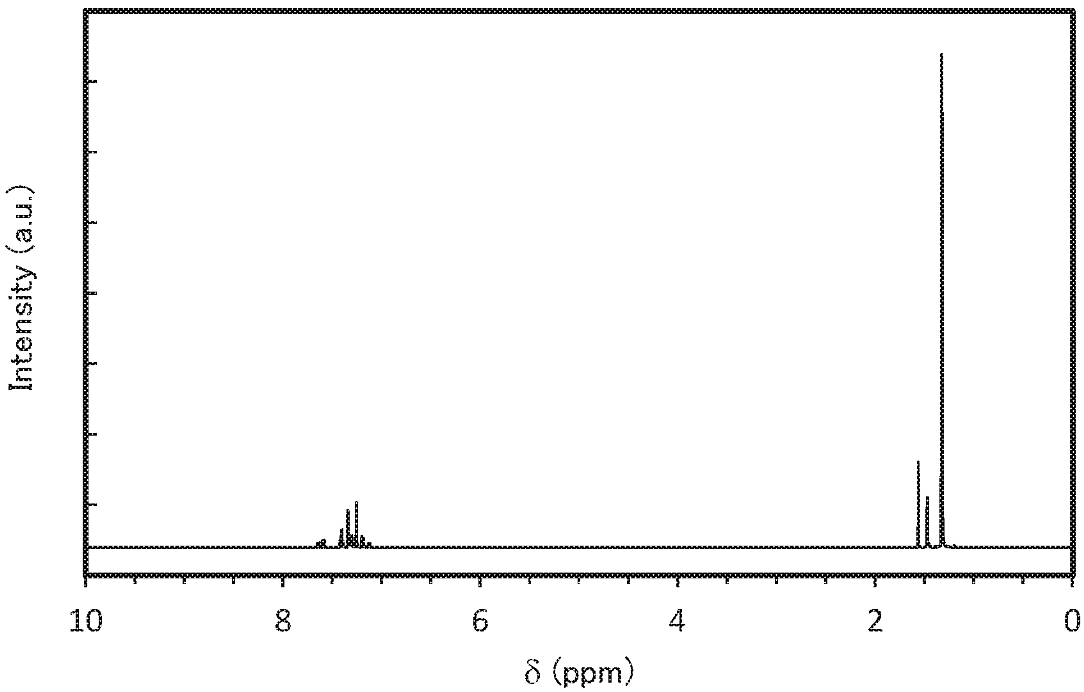
Figure 119B:
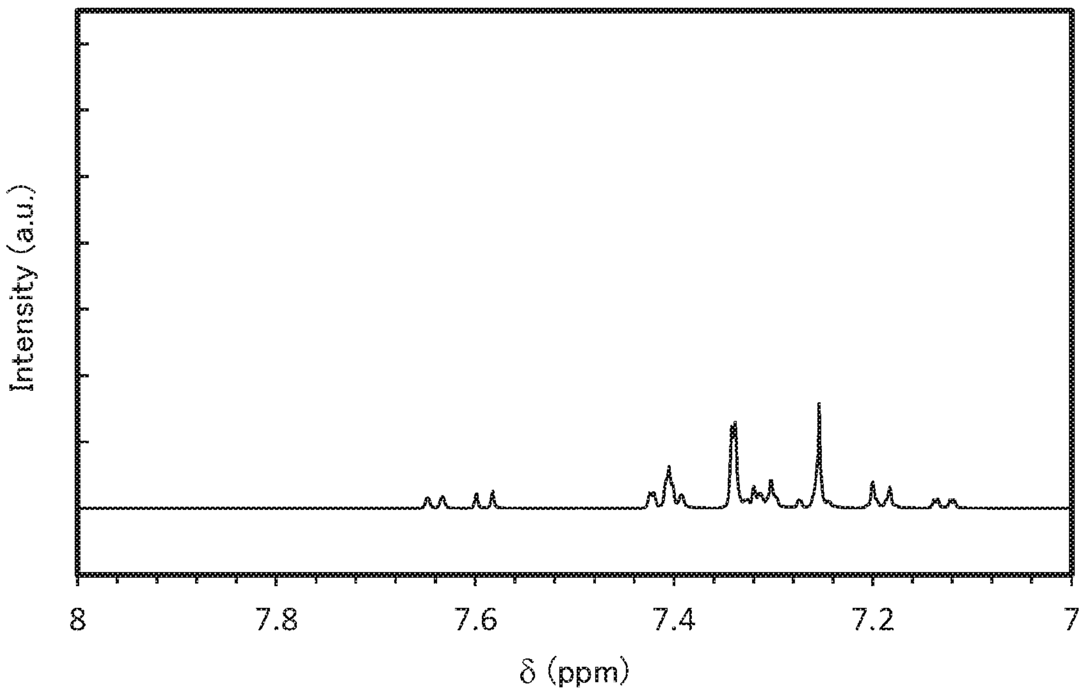

Analysis results by nuclear magnetic resonance spectroscopy (H-NMR) of the white solid obtained in Step 3 are shown below. FIGS. 119A and 119B are the $^1$H-NMR charts. The results show that the organic compound N-(4-tert-butylphenyl)-N-(3,3",5,5"-tetra-tert-butyl-1,1':3',1"-terphenyl-5'-yl)-9,9-dimethyl-9H-fluoren-2-amine (abbreviation: mmtBumTPtBuPAF) was synthesized in this synthesis example.

$^1$H-NMR. δ ($CDCl_3$): 7.64 (d, 1H, J=7.5 Hz), 7.59 (d, 1H, J=8.0 Hz), 7.38-7.43 (m, 4H), 7.29-7.36 (m, 8H), 7.24-7.28 (m, 3H), 7.19 (d, 2H, J=8.5 Hz), 7.13 (dd, 1H, J=1.5 Hz, 8.0 Hz), 1.47 (s, 6H), 1.32 (s, 45H).

Then, 4.8 g of the obtained white solid was purified by a train sublimation method. The purification by sublimation was conducted by heating at 250° C. under a pressure of 2.5 Pa with the argon flow rate of 15 mL/min. After the purification by sublimation, 4.0 g of a pale yellowish white solid was obtained at a collection rate of 83%.

Figure 120:
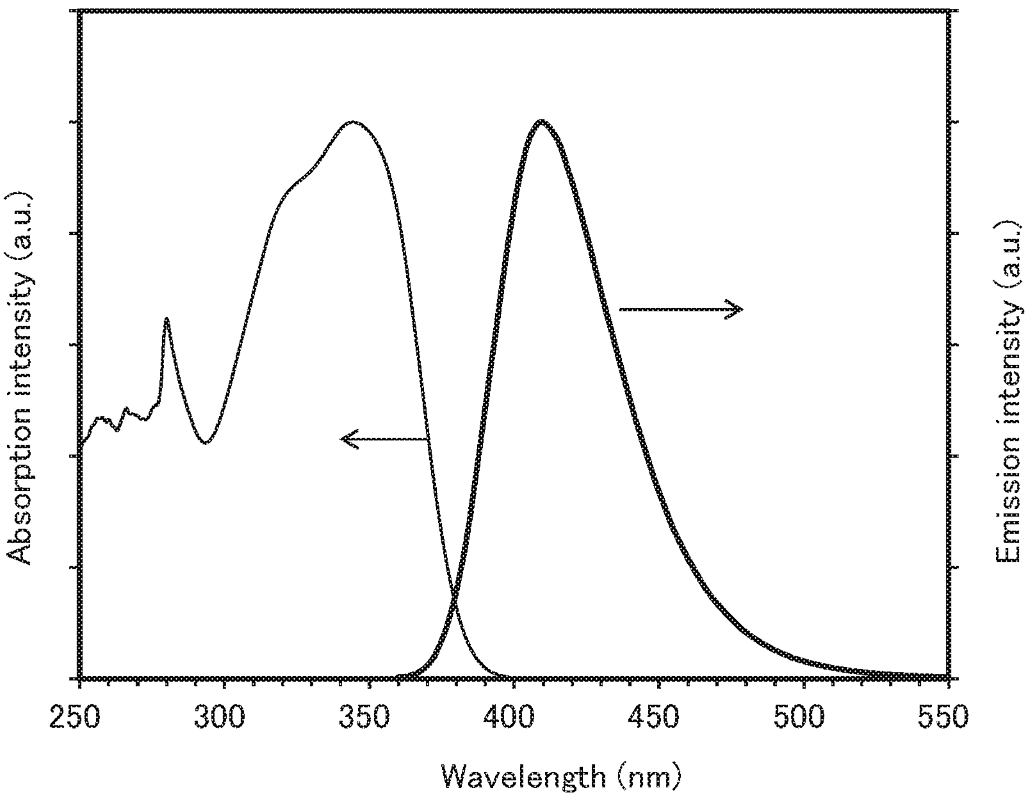

Next, an ultraviolet-visible absorption spectrum (hereinafter, simply referred to as an absorption spectrum) of mmtBumTPtBuPAF in a toluene solution and an emission spectrum thereof were measured. The absorption spectrum was measured at room temperature with an ultraviolet-visible light spectrophotometer (V-550, manufactured by JASCO Corporation) in a state where the toluene solution was put in a quartz cell. The emission spectrum was measured at room temperature with a fluorescence spectrophotometer (FP-8600, manufactured by JASCO Corporation) in a state where the toluene solution was put in a quartz cell. FIG. 120 shows measurement results of the absorption spectrum and emission spectrum. The horizontal axis represents the wavelength and the vertical axes represent the absorption intensity and emission intensity. In FIG. 120, two solid lines are shown; the thin line represents the absorption spectrum, and the thick line represents the emission spectrum. The absorption intensity shown in FIG. 120 is a result obtained by subtraction of an absorption spectrum of only toluene in a quartz cell from the measured absorption spectrum of the toluene solution in the quartz cell.

As shown in FIG. 120, the organic compound mmtBumTPtBuPAF has an emission peak at 409 nm.

FIG. 132 shows the results of measuring the refractive index of mmtBumTPtBuPAF by a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index of an ordinary ray, n, Ordinary, and a refractive index of an extraordinary ray, n, Extra-ordinary are shown in FIG. 132.

FIG. 132 shows that mmtBumTPtBuPAF is a material with a low refractive index: the refractive index of an ordinary ray is within the range of 1.50 to 1.75 in the entire blue light emitting region (from 455 nm to 465 nm), and the refractive index at 633 nm is within the range of 1.45 to 1.70.

Next, Tg of mmtBumTPtBuPAF was measured. Tg was measured using a differential scanning calorimeter (a Perkin-Elmer Co., Ltd. Pyris 1 DSC) in a state where a powder was put on an aluminum cell. As a result, Tg of mmtBumTPtBuPAF was 123° C.

Example 25

In this example, light-emitting devices of one embodiment of the present invention described in the above embodiments and a comparative light-emitting device are described. Structural formulae of organic compounds used in this example are shown below.

[Chemical Formula 105]

(xv)

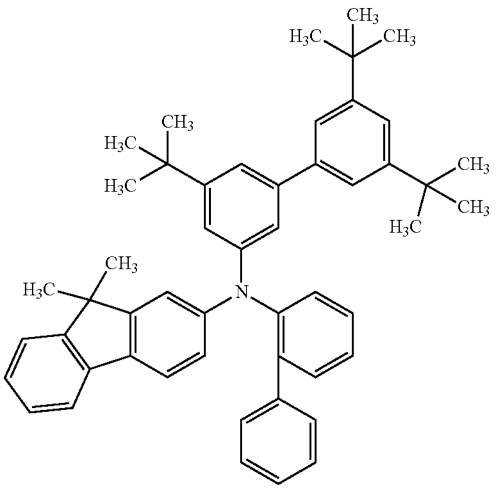

mmtBumBioFBi

-continued (xvi)

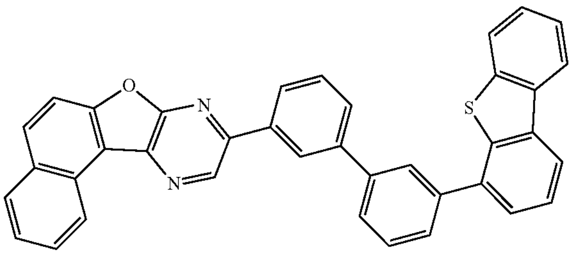

9mDBtBPNfpr (xvii)

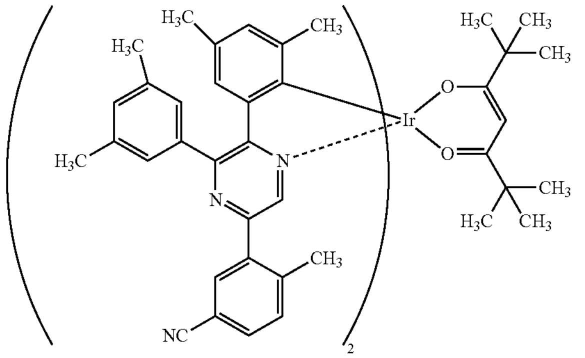

Ir(dmdppr-m5CP)2(dpm)

(ii)

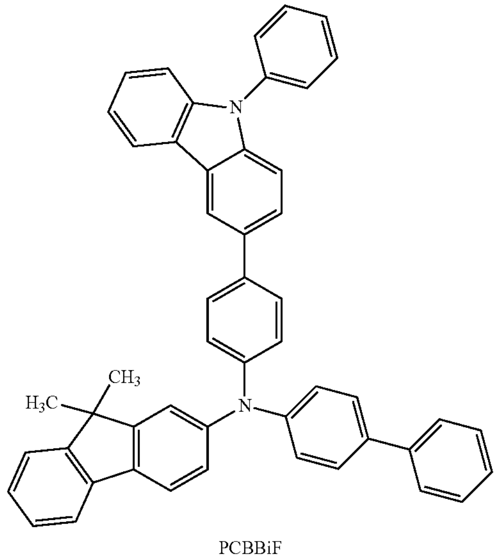

PCBBiF

-continued (v)

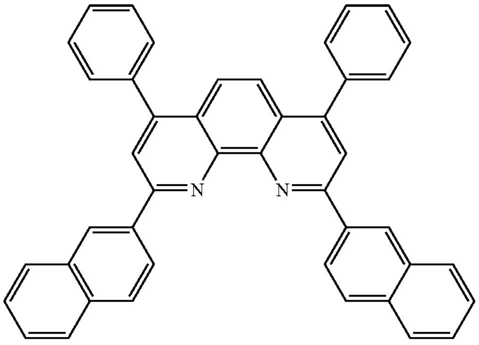

NBPhen (xviii)

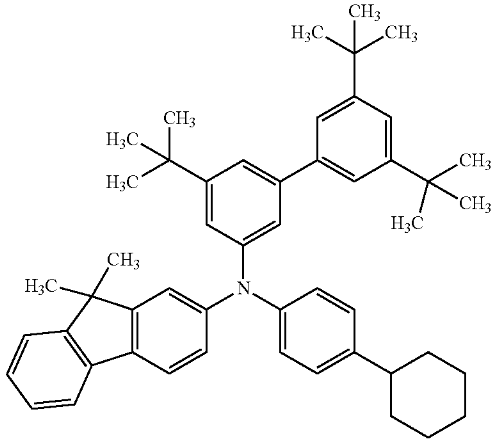

mmtBumBichPAF (Fabrication Method of Light-Emitting Device 11)

First, indium tin oxide containing silicon oxide (ITSO) was deposited over a glass substrate by a sputtering method to form the first electrode 101. The thickness of the first electrode 101 was 110 nm and the electrode area was 2 mm×2 mm.

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N-(1,1'-biphenyl-2-yl)-N-[(3,3',5'-tri-t-butyl)-1,1'-biphenyl-5-yl)-9,9-dimethyl-9H-fluoren-2-amine (abbreviation: mmtBumBioFBi) represented by the structural formula (xv) and ALD-MP001Q (produced by Analysis Atelier Corporation, material serial No. 1520180314) were deposited by co-evaporation to a thickness of 10 nm on the first electrode 101 such that the weight ratio of mmtBumBioFBi to ALD-MP001Q was 1:0.05, whereby the hole-injection layer 111 was formed.

Subsequently, over the hole-injection layer 111, mmtBumBioFBi was deposited by evaporation to a thickness of 55 nm, whereby the hole-transport layer 112 was formed.

Then, 9-[(3'-dibenzothiophen-4-yl)biphenyl-3-yl]naphtho[1',2':4,5]furo[2,3-b]pyrazine (abbreviation: 9mDBtBPNfpr) represented by the structural formula (xvi), N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by the structural formula (ii), and bis{4,6-dimethyl-2-[5-(5-cyano-2-methylphenyl)-3-(3,5-dimethylphenyl)-2-pyrazinyl-K]phenyl-κC}(2,2,6,6-tetramethyl-3,5-heptanedionato-$K_2$O,O')iridium(III) (abbreviation: Ir(dmdppr-m5CP)$_2$(dpm)) were deposited by co-evaporation to a thickness of 40 nm such that the weight ratio of 9mDBtBPNfpr to PCBBiF and [Ir(dmdppr-m5CP)$_2$(dpm)] was 0.7:0.3:0.1, where by the light-emitting layer 113 was formed.

After that, over the light-emitting layer 113, 9mDBtBPNfpr was deposited by evaporation to a thickness of 30 nm, and then 2,9-di(2-naphthyl)-4,7-diphenyl-1,10-phenanthroline (abbreviation: NBPhen) represented by the structural formula (v) was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115. Then, aluminum was deposited by evaporation to a thickness of 200 nm to form the second electrode 102. Thus, the light-emitting device 11 of this example was fabricated.

(Fabrication Method of Light-Emitting Device 12)

The light-emitting device 12 was fabricated in a manner similar to that for the light-emitting device 11 except that mmtBumBioFBi used in the hole-injection layer 111 and the hole-transport layer 112 was replaced with N-[(3,3',5'-tri-t-butyl)-1,1'-biphenyl-5-yl]-N-(4-cyclohexylphenyl)-9,9-dimethyl-9H-fluoren-2-amine (abbreviation: mmtBumBichPAF) represented by the structural formula (xviii).

(Fabrication Method of Comparative Light-Emitting Device 5)

The light-emitting device 5 was fabricated in a manner similar to that for the light-emitting device 11 except that mmtBumBioFBi used in the hole-injection layer 111 and the hole-transport layer 112 was replaced with PCBBiF.

The device structures of the light-emitting devices 11 and 12 and the comparative light-emitting device 5 are listed in the following table.

TABLE 20

| | Thickness | Light-emitting device 11 | Light-emitting device 12 | Comparative light-emitting device 5 |
|---|---|---|---|---|
| Electron-injection layer | 1 nm | | Lif | |
| Electron-transport layer | 10 nm | | NBPhen | |
| | 30 nm | | 9mDBtBPNfpr | |

TABLE 20-continued

| | Thickness | Light-emitting device 11 | Light-emitting device 12 | Comparative light-emitting device 5 |
|---|---|---|---|---|
| Light-emitting layer | 40 nm | 9mDBtBPNfpr:PCBBiF:Ir(dmdppr-m5CP)$_2$(dpm) (0.7:0.3:0.1) | | |
| Hole-transport layer | 55 nm | mmtBumBioFBi | mmtBumBichPAF | PCBBiF |
| Hole-injection layer | 10 nm | mmtBumBioFBi:ALD-MP001Q (1:0.05) | mmtBumBichPAF:ALD-MP001Q (1:0.05) | PCBBiF:ALD-MP001Q (1:0.05) |

The light-emitting devices and the comparative light-emitting devices were sealed using a glass substrate in a glove box containing a nitrogen atmosphere so as not to be exposed to the air (a sealing material was applied to surround the element and UV treatment and heat treatment at 80° C. for 1 hour were performed at the time of sealing). Then, the initial characteristics and reliability of the light-emitting devices were measured. Note that the sealed glass substrate was not subjected to particular treatment for improving outcoupling efficiency.

FIG. 121 shows the current efficiency-luminance characteristics of the light-emitting devices 11 and 12 and the comparative light-emitting device 5. FIG. 122 shows the external quantum efficiency-luminance characteristics thereof. FIG. 123 shows the emission spectra thereof. Luminance, CIE chromaticity, and emission spectra were measured with a spectroradiometer (UR-UL1R manufactured by TOPCON TECHNOHOUSE CORPORATION). The external quantum efficiency was calculated from the luminance and emission spectra measured with the spectroradiometer, on the assumption that the light-emitting devices had Lambertian light-distribution characteristics.

FIGS. 121 and 122 show that the light-emitting devices of one embodiment of the present invention using a material with a low refractive index are EL devices having higher external quantum efficiency than the comparative light-emitting device. The improvement in device efficiency is derived from an improvement in outcoupling efficiency owing to the low refractive index of the hole-transport layers of the light-emitting devices 11 and 12.

Example 26

In this example, a light-emitting device of one embodiment of the present invention described in the above embodiments and a comparative light-emitting device are described. Structural formulae of organic compounds used in this example are shown below.

[Chemical Formula 106]

(xix)

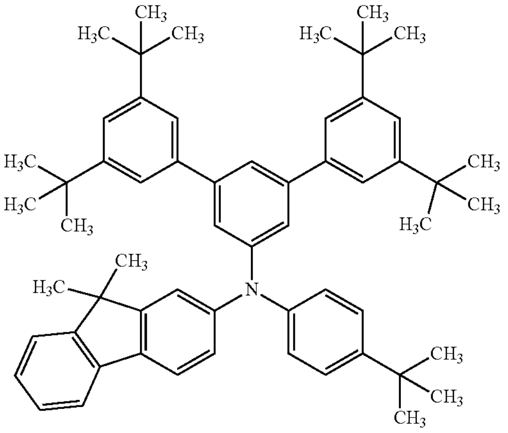

mmtBumTPtBuPAF (ix)

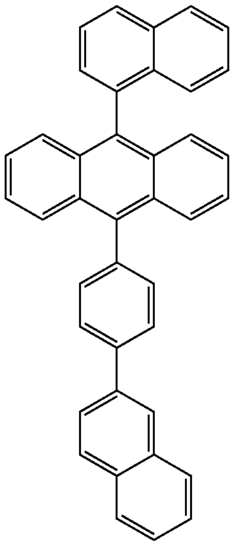

αN-βNPAnth

-continued
(xi)
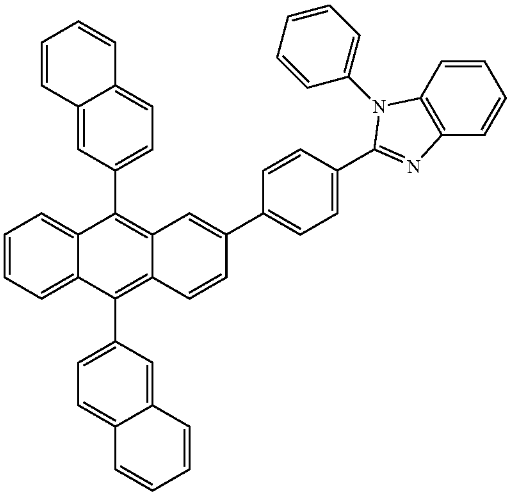
ZADN
(xiii)
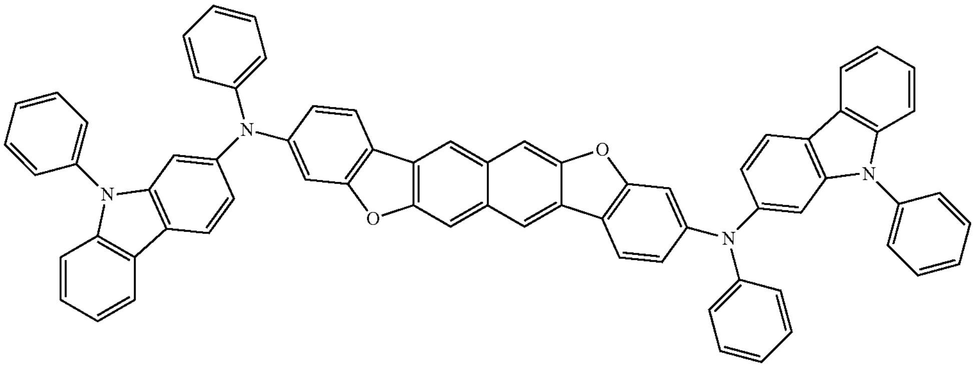
3,10PCA2Nbf(IV)-02
(xii)
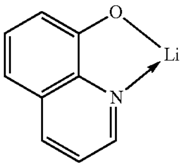
Liq
(ii)
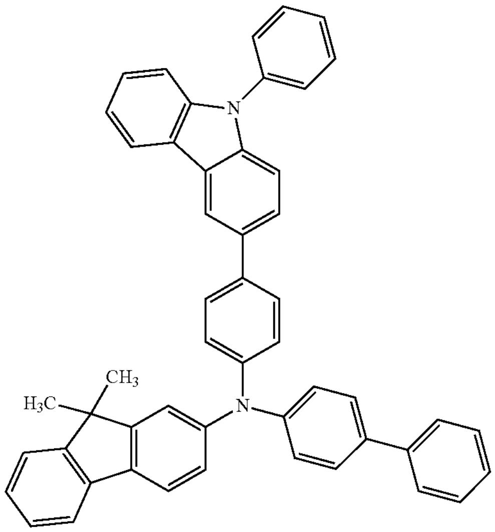
PCBBiF (Fabrication Method of Light-Emitting Device 13)

First, indium tin oxide containing silicon oxide (ITSO) was deposited over a glass substrate by a sputtering method to form the first electrode 101. The thickness of the first electrode 101 was 55 nm and the electrode area was 2 mm×2 mm.

Next, in pretreatment for forming the light-emitting device over a substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N-(4-tert-butylphenyl)-N-(3,3",5,5"-tetra-tert-butyl-1,1':3',1"-terphenyl-5'-yl)-9,9-dimethyl-9H-fluoren-2-amine (abbreviation: mmtBumTPtBuPAF) represented by the structural formula (xix) and ALD-MP001Q (produced by Analysis Atelier Corporation, material serial No. 1S20180314) were deposited by co-evaporation to a thickness of 10 nm on the first electrode 101 such that the weight ratio of mmtBumTPtBuPAF to ALD-MP001Q was 1:0.1, whereby the hole-injection layer 111 was formed.

Subsequently, over the hole-injection layer 111, mmtBumTPtBuPAF was deposited by evaporation to a thickness of 40 nm, whereby the hole-transport layer 112 was formed.

Then, 9-(1-naphthyl)-10-[4-(2-naphthyl)phenyl]anthracene (abbreviation: αN-βNPAnth) represented by the structural formula (ix) and 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02) represented by the structural formula (xiii) were deposited to a thickness of 25 nm by co-evaporation such that the weight ratio of αN-βNPAnth to 3,10PCA2Nbf(IV)-02 was 1:0.015, whereby the light-emitting layer 113 was formed.

After that, over the light-emitting layer 113, 2-{4-[9,10-di(naphthalen-2-yl)-2-anthryl]phenyl}-1-phenyl-1H-benzimidazole (abbreviation: ZADN) represented by the structural formula (xi) and 8-hydroxyquinolinatolithium (abbreviation: Liq) represented by the structural formula (xii) (produced by Chemipro Kasei Kaisha, Ltd., serial No. 181201) were deposited by co-evaporation to a thickness of 25 nm such that the weight ratio of ZADN to Liq was 1:1, whereby the electron-transport layer 114 was formed.

After the formation of the electron-transport layer 114, Liq was deposited by evaporation to a thickness of 1 nm to form the electron-injection layer 115. Then, aluminum was deposited by evaporation to a thickness of 200 nm to form the second electrode 102. Thus, the light-emitting device 13 of this example was fabricated.

(Fabrication Method of Comparative Light-Emitting Device 6)

The light-emitting device 6 was fabricated in a manner similar to that for the light-emitting device 13 except that mmtBumTPtBuPAF used in the hole-injection layer 111 and the hole-transport layer 112 was replaced with PCBBiF.

The device structures of the light-emitting device 13 and the comparative light-emitting device 6 are listed in the following table.

TABLE 21

| | Thickness | Light-emitting device 13 | Comparative light-emitting device 6 |
|---|---|---|---|
| Electron-injection layer | 1 nm | Liq | |
| Electron-transport layer | 25 nm | ZADN:Liq (1:1) | |
| Light-emitting layer | 25 nm | αN-βNPAnth:3,10PCA2Nbf(IV)-02 (1:0.015) | |
| Hole-transport layer | 40 nm | mmtBumTPtBuPAF | PCBBiF |
| Hole-injection layer | 10 nm | mmtBumTPtBuPAF: ALD-MP001Q (1:0.1) | PCBBif: ALD-MP001Q (1:0.1) |

The light-emitting device and the comparative light-emitting device were sealed using a glass substrate in a glove box containing a nitrogen atmosphere so as not to be exposed to the air (a sealing material was applied to surround the element and UV treatment and heat treatment at 80° C. for 1 hour were performed at the time of sealing). Then, the initial characteristics and reliability of the light-emitting devices were measured. Note that the sealed glass substrate was not subjected to particular treatment for improving outcoupling efficiency.

FIG. 124 shows the current efficiency-luminance characteristics of the light-emitting device 13 and the comparative light-emitting device 6. FIG. 125 shows the external quantum efficiency-luminance characteristics thereof. FIG. 126 shows the emission spectra thereof. Luminance and emission spectra were measured with a spectroradiometer (UR-UL1R manufactured by TOPCON TECHNOHOUSE CORPORATION). The external quantum efficiency was calculated from the luminance and emission spectra measured with the spectroradiometer, on the assumption that the light-emitting devices had Lambertian light-distribution characteristics.

FIGS. 124 and 125 show that the light-emitting device of one embodiment of the present invention using a material with a low refractive index is an EL device having higher external qualtum efficiency than the comparative light-emitting device. The improvement in device efficiency is derived from an improvement in outcoupling efficiency owing to the low refractive index of the hole-transport layer of the light-emitting device 13.

This application is based on Japanese Patent Application Serial No. 2019-126017 filed with Japan Patent Office on Jul. 5, 2019, Japanese Patent Application Serial No. 2020-015450 filed with Japan Patent Office on Jan. 31, 2020, Japanese Patent Application Serial No. 2020-067192 filed with Japan Patent Office on Apr. 3, 2020, and Japanese Patent Application Serial No. 2020-078898 filed with Japan Patent Office on Apr. 28, 2020, the entire contents of which are hereby incorporated by reference.

What is claimed is:

1. An organic compound represented by a general formula (G2), (G2)

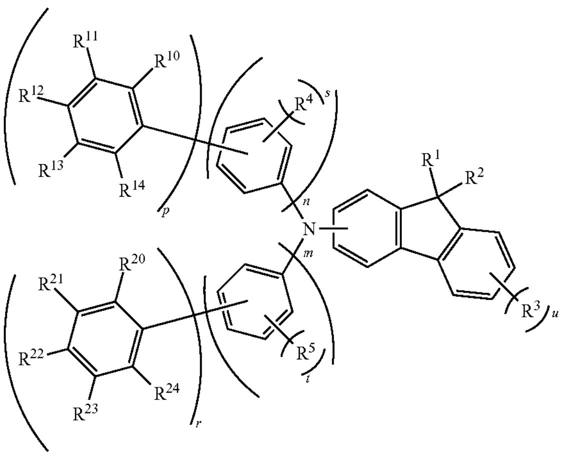

wherein:

n, m, p, and r each independently represent 1 or 2;

s, t, and u each independently represent an integer of 0 to 4;

n+p and m+r are each independently 2 or 3;

$R^4$ and $R^5$ each independently represent hydrogen or a hydrocarbon group having 1 to 3 carbon atoms;

$R^{10}$ to $R^{14}$ and $R^{20}$ to $R^{24}$ each independently represent hydrogen or a hydrocarbon group having 1 to 12 carbon atoms each forming bonds only by $sp^3$ hybrid orbitals;

one or more of $R^{10}$ to $R^{14}$ and $R^{20}$ to $R^{24}$ represent hydrocarbon groups each independently being an alkyl group having 3 to 8 carbon atoms or a monocyclic cycloalkyl group having 6 to 12 carbon atoms;

a total number of carbon atoms contained in each alkyl group having 3 to 8 carbon atoms and each monocyclic cycloalkyl group having 6 to 12 carbon atoms in $R^{10}$ to $R^{14}$ and $R^{20}$ to $R^{24}$ is 8 or more;

a total number of carbon atoms contained in each alkyl group having 3 to 8 carbon atoms and each monocyclic cycloalkyl group having 6 to 12 carbon atoms in either $R^{10}$ to $R^{14}$ or $R^{20}$ to $R^{24}$ is 6 or more;

$R^1$, $R^2$, and $R^3$ each independently represent an alkyl group having 1 to 4 carbon atoms; and at least one of s or t is 0.

2. The organic compound according to claim 1, wherein the alkyl group having 3 to 8 carbon atoms is a tert-butyl group, and wherein the monocyclic cycloalkyl group having 6 to 12 carbon atoms is a cyclohexyl group.

3. The organic compound according to claim 1, wherein u is 0.

4. A light-emitting device comprising the organic compound according to claim 1.

5. A light-emitting apparatus comprising:

the light-emitting device according to claim 4; and at least one of a transistor or a substrate.

6. The organic compound according to claim 1, wherein a proportion of a total number of carbon atoms each forming bonds only by $sp^3$ hybrid orbitals to a total number of carbon atoms in a molecule of the organic compound is higher than or equal to 23% and lower than or equal to 55%.

* * * * *